US012740943B2

(12) United States Patent
Benenato et al.

(10) Patent No.: US 12,740,943 B2
(45) Date of Patent: Sep. 22, 2026

(54) HEADGROUP LIPID COMPOUNDS AND COMPOSITIONS FOR INTRACELLULAR DELIVERY OF THERAPEUTIC AGENTS

(71) Applicant: ModernaTX, Inc., Cambridge, MA (US)

(72) Inventors: Kerry E. Benenato, Cambridge, MA (US); Mark Cornebise, Cambridge, MA (US); Edward Hennessy, Cambridge, MA (US); Andrew McKenzie, Cambridge, MA (US)

(73) Assignee: ModernaTX, Inc., Cambridge, MA (US)

( * ) Notice: Subject to any disclaimer, the term of this patent is extended or adjusted under 35 U.S.C. 154(b) by 943 days.

(21) Appl. No.: 17/761,863

(22) PCT Filed: Sep. 18, 2020

(86) PCT No.: PCT/US2020/051629

§ 371 (c)(1),
(2) Date: Mar. 18, 2022

(87) PCT Pub. No.: WO2021/055849

PCT Pub. Date: Mar. 25, 2021

(65) Prior Publication Data

US 2023/0000773 A1 Jan. 5, 2023

Related U.S. Application Data

(60) Provisional application No. 62/902,928, filed on Sep. 19, 2019.

(51) Int. Cl.

| | |
|---|---|
| ***A61K 9/1272*** | (2025.01) |
| ***A61K 31/7105*** | (2006.01) |
| ***C07C 237/10*** | (2006.01) |
| ***C07C 311/05*** | (2006.01) |
| ***C07D 207/456*** | (2006.01) |
| ***C07D 209/14*** | (2006.01) |
| ***C07D 231/56*** | (2006.01) |
| ***C07D 233/88*** | (2006.01) |
| ***C07D 237/22*** | (2006.01) |
| ***C07D 239/22*** | (2006.01) |
| ***C07D 239/38*** | (2006.01) |
| ***C07D 241/20*** | (2006.01) |
| ***C07D 249/14*** | (2006.01) |
| ***C07D 271/08*** | (2006.01) |
| ***C07D 285/10*** | (2006.01) |
| ***C07D 285/18*** | (2006.01) |
| ***C07D 307/68*** | (2006.01) |
| ***C07D 319/12*** | (2006.01) |
| ***C07F 5/02*** | (2006.01) |
| ***C07F 9/36*** | (2006.01) |

(52) U.S. Cl.
CPC ........ *A61K 9/1272* (2013.01); *A61K 31/7105* (2013.01); *C07C 237/10* (2013.01); *C07C 311/05* (2013.01); *C07D 207/456* (2013.01); *C07D 209/14* (2013.01); *C07D 231/56* (2013.01); *C07D 233/88* (2013.01); *C07D 237/22* (2013.01); *C07D 239/22* (2013.01); *C07D 239/38* (2013.01); *C07D 241/20* (2013.01); *C07D 249/14* (2013.01); *C07D 271/08* (2013.01); *C07D 285/10* (2013.01); *C07D 285/18* (2013.01); *C07D 307/68* (2013.01); *C07D 319/12* (2013.01); *C07F 5/027* (2013.01); *C07F 9/36* (2013.01)

(58) Field of Classification Search
None
See application file for complete search history.

(56) References Cited

U.S. PATENT DOCUMENTS

| | | | |
|---|---|---|---|
| 3,324,182 | A | 6/1967 | De et al. |
| 3,799,876 | A | 3/1974 | White et al. |
| 3,872,171 | A | 3/1975 | Cronin et al. |
| 4,125,544 | A | 11/1978 | Dygos |
| 4,957,735 | A | 9/1990 | Huang |
| 5,807,861 | A | 9/1998 | Klein et al. |
| 6,143,276 | A | 11/2000 | Unger |
| 6,303,378 | B1 | 10/2001 | Bridenbaugh et al. |

(Continued)

FOREIGN PATENT DOCUMENTS

| | | | |
|---|---|---|---|
| AU | 652831 B2 | 9/1994 | |
| CN | 102068701 A | 5/2011 | |

(Continued)

OTHER PUBLICATIONS

Abdelwahed et al., "Freeze-drying of nanoparticles: formulation, process and storage considerations," Advanced Drug Delivery Reviews 58, pp. 1688-1713, Dec. 30, 2006, Epub Oct. 6, 2006.

(Continued)

*Primary Examiner* — Anna R Falkowitz
*Assistant Examiner* — Edwin Coleman Mitchell
(74) *Attorney, Agent, or Firm* — Clark & Elbing LLP

(57) ABSTRACT

The invention features novel lipids and compositions involving the same. Lipid nanoparticles (e.g., empty LNPs or loaded LNPs) include a novel lipid as well as additional lipids such as phospholipids, structural lipids, and PEG lipids. Lipid nanoparticles (e.g., empty LNPs or loaded LNPs) further including therapeutic and/or prophylactics such as RNA are useful in the delivery of therapeutic and/or prophylactics to mammalian cells or organs to, for example, regulate polypeptide, protein, or gene expression.

14 Claims, No Drawings

(56) References Cited

U.S. PATENT DOCUMENTS

| | | | |
|---|---|---|---|
| 6,395,253 | B2 | 5/2002 | Levy et al. |
| 6,652,886 | B2 | 11/2003 | Ahn et al. |
| 6,696,038 | B1 | 2/2004 | Mahato et al. |
| 7,268,120 | B1 | 9/2007 | Horton et al. |
| 7,371,404 | B2 | 5/2008 | Panzner et al. |
| 7,943,168 | B2 | 5/2011 | Schlesinger et al. |
| 8,058,069 | B2 | 11/2011 | Yaworski et al. |
| 8,158,601 | B2 | 4/2012 | Chen et al. |
| 8,420,123 | B2 | 4/2013 | Troiano et al. |
| 8,440,614 | B2 | 5/2013 | Castor |
| 8,449,916 | B1 | 5/2013 | Bellaire et al. |
| 8,450,298 | B2 | 5/2013 | Mahon et al. |
| 8,460,696 | B2 | 6/2013 | Slobodkin et al. |
| 8,460,709 | B2 | 6/2013 | Ausborn et al. |
| 8,563,041 | B2 | 10/2013 | Grayson et al. |
| 8,568,784 | B2 | 10/2013 | Lillard et al. |
| 8,569,256 | B2 | 10/2013 | Heyes et al. |
| 8,580,297 | B2 | 11/2013 | Essler et al. |
| 8,603,499 | B2 | 12/2013 | Zale et al. |
| 8,603,500 | B2 | 12/2013 | Zale et al. |
| 8,603,501 | B2 | 12/2013 | Zale et al. |
| 8,603,534 | B2 | 12/2013 | Zale et al. |
| 8,603,535 | B2 | 12/2013 | Troiano et al. |
| 8,609,142 | B2 | 12/2013 | Troiano et al. |
| 8,613,951 | B2 | 12/2013 | Zale et al. |
| 8,613,954 | B2 | 12/2013 | Zale et al. |
| 8,617,608 | B2 | 12/2013 | Zale et al. |
| 8,618,240 | B2 | 12/2013 | Podobinski et al. |
| 8,637,083 | B2 | 1/2014 | Troiano et al. |
| 8,642,076 | B2 | 2/2014 | Manoharan et al. |
| 8,652,487 | B2 | 2/2014 | Maldonado |
| 8,652,528 | B2 | 2/2014 | Troiano et al. |
| 8,663,599 | B1 | 3/2014 | Sung et al. |
| 8,663,700 | B2 | 3/2014 | Troiano et al. |
| 8,668,926 | B1 | 3/2014 | Mousa et al. |
| 8,685,368 | B2 | 4/2014 | Reineke |
| 8,691,750 | B2 | 4/2014 | Constien et al. |
| 8,697,098 | B2 | 4/2014 | Perumal et al. |
| 8,703,204 | B2 | 4/2014 | Bloom et al. |
| 8,709,483 | B2 | 4/2014 | Farokhzad et al. |
| 8,715,736 | B2 | 5/2014 | Sachdeva et al. |
| 8,715,741 | B2 | 5/2014 | Maitra et al. |
| 8,728,527 | B2 | 5/2014 | Singh |
| 8,734,832 | B2 | 5/2014 | O'Hagan et al. |
| 8,734,846 | B2 | 5/2014 | Ali et al. |
| 8,734,853 | B2 | 5/2014 | Sood et al. |
| 8,802,644 | B2 | 8/2014 | Chen et al. |
| 9,006,487 | B2 | 4/2015 | Anderson et al. |
| 9,029,590 | B2 | 5/2015 | Colletti et al. |
| 9,394,234 | B2 | 7/2016 | Chen et al. |
| 9,717,690 | B2 | 8/2017 | Guild et al. |
| 9,738,593 | B2 | 8/2017 | Ansell et al. |
| 9,867,888 | B2 | 1/2018 | Benenato |
| 9,868,691 | B2 | 1/2018 | Benenato |
| 9,868,692 | B2 | 1/2018 | Benenato |
| 9,868,693 | B2 | 1/2018 | Benenato |
| 10,106,490 | B2 | 10/2018 | Du |
| 10,166,298 | B2 | 1/2019 | Ansell et al. |
| 10,195,156 | B2 | 2/2019 | Benenato et al. |
| 10,266,485 | B2 | 4/2019 | Benenato |
| 10,392,341 | B2 | 8/2019 | Benenato et al. |
| 10,442,756 | B2 | 10/2019 | Benenato et al. |
| 10,799,463 | B2 | 10/2020 | Benenato et al. |
| 10,857,105 | B2 | 12/2020 | Benenato et al. |
| 11,001,861 | B2 | 5/2021 | Martini et al. |
| 11,066,355 | B2 | 7/2021 | Benenato et al. |
| 11,203,569 | B2 | 12/2021 | Almarsson et al. |
| 11,220,476 | B2 | 1/2022 | Benenato et al. |
| 11,504,337 | B2 | 11/2022 | Martini et al. |
| 11,583,504 | B2 | 2/2023 | Brader |
| 11,597,698 | B2 | 3/2023 | Benenato et al. |
| 11,969,506 | B2 | 4/2024 | Patel et al. |
| 12,077,501 | B2 | 9/2024 | Benenato et al. |
| 12,144,895 | B2 | 11/2024 | Brader |
| 12,151,995 | B2 | 11/2024 | Benenato |
| 2003/0073619 | A1 | 4/2003 | Mahato et al. |
| 2003/0092653 | A1 | 5/2003 | Kisich et al. |
| 2004/0142474 | A1 | 7/2004 | Mahato et al. |
| 2005/0222064 | A1 | 10/2005 | Vargeese et al. |
| 2006/0008910 | A1 | 1/2006 | MacLachlan et al. |
| 2006/0083780 | A1 | 4/2006 | Heyes et al. |
| 2006/0172003 | A1 | 8/2006 | Meers et al. |
| 2006/0204566 | A1 | 9/2006 | Smyth-Templeton et al. |
| 2007/0252295 | A1 | 11/2007 | Panzner et al. |
| 2009/0042825 | A1 | 2/2009 | Matar et al. |
| 2009/0042829 | A1 | 2/2009 | Matar et al. |
| 2010/0285112 | A1 | 11/2010 | Novobrantseva et al. |
| 2010/0324120 | A1 | 12/2010 | Chen et al. |
| 2011/0009641 | A1 | 1/2011 | Anderson et al. |
| 2011/0200582 | A1 | 8/2011 | Baryza et al. |
| 2011/0244026 | A1 | 10/2011 | Guild et al. |
| 2012/0136073 | A1 | 5/2012 | Yang et al. |
| 2012/0177724 | A1 | 7/2012 | Irvine et al. |
| 2012/0178702 | A1 | 7/2012 | Huang et al. |
| 2012/0226085 | A1 | 9/2012 | Ishihara et al. |
| 2012/0295832 | A1 | 11/2012 | Constien et al. |
| 2013/0017223 | A1 | 1/2013 | Hope et al. |
| 2013/0064894 | A1 | 3/2013 | Martin et al. |
| 2013/0065942 | A1 | 3/2013 | Matar et al. |
| 2013/0090372 | A1 | 4/2013 | Budzik et al. |
| 2013/0108685 | A1 | 5/2013 | Kuboyama et al. |
| 2013/0115273 | A1 | 5/2013 | Yang et al. |
| 2013/0115274 | A1 | 5/2013 | Knopov et al. |
| 2013/0116307 | A1 | 5/2013 | Heyes et al. |
| 2013/0122104 | A1 | 5/2013 | Yaworski et al. |
| 2013/0123338 | A1 | 5/2013 | Heyes et al. |
| 2013/0129785 | A1 | 5/2013 | Manoharan et al. |
| 2013/0130348 | A1 | 5/2013 | Gu et al. |
| 2013/0142868 | A1 | 6/2013 | Hoekman et al. |
| 2013/0142876 | A1 | 6/2013 | Howard et al. |
| 2013/0150625 | A1 | 6/2013 | Budzik et al. |
| 2013/0156845 | A1 | 6/2013 | Manoharan et al. |
| 2013/0156849 | A1 | 6/2013 | De Fougerolles et al. |
| 2013/0164400 | A1 | 6/2013 | Knopov et al. |
| 2013/0171241 | A1 | 7/2013 | Geall |
| 2013/0172406 | A1 | 7/2013 | Zale et al. |
| 2013/0178541 | A1 | 7/2013 | Stanton et al. |
| 2013/0183244 | A1 | 7/2013 | Hanes et al. |
| 2013/0183355 | A1 | 7/2013 | Jain et al. |
| 2013/0183372 | A1 | 7/2013 | Schutt et al. |
| 2013/0183373 | A1 | 7/2013 | Schutt et al. |
| 2013/0183375 | A1 | 7/2013 | Schutt et al. |
| 2013/0189351 | A1 | 7/2013 | Geall |
| 2013/0195759 | A1 | 8/2013 | Mirkin et al. |
| 2013/0195765 | A1 | 8/2013 | Gho et al. |
| 2013/0195967 | A1 | 8/2013 | Guild et al. |
| 2013/0195968 | A1 | 8/2013 | Geall et al. |
| 2013/0195969 | A1 | 8/2013 | Geall et al. |
| 2013/0202684 | A1 | 8/2013 | Geall et al. |
| 2013/0236500 | A1 | 9/2013 | Zale et al. |
| 2013/0236533 | A1 | 9/2013 | Von Andrian et al. |
| 2013/0236550 | A1 | 9/2013 | Ausborn et al. |
| 2013/0243827 | A1 | 9/2013 | Troiano et al. |
| 2013/0243848 | A1 | 9/2013 | Lobovkina et al. |
| 2013/0243867 | A1 | 9/2013 | Mohapatra et al. |
| 2013/0251766 | A1 | 9/2013 | Zale et al. |
| 2013/0251816 | A1 | 9/2013 | Zale et al. |
| 2013/0251817 | A1 | 9/2013 | Zale et al. |
| 2013/0266617 | A1 | 10/2013 | Mirosevich et al. |
| 2013/0273117 | A1 | 10/2013 | Podobinski et al. |
| 2013/0274504 | A1 | 10/2013 | Colletti et al. |
| 2013/0274523 | A1 | 10/2013 | Bawiec, III et al. |
| 2013/0280334 | A1 | 10/2013 | Karp et al. |
| 2013/0280339 | A1 | 10/2013 | Zale et al. |
| 2013/0295183 | A1 | 11/2013 | Troiano et al. |
| 2013/0295191 | A1 | 11/2013 | Troiano et al. |
| 2013/0302432 | A1 | 11/2013 | Zale et al. |
| 2013/0302433 | A1 | 11/2013 | Troiano et al. |
| 2013/0315831 | A1 | 11/2013 | Shi et al. |
| 2013/0330401 | A1 | 12/2013 | Payne et al. |
| 2013/0338210 | A1 | 12/2013 | Manoharan et al. |
| 2013/0344158 | A1 | 12/2013 | Zale et al. |
| 2014/0017327 | A1 | 1/2014 | Cheng et al. |
| 2014/0017329 | A1 | 1/2014 | Mousa |

(56) References Cited

U.S. PATENT DOCUMENTS

2014/0037573 A1 2/2014 Eliasof et al.
2014/0037660 A1 2/2014 Fotin-Mleczek et al.
2014/0037714 A1 2/2014 Quay et al.
2014/0039032 A1 2/2014 Kuboyama et al.
2014/0044772 A1 2/2014 Maclachlan et al.
2014/0044791 A1 2/2014 Basilion et al.
2014/0045913 A1 2/2014 Kuboyama et al.
2014/0050775 A1 2/2014 Slobodkin et al.
2014/0057109 A1 2/2014 Menchen et al.
2014/0065172 A1 3/2014 Echeverri et al.
2014/0065204 A1 3/2014 Hayes et al.
2014/0065228 A1 3/2014 Yaworski et al.
2014/0079774 A1 3/2014 Brinker et al.
2014/0093575 A1 4/2014 Hammond et al.
2014/0093579 A1 4/2014 Zale et al.
2014/0113137 A1 4/2014 Podobinski et al.
2014/0121263 A1 5/2014 Fitzgerald et al.
2014/0121393 A1 5/2014 Manoharan et al.
2014/0134260 A1 5/2014 Heyes et al.
2014/0141070 A1 5/2014 Geall et al.
2014/0141089 A1 5/2014 Liang
2014/0141483 A1 5/2014 Bossard et al.
2014/0142165 A1 5/2014 Grayson et al.
2014/0142254 A1 5/2014 Fonnum et al.
2014/0161830 A1 6/2014 Anderson et al.
2014/0288160 A1 9/2014 Guild et al.
2014/0308304 A1 10/2014 Manoharan et al.
2015/0174260 A1 6/2015 Yang et al.
2015/0174261 A1 6/2015 Kuboyama et al.
2015/0239926 A1 8/2015 Payne et al.
2015/0284317 A1 10/2015 Colletti et al.
2015/0343062 A1 12/2015 Kuboyama et al.
2015/0376115 A1 12/2015 Ansell et al.
2016/0002178 A1 1/2016 Fenton et al.
2016/0009657 A1 1/2016 Anderson et al.
2016/0022580 A1 1/2016 Ramsay et al.
2016/0151284 A1 6/2016 Heyes et al.
2016/0317458 A1 11/2016 Brito et al.
2016/0361411 A1 12/2016 Gindy et al.
2017/0119904 A1 5/2017 Ansell et al.
2018/0201572 A1 7/2018 Benenato
2018/0273467 A1 9/2018 Benenato
2018/0303925 A1 10/2018 Weissman et al.
2018/0333366 A1 11/2018 Benenato et al.
2018/0369419 A1 12/2018 Benenato et al.
2019/0016669 A1 1/2019 Benenato et al.
2019/0298657 A1 10/2019 Martini et al.
2019/0298658 A1 10/2019 Benenato et al.
2019/0314291 A1 10/2019 Besin et al.
2019/0314292 A1 10/2019 Benenato et al.
2019/0314524 A1 10/2019 Ansell et al.
2019/0336452 A1 11/2019 Brader
2019/0390181 A1 12/2019 Benenato et al.
2020/0069599 A1 3/2020 Smith et al.
2020/0129445 A1 4/2020 Patel et al.
2020/0131116 A1 4/2020 Almarsson et al.
2020/0306191 A1 10/2020 Schariter et al.
2021/0087135 A1 3/2021 Benenato et al.
2021/0154148 A1 5/2021 Benenato et al.
2021/0161829 A1 6/2021 Benenato et al.
2021/0198200 A1 7/2021 Benenato et al.
2022/0073449 A1 3/2022 Almarsson et al.
2022/0106259 A1 4/2022 Benenato et al.
2022/0265857 A1 8/2022 Besin et al.
2022/0380299 A1 12/2022 Benenato et al.
2022/0409536 A1 12/2022 Benenato et al.
2023/0286903 A1 9/2023 Benenato et al.
2023/0364024 A1 11/2023 Brader
2024/0124388 A1 4/2024 Benenato et al.
2024/0226026 A1 7/2024 Benenato

FOREIGN PATENT DOCUMENTS

CN 102204920 A 10/2011
CN 102813929 A 12/2012
CN 104644555 A 5/2015
EP 737750 A2 10/1996
EP 2073848 B1 8/2013
EP 1404860 B1 11/2013
JP 2000169864 A 6/2000
WO WO-1993014778 A1 8/1993
WO WO-1999014346 A2 3/1999
WO WO-9915580 A1 4/1999
WO WO-9954344 A1 10/1999
WO WO-1999052503 A2 10/1999
WO WO-03086280 A2 10/2003
WO WO-2005034979 A2 4/2005
WO WO-2006063249 A2 6/2006
WO WO-2008042973 A2 4/2008
WO WO-2009024599 A1 2/2009
WO WO-2009053686 A1 4/2009
WO WO-2009086558 A1 7/2009
WO WO-2009127060 A1 10/2009
WO WO-2009129385 A1 10/2009
WO WO-2009129395 A1 10/2009
WO WO-2010030739 A1 3/2010
WO WO-2010042877 A1 4/2010
WO WO-2010053572 A2 5/2010
WO WO-2010054406 A1 5/2010
WO WO-2010060818 A1 6/2010
WO WO-2010088537 A2 8/2010
WO WO-2010129709 A1 11/2010
WO WO-2010135207 A1 11/2010
WO WO-2011017548 A1 2/2011
WO WO-2011058990 A1 5/2011
WO WO-2011068810 A1 6/2011
WO WO-2011127255 A1 10/2011
WO WO-2011136368 A1 11/2011
WO WO-2012000104 A1 1/2012
WO WO-2012006376 A2 1/2012
WO WO-2012006378 A1 1/2012
WO WO-2012030901 A1 3/2012
WO WO-2012031043 A1 3/2012
WO WO-2012031046 A2 3/2012
WO WO-2012054365 A2 4/2012
WO WO-2012129483 A1 9/2012
WO WO-2012149252 A2 11/2012
WO WO-2012149255 A2 11/2012
WO WO-2012149265 A2 11/2012
WO WO-2012149282 A2 11/2012
WO WO-2012149301 A2 11/2012
WO WO-2012149376 A2 11/2012
WO WO-2012149393 A2 11/2012
WO WO-2012153338 A2 11/2012
WO WO-2012170889 A1 12/2012
WO WO-2012170930 A1 12/2012
WO WO-2013006825 A1 1/2013
WO WO-2013006834 A1 1/2013
WO WO-2013006837 A1 1/2013
WO WO-2013006838 A1 1/2013
WO WO-2013006842 A2 1/2013
WO WO-2013016058 A1 1/2013
WO WO-2013033438 A2 3/2013
WO WO-2013033563 A1 3/2013
WO WO-2013036835 A1 3/2013
WO WO-2013049328 A1 4/2013
WO WO-2013052167 A2 4/2013
WO WO-2013056132 A2 4/2013
WO WO-2013057715 A1 4/2013
WO WO-2013059496 A1 4/2013
WO WO-2013059922 A1 5/2013
WO WO-2013064911 A2 5/2013
WO WO-2013066903 A1 5/2013
WO WO-2013067537 A1 5/2013
WO WO-2013070872 A1 5/2013
WO WO-2013072929 A2 5/2013
WO WO-2013086322 A1 6/2013
WO WO-2013086354 A1 6/2013
WO WO-2013086373 A1 6/2013
WO WO-2013086526 A1 6/2013
WO WO-2013087083 A1 6/2013
WO WO-2013087791 A1 6/2013
WO WO-2013093648 A2 6/2013
WO WO-2013126803 A1 8/2013

(56) References Cited

FOREIGN PATENT DOCUMENTS

| | | | |
|---|---|---|---|
| WO | WO-2013135359 A1 | 9/2013 | |
| WO | WO-2013143555 A1 | 10/2013 | |
| WO | WO-2013143683 A1 | 10/2013 | |
| WO | WO-2013148186 A1 | 10/2013 | |
| WO | WO-2013148541 A1 | 10/2013 | |
| WO | WO-2013149141 A1 | 10/2013 | |
| WO | WO-2013151650 A1 | 10/2013 | |
| WO | WO-2013155487 A1 | 10/2013 | |
| WO | WO-2013158127 A1 | 10/2013 | |
| WO | WO-2013158579 A1 | 10/2013 | |
| WO | WO-2013155493 A9 | 11/2013 | |
| WO | WO-2013166498 A1 | 11/2013 | |
| WO | WO-2013173693 A1 | 11/2013 | |
| WO | WO-2013177419 A2 | 11/2013 | |
| WO | WO-2013177421 A2 | 11/2013 | |
| WO | WO-2013185069 A1 | 12/2013 | |
| WO | WO-2014007398 A1 | 1/2014 | |
| WO | WO-2014008334 A1 | 1/2014 | |
| WO | WO-2014026284 A1 | 2/2014 | |
| WO | WO-2014028487 A1 | 2/2014 | |
| WO | WO-2014028763 A1 | 2/2014 | |
| WO | WO-2014047649 A1 | 3/2014 | |
| WO | WO-2014048969 A1 | 4/2014 | |
| WO | WO-2014052634 A1 | 4/2014 | |
| WO | WO-2014054026 A1 | 4/2014 | |
| WO | WO-2014071072 A2 | 5/2014 | |
| WO | WO-2014072997 A1 | 5/2014 | |
| WO | WO-2014089486 A1 | 6/2014 | |
| WO | WO-2014144196 A1 | 9/2014 | |
| WO | WO-2014160243 A1 | 10/2014 | |
| WO | WO-2014172045 A1 | 10/2014 | |
| WO | WO-2014182661 A2 | 11/2014 | |
| WO | WO-2014210356 A1 | 12/2014 | |
| WO | WO-2015011633 A1 | 1/2015 | |
| WO | WO-2015095346 A1 | 6/2015 | |
| WO | WO-2015130584 A2 | 9/2015 | |
| WO | WO-2015154002 A1 | 10/2015 | |
| WO | WO-2015199952 A1 | 12/2015 | |
| WO | WO-2016004202 A1 | 1/2016 | |
| WO | WO-2016004318 A1 | 1/2016 | |
| WO | WO-2016118697 A1 | 7/2016 | |
| WO | WO-2016118724 A1 | 7/2016 | |
| WO | WO-2016176330 A1 | 11/2016 | |
| WO | WO-2017004143 A1 | 1/2017 | |
| WO | WO-2017010573 A1 | 1/2017 | |
| WO | WO-2017015630 A2 | 1/2017 | |
| WO | WO-2017031232 A1 | 2/2017 | |
| WO | WO-2017049245 A2 | 3/2017 | |
| WO | WO-2017070616 A2 | 4/2017 | |
| WO | WO-2017070626 A2 | 4/2017 | |
| WO | WO-2017075531 A1 | 5/2017 | |
| WO | WO-2017099823 A1 | 6/2017 | |
| WO | WO-2017100744 A1 | 6/2017 | |
| WO | WO-2017112865 A1 | 6/2017 | |
| WO | WO-2017117528 A1 | 7/2017 | |
| WO | WO-2017127750 A1 | 7/2017 | |
| WO | WO-2017176974 A1 | 10/2017 | |
| WO | WO-2017180917 A2 | 10/2017 | |
| WO | WO-2017192470 A1 | 11/2017 | |
| WO | WO-2017201317 A1 | 11/2017 | |
| WO | WO-2017201325 A1 | 11/2017 | |
| WO | WO-2017201328 A1 | 11/2017 | |
| WO | WO-2017201332 A1 | 11/2017 | |
| WO | WO-2017201333 A1 | 11/2017 | |
| WO | WO-2017201340 A2 | 11/2017 | |
| WO | WO-2017201342 A1 | 11/2017 | |
| WO | WO-2017201346 A1 | 11/2017 | |
| WO | WO-2017201347 A1 | 11/2017 | |
| WO | WO-2017201348 A1 | 11/2017 | |
| WO | WO-2017201349 A1 | 11/2017 | |
| WO | WO-2017201350 A1 | 11/2017 | |
| WO | WO-2017201352 A1 | 11/2017 | |
| WO | WO-2017218704 A1 | 12/2017 | |
| WO | WO-2018078053 A1 | 5/2018 | |
| WO | WO-2018081480 A1 | 5/2018 | |
| WO | WO-2018081638 A1 | 5/2018 | |
| WO | WO-2018089540 A1 | 5/2018 | |
| WO | WO-2018144775 A1 | 8/2018 | |
| WO | WO-2018170260 A1 | 9/2018 | |
| WO | WO-2018170270 A1 | 9/2018 | |
| WO | WO-2018170306 A1 | 9/2018 | |
| WO | WO-2018170322 A1 | 9/2018 | |
| WO | WO-2018170336 A1 | 9/2018 | |
| WO | WO-2018191719 A1 | 10/2018 | |
| WO | WO-2018200943 A1 | 11/2018 | |
| WO | WO-2018225871 A1 | 12/2018 | |
| WO | WO-2018232120 A1 | 12/2018 | |
| WO | WO-2019036008 A1 | 2/2019 | |
| WO | WO-2019036030 A1 | 2/2019 | |
| WO | WO-2019046809 A1 | 3/2019 | |
| WO | WO-2019089828 A1 | 5/2019 | |
| WO | WO-2019136241 A1 * | 7/2019 | ........... A61K 39/395 |
| WO | WO-2019152557 A1 * | 8/2019 | ......... A61K 39/0011 |
| WO | WO-2019193183 A2 | 10/2019 | |
| WO | WO-2019202035 A1 | 10/2019 | |
| WO | WO-2020002525 A1 | 1/2020 | |
| WO | WO-2020061367 A1 | 3/2020 | |
| WO | WO-2020061457 A1 | 3/2020 | |
| WO | WO-2020123300 A2 | 6/2020 | |
| WO | WO-2021055833 A1 | 3/2021 | |
| WO | WO-2021055835 A1 | 3/2021 | |
| WO | WO-2021055849 A1 | 3/2021 | |
| WO | WO-2021204175 A1 | 10/2021 | |
| WO | WO-2022204288 A1 | 9/2022 | |
| WO | WO-2023107669 A1 | 6/2023 | |

OTHER PUBLICATIONS

Akinc, A., et al., "Targeted Delivery of RNAi Therapeutics with Endogenous and Exogenous Ligand-Based Mechanisms," Mol Ther. 2010 18(7):1357-1364.

Akinc et al., Development of LipidoidsiRNA Formulations for Systemic Delivery to the Liver, Molecular Therapy, May 2009, vol. 17, No. 5, pp. 872-879.

Anderson, D.M. et al., Stability of mRNA/cationic lipid lipoplexes in human and rat cerebrospinal fluid: methods and evidence for nonviral mRNA gene delivery to the central nervous system. Hum Gene Ther. Feb. 10, 2003; 14(3):191-202.

Andries, O., et al., Comparison of the gene transfer efficiency of mRNA/GL67 and pDNA/GL67 complexes in respiratory cells. Mol Pharmaceutics. 2012; 9: 2136-2145.

Ashizawa et al., "Liposomal delivery of nucleic acid-based anti-cancer therapeutics: BP-100-1.01," Expert Opin. Drug Deliv., (2014) 12(7):1107-1120.

Bag, J., Recovery of normal protein synthesis in heat-shocked chicken myotubes by liposome-mediated transfer of mRNAs. Can. J. Biochem. Cell Biol. 1985; 63(3): 231-235.

Belliveau et al., "Microfluidic Synthesis of Highly Potent Limit-size Lipid Nanoparticles for In Vivo Delivery of siRNA," Molecular Therapy-Nucleic Acids, 2012, 1, e37, 9 pages.

Berge, S.M. et al., "Pharmaceutical Salts," Journal of Pharmaceutical Sciences, Jan. 1977, vol. 66, No. 1, pp. 1-19.

Bettinger, T. et al., Peptide-mediated RNA delivery: a novel approach for enhanced transfection of primary and post-mitotic cells. Nucleic Acids Res. Sep. 15, 2001;29(18):3882-91.

Bolhassani A., et al. , Improvement of Different Vaccine Delivery Systems for Cancer Therapy, Molecular Cancer, Biomed Central, London, GB, 2011, vol. 10, No. 3, pp. 1-20.

Bonehill, A., et al., Single-step antigen loading and activation of dendritic cells by mRNA electroporation for the purpose of therapeutic vaccination in melanoma patients. Clin Cancer Res. May 2009; 15(10): 3366-3375.

Bouxsein, N.F., et al., Structure and gene silencing activities of monovalent and pentavalent cationic lipid vectors complexed with siRNA. Biochem. 2007; 46(16): 4785-4792.

Chen, D., et al., Rapid discovery of potent siRNA-containing lipid nanoparticles enabled by controlled microfluidic formulation. J Am Chem Soc. 2012; 134: 6948-6951.

(56) References Cited

OTHER PUBLICATIONS

Chen, S. et al., "Development of lipid nanoparticle formulations of siRNA for hepatocyte gene silencing following subcutaneous administration," J Control Release, 2014, 196, 106-112.
Cun, Dongmei, et al., Preparation and characterization of poly(DL-lactide-co-glycolide) nanoparticles for siRNA delivery. International Journal of Pharmaceutics 390 (2010) 70-75.
Dahlman, James E. et al., In vivo endothelial siRNA delivery using polymeric nanoparticles with low molecular weight, Nature Nanotechnology, 2014, pp. 1-8.
Delehanty, James B., Peptides for Specific Intracellular Delivery and Targeting of Nanoparticles: Implications for Developing Nanoparticle-Mediated Drug Delivery, Future Science, Therapeutic Delivery, 2010, vol. 1, No. 3, pp. 411-433.
Dong et al., "Lipopeptide nanoparticles for potent and selective siRNA delivery in rodents and nonhuman primates," PNAS, Mar. 2014, vol. 111, No. 11, 3955-3960; 5753-5754.
El Ouahabi, A., et al., Double long-chain amidine liposome-mediated self replicating RNA transfection. FEBS Letters. Feb. 1996; 380(1-2): 108-112.
Felgner, PL Cationic lipid/polynucleotide condensates for in vitro and in vivo polynucleotide delivery—the cytofectins. J. of Liposome Research. 1993; 3(1): 3-16.
Felgner P.L., et al., "Lipofection: A Highly Efficient, Lipid-Mediated DNA-Transfection Procedure," Proceedings of the National Academy of Sciences USA, vol. 84 (21), Nov. 1987, pp. 7413-7417.
Felgner, PL Particulate systems and polymers for in vitro and in vivo delivery of polynucleotides. Adv. Drug Delivery Rev. 1990; 5(3): 163-187.
Gao, X. et al., Nonviral gene delivery: what we know and what is next. AAPS J. Mar. 23, 2007;9(1):E92-104.
Hashiba et al., "pH-labile PEGylation of siRNA-loaded lipid nanoparticle improves active targeting and gene silencing activity in hepatocytes," Journal of Controlled Release (2017) vol. 262, 239-246.
He, K. et al., Synthesis and Separation of Diastereomers of Ribonucleoside 5'-(alpha-P-Borano)triphosphates. J Org Chem. Aug. 21, 1998 ;63(17):5769-5773.
Hecker, J.G. et al., Non-Viral DNA and mRNA Gene Delivery to the CNS Pre-Operatively for Neuroprotection and Following Neurotrauma. Molecular Therapy. 2004; 9, S258-S258.
Heurtaul T et al., "Physico-chemical stability of colloidal lipid particles," Biomaterials, 2003,24:4283-4300.
Hoerr, I. et al., In vivo application of RNA leads to induction of specific cytotoxic T lymphocytes and antibodies. EurJ Immunol. Jan. 2000;30(1): 1-7.
Jaiswal et al., "Nanostructured lipid carriers and their current application in targeted drug delivery," Artificial Cells, Nanomedicine, and Biotechnology (2016) 44: 27-40.
Jayaraman et al., "Maximizing the Potency of siRNA Lipid Nanoparticles for Hepatic Gene Silencing In Vivo," Angew. Chem. Int. Ed. 2012, 51, 8529-8533.
Juliano, R.L., et al., Cell-targeting and cell-penetrating peptides for delivery of therapeutic and imaging agents. Wiley Interdisciplinary Reviews: Nanomedicine and Nanobiotechnology. May/Jun. 2009; 1(3): 324-335.
Kang, Hyunmin, Inhibition of MDR1 Gene Expression by Chimeric HNA Antisense Oligonucleotides, Nucleic Acids Research, 2004, vol. 32, No. 14, pp. 4411-4419.
Kariko et al., Phosphate-enhanced transfection of cationic lipid-complexed mRNA and plasmid DNA. Biochimica et Biophysica Acta. 1998. 1369:320-34.
Kariko, K., et al., In vivo protein expression from mRNA delivered into adult rat brain. J. of Neuroscience Methods. Jan. 2001; 105(1): 77-86.
Kariko, K., et al., Incorporation of pseudouridine into mRNA yields superior nonimmunogenic vector with increased translational capacity and biological stability, Molecular Therapy, Nature Publishing Group, GB, vol. 16, No. 11,Nov. 1, 2008 (Nov. 1, 2008), pp. 1833-1840.
Keown, WA, et al., [41] Methods for Introducing DNA into Mammalian Cells. Methods in Enzymology, 1990, 185:527-37.
Kirpotin, D.B., et al., Antibody targeting of long-circulating lipidic nanoparticles does not increase tumor localization but does increase internalization in animal models. Cancer Res. 2006; 66: 6732-6740.
Kozielski, Kristen L. et al., Bioreducible Cationic Polymer-Based Nanoparticles for Efficient and Environmentally Triggered Cytoplasmic siRNA Delivery to Primary Human Brain Cancer Cells, ACS Nano, 2014, vol. 8, No. 4, pp. 3232-3241.
Lai, S.K., et al., Mucus-penetrating nanoparticles for drug and gene delivery to mucosal tissues. Adv Drug Deliv Rev. Feb. 27, 2009; 61(2): 158-171.
Lai, S.K., et al., Rapid transport of large polymeric nanoparticles in fresh undiluted human mucus. PNAS. Jan. 30, 2007; 104(5): 1482-1487.
Lee, Justin B. et al., Lipid Nanoparticle siRNA Systems for Silencing The Androgen Receptor In Human Prostate Cancer in Vivo, International Journal of Cancer, 2012, vol. 131, pp. 781-790.
Lehto, T., et al., Cell-penetrating peptides for the delivery of nucleic acids. Expert Opin. Drug Deliv. Jul. 2012; 9(7): 823-836.
Leung et al., "Lipid Nanoparticles for Short Interfering RNA Delivery", Advances in Genetics, 2014, vol. 88, Chapter 4, pp. 71-110.
Lewis, David, Dynamic Polyconjugates (DPC) Technology: An elegant solution to the siRNA delivery problem. Arrowhead Research Corp (NASDAQ: ARWR). Nov. 2011. 6 pages.
Lewis, R., et al., "Studies of the Thermotropie Phase Behavior of Phosphatidylcholines Containing 2-Alkyl Substituted Fatty Alkyl Chains: A New Class of Phosphatidylcholines Forming Inverted Nonlamellar Phases," Biophysical Journal, Apr. 1994, vol. 66, pp. 1088-1103.
Li, L. et al., Overcoming obstacles to develop effective and safe siRNA therapeutics. Expert Opin Biol Ther. May 2009; 9(5): 609-19.
Li, L. et al., Preparation and gene delivery of alkaline amino acids-based cationic liposomes. Arch Pharm Res. Jul. 2008; 31(7):924-31. Epub Aug. 14, 2008.
Lian, T. et al., Trends and developments in liposome drug delivery systems. J Pharm Sci. Jun. 2001;90(6):667-80.
Lopez-Berestein, G. et al., Treatment of systemic fungal infections with liposomal amphotericin B. Arch Intern Med. Nov. 1989;149(11):2533-6.
Love et al., Lipid-like materials for low-dose, in vivo gene silencing, PNAS vol. 107 No. 5, pp. 1864-1869, Feb. 2, 2010, 7 pages.
Luten, D.B., "The Preparation of Aminonitriles and Their Quaternary Ammonium Derivatives", Journal of Organic Chemistry (1939), 3, pp. 588-597.
M. Kanapathipillai, et al., Nanoparticle targeting of anti-cancer drugs that alter intracellular signaling or influence the tumor microenvironment, Adv. Drug Deliv. Rev. (2014), pp. 1-12.
Magee, W .E. et al., Marked stimulation of lymphocyte-mediated attack on tumor cells by target-directed liposomes containing immune RNA, Cancer Res., 1978, 38(4):1173-6.
Malone, R.W. et al., Cationic liposome-mediated RNA transfection. Proc Natl Acad Sci U S A. Aug. 1989;86 (16):6077-81.
Martinon, F. et al., Induction of virus-specific cytotoxic T lymphocytes in vivo by liposome-entrapped mRNA. Eur J Immunol. Jul. 1993;23(7): 1719-22.
Maskarinec et al., "Direct Observation of Poloxamer 188 Insertion into Lipid Monolayers," Biophys J., Mar. 2002, vol. 82, 1453-1459.
Maurer, N., et al., Spontaneous entrapment of polynucleotides upon electrostatic interaction with ethanol-destabilized cationic liposomes. Biophys J. May 2001; 80(5): 2310-2326.
Midoux et al., Lipid-based mRNA vaccine delivery systems. Expert Rev Vaccines. Feb. 2015; 14(2):221-34. doi: 10.1586/14760584.2015.986104. Epub Dec. 26, 2014. Review.
Mishra, R.K. et al., Improved leishmanicidal effect of phosphorothioate antisense oligonucleotides by LDL-mediated delivery. Biochim Biophys Acta. Nov. 7, 1995;1264(2):229-37.
Mockey et al., mRNA-based cancer vaccine: prevention of B16 melanoma progression and metastasis by systemic injection of MART1 mRNA histidylated lipopolyplexes, Cancer Gene Therapy, 2007, 14, pp. 802-814.

(56) References Cited

OTHER PUBLICATIONS

Mohtar et al., "Solid Lipid Nanoparticles of Atovaquone Based on 24 Full-Factorial Design," Iranian Journal of Pharmaceutical Research (2015) 14(4): 989-1000.
Morissette, S. L., "High-Throughput Crystallization: Polymorphs, Salts, Co-Crystals and Solvates of Pharmaceutical Solids," Advanced Drug Delivery Reviews, vol. 56, No. 3, Feb. 2004, pp. 275-300.
Müller et al., "Solid lipid nanoparticles (SLN) for controlled drug delivery—a review of the state of the art," European Journal of Pharmaceutics and Biopharmaceutics, 50 (2000) 161-177.
Müller et al., Solid lipid nanoparticles (SLN) as potential carrier for human use: interaction with human granulocytes, Journal of Controlled Release, 1997, 47: 261-269.
Nair, S. et al., Soluble proteins delivered to dendritic cells via pH-sensitive liposomes induce primary cytotoxic T lymphocyte responses in vitro. J Exp Med. Feb. 1, 1992; 175(2):609-12.
Ohgami, N., et al., "Analysis of Molecular Recognition of the Cholesterol-binding Proteins," Bulletin of Institute for Life and Health Sciences, Japan, 2008 vol. 4, pp. 35-40 (with English abstract, 8 pages).
Okumura, K., et al., Bax mRNA therapy using cationic liposomes for human malignant melanoma. J Gene Med. 2008; 10: 910-917.
Oster, C.G., et al. Comparative study of DNA encapsulation into PLGA microparticles using modified double emulsion methods and spray drying techniques. Journal of Microencapsulation, May 2005; 22(3): 235-244.
Parker et al., Targeting of Polyelectrolyte RNA Complexes to Cell Surface Integrins as an Efficient, Cytoplasmic Transfection Mechanism, Journal of Bioactive and Compatible Polymers, Jul. 2002, pp. 1-10.
Pollard, C,, et al., Type IIFN counteracts the induction of antigen-specific immune responses by lipid-based delivery of mRNA vaccines. Mol Ther. Jan. 2013; 21(1): 251-259.
Pulford, B., et al., Liposome-siRNA-peptide complexes cross the blood-brain barrier and significantly decrease PrP'C on neuronal cells and PrP'RES in infected cell cultures. PLoS ONE. 2010; 5(6): e11085.
Ramteke, K. H. et al., "Solid Lipid Nanoparticle: A Review," IOSR Journal of Pharmacy, Nov.-Dec. 2012, 2(60): 34-44.
Sabnis et al., "A Novel Amino Lipid Series for mRNA Delivery: Improved Endosomal Escape and Sustained Pharmacology and Safety in Non-human Primates," Molecular Therapy, Jun. 2018, vol. 26, No. 6, pp. 1509-1519.
Saha, A. et al., "Phosphate Bioisostere Containing Amphiphiles: A Novel Class of Squaramide-based Lipids," Chemical Communications, Jul. 19, 2016, vol. 52(60), pp. 9438-9441.
Sahay, G. et al., "Efficiency of siRNA delivery by lipid nanoparticles is limited by endocytic recycling," Nat Biotechnol. Jul. 2013 ; 31(7): 653-658.
Saito, R., et al., Distribution of liposomes into brain and rat brain tumor models by convection-enhanced delivery monitored with magnetic resonance imaging. Cancer Res. Apr. 2004; 64: 2572-2579.
Sakuma, S. et al., Mucoadhesion of polystyrene nanoparticles having surface hydrophilic polymeric chains in the gastrointestinal tract. Int J Pharm. Jan. 25, 1999;177(2):161-72.
Schott, J.W., et al., Viral and non-viral approaches for transient delivery of mRNA and proteins. Current Gene Ther. 2011; 11 (5): 382-398.
Semple, S.C., et al., Efficient encapsulation of antisense oligonucleotides in lipid vesicles using ionizable aminolipids: formation of novel small multilamellar vesicle structures. Biochim Biophys Acta. Feb. 9, 2001; 1510(1-2): 152-166.
Semple, S.C., et al., "Rational design of cationic lipids for siRNA delivery", Nature Biotechnology, 2010, vol. 28, No. 2, 172-176.
Shah et al., "Lipid Nanoparticles: Production, Characterization and Stability," Springer International Publishing, 2014, 23 pages.
Shea, R.G. et al., Synthesis, hybridization properties and antiviral activity of lipid-oligodeoxynucleotide conjugates. Nucleic Acids Res. Jul. 11, 1990;18(13):3777-83.
Strobel, I. et al., Human dendritic cells transfected with either RNA or DNA encoding influenza matrix protein M1 differ in their ability to stimulate cytotoxic T lymphocytes. Gene Ther. Dec. 2000; 7(23): 2028-2035.
Svinarchuk, F.P. et al., Inhibition of HIV proliferation in MT-4 cells by antisense oligonucleotide conjugated to lipophilic groups. Biochimie. 1993;75(1-2):49-54.
Tam et al., "Advances in Lipid Nanoparticles for siRNA Delivery," Pharmaceutics 2013, 5, 498-507; doi:10.3390/pharmaceutics5030498.
Tavernier, G., et al., mRNA as gene therapeutic: How to control protein expression. J. of Controlled Release. Mar. 2011; 150(3): 238-247.
Thess et al., Sequence-engineered mRNA Without Chemical Nucleoside Modifications Enables an Effective Protein Therapy in Large Animals. Mol Ther. Sep. 2015;23(9):1456-64. doi: 10.1038/mt.2015. 103. Epub Jun. 8, 2015.
Torchilin, Vladimir et al., Multifunctional and Stimuli-Sensitive Pharmaceutical Nanocarriers, Eur J. Pharm Biopharm, 2009, vol. 71, No. 3, pp. 431-444.
Tracy, M., "Progress in the Development of LNP Delivery for siRNA Advancing LNPs to the Clinic," International Liposome Research Days Meeting, Vancouver, Canada. Aug. 2010, pp. 1-52.
Treat et al., "Liposome Encapsulated Doxorubicin Preliminary Results of Phase I and Phase II Trials," Liposomes in the Therapy of Infectious Disease and Cancer, Lopez-Berestein and Fidler (eds.), (1989) Liss, New York, pp. 353-365.
Uzgun, S., et al., PEGylation improves nanoparticle formation and transfection efficiency of messenger RNA. Pharm Res. Sep. 2011; 28(9); 2223-2232.
Van Tendeloo, V.F. et al., Highly efficient gene delivery by mRNA electroporation in human hematopoietic cells: superiority to lipofection and passive pulsing of mRNA and to electroporation of plasmid cDNA for tumor antigen loading of dendritic cells. Blood. Jul. 1, 2001;98(1):49-56.
Wan et al., Lipid nanoparticle delivery systems for siRNA-based therapeutics. Drug Deliv Transl Res. Feb. 2014;4(1):74-83. doi:10. 1007/s13346-013-0161-z.
Wang et al., Systemic delivery of modified mRNA encoding herpes simplex virus 1 thymidine kinase for targeted cancer gene therapy. Mol Ther. Feb. 2013;21(2):358-67. doi: 10.1038/mt.2012.250. Epub Dec. 11, 2012.
Weilhammer et al., The use of nanolipoprotein particles to enhance the immunostimulatory properties of innate immune agonists against lethal influenza challenge. Biomaterials. Dec. 2013;34(38):10305-18. doi: 10.1016/j.biomaterials.2013.09.038. Epub Sep. 27, 2013.
Yadava, P. et al., "Effect of Lyophilization and Freeze-thawing on the Stability of SiRNA-liposome Complexes," AAPS PharmSciTech, Jun. 2008, 9(2): 335-341.
Yamamoto et al., Current prospects for mRNA gene delivery, European Journal of Pharmaceutics and Biopharmaceutics 71 (2009) 484-489.
Zhang et al., "A novel cationic cardiolipin analogue for gene delivery," Pharmazie, 2006, 61: 10-14.
Zhang et al., "Biodegradable Amino-Ester Nanomaterials for Cas9 mRNA Delivery in Vitro and in Vivo," ACS Applied Materials & Interfaces, Aug. 2017, 9(30): 25481-25487.
Zhigaltsev, I.V., et al., Bottom-Up design and synthesis of limit size lipid nanoparticle systems with aqueous and triglyceride cores using millisecond microfluidic mixing. Langmuir. Feb. 21, 2012; 28(7): 3633-3640.
Zimmermann, E. et al., Electrolyte- and pH-stabilities of aqueous solid lipid nanoparticle (SLN) dispersions in artificial gastrointestinal media. Eur J Pharm Biopharm. Sep. 2001;52(2):203-10.
Zohra, F.T., et al., Drastic effect of nanoapatite particles on liposome-mediated mRNA delivery to mammalian cells. Analytical Biochem. Oct. 2005; 345(1): 164-166.
Zohra, F.T., et al., Effective delivery with enhanced translational activity synergistically accelerates mRNA-based transfection. Biochem Biophys Res Comm. Jun. 2007; 358(1 ): 373-378.
Abrams et al., "Evaluation of Efficacy, Biodistribution, and Inflammation for a Potent SIRNA Nanoparticle: Effect of Dexamethasone Co-treatment," Molecular Therapy, Jan. 2010, vol. 18 , No. 1, 171-180.

(56) References Cited

OTHER PUBLICATIONS

Audic and Chaufer, "Caseinate Based Biodegradable Films with Improved Water Resistance," Journal of Applied Polymer Science, (2010) vol. 117, 1828-1836.
Bowman, "N-Substituted Amino-acids. Part II. The Reductive Alkylation of Amino-acids," Journal of the Chemical Society (1950), pp. 1346-1349.
Burnett et al., "Dialkylaminoalkanol Esters of p-Aminobenzoic Acid," Journal of the American Chemical Society (1937), vol. 59, pp. 2248-2252.
Cao et al., "Approach on quantitative structure-activity relationship for design of a pH neutral carrier containing tertiary amino group," Analytica Chimica Acta (2007) 581: 19-26.
Cornebise, M., et al., Discovery of a Novel Amino Lipid that Improves Lipid Nanoparticle Performance through Specific Interactions with mRNA, Advanced Functional Mater, 2022, 32, 2106727, 12 pages.
Han et al., "An ionizable lipid toolbox for RNA delivery," Nature Communications, 2021,12:7233,6 pages.
Hassett et al., "Optimization of Lipid Nanoparticles for Intramuscular Administration of mRNA Vaccines", Molecular Therapy: Nucleic Acids, Apr. 2019, vol. 15, 11 pages.
Mahidhar et al., "Distance of hydroxyl functionality from the quaternized center influence DNA binding and in vitro gene delivery efficacies of cationic lipids with hydroxyalkyl headgroups," J. Med. Chem. 2004, 47, 23, 5721-5728.
Mann et al., "355. Triethylenediamine (1 : 4-diazabicyclo[2 : 2 : 2]octane) and hexaethylenetetramine. Part III. The interaction of 2 : 2' : 2"-trichlorotriethylamine hydrochloride and dimethylamine," Journal of the Chemical Society, (1957), pp. 1881-1899.
Rehse, K., et al., "Antiaggregatorische und anticoagulante Eigenschaften von Oligoaminen, 12. Mitt.+): Alkyl- und Arylalkylderivate von Putrescin, Spermidin und Spermin", Arch. Pharm. (Weinheim) 323, 287-294 (1990) (with English abstract).
Tao et al., "Mechanistically Probing Lipid-siRNA Nanoparticle-associated Toxicities Identifies Jak Inhibitors Effective in Mitigating Multifaceted Toxic Responses," Molecular Therapy, Mar. 2011, vol. 19, No. 3, 567-575.

* cited by examiner

HEADGROUP LIPID COMPOUNDS AND COMPOSITIONS FOR INTRACELLULAR DELIVERY OF THERAPEUTIC AGENTS

RELATED APPLICATIONS

This application is a U.S. National Phase application, filed under 35 U.S.C. § 371, of International Application No. PCT/US2020/051629, filed Sep. 18, 2020, which claims priority to, and the benefit of, U.S. Provisional Application No. 62/902,928, filed Sep. 19, 2019, the entire contents of which are incorporated herein by reference in their entireties.

FIELD OF DISCLOSURE

The present disclosure provides novel compounds, compositions comprising such compounds, and methods involving lipid nanoparticle compositions to deliver one or more therapeutic and/or prophylactics to and/or produce polypeptides in mammalian cells or organs. In addition to a novel lipid, lipid nanoparticle compositions of the disclosure may include one or more cationic and/or ionizable amino lipids, phospholipids including polyunsaturated lipids, PEG lipids, structural lipids, and/or therapeutic and/or prophylactics in specific fractions.

BACKGROUND OF THE DISCLOSURE

The effective targeted delivery of biologically active substances such as small molecule drugs, proteins, and nucleic acids represents a continuing medical challenge. In particular, the delivery of nucleic acids to cells is made difficult by the relative instability and low cell permeability of such species. Thus, there exists a need to develop methods and compositions to facilitate the delivery of therapeutic and/or prophylactics such as nucleic acids to cells.

Lipid-containing nanoparticle compositions, liposomes, and lipoplexes have proven effective as transport vehicles into cells and/or intracellular compartments for biologically active substances such as small molecule drugs, proteins, and nucleic acids. Such compositions generally include one or more "cationic" and/or amino (ionizable) lipids, phospholipids including polyunsaturated lipids, structural lipids (e.g., sterols), and/or lipids containing polyethylene glycol (PEG lipids). Cationic and/or ionizable lipids include, for example, amine-containing lipids that can be readily protonated. Though a variety of such lipid-containing nanoparticle compositions have been demonstrated, improvements in safety, efficacy, and specificity are still lacking.

SUMMARY OF THE DISCLOSURE

In some aspects, the disclosure relates to a compound of Formula (A):

(A)

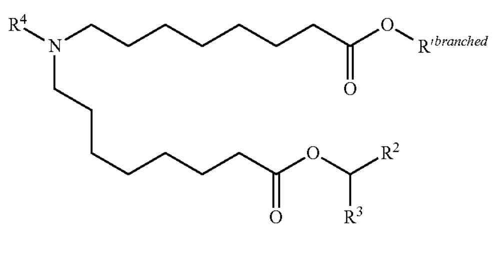

or its N-oxide, or a salt or isomer thereof, wherein:

$R^{\prime branched}$ is

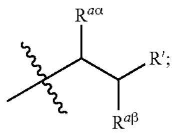

wherein

denotes a point of attachment;

wherein $R^{a\alpha}$ and $R^{a\beta}$ are each independently selected from the group consisting of H and $C_{1-2}$ alkyl, wherein at least one of $R^{a\alpha}$ and $R^{a\beta}$ is a $C_1$ or $C_2$ alkyl;

R' is selected from the group consisting of $C_{1-18}$ alkyl and $C_{2-18}$ alkenyl;

$R^2$ and $R^3$ are each independently selected from the group consisting of $C_{1-14}$ alkyl and $C_{2-14}$ alkenyl;

$R^4$ is $-(CH_2)_nQ$, wherein n is selected from 1, 2, 3, 4, and 5, where Q is selected from $-NR(S(O)(NR))R^{SX}$, $-NRS(O)_2NRR^{SX}$, $-NRC(S)R^{SX}$, $-NRC(O)R^{SX}$, $-NRP(O)(OR^{P\prime})R^P$, $-NRS(O)_2R^{SX}$, $-NC(R)=R^{11}$, $-NC(=NR^{15})R^{11}$, $-NRC(C(O)NR^{14}R^{14\prime})_2$, $-NRC(O)(CH_2)_pC(O)NR^{14}R^{14\prime}(R)=NS(O)_2R^{SX}$, $-S(O)_2NRR^{SX}$, and

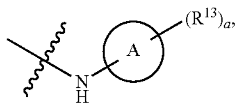

wherein A is a 3-14 membered heterocycle containing one or more heteroatoms selected from N, O and S; p is 0, 1, 2, 3, or 4; and a is 1, 2, 3, 4, or 5; wherein

denotes a point of attachment;

each R is independently selected from the group consisting of H and $C_{1-3}$ alkyl;

$R^{SX}$ is selected from a $C_{3-8}$ carbocycle, a 3-14 membered heterocycle containing one or more heteroatoms selected from N, O and S, $C_{1-6}$ alkyl, $C_{2-6}$ alkenyl, $(CH_2)_{p1}O(CH_2)_{p2}R^{SX1}$, $(CH_2)_{p1}S(CH_2)_{p2}R^{SX1}$, $(CH_2)_{p1}S(O)(CH_2)_{p2}R^{SX1}$, $(CH_2)_{p1}S(O)_2(CH_2)_{p2}R^{SX1}$, $(CH_2)_{p1}S(O)NR^{SX1}$, $(CH_2)_{p1}S(O)_2NR^{SX1}$, and $(CH_2)_{p1}R^{SX1}$, wherein the carbocycle and heterocycle are optionally substituted with one or more groups selected from OH, oxo, $C_{1-6}$ alkyl and $C_{1-6}$ alkoxy;

$R^P$ and $R^{P\prime}$ are each independently selected from H, $C_{1-3}$ alkyl, and $C_{2-3}$ alkenyl;

$R^{SX1}$ is selected from $C_{1-3}$ alkyl, $NR^{14}R^{14\prime}$, $C(O)NR^{14}R^{14\prime}$, $S(O)_2NR^{14}R^{14\prime}$, a $C_{3-8}$ carbocycle, and a 3-14 membered heterocycle containing one or more heteroatoms selected from N, O and S, wherein the carbocycle and heterocycle are each optionally substituted with one or more groups selected from oxo, halo, $C_{1-3}$ alkyl, $C_{1-3}$ alkoxy, ($C_{1-3}$ alkoxy)-$C_{1-3}$ alkyl, $C_{1-6}$ alkylamino, di-($C_{1-6}$ alkyl) amino, and $NH_2$;

$R^{11}$ is selected from the group consisting of $C_{3-6}$ carbocycle and a 3-14 membered heterocycle containing one or more heteroatoms selected from N, O and S, wherein the carbocycle and heterocycle are each optionally substituted with one or more $R^{13}$;

each $R^{13}$ is independently selected from the group consisting of OH, oxo, halo, $C_{1-6}$ alkyl, $C_{1-6}$ alkoxy, $C_{2-6}$ alkenyl, $C_{1-6}$ alkylamino, di-($C_{1-6}$ alkyl) amino, $NH_2$, $C(O)NH_2$, CN, and $NO_2$; wherein $C_{1-6}$ alkyl and $C_{2-6}$ alkenyl are optionally substituted with $C_{1-6}$ alkoxy;

$R^{14}$ and $R^{14\prime}$ are each independently selected from the group consisting of H, OH, $C_{1-6}$ alkyl;

$R^{15}$ is H or OH;

$p_1$ is selected from 1, 2, 3, 4, and 5; and $p_2$ is selected from 1, 2, 3, 4, and 5.

In some aspects, the disclosure relates to a compound of Formula (A-1):

(A-1)

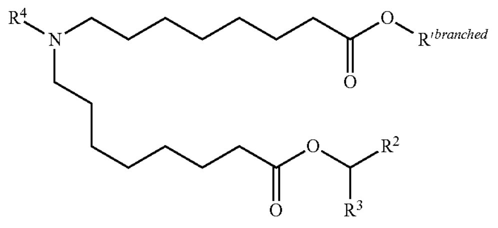

or its N-oxide, or a salt or isomer thereof, wherein:

$R'^{branched}$ is

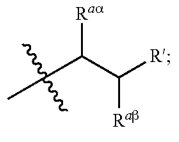

wherein

denotes a point of attachment;

wherein $R^{a\alpha}$ and $R^{a\beta}$ are each independently selected from the group consisting of H and $C_{1-2}$ alkyl, wherein at least one of $R^{a\alpha}$ and $R^{a\beta}$ is a $C_1$ or $C_2$ alkyl;

R' is selected from the group consisting of $C_{1-18}$ alkyl and $C_{2-18}$ alkenyl;

$R^2$ and $R^3$ are each independently selected from the group consisting of $C_{1-14}$ alkyl and $C_{2-14}$ alkenyl;

$R^4$ is $-(CH_2)_nQ$, wherein n is independently selected from 1, 2, 3, 4, and 5, where Q is selected from $NRS(O)_2R^{SX}$ and

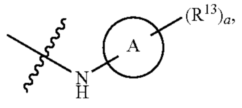

wherein A is a 3-14 membered heterocycle containing one or more heteroatoms selected from N, O and S; and a is 1, 2, 3, or 4; wherein

denotes a point of attachment;

R is selected from H and $C_{1-3}$ alkyl;

$R^{SX}$ is selected from a $C_{3-8}$ carbocycle, a 3-14 membered heterocycle containing one or more heteroatoms selected from N, O and S, $C_{1-6}$ alkyl, $C_{2-6}$ alkenyl, ($C_{1-3}$ alkoxy)$C_{1-3}$ alkyl, $(CH_2)_{p1}O(CH_2)_{p2}R^{SX1}$, and $(CH_2)_{p1}R^{SX1}$, wherein the carbocycle and heterocycle are optionally substituted with one or more groups selected from oxo, $C_{1-6}$ alkyl, and ($C_{1-3}$ alkoxy)$C_{1-3}$ alkyl;

$R^{SX1}$ is selected from $C(O)NR^{14}R^{14\prime}$, a $C_{3-8}$ carbocycle, and a 3-14 membered heterocycle containing one or more heteroatoms selected from N, O and S, wherein the carbocycle and heterocycle are each optionally substituted with one or more groups selected from oxo, halo, $C_{1-3}$ alkyl, ($C_{1-3}$ alkoxy)$C_{1-3}$ alkyl, $C_{1-6}$ alkylamino, di-($C_{1-6}$ alkyl) amino, and $NH_2$;

each $R^{13}$ is selected from the group consisting of OH, oxo, halo, $C_{1-6}$ alkyl, $C_{1-6}$ alkoxy, $C_{2-6}$ alkenyl, $C_{1-6}$ alkylamino, di-($C_{1-6}$ alkyl) amino, $NH_2$, $C(O)NH_2$, CN, and $NO_2$;

$R^{14}$ and $R^{14\prime}$ are each independently selected from the group consisting of H and $C_{1-6}$ alkyl;

$p_1$ is selected from 1, 2, 3, 4, and 5; and $p_2$ is selected from 1, 2, 3, 4, and 5.

DETAILED DESCRIPTION

The disclosure relates to novel lipids and lipid nanoparticles (e.g., empty LNPs or loaded LNPs) including a novel lipid. The disclosure also provides methods of delivering a therapeutic and/or prophylactic to a mammalian cell, specifically delivering a therapeutic and/or prophylactic to a mammalian organ, producing a polypeptide of interest in a mammalian cell, improving levels of protein produced in a mammalian cell as compared to LNPs comprising other lipids, and treating a disease or disorder in a mammal in need thereof. For example, a method of producing a polypeptide of interest in a cell involves contacting a nanoparticle comprising an mRNA with a mammalian cell, whereby the mRNA may be translated to produce the polypeptide of interest. A method of delivering a therapeutic and/or prophylactic to a mammalian cell or organ may involve administration of a nanoparticle composition including the therapeutic and/or prophylactic to a subject, in which the administration involves contacting the cell or organ with the composition, whereby the therapeutic and/or prophylactic is delivered to the cell or organ. Such methods of delivery can be in vitro or in vivo.

The present disclosure provides lipids including a central amine moiety and at least one biodegradable group. The lipids described herein may be advantageously used in lipid nanoparticles (e.g., empty LNPs or loaded LNPs) for the delivery of therapeutic and/or prophylactics to mammalian cells or organs. For example, the lipids described herein have little or no immunogenicity. For example, the lipid compound of Formula (I), (I-1), (A), (A-1), (A-1a), or (A-1b) has a lower immunogenicity as compared to a reference lipid (e.g., MC3, KC2, or DLinDMA). For example, a formulation comprising a lipid disclosed herein and a therapeutic or prophylactic agent has an increased therapeutic index as compared to a corresponding formulation which comprise a reference lipid (e.g., MC3, KC2, or DLinDMA) and the same therapeutic or prophylactic agent.

In some aspects, the disclosure relates to a compound of Formula (I):

(I)

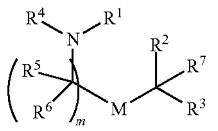

or its N-oxide, or a salt or isomer thereof, wherein:

$R^1$ is selected from the group consisting of $C_{5-30}$ alkyl, $C_{5-20}$ alkenyl, —R*YR*", —YR*", and —R"M'R';

$R^2$ and $R^3$ are independently selected from the group consisting of H, $C_{1-14}$ alkyl, $C_{2-14}$ alkenyl, —R*YR*", —YR*", and —R*OR*", or $R^2$ and $R^3$, together with the atom to which they are attached, form a heterocycle or carbocycle;

$R^4$ is selected from the group consisting of —$(CH_2)_nQ$, —$(CH_2)_nCHQR$, —$(CH_2)_oC(R^{12})_2(CH_2)_{n-o}Q$, —CHQR, —$CQ(R)_2$, and —C(O)NQR, where Q is selected from $NC(R)=R^{11}$, $NC(=NR^{15})R^{11}$, $NRC(C(O)NR^{14}R^{14'})_2$, —$NRC(O)(CH_2)_pC(O)NR^{14}R^{14'}$, and

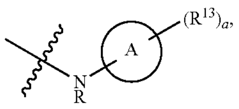

wherein A is $C_{6-10}$ aryl or a heterocycle; and each o is independently selected from 1, 2, 3, and 4; p is 0, 1, 2, 3, or 4; a is 1, 2, 3, or 4; and each n is independently selected from 1, 2, 3, 4, and 5;

each $R^5$ is independently selected from the group consisting of OH, $C_{1-3}$ alkyl, $C_{2-3}$ alkenyl, and H;

each $R^6$ is independently selected from the group consisting of OH, $C_{1-3}$ alkyl, $C_{2-3}$ alkenyl, and H;

M and M' are independently selected from —OC(O)O—, —C(O)O—, —OC(O)—, —OC(O)-M"-C(O)O—, —OC(O)—$NR^M$—C(O)O—, —O-M"-O—, —C(O)N($R^M$)—, —N($R^M$)C(O)—, —OC(O)N($R^M$)—, —N($R^M$)C(O)O—, —$NR^M$C(O)$NR^M$—, —O—N=C($R^M$)—, —C(O)—, —C(S)—, —C(S)S—, —SC(S)—, —CH(OH)—, —P(O)($OR^M$)O—, —$S(O)_2$—, —S—S—, —SO—, —OS—, $S(R^M)_2O$—, —O—$S(R^M)_2$—, —S(O)O—, —OS(O)—, an aryl group, and a heteroaryl group, in which M" is a bond, —$(CH_2)_zC(O)$—, $C_{1-13}$ alkyl, $C_{2-13}$ alkenyl, —B(R)—, —$Si(R)_2$—, —$S(R**)_2$—, or —S(O)—, wherein z is 1, 2, 3, or 4;

$R^7$ is selected from the group consisting of $C_{1-3}$ alkyl, $C_{2-3}$ alkenyl, and H;

$R^{11}$ is selected from the group consisting of $C_{3-6}$ carbocycle and heterocycle, wherein the $C_{3-6}$ carbocycle and heterocycle are each optionally substituted with one or more $R^{13}$;

$R^{12}$ is selected from the group consisting of H, OH, $C_{1-3}$ alkyl, and $C_{2-3}$ alkenyl;

each $R^{13}$ is selected from the group consisting of OH, oxo, halo, $C_{1-6}$ alkyl, $C_{1-6}$ alkoxyl, $C_{2-6}$ alkenyl, $C_{1-6}$ alkylamino, di-($C_{1-6}$ alkyl) amino, $NH_2$, $C(O)NH_2$, CN, and $NO_2$;

each $R^{14}$ is independently selected from the group consisting of H, OH, $C_{1-6}$ alkyl, and $C_{2-3}$ alkenyl;

each $R^{14'}$ is independently selected from the group consisting of H, OH, $C_{1-6}$ alkyl, and $C_{2-3}$ alkenyl;

$R^{15}$ is independently selected from the group consisting of H, OH, $C_{1-6}$ alkyl, and $C_{2-3}$ alkenyl;

each R is independently selected from the group consisting of H, OH, $C_{1-6}$ alkyl, and $C_{2-6}$ alkenyl;

each R' is independently selected from the group consisting of $C_{1-18}$ alkyl, $C_{2-18}$ alkenyl, —R*YR*", —YR*", $(CH_2)_qOR*$, and H;

each $R^M$ is independently selected from the group consisting of H, $C_{1-6}$ alkyl and $C_{2-6}$ alkenyl;

each R" is independently selected from the group consisting of $C_{3-15}$ alkyl and $C_{3-15}$ alkenyl;

each R*" is selected from the group consisting of $C_{1-15}$ alkyl and $C_{2-15}$ alkenyl;

each R* is independently selected from the group consisting of $C_{1-12}$ alkyl and $C_{2-12}$ alkenyl;

each R** is independently selected from the group consisting of H, OH, $C_{1-12}$ alkyl, $C_{2-12}$ alkenyl, $(CH_2)_qOR*$, and $(CH_2)_qOH$;

each Y is independently a $C_{3-6}$ carbocycle;

each q is independently selected from 1, 2, and 3; and m is selected from 5, 6, 7, 8, 9, 10, 11, 12, and 13.

In some aspects, the disclosure relates to a compound of Formula (I-1):

(I-1)

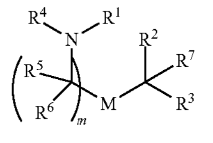

or its N-oxide, or a salt or isomer thereof, wherein:

$R^1$ is R"M'R' and R' is a branched $C_{1-18}$ alkyl;

$R^2$ and $R^3$ are each independently selected from the group consisting of H, $C_{1-14}$ alkyl, $C_{2-14}$ alkenyl, —R*YR*", —YR*", and —R*OR*", or $R^2$ and $R^3$, together with the atom to which they are attached, form a heterocycle or carbocycle;

$R^4$ is —$(CH_2)_nQ$, where Q is

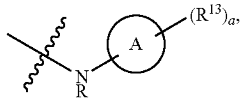

wherein A is $C_{6-10}$ aryl or a heterocycle; a is 1, 2, 3, or 4; and each n is independently selected from 1, 2, 3, 4, and 5;

each $R^5$ is independently selected from the group consisting of OH, $C_{1-3}$ alkyl, $C_{2-3}$ alkenyl, and H;

each $R^6$ is independently selected from the group consisting of OH, $C_{1-3}$ alkyl, $C_{2-3}$ alkenyl, and H;

M and M' are each independently selected from —OC(O)O—, —C(O)O—, —OC(O)—, —OC(O)-M"-C(O)O—, —OC(O)—$NR^M$—C(O)O—, —O-M"-O—, —C(O)N($R^M$)—, —N($R^M$)C(O)—, —OC(O)N($R^M$)—, —N($R^M$)C(O)O—, —$NR^M$C(O)$NR^M$—, —O—N═C($R^M$)—, —C(O)—, —C(S)—, —C(S)S—, —SC(S)—, —CH(OH)—, —P(O)($OR^M$)O—, —$S(O)_2$—, —S—S—, —SO—, —OS—, $S(R^M)_2O$—, —O—$S(R^M)_2$—, —S(O)O—, —OS(O)—, an aryl group, and a heteroaryl group, in which M" is a bond, —$(CH_2)_z$C(O)—, $C_{1-13}$ alkyl, $C_{2-13}$ alkenyl, —B(R)—, —Si$(R^{})_2$—, —S$(R^{**})_2$—, or —S(O)—, wherein z is 1, 2, 3, or 4;

$R^7$ is selected from the group consisting of $C_{1-3}$ alkyl, $C_{2-3}$ alkenyl, and H;

each $R^{13}$ is selected from the group consisting of OH, oxo, halo, $C_{1-6}$ alkyl, $C_{1-6}$ alkoxy, $C_{2-6}$ alkenyl, $C_{1-6}$ alkylamino, di-($C_{1-6}$ alkyl) amino, $NH_2$, C(O)$NH_2$, CN, and $NO_2$;

each $R^M$ is independently selected from the group consisting of H, $C_{1-6}$ alkyl and $C_{2-6}$ alkenyl;

each R" is independently selected from the group consisting of $C_{3-15}$ alkyl and $C_{3-15}$ alkenyl;

each R*" is selected from the group consisting of $C_{1-15}$ alkyl and $C_{2-15}$ alkenyl;

each R* is independently selected from the group consisting of $C_{1-12}$ alkyl and $C_{2-12}$ alkenyl;

each R** is independently selected from the group consisting of H, OH, $C_{1-12}$ alkyl, $C_{2-12}$ alkenyl, $(CH_2)_qOR^*$, and $(CH_2)_qOH$;

each Y is independently a $C_{3-6}$ carbocycle;

m is selected from 5, 6, 7, 8, 9, 10, 11, 12, and 13; and each q is independently selected from 1, 2, and 3.

In some embodiments, a compound of Formula (I), (I-1), (A), or (A-1) has one of the following structures:

(A-1a)

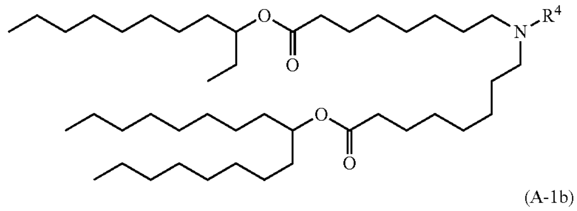

(A-1b)

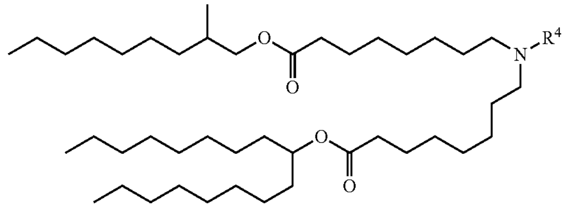

The compounds of any one of formula (I), (I-1), (A), (A-1), (A-1a), or (A-1 b) include one or more of the following features when applicable.

In some embodiments, $M_1$ is M'.

In some embodiments, M and M' are independently —C(O)O— or —OC(O)—.

In some embodiments, at least one of M and M' is —C(O)O— or —OC(O)—.

In certain embodiments, at least one of M and M' is —OC(O)—.

In certain embodiments, M is —OC(O)— and M' is —C(O)O—. In some embodiments, M is —C(O)O— and M' is —OC(O)—. In certain embodiments, M and M' are each —OC(O)—. In some embodiments, M and M' are each —C(O)O—.

In some embodiments, 1 is 1, 3, or 5. In some embodiments, 1 is 1, 3, or 4. In some embodiments, 1 is 5.

In some embodiments, $R^4$ is —$(CH_2)_n$Q.

In some embodiments, Q is

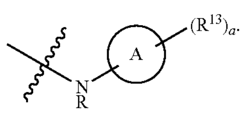

In some embodiments, Q is $NRS(O)_2R^{SX}$.

In some embodiments, $R^{13'}$ is selected from the group consisting of OH, oxo, halo, $C_{1-6}$ alkyl, $C_{1-6}$ alkoxyl, $C_{2-6}$ alkenyl, $C_{1-6}$ alkylamino, di-($C_{1-6}$ alkyl) amino, $NH_2$, C(O)$NH_2$, CN, and $NO_2$, In some embodiments, $R^{13'}$ is selected from $C_{1-6}$ alkyl and $C_{2-6}$ alkenyl substituted with $C_{1-6}$ alkoxyl.

In some embodiments, $R^{13'}$ is $C_{1-3}$-alkyl.

In some embodiments, $R^{SX}$ is selected from $(CH_2)_{p1}O(CH_2)_{p2}R^{SX1}$ and $(CH_2)_{p1}R^{SX1}$.

In some embodiments, $R^{SX1}$ is selected from $C_{2-3}$ alkyl, $C_{2-3}$ alkenyl, and C(O)$NR^{14}R^{14'}$. In some embodiments, $R^{SX1}$ is selected from carbocycle and heterocycle, wherein the carbocycle and heterocycle are each optionally substituted with one or more $R^{13}$. In some embodiments, $R^{SX1}$ is selected from $C_{2-3}$ alkenyl, C(O)$NR^{14}R^{14'}$, and heterocycle, wherein the heterocycle is optionally substituted with one or more $R^{13'}$;

In some embodiments, $R^{SX1}$ is a $C_{6-10}$ aryl. In some embodiments, $R^{SX1}$ is phenyl.

In some embodiments, $R^{SX}$ is $(CH_2)_{p1}R^{SX1}$. In some embodiments, $R^{SX}$ is $(CH_2)_{p1}R^{SX1}$ and p1 is 1. For example, in some embodiments, $R^{SX}$ is $(CH_2)R^{SX1}$.

In some embodiments, $R^{SX1}$ is a heterocycle.

In some embodiments, $R^{SX1}$ is a 4 to 12-membered heterocycloalkyl.

In some embodiments, $R^{SX1}$ is 1,4-dioxan-2-yl.

In some embodiments, $R^{SX1}$ is a 5- or 6-membered heteroaryl.

In some embodiments, $R^{SX1}$ is isoxazol-3-yl.

In some embodiments, $R^{SX1}$ is a 4 to 12-membered heterocycloalkyl.

In some embodiments, $p_1$ is 1 or 2.

In some embodiments, $p_2$ is 1.

In some embodiments, n is 2.

In some embodiments, n is 3.

In some embodiments, n is 4.

In some embodiments, A is a $C_{6-10}$ aryl. In some embodiments, A is phenyl.

In some embodiments, A is a heterocycle.

In some embodiments, A is selected from 1,2,5-thiadiazole, pyrrole, imidazole, imidazoline, 1,2-dihydropyridazine, 1,2,4 triazole, 1,2,5 oxadiazole, 1,2,4-oxadiazole, pyrimidine, pyrazine, pyridazine, pyridine, pyrazole, 2,5-dihydrofuran, 5,6-dihydro-4H-1,2,4-thiadiazine, 2,5-dihydro-1H-imidazole, 2,5-dihydro-1H-pyrrole, and 2,3-dihydro-1H-pyrazole.

In some embodiments, A is selected from 7-H purine, 9-H purine, indole, and indazole.

In some embodiments, A is a 4 to 12-membered heterocycloalkyl.

In some embodiments, A is a 5- or 6-membered heteroaryl.

In some embodiments, one $R^{13}$ is oxo. In some embodiments, two $R^{13}$ are each oxo. In some embodiments, three $R^{13}$ are each oxo.

In some embodiments, one $R^{13}$ is $NH_2$. In some embodiments, two $R^{13}$ are each $NH_2$. In some embodiments, three $R^{13}$ are each $NH_2$.

In some embodiments, one $R^{13}$ is $C_{1-6}$ alkylamino. In some embodiments, two $R^{13}$ are each $C_{1-6}$ alkylamino. In some embodiments, three $R^{13}$ are each $C_{1-6}$ alkylamino. For example, in some embodiments, one $R^{13}$ is methylamino. In some embodiments, two $R^{13}$ are each methylamino. In some embodiments, three $R^{13}$ are each methylamino.

In some embodiments, one $R^{13}$ is $C_{1-6}$ alkyl. In some embodiments, two $R^{13}$ are each $C_{1-6}$ alkyl. In some embodiments, three $R^{13}$ are each $C_{1-6}$ alkyl. For example, in some embodiments, one $R^{13}$ is methyl. In some embodiments, two $R^{13}$ are each methyl. In some embodiments, three $R^{13}$ are each methyl.

In some embodiments, one $R^{13}$ is $C_{1-6}$ alkoxyl. In some embodiments, two $R^{13}$ are each $C_{1-6}$ alkoxyl. In some embodiments, three $R^{13}$ are each $C_{1-6}$ alkoxyl. For example, in some embodiments, one $R^{13}$ is methoxyl. In some embodiments, two $R^{13}$ are each methoxyl. In some embodiments, three $R^{13}$ are each methoxyl.

In some embodiments, one $R^{13}$ is halo. In some embodiments, two $R^{13}$ are each halo. In some embodiments, three $R^{13}$ are each halo. For example, in some embodiments, one $R^{13}$ is fluoro. In some embodiments, two $R^{13}$ are each fluoro. In some embodiments, three $R^{13}$ are each fluoro. For example, in some embodiments, one $R^{13}$ is chloro. In some embodiments, two $R^{13}$ are each chloro. In some embodiments, three $R^{13}$ are each chloro. For example, in some embodiments, one $R^{13}$ is bromo. In some embodiments, two $R^{13}$ are each bromo. In some embodiments, three $R^{13}$ are each bromo. For example, in some embodiments, one $R^{13}$ is iodo. In some embodiments, two $R^{13}$ are each iodo. In some embodiments, three $R^{13}$ are each iodo.

In some embodiments, one $R^{13}$ is CN. In some embodiments, two $R^{13}$ are each CN. In some embodiments, three $R^{13}$ are each CN.

In some embodiments, one $R^{13}$ is $NO_2$. In some embodiments, two $R^{13}$ are each $NO_2$. In some embodiments, three $R^{13}$ are each $NO_2$.

In some embodiments, one $R^{13}$ is $C(O)NH_2$. In some embodiments, two $R^{13}$ are each $C(O)NH_2$. In some embodiments, three $R^{13}$ are each $C(O)NH_2$.

In some embodiments,

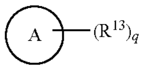

is selected from 1,2,5-thiadiazole 1-oxide, 1,2,5-thiadiazole 1,1-dioxide, 1H-pyrrole-2,5-dione, 1,2-dihydropyridazine-3,6-dione, imidazolidine-2,5-dione, imidazolidine-2,4-dione, imidazolidin-2-one, imidazole-2,5-dione, pyrimidine-2,4,6-trione, pyrimidin-2-one, pyrimidin-4-one, pyrimidine-2,4-dione, pyrimidine-2,4,6-trione, pyridin-2-one, 1,5-dihydro-2H-pyrrol-2-one, 1,2-dihydro-3H-pyrazol-3-one, pyridazine-3,6-dione, 1,9-dihydro-6H-purin-6-one, and imidazole-2,5-dione, each optionally substituted with one or more groups selected from $C_{1-6}$ alkyl, $C_{1-6}$ alkylamino, or halo.

In some embodiments,

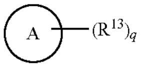

is selected from 1,2,5-thiadiazole 1-oxide, 1,2,5-thiadiazole 1,1-dioxide, 1H-pyrrole-2,5-dione, 1,2-dihydropyridazine-3,6-dione, imidazolidine-2,5-dione, imidazolidine-2,4-dione, imidazolidin-2-one, imidazole-2,5-dione, pyrimidine-2,4,6-trione, pyrimidin-2-one, pyrimidin-4-one, pyrimidine-2,4-dione, pyrimidine-2,4,6-trione, pyridin-2-one, 1,5-dihydro-2H-pyrrol-2-one, 1,2-dihydro-3H-pyrazol-3-one, pyridazine-3,6-dione, 1,9-dihydro-6H-purin-6-one, 2-oxo-2,5-dihydrofuran-3-carbonitrile, 5,6-dihydro-4H-1,2,4-thiadiazine 1,1-dioxide, 1,5-dihydro-2H-imidazol-2-one, 1,3,4-thiadiazol-2-amine, N-methyl-1,2,5-thiadiazol-3-amine, 3-(methylamino)-1,2,5-thiadiazole 1-oxide, 3-(dimethylamino)-1,2,5-thiadiazole 1-oxide, 1-methyl-1H-1,2,4-triazol-3-amine, 3-nitro-1H-pyrrole, and imidazole-2,5-dione.

In some embodiments,

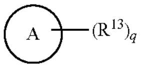

is selected from 1,2,5-thiadiazole 1-oxide, 1,2,5-thiadiazole 1,1-dioxide, 1H-pyrrole-2,5-dione, 1,2-dihydropyridazine-3,6-dione, imidazolidine-2,5-dione, imidazolidine-2,4-dione, imidazolidin-2-one, imidazole-2,5-dione, pyrimidine-2,4,6-trione, pyrimidin-2-one, pyrimidin-4-one, pyrimidine-2,4-dione, pyrimidine-2,4,6-trione, pyridin-2-one, 1,5-dihydro-2H-pyrrol-2-one, 1,2-dihydro-3H-pyrazol-3-one, pyridazine-3,6-dione, 1,9-dihydro-6H-purin-6-one, and imidazole-2,5-dione each substituted with $C_{1-6}$ alkyl.

In some embodiments,

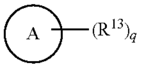

is selected from 1,2,5-thiadiazole 1-oxide, 1,2,5-thiadiazole 1,1-dioxide, 1H-pyrrole-2,5-dione, 1,2-dihydropyridazine-3,6-dione, imidazolidine-2,5-dione, imidazolidine-2,4-dione, imidazolidin-2-one, imidazole-2,5-dione, pyrimidine-2,4,6-trione, pyrimidin-2-one, pyrimidin-4-one, pyrimidine-2,4-dione, pyrimidine-2,4,6-trione, pyridin-2-one, 1,5-dihydro-2H-pyrrol-2-one, 1,2-dihydro-3H-pyrazol-3-one, pyridazine-3,6-dione, 1,9-dihydro-6H-purin-6-one, and imidazole-2,5-dione each substituted with $C_{1-6}$ alkylamino.

In some embodiments,

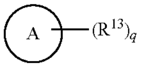

is selected from 1,2,5-thiadiazole 1-oxide, 1,2,5-thiadiazole 1,1-dioxide, 1H-pyrrole-2,5-dione, 1,2-dihydropyridazine-3,6-dione, imidazolidine-2,5-dione, imidazolidine-2,4-dione, imidazolidin-2-one, imidazole-2,5-dione, pyrimidine-2,4,6-trione, pyrimidin-2-one, pyrimidin-4-one, pyrimidine-2,4-dione, pyrimidine-2,4,6-trione, pyridin-2-one, 1,5-dihydro-2H-pyrrol-2-one, 1,2-dihydro-3H-pyrazol-3-one, pyridazine-3,6-dione, 1,9-dihydro-6H-purin-6-one, and imidazole-2,5-dione each substituted with halo.

In some embodiments,

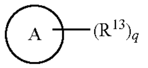

is selected from 1,2,5-thiadiazole 1-oxide, 1,2,5-thiadiazole 1,1-dioxide, 1H-pyrrole-2,5-dione, 1,2-dihydropyridazine-3,6-dione, imidazolidine-2,5-dione, imidazolidine-2,4-dione, imidazolidin-2-one, imidazole-2,5-dione, pyrimidine-2,4,6-trione, pyrimidin-2-one, pyrimidin-4-one, pyrimidine-2,4-dione, pyrimidine-2,4,6-trione, pyridin-2-one, 1,5-dihydro-2H-pyrrol-2-one, 1,2-dihydro-3H-pyrazol-3-one, pyridazine-3,6-dione, 1,9-dihydro-6H-purin-6-one, and imidazole-2,5-dione each substituted with $C_{1-6}$ alkyl and $C_{1-6}$ alkylamino.

In some embodiments,

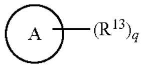

is selected from 1,2,5-thiadiazole 1-oxide, 1,2,5-thiadiazole 1,1-dioxide, 1H-pyrrole-2,5-dione, 1,2-dihydropyridazine-3,6-dione, imidazolidine-2,5-dione, imidazolidine-2,4-dione, imidazolidin-2-one, imidazole-2,5-dione, pyrimidine-2,4,6-trione, pyrimidin-2-one, pyrimidin-4-one, pyrimidine-2,4-dione, pyrimidine-2,4,6-trione, pyridin-2-one, 1,5-dihydro-2H-pyrrol-2-one, 1,2-dihydro-3H-pyrazol-3-one, pyridazine-3,6-dione, 1,9-dihydro-6H-purin-6-one, and imidazole-2,5-dione each substituted with $C_{1-6}$ alkyl and halo.

In some embodiments,

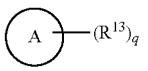

is selected from 1,2,5-thiadiazole 1-oxide, 1,2,5-thiadiazole 1,1-dioxide, 1H-pyrrole-2,5-dione, 1,2-dihydropyridazine-3,6-dione, imidazolidine-2,5-dione, imidazolidine-2,4-dione, imidazolidin-2-one, imidazole-2,5-dione, pyrimidine-2,4,6-trione, pyrimidin-2-one, pyrimidin-4-one, pyrimidine-2,4-dione, pyrimidine-2,4,6-trione, pyridin-2-one, 1,5-dihydro-2H-pyrrol-2-one, 1,2-dihydro-3H-pyrazol-3-one, pyridazine-3,6-dione, 1,9-dihydro-6H-purin-6-one, and imidazole-2,5-dione each substituted with $C_{1-6}$ alkylamino and halo.

In some embodiments, $R^2$ and $R^3$ are independently $C_{3-14}$ alkyl or $C_{3-14}$ alkenyl.

In some embodiments, one $R^{12}$ is H and one $R^{12}$ is $C_{1-3}$ alkyl or $C_{2-3}$ alkenyl. In some embodiments, each $R^{12}$ is $C_{1-3}$ alkyl or $C_{2-3}$ alkenyl. In some embodiments, each $R^{12}$ is $C_{1-3}$ alkyl (e.g. methyl, ethyl or propyl). For example, one $R^{12}$ is methyl and one $R^{12}$ is ethyl or propyl. For example, one $R^{12}$ is ethyl and one $R^{12}$ is methyl or propyl. For example, one $R^{12}$ is propyl and one $R^{12}$ is methyl or ethyl. For example, each $R^{12}$ is methyl. For example, each $R^{12}$ is ethyl. For example, each $R^{12}$ is propyl.

In some embodiments, one $R^{12}$ is H and one $R^{12}$ is OH. In some embodiments, each $R^{12}$ is OH.

In some embodiments, R' is selected from $C_4$ alkyl and $C_4$ alkenyl. In certain embodiments, R' is selected from $C_5$ alkyl and $C_5$ alkenyl. In some embodiments, R' is selected from $C_6$ alkyl and $C_6$ alkenyl. In some embodiments, R' is selected from $C_7$ alkyl and $C_7$ alkenyl. In some embodiments, R' is selected from $C_9$ alkyl and $C_9$ alkenyl.

In some embodiments, R' is selected from $C_4$ alkyl, $C_4$ alkenyl, $C_5$ alkyl, $C_5$ alkenyl, $C_6$ alkyl, $C_6$ alkenyl, $C_7$ alkyl, $C_7$ alkenyl, $C_9$ alkyl, $C_9$ alkenyl, $C_{11}$ alkyl, $C_{11}$ alkenyl, $C_{17}$ alkyl, $C_{17}$ alkenyl, $C_{18}$ alkyl, and $C_{18}$ alkenyl, each of which is either linear or branched.

In some embodiments, R' is $C_4$ alkyl or $C_4$ alkenyl. In some embodiments, R' is $C_5$ alkyl or $C_5$ alkenyl. In some embodiments, R' is $C_6$ alkyl or $C_6$ alkenyl. In some embodiments, R' is $C_7$ alkyl or $C_7$ alkenyl. In some embodiments, R' is $C_8$ alkyl or $C_8$ alkenyl. In some embodiments, R' is $C_9$ alkyl or $C_9$ alkenyl. In some embodiments, R' is $C_{10}$ alkyl or $C_{10}$ alkenyl. In some embodiments, R' is $C_{11}$ alkyl or $C_{11}$ alkenyl.

In other embodiments, R' is selected from $C_{11}$ alkyl and $C_{11}$ alkenyl. In other embodiments, R' is selected from $C_{12}$ alkyl, $C_{12}$ alkenyl, $C_{13}$ alkyl, $C_{13}$ alkenyl, $C_{14}$ alkyl, $C_{14}$ alkenyl, Cis alkyl, Cis alkenyl, $C_{16}$ alkyl, $C_{16}$ alkenyl, $C_{17}$ alkyl, $C_{17}$ alkenyl, Cis alkyl, and Cis alkenyl. In certain embodiments, R' is linear $C_4$-18 alkyl or $C_4$-18 alkenyl. In certain embodiments, R' is branched (e.g., decan-2-yl, undecan-3-yl, dodecan-4-yl, tridecan-5-yl, tetradecan-6-yl, 2-methylundecan-3-yl, 2-methyldecan-2-yl, 3-methylundecan-3-yl, 4-methyldodecan-4-yl or heptadeca-9-yl). In certain embodiments, R' is

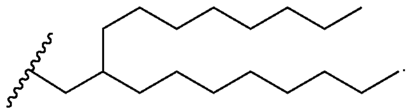 [SMILES: *CC(CCCCCCCC)CCCCCCCC]

In some embodiments, each $R^5$ is H. In some embodiments, each $R^6$ is H. In certain such embodiments, each $R^5$ and each $R^6$ is H.

In some embodiments, $R^7$ is H. In other embodiments, $R^7$ is $C_{1-3}$ alkyl (e.g., methyl, ethyl, propyl, or i-propyl).

In some embodiments, $R^2$ and $R^3$ are independently $C_{5-14}$ alkyl or $C_{5-14}$ alkenyl.

In some embodiments, $R^2$ and $R^3$ are the same. In some embodiments, $R^2$ and $R^3$ are $C_8$ alkyl. In certain embodiments, $R^2$ and $R^3$ are $C_2$ alkyl. In other embodiments, $R^2$ and $R^3$ are $C_3$ alkyl. In some embodiments, $R^2$ and $R^3$ are $C_4$ alkyl. In certain embodiments, $R^2$ and $R^3$ are $C_5$ alkyl. In other embodiments, $R^2$ and $R^3$ are $C_6$ alkyl. In some embodiments, $R^2$ and $R^3$ are $C_7$ alkyl.

In other embodiments, $R^2$ and $R^3$ are different. In certain embodiments, $R^2$ is $C_8$ alkyl. In some embodiments, $R^3$ is $C_{1-7}$ (e.g., $C_1$, $C_2$, $C_3$, $C_4$, $C_5$, $C_6$, or $C_7$ alkyl) or $C_9$ alkyl.

In some embodiments, $R^3$ is $C_1$ alkyl. In some embodiments, $R^3$ is $C_2$ alkyl. In some embodiments, $R^3$ is $C_3$ alkyl. In some embodiments, $R^3$ is $C_4$ alkyl. In some embodiments, $R^3$ is $C_5$ alkyl. In some embodiments, $R^3$ is $C_6$ alkyl. In some embodiments, $R^3$ is $C_7$ alkyl. In some embodiments, $R^3$ is $C_9$ alkyl.

In some embodiments, $R^7$ and $R^3$ are H.

In certain embodiments, $R^2$ is H.

In some embodiments, m is 5, 6, 7, 8, or 9. In some embodiments, m is 5, 7, or 9. For example, in some embodiments, m is 5. For example, in some embodiments, m is 7. For example, in some embodiments, m is 9.

In some embodiments, R is H.

In some embodiments, R is $C_{1-3}$ alkyl substituted with mono- or di-alkylamino, e.g., R is ((dimethylamino)ethyl) amino.

In some embodiments, R is $C_{1-6}$ alkyl substituted with one or more substituents selected from the group consisting of $C_{1-3}$ alkoxyl, amino, and $C_1$-$C_3$ dialkylamino.

In some embodiments, R is unsubstituted $C_{1-3}$ alkyl or unsubstituted $C_{2-3}$ alkenyl.

In some embodiments, the compound of Formula (I), (I-1), (A), (A-1), (A-1a), or (A-1b) is selected from Table 1.

TABLE 1

Amino Lipids

| Cpd | Structure |
|---|---|
| 1 | 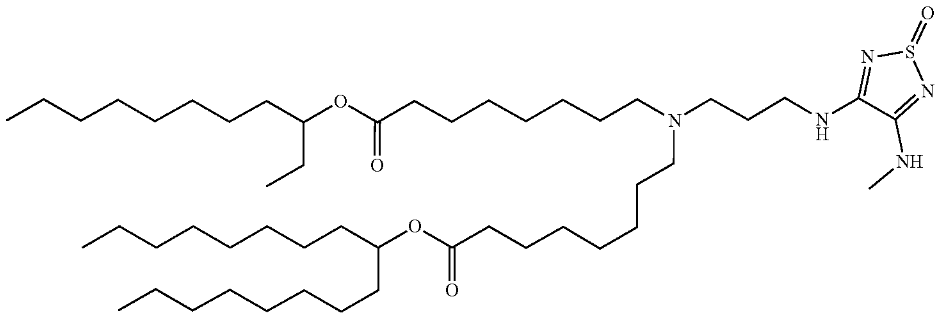 [SMILES: CCCCCCCCC(CC)OC(=O)CCCCCCCN(CCCCCCCC(=O)OC(CCCCCCCC)CCCCCCCC)CCCNC1=NS(=O)N=C1NC] |
| 2 | 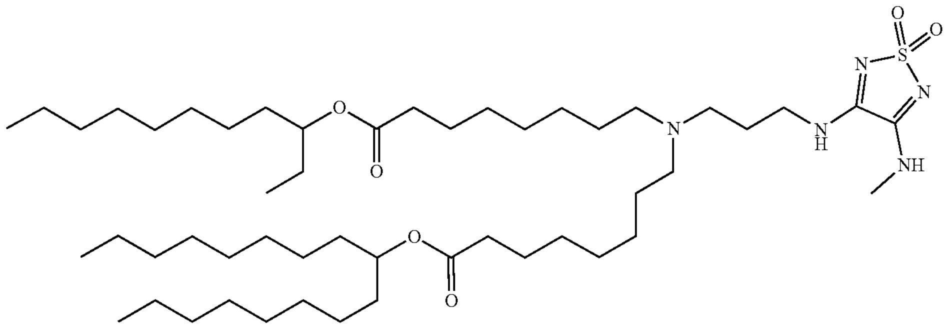 [SMILES: CCCCCCCCC(CC)OC(=O)CCCCCCCN(CCCCCCCC(=O)OC(CCCCCCCC)CCCCCCCC)CCCNC1=NS(=O)(=O)N=C1NC] |
| 3 | 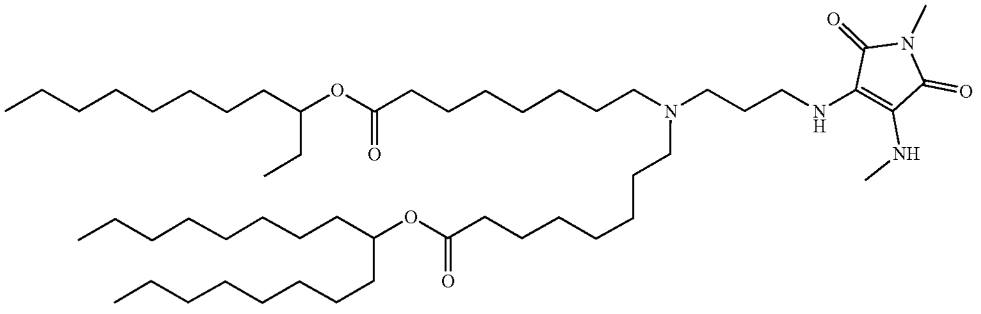 [SMILES: CCCCCCCCC(CC)OC(=O)CCCCCCCN(CCCCCCCC(=O)OC(CCCCCCCC)CCCCCCCC)CCCNC1=C(NC)C(=O)N(C)C1=O] |
| 4 | 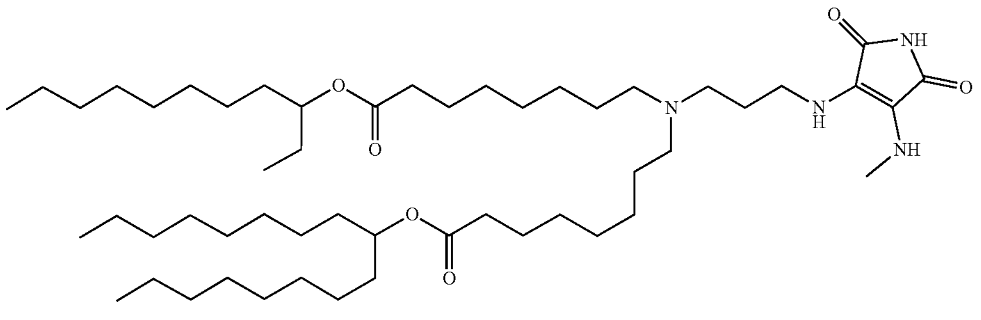 [SMILES: CCCCCCCCC(CC)OC(=O)CCCCCCCN(CCCCCCCC(=O)OC(CCCCCCCC)CCCCCCCC)CCCNC1=C(NC)C(=O)NC1=O] |

TABLE 1-continued
| Amino Lipids | |
|---|---|
| Cpd | Structure |
| 5 | 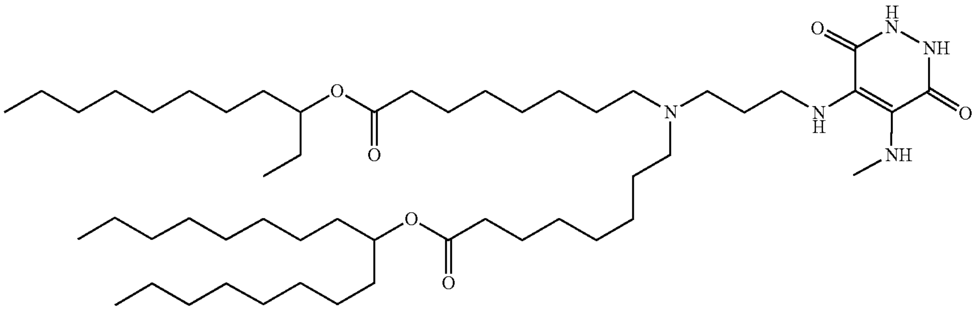 [SMILES: CCCCCCCCC(CC)OC(=O)CCCCCCCN(CCCCCCCC(=O)OC(CCCCCCCC)CCCCCCCC)CCCNc1c(NC)c(=O)[nH][nH]c1=O] |
| 6 | 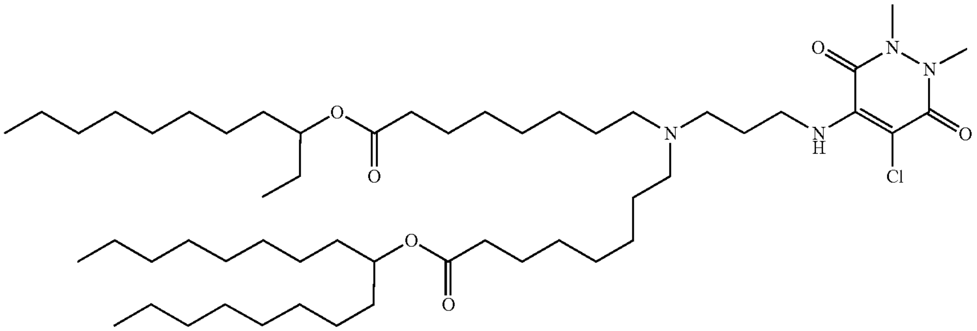 [SMILES: CCCCCCCCC(CC)OC(=O)CCCCCCCN(CCCCCCCC(=O)OC(CCCCCCCC)CCCCCCCC)CCCNc1c(Cl)c(=O)n(C)n(C)c1=O] |
| 7 | 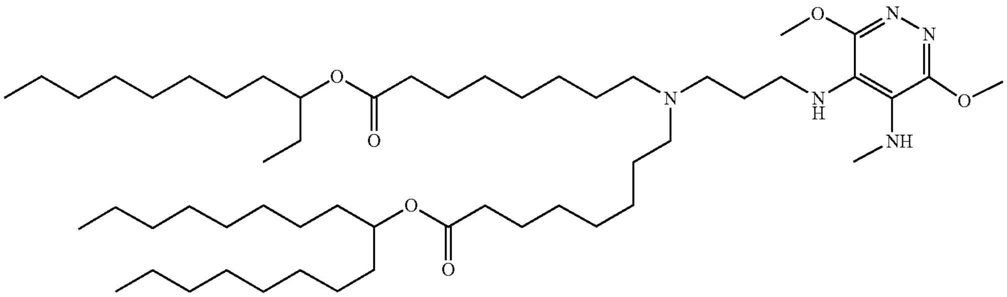 [SMILES: CCCCCCCCC(CC)OC(=O)CCCCCCCN(CCCCCCCC(=O)OC(CCCCCCCC)CCCCCCCC)CCCNc1c(OC)nnc(OC)c1NC] |
| 8 | 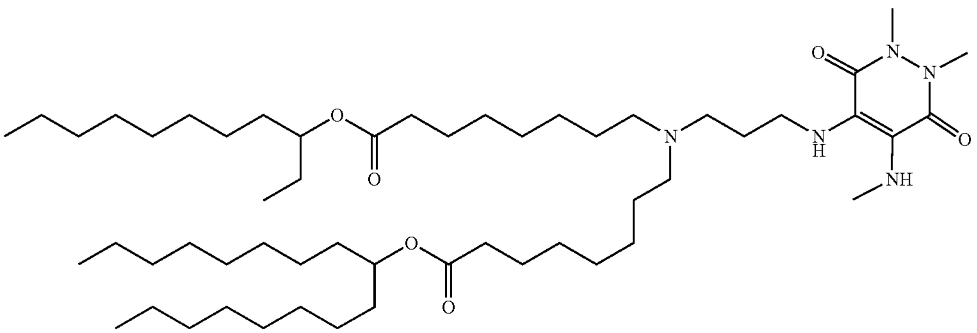 [SMILES: CCCCCCCCC(CC)OC(=O)CCCCCCCN(CCCCCCCC(=O)OC(CCCCCCCC)CCCCCCCC)CCCNc1c(NC)c(=O)n(C)n(C)c1=O] |

TABLE 1-continued
| Amino Lipids | |
|---|---|
| Cpd | Structure |
| 9 | 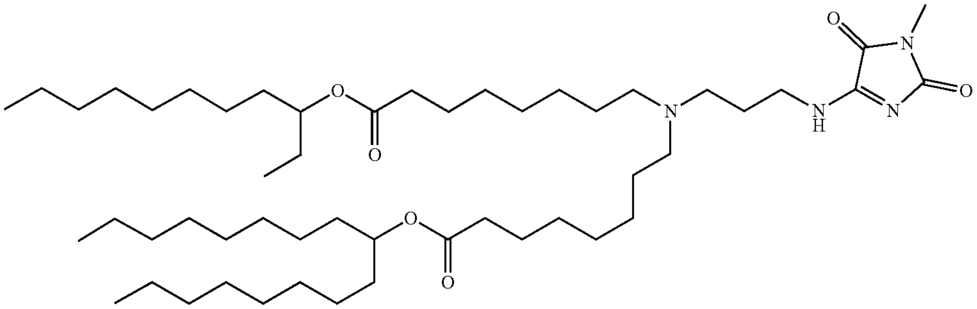 [SMILES: CCCCCCCCC(CC)OC(=O)CCCCCCCN(CCCCCCCC(=O)OC(CCCCCCCC)CCCCCCCC)CCCNC1=NC(=O)N(C)C1=O] |
| 10 | 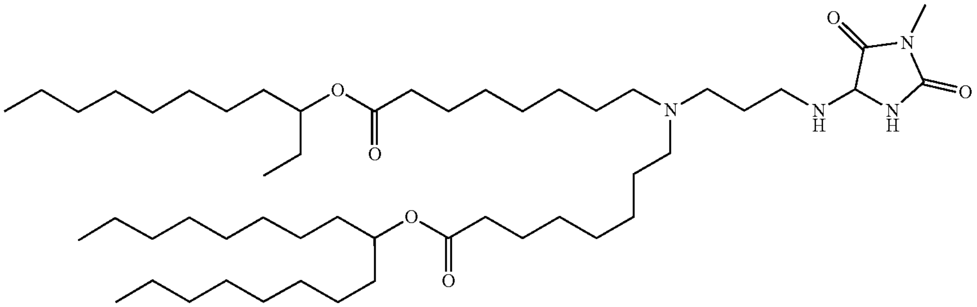 [SMILES: CCCCCCCCC(CC)OC(=O)CCCCCCCN(CCCCCCCC(=O)OC(CCCCCCCC)CCCCCCCC)CCCNC1NC(=O)N(C)C1=O] |
| 11 | 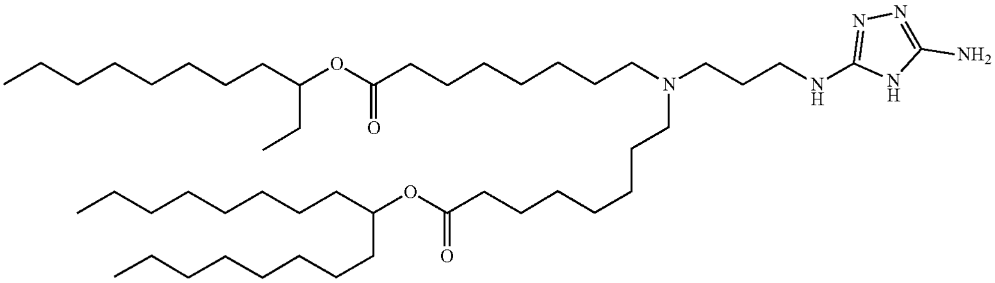 [SMILES: CCCCCCCCC(CC)OC(=O)CCCCCCCN(CCCCCCCC(=O)OC(CCCCCCCC)CCCCCCCC)CCCNc1nnc(N)[nH]1] |
| 12 | 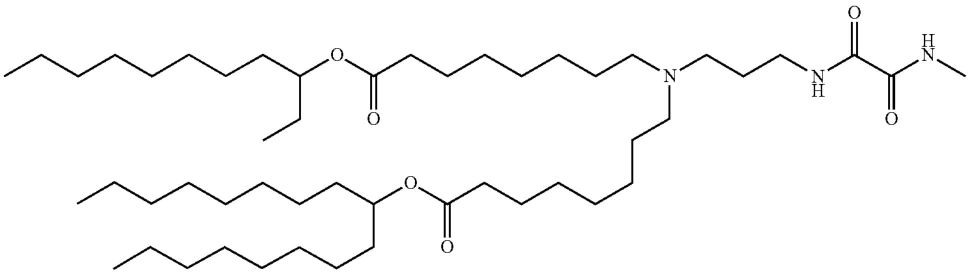 [SMILES: CCCCCCCCC(CC)OC(=O)CCCCCCCN(CCCCCCCC(=O)OC(CCCCCCCC)CCCCCCCC)CCCNC(=O)C(=O)NC] |
| 13 | 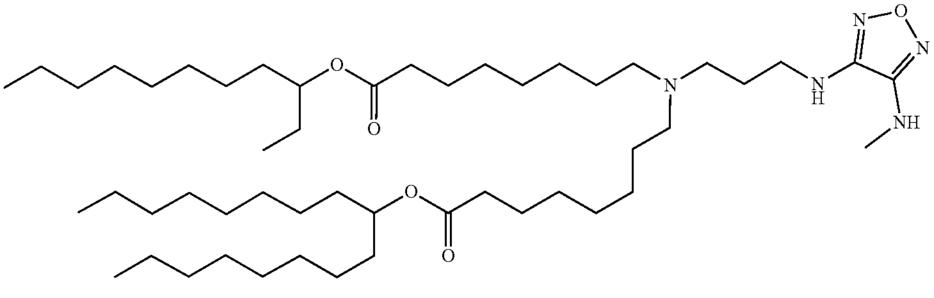 |

TABLE 1-continued
| Amino Lipids | |
|---|---|
| Cpd | Structure |
| 14 | 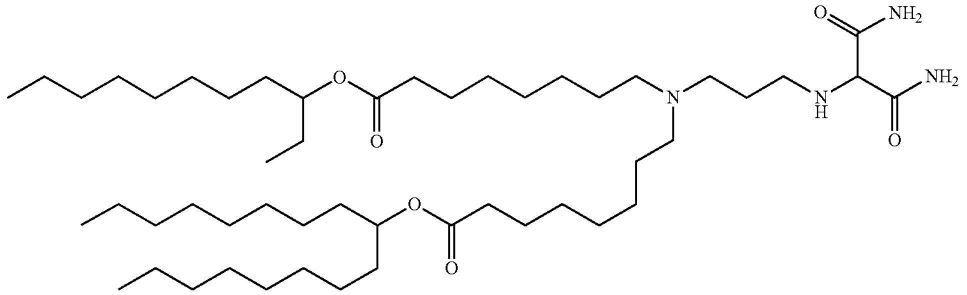 [SMILES: CCCCCCCCC(CC)OC(=O)CCCCCCCN(CCCCCCCC(=O)OC(CCCCCCCC)CCCCCCCC)CCCNC(C(N)=O)C(N)=O] |
| 15 | 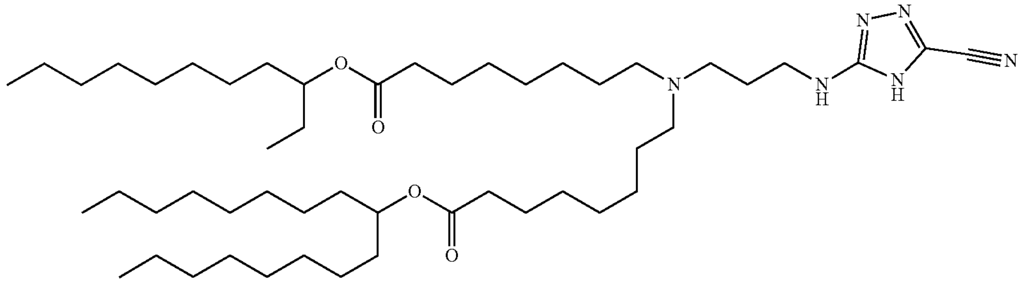 [SMILES: CCCCCCCCC(CC)OC(=O)CCCCCCCN(CCCCCCCC(=O)OC(CCCCCCCC)CCCCCCCC)CCCNc1nnc(C#N)[nH]1] |
| 16 | 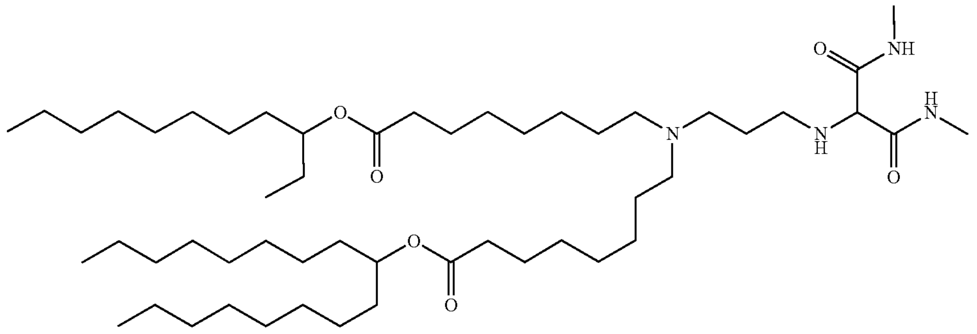 [SMILES: CCCCCCCCC(CC)OC(=O)CCCCCCCN(CCCCCCCC(=O)OC(CCCCCCCC)CCCCCCCC)CCCNC(C(=O)NC)C(=O)NC] |
| 17 | 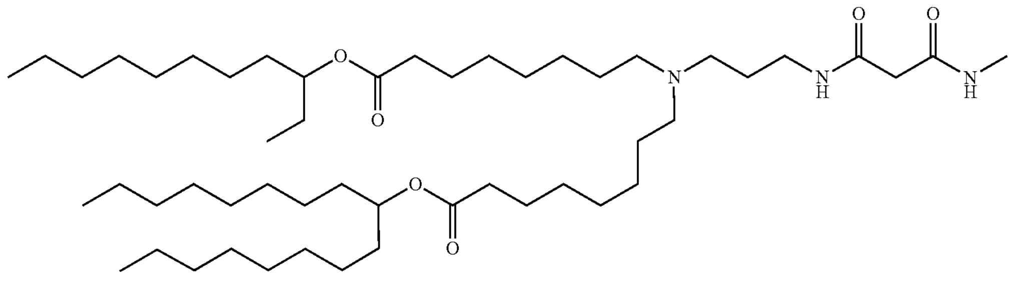 [SMILES: CCCCCCCCC(CC)OC(=O)CCCCCCCN(CCCCCCCC(=O)OC(CCCCCCCC)CCCCCCCC)CCCNC(=O)CC(=O)NC] |
| 18 | 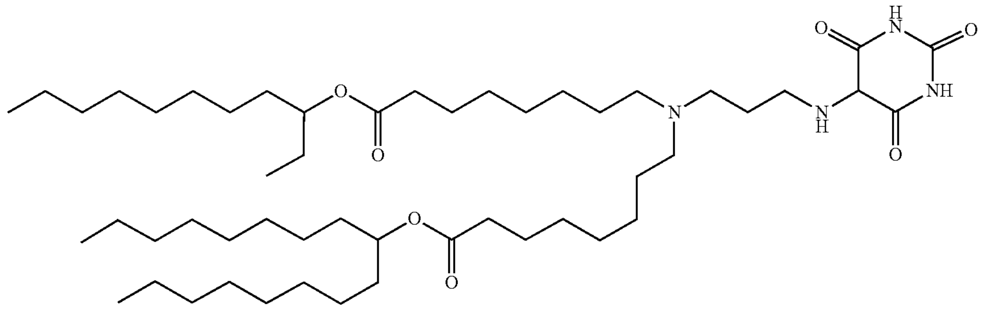 [SMILES: CCCCCCCCC(CC)OC(=O)CCCCCCCN(CCCCCCCC(=O)OC(CCCCCCCC)CCCCCCCC)CCCNC1C(=O)NC(=O)NC1=O] |

TABLE 1-continued
| Amino Lipids | |
|---|---|
| Cpd | Structure |
| 19 | 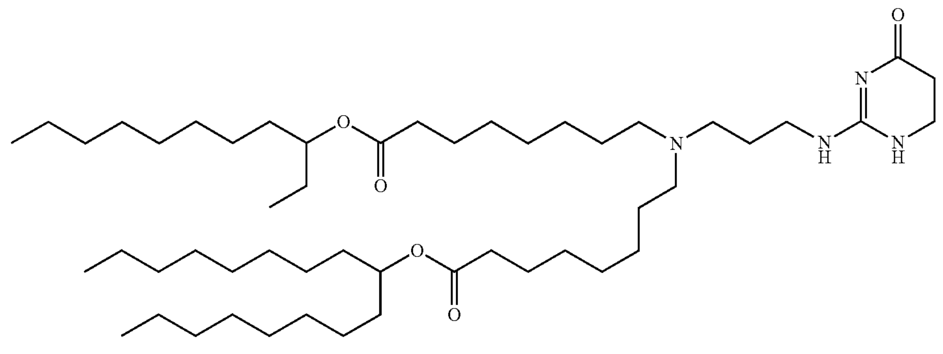 [SMILES: CCCCCCCCC(CC)OC(=O)CCCCCCCN(CCCCCCCC(=O)OC(CCCCCCCC)CCCCCCCC)CCCNC1=NC(=O)CCN1] |
| 20 | 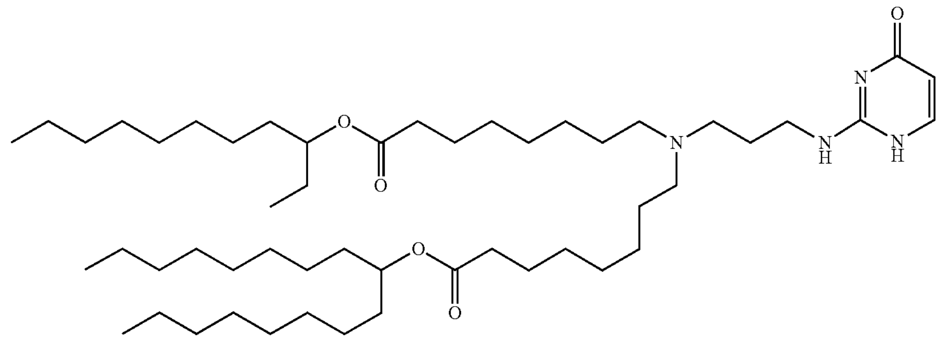 [SMILES: CCCCCCCCC(CC)OC(=O)CCCCCCCN(CCCCCCCC(=O)OC(CCCCCCCC)CCCCCCCC)CCCNc1nc(=O)cc[nH]1] |
| 21 | 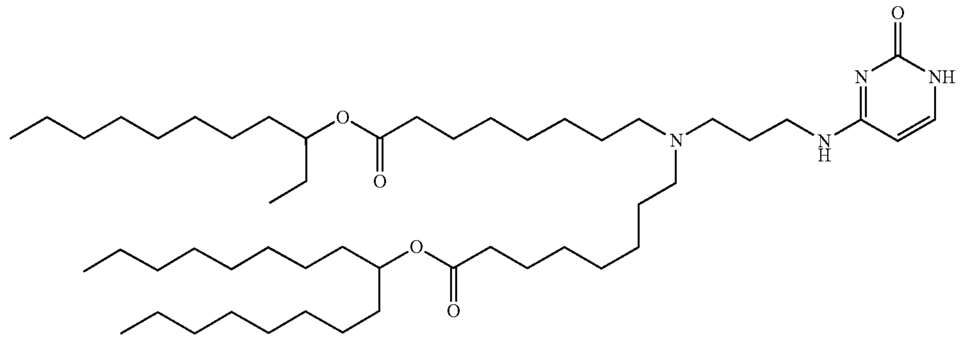 [SMILES: CCCCCCCCC(CC)OC(=O)CCCCCCCN(CCCCCCCC(=O)OC(CCCCCCCC)CCCCCCCC)CCCNc1cc[nH]c(=O)n1] |
| 22 | 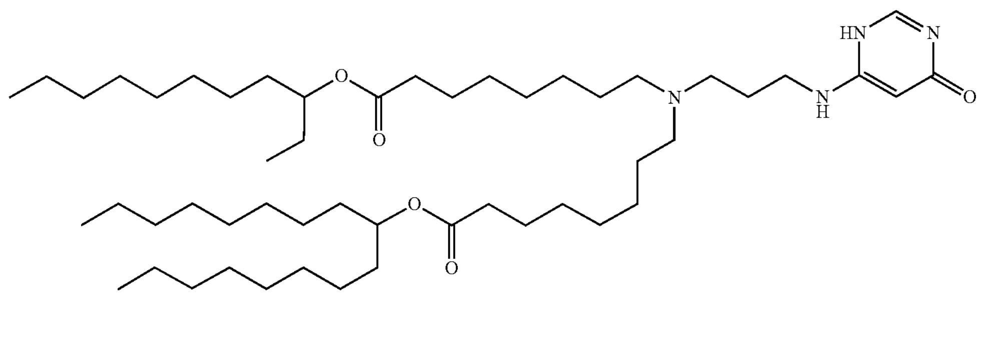 [SMILES: CCCCCCCCC(CC)OC(=O)CCCCCCCN(CCCCCCCC(=O)OC(CCCCCCCC)CCCCCCCC)CCCNc1cc(=O)nc[nH]1] |

TABLE 1-continued
| Amino Lipids | |
|---|---|
| Cpd | Structure |
| 23 | 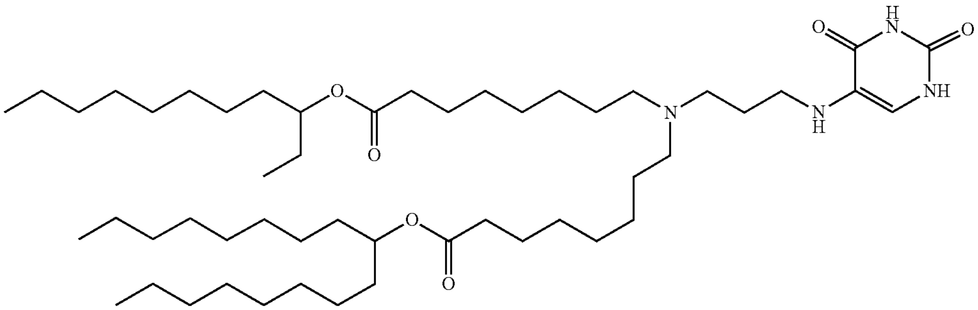 [SMILES: CCCCCCCCC(CC)OC(=O)CCCCCCCN(CCCCCCCC(=O)OC(CCCCCCCC)CCCCCCCC)CCCNc1c[nH]c(=O)[nH]c1=O] |
| 24 | 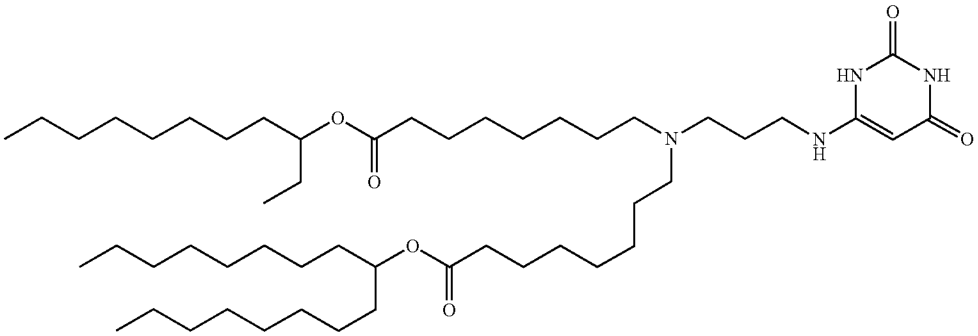 [SMILES: CCCCCCCCC(CC)OC(=O)CCCCCCCN(CCCCCCCC(=O)OC(CCCCCCCC)CCCCCCCC)CCCNc1cc(=O)[nH]c(=O)[nH]1] |
| 25 | 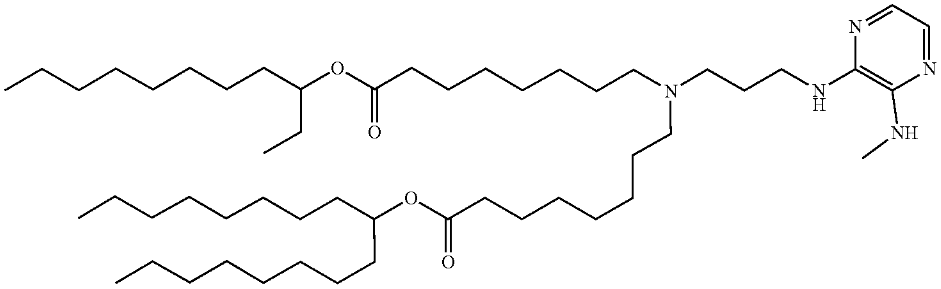 [SMILES: CCCCCCCCC(CC)OC(=O)CCCCCCCN(CCCCCCCC(=O)OC(CCCCCCCC)CCCCCCCC)CCCNc1nccnc1NC] |
| 26 | 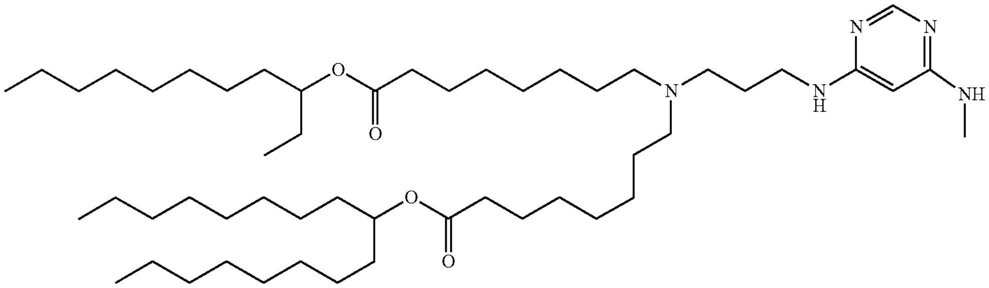 [SMILES: CCCCCCCCC(CC)OC(=O)CCCCCCCN(CCCCCCCC(=O)OC(CCCCCCCC)CCCCCCCC)CCCNc1cc(NC)ncn1] |
| 27 | 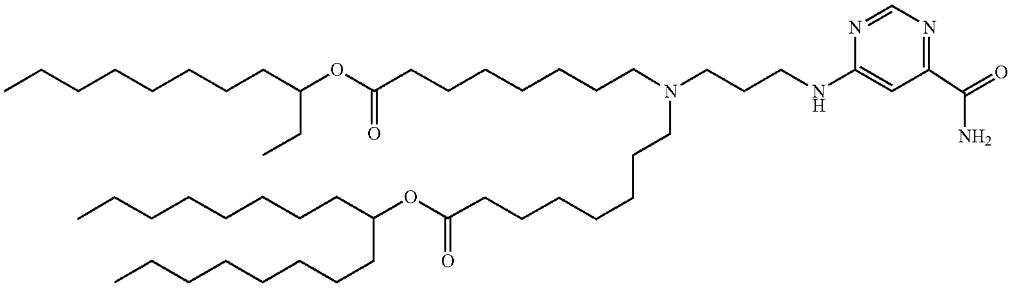 [SMILES: CCCCCCCCC(CC)OC(=O)CCCCCCCN(CCCCCCCC(=O)OC(CCCCCCCC)CCCCCCCC)CCCNc1cc(C(N)=O)ncn1] |

TABLE 1-continued
| Amino Lipids | |
| --- | --- |
| Cpd | Structure |
| 28 | 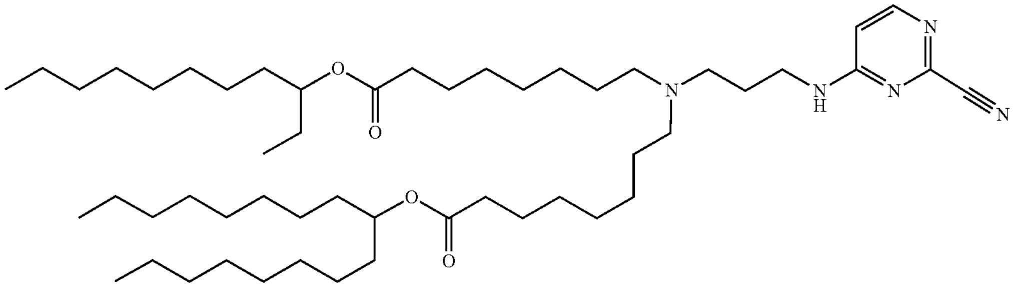 [SMILES: CCCCCCCCC(CC)OC(=O)CCCCCCCN(CCCCCCCC(=O)OC(CCCCCCCC)CCCCCCCC)CCCNc1ccnc(C#N)n1] |
| 29 | 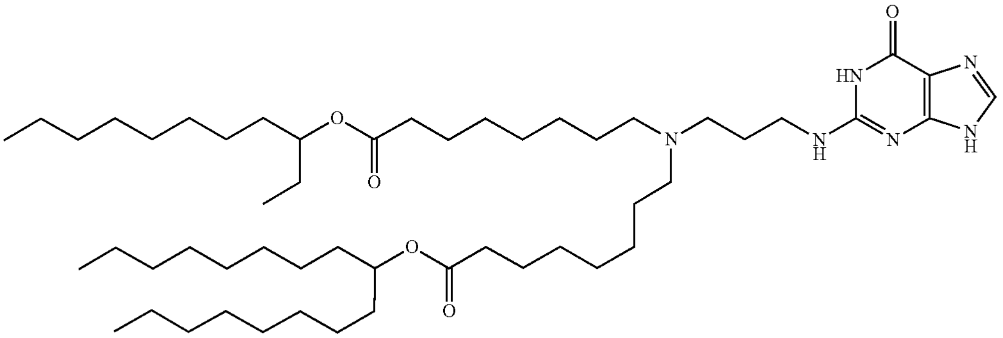 [SMILES: CCCCCCCCC(CC)OC(=O)CCCCCCCN(CCCCCCCC(=O)OC(CCCCCCCC)CCCCCCCC)CCCNc1nc2[nH]cnc2c(=O)[nH]1] |
| 30 | 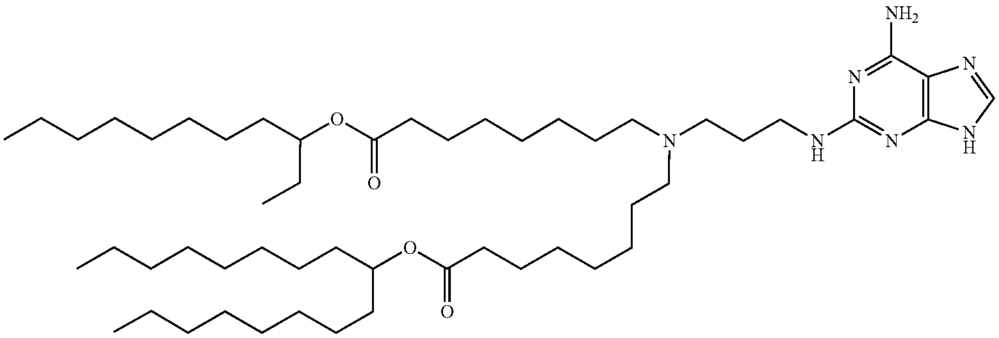 [SMILES: CCCCCCCCC(CC)OC(=O)CCCCCCCN(CCCCCCCC(=O)OC(CCCCCCCC)CCCCCCCC)CCCNc1nc(N)c2nc[nH]c2n1] |
| 31 | 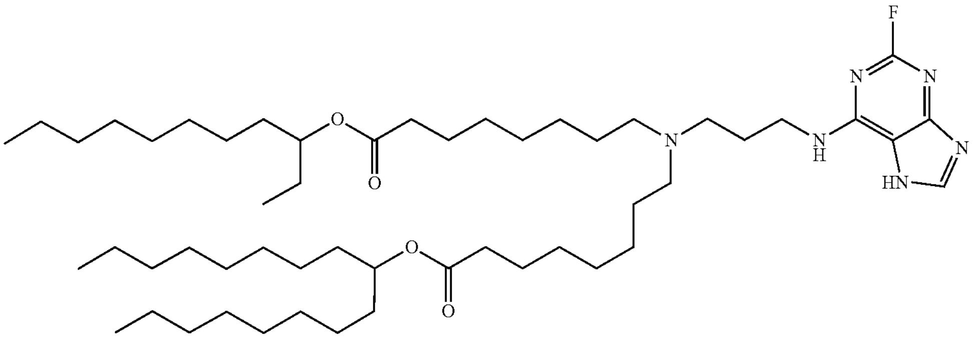 [SMILES: CCCCCCCCC(CC)OC(=O)CCCCCCCN(CCCCCCCC(=O)OC(CCCCCCCC)CCCCCCCC)CCCNc1nc(F)nc2nc[nH]c12] |

TABLE 1-continued
| Amino Lipids | |
|---|---|
| Cpd | Structure |
| 32 | 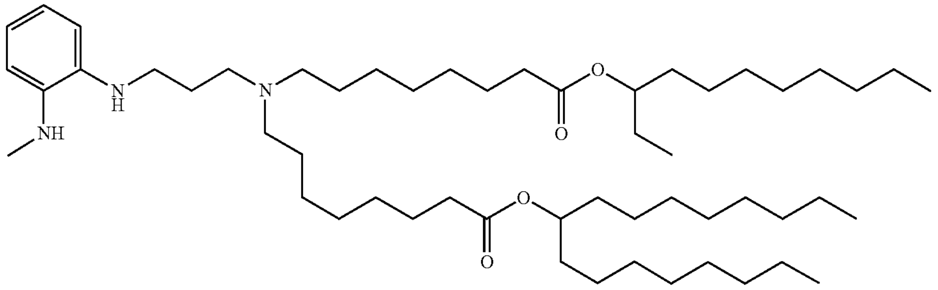 [SMILES: CCCCCCCCC(CC)OC(=O)CCCCCCCN(CCCCCCCC(=O)OC(CCCCCCCC)CCCCCCCC)CCCNc1ccccc1NC] |
| 33 | 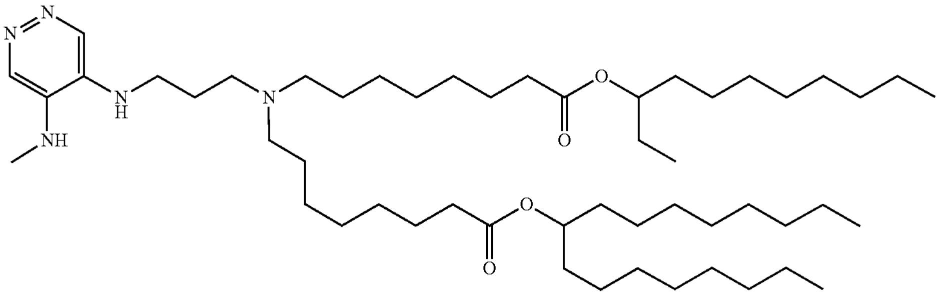 [SMILES: CCCCCCCCC(CC)OC(=O)CCCCCCCN(CCCCCCCC(=O)OC(CCCCCCCC)CCCCCCCC)CCCNc1cnncc1NC] |
| 34 | 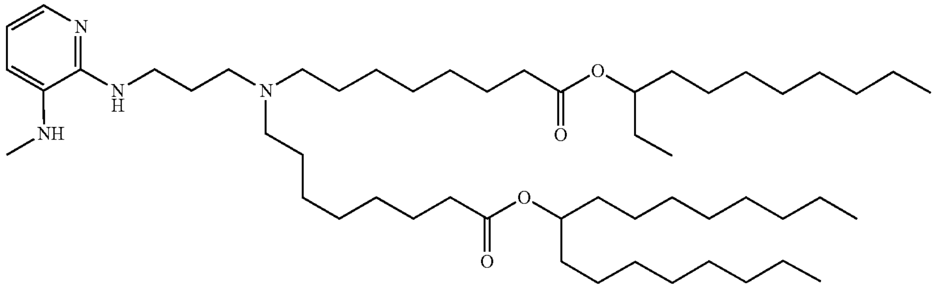 [SMILES: CCCCCCCCC(CC)OC(=O)CCCCCCCN(CCCCCCCC(=O)OC(CCCCCCCC)CCCCCCCC)CCCNc1ncccc1NC] |
| 35 | 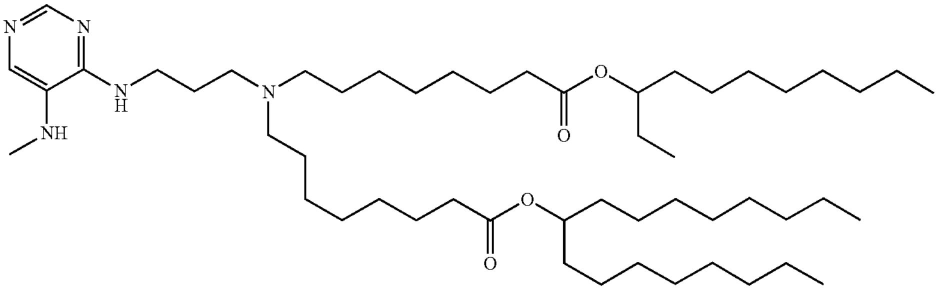 [SMILES: CCCCCCCCC(CC)OC(=O)CCCCCCCN(CCCCCCCC(=O)OC(CCCCCCCC)CCCCCCCC)CCCNc1ncncc1NC] |
| 36 | 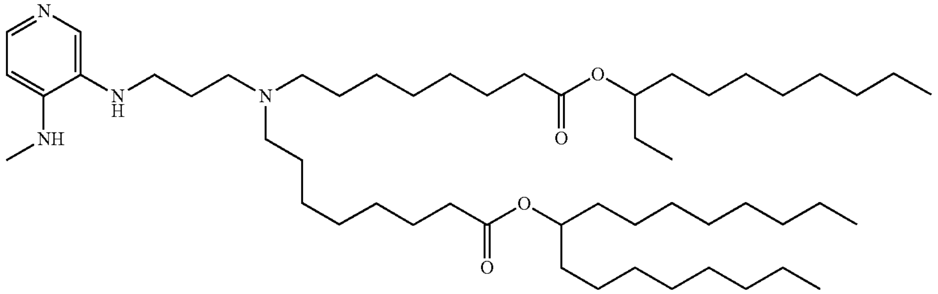 [SMILES: CCCCCCCCC(CC)OC(=O)CCCCCCCN(CCCCCCCC(=O)OC(CCCCCCCC)CCCCCCCC)CCCNc1cnccc1NC] |

TABLE 1-continued
| Amino Lipids | |
|---|---|
| Cpd | Structure |
| 37 | 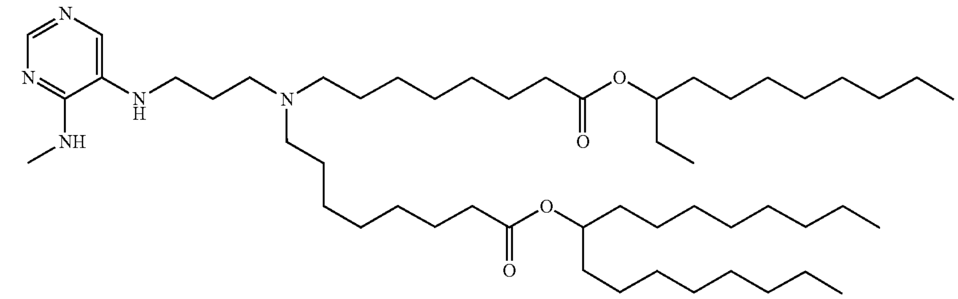 [SMILES: CCCCCCCCC(CC)OC(=O)CCCCCCCN(CCCCCCCC(=O)OC(CCCCCCCC)CCCCCCCC)CCCNc1cncnc1NC] |
| 38 | 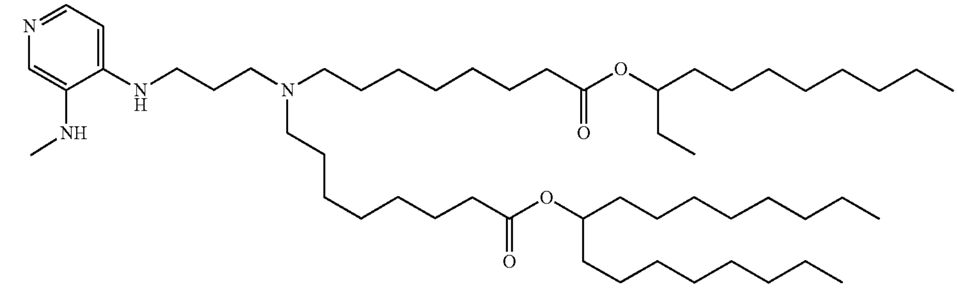 [SMILES: CCCCCCCCC(CC)OC(=O)CCCCCCCN(CCCCCCCC(=O)OC(CCCCCCCC)CCCCCCCC)CCCNc1ccncc1NC] |
| 39 | 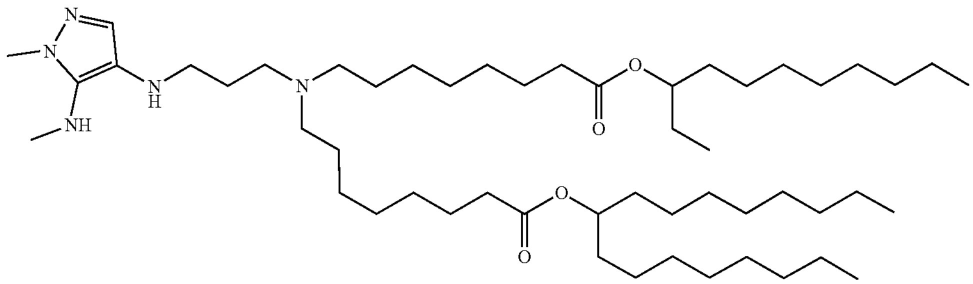 [SMILES: CCCCCCCCC(CC)OC(=O)CCCCCCCN(CCCCCCCC(=O)OC(CCCCCCCC)CCCCCCCC)CCCNc1cnn(C)c1NC] |
| 40 | 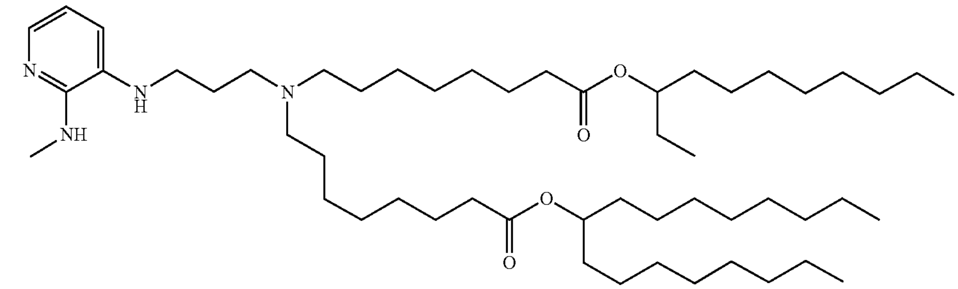 [SMILES: CCCCCCCCC(CC)OC(=O)CCCCCCCN(CCCCCCCC(=O)OC(CCCCCCCC)CCCCCCCC)CCCNc1cccnc1NC] |
| 41 | 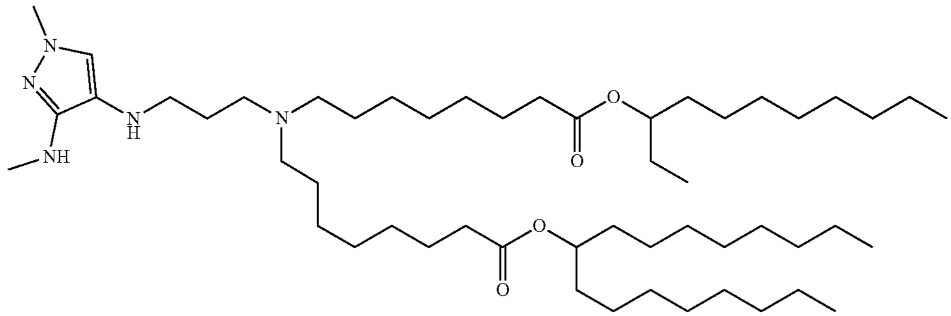 [SMILES: CCCCCCCCC(CC)OC(=O)CCCCCCCN(CCCCCCCC(=O)OC(CCCCCCCC)CCCCCCCC)CCCNc1cn(C)nc1NC] |

TABLE 1-continued
| Amino Lipids | |
|---|---|
| Cpd | Structure |
| 42 | 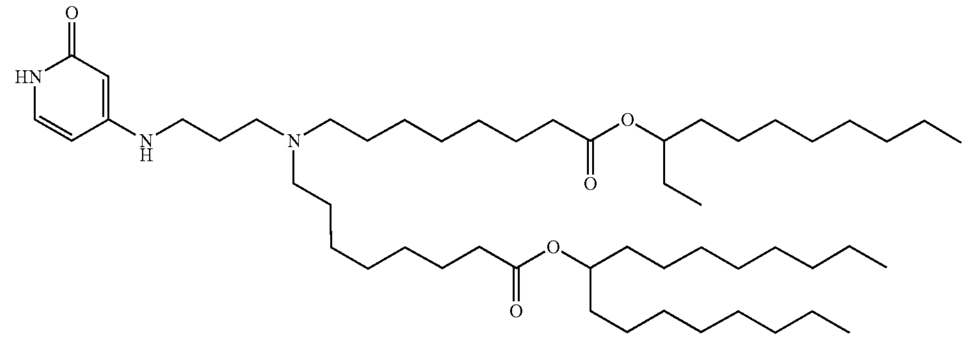 [SMILES: CCCCCCCCC(CC)OC(=O)CCCCCCCN(CCCCCCCC(=O)OC(CCCCCCCC)CCCCCCCC)CCCNc1cc[nH]c(=O)c1] |
| 43 | 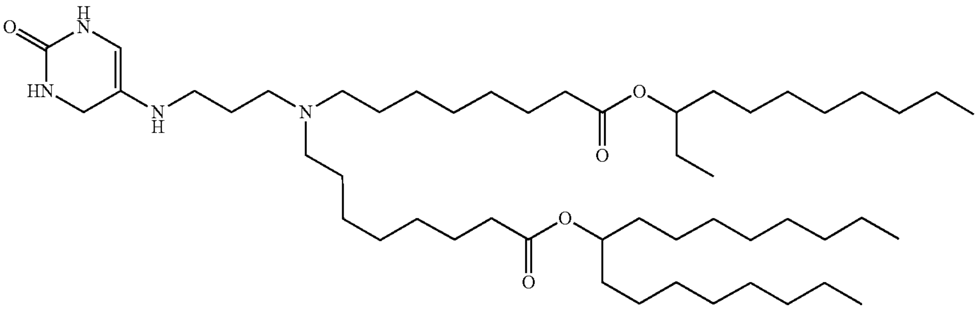 [SMILES: CCCCCCCCC(CC)OC(=O)CCCCCCCN(CCCCCCCC(=O)OC(CCCCCCCC)CCCCCCCC)CCCNC1=CNC(=O)NC1] |
| 44 | 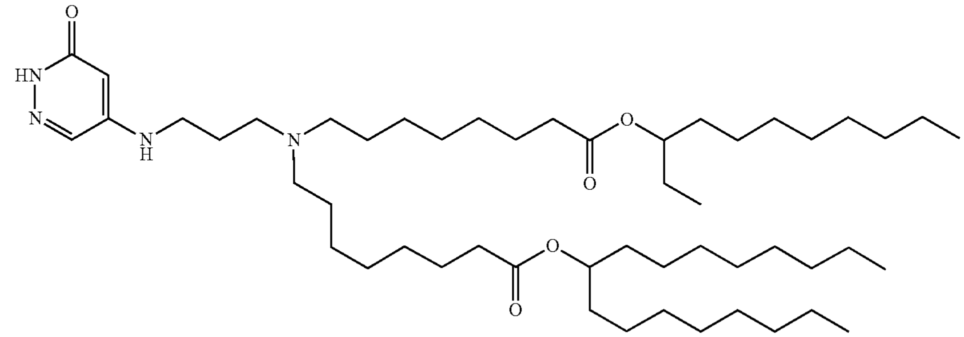 [SMILES: CCCCCCCCC(CC)OC(=O)CCCCCCCN(CCCCCCCC(=O)OC(CCCCCCCC)CCCCCCCC)CCCNc1cn[nH]c(=O)c1] |
| 45 | 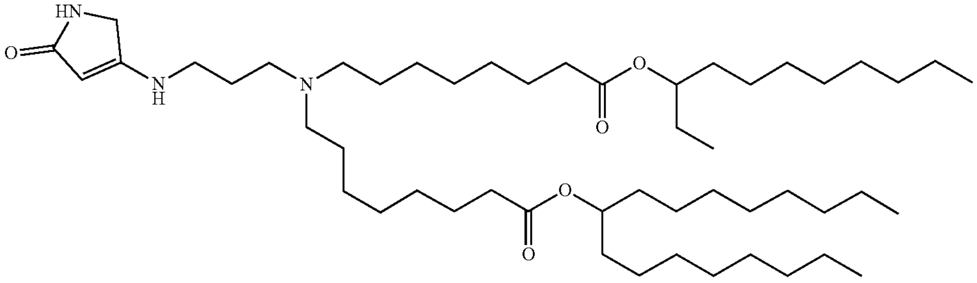 [SMILES: CCCCCCCCC(CC)OC(=O)CCCCCCCN(CCCCCCCC(=O)OC(CCCCCCCC)CCCCCCCC)CCCNC1=CC(=O)NC1] |

TABLE 1-continued
| Amino Lipids | |
|---|---|
| Cpd | Structure |
| 46 | 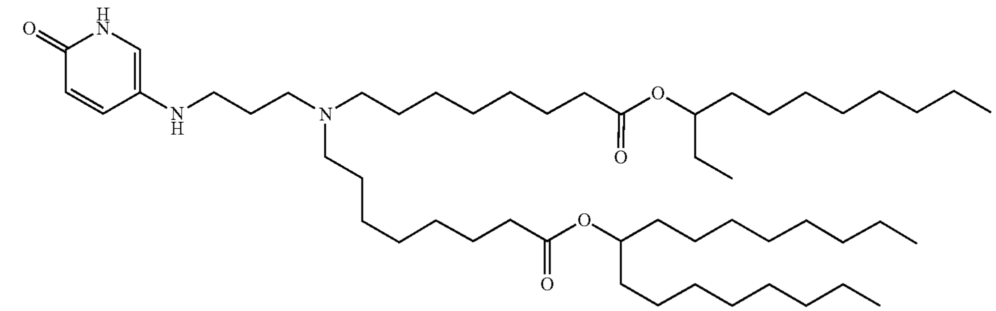 [SMILES: CCCCCCCCC(CC)OC(=O)CCCCCCCN(CCCCCCCC(=O)OC(CCCCCCCC)CCCCCCCC)CCCNc1ccc(=O)[nH]c1] |
| 47 | 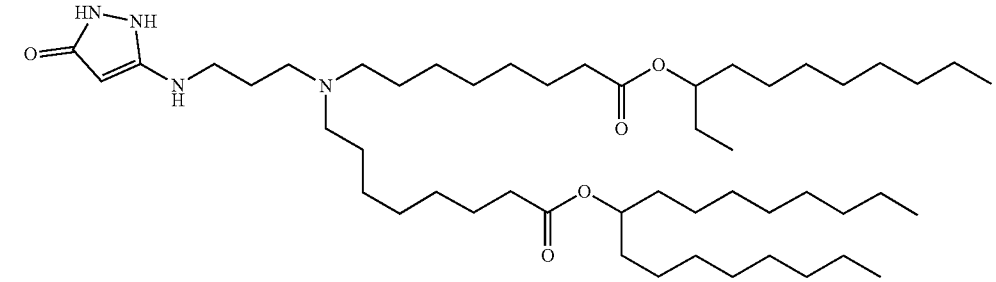 [SMILES: CCCCCCCCC(CC)OC(=O)CCCCCCCN(CCCCCCCC(=O)OC(CCCCCCCC)CCCCCCCC)CCCNc1cc(=O)[nH][nH]1] |
| 48 | 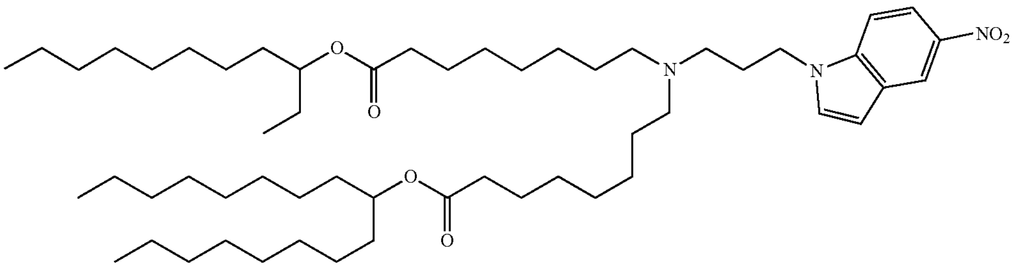 [SMILES: CCCCCCCCC(CC)OC(=O)CCCCCCCN(CCCCCCCC(=O)OC(CCCCCCCC)CCCCCCCC)CCCn1ccc2cc([N+](=O)[O-])ccc21] |
| 49 | 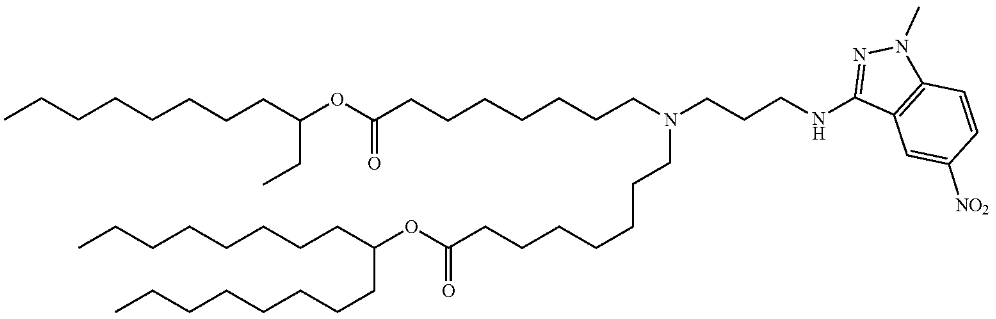 [SMILES: CCCCCCCCC(CC)OC(=O)CCCCCCCN(CCCCCCCC(=O)OC(CCCCCCCC)CCCCCCCC)CCCNc1nn(C)c2ccc([N+](=O)[O-])cc12] |
| 50 | 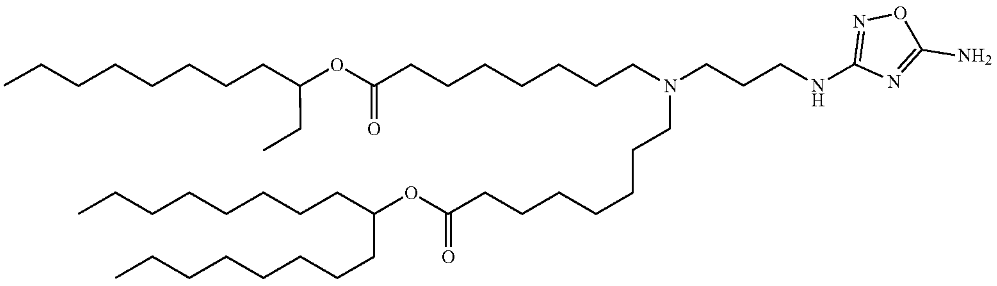 [SMILES: CCCCCCCCC(CC)OC(=O)CCCCCCCN(CCCCCCCC(=O)OC(CCCCCCCC)CCCCCCCC)CCCNc1noc(N)n1] |

TABLE 1-continued
| Amino Lipids | |
|---|---|
| Cpd | Structure |
| 51 | 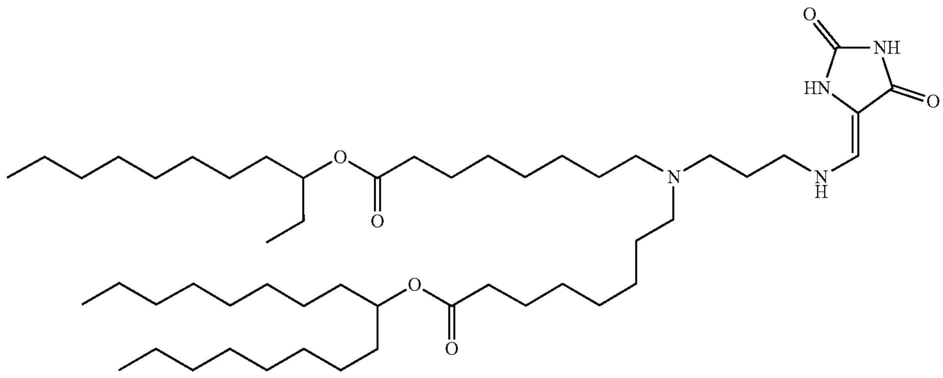 [SMILES: CCCCCCCCC(CC)OC(=O)CCCCCCCN(CCCCCCCC(=O)OC(CCCCCCCC)CCCCCCCC)CCCN/C=C1\NC(=O)NC1=O] |
| 52 | 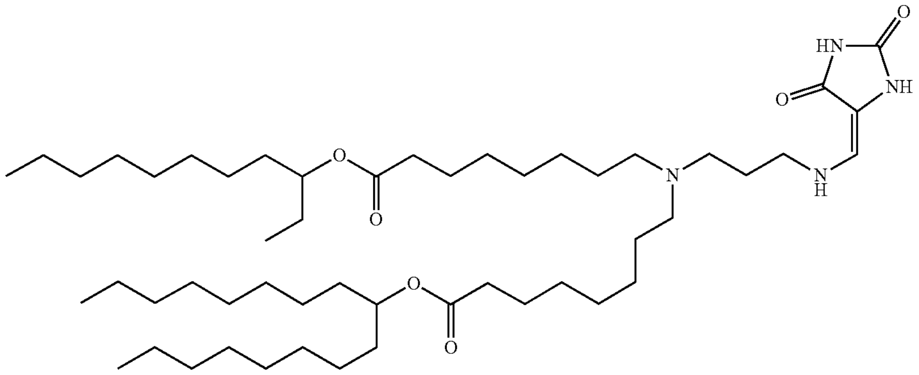 [SMILES: CCCCCCCCC(CC)OC(=O)CCCCCCCN(CCCCCCCC(=O)OC(CCCCCCCC)CCCCCCCC)CCCN/C=C1/NC(=O)NC1=O] |
| 53 | 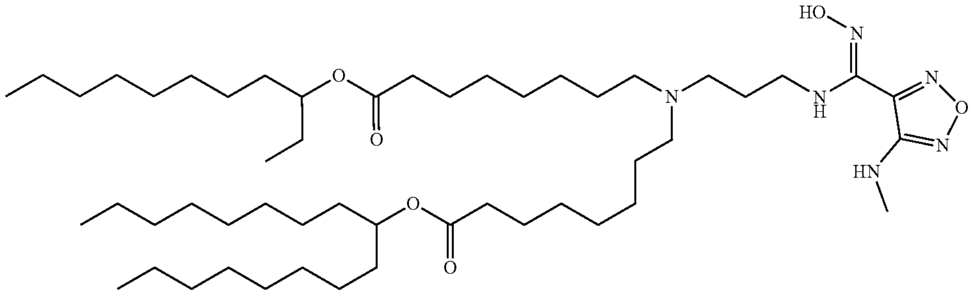 [SMILES: CCCCCCCCC(CC)OC(=O)CCCCCCCN(CCCCCCCC(=O)OC(CCCCCCCC)CCCCCCCC)CCCN/C(=N\O)c1nonc1NC] |
| 54 | 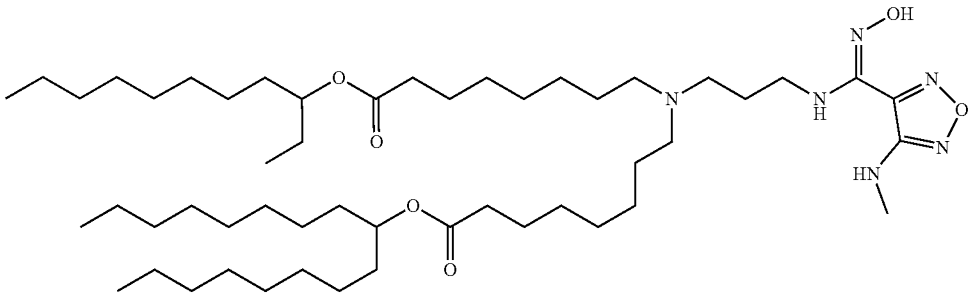 [SMILES: CCCCCCCCC(CC)OC(=O)CCCCCCCN(CCCCCCCC(=O)OC(CCCCCCCC)CCCCCCCC)CCCN/C(=N/O)c1nonc1NC] |

TABLE 1-continued
| Amino Lipids | |
|---|---|
| Cpd | Structure |
| 55 | 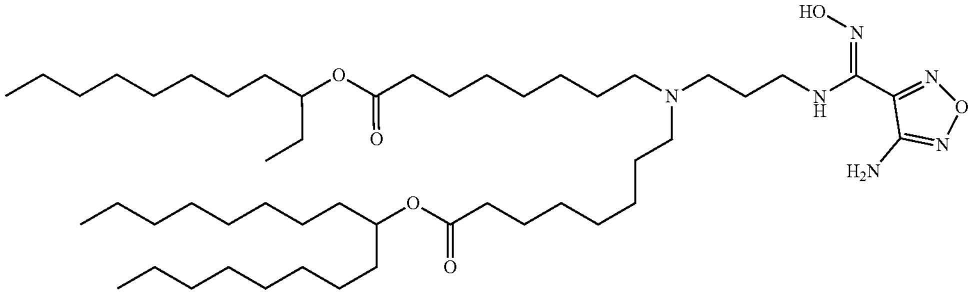 [SMILES: CCCCCCCCC(CC)OC(=O)CCCCCCCN(CCCCCCCC(=O)OC(CCCCCCCC)CCCCCCCC)CCCN/C(=N\O)c1nonc1N] |
| 56 | 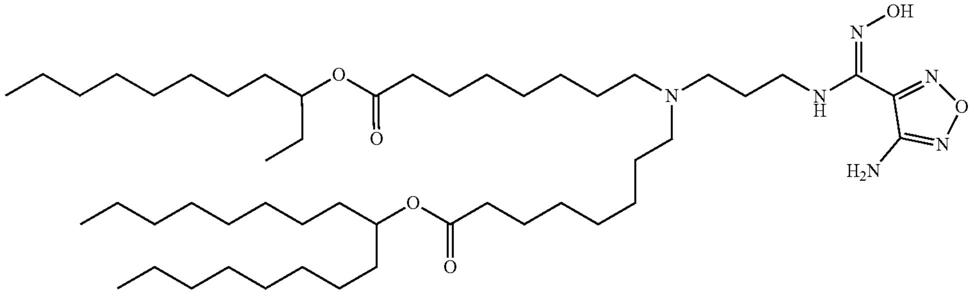 [SMILES: CCCCCCCCC(CC)OC(=O)CCCCCCCN(CCCCCCCC(=O)OC(CCCCCCCC)CCCCCCCC)CCCN/C(=N/O)c1nonc1N] |
| 57 | 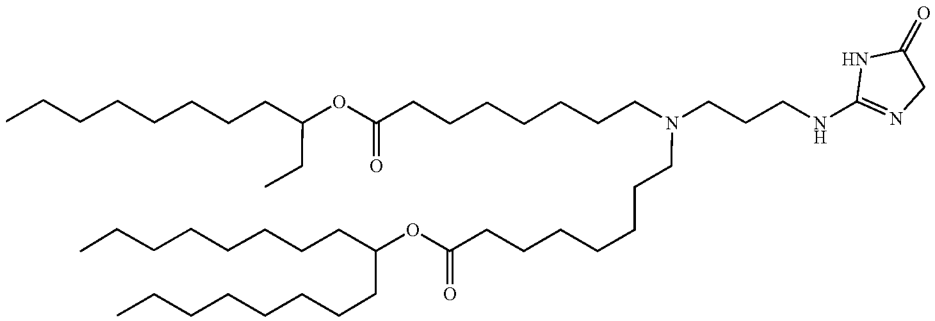 [SMILES: CCCCCCCCC(CC)OC(=O)CCCCCCCN(CCCCCCCC(=O)OC(CCCCCCCC)CCCCCCCC)CCCNC1=NCC(=O)N1] |
| 58 | 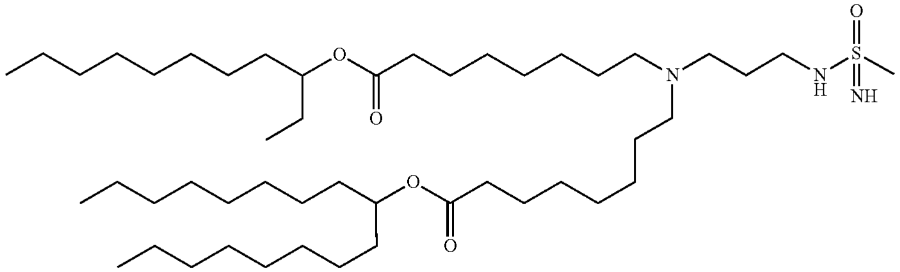 [SMILES: CCCCCCCCC(CC)OC(=O)CCCCCCCN(CCCCCCCC(=O)OC(CCCCCCCC)CCCCCCCC)CCCNS(C)(=N)=O] |
| 59 | 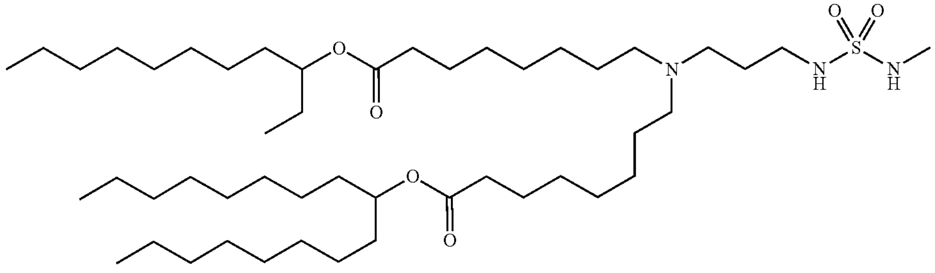 [SMILES: CCCCCCCCC(CC)OC(=O)CCCCCCCN(CCCCCCCC(=O)OC(CCCCCCCC)CCCCCCCC)CCCNS(=O)(=O)NC] |

TABLE 1-continued
| Amino Lipids | |
|---|---|
| Cpd | Structure |
| 60 | 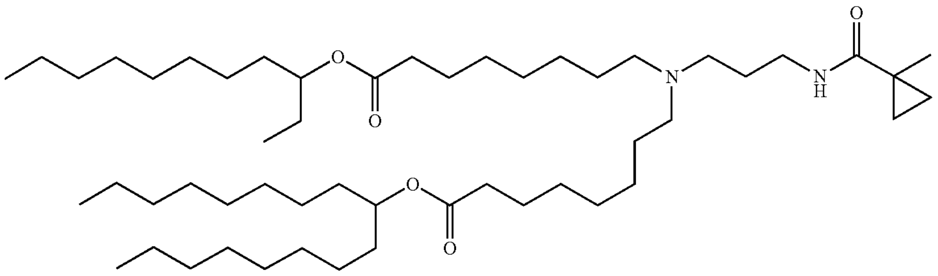 |
| 61 | 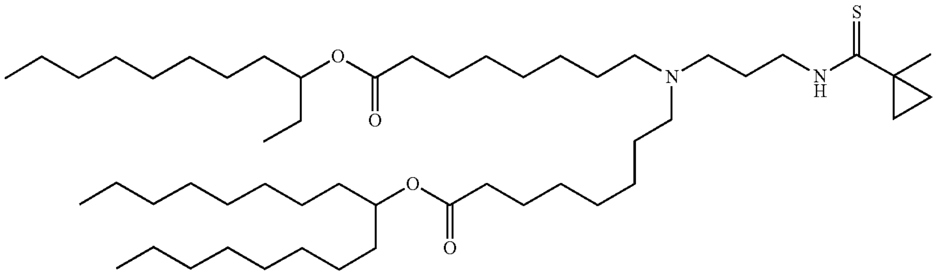 |
| 62 | 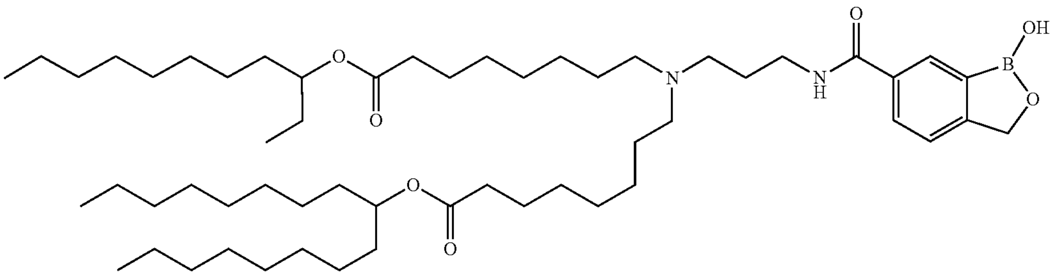 [SMILES: CCCCCCCCC(CC)OC(=O)CCCCCCCN(CCCCCCCC(=O)OC(CCCCCCCC)CCCCCCCC)CCCNC(=O)c1ccc2c(c1)B(O)OC2] |
| 63 | 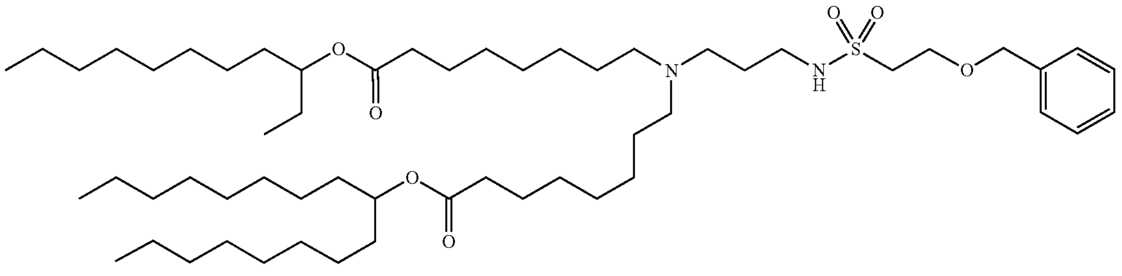 [SMILES: CCCCCCCCC(CC)OC(=O)CCCCCCCN(CCCCCCCC(=O)OC(CCCCCCCC)CCCCCCCC)CCCNS(=O)(=O)CCOCc1ccccc1] |
| 64 | 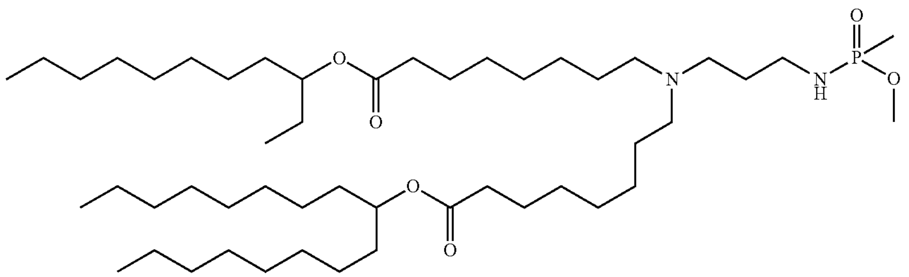 [SMILES: CCCCCCCCC(CC)OC(=O)CCCCCCCN(CCCCCCCC(=O)OC(CCCCCCCC)CCCCCCCC)CCCNP(C)(=O)OC] |

TABLE 1-continued
| Amino Lipids | |
|---|---|
| Cpd | Structure |
| 65 | 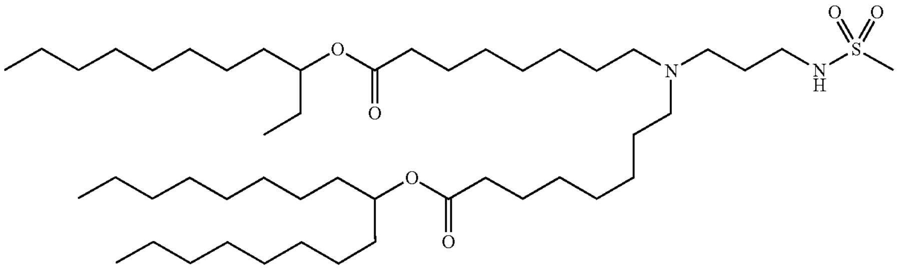 [SMILES: CCCCCCCCC(CC)OC(=O)CCCCCCCN(CCCCCCCC(=O)OC(CCCCCCCC)CCCCCCCC)CCCNS(C)(=O)=O] |
| 66 | 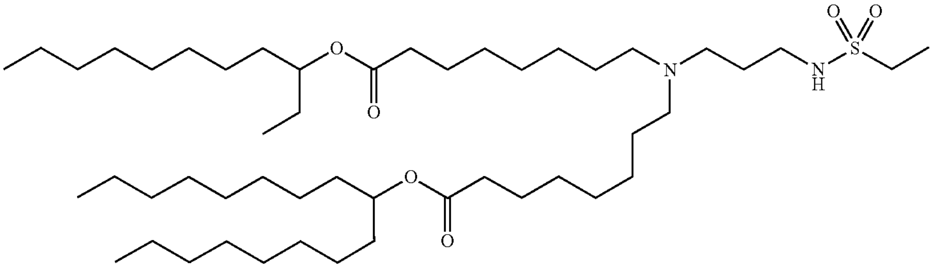 [SMILES: CCCCCCCCC(CC)OC(=O)CCCCCCCN(CCCCCCCC(=O)OC(CCCCCCCC)CCCCCCCC)CCCNS(=O)(=O)CC] |
| 67 | 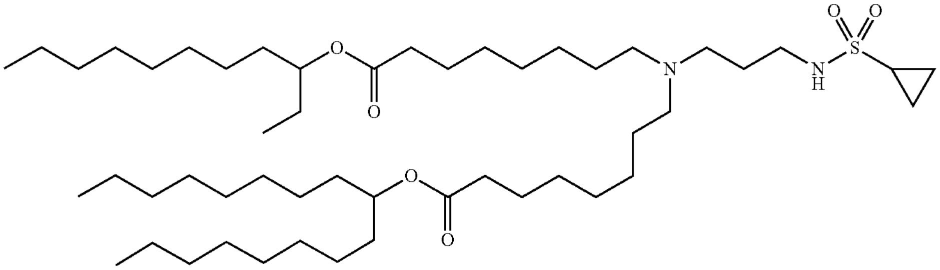 [SMILES: CCCCCCCCC(CC)OC(=O)CCCCCCCN(CCCCCCCC(=O)OC(CCCCCCCC)CCCCCCCC)CCCNS(=O)(=O)C1CC1] |
| 68 | 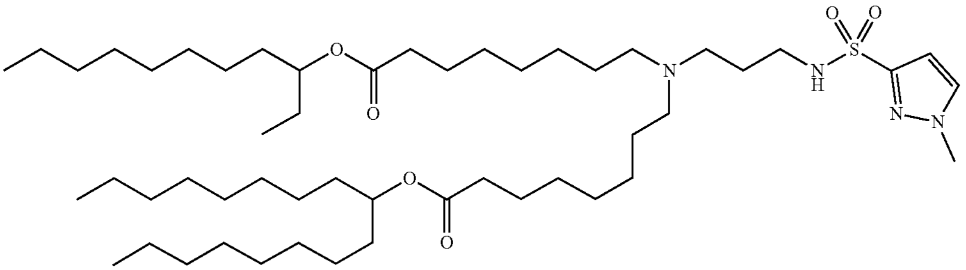 [SMILES: CCCCCCCCC(CC)OC(=O)CCCCCCCN(CCCCCCCC(=O)OC(CCCCCCCC)CCCCCCCC)CCCNS(=O)(=O)c1ccn(C)n1] |
| 69 | 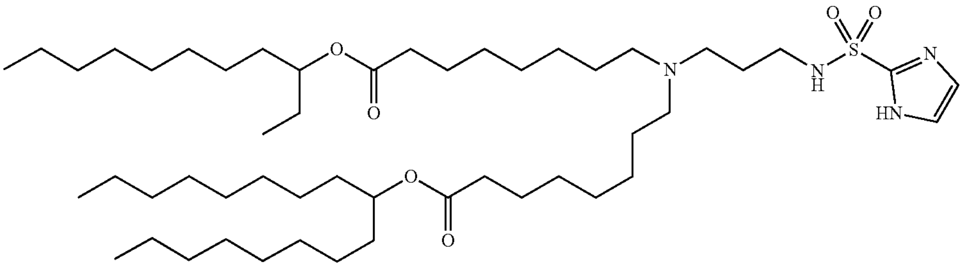 [SMILES: CCCCCCCCC(CC)OC(=O)CCCCCCCN(CCCCCCCC(=O)OC(CCCCCCCC)CCCCCCCC)CCCNS(=O)(=O)c1ncc[nH]1] |

TABLE 1-continued
| Amino Lipids | |
|---|---|
| Cpd | Structure |
| 70 | 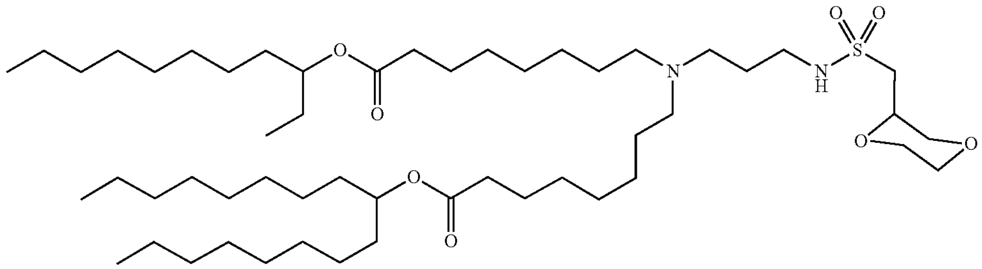 [SMILES: CCCCCCCCC(CC)OC(=O)CCCCCCCN(CCCCCCCC(=O)OC(CCCCCCCC)CCCCCCCC)CCCNS(=O)(=O)CC1COCCO1] |
| 71 | 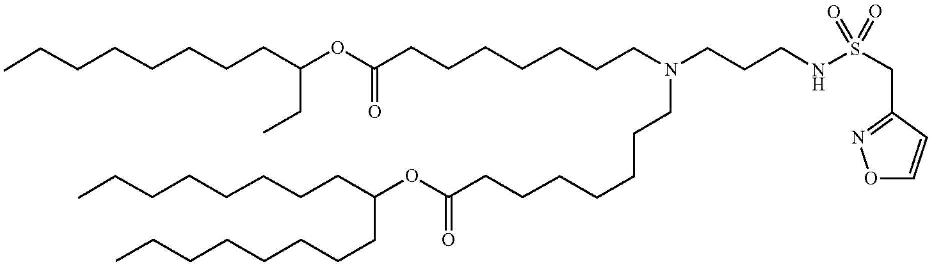 [SMILES: CCCCCCCCC(CC)OC(=O)CCCCCCCN(CCCCCCCC(=O)OC(CCCCCCCC)CCCCCCCC)CCCNS(=O)(=O)Cc1ccon1] |
| 72 | 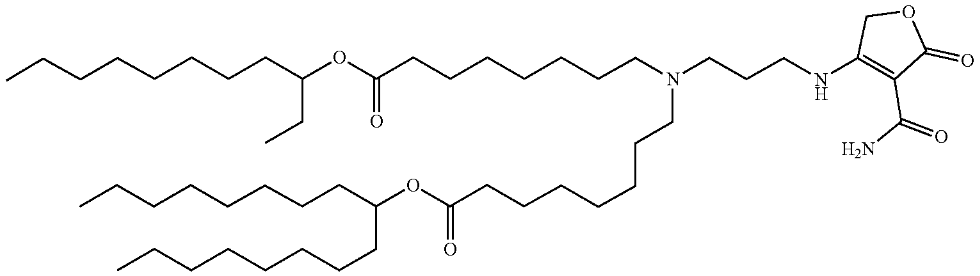 [SMILES: CCCCCCCCC(CC)OC(=O)CCCCCCCN(CCCCCCCC(=O)OC(CCCCCCCC)CCCCCCCC)CCCNC1=C(C(N)=O)C(=O)OC1] |
| 73 | 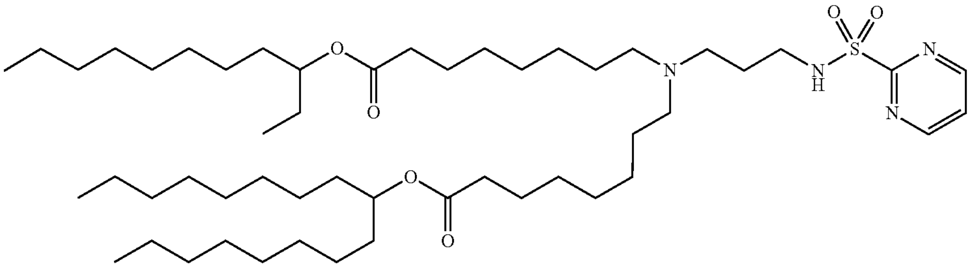 [SMILES: CCCCCCCCC(CC)OC(=O)CCCCCCCN(CCCCCCCC(=O)OC(CCCCCCCC)CCCCCCCC)CCCNS(=O)(=O)c1ncccn1] |
| 74 | 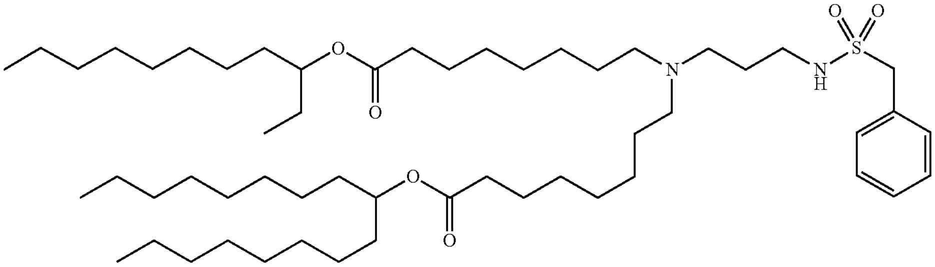 [SMILES: CCCCCCCCC(CC)OC(=O)CCCCCCCN(CCCCCCCC(=O)OC(CCCCCCCC)CCCCCCCC)CCCNS(=O)(=O)Cc1ccccc1] |

TABLE 1-continued
| Amino Lipids | |
|---|---|
| Cpd | Structure |
| 75 | 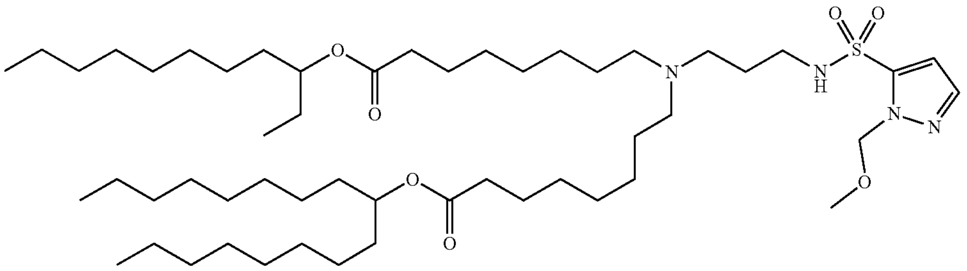 [SMILES: CCCCCCCCC(CC)OC(=O)CCCCCCCN(CCCCCCCC(=O)OC(CCCCCCCC)CCCCCCCC)CCCNS(=O)(=O)c1ccnn1COC] |
| 76 | 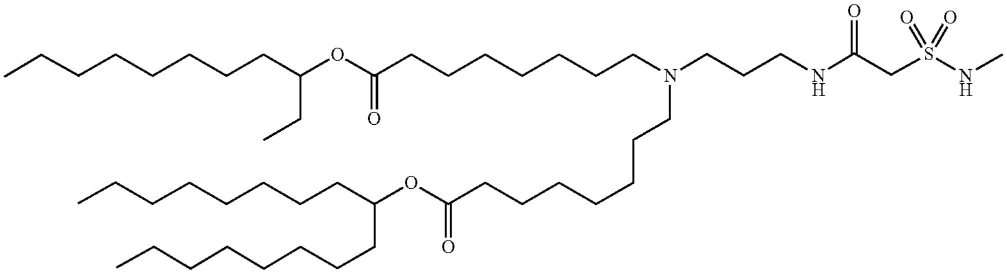 [SMILES: CCCCCCCCC(CC)OC(=O)CCCCCCCN(CCCCCCCC(=O)OC(CCCCCCCC)CCCCCCCC)CCCNC(=O)CS(=O)(=O)NC] |
| 77 | 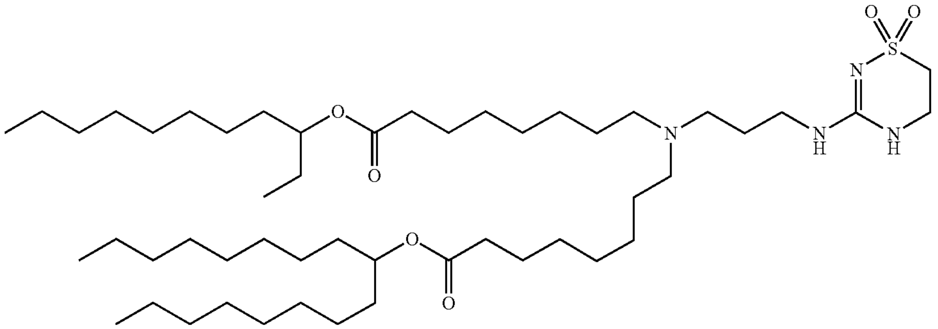 [SMILES: CCCCCCCCC(CC)OC(=O)CCCCCCCN(CCCCCCCC(=O)OC(CCCCCCCC)CCCCCCCC)CCCNC1=NS(=O)(=O)CCN1] |
| 78 | 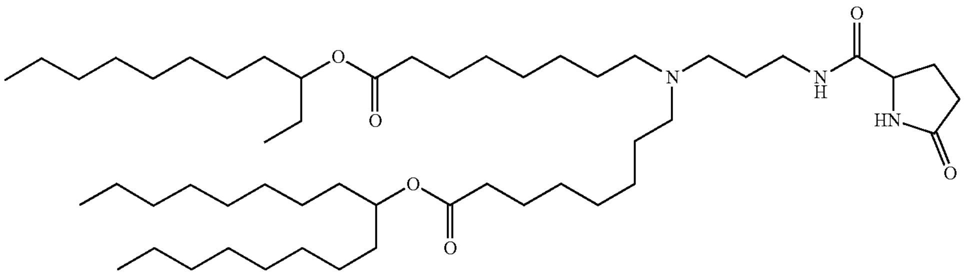 [SMILES: CCCCCCCCC(CC)OC(=O)CCCCCCCN(CCCCCCCC(=O)OC(CCCCCCCC)CCCCCCCC)CCCNC(=O)C1CCC(=O)N1] |
| 79 | 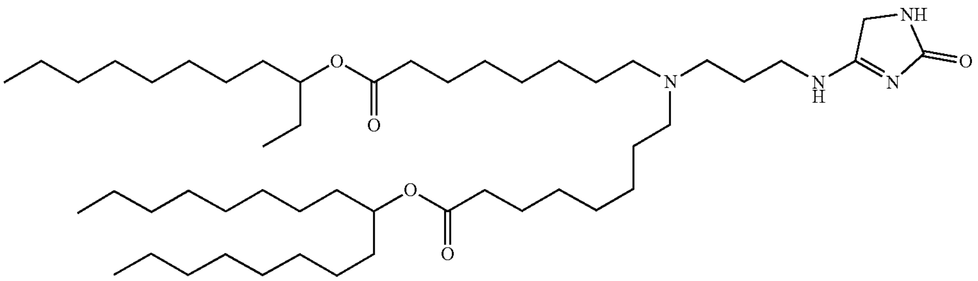 [SMILES: CCCCCCCCC(CC)OC(=O)CCCCCCCN(CCCCCCCC(=O)OC(CCCCCCCC)CCCCCCCC)CCCNC1=NC(=O)NC1] |

TABLE 1-continued
| Amino Lipids | |
|---|---|
| Cpd | Structure |
| 80 | 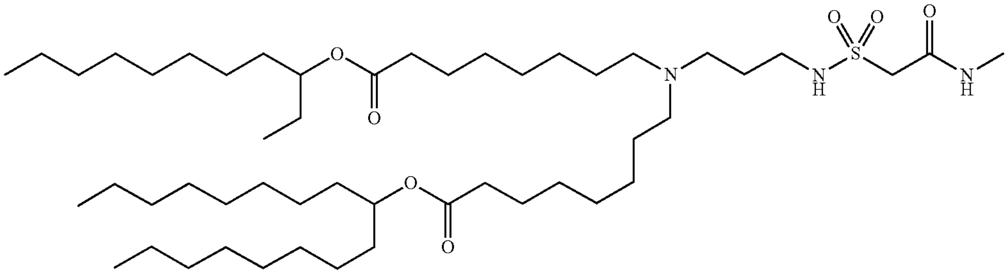 [SMILES: CCCCCCCCC(CC)OC(=O)CCCCCCCN(CCCCCCCC(=O)OC(CCCCCCCC)CCCCCCCC)CCCNS(=O)(=O)CC(=O)NC] |
| 81 | 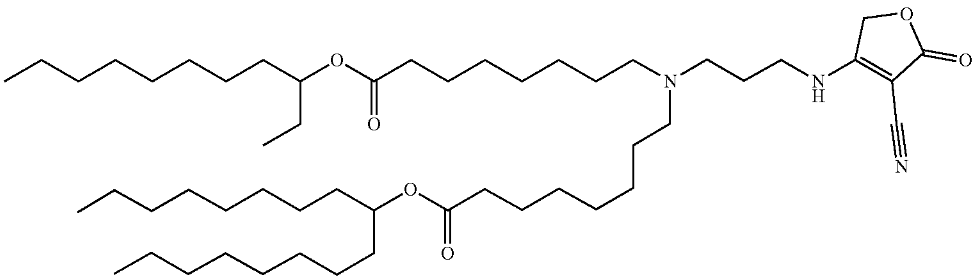 [SMILES: CCCCCCCCC(CC)OC(=O)CCCCCCCN(CCCCCCCC(=O)OC(CCCCCCCC)CCCCCCCC)CCCNC1=C(C#N)C(=O)OC1] |
| 82 | 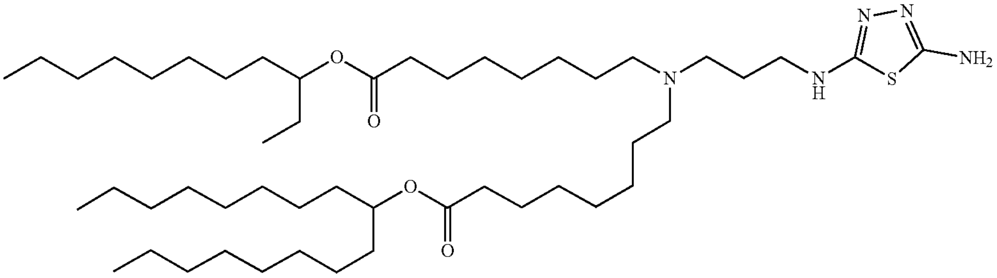 [SMILES: CCCCCCCCC(CC)OC(=O)CCCCCCCN(CCCCCCCC(=O)OC(CCCCCCCC)CCCCCCCC)CCCNc1nnc(N)s1] |
| 83 | 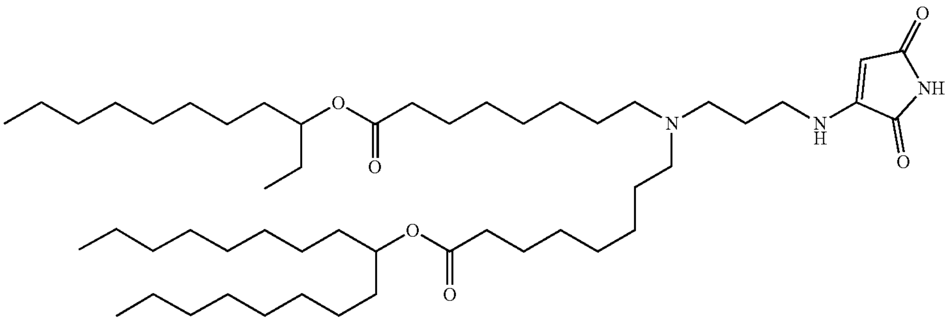 [SMILES: CCCCCCCCC(CC)OC(=O)CCCCCCCN(CCCCCCCC(=O)OC(CCCCCCCC)CCCCCCCC)CCCNC1=CC(=O)NC1=O] |
| 84 | 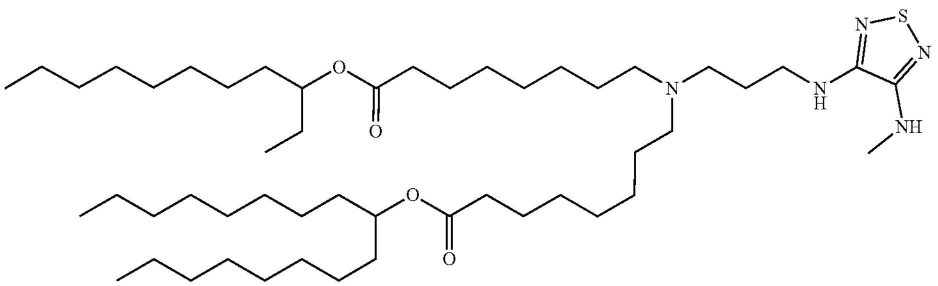 [SMILES: CCCCCCCCC(CC)OC(=O)CCCCCCCN(CCCCCCCC(=O)OC(CCCCCCCC)CCCCCCCC)CCCNc1nsnc1NC] |

TABLE 1-continued
| Amino Lipids | |
|---|---|
| Cpd | Structure |
| 85 | 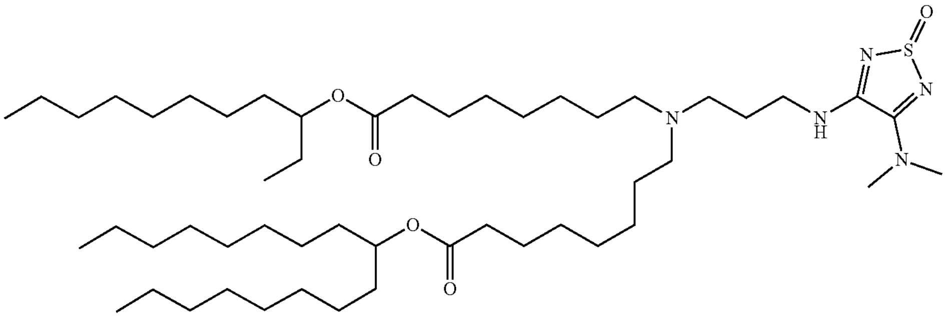 [SMILES: CCCCCCCCC(CC)OC(=O)CCCCCCCN(CCCCCCCC(=O)OC(CCCCCCCC)CCCCCCCC)CCCNC1=NS(=O)N=C1N(C)C] |
| 86 | 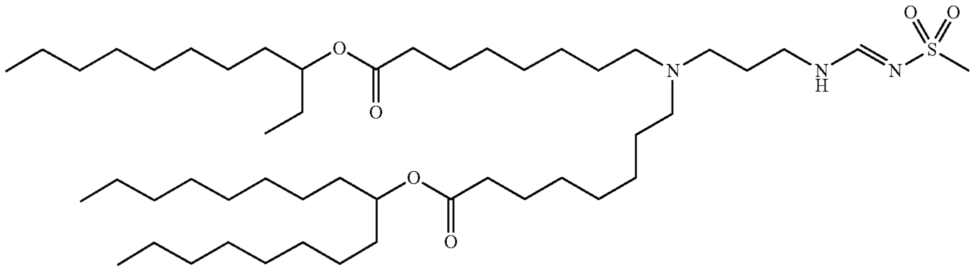 [SMILES: CCCCCCCCC(CC)OC(=O)CCCCCCCN(CCCCCCCC(=O)OC(CCCCCCCC)CCCCCCCC)CCCN/C=N/S(C)(=O)=O] |
| 87 | 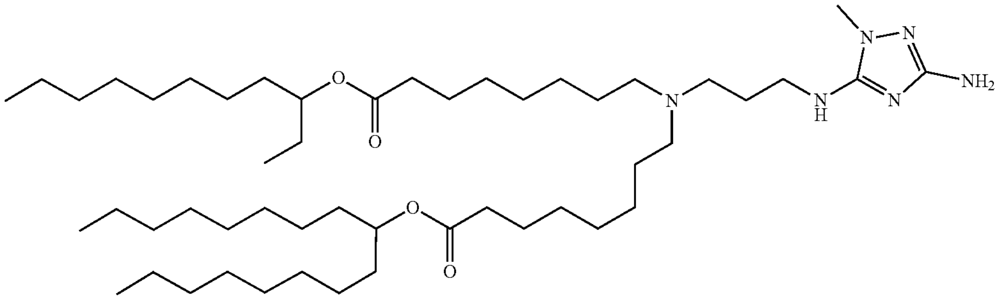 [SMILES: CCCCCCCCC(CC)OC(=O)CCCCCCCN(CCCCCCCC(=O)OC(CCCCCCCC)CCCCCCCC)CCCNc1nc(N)nn1C] |
| 88 | 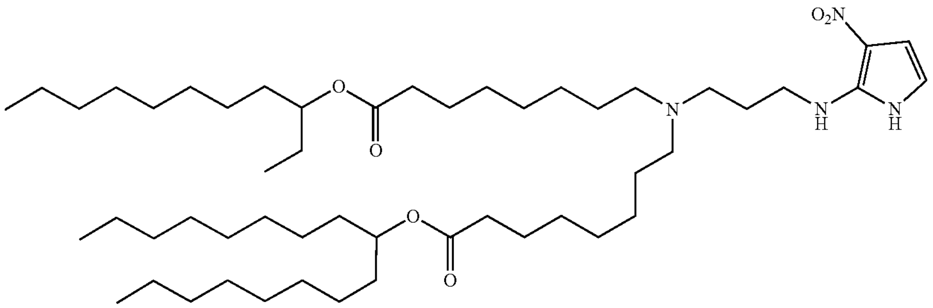 [SMILES: CCCCCCCCC(CC)OC(=O)CCCCCCCN(CCCCCCCC(=O)OC(CCCCCCCC)CCCCCCCC)CCCNc1[nH]ccc1[N+](=O)[O-]] |
| 89 | 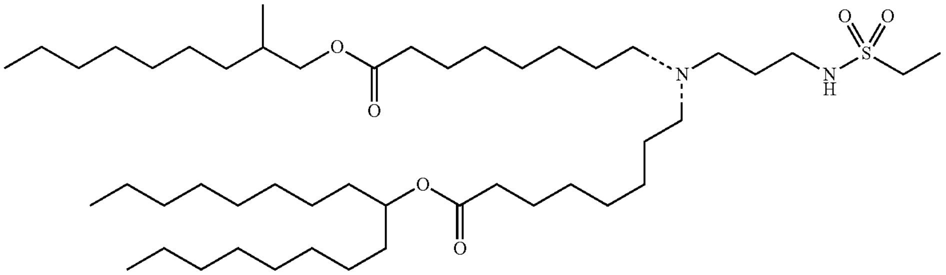 |

TABLE 1-continued
| Amino Lipids | |
|---|---|
| Cpd | Structure |
| 90 | 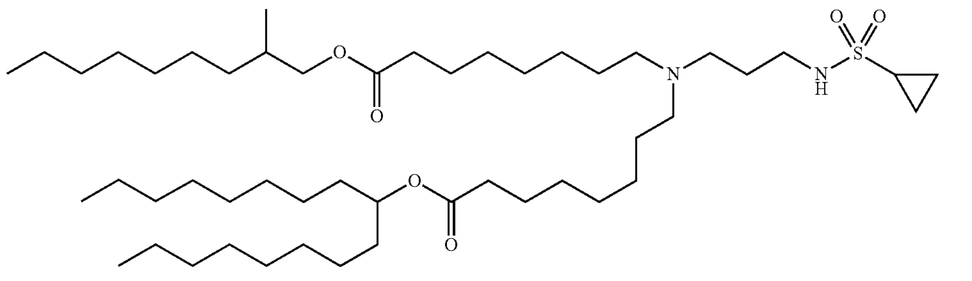 [SMILES: CCCCCCCCC(CCCCCCCC)OC(=O)CCCCCCCN(CCCCCCCC(=O)OCC(C)CCCCCCC)CCCNS(=O)(=O)C1CC1] |
| 91 | 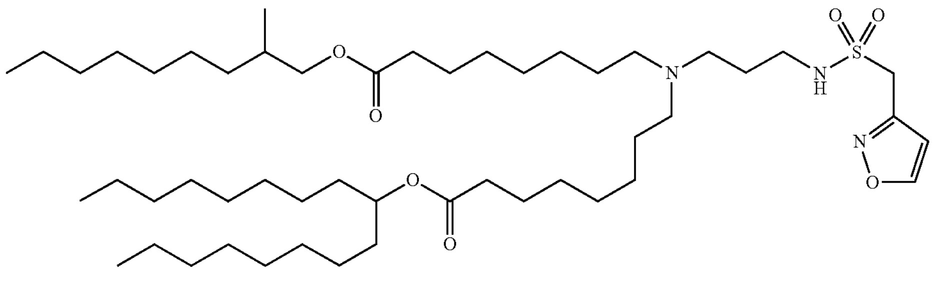 [SMILES: CCCCCCCCC(CCCCCCCC)OC(=O)CCCCCCCN(CCCCCCCC(=O)OCC(C)CCCCCCC)CCCNS(=O)(=O)Cc1ccon1] |
| 92 | 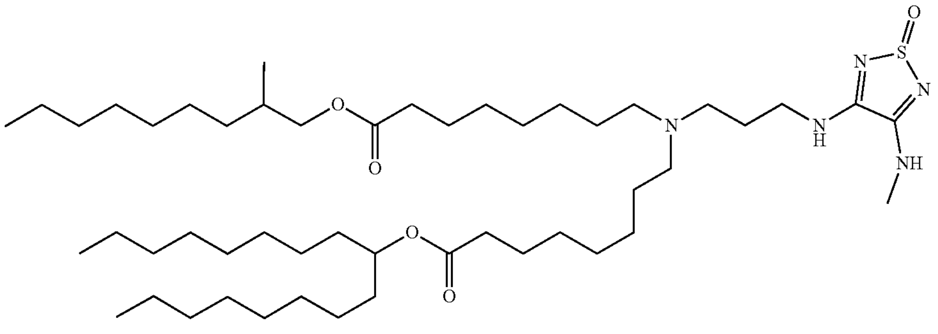 [SMILES: CCCCCCCCC(CCCCCCCC)OC(=O)CCCCCCCN(CCCCCCCC(=O)OCC(C)CCCCCCC)CCCNC1=NS(=O)N=C1NC] |
| 93 | 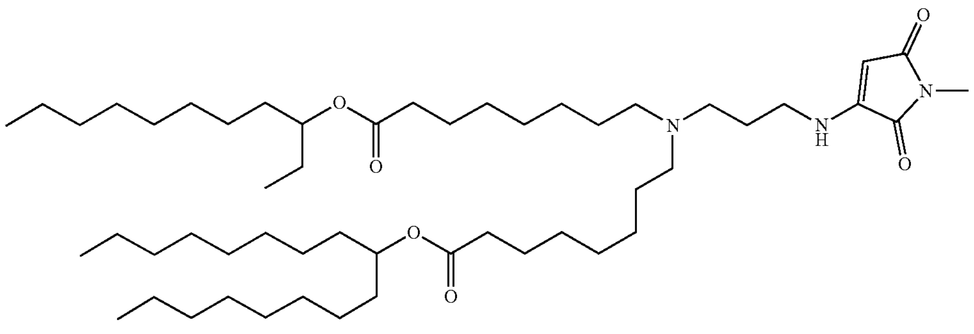 [SMILES: CCCCCCCCC(CC)OC(=O)CCCCCCCN(CCCCCCCC(=O)OC(CCCCCCCC)CCCCCCCC)CCCNC1=CC(=O)N(C)C1=O] |
| 94 | 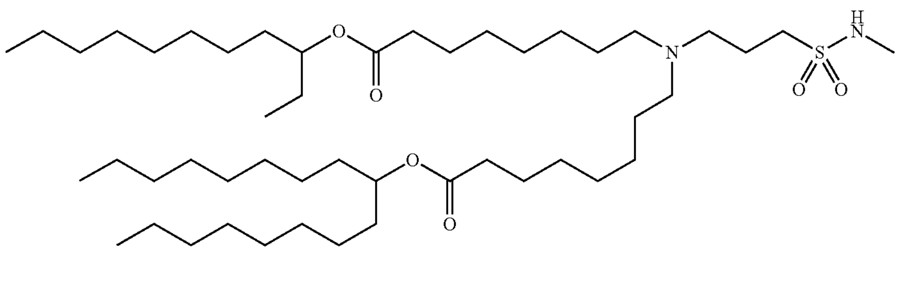 [SMILES: CCCCCCCCC(CC)OC(=O)CCCCCCCN(CCCCCCCC(=O)OC(CCCCCCCC)CCCCCCCC)CCCS(=O)(=O)NC] |

TABLE 1-continued
| Amino Lipids | |
|---|---|
| Cpd | Structure |
| 95 | 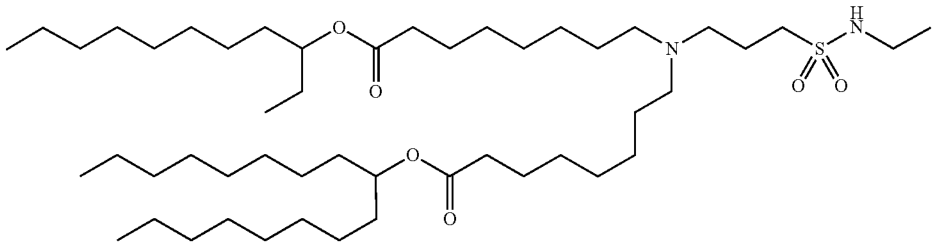 [SMILES: CCCCCCCCC(CC)OC(=O)CCCCCCCN(CCCCCCCC(=O)OC(CCCCCCCC)CCCCCCCC)CCCS(=O)(=O)NCC] |
| 96 | 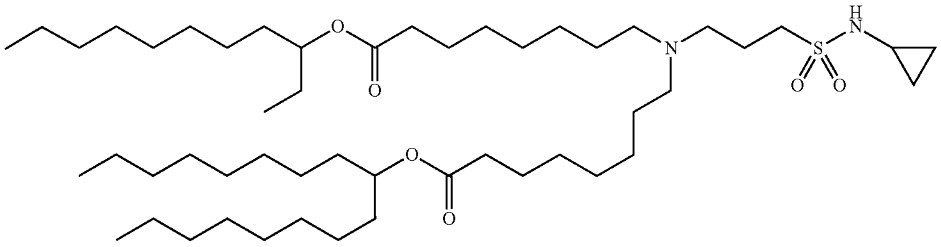 [SMILES: CCCCCCCCC(CC)OC(=O)CCCCCCCN(CCCCCCCC(=O)OC(CCCCCCCC)CCCCCCCC)CCCS(=O)(=O)NC1CC1] |
| 97 | 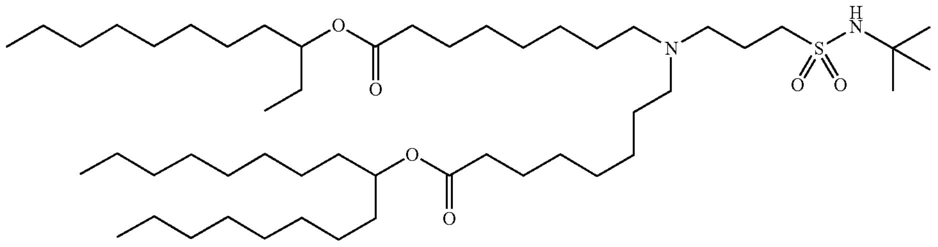 [SMILES: CCCCCCCCC(CC)OC(=O)CCCCCCCN(CCCCCCCC(=O)OC(CCCCCCCC)CCCCCCCC)CCCS(=O)(=O)NC(C)(C)C] |
| 98 | 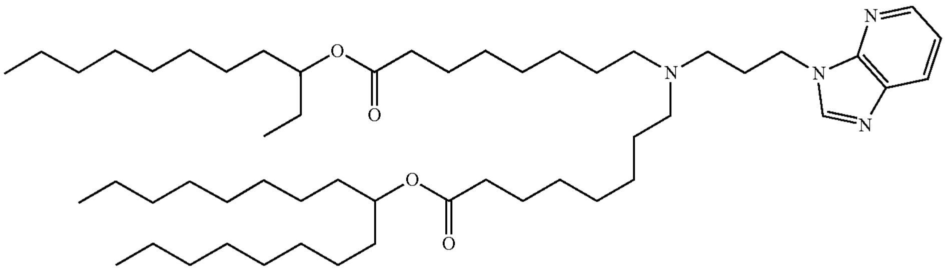 [SMILES: CCCCCCCCC(CC)OC(=O)CCCCCCCN(CCCCCCCC(=O)OC(CCCCCCCC)CCCCCCCC)CCCn1cnc2cccnc21] |
| 99 | 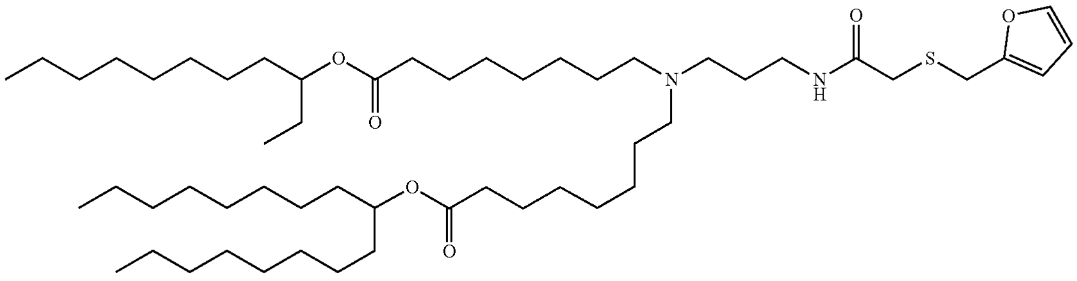 [SMILES: CCCCCCCCC(CC)OC(=O)CCCCCCCN(CCCCCCCC(=O)OC(CCCCCCCC)CCCCCCCC)CCCNC(=O)CSCc1ccco1] |

TABLE 1-continued
| Cpd | Structure |
|---|---|
| | Amino Lipids |
| 100 | 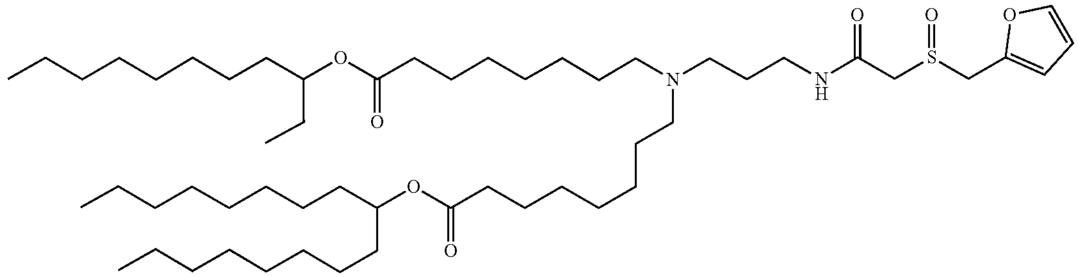 [SMILES: CCCCCCCCC(CC)OC(=O)CCCCCCCN(CCCCCCCC(=O)OC(CCCCCCCC)CCCCCCCC)CCCNC(=O)CS(=O)Cc1ccco1] |
| 101 | 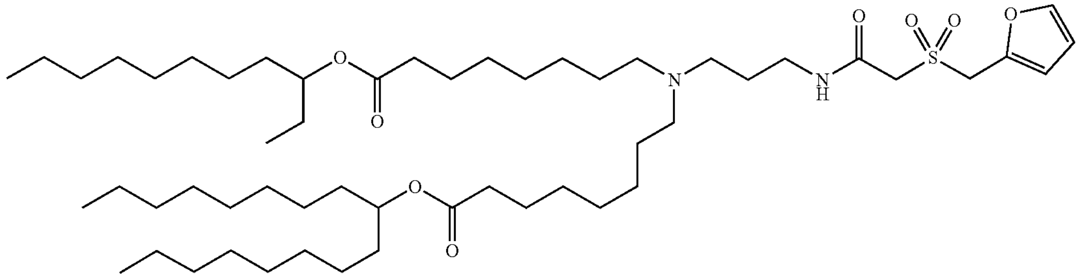 [SMILES: CCCCCCCCC(CC)OC(=O)CCCCCCCN(CCCCCCCC(=O)OC(CCCCCCCC)CCCCCCCC)CCCNC(=O)CS(=O)(=O)Cc1ccco1] |
| 102 | 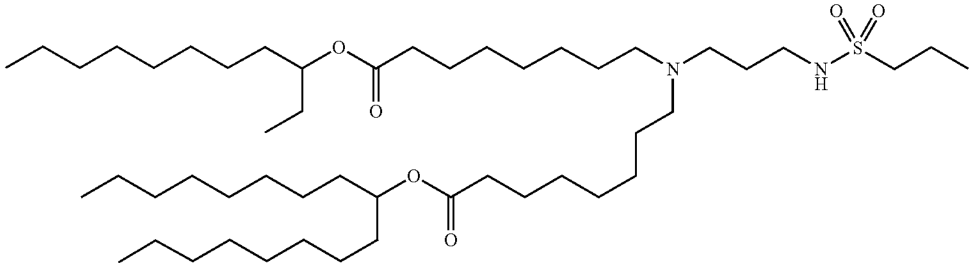 [SMILES: CCCCCCCCC(CC)OC(=O)CCCCCCCN(CCCCCCCC(=O)OC(CCCCCCCC)CCCCCCCC)CCCNS(=O)(=O)CCC] |
| 103 | 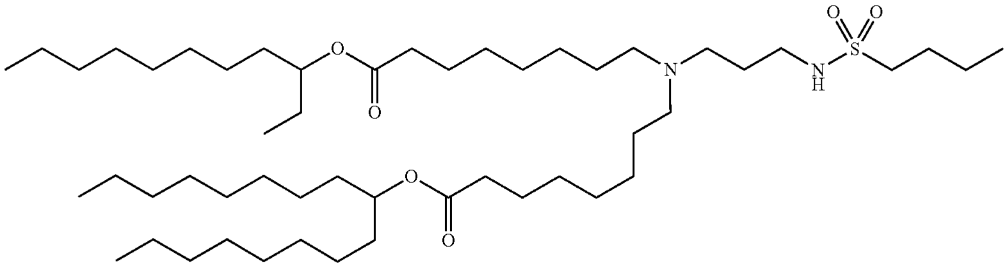 [SMILES: CCCCCCCCC(CC)OC(=O)CCCCCCCN(CCCCCCCC(=O)OC(CCCCCCCC)CCCCCCCC)CCCNS(=O)(=O)CCCC] |
| 104 | 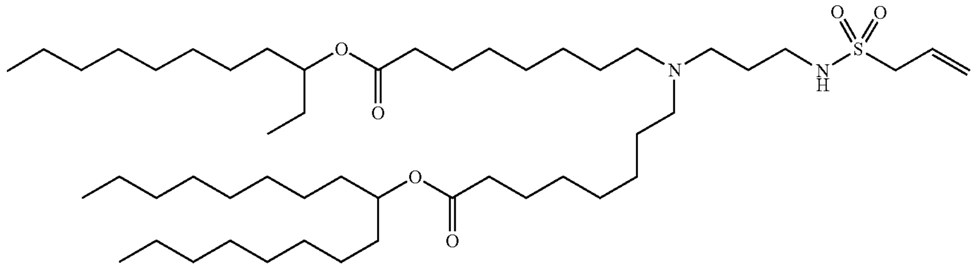 [SMILES: C=CCS(=O)(=O)NCCCN(CCCCCCCC(=O)OC(CC)CCCCCCCC)CCCCCCCC(=O)OC(CCCCCCCC)CCCCCCCC] |

TABLE 1-continued
| Amino Lipids | |
|---|---|
| Cpd | Structure |
| 105 | 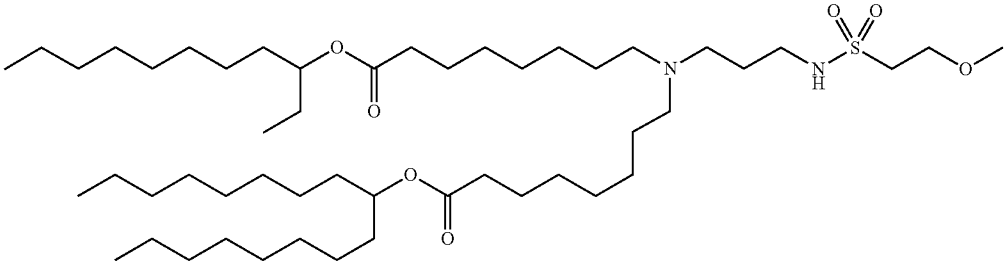 [SMILES: CCCCCCCCC(CC)OC(=O)CCCCCCCN(CCCCCCCC(=O)OC(CCCCCCCC)CCCCCCCC)CCCNS(=O)(=O)CCOC] |
| 106 | 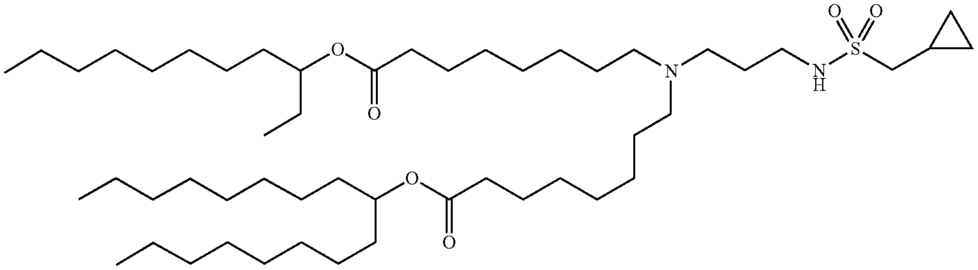 [SMILES: CCCCCCCCC(CC)OC(=O)CCCCCCCN(CCCCCCCC(=O)OC(CCCCCCCC)CCCCCCCC)CCCNS(=O)(=O)CC1CC1] |
| 107 | 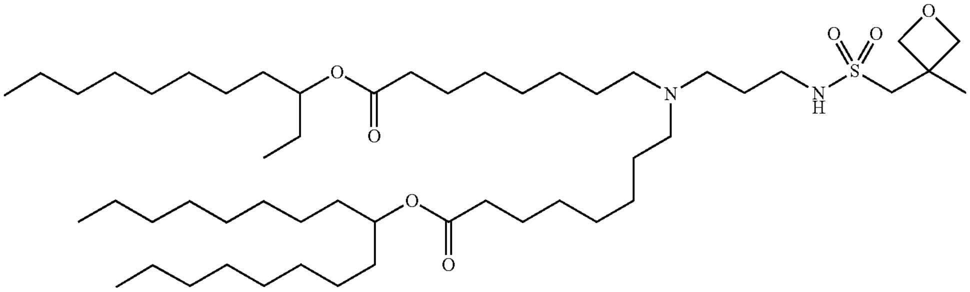 [SMILES: CCCCCCCCC(CC)OC(=O)CCCCCCCN(CCCCCCCC(=O)OC(CCCCCCCC)CCCCCCCC)CCCNS(=O)(=O)CC1(C)COC1] |
| 108 | 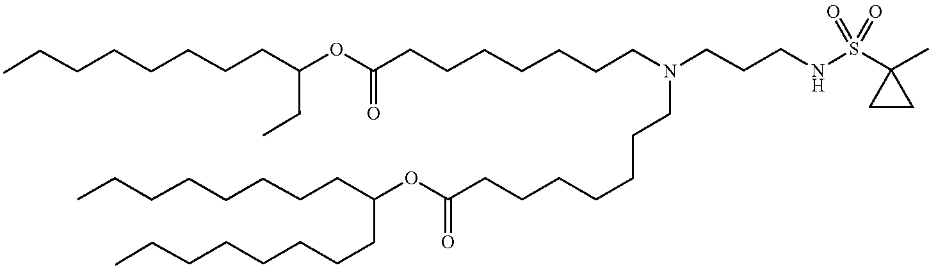 [SMILES: CCCCCCCCC(CC)OC(=O)CCCCCCCN(CCCCCCCC(=O)OC(CCCCCCCC)CCCCCCCC)CCCNS(=O)(=O)C1(C)CC1] |
| 109 | 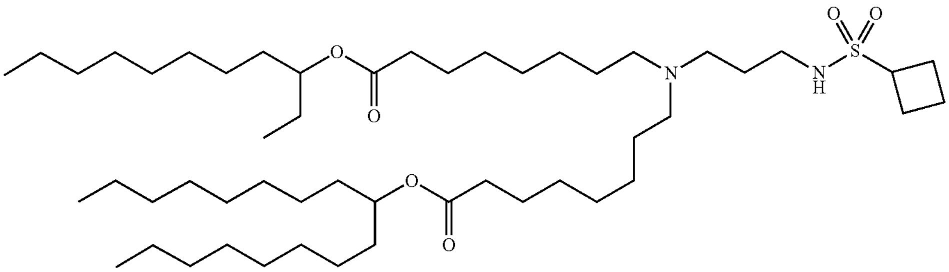 [SMILES: CCCCCCCCC(CC)OC(=O)CCCCCCCN(CCCCCCCC(=O)OC(CCCCCCCC)CCCCCCCC)CCCNS(=O)(=O)C1CCC1] |

TABLE 1-continued
| Amino Lipids | |
|---|---|
| Cpd | Structure |
| 110 | 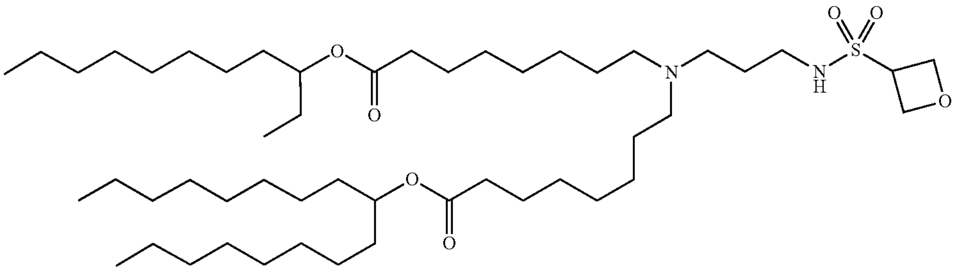 [SMILES: CCCCCCCCC(CC)OC(=O)CCCCCCCN(CCCCCCCC(=O)OC(CCCCCCCC)CCCCCCCC)CCCNS(=O)(=O)C1COC1] |
| 111 | 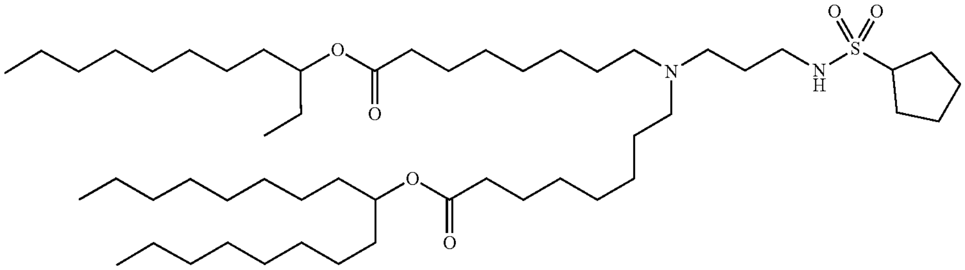 [SMILES: CCCCCCCCC(CC)OC(=O)CCCCCCCN(CCCCCCCC(=O)OC(CCCCCCCC)CCCCCCCC)CCCNS(=O)(=O)C1CCCC1] |
| 112 | 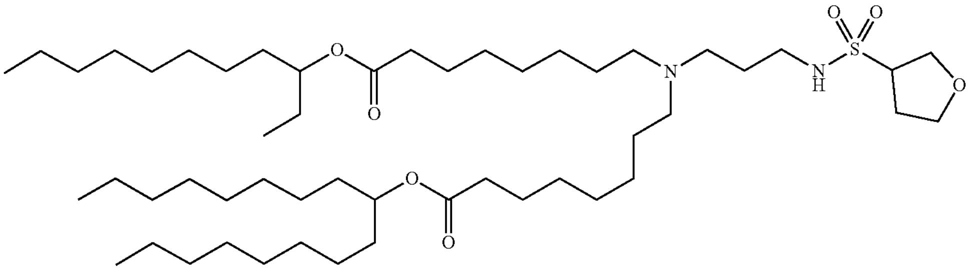 [SMILES: CCCCCCCCC(CC)OC(=O)CCCCCCCN(CCCCCCCC(=O)OC(CCCCCCCC)CCCCCCCC)CCCNS(=O)(=O)C1CCOC1] |
| 113 | 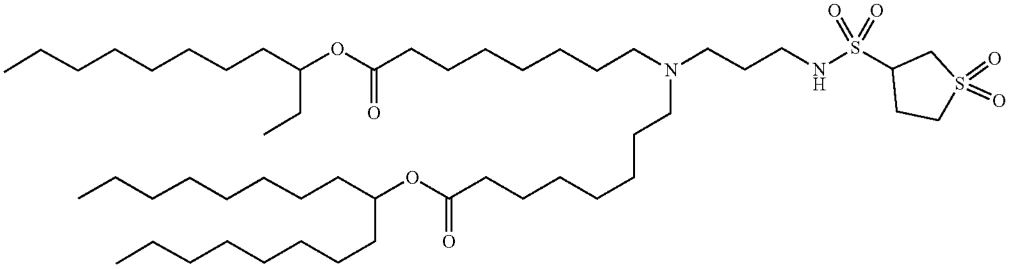 [SMILES: CCCCCCCCC(CC)OC(=O)CCCCCCCN(CCCCCCCC(=O)OC(CCCCCCCC)CCCCCCCC)CCCNS(=O)(=O)C1CCS(=O)(=O)C1] |
| 114 | 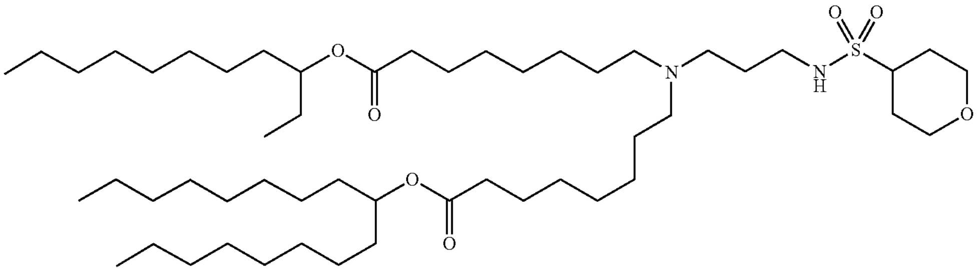 [SMILES: CCCCCCCCC(CC)OC(=O)CCCCCCCN(CCCCCCCC(=O)OC(CCCCCCCC)CCCCCCCC)CCCNS(=O)(=O)C1CCOCC1] |

TABLE 1-continued
Amino Lipids
| Cpd | Structure |
| --- | --- |
| 115 | 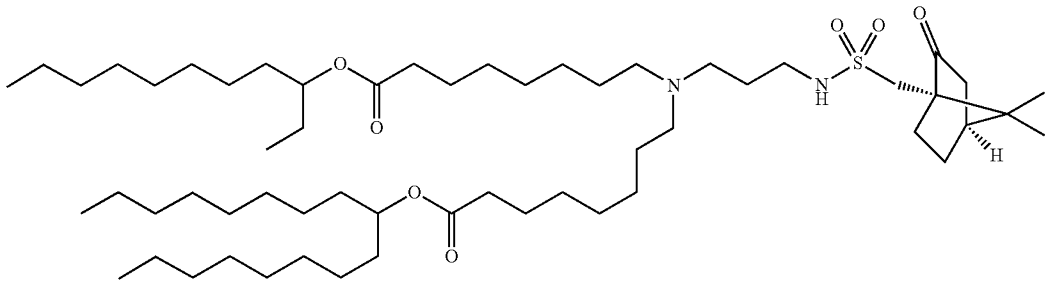 [SMILES: CCCCCCCCC(CC)OC(=O)CCCCCCCN(CCCCCCCC(=O)OC(CCCCCCCC)CCCCCCCC)CCCNS(=O)(=O)C[C@]12CC[C@@H](CC1=O)C2(C)C] |
| 116 | 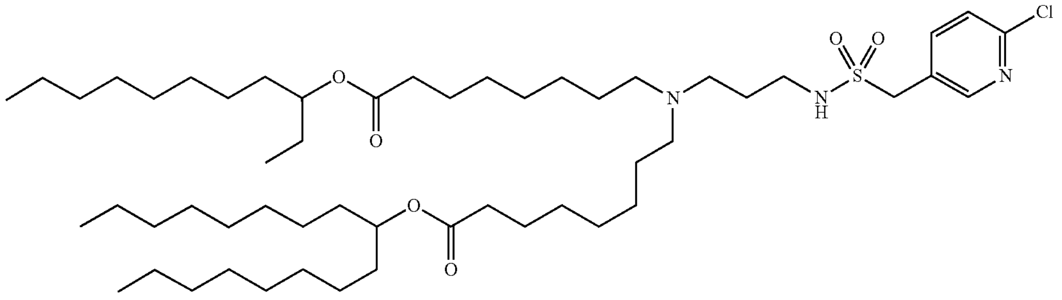 [SMILES: CCCCCCCCC(CC)OC(=O)CCCCCCCN(CCCCCCCC(=O)OC(CCCCCCCC)CCCCCCCC)CCCNS(=O)(=O)Cc1ccc(Cl)nc1] |
| 117 | 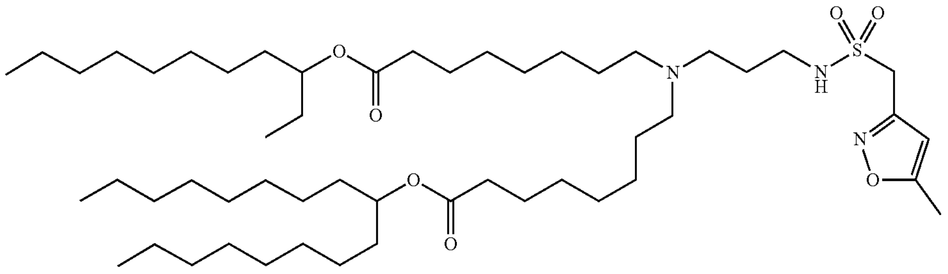 [SMILES: CCCCCCCCC(CC)OC(=O)CCCCCCCN(CCCCCCCC(=O)OC(CCCCCCCC)CCCCCCCC)CCCNS(=O)(=O)Cc1cc(C)on1] |
| 118 | 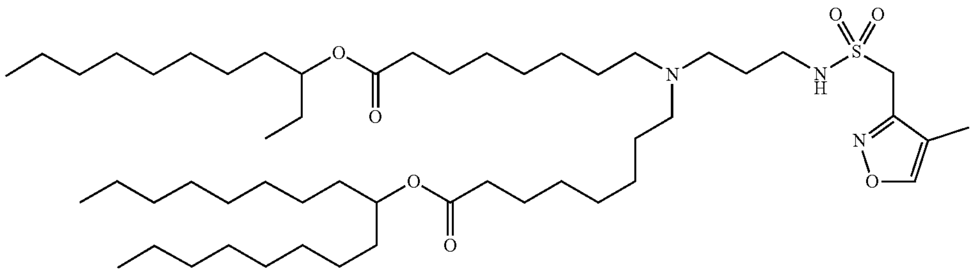 [SMILES: CCCCCCCCC(CC)OC(=O)CCCCCCCN(CCCCCCCC(=O)OC(CCCCCCCC)CCCCCCCC)CCCNS(=O)(=O)Cc1nocc1C] |
| 119 | 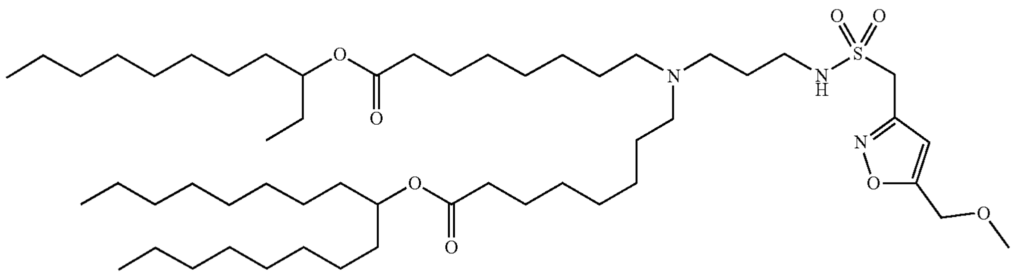 [SMILES: CCCCCCCCC(CC)OC(=O)CCCCCCCN(CCCCCCCC(=O)OC(CCCCCCCC)CCCCCCCC)CCCNS(=O)(=O)Cc1cc(COC)on1] |

The central amine moiety of a lipid according to Formula (I), (I-1), (A), (A-1), (A-1a), or (A-1b) may be protonated at a physiological pH. Thus, a lipid may have a positive or partial positive charge at physiological pH. Such lipids may be referred to as cationic or ionizable (amino)lipids. Lipids may also be zwitterionic, i.e., neutral molecules having both a positive and a negative charge.

Definitions

As used herein, the term "alkyl" or "alkyl group" means a linear or branched, saturated hydrocarbon including one or more carbon atoms (e.g., one, two, three, four, five, six, seven, eight, nine, ten, eleven, twelve, thirteen, fourteen, fifteen, sixteen, seventeen, eighteen, nineteen, twenty, or more carbon atoms), which is optionally substituted. The notation "$C_{1-14}$ alkyl" means an optionally substituted linear or branched, saturated hydrocarbon including 1-14 carbon atoms. Unless otherwise specified, an alkyl group described herein refers to both unsubstituted and substituted alkyl groups.

As used herein, the term "alkenyl" or "alkenyl group" means a linear or branched hydrocarbon including two or more carbon atoms (e.g., two, three, four, five, six, seven, eight, nine, ten, eleven, twelve, thirteen, fourteen, fifteen, sixteen, seventeen, eighteen, nineteen, twenty, or more carbon atoms) and at least one double bond, which is optionally substituted. The notation "$C_{2-14}$ alkenyl" means an optionally substituted linear or branched hydrocarbon including 2-14 carbon atoms and at least one carbon-carbon double bond. An alkenyl group may include one, two, three, four, or more carbon-carbon double bonds. For example, $C_{18}$ alkenyl may include one or more double bonds. A $C_{18}$ alkenyl group including two double bonds may be a linoleyl group. Unless otherwise specified, an alkenyl group described herein refers to both unsubstituted and substituted alkenyl groups.

As used herein, the term "alkynyl" or "alkynyl group" means a linear or branched hydrocarbon including two or more carbon atoms (e.g., two, three, four, five, six, seven, eight, nine, ten, eleven, twelve, thirteen, fourteen, fifteen, sixteen, seventeen, eighteen, nineteen, twenty, or more carbon atoms) and at least one carbon-carbon triple bond, which is optionally substituted. The notation "$C_{2-14}$ alkynyl" means an optionally substituted linear or branched hydrocarbon including 2-14 carbon atoms and at least one carbon-carbon triple bond. An alkynyl group may include one, two, three, four, or more carbon-carbon triple bonds. For example, $C_{18}$ alkynyl may include one or more carbon-carbon triple bonds. Unless otherwise specified, an alkynyl group described herein refers to both unsubstituted and substituted alkynyl groups.

As used herein, the term "carbocycle" or "carbocyclic group" means an optionally substituted mono- or multi-cyclic system including one or more rings of carbon atoms. Rings may be three, four, five, six, seven, eight, nine, ten, eleven, twelve, thirteen, fourteen, fifteen, sixteen, seventeen, eighteen, nineteen, or twenty membered rings. The notation "$C_{3-6}$ carbocycle" means a carbocycle including a single ring having 3-6 carbon atoms. Carbocycles may include one or more carbon-carbon double or triple bonds and may be non-aromatic or aromatic (e.g., cycloalkyl or aryl groups). Examples of carbocycles include cyclopropyl, cyclopentyl, cyclohexyl, phenyl, naphthyl, and 1,2-dihydronaphthyl groups. The term "cycloalkyl" as used herein means a non-aromatic carbocycle and may or may not include any double or triple bond. Unless otherwise specified, carbocycles described herein refers to both unsubstituted and substituted carbocycle groups, i.e., optionally substituted carbocycles. In some embodiments, the carbocycle is a $C_{3-8}$ cycloalkyl. In some embodiments, the carbocycle is a $C_{3-6}$ cycloalkyl. In some embodiments, the carbocycle is a $C_{6-10}$ aryl.

"Aryl" includes groups with aromaticity, including "conjugated," or multicyclic systems with at least one aromatic ring and do not contain any heteroatom in the ring structure. Examples include phenyl, benzyl, 1,2,3,4-tetrahydronaphthalenyl, etc. In some embodiments, an "aryl" is a $C_{6-10}$ carbocycle with aromatity (e.g. an "aryl" is a $C_{6-10}$ aryl).

As used herein, the term "heterocycle" or "heterocyclic group" means an optionally substituted mono- or multi-cyclic system including one or more rings, where at least one ring includes at least one heteroatom. Heteroatoms may be, for example, nitrogen, oxygen, or sulfur atoms. Rings may be three, four, five, six, seven, eight, nine, ten, eleven, twelve, thirteen, or fourteen membered rings. Heterocycles may include one or more double or triple bonds and may be non-aromatic or aromatic (e.g., heterocycloalkyl or heteroaryl groups). Examples of heterocycles include imidazolyl, imidazolidinyl, oxazolyl, oxazolidinyl, thiazolyl, thiazolidinyl, pyrazolidinyl, pyrazolyl, isoxazolidinyl, isoxazolyl, isothiazolidinyl, isothiazolyl, morpholinyl, pyrrolyl, pyrrolidinyl, furyl, tetrahydrofuryl, thiophenyl, pyridinyl, piperidinyl, quinolyl, and isoquinolyl groups. The term "heterocycloalkyl" as used herein means a non-aromatic heterocycle and may or may not include any double or triple bond. Unless otherwise specified, heterocycles described herein refers to both unsubstituted and substituted heterocycle groups, i.e., optionally substituted heterocycles. In some embodiments, the heterocycle is a 4 to 12-membered heterocycloalkyl. In some embodiments, the heterocycle is a 5- or 6-membered heteroaryl.

"Heteroaryl" groups are aryl groups, as defined above, except having from one to four heteroatoms in the ring structure, and may also be referred to as "aryl heterocycles" or "heteroaromatics." As used herein, the term "heteroaryl" is intended to include a stable 5-, 6-, or 7-membered monocyclic or 7-, 8-, 9-, 10-, 11- or 12-membered bicyclic aromatic heterocyclic ring which consists of carbon atoms and one or more heteroatoms, e.g., 1 or 1-2 or 1-3 or 1-4 or 1-5 or 1-6 heteroatoms, or e.g. 1, 2, 3, 4, 5, or 6 heteroatoms, independently selected from the group consisting of nitrogen, oxygen sulfur, and boron. The nitrogen atom may be substituted or unsubstituted (i.e., N or NR wherein R is H or other substituents, as defined). The nitrogen and sulfur heteroatoms may optionally be oxidized (i.e., N→O and $S(O)_p$, where p=1 or 2). It is to be noted that total number of S and O atoms in the aromatic heterocycle is not more than 1.

Examples of heteroaryl groups include pyrrole, furan, thiophene, thiazole, isothiazole, imidazole, triazole, tetrazole, pyrazole, oxazole, isoxazole, pyridine, pyrazine, pyridazine, pyrimidine, and the like.

Furthermore, the terms "aryl" and "heteroaryl" include multicyclic aryl and heteroaryl groups, e.g., tricyclic, bicyclic, e.g., naphthalene, benzoxazole, benzodioxazole, benzothiazole, benzoimidazole, benzothiophene, quinoline, isoquinoline, naphthridine, indole, benzofuran, purine, benzofuran, deazapurine, indolizine.

As used herein, a "biodegradable group" is a group that may facilitate faster metabolism of a lipid in a mammalian entity. A biodegradable group may be selected from the group consisting of, but is not limited to, —C(O)O—, —OC(O)—, —C(O)N(R')—, —N(R')C(O)—, —C(O)—, —C(S)—, —C(S)S—, —SC(S)—, —CH(OH)—, —P(O)

(OR')O—, —$S(O)_2$—, an aryl group, and a heteroaryl group. As used herein, an "aryl group" is an optionally substituted carbocyclic group including one or more aromatic rings. Examples of aryl groups include phenyl and naphthyl groups. As used herein, a "heteroaryl group" is an optionally substituted heterocyclic group including one or more aromatic rings. Examples of heteroaryl groups include pyrrolyl, furyl, thiophenyl, imidazolyl, oxazolyl, and thiazolyl. Both aryl and heteroaryl groups may be optionally substituted. For example, M and M' can be selected from the non-limiting group consisting of optionally substituted phenyl, oxazole, and thiazole. In the formulas herein, M and M' can be independently selected from the list of biodegradable groups above. Unless otherwise specified, aryl or heteroaryl groups described herein refers to both unsubstituted and substituted groups, i.e., optionally substituted aryl or heteroaryl groups.

Alkyl, alkenyl, and cyclyl (e.g., carbocyclyl and heterocyclyl) groups may be optionally substituted unless otherwise specified. Optional substituents may be selected from the group consisting of, but are not limited to, a halogen atom (e.g., a chloride, bromide, fluoride, or iodide group), a carboxylic acid (e.g., —C(O)OH), an alcohol (e.g., a hydroxyl, —OH), an ester (e.g., —C(O)OR or —OC(O)R), an aldehyde (e.g., —C(O)H), a carbonyl (e.g., —C(O)R, alternatively represented by C═O), an acyl halide (e.g., —C(O)X, in which X is a halide selected from bromide, fluoride, chloride, and iodide), a carbonate (e.g., —OC(O)OR), an alkoxy (e.g., —OR), an acetal (e.g., —$C(OR)_2R''''$, in which each OR are alkoxy groups that can be the same or different and R'''' is an alkyl or alkenyl group), a phosphate (e.g., $P(O)_4^{3-}$), a thiol (e.g., —SH), a sulfoxide (e.g., —S(O)R), a sulfuric acid (e.g., —S(O)OH), a sulfonic acid (e.g., —$S(O)_2OH$), a thial (e.g., —C(S)H), a sulfate (e.g., $S(O)_4^{2-}$), a sulfonyl (e.g., —$S(O)_2$—), an amide (e.g., —$C(O)NR_2$, or —N(R)C(O)R), an azido (e.g., —$N_3$), a nitro (e.g., —$NO_2$), a cyano (e.g., —CN), an isocyano (e.g., —NC), an acyloxy (e.g., —OC(O)R), an amino (e.g., —$NR_2$, —NRH, or —$NH_2$), a carbamoyl (e.g., —$OC(O)NR_2$, —OC(O)NRH, or —$OC(O)NH_2$), a sulfonamide (e.g., —$S(O)_2NR_2$, —$S(O)_2NRH$, —$S(O)_2NH_2$, —$N(R)S(O)_2R$, —$N(H)S(O)_2R$, —$N(R)S(O)_2H$, or —$N(H)S(O)_2H$), an alkyl group, an alkenyl group, and a cyclyl (e.g., carbocyclyl or heterocyclyl) group. In any of the preceding, R is an alkyl or alkenyl group, as defined herein. In some embodiments, the substituent groups themselves may be further substituted with, for example, one, two, three, four, five, or six substituents as defined herein. For example, a $C_{1-6}$ alkyl group may be further substituted with one, two, three, four, five, or six substituents as described herein.

Compounds of the disclosure that contain nitrogens can be converted to N-oxides by treatment with an oxidizing agent (e.g., 3-chloroperoxybenzoic acid (mCPBA) and/or hydrogen peroxides) to afford other compounds of the disclosure. Thus, all shown and claimed nitrogen-containing compounds are considered, when allowed by valency and structure, to include both the compound as shown and its N-oxide derivative (which can be designated as N→O or $N^+$—$O^-$). Furthermore, in other instances, the nitrogens in the compounds of the disclosure can be converted to N-hydroxy or N-alkoxy compounds. For example, N-hydroxy compounds can be prepared by oxidation of the parent amine by an oxidizing agent such as m-CPBA. All shown and claimed nitrogen-containing compounds are also considered, when allowed by valency and structure, to cover both the compound as shown and its N-hydroxy (i.e., N—OH) and N-alkoxy (i.e., N—OR, wherein R is substituted or unsubstituted $C_1$-$C_6$ alkyl, $C_1$-$C_6$ alkenyl, $C_1$-$C_6$ alkynyl, 3-14-membered carbocycle or 3-14-membered heterocycle) derivatives.

About, Approximately: As used herein, the terms "approximately" and "about," as applied to one or more values of interest, refer to a value that is similar to a stated reference value. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value). For example, when used in the context of an amount of a given compound in a lipid component of a nanoparticle composition, "about" may mean+/−10% of the recited value. For instance, a nanoparticle composition including a lipid component having about 40% of a given compound may include 30-50% of the compound.

As used herein, the term "compound," is meant to include all isomers and isotopes of the structure depicted. "Isotopes" refers to atoms having the same atomic number but different mass numbers resulting from a different number of neutrons in the nuclei. For example, isotopes of hydrogen include tritium and deuterium. Further, a compound, salt, or complex of the present disclosure can be prepared in combination with solvent or water molecules to form solvates and hydrates by routine methods.

As used herein, the term "contacting" means establishing a physical connection between two or more entities. For example, contacting a mammalian cell with a nanoparticle composition means that the mammalian cell and a nanoparticle are made to share a physical connection. Methods of contacting cells with external entities both in vivo and ex vivo are well known in the biological arts. For example, contacting a nanoparticle composition and a mammalian cell disposed within a mammal may be performed by varied routes of administration (e.g., intravenous, intramuscular, intradermal, and subcutaneous) and may involve varied amounts of lipid nanoparticles (e.g., empty LNPs or loaded LNPs). Moreover, more than one mammalian cell may be contacted by a nanoparticle composition.

As used herein, the term "delivering" means providing an entity to a destination. For example, delivering a therapeutic and/or prophylactic to a subject may involve administering a nanoparticle composition including the therapeutic and/or prophylactic to the subject (e.g., by an intravenous, intramuscular, intradermal, or subcutaneous route). Administration of a nanoparticle composition to a mammal or mammalian cell may involve contacting one or more cells with the nanoparticle composition.

As used herein, the term "enhanced delivery" means delivery of more (e.g., at least 1.5 fold more, at least 2-fold more, at least 3-fold more, at least 4-fold more, at least 5-fold more, at least 6-fold more, at least 7-fold more, at least 8-fold more, at least 9-fold more, at least 10-fold more) of a therapeutic and/or prophylactic by a nanoparticle to a target tissue of interest (e.g., mammalian liver) compared to the level of delivery of a therapeutic and/or prophylactic by a control nanoparticle to a target tissue of interest (e.g., MC3, KC2, or DLinDMA). The level of delivery of a nanoparticle to a particular tissue may be measured by comparing the amount of protein produced in a tissue to the weight of said tissue, comparing the amount of therapeutic and/or prophylactic in a tissue to the weight of said tissue, comparing the amount of protein produced in a tissue to the amount of total protein in said tissue, or comparing the amount of therapeutic and/or prophylactic in a tissue to the amount of total therapeutic and/or prophylactic in said tissue. It will be understood that the enhanced delivery of a nanoparticle to a target tissue need not be determined in a subject being treated, it may be determined in a surrogate such as an animal model (e.g., a rat model). In certain embodiments, a nanoparticle composition including a compound according to Formula (I), (I-1), (A), (A-1), (A-1a), or (A-1b) has substantively the same level of delivery enhancement regardless of administration routes. For example, certain compounds disclosed herein exhibit similar delivery enhancement when they are used for delivering a therapeutic and/or prophylactic either intravenously or intramuscularly. In other embodiments, certain compounds disclosed herein exhibit a higher level of delivery enhancement when they are used for delivering a therapeutic and/or prophylactic intramuscularly than intravenously.

As used herein, the term "specific delivery," "specifically deliver," or "specifically delivering" means delivery of more (e.g., at least 1.5 fold more, at least 2-fold more, at least 3-fold more, at least 4-fold more, at least 5-fold more, at least 6-fold more, at least 7-fold more, at least 8-fold more, at least 9-fold more, at least 10-fold more) of a therapeutic and/or prophylactic by a nanoparticle to a target tissue of interest (e.g., mammalian liver) compared to an off-target tissue (e.g., mammalian spleen). The level of delivery of a nanoparticle to a particular tissue may be measured by comparing the amount of protein produced in a tissue to the weight of said tissue, comparing the amount of therapeutic and/or prophylactic in a tissue to the weight of said tissue, comparing the amount of protein produced in a tissue to the amount of total protein in said tissue, or comparing the amount of therapeutic and/or prophylactic in a tissue to the amount of total therapeutic and/or prophylactic in said tissue. For example, for renovascular targeting, a therapeutic and/or prophylactic is specifically provided to a mammalian kidney as compared to the liver and spleen if 1.5, 2-fold, 3-fold, 5-fold, 10-fold, 15 fold, or 20 fold more therapeutic and/or prophylactic per 1 g of tissue is delivered to a kidney compared to that delivered to the liver or spleen following systemic administration of the therapeutic and/or prophylactic. It will be understood that the ability of a nanoparticle to specifically deliver to a target tissue need not be determined in a subject being treated, it may be determined in a surrogate such as an animal model (e.g., a rat model).

As used herein, "encapsulation efficiency" refers to the amount of a therapeutic and/or prophylactic that becomes part of a nanoparticle composition, relative to the initial total amount of therapeutic and/or prophylactic used in the preparation of a nanoparticle composition. For example, if 97 mg of therapeutic and/or prophylactic are encapsulated in a nanoparticle composition out of a total 100 mg of therapeutic and/or prophylactic initially provided to the composition, the encapsulation efficiency may be given as 97%. As used herein, "encapsulation" may refer to complete, substantial, or partial enclosure, confinement, surrounding, or encasement.

As used herein, "encapsulation", "encapsulated", "loaded", and "associated" may refer to complete, substantial, or partial enclosure, confinement, surrounding, or encasement. As used herein, "encapsulation" or "association" may refer to the process of confining an individual nucleic acid molecule within a nanoparticle and/or establishing a physiochemical relationship between an individual nucleic acid molecule and a nanoparticle. As used herein, an "empty nanoparticle" may refer to a nanoparticle that is substantially free of a therapeutic or prophylactic agent. As used herein, an "empty nanoparticle" or an "empty lipid nanoparticle" may refer to a nanoparticle that is substantially free of a nucleic acid. As used herein, an "empty nanoparticle" or an "empty lipid nanoparticle" may refer to a nanoparticle that is substantially free of a nucleotide or a polypeptide. As used herein, an "empty nanoparticle" or an "empty lipid nanoparticle" may refer to a nanoparticle that consists substantially of only lipid components. As used herein, a "loaded nanoparticle" or a "loaded lipid nanoparticle" (also referred to as a "full nanoparticle" or a "full lipid nanoparticle") may refer to a nanoparticle comprising the components of the empty nanoparticle, and a therapeutic or prophylactic agent. As used herein, a "loaded nanoparticle" or a "loaded lipid nanoparticle" (also referred to as a "full nanoparticle" or a "full lipid nanoparticle") may refer to a nanoparticle comprising the components of the empty nanoparticle, and a nucleotide or polypeptide. As used herein, a "loaded nanoparticle" or a "loaded lipid nanoparticle" (also referred to as a "full nanoparticle" or a "full lipid nanoparticle") may refer to a nanoparticle comprising the components of the empty nanoparticle, and a nucleic acid.

As used herein, "expression" of a nucleic acid sequence refers to translation of an mRNA into a polypeptide or protein and/or post-translational modification of a polypeptide or protein.

As used herein, the term "in vitro" refers to events that occur in an artificial environment, e.g., in a test tube or reaction vessel, in cell culture, in a Petri dish, etc., rather than within an organism (e.g., animal, plant, or microbe).

As used herein, the term "in vivo" refers to events that occur within an organism (e.g., animal, plant, or microbe or cell or tissue thereof).

As used herein, the term "ex vivo" refers to events that occur outside of an organism (e.g., animal, plant, or microbe or cell or tissue thereof). Ex vivo events may take place in an environment minimally altered from a natural (e.g., in vivo) environment.

As used herein, the term "isomer" means any geometric isomer, tautomer, zwitterion, stereoisomer, enantiomer, or diastereomer of a compound. Compounds may include one or more chiral centers and/or double bonds and may thus exist as stereoisomers, such as double-bond isomers (i.e., geometric E/Z isomers) or diastereomers (e.g., enantiomers (i.e., (+) or (−)) or cis/trans isomers). The present disclosure encompasses any and all isomers of the compounds described herein, including stereomerically pure forms (e.g., geometrically pure, enantiomerically pure, or diastereomerically pure) and enantiomeric and stereoisomeric mixtures, e.g., racemates. Enantiomeric and stereomeric mixtures of compounds and means of resolving them into their component enantiomers or stereoisomers are well-known.

"Tautomer" is one of two or more structural isomers that exist in equilibrium and is readily converted from one isomeric form to another. This conversion results in the formal migration of a hydrogen atom accompanied by a switch of adjacent conjugated double bonds. Tautomers exist as a mixture of a tautomeric set in solution. In solutions where tautomerization is possible, a chemical equilibrium of the tautomers will be reached. The exact ratio of the tautomers depends on several factors, including temperature, solvent and pH. The concept of tautomers that are interconvertible by tautomerization is called tautomerism.

Of the various types of tautomerism that are possible, two are commonly observed. In keto-enol tautomerism a simultaneous shift of electrons and a hydrogen atom occurs. Ring-chain tautomerism arises as a result of the aldehyde group (—CHO) in a sugar chain molecule reacting with one of the hydroxy groups (—OH) in the same molecule to give it a cyclic (ring-shaped) form as exhibited by glucose.

Common tautomeric pairs are: ketone-enol, amide-nitrile, lactam-lactim, amide-imidic acid tautomerism in heterocyclic rings (e.g., in nucleobases such as guanine, thymine and cytosine), imine-enamine and enamine-enamine. An example of tautomerism in di-substituted guanidine is shown below.

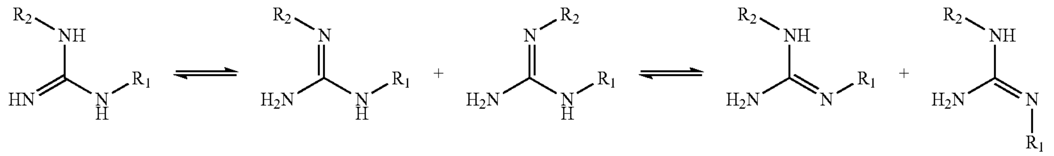

It is to be understood that the compounds of the disclosure may be depicted as different tautomers. It should also be understood that when compounds have tautomeric forms, all tautomeric forms are intended to be included in the scope of the disclosure, and the naming of the compounds does not exclude any tautomer form.

As used herein, a "lipid component" is that component of a nanoparticle composition that includes one or more lipids. For example, the lipid component may include one or more cationic/ionizable, PEGylated, structural, or other lipids, such as phospholipids.

As used herein, a "linker" is a moiety connecting two moieties, for example, the connection between two nucleosides of a cap species. A linker may include one or more groups including but not limited to phosphate groups (e.g., phosphates, boranophosphates, thiophosphates, selenophosphates, and phosphonates), alkyl groups, amidates, or glycerols. For example, two nucleosides of a cap analog may be linked at their 5' positions by a triphosphate group or by a chain including two phosphate moieties and a boranophosphate moiety.

As used herein, "methods of administration" may include intravenous, intramuscular, intradermal, subcutaneous, or other methods of delivering a composition to a subject. A method of administration may be selected to target delivery (e.g., to specifically deliver) to a specific region or system of a body.

As used herein, "modified" means non-natural. For example, an RNA may be a modified RNA. That is, an RNA may include one or more nucleobases, nucleosides, nucleotides, or linkers that are non-naturally occurring. A "modified" species may also be referred to herein as an "altered" species. Species may be modified or altered chemically, structurally, or functionally. For example, a modified nucleobase species may include one or more substitutions that are not naturally occurring.

As used herein, the "N:P ratio" is the molar ratio of ionizable (in the physiological pH range) nitrogen atoms in a lipid to phosphate groups in an RNA, e.g., in a nanoparticle composition including a lipid component and an RNA.

As used herein, a "nanoparticle composition" is a composition comprising one or more lipids. Nanoparticle compositions are typically sized on the order of micrometers or smaller and may include a lipid bilayer. Nanoparticle compositions encompass lipid nanoparticles (LNPs), liposomes (e.g., lipid vesicles), and lipoplexes. For example, a nanoparticle composition may be a liposome having a lipid bilayer with a diameter of 500 nm or less.

As used herein, "naturally occurring" means existing in nature without artificial aid.

As used herein, "patient" refers to a subject who may seek or be in need of treatment, requires treatment, is receiving treatment, will receive treatment, or a subject who is under care by a trained professional for a particular disease or condition.

As used herein, a "PEG lipid" or "PEGylated lipid" refers to a lipid comprising a polyethylene glycol component.

The phrase "pharmaceutically acceptable" is used herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable excipient," as used herein, refers to any ingredient other than the compounds described herein (for example, a vehicle capable of suspending, complexing, or dissolving the active compound) and having the properties of being substantially nontoxic and non-inflammatory in a patient. Excipients may include, for example: anti-adherents, antioxidants, binders, coatings, compression aids, disintegrants, dyes (colors), emollients, emulsifiers, fillers (diluents), film formers or coatings, flavors, fragrances, glidants (flow enhancers), lubricants, preservatives, printing inks, sorbents, suspending or dispersing agents, sweeteners, and waters of hydration. Exemplary excipients include, but are not limited to: butylated hydroxytoluene (BHT), calcium carbonate, calcium phosphate (dibasic), calcium stearate, croscarmellose, cross-linked polyvinyl pyrrolidone, citric acid, crospovidone, cysteine, ethylcellulose, gelatin, hydroxypropyl cellulose, hydroxypropyl methylcellulose, lactose, magnesium stearate, maltitol, mannitol, methionine, methylcellulose, methyl paraben, microcrystalline cellulose, polyethylene glycol, polyvinyl pyrrolidone, povidone, pregelatinized starch, propyl paraben, retinyl palmitate, shellac, silicon dioxide, sodium carboxymethyl cellulose, sodium citrate, sodium starch glycolate, sorbitol, starch (corn), stearic acid, sucrose, talc, titanium dioxide, vitamin A, vitamin E (alpha-tocopherol), vitamin C, xylitol, and other species disclosed herein.

In the present specification, the structural formula of the compound represents a certain isomer for convenience in some cases, but the present disclosure includes all isomers, such as geometrical isomers, optical isomers based on an asymmetrical carbon, stereoisomers, tautomers, and the like, it being understood that not all isomers may have the same level of activity. In addition, a crystal polymorphism may be present for the compounds represented by the formula. It is noted that any crystal form, crystal form mixture, or anhydride or hydrate thereof is included in the scope of the present disclosure.

The term "crystal polymorphs", "polymorphs" or "crystal forms" means crystal structures in which a compound (or a salt or solvate thereof) can crystallize in different crystal packing arrangements, all of which have the same elemental composition. Different crystal forms usually have different X-ray diffraction patterns, infrared spectral, melting points, density hardness, crystal shape, optical and electrical properties, stability and solubility. Recrystallization solvent, rate of crystallization, storage temperature, and other factors may cause one crystal form to dominate. Crystal polymorphs of the compounds can be prepared by crystallization under different conditions.

Compositions may also include salts of one or more compounds. Salts may be pharmaceutically acceptable salts. As used herein, “pharmaceutically acceptable salts” refers to derivatives of the disclosed compounds wherein the parent compound is altered by converting an existing acid or base moiety to its salt form (e.g., by reacting a free base group with a suitable organic acid). Examples of pharmaceutically acceptable salts include, but are not limited to, mineral or organic acid salts of basic residues such as amines; alkali or organic salts of acidic residues such as carboxylic acids; and the like. Representative acid addition salts include acetate, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, fumarate, glucoheptonate, glycerophosphate, hemisulfate, heptonate, hexanoate, hydrobromide, hydrochloride, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, toluenesulfonate, undecanoate, valerate salts, and the like. Representative alkali or alkaline earth metal salts include sodium, lithium, potassium, calcium, magnesium, and the like, as well as nontoxic ammonium, quaternary ammonium, and amine cations, including, but not limited to ammonium, tetramethylammonium, tetraethylammonium, methylamine, dimethylamine, trimethylamine, triethylamine, ethylamine, and the like. The pharmaceutically acceptable salts of the present disclosure include the conventional non-toxic salts of the parent compound formed, for example, from non-toxic inorganic or organic acids. The pharmaceutically acceptable salts of the present disclosure can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred.

As used herein, a “phospholipid” is a lipid that includes a phosphate moiety and one or more carbon chains, such as unsaturated fatty acid chains. A phospholipid may include one or more multiple (e.g., double or triple) bonds (e.g., one or more unsaturations). Particular phospholipids may facilitate fusion to a membrane. For example, a cationic phospholipid may interact with one or more negatively charged phospholipids of a membrane (e.g., a cellular or intracellular membrane). Fusion of a phospholipid to a membrane may allow one or more elements of a lipid-containing composition to pass through the membrane permitting, e.g., delivery of the one or more elements to a cell.

As used herein, the “polydispersity index,” or “PDI” is a ratio that describes the homogeneity of the particle size distribution of a system. A small value, e.g., less than 0.3, indicates a narrow particle size distribution.

As used herein, the term “polypeptide” or “polypeptide of interest” refers to a polymer of amino acid residues typically joined by peptide bonds that can be produced naturally (e.g., isolated or purified) or synthetically. The terms “polypeptide,” “peptide,” and “protein” are used interchangeably herein to refer to polymers of amino acids of any length. The polymer can comprise modified amino acids. The terms also encompass an amino acid polymer that has been modified naturally or by intervention; for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids such as homocysteine, ornithine, p-acetylphenylalanine, D-amino acids, and creatine), as well as other modifications known in the art. The term, as used herein, refers to proteins, polypeptides, and peptides of any size, structure, or function. Polypeptides include encoded polynucleotide products, naturally occurring polypeptides, synthetic polypeptides, homologs, orthologs, paralogs, fragments and other equivalents, variants, and analogs of the foregoing. A polypeptide can be a monomer or can be a multi-molecular complex such as a dimer, trimer or tetramer. They can also comprise single chain or multichain polypeptides. Most commonly disulfide linkages are found in multichain polypeptides. The term polypeptide can also apply to amino acid polymers in which one or more amino acid residues are an artificial chemical analogue of a corresponding naturally occurring amino acid. In some embodiments, a “peptide” can be less than or equal to 50 amino acids long, e.g., about 5, 10, 15, 20, 25, 30, 35, 40, 45, or 50 amino acids long.

As used herein, an “RNA” refers to a ribonucleic acid that may be naturally or non-naturally occurring. For example, an RNA may include modified and/or non-naturally occurring components such as one or more nucleobases, nucleosides, nucleotides, or linkers. An RNA may include a cap structure, a chain terminating nucleoside, a stem loop, a polyA sequence, and/or a polyadenylation signal. An RNA may have a nucleotide sequence encoding a polypeptide of interest.

As used herein, a “DNA” refers to a desoxyribonucleic acid that may be naturally or non-naturally occurring. For example, a DNA may be a synthetic molecule, e.g., a synthetic DNA molecule produced in vitro. In some embodiments, the DNA molecule is a recombinant molecule. As used herein, a “recombinant DNA molecule” refers to a DNA molecule that does not exist as a natural product, but is produced using molecular biology techniques.

As used herein, a “single unit dose” is a dose of any therapeutic administered in one dose/at one time/single route/single point of contact, i.e., single administration event.

As used herein, a “split dose” is the division of single unit dose or total daily dose into two or more doses.

As used herein, a “total daily dose” is an amount given or prescribed in 24 hour period. It may be administered as a single unit dose.

As used herein, “size” or “mean size” in the context of lipid nanoparticles (e.g., empty LNPs or loaded LNPs) refers to the mean diameter of a nanoparticle composition.

As used herein, the term “subject” or “patient” refers to any organism to which a composition in accordance with the disclosure may be administered, e.g., for experimental, diagnostic, prophylactic, and/or therapeutic purposes. Typical subjects include animals (e.g., mammals such as mice, rats, rabbits, non-human primates, and humans) and/or plants.

As used herein, "targeted cells" refers to any one or more cells of interest. The cells may be found in vitro, in vivo, in situ, or in the tissue or organ of an organism. The organism may be an animal, preferably a mammal, more preferably a human and most preferably a patient.

As used herein "target tissue" refers to any one or more tissue types of interest in which the delivery of a therapeutic and/or prophylactic would result in a desired biological and/or pharmacological effect. Examples of target tissues of interest include specific tissues, organs, and systems or groups thereof. In particular applications, a target tissue may be a kidney, a lung, a spleen, vascular endothelium in vessels (e.g., intra-coronary or intra-femoral), or tumor tissue (e.g., via intratumoral injection). An "off-target tissue" refers to any one or more tissue types in which the expression of the encoded protein does not result in a desired biological and/or pharmacological effect. In particular applications, off-target tissues may include the liver and the spleen.

The term "therapeutic agent" or "prophylactic agent" refers to any agent that, when administered to a subject, has a therapeutic, diagnostic, and/or prophylactic effect and/or elicits a desired biological and/or pharmacological effect. Therapeutic agents are also referred to as "actives" or "active agents." Such agents include, but are not limited to, cytotoxins, radioactive ions, chemotherapeutic agents, small molecule drugs, proteins, and nucleic acids.

As used herein, the term "therapeutically effective amount" means an amount of an agent to be delivered (e.g., nucleic acid, drug, composition, therapeutic agent, diagnostic agent, prophylactic agent, etc.) that is sufficient, when administered to a subject suffering from or susceptible to an infection, disease, disorder, and/or condition, to treat, improve symptoms of, diagnose, prevent, and/or delay the onset of the infection, disease, disorder, and/or condition.

As used herein, "transfection" refers to the introduction of a species (e.g., an RNA) into a cell. Transfection may occur, for example, in vitro, ex vivo, or in vivo.

As used herein, the term "treating" refers to partially or completely alleviating, ameliorating, improving, relieving, delaying onset of, inhibiting progression of, reducing severity of, and/or reducing incidence of one or more symptoms or features of a particular infection, disease, disorder, and/or condition. For example, "treating" cancer may refer to inhibiting survival, growth, and/or spread of a tumor. Treatment may be administered to a subject who does not exhibit signs of a disease, disorder, and/or condition and/or to a subject who exhibits only early signs of a disease, disorder, and/or condition for the purpose of decreasing the risk of developing pathology associated with the disease, disorder, and/or condition.

As used herein, the "zeta potential" is the electrokinetic potential of a lipid, e.g., in a particle composition.

Nanoparticle Compositions

The disclosure also features lipid nanoparticles comprising a compound according to Formula (I), (I-1), (A), (A-1), (A-1a), or (A-1b) as described herein.

In some embodiments, the largest dimension of a nanoparticle composition is 1 μm or shorter (e.g., 1 μm, 900 nm, 800 nm, 700 nm, 600 nm, 500 nm, 400 nm, 300 nm, 200 nm, 175 nm, 150 nm, 125 nm, 100 nm, 75 nm, 50 nm, or shorter), e.g., when measured by dynamic light scattering (DLS), transmission electron microscopy, scanning electron microscopy, or another method. Nanoparticle compositions include, for example, lipid nanoparticles (LNPs; e.g., empty LNPs or loaded LNPs), liposomes, lipid vesicles, and lipoplexes. In some embodiments, nanoparticle compositions are vesicles including one or more lipid bilayers. In certain embodiments, a nanoparticle composition includes two or more concentric bilayers separated by aqueous compartments. Lipid bilayers may be functionalized and/or cross-linked to one another. Lipid bilayers may include one or more ligands, proteins, or channels.

Nanoparticle compositions comprise a lipid component including at least one compound according to Formula (I), (I-1), (A), (A-1), (A-1a), or (A-1b). For example, the lipid component of a nanoparticle composition may include one or more of compounds of Table 1. Nanoparticle compositions may also include a variety of other components. For example, the lipid component of a nanoparticle composition may include one or more other lipids in addition to a lipid according to Formula (I), (I-1), (A), (A-1), (A-1a), or (A-1b).

Cationic/Ionizable Lipids

The lipid nanoparticle (e.g., an empty LNP or a loaded LNP) may include one or more cationic and/or ionizable lipids (e.g., lipids that may have a positive or partial positive charge at physiological pH) in addition to a lipid according to Formula (I), (I-1), (A), (A-1), (A-1a), or (A-1b). Cationic and/or ionizable lipids may be selected from the non-limiting group consisting of 3-(didodecylamino)-N1,N1,4-tridodecyl-1-piperazineethanamine (KL10), N1-[2-(didodecylamino)ethyl]-N1,N4,N4-tridodecyl-1,4-piperazinediethanamine (KL22), 14,25-ditridecyl-15,18,21,24-tetraaza-octatriacontane (KL25), 1,2-dilinoleyloxy-N,N-dimethylaminopropane (DLin-DMA), 2,2-dilinoleyl-4-dimethylaminomethyl-[1,3]-dioxolane (DLin-K-DMA), heptatriaconta-6,9,28,31-tetraen-19-yl 4-(dimethylamino) butanoate (DLin-MC3-DMA), 2,2-dilinoleyl-4-(2-dimethylaminoethyl)-[1,3]-dioxolane (DLin-KC2-DMA), 1,2-dioleyloxy-N,N-dimethylaminopropane (DODMA), 2-({8-[(3β)-cholest-5-en-3-yloxy]octyl}oxy)-N,N-dimethyl-3-[(9Z,12Z)-octadeca-9,12-dien-1-yloxy]propan-1-amine (Octyl-CLinDMA), (2R)-2-({8-[(3β)-cholest-5-en-3-yloxy]octyl}oxy)-N,N-dimethyl-3-[(9Z,12Z)-octadeca-9,12-dien-1-yloxy]propan-1-amine (Octyl-CLinDMA (2R)), and (2S)-2-({8-[(3β)-cholest-5-en-3-yloxy]octyl}oxy)-N,N-dimethyl-3-[(9Z,12Z)-octadeca-9,12-dien-1-yloxy]propan-1-amine (Octyl-CLinDMA (2S)). In addition to these, a cationic lipid may also be a lipid including a cyclic amine group.

Structural Lipids

The lipid nanoparticle (e.g., an empty LNP or a loaded LNP) may include one or more structural lipids. Structural lipids can be selected from the group consisting of, but are not limited to, cholesterol, fecosterol, sitosterol, ergosterol, campesterol, stigmasterol, brassicasterol, tomatidine, tomatine, ursolic acid, alpha-tocopherol, and mixtures thereof. In some embodiments, the structural lipid is cholesterol. In some embodiments, the structural lipid includes cholesterol and a corticosteroid (such as prednisolone, dexamethasone, prednisone, and hydrocortisone), or a combination thereof. In some embodiments, the structural lipid is:

(SL-1)

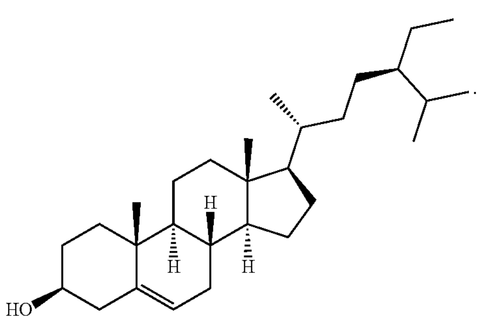

Phospholipids

The lipid nanoparticle (e.g., an empty LNP or a loaded LNP) may include one or more phospholipids, such as one or more (poly)unsaturated lipids. Phospholipids may assemble into one or more lipid bilayers. In general, phospholipids may include a phospholipid moiety and one or more fatty acid moieties. For example, a phospholipid may be a lipid according to Formula (IV):

(IV)

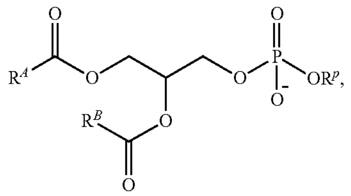

in which $R_p$ represents a phospholipid moiety and $R^A$ and $R^B$ represent fatty acid moieties with or without unsaturation that may be the same or different. A phospholipid moiety may be selected from the non-limiting group consisting of phosphatidyl choline, phosphatidyl ethanolamine, phosphatidyl glycerol, phosphatidyl serine, phosphatidic acid, 2-lysophosphatidyl choline, and a sphingomyelin. A fatty acid moiety may be selected from the non-limiting group consisting of lauric acid, myristic acid, myristoleic acid, palmitic acid, palmitoleic acid, stearic acid, oleic acid, linoleic acid, alpha-linolenic acid, erucic acid, phytanic acid, arachidic acid, arachidonic acid, eicosapentaenoic acid, behenic acid, docosapentaenoic acid, and docosahexaenoic acid. Non-natural species including natural species with modifications and substitutions including branching, oxidation, cyclization, and alkynes are also contemplated. For example, a phospholipid may be functionalized with or cross-linked to one or more alkynes (e.g., an alkenyl group in which one or more double bonds is replaced with a triple bond). Under appropriate reaction conditions, an alkyne group may undergo a copper-catalyzed cycloaddition upon exposure to an azide. Such reactions may be useful in functionalizing a lipid bilayer of a lipid nanoparticle (e.g., an empty LNP or a loaded LNP) to facilitate membrane permeation or cellular recognition or in conjugating a lipid nanoparticle (e.g., an empty LNP or a loaded LNP) to a useful component such as a targeting or imaging moiety (e.g., a dye).

Phospholipids useful in the compositions and methods may be selected from the non-limiting group consisting of 1,2-distearoyl-sn-glycero-3-phosphocholine (DSPC), 1,2-dioleoyl-sn-glycero-3-phosphoethanolamine (DOPE), 1,2-dilinoleoyl-sn-glycero-3-phosphocholine (DLPC), 1,2-dimyristoyl-sn-glycero-phosphocholine (DMPC), 1,2-dioleoyl-sn-glycero-3-phosphocholine (DOPC), 1,2-dipalmitoyl-sn-glycero-3-phosphocholine (DPPC), 1,2-diundecanoyl-sn-glycero-phosphocholine (DUPC), 1-palmitoyl-2-oleoyl-sn-glycero-3-phosphocholine (POPC), 1,2-di-O-octadecenyl-sn-glycero-3-phosphocholine (18:0 Diether PC), 1-oleoyl-2-cholesterylhemisuccinoyl-sn-glycero-3-phosphocholine (OChemsPC), 1-hexadecyl-sn-glycero-3-phosphocholine (C16 Lyso PC), 1,2-dilinolenoyl-sn-glycero-3-phosphocholine, 1,2-diarachidonoyl-sn-glycero-3-phosphocholine, 1,2-didocosahexaenoyl-sn-glycero-3-phosphocholine, 1,2-diphytanoyl-sn-glycero-3-phosphoethanolamine (ME 16.0 PE), 1,2-distearoyl-sn-glycero-3-phosphoethanolamine, 1,2-dilinoleoyl-sn-glycero-3-phosphoethanolamine, 1,2-dilinolenoyl-sn-glycero-3-phosphoethanolamine, 1,2-diarachidonoyl-sn-glycero-3-phosphoethanolamine, 1,2-didocosahexaenoyl-sn-glycero-3-phosphoethanolamine, 1,2-dioleoyl-sn-glycero-3-phospho-rac-(1-glycerol) sodium salt (DOPG), dipalmitoylphosphatidylglycerol (DPPG), palmitoyloleoylphosphatidylethanolamine (POPE), distearoyl-phosphatidyl-ethanolamine (DSPE), dipalmitoyl phosphatidyl ethanolamine (DPPE), dimyristoylphosphoethanolamine (DMPE), 1-stearoyl-2-oleoyl-phosphatidyethanolamine (SOPE), 1-stearoyl-2-oleoyl-phosphatidylcholine (SOPC), sphingomyelin, phosphatidylcholine, phosphatidylethanolamine, phosphatidylserine, phosphatidylinositol, phosphatidic acid, palmitoyloleoyl phosphatidylcholine, lysophosphatidylcholine, lysophosphatidylethanolamine (LPE), and mixtures thereof. In some embodiments, a lipid nanoparticle (e.g., an empty LNP or a loaded LNP) includes DSPC. In certain embodiments, a lipid nanoparticle (e.g., an empty LNP or a loaded LNP) includes DOPE. In some embodiments, a lipid nanoparticle (e.g., an empty LNP or a loaded LNP) includes both DSPC and DOPE.

PEG Lipids

The lipid nanoparticle (e.g., an empty LNP or a loaded LNP) may include one or more PEG or PEG-modified lipids. Such species may be alternately referred to as PEGylated lipids. A PEG lipid is a lipid modified with polyethylene glycol. A PEG lipid may be selected from the non-limiting group consisting of PEG-modified phosphatidylethanolamines, PEG-modified phosphatidic acids, PEG-modified ceramides (PEG-CER), PEG-modified dialkylamines, PEG-modified diacylglycerols (PEG-DEG), PEG-modified dialkylglycerols, and mixtures thereof. For example, a PEG lipid may be PEG-c-DOMG, PEG-DMG, PEG-DLPE, PEG-DMPE, PEG-DPPC, or a PEG-DSPE lipid.

In certain embodiments, the PEG lipid is selected from the group consisting of a PEG-modified phosphatidylethanolamine, a PEG-modified phosphatidic acid, a PEG-modified ceramide, a PEG-modified dialkylamine, a PEG-modified diacylglycerol, and a PEG-modified dialkylglycerol.

In certain embodiments, PEG lipid is selected from the group consisting of 1,2-dimyristoyl-sn-glycerol methoxypolyethylene glycol (PEG-DMG), 1,2-distearoyl-sn-glycero-3-phosphoethanolamine-N-[amino(polyethylene glycol)] (PEG-DSPE), PEG-disteryl glycerol (PEG-DSG), PEG-dipalmetoleyl, PEG-dioleyl, PEG-distearyl, PEG-diacylglycamide (PEG-DAG), PEG-dipalmitoyl phosphatidylethanolamine (PEG-DPPE), or PEG-1,2-dimyristyloxlpropyl-3-amine (PEG-c-DMA). For example, in some embodiments, the PEG lipid is PEG-DMG.

In certain embodiments, the PEG lipid is a compound of Formula (PL-I):

(PL-I)

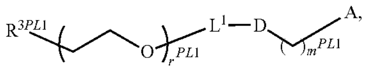

or a salt thereof, wherein:

$R^{3PL1}$ is —$OR^{OPL1}$;

$R^{OPL1}$ is hydrogen, optionally substituted alkyl, or an oxygen protecting group;

$r^{PL1}$ is an integer between 1 and 100, inclusive;

$L^1$ is optionally substituted $C_{1-10}$ alkylene, wherein at least one methylene of the optionally substituted $C_{1-10}$ alkylene is independently replaced with optionally substituted carbocyclylene, optionally substituted heterocyclylene, optionally substituted arylene, optionally substituted heteroarylene, O, $N(R^{NPL1})$, S, C(O), $C(O)N(R^{NPL1})$, $NR^{NPL1}C(O)$, —C(O)O, OC(O), OC(O)O, $OC(O)N(R^{NPL1})$, $NR^{NPL1}C(O)O$, or $NR^{NPL1}C(O)N(R^{NPL1})$;

D is a moiety obtained by click chemistry or a moiety cleavable under physiological conditions;

$m^{PL1}$ is 0, 1, 2, 3, 4, 5, 6, 7, 8, 9, or 10;

A is of the formula:

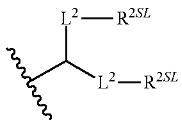

or

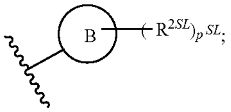

each instance of $L^2$ is independently a bond or optionally substituted $C_{1-6}$ alkylene, wherein one methylene unit of the optionally substituted $C_{1-6}$ alkylene is optionally replaced with O, $N(R^{NPL1})$, S, C(O), $C(O)N(R^{NPL1})$, $NR^{NPL1}C(O)$, C(O)O, OC(O), OC(O)O, —$OC(O)N(R^{NPL1})$, $NR^{NPL1}C(O)O$, or $NR^{NPL1}C(O)N(R^{NPL1})$;

each instance of $R^{2SL}$ is independently optionally substituted $C_{1-30}$ alkyl, optionally substituted $C_{1-30}$ alkenyl, or optionally substituted $C_{1-30}$ alkynyl; optionally wherein one or more methylene units of $R^{2SL}$ are independently replaced with optionally substituted carbocyclylene, optionally substituted heterocyclylene, optionally substituted arylene, optionally substituted heteroarylene, $N(R^{NPL1})$, O, S, C(O), $C(O)N(R^{NPL1})$, $NR^{NPL1}C(O)$, —$NR^{NPL1}C(O)N(R^{NPL1})$, C(O)O, OC(O), OC(O)O, $OC(O)N(R^{NPL1})$, $NR^{NPL1}C(O)O$, C(O)S, —SC(O), $C(=NR^{NPL1})$, $C(=NR^{NPL1})N(R^{NPL1})$, $NR^{NPL1}C(=NR^{NPL1})$, —$NR^{NPL1}C(=NR^{NPL1})N(R^{NPL1})$, C(S), $C(S)N(R^{NPL1})$, $NR^{NPL1}C(S)$, $NR^{NPL1}C(S)N(R^{NPL1})$, S(O), OS(O), S(O)O, OS(O)O, $OS(O)_2$, $S(O)_2O$, $OS(O)_2O$, $N(R^{NPL1})S(O)$, $S(O)N(R^{NPL1})$, —$N(R^{NPL1})S(O)N(R^{NPL1})$, $OS(O)N(R^{NPL1})$, $N(R^{NPL1})S(O)O$, $S(O)_2$, $N(R^{NPL1})S(O)_2$, —$S(O)_2N(R^{NPL1})$, $N(R^{NPL1})S(O)_2N(R^{NPL1})$, $OS(O)_2N(R^{NPL1})$, or $N(R^{NPL1})S(O)_2O$;

each instance of $R^{NPL1}$ is independently hydrogen, optionally substituted alkyl, or a nitrogen protecting group;

Ring B is optionally substituted carbocyclyl, optionally substituted heterocyclyl, optionally substituted aryl, or optionally substituted heteroaryl; and $p^{SL}$ is 1 or 2.

In certain embodiments, the PEG lipid is a compound of Formula (PL-I—OH):

(PL-I-OH)

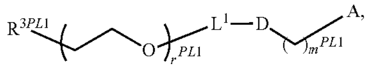

or a salt thereof.

In certain embodiments, the PEG lipid is a compound of Formula (PL-II-OH):

(PL-II-OH)

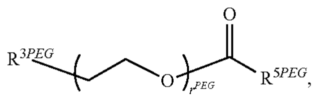

or a salt or isomer thereof, wherein:

$R^{3PEG}$ is —$OR^O$;

$R^O$ is hydrogen, $C_{1-6}$ alkyl or an oxygen protecting group;

$r^{PEG}$ is an integer between 1 and 100;

$R^{5PEG}$ is $C_{10-40}$ alkyl, $C_{10-40}$ alkenyl, or $C_{10-40}$ alkynyl; and optionally one or more methylene groups of $R^{5PEG}$ are independently replaced with $C_{3-10}$ carbocyclylene, 4 to 10 membered heterocyclylene, $C_{6-10}$ arylene, 4 to 10 membered heteroarylene, —$N(R^{NPEG})$—, —O—, —S—, —C(O)—, —$C(O)N(R^{NPEG})$—, —$NR^{NPEG}C(O)$—, —$NR^{NPEG}C(O)N(R^{NPEG})$—, —C(O)O—, —OC(O)—, —OC(O)O—, —$OC(O)N(R^{NPEG})$—, —$NR^{NPEG}C(O)O$—, —C(O)S—, —SC(O)—, —$C(=NR^{NPEG})$—, —$C(=NR^{NPEG})N(R^{NPEG})$—, —$NR^{NPEG}C(=NR^{NPEG})$—, —$NR^{NPEG}C(=NR^{NPEG})N(R^{NPEG})$—, —C(S)—, —$C(S)N(R^{NPEG})$—, —$NR^{NPEG}C(S)$—, —$NR^{NPEG}C(S)N(R^{NPEG})$—, —S(O)—, —OS(O)—, —S(O)O—, —OS(O)O—, —$OS(O)_2$—, —$S(O)_2O$—, —$OS(O)_2O$—, —$N(R^{NPEG})S(O)$—, —$S(O)N(R^{NPEG})$—, —$N(R^{NPEG})S(O)N(R^{NPEG})$—, —$OS(O)N(R^{NPEG})$—, —$N(R^{NPEG})S(O)O$—, —$S(O)_2$—, —$N(R^{NPEG})S(O)_2$—, —$S(O)_2N(R^{NPEG})$—, —$N(R^{NPEG})S(O)_2N(R^{NPEG})$—, —$OS(O)_2N(R^{NPEG})$—, or —$N(R^{NPEG})S(O)_2O$—; and each instance of $R^{NPEG}$ is independently hydrogen, $C_{1-6}$ alkyl, or a nitrogen protecting group.

In certain embodiments, in the PEG lipid of Formula (PL-II-OH), r is an integer between 40 and 50. For example, r is selected from the group consisting of 40, 41, 42, 43, 44, 45, 46, 47, 48, 49 and 50. For example, r is 45.

In certain embodiments, in the PEG lipid of Formula (PL-II-OH), $R^5$ is $C_{17}$ alkyl.

In certain embodiments, the PEG lipid is a compound of Formula (PL-II):

(PL-II)

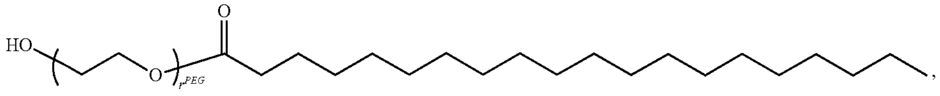

wherein $r^{PEG}$ is an integer between 1 and 100.

In certain embodiments, the PEG lipid is a compound of Formula (PEG-1):

(PEG-1)

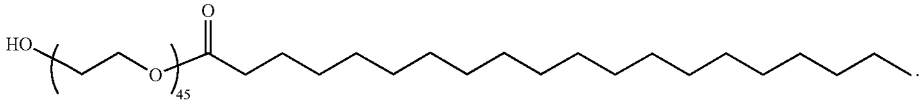

In certain embodiments, the PEG lipid is a compound of Formula (PL-III):

(PL-III)

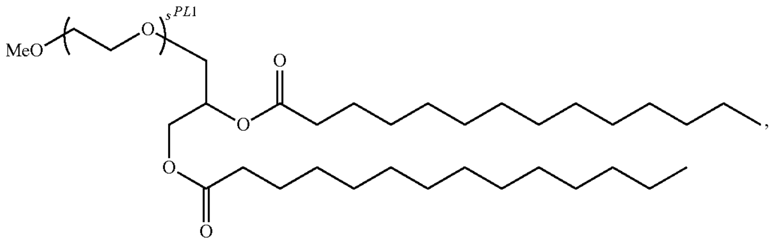

or a salt or isomer thereof, wherein $s^{PL1}$ is an integer between 1 and 100.

In certain embodiments, the PEG lipid is a compound of following formula:

($PEG_{2k}$-DMG)

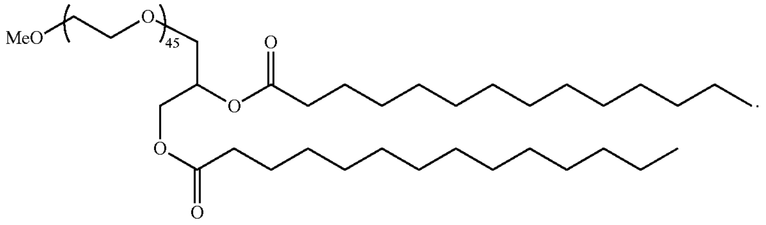

In certain embodiments, the incorporation of lipids of one of formulae (PL-I), PL-I-OH), (PL-II), (PL-II-OH), (PL-III), $PEG_{2k}$-DMG, or PEG-1 in the nanoparticle formulation can improve the pharmacokinetics and/or biodistribution of the lipid nanoparticle formulations. For example, incorporation of lipids of one of formulae (PL-II-OH), (PL-IIa-OH), (PL-II), or PEG-1 in the nanoparticle formulation can reduce the accelerated blood clearance (ABC) effect.

Adjuvants

In some embodiments, a lipid nanoparticle (e.g., an empty LNP or a loaded LNP) that includes one or more lipids described herein may further include one or more adjuvants, e.g., Glucopyranosyl Lipid Adjuvant (GLA), CpG oligodeoxynucleotides (e.g., Class A or B), poly(I:C), aluminum hydroxide, and Pam3CSK4.

Therapeutic Agents

Lipid nanoparticles (e.g., empty LNPs or loaded LNPs) may include one or more therapeutic and/or prophylactics. The disclosure features methods of delivering a therapeutic and/or prophylactic to a mammalian cell or organ, producing a polypeptide of interest in a mammalian cell, and treating a disease or disorder in a mammal in need thereof comprising administering to a mammal and/or contacting a mammalian cell with a lipid nanoparticle (e.g., an empty LNP or a loaded LNP) including a therapeutic and/or prophylactic.

Therapeutic and/or prophylactics include biologically active substances and are alternately referred to as "active agents." A therapeutic and/or prophylactic may be a substance that, once delivered to a cell or organ, brings about a desirable change in the cell, organ, or other bodily tissue or system. Such species may be useful in the treatment of one or more diseases, disorders, or conditions. In some embodiments, a therapeutic and/or prophylactic is a small molecule drug useful in the treatment of a particular disease, disorder, or condition.

In some embodiments, a therapeutic and/or prophylactic is a vaccine, a compound (e.g., a polynucleotide or nucleic acid molecule that encodes a protein or polypeptide or peptide or a protein or polypeptide or protein) that elicits an immune response, and/or another therapeutic and/or prophylactic. Vaccines include compounds and preparations that are capable of providing immunity against one or more conditions related to infectious diseases and can include mRNAs encoding infectious disease derived antigens and/or epitopes. Vaccines also include compounds and preparations that direct an immune response against cancer cells and can include mRNAs encoding tumor cell derived antigens, epitopes, and/or neoepitopes. In some embodiments, a vaccine and/or a compound capable of eliciting an immune response is administered intramuscularly via a composition of the disclosure.

In other embodiments, a therapeutic and/or prophylactic is a protein, for example a protein needed to augment or replace a naturally-occurring protein of interest. Such proteins or polypeptides may be naturally occurring, or may be modified using methods known in the art, e.g., to increase half life. Exemplary proteins are intracellular, transmembrane, or secreted.

Polynucleotides and Nucleic Acids

In some embodiments, the therapeutic agent is an agent that enhances (i.e., increases, stimulates, upregulates) protein expression. Non-limiting examples of types of therapeutic agents that can be used for enhancing protein expression include RNAs, mRNAs, dsRNAs, CRISPR/Cas9 technology, ssDNAs and DNAs (e.g., expression vectors). The agent that upregulates protein expression may upregulate expression of a naturally occurring or non-naturally occurring protein (e.g., a chimeric protein that has been modified to improve half life, or one that comprises desirable amino acid changes). Exemplary proteins include intracellular, transmembrane, or secreted proteins, peptides, or polypeptides.

In some embodiments, the therapeutic agent is a DNA therapeutic agent. The DNA molecule can be a double-stranded DNA, a single-stranded DNA (ssDNA), or a molecule that is a partially double-stranded DNA, i.e., has a portion that is double-stranded and a portion that is single-stranded. In some cases the DNA molecule is triple-stranded or is partially triple-stranded, i.e., has a portion that is triple stranded and a portion that is double stranded. The DNA molecule can be a circular DNA molecule or a linear DNA molecule.

A DNA therapeutic agent can be a DNA molecule that is capable of transferring a gene into a cell, e.g., that encodes and can express a transcript. In other embodiments, the DNA molecule is a synthetic molecule, e.g., a synthetic DNA molecule produced in vitro. In some embodiments, the DNA molecule is a recombinant molecule. Non-limiting exemplary DNA therapeutic agents include plasmid expression vectors and viral expression vectors.

The DNA therapeutic agents described herein, e.g., DNA vectors, can include a variety of different features. The DNA therapeutic agents described herein, e.g., DNA vectors, can include a non-coding DNA sequence. For example, a DNA sequence can include at least one regulatory element for a gene, e.g., a promoter, enhancer, termination element, polyadenylation signal element, splicing signal element, and the like. In some embodiments, the non-coding DNA sequence is an intron. In some embodiments, the non-coding DNA sequence is a transposon. In some embodiments, a DNA sequence described herein can have a non-coding DNA sequence that is operatively linked to a gene that is transcriptionally active. In other embodiments, a DNA sequence described herein can have a non-coding DNA sequence that is not linked to a gene, i.e., the non-coding DNA does not regulate a gene on the DNA sequence.

In some embodiments, in the loaded LNP of the disclosure, the one or more therapeutic and/or prophylactic agents is a nucleic acid. In some embodiments, the one or more therapeutic and/or prophylactic agents is selected from the group consisting of a ribonucleic acid (RNA) and a deoxyribonucleic acid (DNA).

For example, in some embodiments, when the therapeutic and/or prophylactic agents is a DNA, the DNA is selected from the group consisting of a double-stranded DNA, a single-stranded DNA (ssDNA), a partially double-stranded DNA, a triple stranded DNA, and a partially triple-stranded DNA. In some embodiments, the DNA is selected from the group consisting of a circular DNA, a linear DNA, and mixtures thereof.

In some embodiments, in the loaded LNP of the disclosure, the one or more therapeutic and/or prophylactic agents is selected from the group consisting of a plasmid expression vector, a viral expression vector, and mixtures thereof.

For example, in some embodiments, when the therapeutic and/or prophylactic agents is a RNA, the RNA is selected from the group consisting of a single-stranded RNA, a double-stranded RNA (dsRNA), a partially double-stranded RNA, and mixtures thereof. In some embodiments, the RNA is selected from the group consisting of a circular RNA, a linear RNA, and mixtures thereof.

For example, in some embodiments, when the therapeutic and/or prophylactic agents is a RNA, the RNA is selected from the group consisting of a short interfering RNA (siRNA), an asymmetrical interfering RNA (aiRNA), a RNA interference (RNAi) molecule, a microRNA (miRNA), an antagomir, an antisense RNA, a ribozyme, a Dicer-substrate RNA (dsRNA), a small hairpin RNA (shRNA), a messenger RNA (mRNA), locked nucleic acids (LNAs) and CRISPR/Cas9 technology, and mixtures thereof.

For example, in some embodiments, when the therapeutic and/or prophylactic agents is a RNA, the RNA is selected from the group consisting of a small interfering RNA (siRNA), an asymmetrical interfering RNA (aiRNA), a microRNA (miRNA), a Dicer-substrate RNA (dsRNA), a small hairpin RNA (shRNA), a messenger RNA (mRNA), and mixtures thereof.

In some embodiments, the one or more therapeutic and/or prophylactic agents is an mRNA. In some embodiments, the one or more therapeutic and/or prophylactic agents is a modified mRNA (mmRNA).

In some embodiments, the one or more therapeutic and/or prophylactic agents is an mRNA that incorporates a micro-RNA binding site (miR binding site). Further, in some embodiments, an mRNA includes one or more of a stem loop, a chain terminating nucleoside, a polyA sequence, a polyadenylation signal, and/or a 5' cap structure.

An mRNA may be a naturally or non-naturally occurring mRNA. An mRNA may include one or more modified nucleobases, nucleosides, or nucleotides, as described below, in which case it may be referred to as a "modified mRNA" or "mmRNA." As described herein "nucleoside" is defined as a compound containing a sugar molecule (e.g., a pentose or ribose) or derivative thereof in combination with an organic base (e.g., a purine or pyrimidine) or a derivative thereof (also referred to herein as "nucleobase"). As described herein, "nucleotide" is defined as a nucleoside including a phosphate group.

An mRNA may include a 5' untranslated region (5'-UTR), a 3' untranslated region (3'-UTR), and/or a coding region (e.g., an open reading frame). An mRNA may include any suitable number of base pairs, including tens (e.g., 10, 20, 30, 40, 50, 60, 70, 80, 90 or 100), hundreds (e.g., 200, 300, 400, 500, 600, 700, 800, or 900) or thousands (e.g., 1000, 2000, 3000, 4000, 5000, 6000, 7000, 8000, 9000, 10,000) of base pairs. Any number (e.g., all, some, or none) of nucleobases, nucleosides, or nucleotides may be an analog of a canonical species, substituted, modified, or otherwise non-naturally occurring. In certain embodiments, all of a particular nucleobase type may be modified. In some embodiments, all uracils or uridines are modified. When all nucleobases, nucleosides, or nucleotides are modified, e.g., all uracils or uridines, the mRNA can be referred to as "fully modified", e.g., for uracil or uridine.

In some embodiments, an mRNA as described herein may include a 5' cap structure, a chain terminating nucleotide, optionally a Kozak sequence (also known as a Kozak consensus sequence), a stem loop, a polyA sequence, and/or a polyadenylation signal.

A 5' cap structure or cap species is a compound including two nucleoside moieties joined by a linker and may be selected from a naturally occurring cap, a non-naturally occurring cap or cap analog, or an anti-reverse cap analog (ARCA). A cap species may include one or more modified nucleosides and/or linker moieties. For example, a natural mRNA cap may include a guanine nucleotide and a guanine (G) nucleotide methylated at the 7 position joined by a triphosphate linkage at their 5' positions, e.g., m7G(5')ppp (5')G, commonly written as m7GpppG. A cap species may also be an anti-reverse cap analog. A non-limiting list of possible cap species includes m7GpppG, m7Gpppm7G, m73'dGpppG, m27, O3'GpppG, m27, O3'GppppG, m27, O2'GppppG, m7Gpppm7G, m73'dGpppG, m27, O3'GpppG, m27, O3'GppppG, and m27, O2'GppppG.

An mRNA may instead or additionally include a chain terminating nucleoside. For example, a chain terminating nucleoside may include those nucleosides deoxygenated at the 2' and/or 3' positions of their sugar group. Such species may include 3' deoxyadenosine (cordycepin), 3' deoxyuridine, 3' deoxycytosine, 3' deoxyguanosine, 3' deoxythymine, and 2',3' dideoxynucleosides, such as 2',3' dideoxyadenosine, 2',3' dideoxyuridine, 2',3' dideoxycytosine, 2',3' dideoxyguanosine, and 2',3' dideoxythymine. In some embodiments, incorporation of a chain terminating nucleotide into an mRNA, for example at the 3'-terminus, may result in stabilization of the mRNA.

An mRNA may instead or additionally include a stem loop, such as a histone stem loop. A stem loop may include 2, 3, 4, 5, 6, 7, 8, or more nucleotide base pairs. For example, a stem loop may include 4, 5, 6, 7, or 8 nucleotide base pairs. A stem loop may be located in any region of an mRNA. For example, a stem loop may be located in, before, or after an untranslated region (a 5' untranslated region or a 3' untranslated region), a coding region, or a polyA sequence or tail. In some embodiments, a stem loop may affect one or more function(s) of an mRNA, such as initiation of translation, translation efficiency, and/or transcriptional termination.

An mRNA may instead or additionally include a polyA sequence and/or polyadenylation signal. A polyA sequence may be comprised entirely or mostly of adenine nucleotides or analogs or derivatives thereof. A poly A sequence may also comprise stabilizing nucleotides or analogs. For example, a poly A sequence can include deoxythymidine, e.g., inverted (or reverse linkage) deoxythymidine (dT), as a stabilizing nucleotide or analog. Details on using inverted dT and other stabilizing poly A sequence modifications can be found, for example, in WO2017/049275 A2, the content of which is incorporated herein by reference. A polyA sequence may be a tail located adjacent to a 3' untranslated region of an mRNA. In some embodiments, a polyA sequence may affect the nuclear export, translation, and/or stability of an mRNA.

An mRNA may instead or additionally include a microRNA binding site. MicroRNA binding sites (or miR binding sites) can be used to regulate mRNA expression in various tissues or cell types. In exemplary embodiments, miR binding sites are engineered into 3' UTR sequences of an mRNA to regulate, e.g., enhance degradation of mRNA in cells or tissues expressing the cognate miR. Such regulation is useful to regulate or control "off-target" expression it mRNAs, i.e., expression in undesired cells or tissues in vivo. Details on using mir binding sites can be found, for example, in WO 2017/062513 A2, the content of which is incorporated herein by reference.

In some embodiments, an mRNA is a bicistronic mRNA comprising a first coding region and a second coding region with an intervening sequence comprising an internal ribosome entry site (IRES) sequence that allows for internal translation initiation between the first and second coding regions, or with an intervening sequence encoding a self-cleaving peptide, such as a 2A peptide. IRES sequences and 2A peptides are typically used to enhance expression of multiple proteins from the same vector. A variety of IRES sequences are known and available in the art and may be used, including, e.g., the encephalomyocarditis virus IRES.

In some embodiments, an mRNA of the disclosure comprises one or more modified nucleobases, nucleosides, or nucleotides (termed "modified mRNAs" or "mmRNAs"). In some embodiments, modified mRNAs may have useful properties, including enhanced stability, intracellular retention, enhanced translation, and/or the lack of a substantial induction of the innate immune response of a cell into which the mRNA is introduced, as compared to a reference unmodified mRNA. Therefore, use of modified mRNAs may enhance the efficiency of protein production, intracellular retention of nucleic acids, as well as possess reduced immunogenicity.

In some embodiments, an mRNA includes one or more (e.g., 1, 2, 3 or 4) different modified nucleobases, nucleosides, or nucleotides. In some embodiments, an mRNA includes one or more (e.g., 1, 2, 3, 4, 5, 6, 7, 8, 9, 10, 20, 30, 40, 50, 60, 70, 80, 90, 100, or more) different modified nucleobases, nucleosides, or nucleotides. In some embodiments, the modified mRNA may have reduced degradation in a cell into which the mRNA is introduced, relative to a corresponding unmodified mRNA.

In some embodiments, the modified nucleobase is a modified uracil. Exemplary nucleobases and nucleosides having a modified uracil include pseudouridine (ψ), pyridin-4-one ribonucleoside, 5-aza-uridine, 6-aza-uridine, 2-thio-5-aza-uridine, 2-thio-uridine (s2U), 4-thio-uridine (s4U), 4-thio-pseudouridine, 2-thio-pseudouridine, 5-hydroxy-uridine (ho5U), 5-aminoallyl-uridine, 5-halo-uridine (e.g., 5-iodo-uridine or 5-bromo-uridine), 3-methyl-uridine (m3U), 5-methoxy-uridine (mo5U), uridine 5-oxyacetic acid (cmo5U), uridine 5-oxyacetic acid methyl ester (mcmo5U), 5-carboxymethyl-uridine (cm5U), 1-carboxymethyl-pseudouridine, 5-carboxyhydroxymethyl-uridine (chm5U), 5-carboxyhydroxymethyl-uridine methyl ester (mchm5U), 5-methoxycarbonylmethyl-uridine (mcm5U), 5-methoxycarbonylmethyl-2-thio-uridine (mcm5s2U), 5-aminomethyl-2-thio-uridine (nm5s2U), 5-methylaminomethyl-uridine (mnm5U), 5-methylaminomethyl-2-thio-uridine (mnm5s2U), 5-methylaminomethyl-2-seleno-uridine (mnm5se2U), 5-carbamoylmethyl-uridine (ncm5U), 5-carboxymethylaminomethyl-uridine (cmnm5U), 5-carboxymethylaminomethyl-2-thio-uridine (cmnm5s2U), 5-propynyl-uridine, 1-propynyl-pseudouridine, 5-taurinomethyl-uridine (τm5U), 1-taurinomethyl-pseudouridine, 5-taurinomethyl-2-thio-uridine (τm5s2U), 1-taurinomethyl-4-thio-pseudouridine, 5-methyl-uridine (m5U, i.e., having the nucleobase deoxythymine), 1-methyl-pseudouridine (m1ψ), 5-methyl-2-thio-uridine (m5s2U), 1-methyl-4-thio-pseudouridine (m1s4ψ), 4-thio-1-methyl-pseudouridine, 3-methyl-pseudouridine (m3ψ), 2-thio-1-methyl-pseudouridine, 1-methyl-1-deaza-pseudouridine, 2-thio-1-methyl-1-deaza-pseudouridine, dihydrouridine (D), dihydropseudouridine, 5,6-dihydrouridine, 5-methyl-dihydrouridine (m5D), 2-thio-dihydrouridine, 2-thio-dihydropseudouridine, 2-methoxy-uridine, 2-methoxy-4-thio-uridine, 4-methoxy-pseudouridine, 4-methoxy-2-thio-pseudouridine, N1-methyl-pseudouridine, 3-(3-amino-3-carboxypropyl)uridine (acp3U), 1-methyl-3-(3-amino-3-carboxypropyl)pseudouridine (acp3 ψ), 5-(isopentenylaminomethyl)uridine (inm5U), 5-(isopentenylaminomethyl)-2-thio-uridine (inm5s2U), α-thio-uridine, 2'-O-methyl-uridine (Um), 5,2'-O-dimethyl-uridine (m5Um), 2'-O-methyl-pseudouridine (ψam), 2-thio-2'-O-methyl-uridine (s2Um), 5-methoxycarbonylmethyl-2'-O-methyl-uridine (mcm5Um), 5-carbamoylmethyl-2'-O-methyl-uridine (ncm5Um), 5-carboxymethylaminomethyl-2'-O-methyl-uridine (cmnm5Um), 3,2'-O-dimethyl-uridine (m3Um), and 5-(isopentenylaminomethyl)-2'-O-methyl-uridine (inm5Um), 1-thio-uridine, deoxythymidine, 2'-F-ara-uridine, 2'-F-uridine, 2'-OH-ara-uridine, 5-(2-carbomethoxyvinyl) uridine, and 5-[3-(1-E-propenylamino)] uridine.

In some embodiments, the modified nucleobase is a modified cytosine. Exemplary nucleobases and nucleosides having a modified cytosine include 5-aza-cytidine, 6-aza-cytidine, pseudoisocytidine, 3-methyl-cytidine (m3C), $N_4$-acetyl-cytidine (ac4C), 5-formyl-cytidine (f5C), $N_4$-methyl-cytidine (m4C), 5-methyl-cytidine (m5C), 5-halo-cytidine (e.g., 5-iodo-cytidine), 5-hydroxymethyl-cytidine (hm5C), 1-methyl-pseudoisocytidine, pyrrolo-cytidine, pyrrolo-pseudoisocytidine, 2-thio-cytidine (s2C), 2-thio-5-methyl-cytidine, 4-thio-pseudoisocytidine, 4-thio-1-methyl-pseudoisocytidine, 4-thio-1-methyl-1-deaza-pseudoisocytidine, 1-methyl-1-deaza-pseudoisocytidine, zebularine, 5-aza-zebularine, 5-methyl-zebularine, 5-aza-2-thio-zebularine, 2-thio-zebularine, 2-methoxy-cytidine, 2-methoxy-5-methyl-cytidine, 4-methoxy-pseudoisocytidine, 4-methoxy-1-methyl-pseudoisocytidine, lysidine (k2C), α-thio-cytidine, 2'-O-methyl-cytidine (Cm), 5,2'-O-dimethyl-cytidine (mSCm), $N_4$-acetyl-2'-O-methyl-cytidine (ac4Cm), $N_{4,2}$'-O-dimethyl-cytidine (m4Cm), 5-formyl-2'-O-methyl-cytidine (f5Cm), N4,N4,2'-O-trimethyl-cytidine (m42Cm), 1-thio-cytidine, 2'-F-ara-cytidine, 2'-F-cytidine, and 2'-0H-ara-cytidine.

In some embodiments, the modified nucleobase is a modified adenine. Exemplary nucleobases and nucleosides having a modified adenine include α-thio-adenosine, 2-amino-purine, 2, 6-diaminopurine, 2-amino-6-halo-purine (e.g., 2-amino-6-chloro-purine), 6-halo-purine (e.g., 6-chloro-purine), 2-amino-6-methyl-purine, 8-azido-adenosine, 7-deaza-adenine, 7-deaza-8-aza-adenine, 7-deaza-2-amino-purine, 7-deaza-8-aza-2-amino-purine, 7-deaza-2, 6-diaminopurine, 7-deaza-8-aza-2,6-diaminopurine, 1-methyl-adenosine (m1A), 2-methyl-adenine (m2A), N6-methyl-adenosine (m6A), 2-methylthio-N6-methyl-adenosine (ms2m6A), N6-isopentenyl-adenosine (i6A), 2-methylthio-N6-isopentenyl-adenosine (ms2i6A), N6-(cis-hydroxyisopentenyl)adenosine (io6A), 2-methylthio-N6-(cis-hydroxyisopentenyl)adenosine (ms2io6A), N6-glycinylcarbamoyl-adenosine (g6A), N6-threonylcarbamoyl-adenosine (t6A), N6-methyl-N6-threonylcarbamoyl-adenosine (m6t6A), 2-methylthio-N6-threonylcarbamoyl-adenosine (ms2g6A), N6,N6-dimethyl-adenosine (m62A), N6-hydroxynorvalylcarbamoyl-adenosine (hn6A), 2-methylthio-N6-hydroxynorvalylcarbamoyl-adenosine (ms2hn6A), N6-acetyl-adenosine (ac6A), 7-methyl-adenine, 2-methylthio-adenine, 2-methoxy-adenine, α-thio-adenosine, 2'-O-methyl-adenosine (Am), N6,2'-O-dimethyl-adenosine (m6Am), N6,N6,2'-O-trimethyl-adenosine (m62Am), 1,2'-O-dimethyl-adenosine (m1Am), 2'-O-ribosyladenosine (phosphate) (Ar(p)), 2-amino-N6-methyl-purine, 1-thio-adenosine, 8-azido-adenosine, 2'-F-ara-adenosine, 2'-F-adenosine, 2'-OH-ara-adenosine, and N6-(19-amino-pentaoxanonadecyl)-adenosine.

In some embodiments, the modified nucleobase is a modified guanine. Exemplary nucleobases and nucleosides having a modified guanine include a-thio-guanosine, inosine (I), 1-methyl-inosine (m1I), wyosine (imG), methylwyosine (mimG), 4-demethyl-wyosine (imG-14), isowyosine (imG2), wybutosine (yW), peroxywybutosine (o2yW), hydroxywybutosine (OhyW), undermodified hydroxywybutosine (OhyW*), 7-deaza-guanosine, queuosine (Q), epoxyqueuosine (oQ), galactosyl-queuosine (galQ), mannosyl-queuosine (manQ), 7-cyano-7-deaza-guanosine (preQ0), 7-aminomethyl-7-deaza-guanosine (preQ1), archaeosine (G+), 7-deaza-8-aza-guanosine, 6-thio-guanosine, 6-thio-7-deaza-guanosine, 6-thio-7-deaza-8-aza-guanosine, 7-methyl-guanosine (m7G), 6-thio-7-methyl-guanosine, 7-methyl-inosine, 6-methoxy-guanosine, 1-methyl-guanosine (m1G), N2-methyl-guanosine (m2G), N2,N2-dimethyl-guanosine (m22G), N2,7-dimethyl-guanosine (m2,7G), N2, N2,7-dimethyl-guanosine (m2,2,7G), 8-oxo-guanosine, 7-methyl-8-oxo-guanosine, 1-methyl-6-thio-guanosine, N2-methyl-6-thio-guanosine, N2,N2-dimethyl-6-thio-guanosine, α-thio-guanosine, 2'-O-methyl-guanosine (Gm), N2-methyl-2'-O-methyl-guanosine (m2Gm), N2,N2-dimethyl-2'-O-methyl-guanosine (m22Gm), 1-methyl-2'-O-methyl-guanosine (m1Gm), N2,7-dimethyl-2'-O-methyl-guanosine (m2,7Gm), 2'-O-methyl-inosine (Im), 1,2'-0-dimethyl-inosine (m1Im), 2'-O-ribosylguanosine (phosphate) (Gr(p)), 1-thio-guanosine, 06-methyl-guanosine, 2'-F-ara-guanosine, and 2'-F-guanosine.

In some embodiments, an mRNA of the disclosure includes a combination of one or more of the aforementioned modified nucleobases (e.g., a combination of 2, 3 or 4 of the aforementioned modified nucleobases.)

In some embodiments, the modified nucleobase is pseudouridine (ψ), N1-methylpseudouridine (m1ψ), 2-thiouridine, 4'-thiouridine, 5-methylcytosine, 2-thio-1-methyl-1-deaza-pseudouridine, 2-thio-1-methyl-pseudouridine, 2-thio-5-aza-uridine, 2-thio-dihydropseudouridine, 2-thio-dihydrouridine, 2-thio-pseudouridine, 4-methoxy-2-thio-pseudouridine, 4-methoxy-pseudouridine, 4-thio-1-methyl-pseudouridine, 4-thio-pseudouridine, 5-aza-uridine, dihydropseudouridine, 5-methoxyuridine, or 2'-O-methyl uridine. In some embodiments, an mRNA of the disclosure includes a combination of one or more of the aforementioned modified nucleobases (e.g., a combination of 2, 3 or 4 of the aforementioned modified nucleobases.) In some embodiments, the modified nucleobase is N1-methylpseudouridine (m1ψ) and the mRNA of the disclosure is fully modified with N1-methylpseudouridine (m1ψ). In some embodiments, N1-methylpseudouridine (m1ψ) represents from 75-100% of the uracils in the mRNA. In some embodiments, N1-methylpseudouridine (m1ψ) represents 100% of the uracils in the mRNA.

In some embodiments, the modified nucleobase is a modified cytosine. Exemplary nucleobases and nucleosides having a modified cytosine include $N_4$-acetyl-cytidine (ac4C), 5-methyl-cytidine (m5C), 5-halo-cytidine (e.g., 5-iodo-cytidine), 5-hydroxymethyl-cytidine (hm5C), 1-methyl-pseudoisocytidine, 2-thio-cytidine (s2C), 2-thio-5-methyl-cytidine. In some embodiments, an mRNA of the disclosure includes a combination of one or more of the aforementioned modified nucleobases (e.g., a combination of 2, 3 or 4 of the aforementioned modified nucleobases.)

In some embodiments, the modified nucleobase is a modified adenine. Exemplary nucleobases and nucleosides having a modified adenine include 7-deaza-adenine, 1-methyl-adenosine (m1A), 2-methyl-adenine (m2A), N6-methyl-adenosine (m6A). In some embodiments, an mRNA of the disclosure includes a combination of one or more of the aforementioned modified nucleobases (e.g., a combination of 2, 3 or 4 of the aforementioned modified nucleobases.)

In some embodiments, the modified nucleobase is a modified guanine. Exemplary nucleobases and nucleosides having a modified guanine include inosine (I), 1-methyl-inosine (m1I), wyosine (imG), methylwyosine (mimG), 7-deaza-guanosine, 7-cyano-7-deaza-guanosine (preQ0), 7-aminomethyl-7-deaza-guanosine (preQ1), 7-methyl-guanosine (m7G), 1-methyl-guanosine (m1G), 8-oxo-guanosine, 7-methyl-8-oxo-guanosine. In some embodiments, an mRNA of the disclosure includes a combination of one or more of the aforementioned modified nucleobases (e.g., a combination of 2, 3 or 4 of the aforementioned modified nucleobases.)

In some embodiments, the modified nucleobase is 1-methyl-pseudouridine (m1ψ), 5-methoxy-uridine (mo5U), 5-methyl-cytidine (m5C), pseudouridine (ψ), α-thio-guanosine, or α-thio-adenosine. In some embodiments, an mRNA of the disclosure includes a combination of one or more of the aforementioned modified nucleobases (e.g., a combination of 2, 3 or 4 of the aforementioned modified nucleobases.)

In some embodiments, the mRNA comprises pseudouridine (ψ). In some embodiments, the mRNA comprises pseudouridine (ψ) and 5-methyl-cytidine (m5C). In some embodiments, the mRNA comprises 1-methyl-pseudouridine (m1ψ). In some embodiments, the mRNA comprises 1-methyl-pseudouridine (m1ψ) and 5-methyl-cytidine (m5C). In some embodiments, the mRNA comprises 2-thiouridine (s2U). In some embodiments, the mRNA comprises 2-thiouridine and 5-methyl-cytidine (m5C). In some embodiments, the mRNA comprises 5-methoxy-uridine (mo5U). In some embodiments, the mRNA comprises 5-methoxy-uridine (mo5U) and 5-methyl-cytidine (m5C). In some embodiments, the mRNA comprises 2'-O-methyl uridine. In some embodiments, the mRNA comprises 2'-O-methyl uridine and 5-methyl-cytidine (m5C). In some embodiments, the mRNA comprises N6-methyl-adenosine (m6A). In some embodiments, the mRNA comprises N6-methyl-adenosine (m6A) and 5-methyl-cytidine (m5C).

In certain embodiments, an mRNA of the disclosure is uniformly modified (i.e., fully modified, modified throughout the entire sequence) for a particular modification. For example, an mRNA can be uniformly modified with N1-methylpseudouridine (m1ψ) or 5-methyl-cytidine (m5C), meaning that all uridines or all cytosine nucleosides in the mRNA sequence are replaced with N1-methylpseudouridine (m1ψ) or 5-methyl-cytidine (m5C). Similarly, mRNAs of the disclosure can be uniformly modified for any type of nucleoside residue present in the sequence by replacement with a modified residue such as those set forth above.

In some embodiments, an mRNA of the disclosure may be modified in a coding region (e.g., an open reading frame encoding a polypeptide). In other embodiments, an mRNA may be modified in regions besides a coding region. For example, in some embodiments, a 5'-UTR and/or a 3'-UTR are provided, wherein either or both may independently contain one or more different nucleoside modifications. In such embodiments, nucleoside modifications may also be present in the coding region.

The mmRNAs of the disclosure can include a combination of modifications to the sugar, the nucleobase, and/or the internucleoside linkage. These combinations can include any one or more modifications described herein.

Where a single modification is listed, the listed nucleoside or nucleotide represents 100 percent of that A, U, G or C nucleotide or nucleoside having been modified. Where percentages are listed, these represent the percentage of that particular A, U, G or C nucleobase triphosphate of the total amount of A, U, G, or C triphosphate present. For example, the combination: 25% 5-Aminoallyl-CTP+75% CTP/25% 5-Methoxy-UTP+75% UTP refers to a polynucleotide where 25% of the cytosine triphosphates are 5-Aminoallyl-CTP while 75% of the cytosines are CTP; whereas 25% of the uracils are 5-methoxy UTP while 75% of the uracils are UTP. Where no modified UTP is listed then the naturally occurring ATP, UTP, GTP and/or CTP is used at 100% of the sites of those nucleotides found in the polynucleotide. In this example all of the GTP and ATP nucleotides are left unmodified.

The mRNAs of the present disclosure, or regions thereof, may be codon optimized. Codon optimization methods are known in the art and may be useful for a variety of purposes: matching codon frequencies in host organisms to ensure proper folding, bias GC content to increase mRNA stability or reduce secondary structures, minimize tandem repeat codons or base runs that may impair gene construction or expression, customize transcriptional and translational control regions, insert or remove proteins trafficking sequences, remove/add post translation modification sites in encoded proteins (e.g., glycosylation sites), add, remove or shuffle protein domains, insert or delete restriction sites, modify ribosome binding sites and mRNA degradation sites, adjust translation rates to allow the various domains of the protein to fold properly, or to reduce or eliminate problem secondary structures within the polynucleotide. Codon optimization tools, algorithms and services are known in the art; non-limiting examples include services from GeneArt (Life Technologies), DNA2.0 (Menlo Park, CA) and/or proprietary methods. In some embodiments, the mRNA sequence is optimized using optimization algorithms, e.g., to optimize expression in mammalian cells or enhance mRNA stability.

In certain embodiments, the present disclosure includes polynucleotides having at least 80%, at least 85%, at least 90%, at least 95%, at least 98%, or at least 99% sequence identity to any of the polynucleotide sequences described herein.

mRNAs of the present disclosure may be produced by means available in the art, including but not limited to in vitro transcription (IVT) and synthetic methods. Enzymatic (IVT), solid-phase, liquid-phase, combined synthetic methods, small region synthesis, and ligation methods may be utilized. In some embodiments, mRNAs are made using IVT enzymatic synthesis methods. Accordingly, the present disclosure also includes polynucleotides, e.g., DNA, constructs and vectors that may be used to in vitro transcribe an mRNA described herein.

Non-natural modified nucleobases may be introduced into polynucleotides, e.g., mRNA, during synthesis or post-synthesis. In certain embodiments, modifications may be on internucleoside linkages, purine or pyrimidine bases, or sugar. In particular embodiments, the modification may be introduced at the terminal of a polynucleotide chain or anywhere else in the polynucleotide chain; with chemical synthesis or with a polymerase enzyme.

Either enzymatic or chemical ligation methods may be used to conjugate polynucleotides or their regions with different functional moieties, such as targeting or delivery agents, fluorescent labels, liquids, nanoparticles, etc. Therapeutic Agents for Reducing Protein Expression In some embodiments, the therapeutic agent is a therapeutic agent that reduces (i.e., decreases, inhibits, downregulates) protein expression. Non-limiting examples of types of therapeutic agents that can be used for reducing protein expression include mRNAs that incorporate a microRNA binding site(s) (miR binding site), microRNAs (miRNAs), antagomirs, small (short) interfering RNAs (siRNAs) (including shortmers and dicer-substrate RNAs), RNA interference (RNAi) molecules, antisense RNAs, ribozymes, small hairpin RNAs (shRNAs), locked nucleic acids (LNAs) and CRISPR/Cas9 technology.

Peptide/Polypeptide Therapeutic Agents

In some embodiments, the therapeutic agent is a peptide therapeutic agent. In some embodiments the therapeutic agent is a polypeptide therapeutic agent.

In some embodiments, the peptide or polypeptide is naturally-derived, e.g., isolated from a natural source. In other embodiments, the peptide or polypeptide is a synthetic molecule, e.g., a synthetic peptide or polypeptide produced in vitro. In some embodiments, the peptide or polypeptide is a recombinant molecule. In some embodiments, the peptide or polypeptide is a chimeric molecule. In some embodiments, the peptide or polypeptide is a fusion molecule. In some embodiments, the peptide or polypeptide therapeutic agent of the composition is a naturally occurring peptide or polypeptide. In some embodiments, the peptide or polypeptide therapeutic agent of the composition is a modified version of a naturally occurring peptide or polypeptide (e.g., contains less than 3, less than 5, less than 10, less than 15, less than 20, or less than 25 amino substitutions, deletions, or additions compared to its wild type, naturally occurring peptide or polypeptide counterpart).

In some embodiments, in the loaded LNP of the disclosure, the one or more therapeutic and/or prophylactic agents is a polynucleotide or a polypeptide.

Other Components

A lipid nanoparticle (e.g., an empty LNP or a loaded LNP) may include one or more components in addition to those described in the preceding sections. For example, a lipid nanoparticle (e.g., an empty LNP or a loaded LNP) may include one or more small hydrophobic molecules such as a vitamin (e.g., vitamin A or vitamin E) or a sterol.

Lipid nanoparticles (e.g., empty LNPs or loaded LNPs) may also include one or more permeability enhancer molecules, carbohydrates, polymers, surface altering agents, or other components. Carbohydrates may include simple sugars (e.g., glucose) and polysaccharides (e.g., glycogen and derivatives and analogs thereof).

A polymer may be included in and/or used to encapsulate or partially encapsulate a nanoparticle composition. A polymer may be biodegradable and/or biocompatible. A polymer may be selected from, but is not limited to, polyamines, polyethers, polyamides, polyesters, polycarbamates, polyureas, polycarbonates, polystyrenes, polyimides, polysulfones, polyurethanes, polyacetylenes, polyethylenes, polyethyleneimines, polyisocyanates, polyacrylates, polymethacrylates, polyacrylonitriles, and polyarylates. For example, a polymer may include poly(caprolactone) (PCL), ethylene vinyl acetate polymer (EVA), poly(lactic acid) (PLA), poly(L-lactic acid) (PLLA), poly(glycolic acid) (PGA), poly(lactic acid-co-glycolic acid) (PLGA), poly(L-lactic acid-co-glycolic acid) (PLLGA), poly(D,L-lactide) (PDLA), poly(L-lactide) (PLLA), poly(D,L-lactide-co-caprolactone), poly(D,L-lactide-co-caprolactone-co-glycolide), poly(D,L-lactide-co-PEO-co-D,L-lactide), poly(D,L-lactide-co-PPO-co-D,L-lactide), polyalkyl cyanoacrylate, polyurethane, poly-L-lysine (PLL), hydroxypropyl methacrylate (HPMA), polyethyleneglycol, poly-L-glutamic acid, poly(hydroxy acids), polyanhydrides, polyorthoesters, poly(ester amides), polyamides, poly(ester ethers), polycarbonates, polyalkylenes such as polyethylene and polypropylene, polyalkylene glycols such as poly(ethylene glycol) (PEG), polyalkylene oxides (PEO), polyalkylene terephthalates such as poly(ethylene terephthalate), polyvinyl alcohols (PVA), polyvinyl ethers, polyvinyl esters such as poly (vinyl acetate), polyvinyl halides such as poly(vinyl chloride) (PVC), polyvinylpyrrolidone (PVP), polysiloxanes, polystyrene (PS), polyurethanes, derivatized celluloses such as alkyl celluloses, hydroxyalkyl celluloses, cellulose ethers, cellulose esters, nitro celluloses, hydroxypropylcellulose, carboxymethylcellulose, polymers of acrylic acids, such as poly(methyl(meth)acrylate) (PMMA), poly(ethyl(meth)acrylate), poly(butyl(meth)acrylate), poly(isobutyl(meth)acrylate), poly(hexyl(meth)acrylate), poly(isodecyl(meth)acrylate), poly(lauryl(meth)acrylate), poly(phenyl(meth)acrylate), poly(methyl acrylate), poly(isopropyl acrylate), poly(isobutyl acrylate), poly(octadecyl acrylate) and copolymers and mixtures thereof, polydioxanone and its copolymers, polyhydroxyalkanoates, polypropylene fumarate, polyoxymethylene, poloxamers, polyoxamines, poly(ortho)esters, poly(butyric acid), poly (valeric acid), poly(lactide-co-caprolactone), trimethylene carbonate, poly(N-acryloylmorpholine) (PAcM), poly(2-methyl-2-oxazoline) (PMOX), poly(2-ethyl-2-oxazoline) (PEOZ), and polyglycerol.

Surface altering agents may include, but are not limited to, anionic proteins (e.g., bovine serum albumin), surfactants (e.g., cationic surfactants such as dimethyldioctadecyl-ammonium bromide), sugars or sugar derivatives (e.g., cyclodextrin), nucleic acids, polymers (e.g., heparin, polyethylene glycol, and poloxamer), mucolytic agents (e.g., acetylcysteine, mugwort, bromelain, papain, clerodendrum, bromhexine, carbocisteine, eprazinone, mesna, ambroxol, sobrerol, domiodol, letosteine, stepronin, tiopronin, gelsolin, thymosin β4, dornase alfa, neltenexine, and erdosteine), and DNases (e.g., rhDNase). A surface altering agent may be disposed within a nanoparticle and/or on the surface of a lipid nanoparticle (e.g., an empty LNP or a loaded LNP) (e.g., by coating, adsorption, covalent linkage, or other process).

A lipid nanoparticle (e.g., an empty LNP or a loaded LNP) may also comprise one or more functionalized lipids. For example, a lipid may be functionalized with an alkyne group that, when exposed to an azide under appropriate reaction conditions, may undergo a cycloaddition reaction. In particular, a lipid bilayer may be functionalized in this fashion with one or more groups useful in facilitating membrane permeation, cellular recognition, or imaging. The surface of a lipid nanoparticle (e.g., an empty LNP or a loaded LNP) may also be conjugated with one or more useful antibodies. Functional groups and conjugates useful in targeted cell delivery, imaging, and membrane permeation are well known in the art.

In addition to these components, lipid nanoparticles (e.g., empty LNPs or loaded LNPs) may include any substance useful in pharmaceutical compositions. For example, the lipid nanoparticle (e.g., an empty LNP or a loaded LNP) may include one or more pharmaceutically acceptable excipients or accessory ingredients such as, but not limited to, one or more solvents, dispersion media, diluents, dispersion aids, suspension aids, granulating aids, disintegrants, fillers, glidants, liquid vehicles, binders, surface active agents, isotonic agents, thickening or emulsifying agents, buffering agents, lubricating agents, oils, preservatives, and other species. Excipients such as waxes, butters, coloring agents, coating agents, flavorings, and perfuming agents may also be included.

Examples of diluents may include, but are not limited to, calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, and/or combinations thereof. Granulating and dispersing agents may be selected from the non-limiting list consisting of potato starch, corn starch, tapioca starch, sodium starch glycolate, clays, alginic acid, guar gum, citrus pulp, agar, bentonite, cellulose and wood products, natural sponge, cation-exchange resins, calcium carbonate, silicates, sodium carbonate, cross-linked poly(vinyl-pyrrolidone) (crospovidone), sodium carboxymethyl starch (sodium starch glycolate), carboxymethyl cellulose, cross-linked sodium carboxymethyl cellulose (croscarmellose), methylcellulose, pregelatinized starch (starch 1500), microcrystalline starch, water insoluble starch, calcium carboxymethyl cellulose, magnesium aluminum silicate (VEEGUM®), sodium lauryl sulfate, quaternary ammonium compounds, and/or combinations thereof.

Surface active agents and/or emulsifiers may include, but are not limited to, natural emulsifiers (e.g. acacia, agar, alginic acid, sodium alginate, tragacanth, chondrux, cholesterol, xanthan, pectin, gelatin, egg yolk, casein, wool fat, cholesterol, wax, and lecithin), colloidal clays (e.g. bentonite [aluminum silicate] and VEEGUM® [magnesium aluminum silicate]), long chain amino acid derivatives, high molecular weight alcohols (e.g. stearyl alcohol, cetyl alcohol, oleyl alcohol, triacetin monostearate, ethylene glycol distearate, glyceryl monostearate, and propylene glycol monostearate, polyvinyl alcohol), carbomers (e.g. carboxy polymethylene, polyacrylic acid, acrylic acid polymer, and carboxyvinyl polymer), carrageenan, cellulosic derivatives (e.g. carboxymethylcellulose sodium, powdered cellulose, hydroxymethyl cellulose, hydroxypropyl cellulose, hydroxypropyl methylcellulose, methylcellulose), sorbitan fatty acid esters (e.g. polyoxyethylene sorbitan monolaurate [TWEEN® 20], polyoxyethylene sorbitan [TWEEN® 60], polyoxyethylene sorbitan monooleate [TWEEN® 80], sorbitan monopalmitate [SPAN® 40], sorbitan monostearate [SPAN® 60], sorbitan tristearate [SPAN® 65], glyceryl monooleate, sorbitan monooleate [SPAN® 80]), polyoxyethylene esters (e.g. polyoxyethylene monostearate [MYRJ® 45], polyoxyethylene hydrogenated castor oil, polyethoxylated castor oil, polyoxymethylene stearate, and SOLUTOL®), sucrose fatty acid esters, polyethylene glycol fatty acid esters (e.g. CREMOPHOR®), polyoxyethylene ethers, (e.g. polyoxyethylene lauryl ether [BRIJ® 30]), poly(vinyl-pyrrolidone), diethylene glycol monolaurate, triethanolamine oleate, sodium oleate, potassium oleate, ethyl oleate, oleic acid, ethyl laurate, sodium lauryl sulfate, PLURONIC® F 68, POLOXAMER® 188, cetrimonium bromide, cetylpyridinium chloride, benzalkonium chloride, docusate sodium, and/or combinations thereof.

A binding agent may be starch (e.g. cornstarch and starch paste); gelatin; sugars (e.g. sucrose, glucose, dextrose, dextrin, molasses, lactose, lactitol, mannitol); natural and synthetic gums (e.g., acacia, sodium alginate, extract of Irish moss, panwar gum, ghatti gum, mucilage of isapol husks, carboxymethylcellulose, methylcellulose, ethylcellulose, hydroxyethylcellulose, hydroxypropyl cellulose, hydroxypropyl methylcellulose, microcrystalline cellulose, cellulose acetate, poly(vinyl-pyrrolidone), magnesium aluminum silicate (VEEGUM®), and larch arabogalactan); alginates; polyethylene oxide; polyethylene glycol; inorganic calcium salts; silicic acid; polymethacrylates; waxes; water; alcohol; and combinations thereof, or any other suitable binding agent.

Examples of preservatives may include, but are not limited to, antioxidants, chelating agents, antimicrobial preservatives, antifungal preservatives, alcohol preservatives, acidic preservatives, and/or other preservatives. Examples of antioxidants include, but are not limited to, alpha tocopherol, ascorbic acid, ascorbyl palmitate, butylated hydroxyanisole, butylated hydroxytoluene, monothioglycerol, potassium metabisulfite, propionic acid, propyl gallate, sodium ascorbate, sodium bisulfite, sodium metabisulfite, and/or sodium sulfite. Examples of chelating agents include ethylenediaminetetraacetic acid (EDTA), citric acid monohydrate, disodium edetate, dipotassium edetate, edetic acid, fumaric acid, malic acid, phosphoric acid, sodium edetate, tartaric acid, and/or trisodium edetate. Examples of antimicrobial preservatives include, but are not limited to, benzalkonium chloride, benzethonium chloride, benzyl alcohol, bronopol, cetrimide, cetylpyridinium chloride, chlorhexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, and/or thimerosal. Examples of antifungal preservatives include, but are not limited to, butyl paraben, methyl paraben, ethyl paraben, propyl paraben, benzoic acid, hydroxybenzoic acid, potassium benzoate, potassium sorbate, sodium benzoate, sodium propionate, and/or sorbic acid. Examples of alcohol preservatives include, but are not limited to, ethanol, polyethylene glycol, benzyl alcohol, phenol, phenolic compounds, bisphenol, chlorobutanol, hydroxybenzoate, and/or phenylethyl alcohol. Examples of acidic preservatives include, but are not limited to, vitamin A, vitamin C, vitamin E, beta-carotene, citric acid, acetic acid, dehydroascorbic acid, ascorbic acid, sorbic acid, and/or phytic acid. Other preservatives include, but are not limited to, tocopherol, tocopherol acetate, deteroxime mesylate, cetrimide, butylated hydroxyanisole (BHA), butylated hydroxytoluene (BHT), ethylenediamine, sodium lauryl sulfate (SLS), sodium lauryl ether sulfate (SLES), sodium bisulfite, sodium metabisulfite, potassium sulfite, potassium metabisulfite, GLYDANT PLUS®, PHENONIP®, methylparaben, GERMALL® 115, GERMABEN® II, NEOLONE™, KATHON™, and/or EUXYL®.

Examples of buffering agents include, but are not limited to, citrate buffer solutions, acetate buffer solutions, phosphate buffer solutions, ammonium chloride, calcium carbonate, calcium chloride, calcium citrate, calcium glubionate, calcium gluceptate, calcium gluconate, d-gluconic acid, calcium glycerophosphate, calcium lactate, calcium lactobionate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, amino-sulfonate buffers (e.g., HEPES), magnesium hydroxide, aluminum hydroxide, alginic acid, pyrogen-free water, isotonic saline, Ringer's solution, ethyl alcohol, and/or combinations thereof. Lubricating agents may selected from the non-limiting group consisting of magnesium stearate, calcium stearate, stearic acid, silica, talc, malt, glyceryl behenate, hydrogenated vegetable oils, polyethylene glycol, sodium benzoate, sodium acetate, sodium chloride, leucine, magnesium lauryl sulfate, sodium lauryl sulfate, and combinations thereof.

Examples of oils include, but are not limited to, almond, apricot kernel, avocado, babassu, bergamot, black current seed, borage, cade, chamomile, canola, caraway, carnauba, castor, cinnamon, cocoa butter, coconut, cod liver, coffee, corn, cotton seed, emu, eucalyptus, evening primrose, fish, flaxseed, geraniol, gourd, grape seed, hazel nut, hyssop, isopropyl myristate, jojoba, kukui nut, lavandin, lavender, lemon, litsea cubeba, macademia nut, mallow, mango seed, meadowfoam seed, mink, nutmeg, olive, orange, orange roughy, palm, palm kernel, peach kernel, peanut, poppy seed, pumpkin seed, rapeseed, rice bran, rosemary, safflower, sandalwood, sasquana, savoury, sea buckthorn, sesame, shea butter, silicone, soybean, sunflower, tea tree, thistle, tsubaki, vetiver, walnut, and wheat germ oils as well as butyl stearate, caprylic triglyceride, capric triglyceride, cyclomethicone, diethyl sebacate, dimethicone 360, simethicone, isopropyl myristate, mineral oil, octyldodecanol, oleyl alcohol, silicone oil, and/or combinations thereof.

Formulations

Lipid nanoparticles (e.g., empty LNPs or loaded LNPs) may include a lipid component and one or more additional components, such as a therapeutic and/or prophylactic. A lipid nanoparticle (e.g., an empty LNP or a loaded LNP) may be designed for one or more specific applications or targets. The elements of a lipid nanoparticle (e.g., an empty LNP or a loaded LNP) may be selected based on a particular application or target, and/or based on the efficacy, toxicity, expense, ease of use, availability, or other feature of one or more elements. Similarly, the particular formulation of a nanoparticle composition may be selected for a particular application or target according to, for example, the efficacy and toxicity of particular combinations of elements.

The lipid component of a nanoparticle composition may include, for example, a lipid according to Formula (I), (I-1), (A), (A-1), (A-1a), or (A-1b), a phospholipid (such as an unsaturated lipid, e.g., DOPE or DSPC), a PEG lipid, and a structural lipid. The elements of the lipid component may be provided in specific fractions.

In some embodiments, the lipid component of a nanoparticle composition includes a lipid according to Formula (I), (I-1), (A), (A-1), (A-1a), or (A-1b), a phospholipid, a PEG lipid, and a structural lipid. In certain embodiments, the lipid component of the nanoparticle composition includes about 30 mol % to about 60 mol % compound of Formula (I), (I-1), (A), (A-1), (A-1a), or (A-1b), about 0 mol % to about 30 mol % phospholipid, about 18.5 mol % to about 48.5 mol % structural lipid, and about 0 mol % to about 10 mol % of PEG lipid, provided that the total mol % does not exceed 100%. In some embodiments, the lipid component of the nanoparticle composition includes about 35 mol % to about 55 mol % compound of Formula (I), (I-1), (A), (A-1), (A-1a), or (A-1b), about 5 mol % to about 25 mol % phospholipid, about 30 mol % to about 40 mol % structural lipid, and about 0 mol % to about 10 mol % of PEG lipid. In a particular embodiment, the lipid component includes about 50 mol % said compound, about 10 mol % phospholipid, about 38.5 mol % structural lipid, and about 1.5 mol % of PEG lipid. In another particular embodiment, the lipid component includes about 40 mol % said compound, about 20 mol % phospholipid, about 38.5 mol % structural lipid, and about 1.5 mol % of PEG lipid. In some embodiments, the phospholipid may be DOPE or DSPC. In other embodiments, the PEG lipid may be PEG-1, or $PEG_{2k}$-DMG and/or the structural lipid may be cholesterol.

In some embodiments an empty lipid nanoparticle (empty LNP) comprises a compound of Formula (I), (I-1), (A), (A-1), (A-1a), or (A-1b), a phospholipid, a structural lipid, and a PEG lipid.

In some embodiments a loaded lipid nanoparticle (loaded LNP) comprises a compound of Formula (I), (I-1), (A), (A-1), (A-1a), or (A-1b), a phospholipid, a structural lipid, a PEG lipid, and one or more therapeutic and/or prophylactic agents.

In some embodiments, the empty LNP or loaded LNP comprises the compound of Formula (I), (I-1), (A), (A-1), (A-1a), or (A-1b), in an amount from about 40% to about 60%.

In some embodiments, the empty LNP or loaded LNP comprises the phospholipid in an amount from about 0% to about 20%. For example, in some embodiments, the empty LNP or loaded LNP comprises DSPC in an amount from about 0% to about 20%.

In some embodiments, the empty LNP or loaded LNP comprises the structural lipid in an amount from about 30% to about 50%. For example, in some embodiments, the empty LNP or loaded LNP comprises cholesterol in an amount from about 30% to about 50%.

In some embodiments, the empty LNP or loaded LNP comprises the PEG lipid in an amount from about 0% to about 5%. For example, in some embodiments, the empty LNP or loaded LNP comprises PEG-1 or $PEG_{2k}$-DMG in an amount from about 0% to about 5%.

In some embodiments, the empty LNP or loaded LNP comprises about 40 mol % to about 60 mol % of the compound of Formula (I), (I-1), (A), (A-1), (A-1a), or (A-1b), about 0 mol % to about 20 mol % phospholipid, about 30 mol % to about 50 mol % structural lipid, and about 0 mol % to about 5 mol % PEG lipid.

In some embodiments, the empty LNP or loaded LNP comprises about 40 mol % to about 60 mol % of the compound of Formula (I), (I-1), (A), (A-1), (A-1a), or (A-1b), about 0 mol % to about 20 mol % DSPC, about 30 mol % to about 50 mol % cholesterol, and about 0 mol % to about 5 mol % $PEG_{2k}$-DMG. In some embodiments, the empty LNP or loaded LNP comprises about 40 mol % to about 60 mol % of the compound of Table 1, about 0 mol % to about 20 mol % DSPC, about 30 mol % to about 50 mol % cholesterol, and about 0 mol % to about 5 mol % $PEG_{2k}$-DMG.

In some embodiments, the empty LNP or loaded LNP comprises about 40 mol % to about 60 mol % of the compound of Formula (I), (I-1), (A), (A-1), (A-1a), or (A-1b), about 0 mol % to about 20 mol % DSPC, about 30 mol % to about 50 mol % cholesterol, and about 0 mol % to about 5 mol % PEG-1. In some embodiments, the empty LNP or loaded LNP comprises about 40 mol % to about 60 mol % of the compound of Table 1, about 0 mol % to about 20 mol % DSPC, about 30 mol % to about 50 mol % cholesterol, and about 0 mol % to about 5 mol % PEG-1.

In some embodiments, the empty LNP or loaded LNP comprises a compound of Formula (I), (I-1), (A), (A-1), (A-1a), or (A-1b), a phospholipid, a structural lipid, and a PEG lipid, wherein the phospholipid is DSPC and the structural lipid is cholesterol. In some embodiments, the empty LNP or loaded LNP comprises a compound of Table 1, a phospholipid, a structural lipid, and a PEG lipid, wherein the phospholipid is DSPC and the structural lipid is cholesterol.

In some embodiments, the empty LNP or loaded LNP comprises a compound of Formula (I), (I-1), (A), (A-1), (A-1a), or (A-1b), a phospholipid, a structural lipid, and a PEG lipid, wherein the structural lipid is cholesterol and the PEG lipid is $PEG_{2k}$-DMG. In some embodiments, the empty LNP or loaded LNP comprises a compound of Table 1, a phospholipid, a structural lipid, and a PEG lipid, wherein the structural lipid is cholesterol and the PEG lipid is $PEG_{2k}$-DMG.

In some embodiments, the empty LNP or loaded LNP comprises a compound of Formula (I), (I-1), (A), (A-1), (A-1a), or (A-1b), a phospholipid, a structural lipid, and a PEG lipid, wherein the structural lipid is cholesterol and the PEG lipid is PEG-1. In some embodiments, the empty LNP or loaded LNP comprises a compound of Table 1 a phospholipid, a structural lipid, and a PEG lipid, wherein the structural lipid is cholesterol and the PEG lipid is PEG-1.

In some embodiments, the empty LNP or loaded LNP comprises a compound of Formula (I), (I-1), (A), (A-1), (A-1a), or (A-1b), a phospholipid, a structural lipid, and a PEG lipid, wherein the phospholipid is DSPC and the PEG lipid is $PEG_{2k}$-DMG. In some embodiments, the empty LNP or loaded LNP comprises a compound of Table 1, a phospholipid, a structural lipid, and a PEG lipid, wherein the phospholipid is DSPC and the PEG lipid is $PEG_{2k}$-DMG.

In some embodiments, the empty LNP or loaded LNP comprises a compound of Formula (I), (I-1), (A), (A-1), (A-1a), or (A-1b), a phospholipid, a structural lipid, and a PEG lipid, wherein the phospholipid is DSPC and the PEG lipid is PEG-1. In some embodiments, the empty LNP or loaded LNP comprises a compound of Table 1, a phospholipid, a structural lipid, and a PEG lipid, wherein the phospholipid is DSPC and the PEG lipid is PEG-1.

In some embodiments, the empty LNP or loaded LNP comprises a compound of Formula (I), (I-1), (A), (A-1), (A-1a), or (A-1b), a phospholipid, a structural lipid, and a PEG lipid, wherein the phospholipid is DSPC, the structural lipid is cholesterol, and the PEG lipid is $PEG_{2k}$-DMG. In some embodiments, the empty LNP or loaded LNP comprises a compound of Table 1, a phospholipid, a structural lipid, and a PEG lipid, wherein the phospholipid is DSPC, the structural lipid is cholesterol, and the PEG lipid is $PEG_{2k}$-DMG.

In some embodiments, the empty LNP or loaded LNP comprises a compound of Formula (A-1), a phospholipid, a structural lipid, and a PEG lipid, wherein the phospholipid is DSPC, the structural lipid is cholesterol, and the PEG lipid is $PEG_{2k}$-DMG. In some embodiments, the empty LNP or loaded LNP comprises a compound of Table 1, a phospholipid, a structural lipid, and a PEG lipid, wherein the phospholipid is DSPC, the structural lipid is cholesterol, and the PEG lipid is $PEG_{2k}$-DMG.

In some embodiments, the empty LNP or loaded LNP comprises a compound of Formula (I), (I-1), (A), (A-1), (A-1a), or (A-1b), a phospholipid, a structural lipid, and a PEG lipid, wherein the phospholipid is DSPC, the structural lipid is cholesterol, and the PEG lipid is PEG-1.

In some embodiments, the empty LNP or loaded LNP comprises a compound of Formula (A-1), a phospholipid, a structural lipid, and a PEG lipid, wherein the phospholipid is DSPC, the structural lipid is cholesterol, and the PEG lipid is PEG-1. In some embodiments, the empty LNP or loaded LNP comprises a compound of Table 1, a phospholipid, a structural lipid, and a PEG lipid, wherein the phospholipid is DSPC, the structural lipid is cholesterol, and the PEG lipid is PEG-1.

Lipid nanoparticles (e.g., empty LNPs or loaded LNPs) may be designed for one or more specific applications or targets. For example, a nanoparticle composition may be designed to deliver a therapeutic and/or prophylactic such as an RNA to a particular cell, tissue, organ, or system or group thereof in a mammal's body. Physiochemical properties of lipid nanoparticles (e.g., empty LNPs or loaded LNPs) may be altered in order to increase selectivity for particular bodily targets. For instance, particle sizes may be adjusted based on the fenestration sizes of different organs. The therapeutic and/or prophylactic included in a nanoparticle composition may also be selected based on the desired delivery target or targets. For example, a therapeutic and/or prophylactic may be selected for a particular indication, condition, disease, or disorder and/or for delivery to a particular cell, tissue, organ, or system or group thereof (e.g., localized or specific delivery). In certain embodiments, a nanoparticle composition may include an mRNA encoding a polypeptide of interest capable of being translated within a cell to produce the polypeptide of interest. Such a composition may be designed to be specifically delivered to a particular organ. In some embodiments, a composition may be designed to be specifically delivered to a mammalian liver.

The amount of a therapeutic and/or prophylactic in a nanoparticle composition may depend on the size, composition, desired target and/or application, or other properties of the nanoparticle composition as well as on the properties of the therapeutic and/or prophylactic. For example, the amount of an RNA useful in a nanoparticle composition may depend on the size, sequence, and other characteristics of the RNA. The relative amounts of a therapeutic and/or prophylactic and other elements (e.g., lipids) in a nanoparticle composition may also vary. In some embodiments, the wt/wt ratio of the lipid component to a therapeutic and/or prophylactic in a nanoparticle composition may be from about 5:1 to about 60:1, such as 5:1, 6:1, 7:1, 8:1, 9:1, 10:1, 11:1, 12:1, 13:1, 14:1, 15:1, 16:1, 17:1, 18:1, 19:1, 20:1, 25:1, 30:1, 35:1, 40:1, 45:1, 50:1, and 60:1. For example, the wt/wt ratio of the lipid component to a therapeutic and/or prophylactic may be from about 10:1 to about 40:1. In certain embodiments, the wt/wt ratio is about 20:1.

The amount of a therapeutic and/or prophylactic in a nanoparticle composition may, for example, be measured using absorption spectroscopy (e.g., ultraviolet-visible spectroscopy).

In some embodiments, a nanoparticle composition includes one or more RNAs, and the one or more RNAs, lipids, and amounts thereof may be selected to provide a specific N:P ratio. The N:P ratio of the composition refers to the molar ratio of nitrogen atoms in one or more lipids to the number of phosphate groups in an RNA. In general, a lower N:P ratio is preferred. The one or more RNA, lipids, and amounts thereof may be selected to provide an N:P ratio from about 2:1 to about 30:1, such as 2:1, 3:1, 4:1, 5:1, 6:1, 7:1, 8:1, 9:1, 10:1, 12:1, 14:1, 16:1, 18:1, 20:1, 22:1, 24:1, 26:1, 28:1, or 30:1. In certain embodiments, the N:P ratio may be from about 2:1 to about 8:1. In other embodiments, the N:P ratio is from about 5:1 to about 8:1. For example, the N:P ratio may be about 5.0:1, about 5.5:1, about 5.67:1, about 6.0:1, about 6.5:1, or about 7.0:1. For example, the N:P ratio may be about 5.67:1.

Physical Properties

The characteristics of a lipid nanoparticle (e.g., an empty LNP or a loaded LNP) may depend on the components thereof. For example, a lipid nanoparticle (e.g., an empty LNP or a loaded LNP) including cholesterol as a structural lipid may have different characteristics than a lipid nanoparticle (e.g., an empty LNP or a loaded LNP) that includes a different structural lipid. Similarly, the characteristics of a lipid nanoparticle (e.g., an empty LNP or a loaded LNP) may depend on the absolute or relative amounts of its components. For instance, a lipid nanoparticle (e.g., an empty LNP or a loaded LNP) including a higher molar fraction of a phospholipid may have different characteristics than a lipid nanoparticle (e.g., an empty LNP or a loaded LNP) including a lower molar fraction of a phospholipid. Characteristics may also vary depending on the method and conditions of preparation of the nanoparticle composition.

Lipid nanoparticles (e.g., empty LNPs or loaded LNPs) may be characterized by a variety of methods. For example, microscopy (e.g., transmission electron microscopy or scanning electron microscopy) may be used to examine the morphology and size distribution of a nanoparticle composition. Dynamic light scattering or potentiometry (e.g., potentiometric titrations) may be used to measure zeta potentials. Dynamic light scattering may also be utilized to determine particle sizes. Instruments such as the Zetasizer Nano ZS (Malvern Instruments Ltd, Malvern, Worcestershire, UK) may also be used to measure multiple characteristics of a nanoparticle composition, such as particle size, polydispersity index, and zeta potential.

The mean size of a lipid nanoparticle (e.g., an empty LNP or a loaded LNP) may be between 10s of nm and 100s of nm, e.g., measured by dynamic light scattering (DLS). For example, the mean size may be from about 40 nm to about 150 nm, such as about 40 nm, 45 nm, 50 nm, 55 nm, 60 nm, 65 nm, 70 nm, 75 nm, 80 nm, 85 nm, 90 nm, 95 nm, 100 nm, 105 nm, 110 nm, 115 nm, 120 nm, 125 nm, 130 nm, 135 nm, 140 nm, 145 nm, or 150 nm. In some embodiments, the mean size of a lipid nanoparticle (e.g., an empty LNP or a loaded LNP) may be from about 50 nm to about 100 nm, from about 50 nm to about 90 nm, from about 50 nm to about 80 nm, from about 50 nm to about 70 nm, from about 50 nm to about 60 nm, from about 60 nm to about 100 nm, from about 60 nm to about 90 nm, from about 60 nm to about 80 nm, from about 60 nm to about 70 nm, from about 70 nm to about 150 nm, from about 70 nm to about 130 nm, from about 70 nm to about 100 nm, from about 70 nm to about 90 nm, from about 70 nm to about 80 nm, from about 80 nm to about 150 nm, from about 80 nm to about 130 nm, from about 80 nm to about 100 nm, from about 80 nm to about 90 nm, from about 90 nm to about 150 nm, from about 90 nm to about 130 nm, or from about 90 nm to about 100 nm. In certain embodiments, the mean size of a lipid nanoparticle (e.g., an empty LNP or a loaded LNP) may from about 70 nm to about 130 nm or be from about 70 nm to about 100 nm. In a particular embodiment, the mean size may be about 80 nm. In other embodiments, the mean size may be about 100 nm. In other embodiments, the mean size may be about 120 nm.

A lipid nanoparticle (e.g., an empty LNP or a loaded LNP) may be relatively homogenous. A polydispersity index may be used to indicate the homogeneity of a nanoparticle composition, e.g., the particle size distribution of the lipid nanoparticles (e.g., empty LNPs or loaded LNPs). A small (e.g., less than 0.3) polydispersity index generally indicates a narrow particle size distribution. A lipid nanoparticle (e.g., an empty LNP or a loaded LNP) may have a polydispersity index from about 0 to about 0.25, such as 0.01, 0.02, 0.03, 0.04, 0.05, 0.06, 0.07, 0.08, 0.09, 0.10, 0.11, 0.12, 0.13, 0.14, 0.15, 0.16, 0.17, 0.18, 0.19, 0.20, 0.21, 0.22, 0.23, 0.24, or 0.25. In some embodiments, the polydispersity index of a lipid nanoparticle (e.g., an empty LNP or a loaded LNP) may be from about 0.10 to about 0.20.

The zeta potential of a lipid nanoparticle (e.g., an empty LNP or a loaded LNP) may be used to indicate the electrokinetic potential of the composition. For example, the zeta potential may describe the surface charge of a nanoparticle composition. Lipid nanoparticles (e.g., empty LNPs or loaded LNPs) with relatively low charges, positive or negative, are generally desirable, as more highly charged species may interact undesirably with cells, tissues, and other elements in the body. In some embodiments, the zeta potential of a lipid nanoparticle (e.g., an empty LNP or a loaded LNP) may be from about −10 mV to about +20 mV, from about −10 mV to about +15 mV, from about −10 mV to about +10 mV, from about −10 mV to about +5 mV, from about −10 mV to about 0 mV, from about −10 mV to about −5 mV, from about −5 mV to about +20 mV, from about −5 mV to about +15 mV, from about −5 mV to about +10 mV, from about −5 mV to about +5 mV, from about −5 mV to about 0 mV, from about 0 mV to about +20 mV, from about 0 mV to about +15 mV, from about 0 mV to about +10 mV, from about 0 mV to about +5 mV, from about +5 mV to about +20 mV, from about +5 mV to about +15 mV, or from about +5 mV to about +10 mV.

The efficiency of encapsulation of a therapeutic and/or prophylactic describes the amount of therapeutic and/or prophylactic that is encapsulated or otherwise associated with a lipid nanoparticle (e.g., an empty LNP or a loaded LNP) after preparation, relative to the initial amount provided. The encapsulation efficiency is desirably high (e.g., close to 100%). The encapsulation efficiency may be measured, for example, by comparing the amount of therapeutic and/or prophylactic in a solution containing the lipid nanoparticle (e.g., an empty LNP or a loaded LNP) before and after breaking up the lipid nanoparticle (e.g., an empty LNP or a loaded LNP) with one or more organic solvents or detergents. Fluorescence may be used to measure the amount of free therapeutic and/or prophylactic (e.g., RNA) in a solution. For the lipid nanoparticles (e.g., empty LNPs or loaded LNPs) described herein, the encapsulation efficiency of a therapeutic and/or prophylactic may be at least 50%, for example 50%, 55%, 60%, 65%, 70%, 75%, 80%, 85%, 90%, 91%, 92%, 93%, 94%, 95%, 96%, 97%, 98%, 99%, or 100%. In some embodiments, the encapsulation efficiency may be at least 80%. In certain embodiments, the encapsulation efficiency may be at least 90%. In some embodiments, the encapsulation efficiency of the therapeutic and/or prophylactic agent is between 80% and 100%.

Pharmaceutical Compositions

Lipid nanoparticles (e.g., empty LNPs or loaded LNPs) may be formulated in whole or in part as pharmaceutical compositions. Pharmaceutical compositions may include one or more lipid nanoparticles (e.g., empty LNPs or loaded LNPs). In one embodiment, a pharmaceutical composition comprises a population of lipid nanoparticles (e.g., empty LNPs or loaded LNPs). For example, a pharmaceutical composition may include one or more lipid nanoparticles (e.g., empty LNPs or loaded LNPs) including one or more different therapeutic and/or prophylactics. Pharmaceutical compositions may further include one or more pharmaceutically acceptable excipients or accessory ingredients such as those described herein. General guidelines for the formulation and manufacture of pharmaceutical compositions and agents are available, for example, in Remington's *The Science and Practice of Pharmacy,* $21^{st}$ Edition, A. R. Gennaro; Lippincott, Williams & Wilkins, Baltimore, MD, 2006. Conventional excipients and accessory ingredients may be used in any pharmaceutical composition, except insofar as any conventional excipient or accessory ingredient may be incompatible with one or more components of a nanoparticle composition. An excipient or accessory ingredient may be incompatible with a component of a lipid nanoparticle (e.g., an empty LNP or a loaded LNP) if its combination with the component may result in any undesirable biological effect or otherwise deleterious effect.

In some embodiments, one or more excipients or accessory ingredients may make up greater than 50% of the total mass or volume of a pharmaceutical composition including a nanoparticle composition. For example, the one or more excipients or accessory ingredients may make up 50%, 60%, 70%, 80%, 90%, or more of a pharmaceutical convention. In some embodiments, a pharmaceutically acceptable excipient is at least 95%, at least 96%, at least 97%, at least 98%, at least 99%, or 100% pure. In some embodiments, an excipient is approved for use in humans and for veterinary use. In some embodiments, an excipient is approved by United States Food and Drug Administration. In some embodiments, an excipient is pharmaceutical grade. In some embodiments, an excipient meets the standards of the United States Pharmacopoeia (USP), the European Pharmacopoeia (EP), the British Pharmacopoeia, and/or the International Pharmacopoeia.

Relative amounts of the one or more lipid nanoparticles (e.g., empty LNPs or loaded LNPs), the one or more pharmaceutically acceptable excipients, and/or any additional ingredients in a pharmaceutical composition in accordance with the present disclosure will vary, depending upon the identity, size, and/or condition of the subject treated and further depending upon the route by which the composition is to be administered. By way of example, a pharmaceutical composition may comprise between 0.1% and 100% (wt/wt) of one or more lipid nanoparticles (e.g., empty LNPs or loaded LNPs).

In certain embodiments, the lipid nanoparticles (e.g., empty LNPs or loaded LNPs) and/or pharmaceutical compositions of the disclosure are refrigerated or frozen for storage and/or shipment (e.g., being stored at a temperature of 4° C. or lower, such as a temperature between about −150° C. and about 0° C. or between about −80° C. and about −20° C. (e.g., about −5° C., −10° C., −15° C., −20° C., −25° C., −30° C., −40° C., −50° C., −60° C., −70° C., −80° C., −90° C., −130° C. or −150° C.). For example, the pharmaceutical composition comprising a compound of any of Formulae (I), (I-1), (A), (A-1), (A-1a), or (A-1b) is a solution that is refrigerated for storage and/or shipment at, for example, about −20° C., −30° C., −40° C., −50° C., −60° C., −70° C., or −80° C. In certain embodiments, the disclosure also relates to a method of increasing stability of the lipid nanoparticles (e.g., empty LNPs or loaded LNPs) and/or pharmaceutical compositions comprising a compound of any of Formulae (I), (I-1), (A), (A-1), (A-1a), or (A-1b) by storing the lipid nanoparticles (e.g., empty LNPs or loaded LNPs) and/or pharmaceutical compositions at a temperature of 4° C. or lower, such as a temperature between about −150° C. and about 0° C. or between about −80° C. and about −20° C., e.g., about −5° C., −10° C., −15° C., −20° C., −25° C., −30° C., −40° C., −50° C., −60° C., −70° C., −80° C., −90° C., −130° C. or −150° C.). For example, the lipid nanoparticles (e.g., empty LNPs or loaded LNPs) and/or pharmaceutical compositions disclosed herein are stable for about at least 1 week, at least 2 weeks, at least 3 weeks, at least 4 weeks, at least 5 weeks, at least 6 weeks, at least 1 month, at least 2 months, at least 4 months, at least 6 months, at least 8 months, at least 10 months, at least 12 months, at least 14 months, at least 16 months, at least 18 months, at least 20 months, at least 22 months, or at least 24 months, e.g., at a temperature of 4° C. or lower (e.g., between about 4° C. and −20° C.). In some embodiments, the formulation is stabilized for at least 4 weeks at about 4° C. In certain embodiments, the pharmaceutical composition of the disclosure comprises a lipid nanoparticle (e.g., an empty LNP or a loaded LNP) disclosed herein and a pharmaceutically acceptable carrier selected from one or more of Tris, an acetate (e.g., sodium acetate), an citrate (e.g., sodium citrate), saline, PBS, and sucrose. In certain embodiments, the pharmaceutical composition of the disclosure has a pH value between about 7 and 8 (e.g., 6.8 6.9, 7.0, 7.1, 7.2, 7.3, 7.4, 7.5, 7.6, 7.7, 7.8, 7.9 or 8.0, or between 7.5 and 8 or between 7 and 7.8). For example, a pharmaceutical composition of the disclosure comprises a lipid nanoparticle (e.g., an empty LNP or a loaded LNP) disclosed herein, Tris, saline and sucrose, and has a pH of about 7.5-8, which is suitable for storage and/or shipment at, for example, about −20° C. For example, a pharmaceutical composition of the disclosure comprises a lipid nanoparticle (e.g., an empty LNP or a loaded LNP) disclosed herein and PBS and has a pH of about 7-7.8, suitable for storage and/or shipment at, for example, about 4° C. or lower. "Stability," "stabilized," and "stable" in the context of the present disclosure refers to the resistance of lipid nanoparticles (e.g., empty LNPs or loaded LNPs) and/or pharmaceutical compositions disclosed herein to chemical or physical changes (e.g., degradation, particle size change, aggregation, change in encapsulation, etc.) under given manufacturing, preparation, transportation, storage and/or in-use conditions, e.g., when stress is applied such as shear force, freeze/thaw stress, etc.

In some embodiments, a pharmaceutical composition of the disclosure comprises a empty LNP or a loaded LNP, a cryoprotectant, a buffer, or a combination thereof.

In some embodiments, the cryoprotectant comprises one or more cryoprotective agents, and each of the one or more cryoprotective agents is independently a polyol (e.g., a diol or a triol such as propylene glycol (i.e., 1,2-propanediol), 1,3-propanediol, glycerol, (+/−)-2-methyl-2,4-pentanediol, 1,6-hexanediol, 1,2-butanediol, 2,3-butanediol, ethylene glycol, or diethylene glycol), a nondetergent sulfobetaine (e.g., NDSB-201 (3-(1-pyridino)-1-propane sulfonate), an osmolyte (e.g., L-proline or trimethylamine N-oxide dihydrate), a polymer (e.g., polyethylene glycol 200 (PEG 200), PEG 400, PEG 600, PEG 1000, $PEG_{2k}$-DMG, PEG 3350, PEG 4000, PEG 8000, PEG 10000, PEG 20000, polyethylene glycol monomethyl ether 550 (mPEG 550), mPEG 600, mPEG 2000, mPEG 3350, mPEG 4000, mPEG 5000, polyvinylpyrrolidone (e.g., polyvinylpyrrolidone K 15), pentaerythritol propoxylate, or polypropylene glycol P 400), an organic solvent (e.g., dimethyl sulfoxide (DMSO) or ethanol), a sugar (e.g., D-(+)-sucrose, D-sorbitol, trehalose, D-(+)-maltose monohydrate, meso-erythritol, xylitol, myo-inositol, D-(+)-raffinose pentahydrate, D-(+)-trehalose dihydrate, or D-(+)-glucose monohydrate), or a salt (e.g., lithium acetate, lithium chloride, lithium formate, lithium nitrate, lithium sulfate, magnesium acetate, sodium acetate, sodium chloride, sodium formate, sodium malonate, sodium nitrate, sodium sulfate, or any hydrate thereof), or any combination thereof. In some embodiments, the cryoprotectant comprises sucrose. In some embodiments, the cryoprotectant and/or excipient is sucrose. In some embodiments, the cryoprotectant comprises sodium acetate. In some embodiments, the cryoprotectant and/or excipient is sodium acetate. In some embodiments, the cryoprotectant comprises sucrose and sodium acetate.

In some embodiments, wherein the buffer is selected from the group consisting of an acetate buffer, a citrate buffer, a phosphate buffer, a tris buffer, and combinations thereof.

Lipid nanoparticles (e.g., empty LNPs or loaded LNPs) and/or pharmaceutical compositions including one or more lipid nanoparticles (e.g., empty LNPs or loaded LNPs) may be administered to any patient or subject, including those patients or subjects that may benefit from a therapeutic effect provided by the delivery of a therapeutic and/or prophylactic to one or more particular cells, tissues, organs, or systems or groups thereof. Although the descriptions provided herein of lipid nanoparticles (e.g., empty LNPs or loaded LNPs) and pharmaceutical compositions including lipid nanoparticles (e.g., empty LNPs or loaded LNPs) are principally directed to compositions which are suitable for administration to humans, it will be understood by the skilled artisan that such compositions are generally suitable for administration to any other mammal. Modification of compositions suitable for administration to humans in order to render the compositions suitable for administration to various animals is well understood, and the ordinarily skilled veterinary pharmacologist can design and/or perform such modification with merely ordinary, if any, experimentation. Subjects to which administration of the compositions is contemplated include, but are not limited to, humans, other primates, and other mammals, including commercially relevant mammals such as cattle, pigs, hoses, sheep, cats, dogs, mice, and/or rats. The subject lipid nanoparticles can also be employed for in vitro and ex vivo uses.

A pharmaceutical composition including one or more lipid nanoparticles (e.g., empty LNPs or loaded LNPs) may be prepared by any method known or hereafter developed in the art of pharmacology. In general, such preparatory methods include bringing the active ingredient into association with an excipient and/or one or more other accessory ingredients, and then, if desirable or necessary, dividing, shaping, and/or packaging the product into a desired single- or multi-dose unit.

A pharmaceutical composition in accordance with the present disclosure may be prepared, packaged, and/or sold in bulk, as a single unit dose, and/or as a plurality of single unit doses. As used herein, a "unit dose" is discrete amount of the pharmaceutical composition comprising a predetermined amount of the active ingredient (e.g., nanoparticle composition). The amount of the active ingredient is generally equal to the dosage of the active ingredient which would be administered to a subject and/or a convenient fraction of such a dosage such as, for example, one-half or one-third of such a dosage.

Pharmaceutical compositions may be prepared in a variety of forms suitable for a variety of routes and methods of administration. For example, pharmaceutical compositions may be prepared in liquid dosage forms (e.g., emulsions, microemulsions, nanoemulsions, solutions, suspensions, syrups, and elixirs), injectable forms, solid dosage forms (e.g., capsules, tablets, pills, powders, and granules), dosage forms for topical and/or transdermal administration (e.g., ointments, pastes, creams, lotions, gels, powders, solutions, sprays, inhalants, and patches), suspensions, powders, and other forms.

Liquid dosage forms for oral and parenteral administration include, but are not limited to, pharmaceutically acceptable emulsions, microemulsions, nanoemulsions, solutions, suspensions, syrups, and/or elixirs. In addition to active ingredients, liquid dosage forms may comprise inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, oral compositions can include additional therapeutic and/or prophylactics, additional agents such as wetting agents, emulsifying and suspending agents, sweetening, flavoring, and/or perfuming agents. In certain embodiments for parenteral administration, compositions are mixed with solubilizing agents such as Cremophor®, alcohols, oils, modified oils, glycols, polysorbates, cyclodextrins, polymers, and/or combinations thereof.

Injectable preparations, for example, sterile injectable aqueous or oleaginous suspensions may be formulated according to the known art using suitable dispersing agents, wetting agents, and/or suspending agents. Sterile injectable preparations may be sterile injectable solutions, suspensions, and/or emulsions in nontoxic parenterally acceptable diluents and/or solvents, for example, as a solution in 1,3-butanediol. Among the acceptable vehicles and solvents that may be employed are water, Ringer's solution, U.S.P., and isotonic sodium chloride solution. Sterile, fixed oils are conventionally employed as a solvent or suspending medium. For this purpose any bland fixed oil can be employed including synthetic mono- or diglycerides. Fatty acids such as oleic acid can be used in the preparation of injectables.

Injectable formulations can be sterilized, for example, by filtration through a bacterial-retaining filter, and/or by incorporating sterilizing agents in the form of sterile solid compositions which can be dissolved or dispersed in sterile water or other sterile injectable medium prior to use.

In order to prolong the effect of an active ingredient, it is often desirable to slow the absorption of the active ingredient from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle. Injectable depot forms are made by forming microencapsulated matrices of the drug in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly(anhydrides). Depot injectable formulations are prepared by entrapping the drug in liposomes or microemulsions which are compatible with body tissues.

Compositions for rectal or vaginal administration are typically suppositories which can be prepared by mixing compositions with suitable non-irritating excipients such as cocoa butter, polyethylene glycol or a suppository wax which are solid at ambient temperature but liquid at body temperature and therefore melt in the rectum or vaginal cavity and release the active ingredient.

Solid dosage forms for oral administration include capsules, tablets, pills, films, powders, and granules. In such solid dosage forms, an active ingredient is mixed with at least one inert, pharmaceutically acceptable excipient such as sodium citrate or dicalcium phosphate and/or fillers or extenders (e.g. starches, lactose, sucrose, glucose, mannitol, and silicic acid), binders (e.g., carboxymethylcellulose, alginates, gelatin, polyvinylpyrrolidinone, sucrose, and acacia), humectants (e.g., glycerol), disintegrating agents (e.g., agar, calcium carbonate, potato or tapioca starch, alginic acid, certain silicates, and sodium carbonate), solution retarding agents (e.g., paraffin), absorption accelerators (e.g., quaternary ammonium compounds), wetting agents (e.g., cetyl alcohol and glycerol monostearate), absorbents (e.g., kaolin and bentonite clay, silicates), and lubricants (e.g., talc, calcium stearate, magnesium stearate, solid polyethylene glycols, sodium lauryl sulfate), and mixtures thereof. In the case of capsules, tablets and pills, the dosage form may comprise buffering agents.

Solid compositions of a similar type may be employed as fillers in soft and hard-filled gelatin capsules using such excipients as lactose or milk sugar as well as high molecular weight polyethylene glycols and the like. Solid dosage forms of tablets, dragees, capsules, pills, and granules can be prepared with coatings and shells such as enteric coatings and other coatings well known in the pharmaceutical formulating art. They may optionally comprise opacifying agents and can be of a composition that they release the active ingredient(s) only, or preferentially, in a certain part of the intestinal tract, optionally, in a delayed manner. Examples of embedding compositions which can be used include polymeric substances and waxes. Solid compositions of a similar type may be employed as fillers in soft and hard-filled gelatin capsules using such excipients as lactose or milk sugar as well as high molecular weight polyethylene glycols and the like.

Dosage forms for topical and/or transdermal administration of a composition may include ointments, pastes, creams, lotions, gels, powders, solutions, sprays, inhalants, and/or patches. Generally, an active ingredient is admixed under sterile conditions with a pharmaceutically acceptable excipient and/or any needed preservatives and/or buffers as may be required. Additionally, the present disclosure contemplates the use of transdermal patches, which often have the added advantage of providing controlled delivery of a compound to the body. Such dosage forms may be prepared, for example, by dissolving and/or dispensing the compound in the proper medium. Alternatively or additionally, rate may be controlled by either providing a rate controlling membrane and/or by dispersing the compound in a polymer matrix and/or gel.

Suitable devices for use in delivering intradermal pharmaceutical compositions described herein include short needle devices. Intradermal compositions may be administered by devices which limit the effective penetration length of a needle into the skin. Jet injection devices which deliver liquid compositions to the dermis via a liquid jet injector and/or via a needle which pierces the stratum corneum and produces a jet which reaches the dermis are suitable. Ballistic powder/particle delivery devices which use compressed gas to accelerate vaccine in powder form through the outer layers of the skin to the dermis are suitable. Alternatively or additionally, conventional syringes may be used in the classical mantoux method of intradermal administration.

Formulations suitable for topical administration include, but are not limited to, liquid and/or semi liquid preparations such as liniments, lotions, oil in water and/or water in oil emulsions such as creams, ointments and/or pastes, and/or solutions and/or suspensions. Topically-administrable formulations may, for example, comprise from about 1% to about 10% (wt/wt) active ingredient, although the concentration of active ingredient may be as high as the solubility limit of the active ingredient in the solvent. Formulations for topical administration may further comprise one or more of the additional ingredients described herein.

A pharmaceutical composition may be prepared, packaged, and/or sold in a formulation suitable for pulmonary administration via the buccal cavity. Such a formulation may comprise dry particles which comprise the active ingredient. Such compositions are conveniently in the form of dry powders for administration using a device comprising a dry powder reservoir to which a stream of propellant may be directed to disperse the powder and/or using a self-propelling solvent/powder dispensing container such as a device comprising the active ingredient dissolved and/or suspended in a low-boiling propellant in a sealed container. Dry powder compositions may include a solid fine powder diluent such as sugar and are conveniently provided in a unit dose form.

Low boiling propellants generally include liquid propellants having a boiling point of below 65° F. at atmospheric pressure. Generally the propellant may constitute 50% to 99.9% (wt/wt) of the composition, and active ingredient may constitute 0.1% to 20% (wt/wt) of the composition. A propellant may further comprise additional ingredients such as a liquid non-ionic and/or solid anionic surfactant and/or a solid diluent (which may have a particle size of the same order as particles comprising the active ingredient).

Pharmaceutical compositions formulated for pulmonary delivery may provide an active ingredient in the form of droplets of a solution and/or suspension. Such formulations may be prepared, packaged, and/or sold as aqueous and/or dilute alcoholic solutions and/or suspensions, optionally sterile, comprising active ingredient, and may conveniently be administered using any nebulization and/or atomization device. Such formulations may further comprise one or more additional ingredients including, but not limited to, a flavoring agent such as saccharin sodium, a volatile oil, a buffering agent, a surface active agent, and/or a preservative such as methylhydroxybenzoate. Droplets provided by this route of administration may have an average diameter in the range from about 1 nm to about 200 nm.

Formulations described herein as being useful for pulmonary delivery are useful for intranasal delivery of a pharmaceutical composition. Another formulation suitable for intranasal administration is a coarse powder comprising the active ingredient and having an average particle from about 0.2 μm to 500 μm. Such a formulation is administered in the manner in which snuff is taken, i.e. by rapid inhalation through the nasal passage from a container of the powder held close to the nose.

Formulations suitable for nasal administration may, for example, comprise from about as little as 0.1% (wt/wt) and as much as 100% (wt/wt) of active ingredient, and may comprise one or more of the additional ingredients described herein. A pharmaceutical composition may be prepared, packaged, and/or sold in a formulation suitable for buccal administration. Such formulations may, for example, be in the form of tablets and/or lozenges made using conventional methods, and may, for example, 0.1% to 20% (wt/wt) active ingredient, the balance comprising an orally dissolvable and/or degradable composition and, optionally, one or more of the additional ingredients described herein. Alternately, formulations suitable for buccal administration may comprise a powder and/or an aerosolized and/or atomized solution and/or suspension comprising active ingredient. Such powdered, aerosolized, and/or aerosolized formulations, when dispersed, may have an average particle and/or droplet size in the range from about 0.1 nm to about 200 nm, and may further comprise one or more of any additional ingredients described herein.

A pharmaceutical composition may be prepared, packaged, and/or sold in a formulation suitable for ophthalmic administration. Such formulations may, for example, be in the form of eye drops including, for example, a 0.1/1.0% (wt/wt) solution and/or suspension of the active ingredient in an aqueous or oily liquid excipient. Such drops may further comprise buffering agents, salts, and/or one or more other of any additional ingredients described herein. Other ophthalmically-administrable formulations which are useful include those which comprise the active ingredient in microcrystalline form and/or in a liposomal preparation. Ear drops and/or eye drops are contemplated as being within the scope of this present disclosure.

mRNA Therapies mRNA as a drug modality has the potential to deliver secreted proteins as well as intracellular proteins and transmembrane proteins. mRNA as a drug modality has the potential to deliver transmembrane and intracellular proteins, i.e., targets that standard biologics are unable to access owing to their inability to cross the cell membrane when delivered in protein form. One major challenge to making mRNA based therapies a reality is the identification of an optimal delivery vehicle. Due to its large size, chemical instability and potential immunogenicity, mRNA requires a delivery vehicle that can offer protection from endo- and exo-nucleases, as well as shield the cargo from immune sentinels. Lipid nanoparticles (LNPs) have been identified as a leading option in this regard.

Key performance criteria for a lipid nanoparticle delivery system are to maximize cellular uptake and enable efficient release of mRNA from the endosome. In one embodiment, the subject LNPs comprising the novel lipids disclosed herein, demonstrate improvements in at least one of cellular uptake and endosomal release. At the same time the LNP must provide a stable drug product and be able to be dosed safely at therapeutically relevant levels. LNPs are multi-component systems which typically consist of an amino lipid, phospholipid, cholesterol, and a PEG-lipid. Each component is required for aspects of efficient delivery of the nucleic acid cargo and stability of the particle. The key component thought to drive cellular uptake, endosomal escape, and tolerability is the amino lipid. Cholesterol and the PEG-lipid contribute to the stability of the drug product both in vivo and on the shelf, while the phospholipid provides additional fusogenicity to the LNP, thus helping to drive endosomal escape and rendering the nucleic acid bioavailable in the cytosol of cells.

Several amino lipid series have been developed for oligonucleotide delivery over the past couple of decades, including the amino lipid MC3 (DLin-MC3-DMA). MC3-based LNPs have been shown to be effective in delivering mRNA. LNPs of this class are quickly opsonized by apolipoprotein E (ApoE) when delivered intravenously, which enables cellular uptake by the low density lipoprotein receptor (LDLr). However, concerns remain that MC3's long tissue half-life could contribute to unfavorable side effects hindering its use for chronic therapies. In addition, extensive literature evidence suggests that chronic dosing of lipid nanoparticles can produce several toxic sides effects including complement activation-related pseudo allergy (CARPA) and liver damage. Hence, to unleash the potential of mRNA and other nucleic acid, nucleotide or peptide based therapies for humans, a class of LNPs with increased delivery efficiency along with a metabolic and toxicity profile that would enable chronic dosing in humans is needed.

The ability to treat a broad swath of diseases requires the flexibility to safely dose chronically at varying dose levels. Through systematic optimization of the amino lipid structure, the compounds of the disclosure were identified as compounds that balance chemical stability, improved efficiency of delivery due to improved endosomal escape, rapid in vivo metabolism, and a clean toxicity profile. The combination of these features provides a drug candidate that can be dosed chronically without activation of the immune system. Initial rodent screens led to the identification of a lead lipid with good delivery efficiency and pharmacokinetics. The lead LNP was profiled further in non-human primate for efficiency of delivery after single and repeat dosing. Finally, the optimized LNPs were evaluated in one-month repeat dose toxicity studies in rat and non-human primate. Without wishing to be bound by theory, the novel ionizable lipids of the instant disclosure have the improved cellular delivery, improved protein expression, and improved biodegradability properties that can lead to greater than 2 fold, 5 fold, 10 fold, 15 fold, or 20 fold increase in mRNA expression in cells as compared to LNPs which lack a lipid of the invention. In another embodiment, an LNP comprising a lipid of the invention can result in specific (e.g., preferential) delivery to a certain cell type or types as compared other cell types, thereby resulting in a greater than 2 fold, 5 fold, 10 fold, 15 fold, or 20 fold increase in mRNA expression in certain cells or tissues as compared to LNPs which lack a lipid of the invention. These improvements over the art allow for the safe and effective use of mRNA-based therapies in acute and chronic diseases.

Methods

In some aspects, the disclosure provides a method of delivering a therapeutic and/or prophylactic to a cell (e.g., a mammalian cell). This method includes the step of contacting the cell with a loaded LNP or a pharmaceutical composition of the disclosure, whereby the therapeutic and/or prophylactic is delivered to the cell. In some embodiments, the cell is in a subject and the contacting comprises administering the cell to the subject. In some embodiments, the method comprises the step of administering to the subject a lipid nanoparticle comprising a compound of Formula (I), (I-1), (A), (A-1), (A-1a), or (A-1b), a phospholipid, a structural lipid, a PEG lipid, and one or more therapeutic and/or prophylactic agents, whereby the therapeutic and/or prophylactic is delivered to the cell.

In some embodiments, the disclosure provides a method of delivering a therapeutic and/or prophylactic to a cell within a subject, wherein the method comprises the step of administering to the subject a lipid nanoparticle comprising a compound of Formula (I), (I-1), (A), (A-1), (A-1a), or (A-1b), DSPC, cholesterol, and $PEG_{2k}$-DMG, and one or more therapeutic and/or prophylactic agents selected from a nucleotide, a polypeptide, and a nucleic acid (e.g., an RNA).

For example, in some embodiments, the disclosure provides a method of delivering a therapeutic and/or prophylactic to a cell within a subject, wherein the method comprises the step of administering to the subject a lipid nanoparticle comprising a compound of Formula (A-1), DSPC, cholesterol, and $PEG_{2k}$-DMG, and one or more therapeutic and/or prophylactic agents selected from a nucleotide, a polypeptide, and a nucleic acid (e.g., an RNA).

In some embodiments, the disclosure provides a method of delivering a therapeutic and/or prophylactic to a cell within a subject, wherein the method comprises the step of administering to the subject a lipid nanoparticle comprising a compound of Formula (I), (I-1), (A), (A-1), (A-1a), or (A-1b), DSPC, cholesterol, and PEG-1, and one or more therapeutic and/or prophylactic agents selected from a nucleotide, a polypeptide, and a nucleic acid (e.g., an RNA). For example, in some embodiments, the disclosure provides a method of delivering a therapeutic and/or prophylactic to a cell within a subject, wherein the method comprises the step of administering to the subject a lipid nanoparticle comprising a compound of Formula (A-1), DSPC, cholesterol, and PEG-1, and one or more therapeutic and/or prophylactic agents selected from a nucleotide, a polypeptide, and a nucleic acid (e.g., an RNA).

In some aspects, the disclosure provides a method of delivering (e.g., specifically delivering) a therapeutic and/or prophylactic to a mammalian organ or tissue (e.g., a liver, kidney, spleen, or lung). This method includes the step of contacting the cell with a loaded LNP or a pharmaceutical composition of the disclosure, whereby the therapeutic and/or prophylactic is delivered to the target organ or tissue. In some embodiments, the method comprises the step of administering to the subject a lipid nanoparticle comprising a compound of Formula (I), (I-1), (A), (A-1), (A-1a), or (A-1b), a phospholipid, a structural lipid, a PEG lipid, and one or more therapeutic and/or prophylactic agents, whereby the therapeutic and/or prophylactic is delivered to the target organ or tissue.

In some embodiments, the disclosure provides a method of specifically delivering a therapeutic and/or prophylactic to an organ of a subject, wherein the method comprises the step of administering to the subject a lipid nanoparticle comprising a compound of Formula (I), (I-1), (A), (A-1), (A-1a), or (A-1b), DSPC, cholesterol, and $PEG_{2k}$-DMG, and one or more therapeutic and/or prophylactic agents selected from a nucleotide, a polypeptide, and a nucleic acid (e.g., an RNA). For example, in some embodiments, the disclosure provides a method of specifically delivering a therapeutic and/or prophylactic to an organ of a subject, wherein the method comprises the step of administering to the subject a lipid nanoparticle comprising a compound of Formula (A-1), DSPC, cholesterol, and $PEG_{2k}$-DMG, and one or more therapeutic and/or prophylactic agents selected from a nucleotide, a polypeptide, and a nucleic acid (e.g., an RNA).

In some embodiments, the disclosure provides a method of specifically delivering a therapeutic and/or prophylactic to an organ of a subject, wherein the method comprises the step of administering to the subject a lipid nanoparticle comprising a compound of Formula (I), (I-1), (A), (A-1), (A-1a), or (A-1b), DSPC, cholesterol, and PEG-1, and one or more therapeutic and/or prophylactic agents selected from a nucleotide, a polypeptide, and a nucleic acid (e.g., an RNA). For example, in some embodiments, the disclosure provides a method of specifically delivering a therapeutic and/or prophylactic to an organ of a subject, wherein the method comprises the step of administering to the subject a lipid nanoparticle comprising a compound of Formula (A-1), DSPC, cholesterol, and PEG-1, and one or more therapeutic and/or prophylactic agents selected from a nucleotide, a polypeptide, and a nucleic acid (e.g., an RNA).

In some aspects, the disclosure features a method for the enhanced delivery of a therapeutic and/or prophylactic (e.g., an mRNA) to a target tissue (e.g., a liver, spleen, or lung). This method includes the step of contacting the cell with a loaded LNP or a pharmaceutical composition of the disclosure, whereby the therapeutic and/or prophylactic is delivered to the target tissue (e.g., a liver, kidney, spleen, or lung). In some embodiments, the method comprises the step of administering to the subject a lipid nanoparticle comprising a compound of Formula (I), (I-1), (A), (A-1), (A-1a), or (A-1b), a phospholipid, a structural lipid, a PEG lipid, and one or more therapeutic and/or prophylactic agents, whereby the therapeutic and/or prophylactic is delivered to the target tissue (e.g., a liver, kidney, spleen, or lung).

In some embodiments, the disclosure provides a method for the enhanced delivery of a therapeutic and/or prophylactic to a target tissue, wherein the method comprises the step of administering to the subject a lipid nanoparticle comprising a compound of Formula (I), (I-1), (A), (A-1), (A-1a), or (A-1b), DSPC, cholesterol, and $PEG_{2k}$-DMG, and one or more therapeutic and/or prophylactic agents selected from a nucleotide, a polypeptide, and a nucleic acid (e.g., an RNA). For example, in some embodiments, the disclosure provides a method for the enhanced delivery of a therapeutic and/or prophylactic to a target tissue, wherein the method comprises the step of administering to the subject a lipid nanoparticle comprising a compound of Formula (A-1), DSPC, cholesterol, and $PEG_{2k}$-DMG, and one or more therapeutic and/or prophylactic agents selected from a nucleotide, a polypeptide, and a nucleic acid (e.g., an RNA).

In some embodiments, the disclosure provides a method for the enhanced delivery of a therapeutic and/or prophylactic to a target tissue, wherein the method comprises the step of administering to the subject a lipid nanoparticle comprising a compound of Formula (I), (I-1), (A), (A-1), (A-1a), or (A-1b), DSPC, cholesterol, and PEG-1, and one or more therapeutic and/or prophylactic agents selected from a nucleotide, a polypeptide, and a nucleic acid (e.g., an RNA). For example, in some embodiments, the disclosure provides a method for the enhanced delivery of a therapeutic and/or prophylactic to a target tissue, wherein the method comprises the step of administering to the subject a lipid nanoparticle comprising a compound of Formula (A-1), DSPC, cholesterol, and PEG-1, and one or more therapeutic and/or prophylactic agents selected from a nucleotide, a polypeptide, and a nucleic acid (e.g., an RNA).

In some aspects, the disclosure provides a method of producing a polypeptide of interest in a cell (e.g., a mammalian cell). This method includes the step of contacting the cell with a loaded LNP or a pharmaceutical composition of the disclosure, wherein the loaded LNP or pharmaceutical composition comprises an mRNA, whereby the mRNA is capable of being translated in the cell to produce the polypeptide. In some embodiments, the cell is in a subject and the contacting comprises administering the cell to the subject. In some embodiments, the method comprises the step of administering to the subject a lipid nanoparticle comprising a compound of Formula (I), (I-1), (A), (A-1), (A-1a), or (A-1b), a phospholipid, a structural lipid, a PEG lipid, and an mRNA, whereby the mRNA is capable of being translated in the cell to produce the polypeptide.

In some embodiments, the disclosure provides a method of producing a polypeptide of interest in a cell, wherein the method comprises the step of administering to the subject a lipid nanoparticle comprising a compound of Formula (I), (I-1), (A), (A-1), (A-1a), or (A-1b), DSPC, cholesterol, and $PEG_{2k}$-DMG, and an mRNA. For example, in some embodiments, the disclosure provides a method of producing a polypeptide of interest in a cell, wherein the method comprises the step of administering to the subject a lipid nanoparticle comprising a compound of Table 1, DSPC, cholesterol, and $PEG_{2k}$-DMG, and an mRNA. For example, in some embodiments, the disclosure provides a method of producing a polypeptide of interest in a cell, wherein the method comprises the step of administering to the subject a lipid nanoparticle comprising a compound of Formula (A-1), DSPC, cholesterol, and $PEG_{2k}$-DMG, and an mRNA.

In some embodiments, the disclosure provides a method of producing a polypeptide of interest in a cell, wherein the method comprises the step of administering to the subject a lipid nanoparticle comprising a compound of Formula (I), (I-1), (A), (A-1), (A-1a), or (A-1b), DSPC, cholesterol, and PEG-1, and an mRNA. For example, in some embodiments, the disclosure provides a method of producing a polypeptide of interest in a cell, wherein the method comprises the step of administering to the subject a lipid nanoparticle comprising a compound of Formula (A-1), DSPC, cholesterol, and PEG-1, and an mRNA. For example, in some embodiments, the disclosure provides a method of producing a polypeptide of interest in a cell, wherein the method comprises the step of administering to the subject a lipid nanoparticle comprising a compound of Table 1, DSPC, cholesterol, and PEG-1, and an mRNA.

In some aspects, the disclosure provides a method of treating a disease or disorder in a mammal (e.g., a human) in need thereof. The method includes the step of administering to the mammal a therapeutically effective amount of loaded LNP or a pharmaceutical composition of the disclosure. In some embodiments, the method comprises the step of administering to the subject a lipid nanoparticle comprising a compound of Formula (I), (I-1), (A), (A-1), (A-1a), or (A-1b), a phospholipid, a structural lipid, a PEG lipid, and one or more therapeutic and/or prophylactic agents, whereby the therapeutic and/or prophylactic is delivered to the cell. In some embodiments, the disease or disorder is characterized by dysfunctional or aberrant protein or polypeptide activity. For example, the disease or disorder is selected from the group consisting of rare diseases, infectious diseases, cancer and proliferative diseases, genetic diseases, autoimmune diseases, diabetes, neurodegenerative diseases, cardio- and reno-vascular diseases, and metabolic diseases.

In some embodiments, the disclosure provides a method of treating a disease or disorder in a subject, wherein the method comprises the step of administering to the subject a lipid nanoparticle comprising a compound of Formula (I), (I-1), (A), (A-1), (A-1a), or (A-1b), DSPC, cholesterol, and $PEG_{2k}$-DMG, and one or more therapeutic and/or prophylactic agents selected from a nucleotide, a polypeptide, and a nucleic acid (e.g., an RNA). For example, in some embodiments, the disclosure provides a method of treating a disease or disorder in a subject, wherein the method comprises the step of administering to the subject a lipid nanoparticle comprising a compound of Formula (A-1), DSPC, cholesterol, and $PEG_{2k}$-DMG, and one or more therapeutic and/or prophylactic agents selected from a nucleotide, a polypeptide, and a nucleic acid (e.g., an RNA). For example, in some embodiments, the disclosure provides a method of treating a disease or disorder in a subject, wherein the method comprises the step of administering to the subject a lipid nanoparticle comprising a compound of Table 1, DSPC, cholesterol, and $PEG_{2k}$-DMG, and one or more therapeutic and/or prophylactic agents selected from a nucleotide, a polypeptide, and a nucleic acid (e.g., an RNA).

In some embodiments, the disclosure provides a method of treating a disease or disorder in a subject, wherein the method comprises the step of administering to the subject a lipid nanoparticle comprising a compound of Formula (I), (I-1), (A), (A-1), (A-1a), or (A-1b), DSPC, cholesterol, and PEG-1, and one or more therapeutic and/or prophylactic agents selected from a nucleotide, a polypeptide, and a nucleic acid (e.g., an RNA). For example, in some embodiments, the disclosure provides a method of treating a disease or disorder in a subject, wherein the method comprises the step of administering to the subject a lipid nanoparticle comprising a compound of Formula (A-1), DSPC, cholesterol, and PEG-1, and one or more therapeutic and/or prophylactic agents selected from a nucleotide, a polypeptide, and a nucleic acid (e.g., an RNA). For example, in some embodiments, the disclosure provides a method of treating a disease or disorder in a subject, wherein the method comprises the step of administering to the subject a lipid nanoparticle comprising a compound of Table 1, DSPC, cholesterol, and PEG-1, and one or more therapeutic and/or prophylactic agents selected from a nucleotide, a polypeptide, and a nucleic acid (e.g., an RNA).

In yet another aspect, the disclosure features a method of lowering immunogenicity comprising introducing loaded LNP or a pharmaceutical composition of the disclosure into cells, wherein the loaded LNP or a pharmaceutical composition reduces the induction of the cellular immune response of the cells to the loaded LNP or a pharmaceutical composition, as compared to the induction of the cellular immune response in cells induced by a reference composition. In some embodiments, the cell is in a subject and the contacting comprises administering the cell to the subject. In some embodiments, the method comprises the step of administering to the subject a lipid nanoparticle comprising a compound of Formula (I), (I-1), (A), (A-1), (A-1a), or (A-1b), a phospholipid, a structural lipid, a PEG lipid, and one or more therapeutic and/or prophylactic agents selected from a nucleotide, a polypeptide, and a nucleic acid (e.g., an RNA), wherein the lipid nanoparticle comprising a compound of Formula (I), (I-1), (A), (A-1), (A-1a), or (A-1b) reduces the induction of the cellular immune response of the cells to the lipid nanoparticle comprising a compound of Formula (I), (I-1), (A), (A-1), (A-1a), or (A-1b), as compared to the induction of the cellular immune response in cells induced by a reference composition. For example, the cellular immune response is an innate immune response, an adaptive immune response, or both.

In some embodiments, the disclosure provides a method of lowering immunogenicity in a subject, wherein the method comprises the step of administering to the subject a lipid nanoparticle comprising a compound of Formula (I), (I-1), (A), (A-1), (A-1a), or (A-1b), DSPC, cholesterol, and $PEG_{2k}$-DMG, and one or more therapeutic and/or prophylactic agents selected from a nucleotide, a polypeptide, and a nucleic acid (e.g., an RNA). For example, in some embodiments, the disclosure provides a method of lowering immunogenicity in a subject, wherein the method comprises the step of administering to the subject a lipid nanoparticle comprising a compound of Formula (A-1), DSPC, cholesterol, and $PEG_{2k}$-DMG, and one or more therapeutic and/or prophylactic agents selected from a nucleotide, a polypeptide, and a nucleic acid (e.g., an RNA). For example, in some embodiments, the disclosure provides a method of lowering immunogenicity in a subject, wherein the method comprises the step of administering to the subject a lipid nanoparticle comprising a compound of Table 1, DSPC, cholesterol, and $PEG_{2k}$-DMG, and one or more therapeutic and/or prophylactic agents selected from a nucleotide, a polypeptide, and a nucleic acid (e.g., an RNA).

In some embodiments, the disclosure provides a method of lowering immunogenicity in a subject, wherein the method comprises the step of administering to the subject a lipid nanoparticle comprising a compound of Formula (I), (I-1), (A), (A-1), (A-1a), or (A-1b), DSPC, cholesterol, and PEG-1, and one or more therapeutic and/or prophylactic agents selected from a nucleotide, a polypeptide, and a nucleic acid (e.g., an RNA). For example, in some embodiments, the disclosure provides a method of lowering immunogenicity in a subject, wherein the method comprises the step of administering to the subject a lipid nanoparticle comprising a compound of Formula (A-1), DSPC, cholesterol, and PEG-1, and one or more therapeutic and/or prophylactic agents selected from a nucleotide, a polypeptide, and a nucleic acid (e.g., an RNA). For example, in some embodiments, the disclosure provides a method of lowering immunogenicity in a subject, wherein the method comprises the step of administering to the subject a lipid nanoparticle comprising a compound of Table 1, DSPC, cholesterol, and PEG-1, and one or more therapeutic and/or prophylactic agents selected from a nucleotide, a polypeptide, and a nucleic acid (e.g., an RNA).

The disclosure also includes methods of synthesizing a compound of Formula (I), (I-1), (A), (A-1), (A-1a), or (A-1b), and methods of making a lipid nanoparticle (e.g., an empty LNP or a loaded LNP) including a lipid component comprising the compound of Formula (I), (I-1), (A), (A-1), (A-1a), or (A-1 b).

Methods of Producing Polypeptides in Cells

The present disclosure provides methods of producing a polypeptide of interest in a mammalian cell. Methods of producing polypeptides involve contacting a cell with a lipid nanoparticle (e.g., an empty LNP or a loaded LNP) including an mRNA encoding the polypeptide of interest. Upon contacting the cell with the nanoparticle composition, the mRNA may be taken up and translated in the cell to produce the polypeptide of interest.

In general, the step of contacting a mammalian cell with a lipid nanoparticle (e.g., an empty LNP or a loaded LNP) including an mRNA encoding a polypeptide of interest may be performed in vivo, ex vivo, in culture, or in vitro. The amount of lipid nanoparticle (e.g., an empty LNP or a loaded LNP) contacted with a cell, and/or the amount of mRNA therein, may depend on the type of cell or tissue being contacted, the means of administration, the physiochemical characteristics of the lipid nanoparticle (e.g., an empty LNP or a loaded LNP) and the mRNA (e.g., size, charge, and chemical composition) therein, and other factors. In general, an effective amount of the lipid nanoparticle (e.g., an empty LNP or a loaded LNP) will allow for efficient polypeptide production in the cell. Metrics for efficiency may include polypeptide translation (indicated by polypeptide expression), level of mRNA degradation, and immune response indicators.

The step of contacting a lipid nanoparticle (e.g., an empty LNP or a loaded LNP) including an mRNA with a cell may involve or cause transfection. A phospholipid including in the lipid component of a lipid nanoparticle (e.g., an empty LNP or a loaded LNP) may facilitate transfection and/or increase transfection efficiency, for example, by interacting and/or fusing with a cellular or intracellular membrane. Transfection may allow for the translation of the mRNA within the cell.

In some embodiments, the lipid nanoparticles (e.g., empty LNPs or loaded LNPs) described herein may be used therapeutically. For example, an mRNA included in a lipid nanoparticle (e.g., an empty LNP or a loaded LNP) may encode a therapeutic polypeptide (e.g., in a translatable region) and produce the therapeutic polypeptide upon contacting and/or entry (e.g., transfection) into a cell. In other embodiments, an mRNA included in a lipid nanoparticle (e.g., an empty LNP or a loaded LNP) may encode a polypeptide that may improve or increase the immunity of a subject. For example, an mRNA may encode a granulocyte-colony stimulating factor or trastuzumab.

In certain embodiments, an mRNA included in a lipid nanoparticle (e.g., an empty LNP or a loaded LNP) may encode a recombinant polypeptide that may replace one or more polypeptides that may be substantially absent in a cell contacted with the nanoparticle composition. The one or more substantially absent polypeptides may be lacking due to a genetic mutation of the encoding gene or a regulatory pathway thereof. Alternatively, a recombinant polypeptide produced by translation of the mRNA may antagonize the activity of an endogenous protein present in, on the surface of, or secreted from the cell. An antagonistic recombinant polypeptide may be desirable to combat deleterious effects caused by activities of the endogenous protein, such as altered activities or localization caused by mutation. In another alternative, a recombinant polypeptide produced by translation of the mRNA may indirectly or directly antagonize the activity of a biological moiety present in, on the surface of, or secreted from the cell. Antagonized biological moieties may include, but are not limited to, lipids (e.g., cholesterol), lipoproteins (e.g., low density lipoprotein), nucleic acids, carbohydrates, and small molecule toxins. Recombinant polypeptides produced by translation of the mRNA may be engineered for localization within the cell, such as within a specific compartment such as the nucleus, or may be engineered for secretion from the cell or for translocation to the plasma membrane of the cell.

In some embodiments, contacting a cell with a lipid nanoparticle (e.g., an empty LNP or a loaded LNP) including an mRNA may reduce the innate immune response of a cell to an exogenous nucleic acid. A cell may be contacted with a first lipid nanoparticle (e.g., an empty LNP or a loaded LNP) including a first amount of a first exogenous mRNA including a translatable region and the level of the innate immune response of the cell to the first exogenous mRNA may be determined. Subsequently, the cell may be contacted with a second composition including a second amount of the first exogenous mRNA, the second amount being a lesser amount of the first exogenous mRNA compared to the first amount. Alternatively, the second composition may include a first amount of a second exogenous mRNA that is different from the first exogenous mRNA. The steps of contacting the cell with the first and second compositions may be repeated one or more times. Additionally, efficiency of polypeptide production (e.g., translation) in the cell may be optionally determined, and the cell may be re-contacted with the first and/or second composition repeatedly until a target protein production efficiency is achieved.

Methods of Delivering Therapeutic Agents to Cells and Organs

The present disclosure provides methods of delivering a therapeutic and/or prophylactic to a mammalian cell or organ. Delivery of a therapeutic and/or prophylactic to a cell involves administering a lipid nanoparticle (e.g., an empty LNP or a loaded LNP) including the therapeutic and/or prophylactic to a subject, where administration of the composition involves contacting the cell with the composition. For example, a protein, cytotoxic agent, radioactive ion, chemotherapeutic agent, or nucleic acid (such as an RNA, e.g., mRNA) may be delivered to a cell or organ. In the instance that a therapeutic and/or prophylactic is an mRNA, upon contacting a cell with the nanoparticle composition, a translatable mRNA may be translated in the cell to produce a polypeptide of interest. However, mRNAs that are substantially not translatable may also be delivered to cells. Substantially non-translatable mRNAs may be useful as vaccines and/or may sequester translational components of a cell to reduce expression of other species in the cell.

In some embodiments, a lipid nanoparticle (e.g., an empty LNP or a loaded LNP) may target a particular type or class of cells (e.g., cells of a particular organ or system thereof). For example, a lipid nanoparticle (e.g., an empty LNP or a loaded LNP) including a therapeutic and/or prophylactic of interest may be specifically delivered to a mammalian liver, kidney, spleen, or lung. Specific delivery to a particular class of cells, an organ, or a system or group thereof implies that a higher proportion of lipid nanoparticles (e.g., loaded LNPs) including a therapeutic and/or prophylactic are delivered to the destination (e.g., tissue) of interest relative to other destinations. In some embodiments, specific delivery of a loaded LNP comprising an mRNA may result in a greater than 2 fold, 5 fold, 10 fold, 15 fold, or 20 fold increase in mRNA expression in cells of the targeted destination (e.g., tissue of interest, such as a liver) as compared to cells of another destination (e.g., the spleen). In some embodiments, the tissue of interest is selected from the group consisting of a liver, a kidney, a lung, a spleen, and tumor tissue (e.g., via intratumoral injection).

In some embodiments, specific delivery of an mRNA comprised in a loaded LNP of the disclosure (i.e., a lipid nanoparticle formulated with a compound of the disclosure) may result in a greater than 2 fold, 5 fold, 10 fold, 15 fold, or 20 fold increase in mRNA expression as compared to delivery of an mRNA comprised in an LNP formulated with another lipid (i.e., without any of the lipids of Formula (I), (I-1), (A), (A-1), (A-1a), or (A-1b)).

As another example of targeted or specific delivery, an mRNA that encodes a protein-binding partner (e.g., an antibody or functional fragment thereof, a scaffold protein, or a peptide) or a receptor on a cell surface may be included in a nanoparticle composition. An mRNA may additionally or instead be used to direct the synthesis and extracellular localization of lipids, carbohydrates, or other biological moieties. Alternatively, other therapeutic and/or prophylactics or elements (e.g., lipids or ligands) of a lipid nanoparticle (e.g., an empty LNP or a loaded LNP) may be selected based on their affinity for particular receptors (e.g., low density lipoprotein receptors) such that a lipid nanoparticle (e.g., an empty LNP or a loaded LNP) may more readily interact with a target cell population including the receptors. For example, ligands may include, but are not limited to, members of a specific binding pair, antibodies, monoclonal antibodies, Fv fragments, single chain Fv (scFv) fragments, Fab' fragments, F(ab')2 fragments, single domain antibodies, camelized antibodies and fragments thereof, humanized antibodies and fragments thereof, and multivalent versions thereof; multivalent binding reagents including mono- or bi-specific antibodies such as disulfide stabilized Fv fragments, scFv tandems, diabodies, tribodies, or tetrabodies; and aptamers, receptors, and fusion proteins.

In some embodiments, a ligand may be a surface-bound antibody, which can permit tuning of cell targeting specificity. This is especially useful since highly specific antibodies can be raised against an epitope of interest for the desired targeting site. In some embodiments, multiple antibodies are expressed on the surface of a cell, and each antibody can have a different specificity for a desired target. Such approaches can increase the avidity and specificity of targeting interactions.

A ligand can be selected, e.g., by a person skilled in the biological arts, based on the desired localization or function of the cell.

Targeted cells may include, but are not limited to, hepatocytes, epithelial cells, hematopoietic cells, epithelial cells, endothelial cells, lung cells, bone cells, stem cells, mesenchymal cells, neural cells, cardiac cells, adipocytes, vascular smooth muscle cells, cardiomyocytes, skeletal muscle cells, beta cells, pituitary cells, synovial lining cells, ovarian cells, testicular cells, fibroblasts, B cells, T cells, reticulocytes, leukocytes, granulocytes, and tumor cells.

In some embodiments, a lipid nanoparticle (e.g., an empty LNP or a loaded LNP) may target hepatocytes. Apolipoproteins such as apolipoprotein E (apoE) have been shown to associate with neutral or near neutral lipid-containing lipid nanoparticles (e.g., empty LNPs or loaded LNPs) in the body, and are known to associate with receptors such as low-density lipoprotein receptors (LDLRs) found on the surface of hepatocytes. Thus, a lipid nanoparticle (e.g., an empty LNP or a loaded LNP) including a lipid component with a neutral or near neutral charge that is administered to a subject may acquire apoE in a subject's body and may subsequently deliver a therapeutic and/or prophylactic (e.g., an RNA) to hepatocytes including LDLRs in a targeted manner.

Methods of Treating Diseases and Disorders

Lipid nanoparticles (e.g., empty LNPs or loaded LNPs) may be useful for treating a disease, disorder, or condition. In particular, such compositions may be useful in treating a disease, disorder, or condition characterized by missing or aberrant protein or polypeptide activity. For example, a lipid nanoparticle (e.g., an empty LNP or a loaded LNP) comprising an mRNA encoding a missing or aberrant polypeptide may be administered or delivered to a cell. Subsequent translation of the mRNA may produce the polypeptide, thereby reducing or eliminating an issue caused by the absence of or aberrant activity caused by the polypeptide. Because translation may occur rapidly, the methods and compositions may be useful in the treatment of acute diseases, disorders, or conditions such as sepsis, stroke, and myocardial infarction. A therapeutic and/or prophylactic included in a lipid nanoparticle (e.g., an empty LNP or a loaded LNP) may also be capable of altering the rate of transcription of a given species, thereby affecting gene expression.

Diseases, disorders, and/or conditions characterized by dysfunctional or aberrant protein or polypeptide activity for which a composition may be administered include, but are not limited to, rare diseases, infectious diseases (as both vaccines and therapeutics), cancer and proliferative diseases, genetic diseases, autoimmune diseases, diabetes, neurodegenerative diseases, cardio- and reno-vascular diseases, and metabolic diseases. Multiple diseases, disorders, and/or conditions may be characterized by missing (or substantially diminished such that proper protein function does not occur) protein activity. Such proteins may not be present, or they may be essentially non-functional. The present disclosure provides a method for treating such diseases, disorders, and/or conditions in a subject by administering a lipid nanoparticle (e.g., an empty LNP or a loaded LNP) including an RNA and a lipid component including a lipid according to Formula (I), (I-1), (A), (A-1), (A-1a), or (A-1b), a phospholipid (optionally unsaturated), a PEG lipid, and a structural lipid, wherein the RNA may be an mRNA encoding a polypeptide that antagonizes or otherwise overcomes an aberrant protein activity present in the cell of the subject.

The disclosure provides methods involving administering lipid nanoparticles (e.g., empty LNPs or loaded LNPs) including one or more therapeutic and/or prophylactic agents and pharmaceutical compositions including the same. The terms therapeutic and prophylactic can be used interchangeably herein with respect to features and embodiments of the present disclosure. Therapeutic compositions, or imaging, diagnostic, or prophylactic compositions thereof, may be administered to a subject using any reasonable amount and any route of administration effective for preventing, treating, diagnosing, or imaging a disease, disorder, and/or condition and/or any other purpose. The specific amount administered to a given subject may vary depending on the species, age, and general condition of the subject; the purpose of the administration; the particular composition; the mode of administration; and the like. Compositions in accordance with the present disclosure may be formulated in dosage unit form for ease of administration and uniformity of dosage. It will be understood, however, that the total daily usage of a composition of the present disclosure will be decided by an attending physician within the scope of sound medical judgment. The specific therapeutically effective, prophylactically effective, or otherwise appropriate dose level (e.g., for imaging) for any particular patient will depend upon a variety of factors including the severity and identify of a disorder being treated, if any; the one or more therapeutic and/or prophylactics employed; the specific composition employed; the age, body weight, general health, sex, and diet of the patient; the time of administration, route of administration, and rate of excretion of the specific pharmaceutical composition employed; the duration of the treatment; drugs used in combination or coincidental with the specific pharmaceutical composition employed; and like factors well known in the medical arts.

A loaded LNP may be administered by any route. In some embodiments, compositions, including prophylactic, diagnostic, or imaging compositions including one or more loaded LNPs described herein, are administered by one or more of a variety of routes, including oral, intravenous, intramuscular, intra-arterial, subcutaneous, trans- or intradermal, interdermal, intraperitoneal, mucosal, nasal, intratumoral, intranasal; by inhalation; as an oral spray and/or powder, nasal spray, and/or aerosol, and/or through a portal vein catheter. In some embodiments, a composition may be administered intravenously, intramuscularly, intradermally, intra-arterially, intratumorally, subcutaneously, or by any other parenteral route of administration or by inhalation. However, the present disclosure encompasses the delivery or administration of compositions described herein by any appropriate route taking into consideration likely advances in the sciences of drug delivery. In general, the most appropriate route of administration will depend upon a variety of factors including the nature of the loaded LNP including one or more therapeutic and/or prophylactics (e.g., its stability in various bodily environments such as the bloodstream and gastrointestinal tract), the condition of the patient (e.g., whether the patient is able to tolerate particular routes of administration), etc.

In certain embodiments, compositions in accordance with the present disclosure may be administered at dosage levels sufficient to deliver from about 0.0001 mg/kg to about 10 mg/kg, from about 0.001 mg/kg to about 10 mg/kg, from about 0.005 mg/kg to about 10 mg/kg, from about 0.01 mg/kg to about 10 mg/kg, from about 0.05 mg/kg to about 10 mg/kg, from about 0.1 mg/kg to about 10 mg/kg, from about 1 mg/kg to about 10 mg/kg, from about 2 mg/kg to about 10 mg/kg, from about 5 mg/kg to about 10 mg/kg, from about 0.0001 mg/kg to about 5 mg/kg, from about 0.001 mg/kg to about 5 mg/kg, from about 0.005 mg/kg to about 5 mg/kg, from about 0.01 mg/kg to about 5 mg/kg, from about 0.05 mg/kg to about 5 mg/kg, from about 0.1 mg/kg to about 5 mg/kg, from about 1 mg/kg to about 5 mg/kg, from about 2 mg/kg to about 5 mg/kg, from about 0.0001 mg/kg to about 2.5 mg/kg, from about 0.001 mg/kg to about 2.5 mg/kg, from about 0.005 mg/kg to about 2.5 mg/kg, from about 0.01 mg/kg to about 2.5 mg/kg, from about 0.05 mg/kg to about 2.5 mg/kg, from about 0.1 mg/kg to about 2.5 mg/kg, from about 1 mg/kg to about 2.5 mg/kg, from about 2 mg/kg to about 2.5 mg/kg, from about 0.0001 mg/kg to about 1 mg/kg, from about 0.001 mg/kg to about 1 mg/kg, from about 0.005 mg/kg to about 1 mg/kg, from about 0.01 mg/kg to about 1 mg/kg, from about 0.05 mg/kg to about 1 mg/kg, from about 0.1 mg/kg to about 1 mg/kg, from about 0.0001 mg/kg to about 0.25 mg/kg, from about 0.001 mg/kg to about 0.25 mg/kg, from about 0.005 mg/kg to about 0.25 mg/kg, from about 0.01 mg/kg to about 0.25 mg/kg, from about 0.05 mg/kg to about 0.25 mg/kg, or from about 0.1 mg/kg to about 0.25 mg/kg of a therapeutic and/or prophylactic (e.g., an mRNA) in a given dose, where a dose of 1 mg/kg (mpk) provides 1 mg of a therapeutic and/or prophylactic per 1 kg of subject body weight. In some embodiments, a dose of about 0.001 mg/kg to about 10 mg/kg of a therapeutic and/or prophylactic of a loaded LNP may be administered. In other embodiments, a dose of about 0.005 mg/kg to about 2.5 mg/kg of a therapeutic and/or prophylactic may be administered. In certain embodiments, a dose of about 0.1 mg/kg to about 1 mg/kg may be administered. In other embodiments, a dose of about 0.05 mg/kg to about 0.25 mg/kg may be administered. A dose may be administered one or more times per day, in the same or a different amount, to obtain a desired level of mRNA expression and/or therapeutic, diagnostic, prophylactic, or imaging effect. The desired dosage may be delivered, for example, three times a day, two times a day, once a day, every other day, every third day, every week, every two weeks, every three weeks, or every four weeks. In certain embodiments, the desired dosage may be delivered using multiple administrations (e.g., two, three, four, five, six, seven, eight, nine, ten, eleven, twelve, thirteen, fourteen, or more administrations). In some embodiments, a single dose may be administered, for example, prior to or after a surgical procedure or in the instance of an acute disease, disorder, or condition.

Lipid nanoparticles (e.g., empty LNPs or loaded LNPs) including one or more therapeutic and/or prophylactics may be used in combination with one or more other therapeutic, prophylactic, diagnostic, or imaging agents. By "in combination with," it is not intended to imply that the agents must be administered at the same time and/or formulated for delivery together, although these methods of delivery are within the scope of the present disclosure. For example, one or more lipid nanoparticles (e.g., empty LNPs or loaded LNPs) including one or more different therapeutic and/or prophylactics may be administered in combination. Compositions can be administered concurrently with, prior to, or subsequent to, one or more other desired therapeutics or medical procedures. In general, each agent will be administered at a dose and/or on a time schedule determined for that agent. In some embodiments, the present disclosure encompasses the delivery of compositions, or imaging, diagnostic, or prophylactic compositions thereof in combination with agents that improve their bioavailability, reduce and/or modify their metabolism, inhibit their excretion, and/or modify their distribution within the body.

It will further be appreciated that therapeutically, prophylactically, diagnostically, or imaging active agents utilized in combination may be administered together in a single composition or administered separately in different compositions. In general, it is expected that agents utilized in combination will be utilized at levels that do not exceed the levels at which they are utilized individually. In some embodiments, the levels utilized in combination may be lower than those utilized individually.

The particular combination of therapies (therapeutics or procedures) to employ in a combination regimen will take into account compatibility of the desired therapeutics and/or procedures and the desired therapeutic effect to be achieved. It will also be appreciated that the therapies employed may achieve a desired effect for the same disorder (for example, a composition useful for treating cancer may be administered concurrently with a chemotherapeutic agent), or they may achieve different effects (e.g., control of any adverse effects, such as infusion related reactions).

A lipid nanoparticle (e.g., an empty LNP or a loaded LNP) may be used in combination with an agent to increase the effectiveness and/or therapeutic window of the composition. Such an agent may be, for example, an anti-inflammatory compound, a steroid (e.g., a corticosteroid), a statin, an estradiol, a BTK inhibitor, an S1P1 agonist, a glucocorticoid receptor modulator (GRM), or an anti-histamine. In some embodiments, a lipid nanoparticle (e.g., an empty LNP or a loaded LNP) may be used in combination with dexamethasone, methotrexate, acetaminophen, an H1 receptor blocker, or an H2 receptor blocker. In some embodiments, a method of treating a subject in need thereof or of delivering a therapeutic and/or prophylactic to a subject (e.g., a mammal) may involve pre-treating the subject with one or more agents prior to administering a nanoparticle composition. For example, a subject may be pre-treated with a useful amount (e.g., 10 mg, 20 mg, 30 mg, 40 mg, 50 mg, 60 mg, 70 mg, 80 mg, 90 mg, 100 mg, or any other useful amount) of dexamethasone, methotrexate, acetaminophen, an H1 receptor blocker, or an H2 receptor blocker. Pre-treatment may occur 24 or fewer hours (e.g., 24 hours, 20 hours, 16 hours, 12 hours, 8 hours, 4 hours, 2 hours, 1 hour, 50 minutes, 40 minutes, 30 minutes, 20 minutes, or 10 minutes) before administration of the lipid nanoparticle (e.g., an empty LNP or a loaded LNP) and may occur one, two, or more times in, for example, increasing dosage amounts.

Those skilled in the art will recognize, or be able to ascertain using no more than routine experimentation, many equivalents to the specific embodiments in accordance with the disclosure described herein. The scope of the present disclosure is not intended to be limited to the above Description, but rather is as set forth in the appended claims.

In the claims, articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The disclosure includes embodiments in which exactly one member of the group is present in, employed in, or otherwise relevant to a given product or process. The disclosure includes embodiments in which more than one, or all, of the group members are present in, employed in, or otherwise relevant to a given product or process. As used herein, the expressions "one or more of A, B, or C," "one or more A, B, or C," "one or more of A, B, and C," "one or more A, B, and C", "selected from A, B, and C," "selected from the group consisting of A, B, and C," and the like are used interchangeably and all refer to a selection from a group consisting of A, B, and/or C, i.e., one or more As, one or more Bs, one or more Cs, or any combination thereof, unless otherwise specified.

It is also noted that the term "comprising" is intended to be open and permits but does not require the inclusion of additional elements or steps. When the term "comprising" is used herein, the terms "consisting essentially of" and "consisting of" are thus also encompassed and disclosed. Throughout the description, where compositions are described as having, including, or comprising specific components, it is contemplated that compositions also consist essentially of, or consist of, the recited components. Similarly, where methods or processes are described as having, including, or comprising specific process steps, the processes also consist essentially of, or consist of, the recited processing steps. Further, it should be understood that the order of steps or order for performing certain actions is immaterial so long as the invention remains operable. Moreover, two or more steps or actions can be conducted simultaneously.

Where ranges are given, endpoints are included. Furthermore, it is to be understood that unless otherwise indicated or otherwise evident from the context and understanding of one of ordinary skill in the art, values that are expressed as ranges can assume any specific value or sub-range within the stated ranges in different embodiments of the disclosure, to the tenth of the unit of the lower limit of the range, unless the context clearly dictates otherwise.

The synthetic processes of the disclosure can tolerate a wide variety of functional groups, therefore various substituted starting materials can be used. The processes generally provide the desired final compound at or near the end of the overall process, although it may be desirable in certain instances to further convert the compound to a pharmaceutically acceptable salt thereof.

Compounds of the present disclosure can be prepared in a variety of ways using commercially available starting materials, compounds known in the literature, or from readily prepared intermediates, by employing standard synthetic methods and procedures either known to those skilled in the art, or which will be apparent to the skilled artisan in light of the teachings herein. Standard synthetic methods and procedures for the preparation of organic molecules and functional group transformations and manipulations can be obtained from the relevant scientific literature or from standard textbooks in the field. Although not limited to any one or several sources, classic texts such as Smith, M. B., March, J., *March's Advanced Organic Chemistry: Reactions, Mechanisms, and Structure,* 5$^{th}$ edition, John Wiley & Sons: New York, 2001; Greene, T. W., Wuts, P. G. M., *Protective Groups in Organic Synthesis,* 3$^{rd}$ edition, John Wiley & Sons: New York, 1999; R. Larock, *Comprehensive Organic Transformations*, VCH Publishers (1989); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995), incorporated by reference herein, are useful and recognized reference textbooks of organic synthesis known to those in the art. The following descriptions of synthetic methods are designed to illustrate, but not to limit, general procedures for the preparation of compounds of the present disclosure.

The compounds of this disclosure having any of the formulae described herein may be prepared according to the procedures illustrated in Schemes 1, 2, and 3 below, from commercially available starting materials or starting materials which can be prepared using literature procedures. The variables in the schemes (e.g., $R^1$, $R^2$, and $R^3$ etc. are as defined herein). One of ordinary skill in the art will note that, during the reaction sequences and synthetic schemes described herein, the order of certain steps may be changed, such as the introduction and removal of protecting groups.

One of ordinary skill in the art will recognize that certain groups may require protection from the reaction conditions via the use of protecting groups. Protecting groups may also be used to differentiate similar functional groups in molecules. A list of protecting groups and how to introduce and remove these groups can be found in Greene, T. W., Wuts, P. G. M., *Protective Groups in Organic Synthesis,* 3rd edition, John Wiley & Sons: New York, 1999.

Preferred protecting groups include, but are not limited to:

For a hydroxyl moiety: TBS, benzyl, THP, Ac;

For carboxylic acids: benzyl ester, methyl ester, ethyl ester, allyl ester;

For amines: Fmoc, Cbz, BOC, DMB, Ac, Bn, Tr, Ts, trifluoroacetyl, phthalimide, benzylideneamine;

For diols: Ac (×2) TBS (×2), or when taken together acetonides;

For thiols: Ac;

For benzimidazoles: SEM, benzyl, PMB, DMB;

For aldehydes: di-alkyl acetals such as dimethoxy acetal or diethyl acetyl.

In the reaction schemes described herein, multiple stereoisomers may be produced. When no particular stereoisomer is indicated, it is understood to mean all possible stereoisomers that could be produced from the reaction. A person of ordinary skill in the art will recognize that the reactions can be optimized to give one isomer preferentially, or new schemes may be devised to produce a single isomer. If mixtures are produced, techniques such as preparative thin layer chromatography, preparative HPLC, preparative chiral HPLC, or preparative SFC may be used to separate the isomers.

Scheme 1

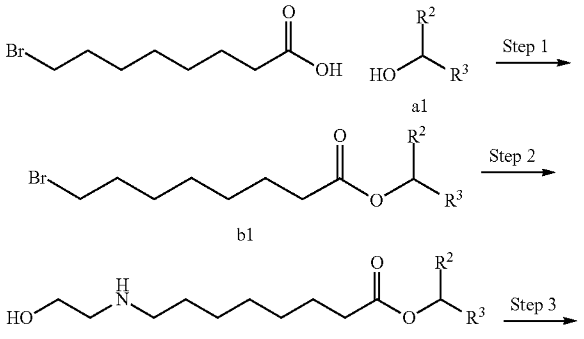

a1 b1 c1

-continued

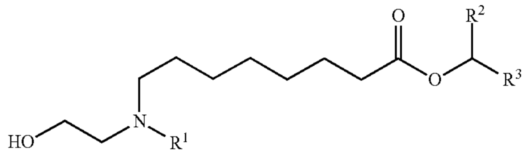

d1

As illustrated in Scheme 1 above, 8-bromooctanoic acid reacts with an alcohol a1 (e.g., heptadecan-9-ol) to afford an ester b1 (e.g., heptadecan-9-yl 8-bromooctanoate). Step 1 can take place in an organic solvent (e.g., dichloromethane) in the presence of, e.g., N-(3-dimethylaminopropyl)-N-ethylcarbodiimide hydrochloride, N,N-diisopropylethylamine and DMAP. Step 1 can take place at room temperature for 18 h. Next, ester b1 reacts with 2-aminoethan-1-ol to afford amine c1 (e.g., heptadecan-9-yl 8-((2-hydroxyethyl)amino) octanoate). Step 2 can take place in ethanol at, e.g., a temperature of about 60° C. Then amine c1 reacts with an bromoalkyl $R^1$—Br (e.g., 1-bromotetradecane) to afford compound d1 (e.g., heptadecan-9-yl 8-((2-hydroxyethyl) (tetradecyl)amino)octanoate). Step 3 can take place in ethanol in the presence of N,N-diisopropylethylamine.

Scheme 2

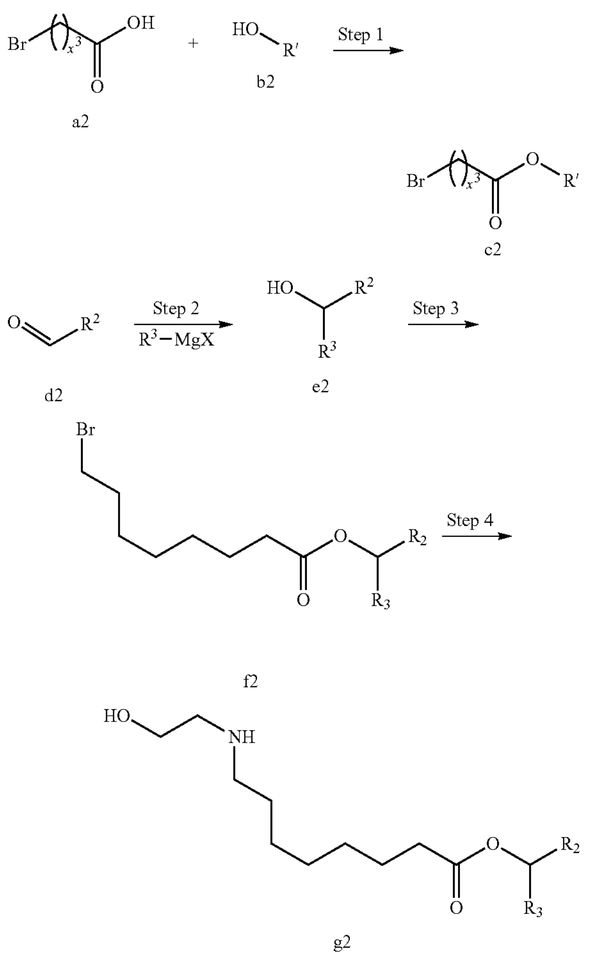

a2 b2 c2 d2 e2 f2 g2

-continued

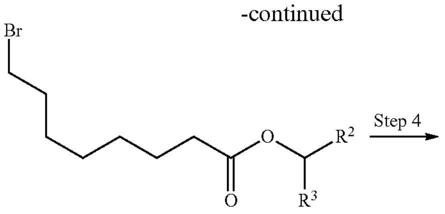

f2

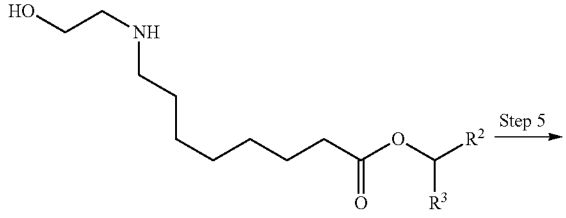

g2

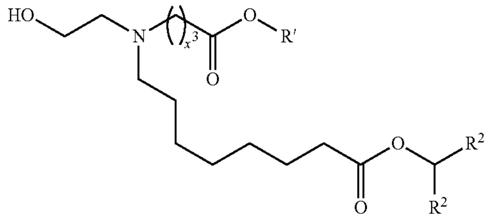

h2

As illustrated in Scheme 2 above, an acid a2 ($x^3$ is an integer between 1 and 7; e.g., 8-bromooctanoic acid) reacts with an alcohol b2 (e.g., nonan-1-ol) to afford an ester c2 (e.g., nonyl-8-bromooctanoate). Step 1 can take place in an organic solvent (e.g., dichloromethane) in the presence of, e.g., N-(3-dimethylaminopropyl)-N-ethylcarbodiimide hydrochloride, N,N-diisopropylethylamine and DMAP. Alcohol e2 (e.g., heptadecan-9-ol) can be obtained from reacting aldehyde d2 (e.g., nonanal) with a Grignard reagent $R^3$—MgX (e.g., n-$C_8H_{17}MgBr$) via Step 2. Next, 8-bromooctanoic acid reacts with an alcohol e2 (e.g., heptadecan-9-ol) to afford an ester 12 (e.g., heptadecan-9-yl 8-bromooctanoate). Step 3 can take place in an organic solvent (e.g., dichloromethane) in the presence of, e.g., N-(3-dimethylaminopropyl)-N'-ethylcarbodiimide hydrochloride, N,N-diisopropylethylamine and DMAP. Next, ester 12 reacts with 2-aminoethan-1-ol to afford amine g2 (e.g., heptadecan-9-yl 8-((2-hydroxyethyl)amino)octanoate). Step 4 can take place in ethanol in the presence of i-$Pr_2EtN$. Then amine g2 reacts with ester c2 (e.g., nonyl-8-bromooctanoate) to afford compound h2 (e.g., heptadecan-9-yl 8-((2-hydroxyethyl)(8-(nonyloxy)-8-oxooctyl)amino)octanoate). Step 5 can take place in an organic solvent (e.g., a mixture of CPME and MeCN), in the presence of a base (such as an inorganic base (e.g., $K_2CO_3$) or non-nucleophilic organic base (e.g., i-$Pr_2EtN$)) and a catalyst (e.g., an iodide such as KI or NaI) at, e.g., an elevated temperature (such as at about 70-90° C., e.g., about 80° C.).

Scheme 3

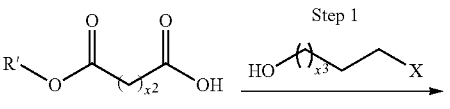

a3

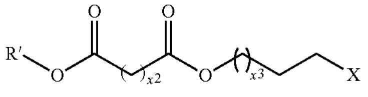

b3

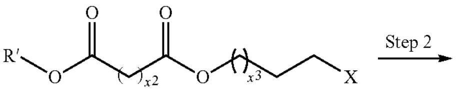

b3

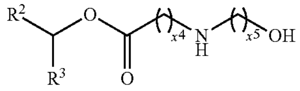

c3

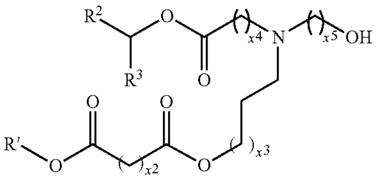

d3

As illustrated in Scheme 3 above, a haloalkanol ($x^3$ is an integer between 1 and 12, e.g., 6-bromohexan-1-ol) is reacted with a starting material a3 ($x^2$ is an integer between 1 and 6, e.g., 4-(hexyloxy)-4-oxobutanoic acid) to afford a halogenated diester b3 (e.g., 6-bromohexyl hexyl succinate). Compound a3 can be obtained by reaction of an alcohol (e.g., hexan-1-ol) with an acid anhydride (e.g. succinic anhydride, dihydro-2H-pyran-2,6(3H)-dione, 3-(tert-butoxy)-3-oxopropanoic acid, 4-(tert-butoxy)-3-methyl-4-oxobutanoic acid, or 4-(tert-butoxy)-2-methyl-4-oxobutanoic acid). Step 1 can take place in an organic solvent (e.g., dichloromethane) in the presence of, e.g., N-(3-dimethylaminopropyl)-N'-ethylcarbodiimide hydrochloride, N,N-diisopropylethylamine and DMAP. Next, halogenated diester b3 reacts with an amine c3 ($x^4$ is an integer between 5 and 13, $x^5$ is an integer between 1 and 5, e.g., heptadecan-9-yl 8-((2-hydroxyethyl)amino)octanoate) to afford the product d3. Step 2 can take place in an organic solvent (e.g., a mixture of CPME and MeCN), in the presence of a base (such as an inorganic base (e.g., $K_2CO_3$) and a catalyst (e.g., an iodide such as KI) and an ether solvent (e.g., cyclopentyl methyl ether), at an elevated temperature (e.g., about 90° C.).

A person of ordinary skill in the art will recognize that in the above schemes the order of certain steps may be interchangeable.

In certain aspects, the disclosure also includes methods of synthesizing a compound of any of Formulae (I), (I-1), (A), (A-1), (A-1a), or (A-1b) and intermediate(s) for synthesizing the compound.

In some embodiments, the method of synthesizing a compound of the disclosure includes reacting a compound of Formula (X2):

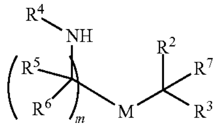

with $R^1$—Br to afford the compound of the disclosure, wherein each variables are as defined herein. For example, m is 5, 6, 7, 8, or 9, preferably 5, 7, or 9. For example, each of $R^5$, $R^6$, and $R^7$ is H. For example, M is —C(O)O— or —OC(O)—. For example, $R^4$ is unsubstituted $C_{1-3}$ alkyl, or —$(CH_2)_n$Q, in which n is 2, 3, or 4 and Q is OH, —NHC(S)N(R)$_2$, —NHC(O)N(R)$_2$, —N(R)C(O)R, or —N(R)S(O)$_2$R. For example, the reaction of the compound of Formula (X2) with $R^1$—Br takes place in the presence of a base (such as an inorganic base (e.g., $K_2CO_3$) or non-nucleophilic organic base (e.g., i-$Pr_2$EtN)). For example, the reaction takes place in the presence of an inorganic base (e.g., $K_2CO_3$) and a catalyst (e.g., an iodide such as KI or NaI). For example, the reaction takes place at an elevated temperature, e.g., about 50-100° C., 70-90° C., or about 80° C.).

The method may also include reacting a compound of Formula (X1):

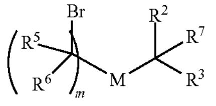

with $R^4NH_2$ to afford a compound of Formula (X2), wherein each variables are as defined herein.

In some embodiments, the intermediate(s) include those having any of Formulae (X1) and (X2):

(X1)

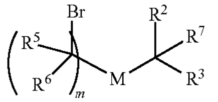

or (X2)

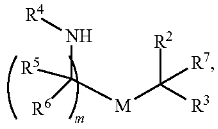

wherein each variables are as defined herein. For example, the intermediate includes heptadecan-9-yl 8-bromooctanoate, and heptadecan-9-yl 8-((2-hydroxyethyl)amino)octanoate, and morphic forms thereof (e.g., a crystalline form).

In addition, it is to be understood that any particular embodiment of the present disclosure that falls within the prior art may be explicitly excluded from any one or more of the claims. Since such embodiments are deemed to be known to one of ordinary skill in the art, they may be excluded even if the exclusion is not set forth explicitly herein.

All cited sources, for example, references, publications, databases, database entries, and art cited herein, are incorporated into this application by reference, even if not expressly stated in the citation. In case of conflicting statements of a cited source and the instant application, the statement in the instant application shall control.

EXAMPLES

Example 1: Synthesis of Compounds of Table 1

A. General Considerations

All solvents and reagents used were obtained commercially and used as such unless noted otherwise. $^1$H NMR spectra were recorded in $CDCl_3$, at 300 K using a Bruker Ultrashield 300 MHz instrument. Chemical shifts are reported as parts per million (ppm) relative to TMS (0.00) for $^1$H. Silica gel chromatographies were performed on ISCO CombiFlash Rf+ Lumen Instruments using ISCO RediSep Rf Gold Flash Cartridges (particle size: 20-40 microns). Reverse phase chromatographies were performed on ISCO CombiFlash Rf+ Lumen Instruments using RediSep Rf Gold C18 High Performance columns. All final compounds were determined to be greater than 85% pure via analysis by reverse phase UPLC-MS (retention times, RT, in minutes) using Waters Acquity UPLC instrument with DAD and ELSD and a ZORBAX Rapid Resolution High Definition (RRHD) SB-C18 LC column, 2.1 mm, 50 mm, 1.8 μm, and a gradient of 65 to 100% acetonitrile in water with 0.1% TFA over 5 minutes at 1.2 mL/min. Injection volume was 5 μL and the column temperature was 80° C. Detection was based on electrospray ionization (ESI) in positive mode using Waters SQD mass spectrometer (Milford, MA, USA) and evaporative light scattering detector.

The procedures described below are useful in the synthesis of compounds of Table 1.

The following abbreviations are employed herein:

THF: Tetrahydrofuran
MeCN: Acetonitrile
LAH: Lithium Aluminum Hydride
DCM: Dichloromethane
DMAP: 4-Dimethylaminopyridine
LDA: Lithium Diisopropylamide
rt: Room Temperature
DME: 1,2-Dimethoxyethane
n-BuLi: n-Butyllithium
CPME: Cyclopentyl methyl ether
i-$Pr_2$EtN: N,N-Diisopropylethylamine

AA. Compound 1: Heptadecan-9-yl 8-((3-((4-(methylamino)-1-oxido-1,2,5-thiadiazol-3-yl)amino)propyl)(8-oxo-8-(undecan-3-yloxy)octyl) amino)octanoate Undecan-3-yl 8-bromooctanoate

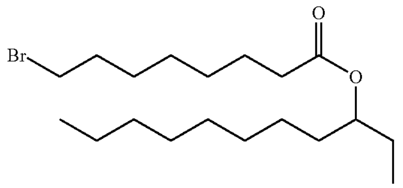

Chemical Formula: $C_{19}H_{37}BrO_2$
Molecular Weight: 377.41

To a solution of 3-undecanol (4.14 g, 24 mmol), 8-bromooctanoic acid (8.01 g, 36 mmol) and 4-(dimethylamino)pyridine (DMAP; 0.58 g, 4.8 mmol) in dichloromethane (DCM; 50 mL) at 0° C. was added 1-ethyl-3-(3-dimethylaminopropyl)carbodiimide hydrochloride (EDC-HCl; 6.9 g, 36 mmol) and the reaction mixture stirred at room temperature overnight. The reaction mixture was cooled to 0° C. and a solution of hydrochloric acid (10 mL conc. HCl, 90 mL water, 7.5 g sodium chloride) was added very slowly over 20 minutes. Once addition was complete 200 mL of a 1:1 mixture of acetonitrile and hexane was added, the layers separated, the organic layer dried ($MgSO_4$) and conc. to give an oil. This was dissolved in hexane (100 mL) and washed with a mixture of acetonitrile (100 mL) and an aqueous 5% sodium bicarbonate solution (100 mL). The hexane layer was separated, filtered through Celite, the filter solids washed with hexane and the filtrate conc. to give undecan-3-yl 8-bromooctanoate (8.76 g, 97%) as a colorless liquid containing ca. 15% chloride by H-NMR. $^1H$ NMR (300 MHz, $CDCl_3$): δ ppm 4.82-4.76 (m, 1H); 3.39 (t, 2H, J=6.7 Hz); 2.44 (t, 0.3H, J=7.4 Hz, for $C\underline{H_2}Cl$); 2.28 (t, 2H, J=7.5 Hz, for $C\underline{H_2}Br$); 1.88-1.79 (m, 2H); 1.70-1.42 (m, 6H); 1.38-1.17 (m, 18H); 0.88-0.82 (m, 6H).

Heptadecan-9-yl 8-((3-((tert-butoxycarbonyl)amino) propyl)amino)octanoate

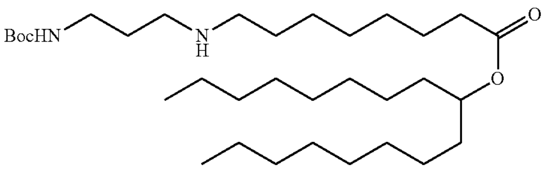

Chemical Formula: $C_{33}H_{66}N_2O_4$
Molecular Weight: 554.90

A solution of heptadecan-9-yl 8-bromooctanoate (69.2 g, 0.15 mole) and tert-butyl (3-aminopropyl)carbamate (130.6 g, 0.75 mole) in 500 mL ethanol was heated to 65° C. overnight. The reaction mixture was conc. and the residue purified by silica gel chromatography (0-20% methanol in DCM) to give heptadecan-9-yl 8-((3-((tert-butoxycarbonyl) amino)propyl)amino)octanoate (62 g, 74%) as a pale yellow oil. MS (CI): m/z ($MH^+$) 555.5 for $C_{33}H_{66}N_2O_4$. $^1H$ NMR (300 MHz, $CDCl_3$): δ ppm 5.15 (bs, 1H); 4.85 (quint., 1H, J=6.0 Hz); 3.17 (m, 2H); 2.65 (t, 2H, J=6.6 Hz); 2.56 (t, 2H, J=6.8 Hz); 2.26 (t, 2H, J=7.6 Hz); 1.68-1.56 (m, 6H); 1.46 (m, 5H); 1.43 (s, 9H); 1.24 (m, 30H); 0.86 (t, 6H, J=6.6 Hz).

Heptadecan-9-yl 8-((3-((tert-butoxycarbonyl)amino) propyl)(8-oxo-8-(undecan-3-yloxy)octyl)amino) octanoate

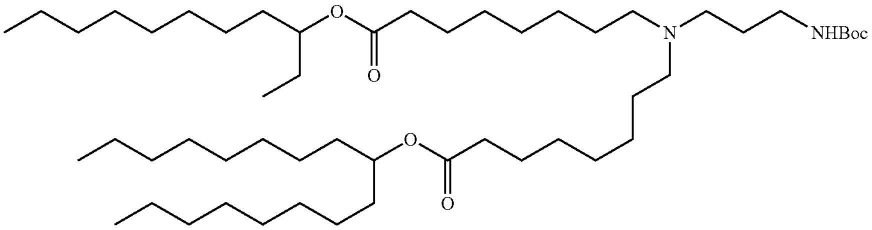

Chemical Formula: $C_{52}H_{102}N_2O_6$
Molecular Weight: 851.40

-

A solution of heptadecan-9-yl 8-((3-((tert-butoxycarbonyl)amino)propyl)amino)octanoate (6.0 g, 12 mmol) and undecan-3-yl 8-bromooctanoate (4.27 g, 11 mmol) in 100 mL of a 1:1 mixture of cyclopentyl methyl ether and acetonitrile was added potassium carbonate (6.02 g, 43 mmol) and potassium iodide (1.97 g, 12 mmol) to give a white mixture. This was heated to 86° C. and stirred for 18 hours. The mixture was allowed to cool to room temp., filtered through Celite, the filter solids washed with ethyl acetate and the filtrate conc. The residue was purified by silica gel chromatography (0-100% ethyl acetate in hexanes) to give heptadecan-9-yl 8-((3-((tert-butoxycarbonyl)amino) propyl)(8-oxo-8-(undecan-3-yloxy)octyl)amino)octanoate (6.8 g, 74%) as an oil. MS (CI): m/z ($MH^+$) 851.7 for $C_{52}H_{102}N_2O_6$. $^1H$ NMR (300 MHz, $CDCl_3$): δ ppm 5.66 (m, 1H); 4.87-4.80 (m, 2H); 3.17 (m, 2H); 2.42 (t, 2H, J=6.3 Hz); 2.35-2.24 (m, 8H); 1.64-1.56 (m, 12H); 1.53-1.44 (m, 9H); 1.44-1.36 (m, 3H); 1.42 (s, 9H); 1.32-1.12 (m, 42H); 0.86 (t, 12H, J=6.4 Hz).

Heptadecan-9-yl 8-((3-aminopropyl)(8-oxo-8-(undecan-3-yloxy)octyl) amino)octanoate

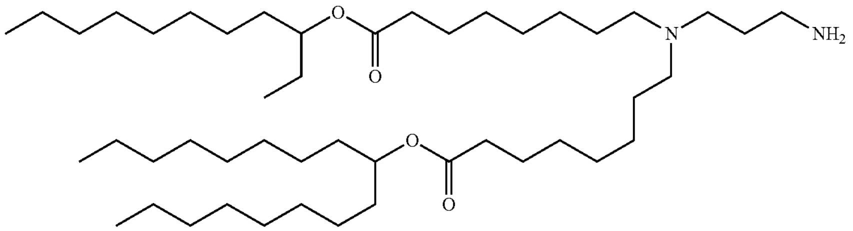

Chemical Formula: $C_{47}H_{94}N_2O_4$
Molecular Weight: 751.28

To a solution of heptadecan-9-yl 8-((3-((tert-butoxycarbonyl)amino)propyl)(8-oxo-8-(undecan-3-yloxy)octyl) amino)octanoate (6.8 g, 7.99 mmol) in 30 mL dichloromethane at 0° C. was added trifluoroacetic acid (10 mL) dropwise and the reaction mixture stirred at room temperature overnight. The reaction was cooled to 0° C. and slowly quenched with a saturated aqueous sodium bicarbonate solution. The organic layer was washed sequentially with a saturated aqueous sodium bicarbonate solution, a 0.1 N sodium hydroxide solution and brine. After drying with anhydrous sodium sulfate, the solvent was removed under vacuum to give heptadecan-9-yl 8-((3-aminopropyl)(8-oxo-8-(undecan-3-yloxy)octyl)amino)octanoate (5.7 g, 97%) as an oil which was used in subsequent steps without further purification. Optionally the material can be converted to the bis-oxalate salt for storage. MS (CI): m/z ($MH^+$) 751.7 for $C_{47}H_{94}N_2O_4$. $^1H$ NMR (300 MHz, $CDCl_3$): δ ppm 4.87-4.79 (m, 2H); 2.70 (t, 2H, J=6.8 Hz); 2.42-2.33 (m, 6H); 2.27 (dt, 4H, J=7.4 Hz, 2.8 Hz); 1.68-1.46 (m, 22H); 1.44-1.35 (m, 4H); 1.34-1.16 (m, 42H); 0.88-0.84 (m, 12H).

3-Methoxy-4-(methylamino)-1,2,5-thiadiazole 1-oxide

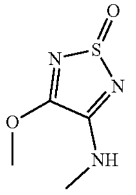

Chemical Formula: $C_4H_7N_3O_2S$
Molecular Weight: 161.18

To a solution of 500 mg (3.0 mmol) 3,4-dimethoxy-1,2,5-thiadiazole 1-oxide (Enamine LLC, Monmouth Jct., NJ) in 10 mL methanol was added 1.5 mL (3 mmol) of a 2M methylamine solution in THF dropwise over five minutes and the resulting orange solution stirred at room temp overnight. No starting material remained by TLC so the solution was conc. and the residue purified by silica gel chromatography (50% hexanes/50% EtOAc going to 100% EtOAc) to give 3-methoxy-4-(methylamino)-1,2,5-thiadiazole 1-oxide (340 mg, 2.11 mmol, 70%) as a pale yellow solid. $^1H$-NMR (300 MHz, $CDCl_3$) ppm δ: 5.73 (br s, 1H); 4.14 (s, 3H); 3.12 (d, 3H, J=5.1 Hz).

Heptadecan-9-yl 8-((3-((4-(methylamino)-1-oxido-1,2,5-thiadiazol-3-yl)amino)propyl)(8-oxo-8-(undecan-3-yloxy)octyl)amino)octanoate

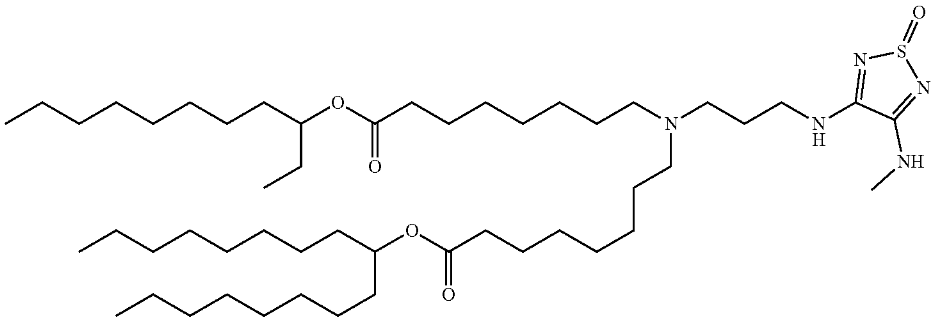

Chemical Formula: $C_{50}H_{97}N_5O_5S$
Molecular Weight: 880.42

To a solution of heptadecan-9-yl 8-((3-aminopropyl)(8-oxo-8-(undecan-3-yloxy)octyl)amino)octanoate bis oxalate (250 mg, 0.27 mmol) in 5 mL 2-propanol was added N,N-diisopropylethylamine (190 uL, 1.1 mmol) followed by 3-methoxy-4-(methylamino)-1,2,5-thiadiazole 1-oxide (52 mg, 0.32 mmol) and the pale yellow mixture stirred at room temp. overnight. The solution was conc. in a stream of nitrogen and the residue dissolved in DCM. The solution was washed once with a saturated aqueous sodium bicarbonate solution, dried ($MgSO_4$), filtered and the filtrate conc. to a pale yellow oil. This was purified by silica gel chromatography (0-100% (mixture of 1% $NH_4OH$, 20% MeOH in dichloromethane) in dichloromethane) to give heptadecan-9-yl 8-((3-((4-(methylamino)-1-oxido-1,2,5-thiadiazol-3-yl)amino)propyl)(8-oxo-8-(undecan-3-yloxy)octyl) amino)octanoate (215 mg, 0.24 mmol, 91%) as a colorless oil. UPLC/ELSD: RT=3.05 min. MS (ES): m/z ($MH^+$) 880.57 for $C_{50}H_{97}N_5O_5S$. $^1H$ NMR (300 MHz, $CDCl_3$) δ: ppm 8.17 (br s, 1H); 7.91 (br s, 1H); 4.90-4.76 (m, 2H); 3.55-3.46 (m, 1H); 3.37-3.28 (m, 1H); 2.98 (s, 3H); 2.60-2.35 (m, 6H); 2.28 (dt, 4H, J=7.4 Hz, 2.9 Hz); 1.90-1.76 (m, 2H); 1.70-1.38 (m, 17H); 1.37-1.13 (m, 49H); 0.87-0.85 (m, 12H).

AB. Compound 2: Heptadecan-9-yl 8-((3-((4-(methylamino)-1,1-dioxido-1,2,5-thiadiazol-3-yl)amino)propyl)(8-oxo-8-(undecan-3-yloxy)octyl)amino)octanoate 3-Ethoxy-4-(methylamino)-1,2,5-thiadiazole 1,1-dioxide

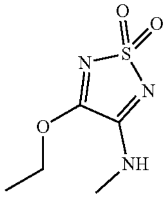

Chemical Formula: $C_5H_9N_3O_3S$
Molecular Weight: 191.21

To a suspension of 500 mg (2.3 mmol) 3,4-diethoxy-1,2,5-thiadiazole 1,1-dioxide (AstaTech, Bristol, PA) in 20 mL diethyl ether was added 1.5 mL (3 mmol) of a 2M methylamine solution in THF dropwise over five minutes and the resulting thick white mixture stirred at room temp overnight. No starting material remained by TLC so the solution was conc., the residue redissolved in DCM, passed through a cotton plug and the filtrate purified by silica gel chromatography (50-100% EtOAc in hexanes) to give 3-ethoxy-4-(methylamino)-1,2,5-thiadiazole 1,1-dioxide (165 mg, 0.86 mmol, 37%) as a white solid. $^{1}$H-NMR (300 MHz, $CDCl_3$) ppm δ: 9.30 (br s, 1H); 4.51 (q, 2H, J=14.2, 7.0 Hz); 2.90 (s, 3H); 1.41 (t, 3H, J=7.1 Hz).

Heptadecan-9-yl 8-((3-((4-(methylamino)-1,1-dioxido-1,2,5-thiadiazol-3-yl)amino)propyl)(8-oxo-8-(undecan-3-yloxy)octyl)amino)octanoate

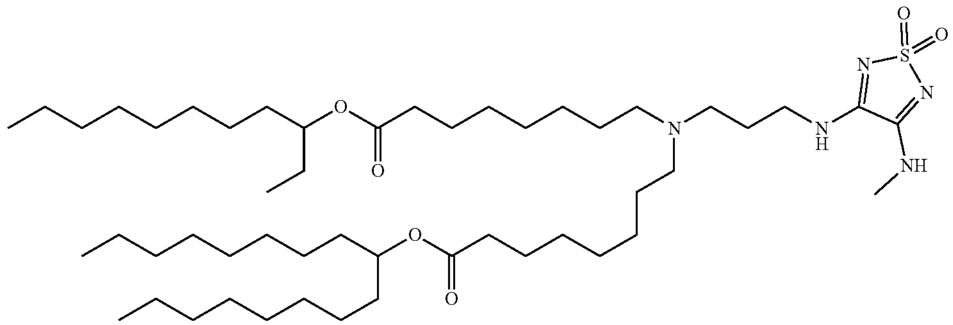

Chemical Formula: $C_{50}H_{97}N_5O_6S$
Molecular Weight: 896.42

To a solution of heptadecan-9-yl 8-((3-aminopropyl)(8-oxo-8-(undecan-3-yloxy)octyl)amino)octanoate bis oxalate (250 mg, 0.27 mmol) in 5 mL methanol was added N,N-diisopropylethylamine (DIEA; 190 uL, 1.1 mmol) followed by 3-ethoxy-4-(methylamino)-1,2,5-thiadiazole 1,1-dioxide (62 mg, 0.32 mmol) and the resulting colorless solution stirred at room temp overnight. The reaction was conc. in a stream of nitrogen, the resulting white solids dissolved in DCM and washed once with a saturated aqueous sodium bicarbonate solution. The organics were dried ($Na_2SO_4$), filtered and the filtrate conc. to a colorless oil. This was purified by silica gel chromatography (100% DCM going to 50% DCM/50% 80:20:1 DCM/MeOH/$NH_4OH$, then to 100% 80:20:1 DCM/MeOH/$NH_4OH$) to give heptadecan-9-yl 8-((3-((4-(methylamino)-1,1-dioxido-1,2,5-thiadiazol-3-yl)amino)propyl)(8-oxo-8-(undecan-3-yloxy)octyl)amino)octanoate (218 mg, 0.24 mmol, 91%) as a colorless syrup. UPLC/ELSD: RT=3.09 min. MS (ES): m/z ($MH^+$) 896.47 for $C_{50}H_{97}N_5O6S$. $^{1}$H NMR (300 MHz, $CDCl_3$) δ: ppm 6.13 (br s, 2H); 4.82 (m, 2H); 3.51 (t, 2H, J=6.4 Hz); 3.06 (s, 3H); 2.67 (t, 2H, J=6.0 Hz); 2.59 (m, 4H); 2.30 (dt, 4H, J=7.4 Hz, 3.1 Hz); 1.87 (m, 2H); 1.69-1.42 (m, 16H); 1.40-1.16 (m, 48H); 0.92-0.81 (m, 12H).

AC. Compound 17: Heptadecan-9-yl 8-({3-[2-(methylcarbamoyl)acetamido]propyl}[8-oxo-8-(undecan-3-yloxy)octyl]amino)octanoate

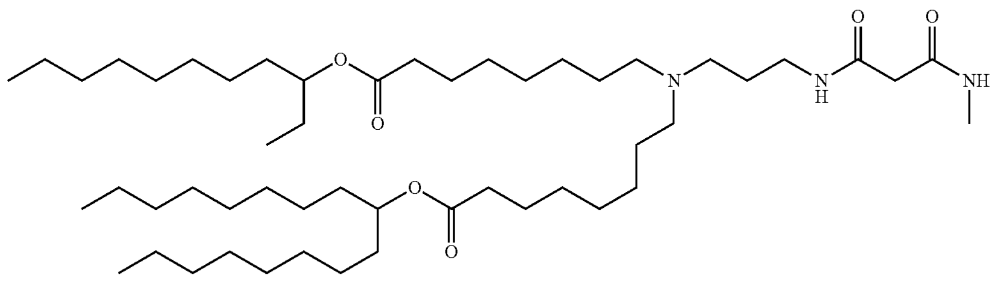

Chemical Formula: $C_{51}H_{99}N_3O_6$
Molecular Weight: 850.37

To solution of heptadecan-9-yl 8-((3-aminopropyl)(8-oxo-8-(undecan-3-yloxy)octyl)amino)octanoate (200 mg, 0.27 mmol) and malonic acid monomethyl amide (33 mg, 0.7 mmol) in 5 mL dry DCM was added 4-(dimethylamino) pyridine (DMAP; 3 mg, 0.03 mmol) followed by 1-ethyl-3-(3-dimethylaminopropyl)carbodiimide hydrochloride (EDC-HCl) (78 mg, 0.4 mmol) and finally N,N-diisopropylethylamine (DIEA; 200 uL, 1.1 mmol). The resulting colorless mixture was stirred at room temp for four days. The solution was diluted with DCM, washed once with a saturated aqueous sodium bicarbonate solution, dried ($Na_2SO_4$), filtered and the filtrate conc. to a pale yellow oil. This was purified by silica gel chromatography (100% DCM going to 100% 80:20:1 DCM/MeOH/ammonium hydroxide) to give heptadecan-9-yl 8-((3-(2-(methylcarbamoyl)acetamido)propyl)(8-oxo-8-(undecan-3-yloxy)octyl)amino)octanoate (165 mg, 0.18 mmol, 69%) as a colorless syrup. UPLC/ELSD: RT=3.03 min. MS (ES): m/z ($MH^+$) 850.85 for $C_{51}H_{99}N_3O_6$. $^1$H NMR (300 MHz, $CDCl_3$) δ: ppm 8.13 (t, 1H, J=3.8 Hz); 7.48 (br s, 1H); 4.83 (m, 2H); 3.34 (q, 2H, J=11.3 Hz, 5.6 Hz); 3.10 (s, 2H); 2.82 (d, 3H, J=4.8 Hz); 2.54 (br s, 2H); 2.40 (br s, 3H); 2.28 (td, 4H, J=7.4 Hz, 3 Hz); 1.77-1.38 (m, 19H); 1.37-1.12 (m, 48H); 0.94-0.81 (m, 12H).

AD. Compound 12: Heptadecan-9-yl 8-((3-(2-(methylamino)-2-oxoacetamido)propyl)(8-oxo-8-(undecan-3-yloxy)octyl)amino)octanoate

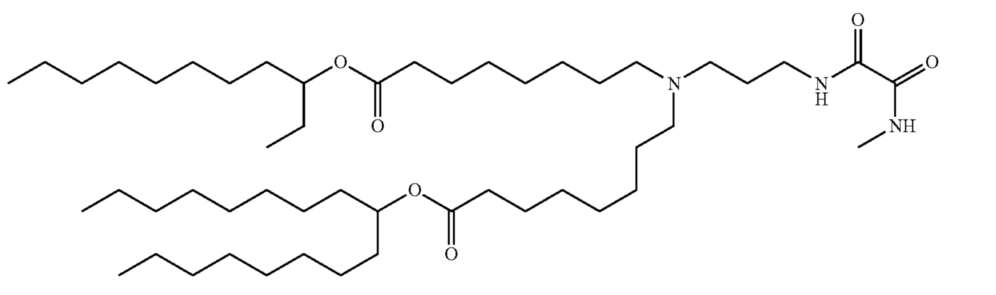

Chemical Formula: $C_{50}H_{97}N_3O_6$
Molecular Weight: 836.34

Heptadecan-9-yl 8-((3-aminopropyl)(8-oxo-8-(undecan-3-yloxy)octyl)amino)octanoate (200 mg, 0.27 mmol) and oxalic acid monomethyl amide (36 mg, 0.33 mmol) were reacted analogously to compound 17 to give heptadecan-9-yl 8-((3-(2-(methylamino)-2-oxoacetamido)propyl)(8-oxo-8-(undecan-3-yloxy)octyl)amino)octanoate (55 mg, 0.06 mmol, 24%) as a colorless liquid. UPLC/ELSD: RT=3.02 min. MS (ES): m/z ($MH^+$) 836.66 for $C_{50}H_{97}N_3O_6$. $^1H$ NMR (300 MHz, $CDCl_3$) δ: ppm 8.51 (br s, 1H); 7.44 (d, 1H, J=4.8 Hz); 4.82 (m, 2H); 3.37 (q, 2H, J=12.2 Hz, 6 Hz); 2.89 (d, 3H, J=5.2 Hz); 2.60-2.33 (m, 5H); 2.27 (td, 4H, J=7.4 Hz, 2.8 Hz); 1.79-1.40 (m, 17H); 1.39-1.14 (m, 50H); 0.94-0.81 (m, 12H).

AE. Compound 6: Heptadecan-9-yl 8-((3-((5-chloro-1,2-dimethyl-3,6-dioxo-1,2,3,6-tetrahydropyridazin-4-yl)amino)propyl)(8-oxo-8-(undecan-3-yloxy)octyl)amino)octanoate

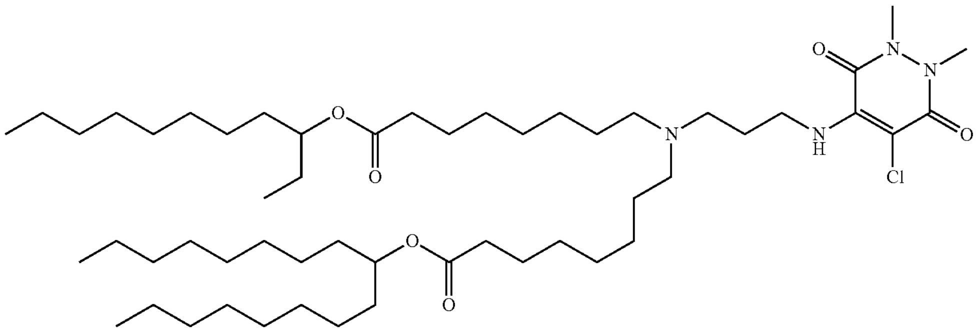

Chemical Formula: $C_{53}H_{99}ClN_4O_6$
Molecular Weight: 923.85

To a solution of heptadecan-9-yl 8-((3-aminopropyl)(8-oxo-8-(undecan-3-yloxy)octyl)amino)octanoate bis oxalate (250 mg, 0.27 mmol) and 4,5-dichloro-1,2-dimethylpyridazinone (76 mg, 0.36 mmol) in 4 mL ethanol was added triethylamine (150 uL, 1.09 mmol) to give a yellow mixture. This was heated to 100° C. in a sealed tube and stirred for 24 hours, then allowed to cool to room temp. The resulting mixture was conc. in a stream of nitrogen, the residue dissolved in DCM and washed once with a saturated aqueous sodium bicarbonate solution. The phases were separated, the aqueous extracted once with DCM, the organics combined, dried ($Na_2SO_4$), filtered and the filtrate conc. to a yellow oil. This was purified by silica gel chromatography (100% DCM going to 100% 80:20:1 DCM/MeOH/ammonium hydroxide) to give heptadecan-9-yl 8-((3-((5-chloro-1,2-dimethyl-3,6-dioxo-1,2,3,6-tetrahydropyridazin-4-yl)amino)propyl)(8-oxo-8-(undecan-3-yloxy)octyl)amino)octanoate (123 mg, 0.13 mmol, 50%) as a yellow oil which solidified to a pale yellow solid on standing. UPLC/ELSD: RT=3.04 min. MS (ES): m/z ($MH^+$) 923.75 for $C_{53}H_{99}ClN_4O_6$. $^1H$ NMR (300 MHz, $CDCl_3$) δ: ppm 6.71 (br s, 1H); 4.83 (m, 2H); 3.84 (q, 2H, J=12.5 Hz, 6.4 Hz); 3.71 (s, 2H); 3.60 (d, 6H, J=4.3 Hz); 2.49 (br s, 2H); 2.39 (br s, 3H); 2.27 (td, 4H, J=7.4 Hz, 2.8 Hz); 1.73 (br s, 2H); 1.68-1.37 (m, 18H); 1.36-1.13 (m, 48H); 0.93-0.81 (m, 12H).

AF. Compound 24: Heptadecan-9-yl 8-((3-((2,6-dioxo-1,2,3,6-tetrahydropyrimidin-4-yl)amino)propyl)(8-oxo-8-(undecan-3-yloxy)octyl)amino)octanoate

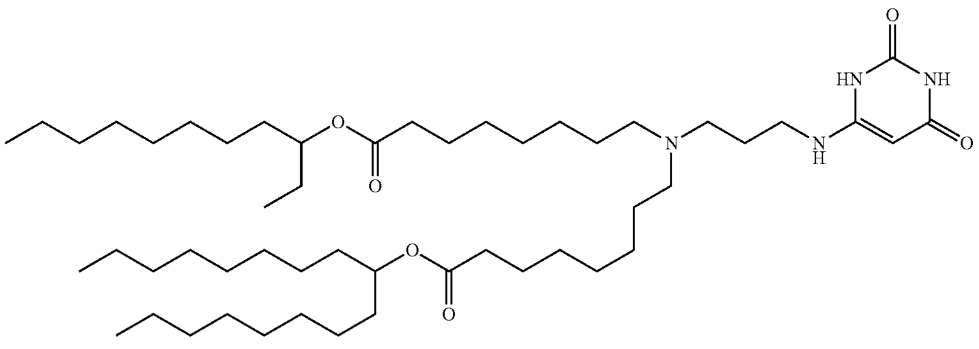

Chemical Formula: $C_{51}H_{96}N_4O_6$
Molecular Weight: 861.35

To a solution of heptadecan-9-yl 8-((3-aminopropyl)(8-oxo-8-(undecan-3-yloxy)octyl)amino)octanoate (290 mg, 0.39 mmol) in 1 butanol was added 6-chloropyrimidine-2, 4(1H,3H)-dione (0.016 g, 0.11 mmol), the resulting mixture heated to reflux (133° C.) and stirred for 2 days. The reaction was allowed to cool to room temp, conc., and codistilled once with toluene. The residue was purified by silica gel chromatography (0-20% MeOH with 1% $NH_3$ in DCM) to give heptadecan-9-yl 8-((3-((2,6-dioxo-1,2,3,6-tetrahydropyrimidin-4-yl)amino)propyl)(8-oxo-8-(undecan-3-yloxy)octyl)amino)octanoate (63 mg, 0.07 mmol, 66%). MS (ES): m/z ($MH^+$) 861.7 for $C_{51}H_{96}N_4O_6$. $^1H$ NMR (300 MHz, $CDCl_3$): ppm δ 5.36 (s, 1H), 4.94-4.77 (m, 2H), 3.25-3.15 (m, 2H), 2.67-2.37 (m, 6H), 2.37-2.24 (m, 4H), 1.83-1.42 (m, 18H), 1.41-1.21 (m, 48H), 0.96-0.82 (m, 12H).

AG. Compound 11: Heptadecan-9-yl 8-((3-((5-amino-4H-1,2,4-triazol-3-yl)amino)propyl)(8-oxo-8-(undecan-3-yloxy)octyl)amino)octanoate Heptadecan-9-yl (E/Z)-8-((3-(((cyanoimino)(phenoxy)methyl)amino)propyl)(8-oxo-8-(undecan-3-yloxy)octyl)amino)octanoate

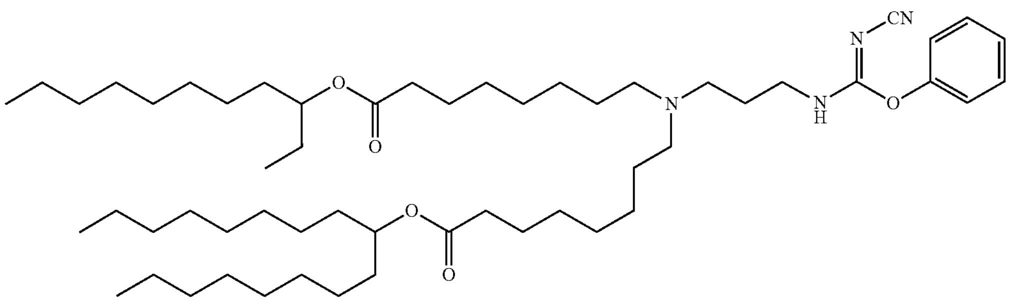

Chemical Formula: $C_{55}H_{98}N_4O_5$
Molecular Weight: 895.41

To a solution of heptadecan-9-yl 8-((3-aminopropyl)(8-oxo-8-(undecan-3-yloxy)octyl)amino)octanoate (0.25 g, 0.33 mmol) in 3 mL 2-propanol was added triethylamine (0.046 ml, 0.33 mmol) and diphenyl cyanocarbonimidate (0.079 g, 0.33 mmol) and the solution stirred at room temp for two hours. The reaction was conc. and the residue purified by silica gel chromatography (0-20% MeOH with 1% $NH_3$ in DCM) to give heptadecan-9-yl(E/Z)-8-((3-(((cyanoimino)(phenoxy)methyl)amino)propyl)(8-oxo-8-(undecan-3-yloxy)octyl)amino)octanoate (0.2 g, 0.2 mmol, 67%) as an oil. MS (ES): m/z ($MH^+$) 895.77 for $C_{55}H_{98}N_4O_5$.

Heptadecan-9-yl 8-((3-((5-amino-4H-1,2,4-triazol-3-yl)amino)propyl)(8-oxo-8-(undecan-3-yloxy)octyl)amino)octanoate

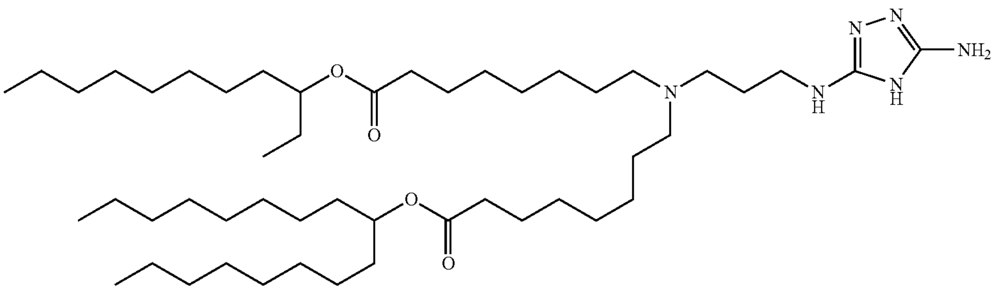

Chemical Formula: $C_{49}H_{96}N_6O_4$
Molecular Weight: 833.35

To a solution of heptadecan-9-yl (E/Z)-8-((3-(((cyanoimino)(phenoxy)methyl)amino)propyl)(8-oxo-8-(undecan-3-yloxy)octyl)amino)octanoate (0.193 g, 0.22 mmol) in ethanol (3 mL) was added 80% hydrazine hydrate (0.012 mL, 0.237 mmol) and the resulting solution stirred at room temp for two days. The reaction was conc. and the residue purified in silica gel chromatography (0-20% MeOH with 1% $NH_3$ in DCM) to give heptadecan-9-yl 8-((3-((5-amino-4H-1,2,4-triazol-3-yl)amino)propyl)(8-oxo-8-(undecan-3-yloxy)octyl)amino)octanoate (0.175 g, 0.21 mmol, 97%) as an oil. MS (ES): m/z ($MH^+$) 833.76 for $C_{49}H_{92}N_6O_4$. $^1H$ NMR (300 MHz, $CDCl_3$): δ 4.92-4.77 (m, 2H), 4.08 (brs, 2H), 3.29-3.22 (m, 2H), 2.55-2.39 (m, 6H), 2.34-2.24 (m, 4H), 1.76-1.40 (m, 20H), 1.36-1.20 (m, 48H), 0.94-0.83 (m, 12H).

AH. Compound 14: Heptadecan-9-yl 8-((3-((1,3-diamino-1,3-dioxopropan-2-yl)amino)propyl)(8-oxo-8-(undecan-3-yloxy)octyl)amino)octanoate

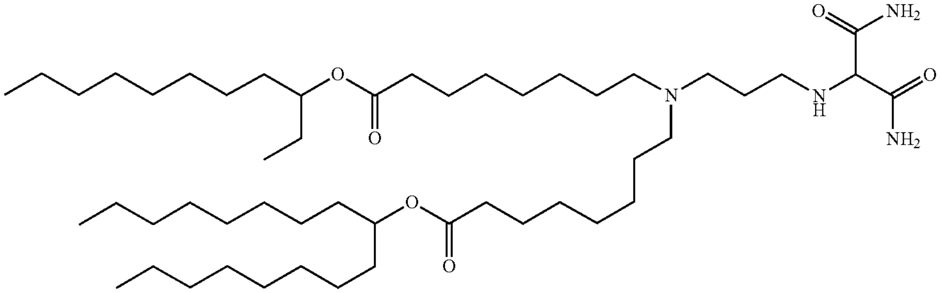

Chemical Formula: $C_{50}H_{98}N_4O_6$
Molecular Weight: 851.36

To a mixture of heptadecan-9-yl 8-((3-aminopropyl)(8-oxo-8-(undecan-3-yloxy)octyl)amino)octanoate bis oxalate (250 mg, 0.27 mmol) in 5 mL 2-Me-THF was added 1 mL of a saturated aqueous sodium bicarbonate solution and the bilayer stirred vigorously for five minutes. To this was added 2-bromomalonamide (Princeton Biomolecular Research, Monmouth Junction, NJ) (60 mg, 0.32 mmol) and the mixture stirred vigorously at room temp for 48 hours. The organic layer was pipetted away and retained, the remaining aqueous extracted twice with DCM, the organics combined, dried ($Na_2SO_4$), filtered and the filtrate conc. to a colorless oil. This was purified by silica gel chromatography (100% DCM going to 100% 80:20:1 DCM/MeOH/ammonium hydroxide) to give heptadecan-9-yl 8-((3-((1,3-diamino-1,3-dioxopropan-2-yl)amino)propyl)(8-oxo-8-(undecan-3-yloxy)octyl)amino)octanoate (145 mg, 0.16 mmol, 60%) as a colorless syrup. UPLC/ELSD: RT=2.83 min. MS (ES): m/z ($MH^+$) 851.59 for $C_{50}H_{98}N_4O_6$. $^1H$ NMR (300 MHz, $CDCl_3$) δ: ppm 7.68 (d, 2H, J=3.4 Hz); 5.60 (d, 2H, J=3.4 Hz); 4.83 (m, 2H); 3.68 (s, 1H); 2.65 (t, 2H, J=6.7 Hz); 2.47 (t, 2H, J=6.8 Hz); 2.37 (m, 4H); 2.27 (td, 4H, J=7.4 Hz, 2.9 Hz); 1.72-1.36 (m, 18H); 1.35-1.14 (m, 48H); 0.95-0.80 (m, 12H).

AI. Compound 21: Heptadecan-9-yl 8-((3-((2-oxo-1,2-dihydropyrimidin-4-yl)amino)propyl)(8-oxo-8-(undecan-3-yloxy)octyl)amino)octanoate

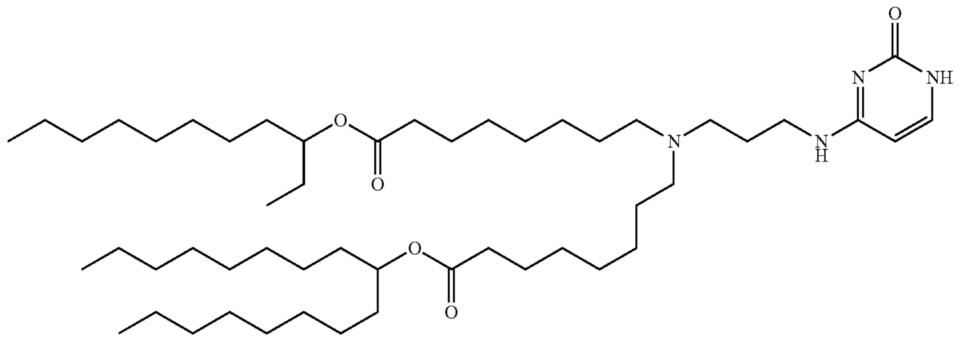

Chemical Formula: $C_{51}H_{96}N_4O_5$
Molecular Weight: 845.35

To a solution of heptadecan-9-yl 8-((3-aminopropyl)(8-oxo-8-(undecan-3-yloxy)octyl)amino)octanoate (240 mg, 0.32 mmol) in 5 mL ethanol was added 4-(methylthio)-2(1R)-pyrimidinone (106 mg, 0.73 mmol), the pale yellow mixture heated to reflux (95° C.) and stirred for three days. The solution was allowed to cool to room temp., conc. in a stream of nitrogen and the residue purified by silica gel chromatography (100% DCM going to 100% 80:20:1 DCM/MeOH/ammonium hydroxide) to give heptadecan-9-yl 8-((3-((2-oxo-1,2-dihydropyrimidin-4-yl)amino)propyl)(8-oxo-8-(undecan-3-yloxy)octyl)amino)octanoate (166 mg, 0.18 mmol, 57%) as a yellow oil. UPLC/ELSD: RT=2.83 min. MS (ES): m/z ($MH^+$) 846.41 for $C_{51}H_{96}N_4O_5$. $^1H$ NMR (300 MHz, $CDCl_3$) δ: ppm 11.76 (br s, 1H); 7.57 (s, 0.8H); 7.40 (s, 0.2H); 7.20 (d, 1H, J=6.9 Hz); 5.68 (d, 0.2H, J=6.7 Hz); 5.43 (d, 0.8H, J=6.7 Hz); 4.83 (m, 2H); 3.57 (m, 1.6H); 3.25 (br s, 0.4H); 2.55 (m, 2H); 2.38 (t, 4H, J=6.6 Hz); 2.27 (td, 4H, J=7.4 Hz, 2.6 Hz); 1.80-1.37 (m, 18H); 1.36-1.13 (m, 48H); 0.94-0.79 (m, 12H).

AJ. Compound 9: Heptadecan-9-yl 8-((3-((1-methyl-2,5-dioxo-2,5-dihydro-1H-imidazol-4-yl)amino)propyl)(8-oxo-8-(undecan-3-yloxy)octyl)amino)octanoate

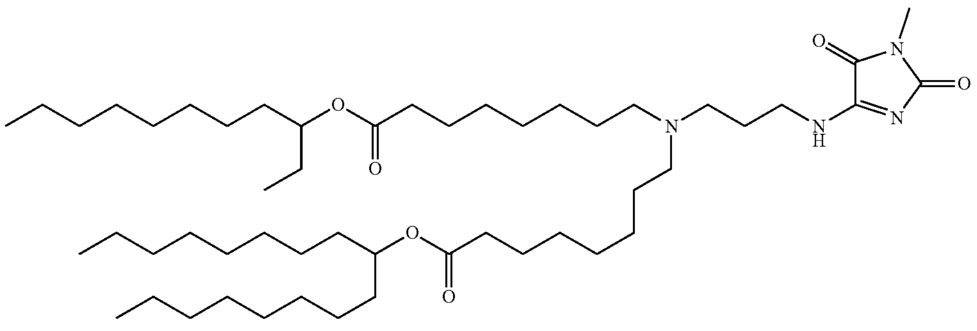

Chemical Formula: $C_{51}H_{96}N_4O_6$
Molecular Weight: 861.35

To a solution of heptadecan-9-yl 8-((3-aminopropyl)(8-oxo-8-(undecan-3-yloxy)octyl)amino)octanoate (200 mg, 0.27 mmol) and 1-methylimidazolidine-2,4,5-trione (0.035 g, 0.27 mmol) in 7 mL DCM was added triethylamine (0.098 mL, 0.68 mmol), followed by trimethylsilyl chloride (0.099 mL, 0.574 mmol) and imidazole (0.02 g, 0.3 mmol) with stirring to give a pale yellow mixture. To this was added DMAP (5 mg, cat.), the reaction heated to 51° C. and stirred for three hours. The reaction was then allowed to cool to room temp, diluted with DCM, washed once with water, dried ($Na_2SO_4$), filtered and the filtrate conc. The residue was purified by silica gel chromatography (100% DCM to 20% MeOH in DCM with 1.5% $NH_3$) to give heptadecan-9-yl 8-((3-((1-methyl-2,5-dioxo-2,5-dihydro-1H-imidazol-4-yl)amino)propyl)(8-oxo-8-(undecan-3-yloxy)octyl)amino)octanoate (0.11 g, 0.13 mmol, 47%) as a waxy solid. MS (ES): m/z ($MH^+$) 861.75 for $C_{51}H_{96}N_4O_6$. $^1H$ NMR (300 MHz, $CDCl_3$): δ 4.93-4.76 (m, 2H), 3.74-3.63 (m, 2H), 3.09 (s, 3H), 2.73-2.65 (m, 2H), 2.53-2.41 (m, 4H), 2.34-2.22 (m, 4H), 1.87-1.75 (m, 2H), 1.70-1.45 (m, 18H), 1.37-1.22 (m, 48H), 0.95-0.81 (m, 12H).

AK. Compound 50: Heptadecan-9-yl 8-((3-((5-amino-1,2,4-oxadiazol-3-yl)amino)propyl)(8-oxo-8-(undecan-3-yloxy)octyl)amino)octanoate

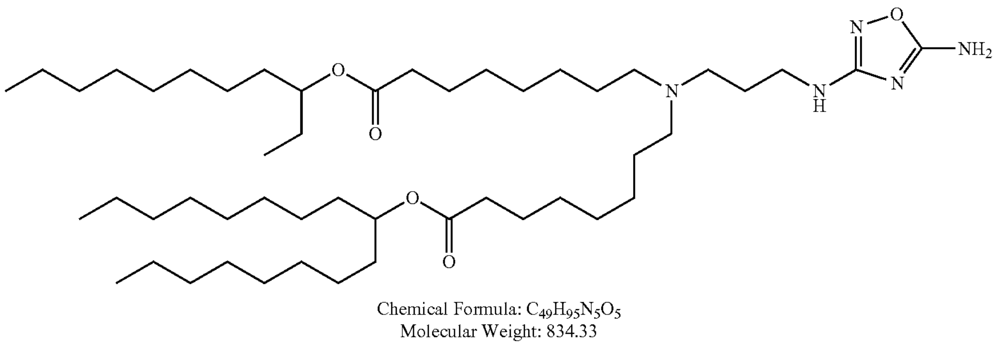 [SMILES: CCCCCCCCC(CC)OC(=O)CCCCCCCN(CCCCCCCC(=O)OC(CCCCCCCC)CCCCCCCC)CCCNc1noc(N)n1]

Chemical Formula: $C_{49}H_{95}N_5O_5$
Molecular Weight: 834.33

Compound 50 was prepared analogously to compound 11 but using hydroxylamine instead of hydrazine hydrate. Following an aqueous workup the residue was purified by silica gel chromatography (100% DCM to 20% MeOH in DCM with 1% $NH_3$) to give heptadecan-9-yl 8-((3-((5-amino-1,2,4-oxadiazol-3-yl)amino)propyl)(8-oxo-8-(undecan-3-yloxy)octyl)amino)octanoate (50 mg, 0.06 mmol, 54%) as an oil. MS (ES): m/z ($MH^+$) 861.75 for $C_{49}H_{95}N_5O_5$. $^1H$ NMR (300 MHz, $CDCl_3$) δ: ppm 0.74 (brs, 1H), 4.94-4.76 (m, 2H), 4.17 (s, 2H), 3.53-3.40 (m, 2H), 2.68-2.54 (m, 2H), 2.51-2.36 (m, 4H), 2.36-2.21 (m, 4H), 1.84-1.38 (m, 20H), 1.38-1.19 (m, 48H), 0.94-0.80 (m, 12H).

Ala. Compound 29: Heptadecan-9-yl 8-((3-((6-oxo-6,9-dihydro-1H-purin-2-yl)amino)propyl)(8-oxo-8-(undecan-3-yloxy)octyl)amino)octanoate

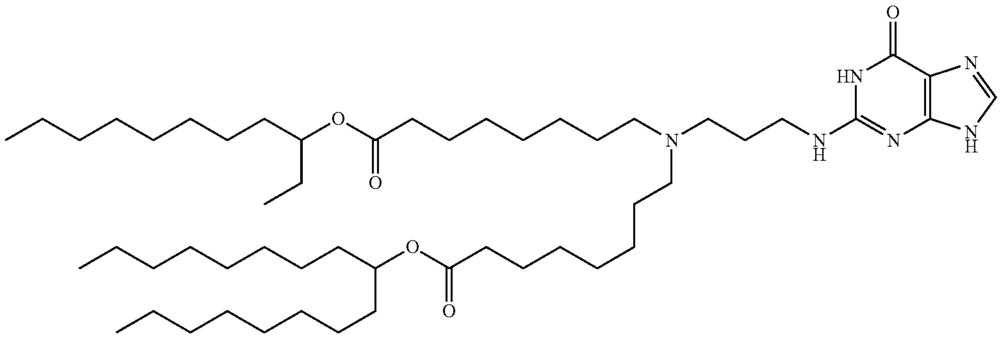

Chemical Formula: $C_{52}H_{96}N_6O_5$
Molecular Weight: 885.38

To a solution of solution of heptadecan-9-yl 8-((3-aminopropyl)(8-oxo-8-(undecan-3-yloxy)octyl)amino)octanoate (240 mg, 0.32 mmol) in 4 mL methoxyethanol was added 2-bromohypoxanthine (110 mg, 0.48 mmol) and the pale yellow mixture subjected to microwave irradiation at 120° C. for four hours. The mixture was diluted with DCM, washed three times with water, the organics dried ($Na_2SO_4$), filtered and the filtrate conc. to a yellow oil. This was triturated with methanol, filtered, and the filtrate conc. to a pale yellow solid. This was purified by silica gel chromatography (100% DCM going to 100% 80:20:1 DCM/MeOH/ammonium hydroxide) to give heptadecan-9-yl 8-((3-((6-oxo-6,9-dihydro-1H-purin-2-yl)amino)propyl)(8-oxo-8-(undecan-3-yloxy)octyl)amino)octanoate (37 mg, 0.04 mmol, 12%) as a white solid. UPLC/ELSD: RT=2.80 min. MS (ES): m/z ($MH^+$) 885.63 for $C_{52}H_{96}N_6O_5$. $^1H$ NMR (300 MHz, $CDCl_3$) δ: ppm 7.74 (br s, 2H); 4.83 (m, 2H); 3.44 (br s, 2H); 2.79-2.36 (m, 6H); 2.27 (td, 4H, J=7.4 Hz, 2.1 Hz); 1.85 (m, 2H); 1.70-1.39 (m, 16H); 1.38-1.13 (m, 50H); 0.94-0.78 (m, 12H).

AM. Compound 48: Heptadecan-9-yl 8-((3-(5-nitro-1H-indol-1-yl)propyl)(8-oxo-8-(undecan-3-yloxy)octyl)amino)octanoate

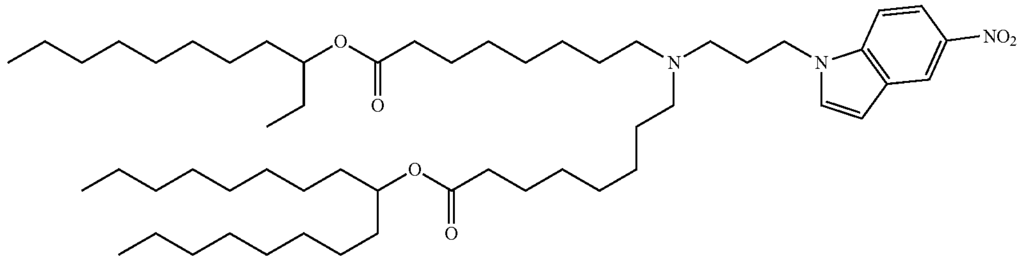

Chemical Formula: $C_{55}H_{97}N_3O_6$
Molecular Weight: 896.40

MS (ES): m/z ($MH^+$) 896.78 for $C_{55}H_{97}N_3O_6$. $^1H$ NMR (300 MHz, $CDCl_3$): δ 8.52 (d, 1H, J=4 Hz), 8.03 (dd, 1H, J=12 Hz, 8 Hz), 7.32 (d, 1H, J=12 Hz), 7.2 (d, 1H, J=4 Hz), 6.60 (d, 1H, J=4 Hz), 4.84-4.64 (m, 3H), 4.16 (t, 2H, J=8 Hz), 2.31-2.18 (m, 12H), 1.93-1.85 (m, 3H), 1.57-1.42 (m, 16H), 1.31-1.18 (m, 70H), 0.82-0.78 (m, 12H).

AN. Compound 55: Heptadecan-9-yl (E/Z)-8-((3-(4-amino-N'-hydroxy-1,2,5-oxadiazole-3-carboximidamido)propyl)(8-oxo-8-(undecan-3-yloxy)octyl)amino)octanoate

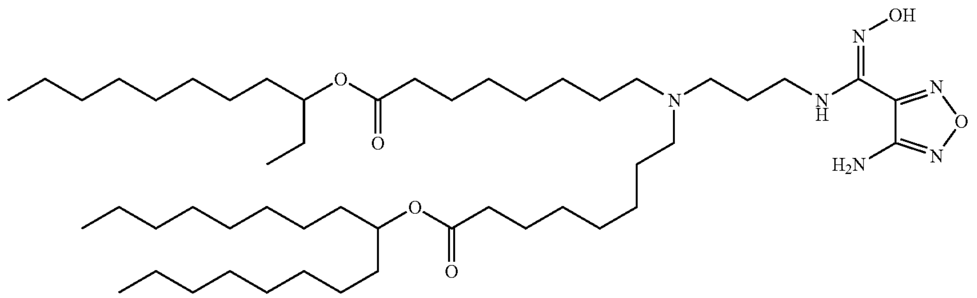

Chemical Formula: $C_{50}H_{96}N_6O_6$
Molecular Weight: 877.35

To a solution of solution of heptadecan-9-yl 8-((3-aminopropyl)(8-oxo-8-(undecan-3-yloxy)octyl)amino)octanoate (250 mg, 0.33 mmol) in 4 mL DCM at 0° C. was added (E/Z)-4-amino-N-hydroxy-1,2,5-oxadiazole-3-carbonimidoyl chloride (53 mg, 0.33 mmol) in one portion with stirring to give a white mixture. After five minutes 70 uL (0.49 mmol) triethylamine (70 uL, 0.49 mmol) was added and after another five minutes the cooling bath was removed. After 60 minutes the pale yellow solution was diluted with DCM, washed once with a 50% saturated aqueous sodium bicarbonate solution, the organics dried ($Na_2SO_4$), filtered and the filtrate conc. to a pale yellow oil. This was purified by silica gel chromatography (100% DCM going to 100% DCM/MeOH/c. $NH_4OH$ (aq) 80:20:1) to give heptadecan-9-yl(E/Z)-8-((3-(4-amino-N'-hydroxy-1,2,5-oxadiazole-3-carboximidamido)propyl)(8-oxo-8-(undecan-3-yloxy)octyl)amino)octanoate (190 mg, 0.21 mmol, 63%) as a slightly yellow oil. UPLC/ELSD: RT=3.01 min. MS (ES): m/z ($MH^+$) 877.49 for $C_{50}H_{96}N_6O_6$. $^1H$ NMR (300 MHz, $CDCl_3$) δ: ppm 6.29 (br s, 1H); 5.23 (s, 2H); 4.84 (m, 2H); 3.69 (q, 2H, J=11.4 Hz, 5.4 Hz); 2.55 (m, 2H); 2.42 (m, 3H); 2.29 (td, 4H, J=7.4 Hz, 3.0 Hz); 1.73 (m, 2H); 1.68-1.40 (m, 16H); 1.39-1.12 (m, 50H); 0.97-0.79 (m, 12H).

AO. Compound 25. Heptadecan-9-yl 8-((3-((3-(methylamino)pyrazin-2-yl)amino)propyl)(8-oxo-8-(undecan-3-yloxy)octyl)amino)octanoate, trifluoroacetate Salt

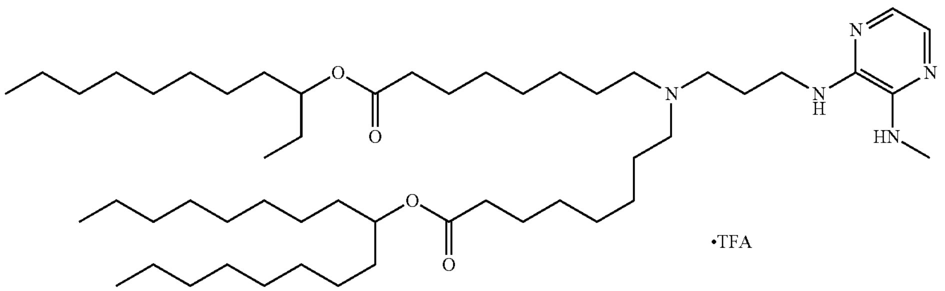

Chemical Formula: $C_{52}H_{99}N_5O_4$•TFA
Molecular Weight: 972.42

To a mixture of heptadecan-9-yl 8-((3-aminopropyl)(8-oxo-8-(undecan-3-yloxy)octyl)amino)octanoate (600 mg, 0.79 mmol) and 3-chloro-N-methylpyrazin-2-amine (171 mg, 1.19 mmol) in n-BuOH (10 mL) was added DIPEA (0.7 mL, 3.98 mmol). The resulting mixture was stirred at 160° C. in a microwave reactor for 16 h. After cooling to room temperature, the mixture was concentrated. To more batches (600 mg×2) of 2 were also carried out and the crude mixture was combined with the above batch for purification. The combined crude product was purified by silica gel chromatography (×3) with 0-10% of methanol in dichloromethane and a reverse phase chromatography with ACN-H2O (0.1% TFA) to give heptadecan-9-yl 8-((3-((3-(methylamino)pyrazin-2-yl)amino)propyl)(8-oxo-8-(undecan-3-yloxy)octyl)amino)octanoate trifluoroacetate salt (59 mg, 3%) as a light brown oil. m/z ($MH^+$) 858.7 for $C_{52}H_{99}N_5O_4$. $^1$H NMR (300 MHz, $CD_2Cl_2$): δ 0.84-0.89 (m, 12H); 1.23-1.85 (m, 65H); 5.22-5.25 (m, 6H); 3.01-3.60 (m, 11H); 4.78-4.82 (m, 2H); 7.22-7.33 (m, 2H); 8.2 (br m, 1H); 11.1 (br m, 1H).

AP. Compound 34. Heptadecan-9-yl 8-((3-((3-(methylamino)pyridin-2-yl)amino)propyl)(8-oxo-8-(undecan-3-yloxy)octyl)amino)octanoate Heptadecan-9-yl 8-((3-((3-nitropyridin-2-yl)amino)propyl)(8-oxo-8-(undecan-3-yloxy)octyl)amino)octanoate

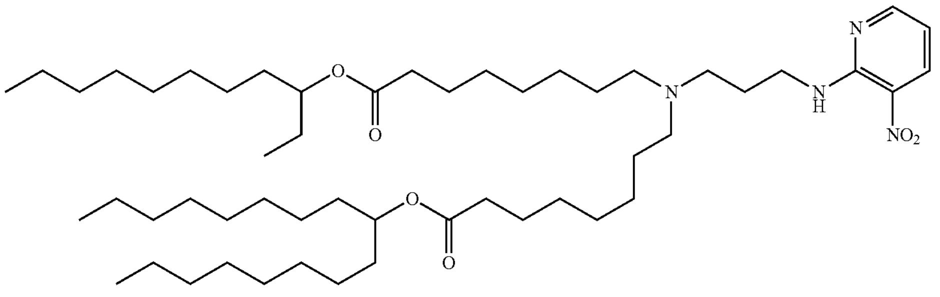

Chemical Formula: $C_{52}H_{96}N_4O_6$
Molecular Weight: 873.36

A mixture of heptadecan-9-yl 8-((3-aminopropyl)(8-oxo-8-(undecan-3-yloxy)octyl)amino)octanoate (340 mg, 0.45 mmol) and 2-chloro-3-nitropyridine (144 mg, 0.9 mmol) in n-BuOH (5 mL) was heated at 90° C. in a sealed tube for 16 h. After cooling, the mixture was concentrated and purified by silica gel chromatography with 0-10% of methanol in dichloromethane to give heptadecan-9-yl 8-((3-((3-nitropyridin-2-yl)amino)propyl)(8-oxo-8-(undecan-3-yloxy)octyl)amino)octanoate (363 mg, 91%). $^1$H NMR (300 MHz, $CDCl_3$): δ 0.84-0.88 (m, 12H); 1.14-1.79 (m, 64H); 2.24-2.45 (m, 10H); 3.15-3.21 (m, 2H); 3.70-3.79 (m, 2H); 4.80-4.85 (m, 2H); 6.65 (br m, 1H); 8.32-8.39 (m, 3H).

Heptadecan-9-yl 8-((3-((3-aminopyridin-2-yl)amino)propyl)(8-oxo-8-(undecan-3-yloxy)octyl)amino)octanoate

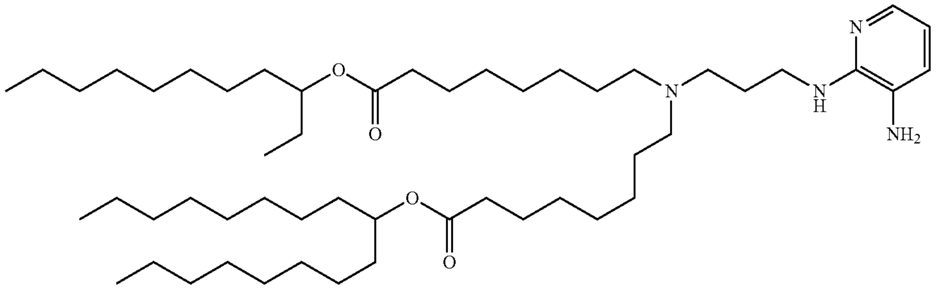

Chemical Formula: $C_{52}H_{98}N_4O_4$
Molecular Weight: 843.38

A mixture of heptadecan-9-yl 8-((3-((3-nitropyridin-2-yl)amino)propyl)(8-oxo-8-(undecan-3-yloxy)octyl)amino)octanoate (340 mg, 0.41 mmol) in MeOH (40 mL) was hydrogenated in the presence of Pd/C catalyst (10%, 50 mg) under $H_2$ atmosphere at ambient temperature for 4 h. The mixture was filtered through Celite and washed with MeOH. The filtrate was concentrated to give heptadecan-9-yl 8-((3-((3-aminopyridin-2-yl)amino)propyl)(8-oxo-8-(undecan-3-yloxy)octyl)amino)octanoate (310 mg, 89%). $^1$H NMR (300 MHz, $CDCl_3$): δ 0.84-0.88 (m, 12H); 1.13-2.01 (m, 70H); 2.24-2.26 (m, 4H); 2.35-2.80 (m, 4H); 3.50-3.58 (m, 3H); 4.80-4.85 (m, 2H); 6.46-6.48 (m, 1H); 6.76-6.79 (m, 1H); 7.65-7.66 (m, 1H).

Heptadecan-9-yl 8-((3-((3-(methylamino)pyridin-2-yl)amino)propyl)(8-oxo-8-(undecan-3-yloxy)octyl)amino)octanoate

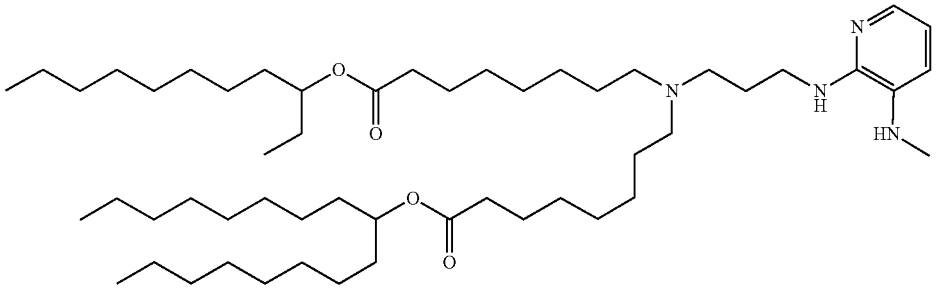

Chemical Formula: $C_{53}H_{100}N_4O_4$
Molecular Weight: 857.41

To a solution of heptadecan-9-yl 8-((3-((3-aminopyridin-2-yl)amino)propyl)(8-oxo-8-(undecan-3-yloxy)octyl) amino)octanoate (206 mg, 0.24 mmol) in MeOH:THF:water (3 mL:1 mL:1.5 mL) was added Pd/C (10%. 26.5 mg, 0.02 mmole) and $N_2$ bubbled through the solution for 5 min. To this mixture was added formaldehyde (36%, 37 μL, 0.48 mmol) and the resulting mixture was stirred at room temperature for 3 h. The mixture was again bubbled with $N_2$ for 5 min before adding ammonium formate (340 mg, 4.88 mmol) and the mixture stirred overnight at room temperature. The mixture was filtered through Celite and washed with $CH_2Cl_2$. The filtrate was washed with water, dried over anhydrous $Na_2SO_4$ and evaporated. The reaction was repeated with 190 mg (0.22 mmol) heptadecan-9-yl 8-((3-aminopropyl)(8-oxo-8-(undecan-3-yloxy)octyl)amino)octanoate following the above procedure. The two batches were combined for purification by silica gel chromatography with 0-10% methanol in dichloromethane to give heptadecan-9-yl 8-((3-((3-(methylamino)pyridin-2-yl)amino)propyl)(8-oxo-8-(undecan-3-yloxy)octyl)amino)octanoate (157 mg, 40%) as a brown oil. m/z ($MH^+$) 857.7 for $C_{53}H_{100}N_4O_4$. $^1$H NMR (300 MHz, $CDCl_3$): δ 0.84-0.88 (m, 12H); 1.14-1.89 (m, 66H); 2.2-2.45 (m, 10H); 2.8 (d, 3H, J=5.2 Hz); 3.01-3.18 (br m, 1H); 3.44-3.48 (m, 2H); 4.79-4.85 (m, 2H); 5.40 (br s, 1H); 6.57-6.67 (m, 2H); 7.62-7.66 (m, 1H).

AQ. Compound 35. Heptadecan-9-yl 8-((3-((5-(methylamino)pyrimidin-4-yl)amino)propyl)(8-oxo-8-(undecan-3-yloxy)octyl)amino)octanoate 4-Chloro-N-methylpyrimidin-5-amine

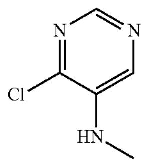

Chemical Formula: $C_5H_6ClN_3$
Molecular Weight: 143.57

To a solution of 4-chloropyrimidin-5-amine (1 g, 7.75 mmol) in 17 mL of trimethyl orthoformate was added 3 drops of TFA. The reaction mixture was stirred at 130° C. for 2 h. After cooling, the excess solvent was evaporated and dried. To this crude product in THF (100 mL) was added sodium triacetoxy borohydride (6.5 g, 31 mmol) and AcOH (620 μL, 10.9 mmol) and the resultant mixture was stirred overnight at room temperature. The mixture was diluted with EtOAc (50 mL), washed with water, dried over anhydrous $Na_2SO_4$ and concentrated. The crude product was purified by silica gel chromatography with 0-10% methanol in dichloromethane to give 4-chloro-N-methylpyrimidin-5-amine (79 mg, 7%). $^1$H NMR (300 MHz, $CDCl_3$): δ 2.96 (d, 3H, J=5.2 Hz)); 4.25 (br s, 1H); 8.02 (s, 1H); 8.36 (s, 1H).

Heptadecan-9-yl 8-((3-((5-(methylamino)pyrimidin-4-yl)amino)propyl)(8-oxo-8-(undecan-3-yloxy)octyl) amino)octanoate

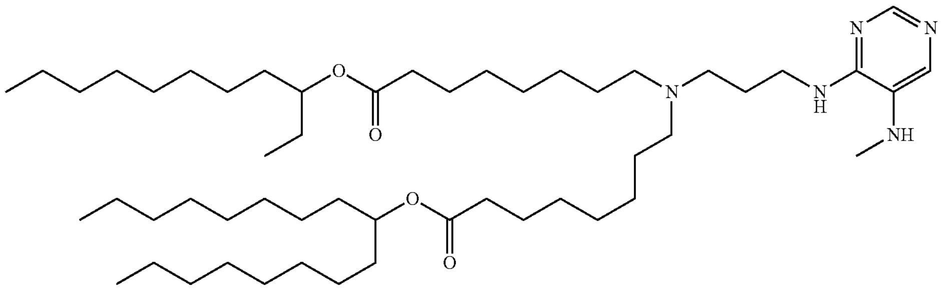

Chemical Formula: $C_{52}H_{99}N_5O_4$
Molecular Weight: 858.40

To a mixture of heptadecan-9-yl 8-((3-aminopropyl)(8-oxo-8-(undecan-3-yloxy)octyl)amino)octanoate (400 mg, 0.53 mmol) and 4-chloro-N-methylpyrimidin-5-amine (115 mg, 0.79 mmol) in n-BuOH (6 mL) was added DIPEA (0.47 mL, 2.65 mmol). The resultant mixture was stirred at 130° C. in a microwave reactor for 16 h. After cooling to room temperature, the mixture was concentrated and purified by silica gel chromatography with 0-10% of methanol in dichloromethane to give heptadecan-9-yl 8-((3-((5-(methylamino)pyrimidin-4-yl)amino)propyl)(8-oxo-8-(undecan-3-yloxy)octyl)amino)octanoate (150 mg, 33%) as light brown oil. m/z ($MH^+$) 858.7 for $C_{52}H_{99}N_5O_4$. $^1H$ NMR (300 MHz, $CDCl_3$): δ 0.85-0.87 (m, 12H); 1.24-1.88 (m, 67H); 2.25-2.65 (m, 10H), 2.82 (s, 3H); 3.41-3.50 (m, 2H); 4.78-4.91 (m, 2H); 6.8 (br s, 1H); 7.56 (s, 1H); 8.23 (s, 1H).

AR. Compound 45. Heptadecan-9-yl 8-((3-((5-oxo-2,5-dihydro-1H-pyrrol-3-yl)amino)propyl)(8-oxo-8-(undecan-3-yloxy)octyl)amino)octanoate

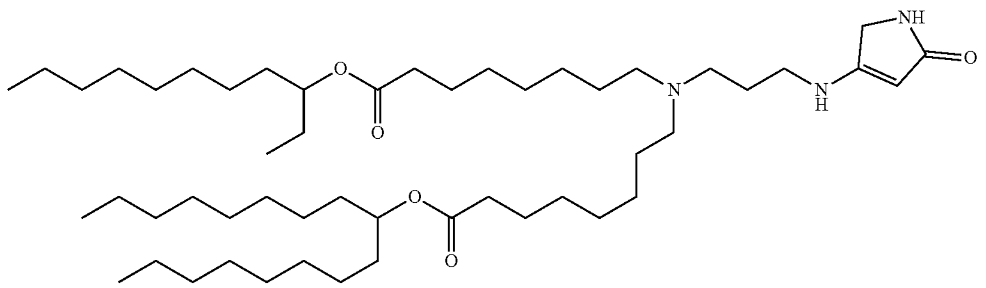

Chemical Formula: $C_{51}H_{97}N_3O_5$
Molecular Weight: 832.35

A mixture of heptadecan-9-yl 8-((3-aminopropyl)(8-oxo-8-(undecan-3-yloxy)octyl)amino)octanoate (365 mg, 0.47 mmol) and tetramic acid (64 mg, 0.64 mmol) in EtOH: AcOH (9:1, 3.5 mL) was stirred at 75° C. in a microwave reactor for 35 min. After cooling to room temperature, the mixture was diluted with $CH_2Cl_2$ (100 mL) and washed with saturated aq. $NaHCO_3$ (30 mL) and saturated aq. $Na_2CO_3$ (11 mL). The organic layer was separated and washed with brine, dried over anhydrous $Na_2SO_4$ and concentrated. The crude product was purified by silica gel chromatography with dichloromethane to dichloromethane/methanol/$NH_4OH$ (90:10:1) to give heptadecan-9-yl 8-((3-((5-oxo-2,5-dihydro-1H-pyrrol-3-yl)amino)propyl)(8-oxo-8-(undecan-3-yloxy)octyl)amino)octanoate (290 mg, 72%) as light yellow oil. m/z ($MH^+$) 832.7 for $C_{51}H_{97}N_3O_5$. $^1H$ NMR (300 MHz, $CDCl_3$): δ 0.86 (m, 12H); 1.11-1.80 (m, 66H); 2.25-2.60 (m, 10H); 3.13-3.16 (m, 2H); 3.85 (s, 2H); 4.62 (s, 1H); 4.8-4.91 (m, 3H); 6.53-5.59 (m, 1H).

AS. Compound 48: Heptadecan-9-yl 8-((3-(5-nitro-1H-indol-1-yl)propyl)(8-oxo-8-(undecan-3-yloxy)octyl)amino)octanoate

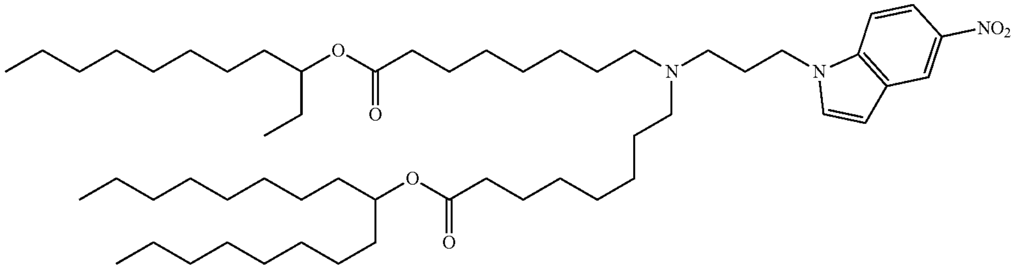

Chemical Formula: $C_{55}H_{97}N_3O_6$
Molecular Weight: 896.40

Nitro indole (0.03 g, 0.185 mmol) was dissolved in 3 mL DMF and cooled to 5 C. NaH 60% in oil (0.016 g, 0.39 mmol) in 3 mL DMF was added and stirred for 30 min in an ice bath. The solution was allowed to come to the RT and heptadecan-9-yl 8-((3-bromopropyl)(8-oxo-8-(undecan-3-yloxy)octyl)amino)octanoate (0.157 g, 0.2 mmol) in 1 mL DMF was added. The reaction was then heated at 93 C for 22 h then allowed to cool to room temp. The mixture was diluted with ethyl acetate and washed with water followed by brine. Organic layer was evaporated and the residue was purified using neutral $Al_2O_3$ column chromatography (A:100% DCM to B: 20% MeOH in DCM with 1% $NH_3$ over 25 min) to give heptadecan-9-yl 8-((3-(5-nitro-1H-indol-1-yl)propyl)(8-oxo-8-(undecan-3-yloxy)octyl)amino)octanoate (30 mg, 18.5%) as a yellow oil. MS (ES): m/z ($MH^+$) 896.78 for $C_{55}H_{97}N_3O_6$. $^1H$ NMR (300 MHz, $CDCl_3$): δ 8.52 (d, 1H, J=4 Hz), 8.03 (dd, 1H, J=12 Hz, 8 Hz), 7.32 (d, 1H, J=12 Hz), 7.2 (d, 1H, J=4 Hz), 6.60 (d, 1H, J=4 Hz), 4.84-4.64 (m, 3H), 4.16 (t, 2H, J=8 Hz), 2.31-2.18 (m, 12H), 1.93-1.85 (m, 3H), 1.57-1.42 (m, 16H), 1.31-1.18 (m, 70H), 0.82-0.78 (m, 12H).

AT. Compound 50: Heptadecan-9-yl 8-((3-((5-amino-1,2,4-oxadiazol-3-yl)amino)propyl)(8-oxo-8-(undecan-3-yloxy)octyl)amino)octanoate

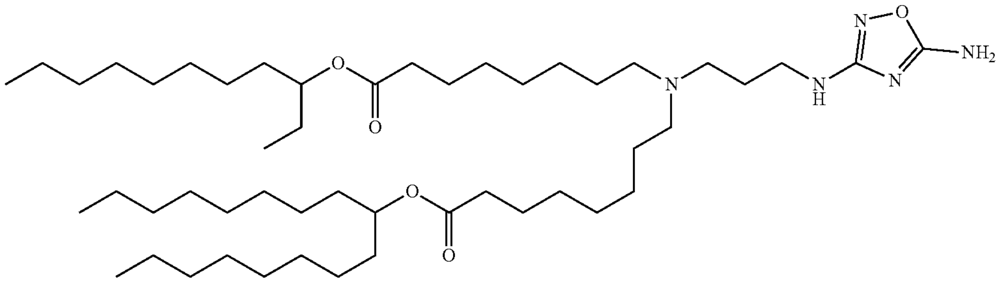

Chemical Formula: $C_{49}H_{95}N_5O_5$
Molecular Weight: 834.33

Compound 11 was prepared analogously to compound 7 but using hydroxylamine instead of hydrazine hydrate. Following an aqueous workup the residue was purified by silica gel chromatography (100% DCM to 20% MeOH in DCM with 1% $NH_3$) to give heptadecan-9-yl 8-((3-((5-amino-1,2,4-oxadiazol-3-yl)amino)propyl)(8-oxo-8-(undecan-3-yloxy)octyl)amino)octanoate (50 mg, 0.06 mmol, 54%) as an oil. MS (ES): m/z ($MH^+$) 861.75 for $C_{49}H_{95}N_5O_5$. $^1H$ NMR (300 MHz, $CDCl_3$) δ: ppm 0.74 (brs, 1H), 4.94-4.76 (m, 2H), 4.17 (s, 2H), 3.53-3.40 (m, 2H), 2.68-2.54 (m, 2H), 2.51-2.36 (m, 4H), 2.36-2.21 (m, 4H), 1.84-1.38 (m, 20H), 1.38-1.19 (m, 48H), 0.94-0.80 (m, 12H).

AU. Compound 55/56: Heptadecan-9-yl (E/Z)-8-((3-(4-amino-N'-hydroxy-1,2,5-oxadiazole-3-carboximidamido)propyl)(8-oxo-8-(undecan-3-yloxy)octyl)amino)octanoate

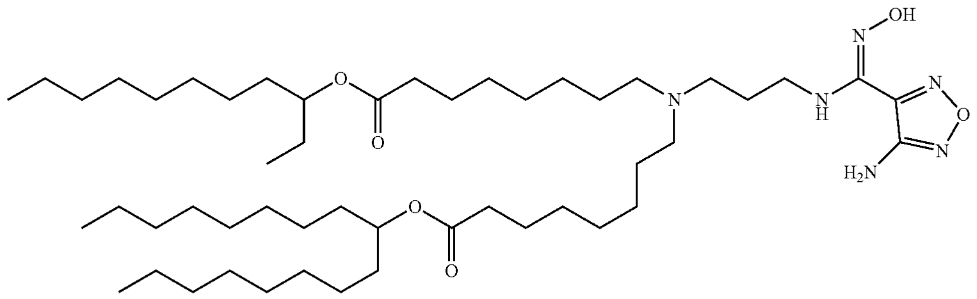

Chemical Formula: $C_{50}H_{96}N_6O_6$
Molecular Weight: 877.35

To a solution of solution of heptadecan-9-yl 8-((3-aminopropyl)(8-oxo-8-(undecan-3-yloxy)octyl)amino)octanoate (250 mg, 0.33 mmol) in 4 mL DCM at 0° C. was added (E/Z)-4-amino-N-hydroxy-1,2,5-oxadiazole-3-carbonimidoyl chloride (53 mg, 0.33 mmol) in one portion with stirring to give a white mixture. After five minutes 70 uL (0.49 mmol) triethylamine (70 uL, 0.49 mmol) was added and after another five minutes the cooling bath was removed. After 60 minutes the pale yellow solution was diluted with DCM, washed once with a 50% saturated aqueous sodium bicarbonate solution, the organics dried ($Na_2SO_4$), filtered and the filtrate conc. to a pale yellow oil. This was purified by silica gel chromatography (100% DCM going to 100% DCM/MeOH/c. $NH_4OH$ (aq) 80:20:1) to give heptadecan-9-yl(E/Z)-8-((3-(4-amino-N'-hydroxy-1,2,5-oxadiazole-3-carboximidamido)propyl)(8-oxo-8-(undecan-3-yloxy)octyl)amino)octanoate (190 mg, 0.21 mmol, 63%) as a slightly yellow oil. UPLC/ELSD: RT=3.01 min. MS (ES): m/z ($MH^+$) 877.49 for $C_{50}H_{96}N_6O_6$. $^1H$ NMR (300 MHz, $CDCl_3$) δ: ppm 6.29 (br s, 1H); 5.23 (s, 2H); 4.84 (m, 2H); 3.69 (q, 2H, J=11.4 Hz, 5.4 Hz); 2.55 (m, 2H); 2.42 (m, 3H); 2.29 (td, 4H, J=7.4 Hz, 3.0 Hz); 1.73 (m, 2H); 1.68-1.40 (m, 16H); 1.39-1.12 (m, 50H); 0.97-0.79 (m, 12H).

AV. Compound 57. Heptadecan-9-yl 8-((3-((4-oxo-4,5-dihydro-1H-imidazol-2-yl)amino)propyl)(8-oxo-8-(undecan-3-yloxy)octyl)amino)octanoate 2-(Methylthio)-1,5-dihydro-4H-imidazol-4-one

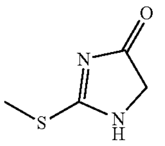

Chemical Formula: $C_4H_6N_2OS$
Molecular Weight: 130.17

To a mixture of 2-thiohydantoin (840 mg, 7.23 mmol) in MeOH (14 mL) was added $CH_3I$ (0.54 mL, 8.68 mmol) portion wise at 0° C. The resultant mixture was stirred overnight at room temperature. The solvents were evaporated and the $^1$H-NMR showed the product 2-(methylthio)-1,5-dihydro-4H-imidazol-4-one and unreacted starting material in the ratio of 4:1. This crude product was used in the next step without further purification.

Heptadecan-9-yl 8-((3-((4-oxo-4,5-dihydro-1H-imidazol-2-yl)amino)propyl)(8-oxo-8-(undecan-3-yloxy)octyl)amino)octanoate

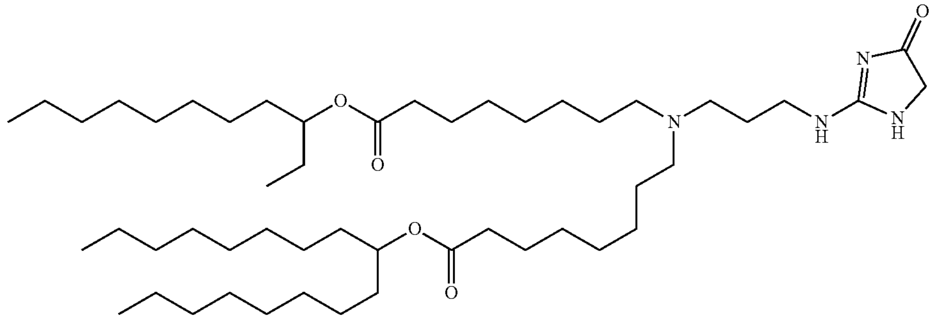

Chemical Formula: $C_{50}H_{96}N_4O_5$
Molecular Weight: 833.34

A mixture of heptadecan-9-yl 8-((3-aminopropyl)(8-oxo-8-(undecan-3-yloxy)octyl)amino)octanoate (400 mg, 0.53 mmol) and 2-(methylthio)-1,5-dihydro-4H-imidazol-4-one (320 mg, 1.06 mmol) in n-BuOH (35 mL) was stirred at 160° C. in a microwave reactor for 25 min. After cooling to room temperature, the mixture was diluted with $CH_2Cl_2$ (100 mL) and washed with saturated aq. $NaHCO_3$ (30 mL) and saturated aq. $Na_2CO_3$ (11 mL). The organic layer was separated and washed with brine, dried over anhydrous $Na_2SO_4$ and concentrated. The reaction was repeated with 120 mg (0.16 mmol) of heptadecan-9-yl 8-((3-aminopropyl)(8-oxo-8-(undecan-3-yloxy)octyl)amino)octanoate and the crude mixture was combined with the above batch for purification. The combined crude product was purified three times by silica gel chromatography with 0-10% of methanol in dichloromethane to give heptadecan-9-yl 8-((3-((4-oxo-4,5-dihydro-1H-imidazol-2-yl)amino)propyl)(8-oxo-8-(undecan-3-yloxy)octyl)amino)octanoate (235 mg, 41%) as a brown oil. m/z ($MH^+$) 834.7 for $C_{50}H_{96}N_4O_5$. $^1$H NMR (300 MHz, $CDCl_3$): δ 0.84-0.93 (m, 12H); 1.15-1.85 (m, 67H); 2.3-2.60 (m, 10H); 3.51-3.55 (m, 2H); 3.94 (s, 2H); 4.8-4.85 (m, 2H); 5.32-5.38 (m, 1H).

AW. Compound 58. Heptadecan-9-yl 8-((3-(methylsulfonoamidimidamido)propyl)(8-oxo-8-(undecan-3-yloxy)octyl)amino)octanoate N-(tert-Butyldimethylsilyl)methanesulfonamide

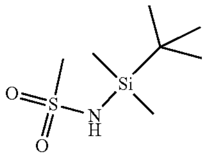

Chemical Formula: $C_7H_{19}NO_2SSi$
Molecular Weight: 209.38

To a stirred mixture of methanesulfonamide (2 g, 21 mmol) and TBDMS-chloride (4.8 g, 31.5 mmol) in $CHCl_3$ (30 mL) at 0° C. was added TEA (4.4 mL, 31.5 mmol). The resultant mixture was stirred at ambient temperature for 16 h, concentrated, the residue diluted with water and extracted with EtOAc. The organic layer was washed with brine, dried over anhydrous $Na_2SO_4$ and concentrated to give N-(tert-butyldimethylsilyl)methanesulfonamide (4.1 g, 93%) which was used in the next step without further purification. $^1$H NMR (300 MHz, $CDCl_3$): δ 0.28 (s, 6H); 0.93 (s, 9H); 3.0 (s, 3H).

Heptadecan-9-yl 8-((3-(N'-(tert-butyldimethylsilyl) methylsulfonoamidimidamido)propyl)(8-oxo-8-(undecan-3-yloxy)octyl)amino)octanoate

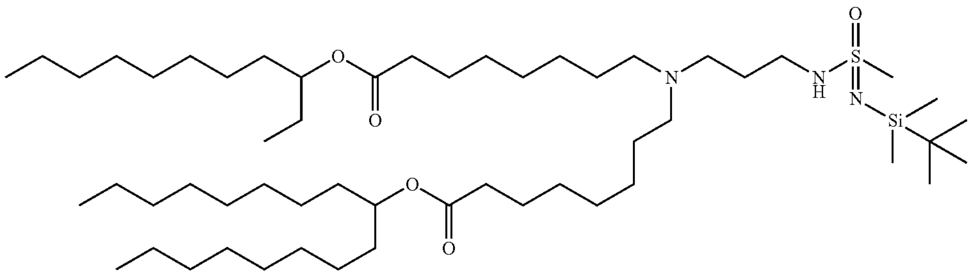

Chemical Formula: $C_{54}H_{111}N_3O_5SSi$
Molecular Weight: 942.64

A suspension of triphenylphosphine dibromide (3.66 g, 8.67 mmol) and triethylamine (1.8 mL, 11.85 mmol) in $CHCl_3$ (11 mL) was stirred at room temperature for 10 min and cooled to 0° C. To this mixture was added N-(tert-butyldimethylsilyl)methanesulfonamide (1.6 g, 7.65 mmol) in $CHCl_3$ (5 mL) and the resultant mixture was stirred at 0° C. for 20 min to give a brown solution. A solution of heptadecan-9-yl 8-((3-aminopropyl)(8-oxo-8-(undecan-3-yloxy)octyl)amino)octanoate (575 mg, 0.76 mmol) in $CHCl_3$ (5 mL) was added to the above mixture at 0° C. and the reaction stirred for 1 h at room temperature. The mixture was concentrated under a stream of nitrogen and the residue purified by silica gel chromatography with dichloromethane/methanol/$NH_4OH$ (90:10:1) 0-100% in dichloromethane to give heptadecan-9-yl 8-((3-(N-(tert-butyldimethylsilyl) methylsulfonoamidimidamido)propyl)(8-oxo-8-(undecan-3-yloxy)octyl)amino)octanoate (99 mg, 14%). $^1H$ NMR (300 MHz, $CDCl_3$): δ −0.01 (s, 12H); 0.09 (m, 4H); 0.84-0.88 (m, 18H); 1.24-1.60 (m, 66H); 2.93-3.26 (m, 8H); 4.79-4.84 (m, 2H); 10.09 (br s, 1H).

Heptadecan-9-yl 8-((3-(methylsulfonoamidimidamido)propyl)(8-oxo-8-(undecan-3-yloxy)octyl) amino)octanoate

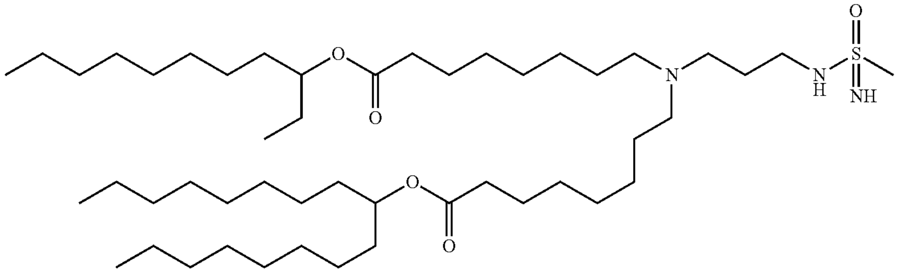

Chemical Formula: $C_{48}H_{97}N_3O_5S$
Molecular Weight: 828.38

A solution of heptadecan-9-yl 8-((3-(N-(tert-butyldimethylsilyl)methylsulfonoamidimidamido)propyl)(8-oxo-8-(undecan-3-yloxy)octyl)amino)octanoate (127 mg, 0.13 mmol) in 4 mL 4N HCl (16 mmol) was stirred at room temperature for 2 h. The resulting mixture was concentrated, treated with $NaHCO_3$:$Na_2CO_3$ (sat. 20 mL. 8:2) and extracted with $CH_2Cl_2$. The organic layer was washed with brine, dried over anhydrous $Na_2SO_4$ and concentrated to give heptadecan-9-yl 8-((3-(methylsulfonoamidimidamido)propyl)(8-oxo-8-(undecan-3-yloxy)octyl)amino)octanoate (94 mg, 85%) as a brown oil. m/z ($MH^+$) 828.7 for $C_{48}H_{97}N_3O_5S$. $^1H$ NMR (300 MHz, $CDCl_3$): δ 0.84-0.88 (m, 12H); 1.13-1.80 (m, 68H); 2.24-2.30 (m, 10H); 2.95 (s, 3H); 3.18-3.20 (m, 2H); 4.80-4.85 (m, 2H).

AX. Compound 59. Heptadecan-9-yl 8-((3-((N-methylsulfamoyl)amino)propyl)(8-oxo-8-(undecan-3-yloxy)octyl)amino)octanoate

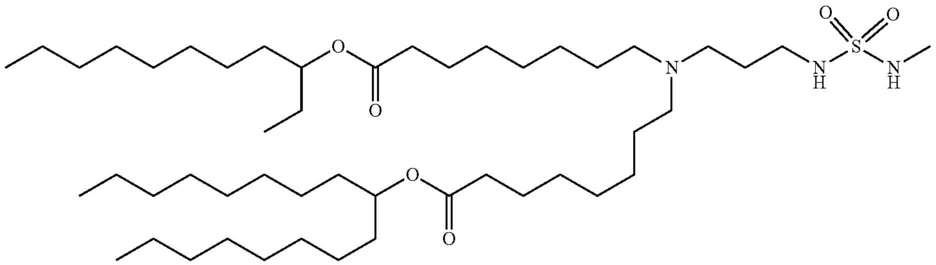

Chemical Formula: $C_{48}H_{97}N_3O_6S$
Molecular Weight: 844.38

To a solution of solution of heptadecan-9-yl 8-((3-aminopropyl)(8-oxo-8-(undecan-3-yloxy)octyl)amino)octanoate (250 mg, 0.33 mmol) and triethylamine (70 uL, 0.49 mmol) in 5 mL DCM at 0° C. was added methylsulfamoyl chloride (35 uL, 0.4 mmol) dropwise with stirring to give a colorless solution. After 60 minutes the cooling bath was removed and the reaction stirred at room temp for 60 minutes. The reaction was diluted with DCM and washed once with a saturated aqueous sodium bicarbonate solution. The organics were dried ($Na_2SO_4$), filtered and the filtrate conc. to a colorless oil. This was purified by silica gel chromatography (100% DCM going to 100% 80:20:1 DCM/MeOH/$NH_4OH$) to give heptadecan-9-yl 8-((3-((N-methylsulfamoyl)amino)propyl)(8-oxo-8-(undecan-3-yloxy)octyl)amino)octanoate (130 mg, 0.15 mmol, 46%) as a colorless oil. UPLC/ELSD: RT=2.98 min. MS (ES): m/z ($MH^+$) 844.56 for $C_{48}H_{97}N_5O_6S$. $^1H$ NMR (300 MHz, $CDCl_3$) δ: ppm 6.91 (br s, 1H); 4.80 (m, 2H); 4.01 (br s, 1H); 3.11 (t, 2H, J=6.2 Hz); 2.68 (s, 3H); 2.53 (t, 2H, J=5.1 Hz); 2.36 (br t, 4H, J=7.1 Hz); 2.25 (dt, 4H, J=7.4 Hz, 3.0 Hz); 1.75-1.38 (m, 18H); 1.36-1.13 (m, 48H); 0.92-0.79 (m, 12H).

AY. Compound 60. Heptadecan-9-yl 8-((3-(1-methylcyclopropane-1-carboxamido)propyl)(8-oxo-8-(undecan-3-yloxy)octyl)amino)octanoate

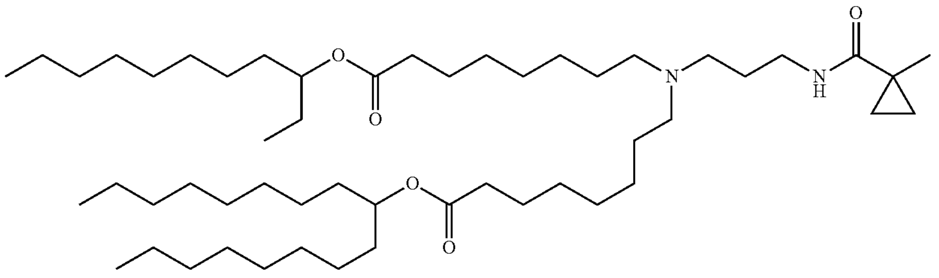

Chemical Formula: $C_{52}H_{100}N_2O_5$
Molecular Weight: 833.38

To a solution of solution of heptadecan-9-yl 8-((3-aminopropyl)(8-oxo-8-(undecan-3-yloxy)octyl)amino)octanoate (400 mg, 0.53 mmol) and triethylamine (115 uL, 0.8 mmol) in 5 mL DCM at 0° C. was added 1-methylcyclopropane-1-carbonyl chloride (65 uL, 0.63 mmol) dropwise with stirring to give a colorless solution. After 90 minutes at 0° C. the reaction was complete so the reaction was diluted with DCM and washed once with a saturated aqueous sodium bicarbonate solution. The organics were dried ($Na_2SO_4$), filtered and the filtrate conc. to a colorless oil. This was purified by silica gel chromatography (100% DCM going to 100% 80:20:1 DCM/MeOH/$NH_4OH$) to give heptadecan-9-yl 8-((3-(1-methylcyclopropane-1-carboxamido)propyl)(8-oxo-8-(undecan-3-yloxy)octyl)amino)octanoate (267 mg, 0.3 mmol, 58%) as a colorless oil. UPLC/ELSD: RT=3.14 min. MS (ES): m/z ($MH^+$) 833.82 for $C_{52}H_{100}N_2O_5$. $^1H$ NMR (300 MHz, $CDCl_3$) δ: ppm 7.43 (br s, 1H); 4.83 (m, 2H); 3.33 (q, 2H, J=5.6 Hz); 2.51 (t, 2H, J=5.2 Hz); 2.41 (br t, 4H, J=7.1 Hz); 2.28 (dt, 4H, J=7.4 Hz, 2.9 Hz); 1.76-1.38 (m, 18H); 1.37-1.17 (m, 51H); 1.15 (q, 2H, J=3.4 Hz); 0.94-0.80 (m, 12H); 0.51 (q, 2H, J=3.4 Hz).

AZ. Compound 61. Heptadecan-9-yl 8-((3-(1-methylcyclopropane-1-carbothioamido)propyl)(8-oxo-8-(undecan-3-yloxy)octyl)amino)octanoate

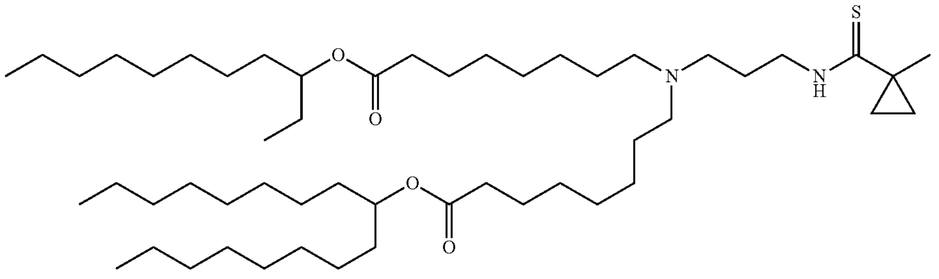

Chemical Formula: $C_{52}H_{100}N_2O_4S$
Molecular Weight: 849.44

To a solution of heptadecan-9-yl 8-((3-(1-methylcyclopropane-1-carboxamido)propyl)(8-oxo-8-(undecan-3-yloxy)octyl)amino)octanoate (210 mg, 0.25 mmol) in 5 mL dry 1,4-dioxane was added Lawesson's reagent (60 mg, 0.14 mmol), the solution heated to reflux and stirred for 24 hours, after which the reaction had progressed ~25%. Heating was continued for another 48 hours after which the reaction had stalled at ~50% complete. Additional Lawesson's reagent (60 mg, 0.14 mmol) was added and the reaction stirred at reflux for 48 hours after which no starting material remained by LC/MS. The reaction was allowed to cool to room temp., conc. and the residue dissolved in DCM. The solution was washed twice with a saturated aqueous sodium bicarbonate solution, once with water, dried ($Na_2SO_4$), filtered and the filtrate conc. to a dark yellow oil. This was chromatographed on silica gel with 100% DCM going to 100% 80:20:1 DCM/MeOH/ammonium hydroxide. The product-containing fractions appeared cloudy so they were conc. and the residue chromatographed on silica gel with 100% DCM going to 50% DCM/50% 80:20:1 DCM/MeOH/ammonium hydroxide to give heptadecan-9-yl 8-((3-(1-methylcyclopropane-1-carbothioamido)propyl)(8-oxo-8-(undecan-3-yloxy)octyl)amino)octanoate (159 mg, 0.18 mmol, 71%) as a yellow oil. UPLC/ELSD: RT=3.13 min. MS (ES): m/z ($MH^+$) 849.61 for $C_{52}H_{100}N_2O_4S$. $^1H$ NMR (300 MHz, $CDCl_3$) δ: ppm 9.98 (br s, 1H); 4.83 (m, 2H); 3.75 (m, 2H); 2.61 (br s, 2H); 2.46 (br t, 4H, J=7.0 Hz); 2.28 (dt, 4H, J=7.4 Hz, 2.9 Hz); 1.76 (br s, 2H); 1.70-1.40 (m, 18H); 1.38 (s, 3H); 1.36-1.13 (m, 50H); 0.94-0.79 (m, 12H); 0.74 (q, 2H, J=3.5 Hz).

BA. Compound 62. Heptadecan-9-yl 8-((3-(1-hydroxy-1,3-dihydrobenzo[c][1,2]oxaborole-6-carboxamido)propyl)(8-oxo-8-(undecan-3-yloxy)octyl)amino)octanoate

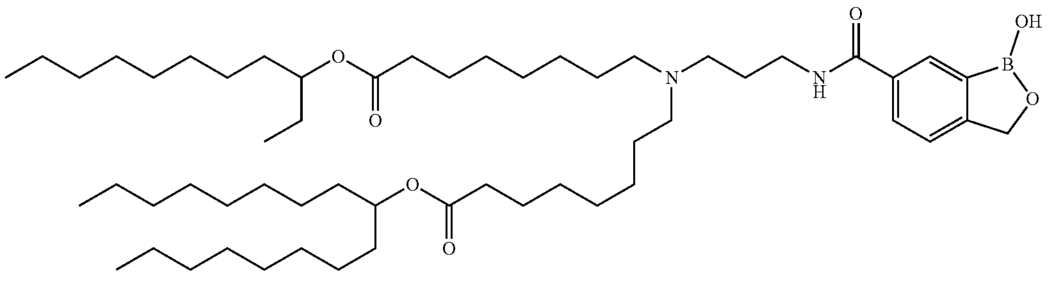

Chemical Formula: $C_{55}H_{99}BN_2O_7$
Molecular Weight: 911.21

To a solution of heptadecan-9-yl 8-((3-aminopropyl)(8-oxo-8-(undecan-3-yloxy)octyl)amino)octanoate (180 mg, 0.24 mmol) and 1-hydroxy-1,3-dihydrobenzo[c][1,2]oxaborole-6-carboxylic acid (54 mg, 0.29 mmol) in 5 mL DCM was added DMAP (3 mg, 0.02 mmol) and EDC-HCl (70 mg, 0.36 mmol) followed by DIEA (175 uL, 0.97 mmol). The resulting mixture was stirred at room temp for 48 hours after which no starting material remained by LC/MS. The solution was diluted with DCM, washed once with a saturated aqueous sodium bicarbonate solution, dried ($Na_2SO_4$), filtered and the filtrate conc. to a colorless oil/white solid mixture. This was chromatographed on silica gel with 100% DCM going to 100% 80:20:1 DCM/MeOH/ammonium hydroxide, then 50:50:1 DCM/MeOH/ammonium hydroxide to give a white solid/colorless syrup mixture. This material was again chromatographed on silica gel with 100% DCM going to 100% 50:50:1 DCM/MeOH/ammonium hydroxide. The product-containing fractions were combined, conc. and the residue triturated with diethyl ether. The precipitated solids were removed via filtration and the filtrate conc. to give heptadecan-9-yl 8-((3-(1-hydroxy-1,3-dihydrobenzo[c][1,2]oxaborole-6-carboxamido)propyl)(8-oxo-8-(undecan-3-yloxy)octyl)amino)octanoate (66 mg, 0.07 mmol, 28%) as a colorless syrup. UPLC/ELSD: RT=3.02 min. MS (ES): m/z ($MH^+$) 911.53 for $C_{55}H_{99}BN_2O_7$. $^1H$ NMR (300 MHz, $CDCl_3$) δ: ppm 8.76 (br s, 1H); 8.59 (br s, 1H); 8.01 (d, 1H, J=7.9 Hz); 7.36 (d, 1H, J=7.9 Hz); 5.07 (s, 2H); 4.81 (m, 2H); 4.71 (s, 1H); 3.60 (m, 2H); 2.96 (br s, 2H); 2.81 (br s, 4H); 2.24 (dt, 4H, J=5.6 Hz, 1.8 Hz); 2.05 (br s, 2H); 1.75-1.39 (m, 16H); 1.38-1.12 (m, 49H); 0.94-0.78 (m, 12H).

BB. Compound 63. Heptadecan-9-yl 8-((3-((2-(benzyloxy)ethyl)sulfonamido)propyl)(8-oxo-8-(undecan-3-yloxy)octyl)amino)octanoate

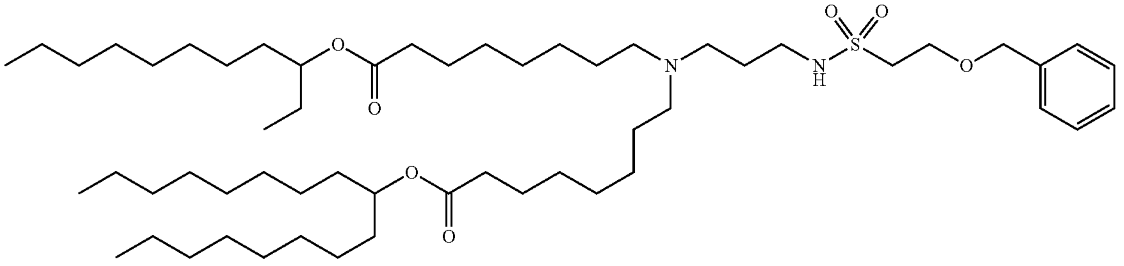

Chemical Formula: $C_{56}H_{104}N_2O_7S$
Molecular Weight: 949.52

To a solution of solution of heptadecan-9-yl 8-((3-aminopropyl)(8-oxo-8-(undecan-3-yloxy)octyl)amino)octanoate (500 mg, 0.66 mmol) and triethylamine (140 uL, 0.99 mmol) in 10 mL DCM at 0° C. was added 2-(benzyloxy)ethanesulfonyl chloride (120 uL, 0.72 mmol) dropwise with stirring to give a colorless solution. After two hours the cooling bath was removed and the reaction stirred at room temp for two hours. The reaction was diluted with DCM and washed once with a saturated aqueous sodium bicarbonate solution. The organics were dried ($Na_2SO_4$), filtered and the filtrate conc. to a colorless oil. This was purified by silica gel chromatography (100% DCM going to 100% 80:20:1 DCM/MeOH/$NH_4OH$) to give heptadecan-9-yl 8-((3-((2-(benzyloxy)ethyl)sulfonamido)propyl)(8-oxo-8-(undecan-3-yloxy)octyl)amino)octanoate (480 mg, 0.5 mmol, 76%) as a pale yellow oil. UPLC/ELSD: RT=3.09 min. MS (ES): m/z (MH+) 949.77 for $C_{56}H_{104}N_2O_7S$. $^1H$ NMR (300 MHz, $CDCl_3$) δ: ppm 7.33 (m, 5H); 4.83 (m, 2H); 4.54 (s, 2H); 3.88 (t, 2H, J=6.2 Hz); 3.27 (t, 2H, J=6.2 Hz); 3.17 (t, 2H, J=6.0 Hz); 2.47 (t, 2H, J=5.3 Hz); 2.34 (br t, 4H, J=5.3 Hz); 2.28 (dt, 4H, J=6.0 Hz, 2.9 Hz); 1.70-1.37 (m, 18H); 1.36-1.15 (m, 48H); 0.96-0.80 (m, 12H).

BC. Compound 64. Heptadecan-9-yl 8-((3-((methoxy(methyl)phosphoryl)amino)propyl)(8-oxo-8-(undecan-3-yloxy)octyl)amino)octanoate Methyl Methylphosphonochloridate

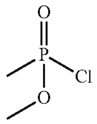

Chemical Formula: $C_2H_6ClO_2P$
Molecular Weight: 128.49

To a solution of dimethyl methylphosphonate (1 mL, 8.9 mmol) in 20 mL dry benzene at 0° C. was added phosphorus pentachloride (2 g, 9 mmol) in portions over ten minutes. Once addition was complete the white mixture was stirred vigorously at 0° C. for 60 minutes then reduced under vacuum to a colorless, translucent oil. This was distilled in vacuo to give methyl methylphosphonochloridate (725 mg, 5 mmol, 57%) as a colorless liquid that was 90% pure by H-NMR; carried through without further purification. $^1H$-NMR: (300 MHz, $CDCl_3$) δ ppm 3.87 (d, J=13.5 Hz, 3H); 1.98 (d, J=17.6 Hz, 3H).

Heptadecan-9-yl 8-((3-((methoxy(methyl)phosphoryl)amino)propyl)(8-oxo-8-(undecan-3-yloxy)octyl) amino)octanoate

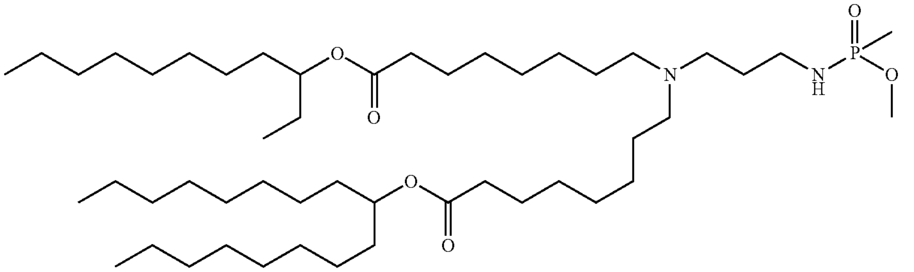

Chemical Formula: $C_{49}H_{99}N_2O_6P$
Molecular Weight: 843.31

To a solution of heptadecan-9-yl 8-((3-aminopropyl)(8-oxo-8-(undecan-3-yloxy)octyl)amino)octanoate (180 mg, 0.24 mmol) in 5 mL dry DCM at 0° C. was added triethylamine (100 uL, 0.71 mmol) followed by methyl methylphosphonochloridate (50 uL, 0.48 mmol) dropwise. The resulting colorless solution was stirred at 0° C. for 5 minutes, then allowed to warm to room temp. and stirred for 30 minutes, after which no starting material remained by LC/MS. The pale yellow solution was diluted with DCM and washed once with a saturated aqueous sodium bicarbonate solution. The organic layer was separated, dried ($Na_2SO_4$), filtered, and the filtrate conc. to a yellow oil. This was chromatographed on silica gel with 100% DCM going to 100% 80:20:1 DCM/MeOH/ammonium hydroxide, the product-containing fractions pooled and conc. The residue was chromatographed on silica gel with 100% hexanes going to 100% EtOAc to give heptadecan-9-yl 8-((3-((methoxy(methyl)phosphoryl)amino)propyl)(8-oxo-8-(undecan-3-yloxy)octyl)amino)octanoate (72 mg, 0.08 mmol, 32%) as a colorless oil. UPLC/ELSD: RT=3.05 min. MS (ES): m/z (MH+) 843.44 for $C_{49}H_{99}N_2O_6P$. $^1H$ NMR (300 MHz, $CDCl_3$): δ 4.84 (m, 2H); 4.01 (br s, 1H); 3.62 (d, 3H, J=11.2 Hz); 3.54 (m, 1H); 2.97 (m, 2H); 2.47 (t, 2H, J=6.5 Hz); 2.36 (br t, 4H, J=7.1 Hz); 2.28 (dt, 4H, J=6.0 Hz, 2.9 Hz); 1.71-1.46 (m, 18H); 1.43 (d, 3H, J=16.5); 1.36-1.13 (m, 48H); 0.92-0.81 (m, 12H).

BD. Compound 65: Heptadecan-9-yl 8-((3-(methylsulfonamido)propyl)(8-oxo-8-(undecan-3-yloxy)octyl)amino)octanoate

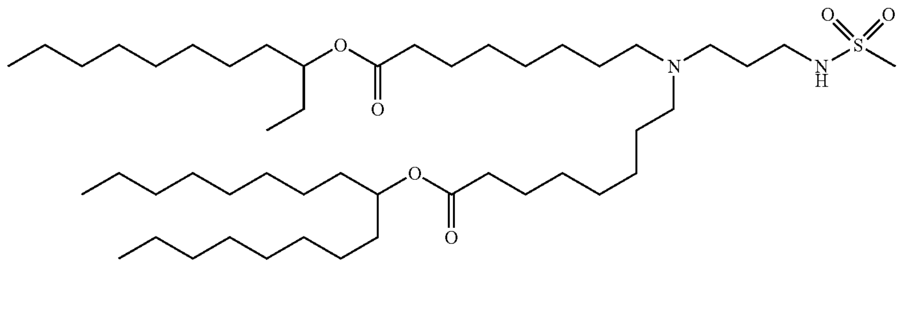

Chemical Formula: $C_{48}H_{96}N_2O_6S$
Molecular Weight: 829.36

To a solution of heptadecan-9-yl 8-((3-aminopropyl)(8-oxo-8-(undecan-3-yloxy)octyl) amino)octanoate (150 mg, 0.2 mmol) and triethylamine (33.39 μL, 0.24 mmol) in DCM (5 mL) at 0° C. was added methanesulfonyl chloride (27.443 mg, 0.24 mmol). The reaction mixture stirred at 0° C. for 1 h and at room temperature for 4 h. The reaction mixture was diluted with additional DCM (10 mL) and washed with saturated sodium bicarbonate solution (15 mL) followed by brine solution (15 mL). The DCM layer was separated and dried over magnesium sulfate. The solution was concentrated and purified by silica gel chromatography (0-100% (mixture of 1% $NH_4OH$, 20% MeOH in DCM) in DCM) to give heptadecan-9-yl 8-((3-(methylsulfonamido)propyl)(8-oxo-8-(undecan-3-yloxy)octyl)amino)octanoate (100.1 mg, 60%) as an oil. UPLC/ELSD: RT=2.97 min. MS (CI): m/z ($MH^+$) 829.384 for $C_{48}H_{96}N_2O_6S$. $^1$H NMR (300 MHz, $CDCl_3$): δ ppm 7.16 (br s, 1H); 4.83-4.75 (m, 2H); 3.23 (t, 2H, J=5.6 Hz); 2.89 (s, 3H); 2.55 (t, 2H, J=3.4 Hz); 2.38 (t, 4H, J=7.0 Hz); 2.28 (td, 4H, J=7.4, 3 Hz); 1.77-1.38 (m, 18H); 1.38-1.17 (m, 48H); 0.95-0.80 (m, 12H).

BE. Compound 66: Heptadecan-9-yl 8-((3-(ethylsulfonamido)propyl)(8-oxo-8-(undecan-3-yloxy)octyl)amino)octanoate To a solution of heptadecan-9-yl 8-((3-aminopropyl)(8-oxo-8-(undecan-3-yloxy)octyl) amino)octanoate (111.9 mg, 0.149 mmol) and triethylamine (24.91 μL, 0.179 mmol) in DCM (3.73 mL) at 0° C. was added ethanesulfonyl chloride (22.98 mg, 0.179 mmol). The reaction mixture stirred at 0° C. for 1 h and at room temperature for 4 h. The reaction mixture was diluted with additional DCM (10 mL) and washed with saturated sodium bicarbonate solution (15 mL) followed by brine solution (15 mL). The DCM layer was separated and dried over magnesium sulfate. The solution was concentrated and purified by silica gel chromatography (0-100% (mixture of 1% $NH_4OH$, 20% MeOH in DCM) in DCM) to give heptadecan-9-yl 8-((3-(ethylsulfonamido)propyl)(8-oxo-8-(undecan-3-yloxy)octyl)amino)octanoate (99.1 mg, 79%) as an oil. UPLC/ELSD: RT=2.99 min. MS (CI): m/z ($MH^+$) 843.322 for $C_{49}H_{98}N_2O_6S$. $^1$H NMR (300 MHz, $CDCl_3$): δ ppm 6.95 (br s, 1H); 4.96-4.75 (m, 2H); 3.20 (t, 2H, J=5.6 Hz); 2.98 (q, 2H, J=7.4 Hz); 2.55 (t, 2H, J=5.1 Hz); 2.38 (t, 4H, J=7.1 Hz); 2.28 (td, 4H, J=7.4, 3.0 Hz); 1.78-1.39 (m, 18H); 1.38-1.17 (m, 51H); 0.95-0.80 (m, 12H).

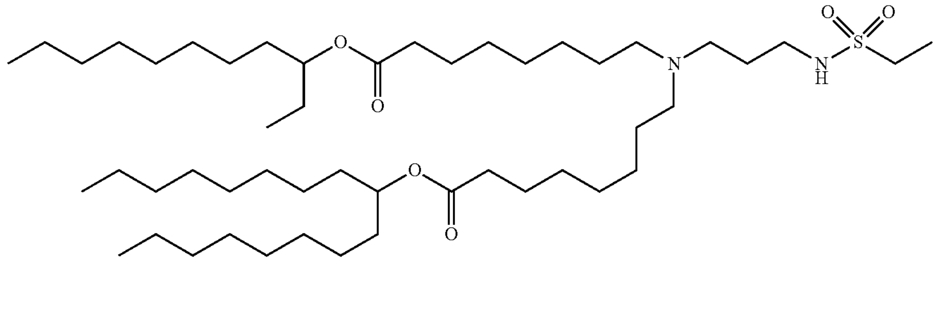

Chemical Formula: $C_{49}H_{98}N_2O_6S$
Molecular Weight: 843.39

BF. Compound 67: Heptadecan-9-yl 8-((3-(cyclopropanesulfonamido)propyl)(8-oxo-8-(undecan-3-yloxy)octyl)amino)octanoate

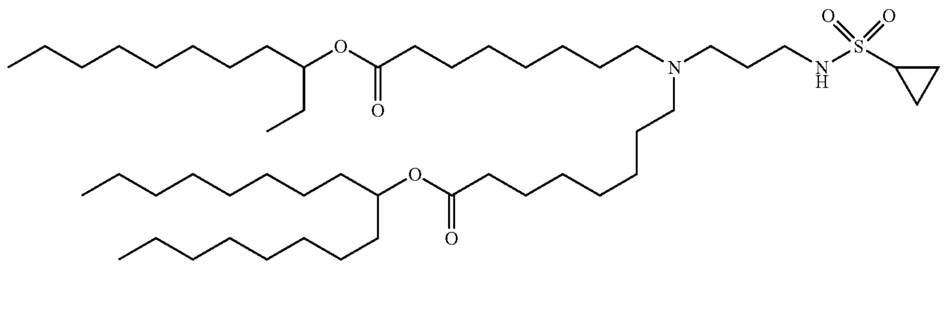

Chemical Formula: $C_{50}H_{98}N_2O_6S$
Molecular Weight: 855.40

To a solution of heptadecan-9-yl 8-((3-aminopropyl)(8-oxo-8-(undecan-3-yloxy)octyl) amino)octanoate (150 mg, 0.2 mmol) and triethylamine (33.99 μL, 0.24 mmol) in DCM (5 mL) at 0° C. was added cyclopropanesulfonyl chloride (33.682 mg, 0.24 mmol) in DCM (1 mL). The reaction mixture stirred at 0° C. for 1 h and at room temperature for 6 h. The reaction mixture was diluted with additional DCM (10 mL) and washed with saturated sodium bicarbonate solution (15 mL) followed by brine solution (15 mL). The DCM layer was separated and dried over magnesium sulfate. The solution was concentrated and purified by silica gel chromatography (0-100% (mixture of 1% $NH_4OH$, 20% MeOH in DCM) in DCM) to give heptadecan-9-yl 8-((3-(cyclopropanesulfonamido)propyl)(8-oxo-8-(undecan-3-yloxy)octyl)amino)octanoate (140.7 mg, 82%) as an oil. UPLC/ELSD: RT=2.99 min. MS (CI): m/z ($MH^+$) 855.410 for $C_{50}H_{98}N_2O_6S$. $^1H$ NMR (300 MHz, $CDCl_3$): δ ppm 6.97 (br s, 1H); 5.02-4.73 (m, 2H); 3.26 (t, 2H, J=5.5 Hz); 2.56 (br s, 2H); 2.55 (t, 2H, J=5.0 Hz); 2.47-2.33 (m, 5H); 2.28 (td, 4H, J=7.4, 3.0 Hz); 1.79-1.39 (m, 18H); 1.38-1.17 (m, 50H); 0.94-0.79 (m, 12H).

BG. Compound 68: Heptadecan-9-yl 8-((3-((1-methyl-1H-pyrazole)-3-sulfonamido)propyl)(8-oxo-8-(undecan-3-yloxy)octyl)amino)octanoate To a solution of heptadecan-9-yl 8-((3-aminopropyl)(8-oxo-8-(undecan-3-yloxy)octyl) amino)octanoate (150 mg, 0.2 mmol) and triethylamine (33.99 μL, 0.24 mmol) in DCM (5 mL) at 0° C. was added 1-methylpyrazole-3-sulfonyl chloride (43.273 mg, 0.24 mmol). The reaction mixture stirred at 0° C. for 1 h and at room temperature for 4 h. The reaction mixture was diluted with additional DCM (10 mL) and washed with saturated sodium bicarbonate solution (15 mL) followed by brine solution (15 mL). The DCM layer was separated and dried over magnesium sulfate. The solution was concentrated and purified by silica gel chromatography (0-100% (mixture of 1% $NH_4OH$, 20% MeOH in DCM) in DCM) to give heptadecan-9-yl 8-((3-((1-methyl-1H-pyrazole)-3-sulfonamido)propyl)(8-oxo-8-(undecan-3-yloxy)octyl)amino)octanoate (147.8 mg, 83%) as an oil. UPLC/ELSD: RT=2.93 min. MS (CI): m/z ($MH^+$) 895.376 for $C_{51}H_{98}N_4O_6S$. $^1H$ NMR (300 MHz, $CDCl_3$): δ ppm 7.44 (br s, 1H); 7.40 (d, 1H, J=2.2 Hz); 6.64 (d, 1H, J=2.3 Hz); 4.93-4.73 (m, 2H); 3.96 (s, 3H); 3.21 (t, 2H, J=5.4 Hz); 2.48 (br s, 2H); 2.41-2.23 (m, 8H); 1.72-1.37 (m, 18H); 1.36-1.14 (m, 48H); 0.97-0.78 (m, 12H).

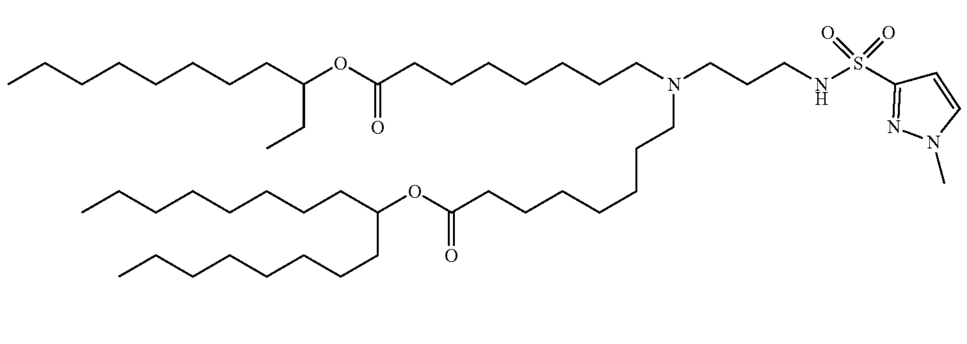

Chemical Formula: $C_{51}H_{98}N_4O_6S$
Molecular Weight: 895.43

BH. Compound 69: Heptadecan-9-yl 8-((3-(1H-imidazole-2-sulfonamido)propyl)(8-oxo-8-(undecan-3-yloxy)octyl)amino)octanoate

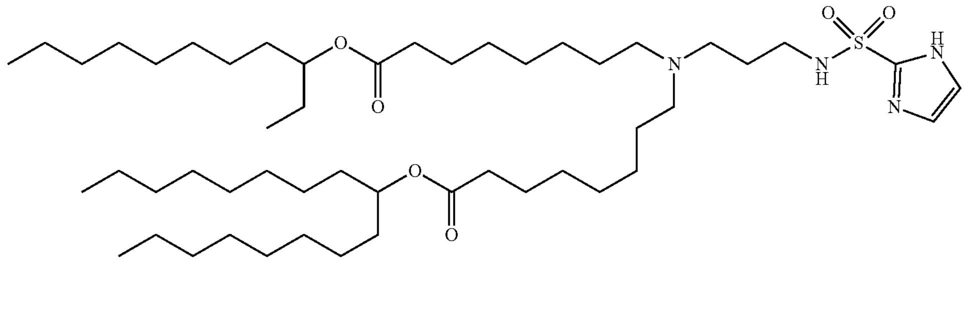

Chemical Formula: $C_{50}H_{96}N_4O_6S$
Molecular Weight: 881.40

To a solution of heptadecan-9-yl 8-((3-aminopropyl)(8-oxo-8-(undecan-3-yloxy)octyl) amino)octanoate (150 mg, 0.2 mmol) and triethylamine (66.79 μL, 0.48 mmol) in DCM (5 mL) at 0° C. was added 1H-imidazole-2-sulfonyl chloride hydrochloride (48.647 mg, 0.24 mmol) in DCM (1 mL). The reaction mixture stirred at 0° C. for 1 h and at room temperature for 4 h. The reaction mixture was diluted with additional DCM (10 mL) and washed with saturated sodium bicarbonate solution (15 mL) followed by brine solution (15 mL). The DCM layer was separated and dried over magnesium sulfate. The solution was concentrated and purified by silica gel chromatography (0-100% (mixture of 1% $NH_4OH$, 20% MeOH in DCM) in DCM) to give heptadecan-9-yl 8-((3-(1H-imidazole-2-sulfonamido)propyl)(8-oxo-8-(undecan-3-yloxy)octyl)amino)octanoate (94.4 mg, 54%) as an oil. UPLC/ELSD: RT=2.89 min. MS (CI): m/z ($MH^+$) 881.314 for $C_{50}H_{96}N_4O_6S$. $^1H$ NMR (300 MHz, $CDCl_3$): δ ppm 7.10 (s, 2H); 4.96-4.75 (m, 2H); 3.41 (t, 2H, J=5.5 Hz); 2.51 (t, 3H, J=5.2 Hz); 2.39-0.24 (m, 8H); 1.75-1.44 (m, 15H); 1.43-1.14 (m, 50H); 0.95-0.81 (m, 12H).

BI. Compound 70: Heptadecan-9-yl 8-((3-((((R)-1,4-dioxan-2-yl)methyl)sulfonamido)propyl)(8-oxo-8-(undecan-3-yloxy)octyl)amino)octanoate To a solution of heptadecan-9-yl 8-((3-aminopropyl)(8-oxo-8-(undecan-3-yloxy)octyl) amino)octanoate (150 mg, 0.2 mmol) and triethylamine (33.39 μL, 0.24 mmol) in DCM (5 mL) at 0° C. was added 1,4-dioxan-2-ylmethanesulfonyl chloride (48.069 mg, 0.24 mmol) in DCM (1 mL). The reaction mixture stirred at 0° C. for 1 h and at room temperature for 4 h. The reaction mixture was diluted with additional DCM (10 mL) and washed with saturated sodium bicarbonate solution (15 mL) followed by brine solution (15 mL). The DCM layer was separated and dried over magnesium sulfate. The solution was concentrated and purified by silica gel chromatography (0-100% (mixture of 1% $NH_4OH$, 20% MeOH in DCM) in DCM) to give heptadecan-9-yl 8-((3-((((R)-1,4-dioxan-2-yl)methyl)sulfonamido)propyl) (8-oxo-8-(undecan-3-yloxy)octyl)amino)octanoate (101.5 mg, 56%) as an oil. UPLC/ELSD: RT=3.02 min. MS (CI): m/z ($MH^+$) 915.358 for $C_{52}H_{102}N_2O_8S$. $^1H$ NMR (300 MHz, $CDCl_3$): δ ppm 6.83 (br s, 1H); 4.95-4.75 (m, 2H); 4.18-4.05 (m, 1H); 3.88 (dd, 2H, J=11.4, 2.3 Hz); 3.82-3.53 (m, 4H); 3.43-3.32 (m, 1H); 3.29-3.08 (m, 3H) 2.53 (t, 2H, J=5.4 Hz); 2.38 (t, 4H, J=7.0 Hz); 2.28 (td, 4H, J=7.4, 3.0 Hz); 1.76-1.38 (m, 18H); 1.37-1.17 (m, 48H); 0.97-0.78 (m, 12H).

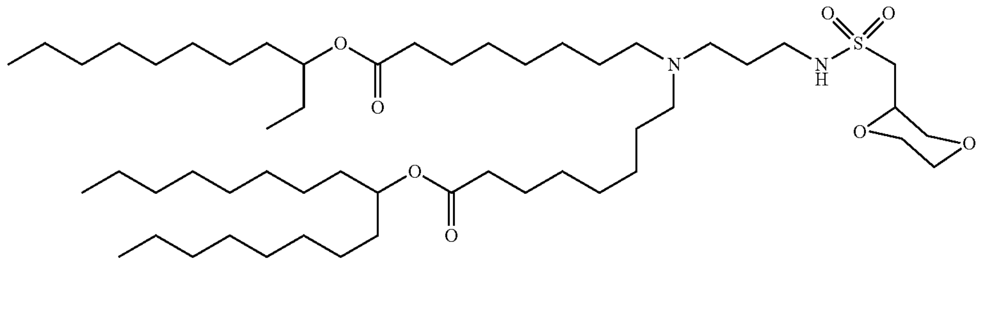

Chemical Formula: $C_{52}H_{102}N_2O_8S$
Molecular Weight: 915.45

BJ. Compound 71: Heptadecan-9-yl 8-((3-((isoxazol-3-ylmethyl)sulfonamido)propyl)(8-oxo-8-(undecan-3-yloxy)octyl)amino)octanoate

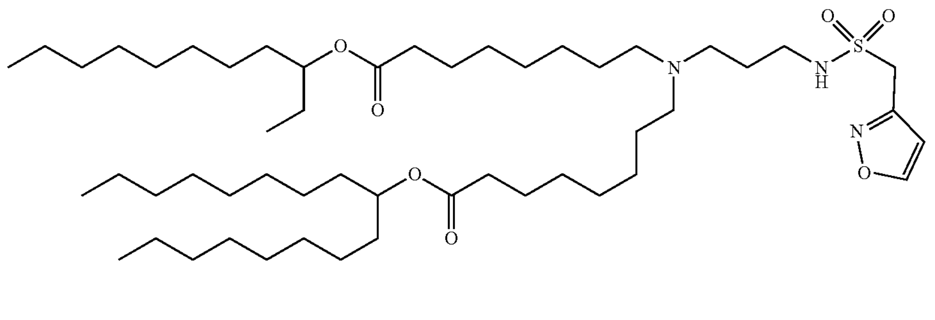

Chemical Formula: $C_{51}H_{97}N_3O_7S$
Molecular Weight: 896.41

To a solution of heptadecan-9-yl 8-((3-aminopropyl)(8-oxo-8-(undecan-3-yloxy)octyl) amino)octanoate (150 mg, 0.2 mmol) and triethylamine (33.39 μL, 0.24 mmol) in DCM (5 mL) at 0° C. was added 1,2-oxazol-3-ylmethanesulfonyl chloride (43.507 mg, 0.24 mmol). The reaction mixture stirred at 0° C. for 1 h and at room temperature for 4 h. The reaction mixture was diluted with additional DCM (10 mL) and washed with saturated sodium bicarbonate solution (15 mL) followed by brine solution (15 mL). The DCM layer was separated and dried over magnesium sulfate. The solution was concentrated and purified by silica gel chromatography (0-100% (mixture of 1% $NH_4OH$, 20% MeOH in DCM) in DCM) to give heptadecan-9-yl 8-((3-((isoxazol-3-ylmethyl)sulfonamido)propyl)(8-oxo-8-(undecan-3-yloxy)octyl)amino)octanoate (95.1 mg, 53%) as an oil. UPLC/ELSD: RT=2.99 min. MS (CI): m/z ($MH^+$) 896.362 for $C_{51}H_{97}N_3O_7S$. $^1H$ NMR (300 MHz, $CDCl_3$): δ ppm 8.44 (s, 1H); 7.64 (br s, 1H); 6.62 (s, 1H); 4.95-4.74 (m, 2H); 4.36 (s, 2H); 3.18 (t, 2H, J=5.6 Hz); 2.52 (t, 2H, J=4.8 Hz); 2.38-2.24 (m, 8H); 1.70-1.44 (m, 16H); 1.41-1.15 (m, 50H); 0.94-0.82 (m, 12H).

BK. Compound 72. Heptadecan-9-yl 8-((3-((4-carbamoyl-5-oxo-2,5-dihydrofuran-3-yl)amino)propyl)(8-oxo-8-(undecan-3-yloxy)octyl)amino)octanoate Methyl 2-cyano-3,3-bis(methylthio)acrylate

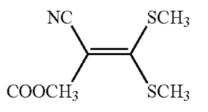

Chemical Formula: $C_7H_9NO_2S_2$
Molecular Weight: 203.27

To an ice cold solution of sodium hydride (4.1 g, 60% in paraffin oil, 105 mmol) in THF (100 mL) was added methyl cyanoacetate (10 g, 100 mmol) dropwise during 15 min. After complete addition, the resultant white solid was vigorously stirred for another 15 min. To this solution was added $CS_2$ (7.6 g, 100 mmol) dropwise while the mixture was kept at 20° C. The reaction mixture slowly changed from a white solid to a yellow liquid. At this point, methyl iodide (15.5 mL, 250 mmol) was added dropwise over a period of 30 min. The resultant mixture was stirred for another 15 min at room temperature. The solvents removed under vacuo and the residue was poured onto crushed ice. The solid was filtered and washed with water and dried. The crude product was crystallized from EtOAc-hexanes to give methyl 2-cyano-3,3-bis(methylthio)acrylate (12.5 g, 61%). $^1H$ NMR (300 MHz, $CDCl_3$): δ 2.59 (s, 3H); 2.74 (s, 3H); 3.81 (s, 3H).

Methyl (E/Z)-2-cyano-3-(methylthio)-4-nitrobut-2-enoate

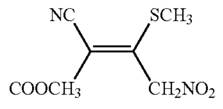

Chemical Formula: $C_7H_8N_2O_4S$
Molecular Weight: 216.2

To solution of methyl 2-cyano-3,3-bis(methylthio)acrylate (12 g, 59 mmol) and nitromethane (3.19 mL, 59 mmol) in DMF (100 mL) was added $K_2CO_3$ (14.3 g, 104 mmol). The resultant mixture was stirred at room temperature for 4 h. The mixture was poured into ice-cold water and the pH was adjusted to 2 with 10% HCl solution. The precipitate was isolated via filtration, washed with water and dried under vacuum to give methyl (E/Z)-2-cyano-3-(methylthio)-4-nitrobut-2-enoate (10 g, 79%). The $^1H$-NMR indicated it is a mixture of isomers in a ratio of 1:3. $^1H$ NMR (300 MHz, $CDCl_3$): δ 2.51-2.65 (m, 3H); 3.48-3.89 (m, 3H); 5.65-5.92 (m, 2H).

4-(Methylthio)-2-oxo-2,5-dihydrofuran-3-carboxamide

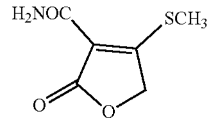

Chemical Formula: $C_6H_7NO_3S$
Molecular Weight: 173.2

To a solution of $H_2SO_4$ (60 mL) at 0° C. was added methyl (E/Z)-2-cyano-3-(methylthio)-4-nitrobut-2-enoate (10 g, 46.2 mmol) in small portions. The resultant mixture was stirred at room temperature for 5 h. Then the mixture was poured onto crushed ice and extracted with $CH_2Cl_2$ (3×500 mL). The combined organic layers were dried over anhydrous $Na_2SO_4$, filtered and concentrated. The crude product was purified by crystallization from an acetone/$CH_2Cl_2$ mixture give 4-(methylthio)-2-oxo-2,5-dihydrofuran-3-carboxamide (3 g, 38%). $^1H$ NMR (300 MHz, $CDCl_3$): δ 2.43 (s, 3H); 4.99 (s, 2H).

Heptadecan-9-yl 8-((3-((4-carbamoyl-5-oxo-2,5-dihydrofuran-3-yl)amino)propyl)(8-oxo-8-(undecan-3-yloxy)octyl)amino)octanoate

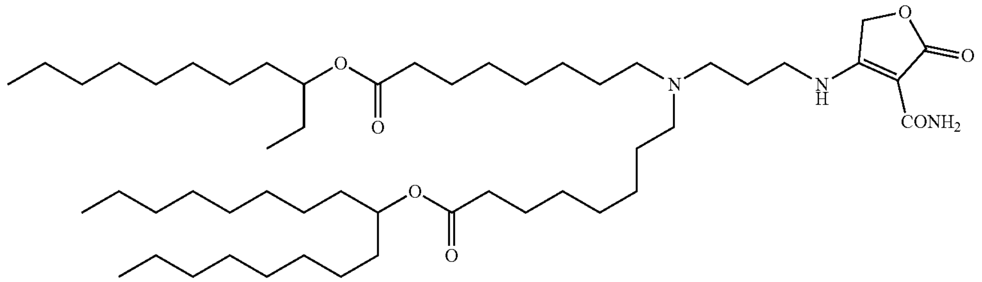

Chemical Formula: $C_{52}H_{97}N_3O_7$
Molecular Weight: 876.4

A mixture of heptadecan-9-yl 8-((3-aminopropyl)(8-oxo-8-(undecan-3-yloxy)octyl)amino)octanoate (300 mg, 0.4 mmol) and 4-(methylthio)-2-oxo-2,5-dihydrofuran-3-carboxamide (83 mg, 0.48 mmol) in n-BuOH (5 mL) was heated to 160° C. in a microwave reactor for 1 h. After the completion of the reaction, the mixture was concentrated and the crude product purified by silica gel chromatography with 0-10% methanol in dichloromethane to give heptadecan-9-yl 8-((3-((4-carbamoyl-5-oxo-2,5-dihydrofuran-3-yl)amino)propyl)(8-oxo-8-(undecan-3-yloxy)octyl)amino)octanoate (180 mg, 52%) as a brown oil. m/z ($MH^+$) 876.7 for $C_{52}H_{97}N_3O_7$. $^1H$ NMR (300 MHz, $CDCl_3$): δ 0.83-0.88 (m, 12H); 1.15-1.8 (m, 66H); 2.25-2.5 (m, 10H); 3.22-3.29 (m, 2H); 4.72-4.91 (m, 4H); 5.22 (br s, 1H); 7.37 (br s, 1H); 8.71-8.75 (m, 1H).

BL. Compound 73: Heptadecan-9-yl 8-((8-oxo-8-(undecan-3-yloxy)octyl)(3-(pyrimidine-2-sulfonamido)propyl)amino)octanoate

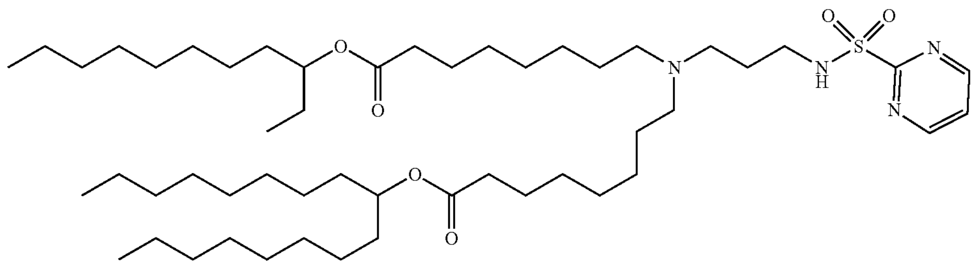

Chemical Formula: $C_{51}H_{96}N_4O_6S$
Molecular Weight: 893.41

To a solution of heptadecan-9-yl 8-((3-aminopropyl)(8-oxo-8-(undecan-3-yloxy)octyl) amino)octanoate (150 mg, 0.2 mmol) and triethylamine (33.39 μL, 0.24 mmol) in DCM (5 mL) at 0° C. was added pyrimidine-2-sulfonyl fluoride (38.847 mg, 0.24 mmol). The reaction mixture stirred at 0° C. for 1 h and at room temperature overnight. The reaction mixture was diluted with additional DCM (10 mL) and washed with saturated sodium bicarbonate solution (15 mL) followed by brine solution (15 mL). The DCM layer was separated and dried over magnesium sulfate. The solution was concentrated and purified by silica gel chromatography (0-100% (mixture of 1% $NH_4OH$, 20% MeOH in DCM) in DCM) to give heptadecan-9-yl 8-((8-oxo-8-(undecan-3-yloxy)octyl)(3-(pyrimidine-2-sulfonamido)propyl)amino) octanoate (82.2 mg, 46%) as an oil. UPLC/ELSD: RT=2.99 min. MS (CI): m/z ($MH^+$) 893.279 for $C_{51}H_{96}N_4O_6S$. $^1H$ NMR (300 MHz, $CDCl_3$): δ ppm 8.90 (d, 2H, J=4.8 Hz); 8.16 (br s, 1H); 7.48 (t, 1H, J=4.9 Hz); 4.93-4.74 (m, 2H); 4.17 (t, 2H, J 6.6 Hz); 3.40 (t, 2H, J=5.6 Hz); 2.56 (s, 2H); 2.25-2.22 (m, 8H); 1.78-1.37 (m, 18H); 1.36-1.15 (m, 46H); 0.96-0.80 (m, 12H).

BM. Compound 74: Heptadecan-9-yl 8-((8-oxo-8-(undecan-3-yloxy)octyl)(3-((phenylmethyl)sulfonamido)propyl)amino)octanoate To a solution of heptadecan-9-yl 8-((3-aminopropyl)(8-oxo-8-(undecan-3-yloxy)octyl) amino)octanoate (150 mg, 0.2 mmol) and triethylamine (33.39 μL, 0.24 mmol) in DCM (5 mL) at 0° C. was added phenylmethanesulfonyl chloride (45.676 mg, 0.24 mmol) in DCM (1 mL). The reaction mixture stirred at 0° C. for 1 h and at room temperature overnight. The reaction mixture was diluted with additional DCM (10 mL) and washed with saturated sodium bicarbonate solution (15 mL) followed by brine solution (15 mL). The DCM layer was separated and dried over magnesium sulfate. The solution was concentrated and purified by silica gel chromatography (0-100% (mixture of 1% $NH_4OH$, 20% MeOH in DCM) in DCM) to give heptadecan-9-yl 8-((8-oxo-8-(undecan-3-yloxy)octyl)(3-((phenylmethyl)sulfonamido)propyl)amino)octanoate (150.5 mg, 83%) as an oil. UPLC/ELSD: RT=3.01 min. MS (CI): m/z ($MH^+$) 905.367 for $C_{54}H_{100}N_2O_6S$. $^1H$ NMR (300 MHz, $CDCl_3$): δ ppm 7.44-7.32 (m, 5H); 6.99 (br s, 1H); 4.94-4.71 (m, 2H); 4.20 (s, 2H); 3.04 (t, 2H, J=5.7 Hz); 2.47 (m, 2H); 2.28 (td, 8H, J=7.4, 3 Hz); 1.74-1.42 (m, 18H); 1.41-1.13 (m, 48H); 0.97-0.81 (m, 12H).

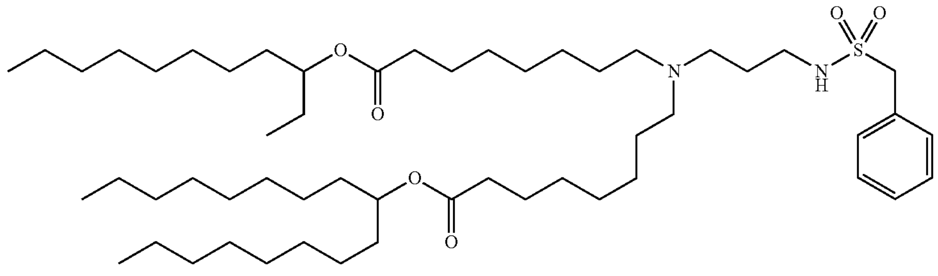

Chemical Formula: $C_{54}H_{100}N_2O_6S$
Molecular Weight: 905.46

BN. Compound 75: Heptadecan-9-yl 8-((3-((1-(methoxymethyl)-1H-pyrazole)-5-sulfonamido)propyl)(8-oxo-8-(undecan-3-yloxy)octyl)amino)octanoate

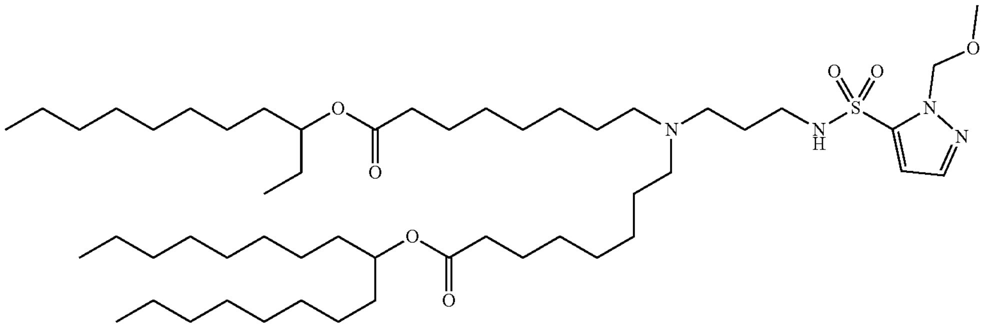

Chemical Formula: $C_{52}H_{100}N_4O_7S$
Molecular Weight: 925.45

To a solution of heptadecan-9-yl 8-((3-aminopropyl)(8-oxo-8-(undecan-3-yloxy)octyl) amino)octanoate (150 mg, 0.2 mmol) and triethylamine (33.39 μL, 0.24 mmol) in DCM (5 mL) at 0° C. was added 2-(methoxymethyl)pyrazole-3-sulfonyl chloride (50.465 mg, 0.24 mmol). The reaction mixture stirred at 0° C. for 1 h and at room temperature overnight. The reaction mixture was diluted with additional DCM (10 mL) and washed with saturated sodium bicarbonate solution (15 mL) followed by brine solution (15 mL). The DCM layer was separated and dried over magnesium sulfate. The solution was concentrated and purified by silica gel chromatography (0-100% (mixture of 1% $NH_4OH$, 20% MeOH in DCM) in DCM) to give heptadecan-9-yl 8-((3-((1-(methoxymethyl)-1H-pyrazole)-5-sulfonamido)propyl)(8-oxo-8-(undecan-3-yloxy)octyl)amino)octanoate (151.3 mg, 82%) as an oil. UPLC/ELSD: RT=2.90 min. MS (CI): m/z ($MH^+$) 925.554 for $C_{52}H_{100}N_4O_7S$. $^1$H NMR (300 MHz, $CDCl_3$): δ ppm 7.69 (br s, 1H); 7.63 (d, 1H, J=2.4 Hz); 6.75 (d, 1H, J=2.4 Hz); 5.44 (s, 2H); 4.91-4.75 (m, 2H); 3.35 (s, 3H); 3.24 (t, 2H, J=5.6 Hz); 2.48 (t, 2H, J=5.4 Hz)); 2.43-2.22 (m, 8H); 1.71-1.37 (m, 18H); 1.36-1.17 (m, 48H); 0.97-0.81 (m, 12H).

BO. Compound 76: Heptadecan-9-yl 8-((3-(2-(N-methylsulfamoyl)acetamido)propyl)(8-oxo-8-(undecan-3-yloxy)octyl)amino)octanoate To a solution of heptadecan-9-yl 8-((3-aminopropyl)(8-oxo-8-(undecan-3-yloxy)octyl) amino)octanoate (150 mg, 0.2 mmol) and (methylsulfamoyl)acetic acid (36.693 mg, 0.24 mmol) in DCM (5 mL) at 0° C. was added EDC-HCl (37.195 mg, 0.24 mmol) and DMAP (4.878 mg, 0.04 mmol) in DCM (1 mL). The reaction mixture stirred at 0° C. and moved to room temperature to stir overnight. The reaction mixture was diluted with additional DCM (10 mL) and washed with saturated sodium bicarbonate solution (15 mL) followed by brine solution (15 mL). The DCM layer was separated and dried over magnesium sulfate. The solution was concentrated and purified by silica gel chromatography (0-100% (mixture of 1% $NH_4OH$, 20% MeOH in DCM) in DCM) to give heptadecan-9-yl 8-((3-(2-(N-methylsulfamoyl)acetamido)propyl)(8-oxo-8-(undecan-3-yloxy)octyl) amino)octanoate (123.7 mg, 70%) as an oil. UPLC/ELSD: RT=3.01 min. MS (CI): m/z (MEV) 886.371 for $C_{50}H_{99}N_3O_7S$. $^1$H NMR (300 MHz, $CDCl_3$): δ ppm 8.31 (s, 1H); 5.02 (s, 1H), 5.01-4.76 (m, 2H); 3.78 (s, 2H); 3.41 (m, 2H); 2.87 (s, 3H); 2.56 (t, 2H, J=5.3 Hz); 2.42 (t, 4H, J=7.1 Hz); 2.31 (td, 4H, J=7.4, 3 Hz); 1.74-1.42 (m, 18H); 1.41-1.13 (m, 48H); 0.97-0.81 (m, 12H).

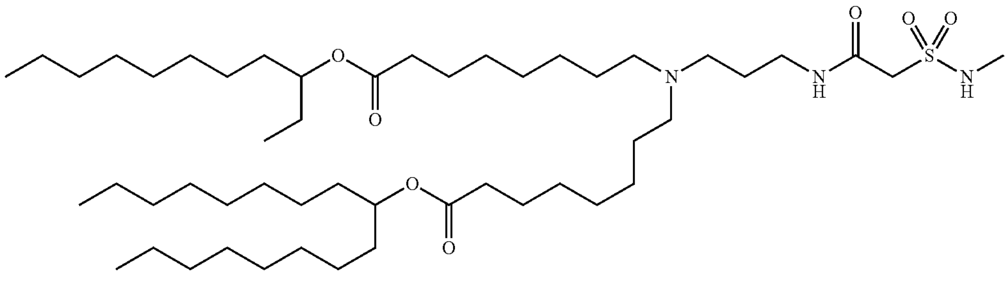

Chemical Formula: $C_{50}H_{99}N_3O_7S$
Molecular Weight: 886.42

BP. Compound 77. Heptadecan-9-yl 8-((3-((1,1-dioxido-5,6-dihydro-4H-1,2,4-thiadiazin-3-yl) amino)propyl)(8-oxo-8-(undecan-3-yloxy)octyl) amino)octanoate 3-(Methylthio)-5,6-dihydro-4H-1,2,4-thiadiazine 1,1-dioxide

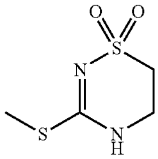

Chemical Formula: $C_4H_8N_2O_2S_2$
Molecular Weight: 180.24

To a stirred mixture of 2-chloroethanesulfonyl chloride (8.2 g, 50 mmol) in EtOAc (250 mL) was added S-methylisothiourea (7.05 g, 25 mmol) followed by $Na_2CO_3$ (8 g, 75 mmol), $K_2CO_3$ (10.5 g, 75 mmol) and $NaHCO_3$ (13 g, 155 mmol). The resultant mixture was stirred at ambient temperature for 48 h. The solids were filtered off and the filter cake washed with hot EtOAc (600 mL). The filtrate was concentrated and recrystallized in EtOH to give 1.0 g of 3-(methylthio)-5,6-dihydro-4H-1,2,4-thiadiazine 1,1-dioxide with 70% purity (by $^1$H-NMR). This was used in the next step without further purification. $^1$H NMR (300 MHz, $CDCl_3$): δ 2.45 (s, 3H); 3.22-3.29 (m, 2H); 3.87-3.90 (m, 2H), 5.86-5.89 (m, 1H).

Heptadecan-9-yl 8-((3-((1,1-dioxido-5,6-dihydro-4H-1,2,4-thiadiazin-3-yl)amino)propyl)(8-oxo-8-(undecan-3-yloxy)octyl)amino)octanoate

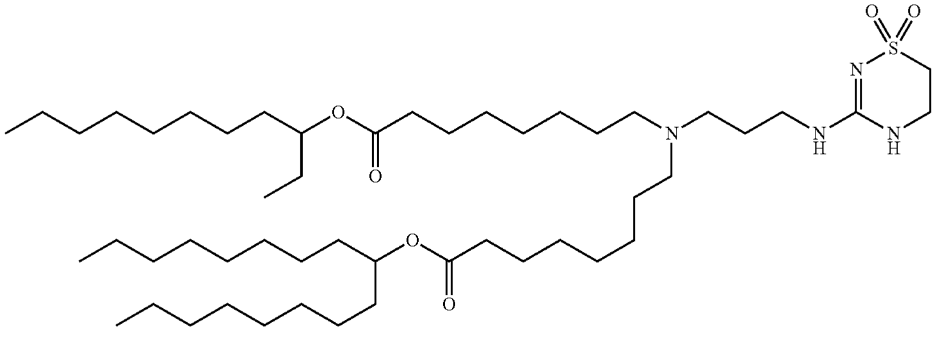

Chemical Formula: $C_{50}H_{98}N_4O_6S$
Molecular Weight: 883.42

A mixture of heptadecan-9-yl 8-((3-aminopropyl)(8-oxo-8-(undecan-3-yloxy)octyl)amino)octanoate (720 mg, 0.95 mmol) and 3-(methylthio)-5,6-dihydro-4H-1,2,4-thiadiazine 1,1-dioxide (560 mg, 3.10 mmol) was heated at 150-155° C. in a sealed tube for 6 h. After cooling, the mixture was concentrated and purified by silica gel chromatography with 0-10% methanol in dichloromethane to give heptadecan-9-yl 8-((3-((1,1-dioxido-5,6-dihydro-4H-1,2,4-thiadiazin-3-yl)amino)propyl)(8-oxo-8-(undecan-3-yloxy)octyl)amino) octanoate (173 mg, 21%) as brown oil. m/z ($MH^+$) 883.8 for $C_{50}H_{98}N_4O_6S$. $^1$H NMR (300 MHz, $CDCl_3$): δ 0.84-0.88 (m, 12H); 1.14-1.79 (m, 67H); 2.24-2.30 (m, 4H); 2.40-2.45 (m, 6H); 3.15-3.21 (m, 2H); 3.35-3.37 (m, 2H); 3.70-3.74 (m, 2H); 4.80-4.85 (m, 2H); 6.45 (br s, 1H).

BQ. Compound 78. Heptadecan-9-yl 8-((8-oxo-8-(undecan-3-yloxy)octyl)(3-(5-oxopyrrolidine-2-carboxamido)propyl)amino)octanoate

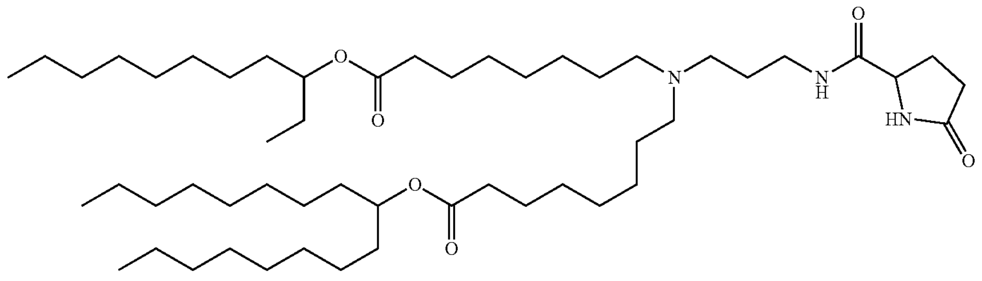

Chemical Formula: $C_{52}H_{99}N_3O_6$
Molecular Weight: 862.4

A mixture of heptadecan-9-yl 8-((3-aminopropyl)(8-oxo-8-(undecan-3-yloxy)octyl)amino)octanoate (150 mg, 0.199 mmol), 5-oxopyrrolidine-2-carboxylic acid (38 mg, 0.299 mmol), EDCI (57 mg, 0.299 mmol), HOBt (40 mg, 0.299 mmol) and TEA (55 μL, 0.398 mmol) in acetonitrile (3 mL) was stirred overnight at room temperature. The mixture was diluted with EtOAc (10 mL), washed with water and brine. The organic layer was dried over anhydrous $Na_2SO_4$ and evaporated. The reaction was repeated with 50 mg (0.07 mmol) of heptadecan-9-yl 8-((3-aminopropyl)(8-oxo-8-(undecan-3-yloxy)octyl)amino)octanoate following the above procedure. The combined crude product was purified by silica gel chromatography with 0-10% methanol in dichloromethane to give heptadecan-9-yl 8-((8-oxo-8-(undecan-3-yloxy)octyl)(3-(5-oxopyrrolidine-2-carboxamido)propyl)amino)octanoate (155 mg, 68%) as a light brown oil. m/z ($MH^+$) 862.7 for $C_{52}H_{99}N_3O_6$. $^1H$ NMR (300 MHz, $CDCl_3$): δ 0.86-0.88 (m, 12H); 1.24-1.89 (m, 66H); 2.1-2.8 (m, 14H); 3.3-3.4 (m, 2H); 4.1-4.15 (m, 1H); 4.79-4.84 (m, 2H); 6.58 (br s, 1H); 7.9 (br s, 1H).

BR. Compound 51/52. Heptadecan-9-yl (E/Z)-8-((3-(((2,5-dioxoimidazolidin-4-ylidene)methyl)amino)propyl)(8-oxo-8-(undecan-3-yloxy)octyl)amino)octanoate (E/Z)-5-(Bromomethylene)imidazolidine-2,4-dione

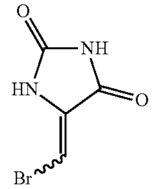

Chemical Formula: $C_4H_3BrN_2O_2$
Molecular Weight: 191.0

A mixture of 3-bromopyruvic acid (2 g, 11.9 mmol), urea (0.72 g, 11.9 mmole) and $BF_3 \cdot Et_2O$ (0.6 mL, 4.7 mmol) in acetonitrile (25 mL) was refluxed for 9 h. The reaction mixture was cooled to room temperature, the precipitate isolated via filtration, washed with acetonitrile (20 mL) and air-dried. This solid was triturated with EtOH to give (E/Z)-5-(bromomethylene)imidazolidine-2,4-dione (420 mg, 18%). $^1H$ NMR (300 MHz, DMSO-d6): 6.55 (s, 12H); 10.63 (br s, 1H); 11.31 (br s, 1H).

Heptadecan-9-yl (E/Z)-8-((3-(((2,5-dioxoimidazolidin-4-ylidene)methyl)amino)propyl)(8-oxo-8-(undecan-3-yloxy)octyl)amino)octanoate

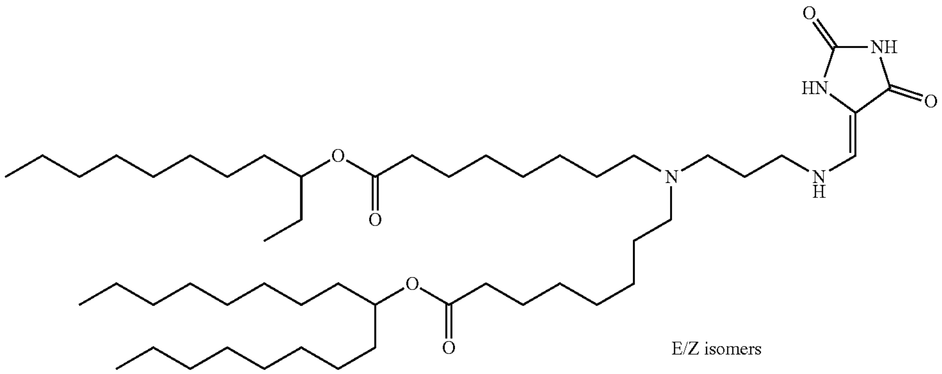

E/Z isomers

Chemical Formula: $C_{51}H_{96}N_4O_6$
Molecular Weight: 861.35

A mixture of heptadecan-9-yl 8-((3-aminopropyl)(8-oxo-8-(undecan-3-yloxy)octyl)amino)octanoate (400 mg, 0.53 mmol), (E/Z)-5-(bromomethylene)imidazolidine-2,4-dione (119 mg, 0.63 mmol) and TEA (0.4 mL) in EtOH (4 mL) was stirred overnight at room temperature and then at 60° C. for 1 h in a microwave reactor. The mixture was cooled to room temperature, diluted with $CH_2Cl_2$ (20 mL) and washed with sat. $NaHCO_3$ and brine. The organic layer was dried over anhydrous $Na_2SO_4$ and evaporated. The crude product was purified by silica gel chromatography with 0-10% methanol in dichloromethane to give heptadecan-9-yl(E/Z)-8-((3-(((2,5-dioxoimidazolidin-4-ylidene)methyl)amino)propyl)(8-oxo-8-(undecan-3-yloxy)octyl)amino)octanoate (352 mg, 77%) as a light yellow oil. m/z ($MH^+$) 861.8 for $C_{51}H_{96}N_4O_6$. $^1H$ NMR (300 MHz, $CDCl_3$): δ 0.84-0.88 (m, 12H); 1.11-1.89 (m, 67H); 2.2-2.7 (m, 10H); 3.1-3.2 (m, 2H); 4.79-4.84 (m, 2H); 6.49 (br s, 1H); 6.6-6.7 (m, 1H); 9.0 (br s, 1H).

BS. Compound 79. Heptadecan-9-yl 8-((3-((2-oxo-2,5-dihydro-1H-imidazol-4-yl)amino)propyl)(8-oxo-8-(undecan-3-yloxy)octyl)amino)octanoate 4-Thioxoimidazolidin-2-one

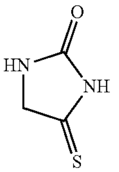

Chemical Formula: $C_4H_3N_2OS$
Molecular Weight: 116.1

A mixture of hydantoin (1.6 g, 13.8 mmol) and $P_4S_{10}$ (3.67 g, 8.2 mmol) in dioxane (25 mL) was heated at 70-80° C. for 90 min. The reaction mixture was cooled to room temperature, the solids filtered away and washed with dioxane (55 mL). The filtrate was then filtered through a pad of diatomaceous earth, washed with dioxane (50 mL) and concentrated. The crude product was purified by trituration ($CH_2Cl_2$) followed by silica gel chromatography with 0-10% methanol in dichloromethane to give 4-thioxoimidazolidin-2-one (680 mg, 39%). $^1H$ NMR (300 MHz, DMSO-$d_6$): δ 3.55 (s, 2H); 6.9 (br s, 2H).

4-(Methylthio)-1,5-dihydro-2H-imidazol-2-one

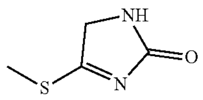

Chemical Formula: $C_4H_6N_2OS$
Molecular Weight: 130.2

To a mixture of 4-thioxoimidazolidin-2-one (550 mg, 13.8 mmol) in MeOH (12 mL) was added $CH_3I$ (1.24 mL, 19.9 mmole). The resultant mixture was stirred overnight at room temperature. After the reaction, the mixture was concentrated and dried to give 4-(methylthio)-1,5-dihydro-2H-imidazol-2-one. The $^1H$-NMR showed 60% conversion to product so this material was used in the next step without further purification.

Heptadecan-9-yl 8-((3-((2-oxo-2,5-dihydro-1H-imidazol-4-yl)amino)propyl)(8-oxo-8-(undecan-3-yloxy)octyl)amino)octanoate

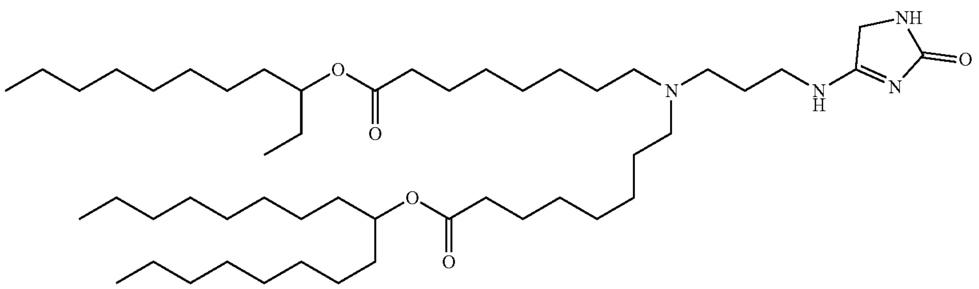

Chemical Formula: $C_{50}H_{96}N_4O_5$
Molecular Weight: 833.3

A mixture of heptadecan-9-yl 8-((3-aminopropyl)(8-oxo-8-(undecan-3-yloxy)octyl)amino)octanoate (100 mg, 0.13 mmol) and 4-(methylthio)-1,5-dihydro-2H-imidazol-2-one (180 mg, 1.38 mmol) in BuOH (2 mL) was heated at 160° C. for 40 min in a microwave reactor. The reaction was repeated (with 250 mg (0.32 mmol) and 400 mg (52 mmol) of heptadecan-9-yl 8-((3-aminopropyl)(8-oxo-8-(undecan-3-yloxy)octyl)amino)octanoate) following the above procedure. All the three crude products were combined and concentrated. The crude residue was diluted with $CH_2Cl_2$ (50 mL) and washed with sat. $NaHCO_3$ and brine. The organic layer was dried over anhydrous $Na_2SO_4$ and evaporated. The crude product was purified by silica gel chromatography with 0-10% methanol to dichloromethane to give heptadecan-9-yl 8-((3-((2-oxo-2,5-dihydro-1H-imidazol-4-yl)amino)propyl)(8-oxo-8-(undecan-3-yloxy)octyl)amino) octanoate (180 mg, 22%) as a brown oil. m/z ($MH^+$) 834.8 for $C_{50}H_{96}N_4O_5$. $^1$H NMR (300 MHz, $CDCl_3$): δ 0.84-0.88 (m, 12H); 1.15-1.81 (m, 67H); 2.24-2.4 (m, 10H); 3.51-3.56 (m, 2H); 3.94 (s, 2H); 4.8-4.85 (m, 2H); 5.35 (br s, 1H).

BT. Compound 80. Heptadecan-9-yl 8-((3-((2-(methylamino)-2-oxoethyl)sulfonamido)propyl)(8-oxo-8-(undecan-3-yloxy)octyl)amino)octanoate Heptadecan-9-yl 8-((3-((2-methoxy-2-oxoethyl)sulfonamido)propyl)(8-oxo-8-(undecan-3-yloxy)octyl)amino)octanoate

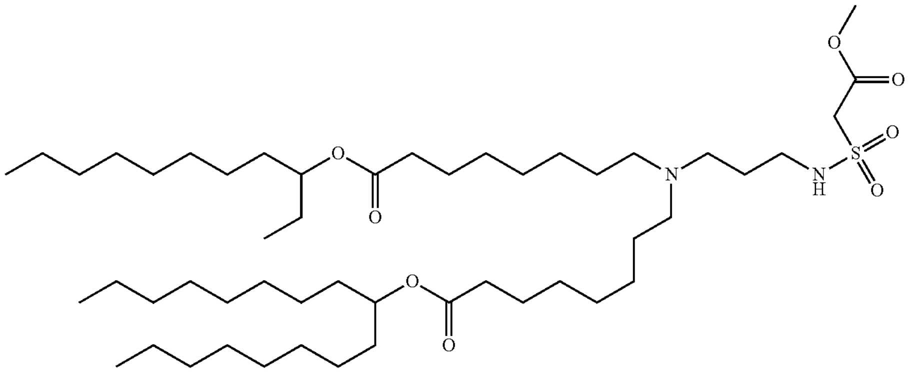

Chemical Formula: $C_{50}H_{98}N_2O_8S$
Molecular Weight: 887.4

To a mixture of heptadecan-9-yl 8-((3-aminopropyl)(8-oxo-8-(undecan-3-yloxy)octyl)amino)octanoate (100 mg, 0.13 mmol) and methyl 2-(chlorosulfonyl)acetate (23 mg, 0.13 mmol) in $CH_2Cl_2$ (5 mL) was added TEA (0.22 mL, 0.15 mmol) and the reaction mixture heated to 50° C. for 2 h. After the completion of the reaction, the mixture was diluted with $CH_2Cl_2$ (25 mL) and washed with water and brine. The organic layer was dried over anhydrous $Na_2SO_4$ and evaporated to give heptadecan-9-yl 8-((3-((2-methoxy-2-oxoethyl)sulfonamido)propyl)(8-oxo-8-(undecan-3-yloxy)octyl)amino)octanoate (80 mg, 69%). The MS spectrum showed the product and used in next step without further purification.

Heptadecan-9-yl 8-((3-((2-(methylamino)-2-oxoethyl)sulfonamido)propyl)(8-oxo-8-(undecan-3-yloxy)octyl)amino)octanoate

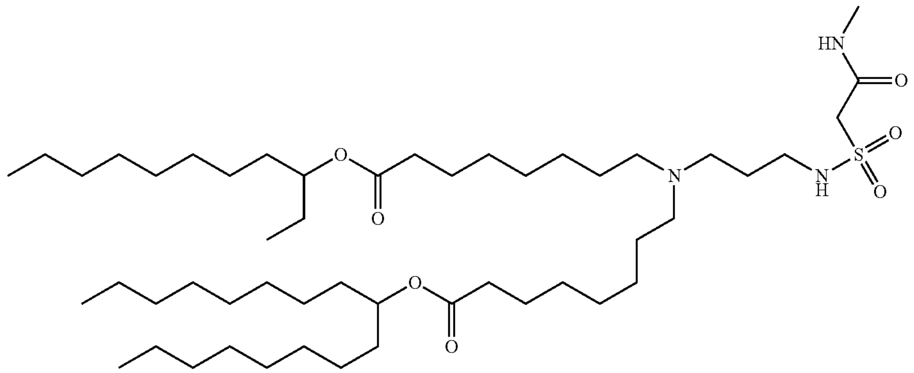

Chemical Formula: $C_{50}H_{99}N_3O_7S$
Molecular Weight: 886.4

A mixture of heptadecan-9-yl 8-((3-((2-methoxy-2-oxoethyl)sulfonamido)propyl)(8-oxo-8-(undecan-3-yloxy)octyl)amino)octanoate (80 mg, 0.09 mmol) and methylamine (0.45 mL, 2M in MeOH, 0.9 mmol) in MeOH (2 mL) was heated to 110° C. in a sealed tube for 16 h. After the completion of the reaction, the mixture was concentrated. The reaction was repeated with 160 mg (0.18 mmol) heptadecan-9-yl 8-((3-((2-methoxy-2-oxoethyl)sulfonamido)propyl)(8-oxo-8-(undecan-3-yloxy)octyl)amino)octanoate following the above procedure. The combined crude product was purified by silica gel chromatography with 0-10% methanol in dichloromethane to give heptadecan-9-yl 8-((3-((2-(methylamino)-2-oxoethyl)sulfonamido)propyl)(8-oxo-8-(undecan-3-yloxy)octyl)amino)octanoate (170 mg, 71%) as a light yellow oil. m/z ($MH^+$) 886.7 for $C_{50}H_{99}N_3O_7S$. $^1H$ NMR (300 MHz, $CDCl_3$): δ 0.82-0.86 (m, 12H); 1.22-1.8 (m, 67H); 2.24-2.25 (m, 4H), 2.4-2.51 (m, 4H); 2.6-2.7 (m, 2H); 2.81 (d, 3H, J=6.6 Hz); 3.19-3.29 (m, 2H); 3.88 (s, 2H); 4.81-4.85 (m, 2H); 6.9 (br s, 1H).

BU. Compound 16. Heptadecan-9-yl 8-((3-((1,3-bis(methylamino)-1,3-dioxopropan-2-yl)amino)propyl)(8-oxo-8-(undecan-3-yloxy)octyl)amino)octanoate Trifluoroacetate Salt $N^1$,$N^3$-Dimethylmalonamide

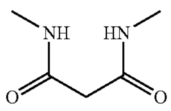

Chemical Formula: $C_5H_{10}N_2O_2$
Molecular Weight: 130.1

A mixture of dimethyl malonate (12.5 g, 132.1 mmol) and methyl amine (30 g, 40% aq) was stirred at room temperature overnight. The solvents were evaporated and the residue dried over P2O5 to obtain $N^1$,$N^3$-dimethylmalonamide (10.2 g, 83%). $^1$H NMR (300 MHz, DMSO-$d_6$): δ 2.56 (d, 6H, J=4.6 Hz); 2.96 (s, 2H); 7.92 (br s, 2H).

2-Bromo-$N^1$,$N^3$-dimethylmalonamide

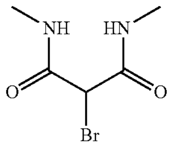

Chemical Formula: $C_5H_9BrN_2O_2$
Molecular Weight: 209.0

A mixture of $N^1$,$N^3$-dimethylmalonamide (1 g, 7.68 mmol) and bromine (0.39 mL, 7.68 mmol) in $CHCl_3$ (15 mL) was heated at 50° C. overnight. The solvents were evaporated and the crude product was purified by silica gel column chromatography eluting with 0-100% ethyl acetate in hexanes to give 2-bromo-$N^1$,$N^3$-dimethylmalonamide (450 mg, 28%). $^1$H NMR (300 MHz, DMSO-$d_6$): δ 2.61 (d, 6H, J=4.6 Hz); 4.73 (s, 2H); 8.22 (br s, 2H).

Heptadecan-9-yl 8-((3-((1,3-bis(methylamino)-1,3-dioxopropan-2-yl)amino)propyl)(8-oxo-8-(undecan-3-yloxy)octyl)amino)octanoate Trifluoroacetate Salt

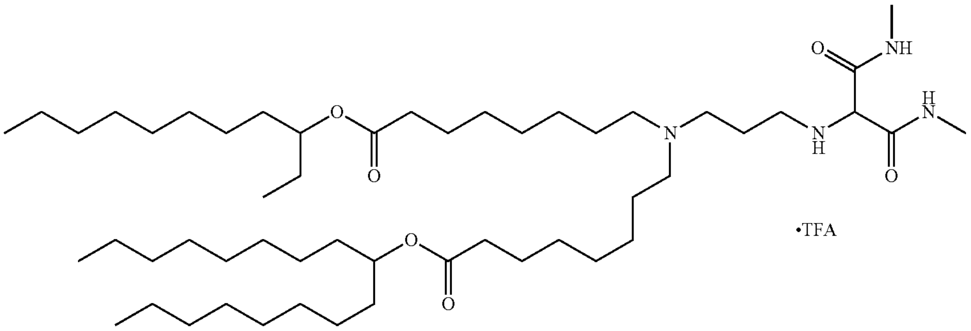

Chemical Formula: $C_{52}H_{102}N_4O_6$•TFA
Molecular Weight: 993.4

To a mixture of heptadecan-9-yl 8-((3-aminopropyl)(8-oxo-8-(undecan-3-yloxy)octyl)amino)octanoate (50 mg, 0.06 mmol) and 2-bromo-$N^1$,$N^3$-dimethylmalonamide (28 mg, 0.13 mmol) in n-BuOH (1 mL) was added DIPEA (35 μL, 0.2 mmol). The resultant mixture was heated to 130° C. in a sealed tube for 16 h. After the completion of the reaction, the mixture was concentrated. The reaction was repeated three more times with 150 mg (0.18 mmol) heptadecan-9-yl 8-((3-aminopropyl)(8-oxo-8-(undecan-3-yloxy)octyl)amino)octanoate each following the above procedure. The combined crude product was purified by silica gel chromatography with 0-10% methanol to dichloromethane and by C8 reverse phase chromatography with acetonitrile-water (0.1% TFA) to give heptadecan-9-yl 8-((3-((1,3-bis(methylamino)-1,3-dioxopropan-2-yl)amino)propyl)(8-oxo-8-(undecan-3-yloxy)octyl)amino)octanoate trifluoroacetic acid salt (185 mg, 28% from four batches) as a colorless oil. m/z ($MH^+$) 879.7 for $C_{52}H_{102}N_4O_6$·TFA. $^1$H NMR (300 MHz, $CDCl_3$): δ 0.83-0.88 (m, 12H); 1.24-1.8 (m, 63H); 2.27-2.3 (m, 6H); 2.8 (d, 6H, J=4.4 Hz); 2.95-3.19 (m, 4H); 3.19-3.29 (m, 4H); 4.79-4.87 (m, 2H); 5.07 (s, 1H); 7.5 (br s, 3H); 8.34-8.36 (m, 2H).

BV. Compound 81. Heptadecan-9-yl 8-((3-((4-cyano-5-oxo-2,5-dihydrofuran-3-yl)amino)propyl)(8-oxo-8-(undecan-3-yloxy)octyl)amino)octanoate Trifluoroacetate Salt

4-(Methylthio)-2-oxo-2,5-dihydrofuran-3-carbonitrile

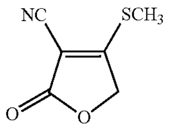

Chemical Formula: $C_6H_5NO_2S$
Molecular Weight: 155.2

A mixture of 4-(methylthio)-2-oxo-2,5-dihydrofuran-3-carboxamide (500 mg, 2.9 mmol) and $POCl_3$ (10 mL) was refluxed for 10 min. After the reaction excess solvent was removed by rotary evaporator and the residue poured onto ice-cold water. This mixture was extracted with $CH_2Cl_2$ (3×50 mL). The combined organic layers were dried over anhydrous $Na_2SO_4$, filtered and evaporated to give 4-(methylthio)-2-oxo-2,5-dihydrofuran-3-carbonitrile (400 mg, 89%). $^1H$ NMR (300 MHz, $CDCl_3$): δ 2.8 (s, 3H); 4.96 (s, 2H).

Heptadecan-9-yl 8-((3-((4-cyano-5-oxo-2,5-dihydrofuran-3-yl)amino)propyl)(8-oxo-8-(undecan-3-yloxy)octyl)amino)octanoate Trifluoroacetate Salt

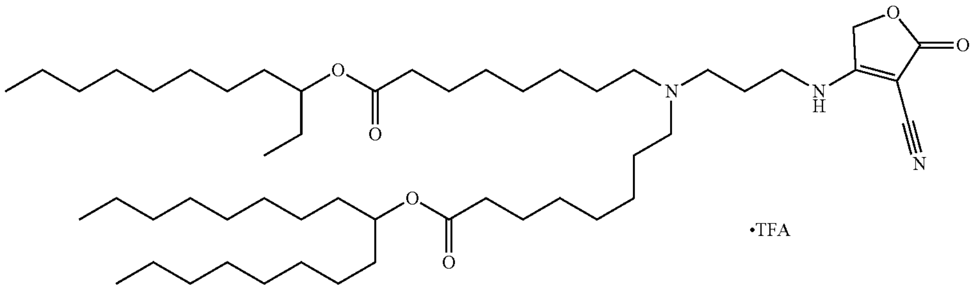

•TFA

Chemical Formula: $C_{25}H_{95}N_3O_6$•TFA
Molecular Weight: 972.4

A mixture of heptadecan-9-yl 8-((3-aminopropyl)(8-oxo-8-(undecan-3-yloxy)octyl)amino)octanoate (300 mg, 0.4 mmol) and 4-(methylthio)-2-oxo-2,5-dihydrofuran-3-carbonitrile (74 mg, 0.48 mmol) in n-BuOH (5 mL) was heated to 160° C. in a microwave reactor for 1 h. After the completion of the reaction, the mixture was concentrated. The reaction was repeated with 200 mg (0.26 mmol) of heptadecan-9-yl 8-((3-aminopropyl)(8-oxo-8-(undecan-3-yloxy)octyl)amino)octanoate as above and the combined crude material was first purified by silica gel chromatography with 0-10% methanol in dichloromethane and then by C8 reverse phase chromatography (acetonitrile-water, 0.1% TFA) to give heptadecan-9-yl 8-((3-((4-cyano-5-oxo-2,5-dihydrofuran-3-yl)amino)propyl)(8-oxo-8-(undecan-3-yloxy)octyl)amino)octanoate trifluoroacetate salt (155 mg, 24%) as a brown oil. m/z ($MH^+$) 858.7 for $C_{52}H_{95}N_3O_6$·TFA. $^1H$ NMR (300 MHz, $CDCl_3$): δ 0.83-0.89 (m, 12H); 1.15-2.8 (m, 64H); 2.26-2.3 (m, 6H); 2.9-3.1 (m, 4H); 3.21-3.32 (m, 2H); 3.74-3.76 (m, 2H); 4.79-4.85 (m, 4H); 9.13-9.21 (m, 1H); 11.5 (br s, 1H).

BW. Compound 82. Heptadecan-9-yl 8-((3-((5-amino-1,3,4-thiadiazol-2-yl)amino)propyl)(8-oxo-8-(undecan-3-yloxy)octyl)amino)octanoate Trifluoroacetate Salt

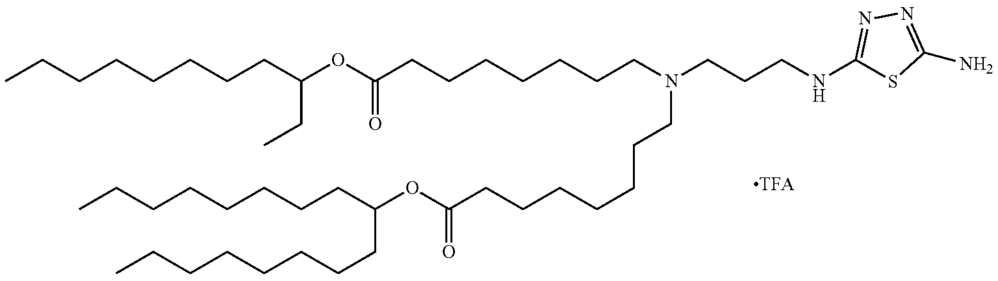

Chemical Formula: $C_{49}H_{95}N_5O_4S$•TFA
Molecular Weight: 964.4

To a mixture of heptadecan-9-yl 8-((3-aminopropyl)(8-oxo-8-(undecan-3-yloxy)octyl)amino)octanoate (300 mg, 0.4 mmol) and 5-bromo-1,3,4-thiadiazol-2-amine (108 mg, 0.6 mmol) in n-BuOH (5 mL) was added DIPEA (0.28 mL, 1.6 mmol) and the resultant mixture was heated at 150° C. in a sealed tube for 4 h. After the completion of the reaction, the mixture was concentrated and was first purified by silica gel chromatography with 0-10% methanol in dichloromethane and then by C8 reverse phase chromatography (acetonitrile-water, 0.1% TFA) to give heptadecan-9-yl 8-((3-((5-amino-1,3,4-thiadiazol-2-yl)amino)propyl)(8-oxo-8-(undecan-3-yloxy)octyl)amino)octanoate trifluoroacetate salt (140 mg, 36%) as a light yellow oil. m/z ($MH^+$) 850.7 for $C_{49}H_{95}N_5O_4S$.TFA. $^1H$ NMR (300 MHz, $CDCl_3$): δ 0.83-0.89 (m, 12H); 1.15-1.8 (m, 66H); 2.0-2.3 (m, 6H); 2.9-3.2 (m, 6H); 3.48-3.51 (m, 1H); 4.79-4.89 (m, 2H); 5.01-5.23 (m, 2H); 7.9 (br s, 1H).

BX. Compound 84. Heptadecan-9-yl 8-((3-((4-(methylamino)-1,2,5-thiadiazol-3-yl)amino)propyl)(8-oxo-8-(undecan-3-yloxy)octyl)amino)octanoate

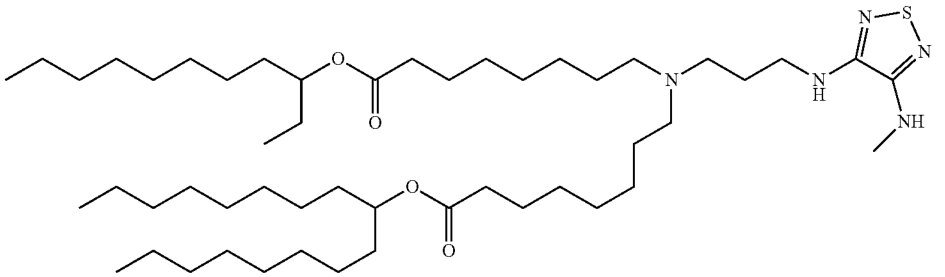

Chemical Formula: $C_{50}H_{97}N_5O_4S$
Molecular Weight: 864.4

To a mixture of heptadecan-9-yl 8-((3-((4-(methylamino)-1-oxido-1,2,5-thiadiazol-3-yl)amino)propyl)(8-oxo-8-(undecan-3-yloxy)octyl) amino)octanoate (250 mg, 0.28 mmol)) in $CH_2Cl_2$ (30 mL) was added $PPh_3$ (223 mg, 0.85 mmol) followed by $CCl_4$ (0.27 mL, 2.84 mmol) at 0° C. The resulting mixture was stirred at room temperature for 4 h. After completion of the reaction (confirmed by TLC and MS), the solvents were removed in a rotary evaporator and the residue purified by silica gel chromatography with 0-10% methanol to dichloromethane to give heptadecan-9-yl 8-((3-((4-(methylamino)-1,2,5-thiadiazol-3-yl)amino)propyl)(8-oxo-8-(undecan-3-yloxy)octyl)amino)octanoate (165 mg, 58%) as a pale yellow oil. m/z ($MH^+$) 864.7 for $C_{50}H_{97}N_5O_4S$. $^1H$ NMR (300 MHz, $CDCl_3$): δ 0.81-0.89 (m, 12H); 1.15-1.69 (m, 64H); 2.05-2.29 (m, 6H); 2.8-3.19 (m, 9H); 3.49-3.54 (m, 2H); 4.80-4.87 (m, 2H); 6.23 (br s, 1H); 6.9 (br s, 1H).

BY. Compound 85. Heptadecan-9-yl 8-((3-((4-(dimethylamino)-1-oxido-1,2,5-thiadiazol-3-yl)amino)propyl)(8-oxo-8-(undecan-3-yloxy)octyl)amino)octanoate Heptadecan-9-yl 8-((3-((4-methoxy-1-oxido-1,2,5-thiadiazol-3-yl)amino)propyl)(8-oxo-8-(undecan-3-yloxy)octyl)amino)octanoate

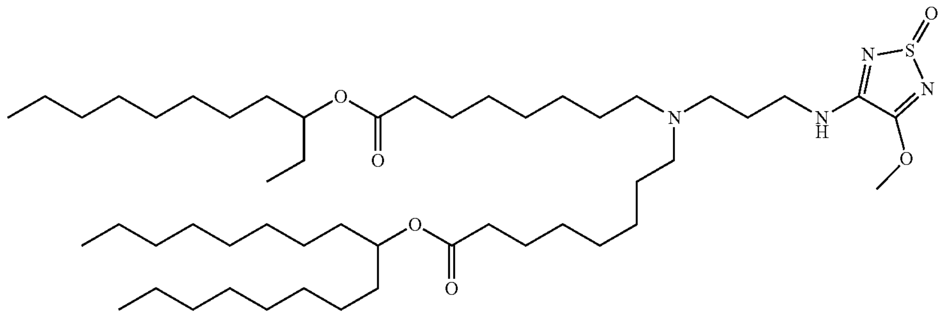

Chemical Formula: $C_{50}H_{96}N_4O_6S$
Molecular Weight: 881.4

To a mixture of heptadecan-9-yl 8-((3-aminopropyl)(8-oxo-8-(undecan-3-yloxy)octyl)amino)octanoate (123 mg, 0.75 mmol)) in methanol (3 mL) was added 3,4-dimethoxy-1,2,5-thiadiazole 1-oxide (285 mg, 0.37 mmol). The resultant mixture was stirred at room temperature for 1 h. After completion of the reaction solvents were removed in a rotary evaporator and the residue purified by silica gel chromatography with 0-10% methanol in dichloromethane to give heptadecan-9-yl 8-((3-((4-methoxy-1-oxido-1,2,5-thiadiazol-3-yl)amino)propyl)(8-oxo-8-(undecan-3-yloxy)octyl)amino)octanoate (3, 192 mg, 29%). $^1H$ NMR (300 MHz, $CDCl_3$): δ 0.83-0.89 (m, 12H); 1.15-1.82 (m, 66H); 2.2-2.65 (m, 10H); 3.54-3.58 (m, 2H); 4.09 (s, 3H); 4.80-4.87 (m, 2H); 9.3 (br s, 1H).

Heptadecan-9-yl 8-((3-((4-(dimethylamino)-1-oxido-1,2,5-thiadiazol-3-yl)amino)propyl)(8-oxo-8-(undecan-3-yloxy)octyl)amino)octanoate

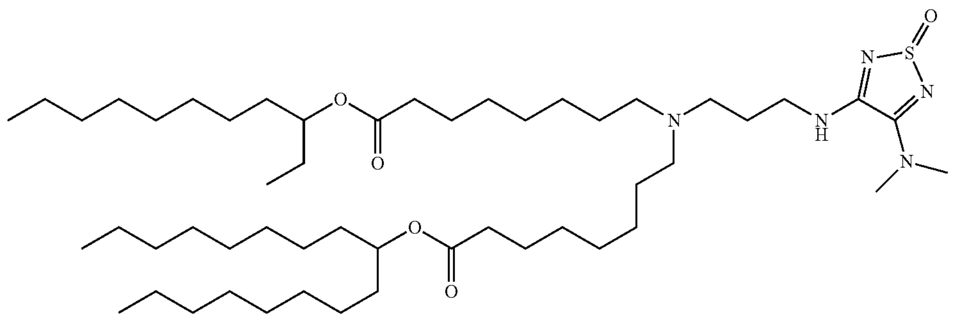

Chemical Formula: $C_{51}H_{99}N_5O_5S$
Molecular Weight: 894.4

To a mixture of heptadecan-9-yl 8-((3-((4-methoxy-1-oxido-1,2,5-thiadiazol-3-yl)amino)propyl)(8-oxo-8-(undecan-3-yloxy)octyl)amino)octanoate (186 mg, 0.21 mmol)) in methanol (3 mL) was added dimethylamine (1.06 mL, 2.1 mmol, 2M in MeOH). The resulting mixture was stirred at room temperature overnight. After completion of the reaction (confirmed by TLC and MS), the solvents were removed in a rotary evaporator and the residue purified by silica gel chromatography with 0-10% methanol in dichloromethane to give heptadecan-9-yl 8-((3-((4-(dimethylamino)-1-oxido-1,2,5-thiadiazol-3-yl)amino)propyl)(8-oxo-8-(undecan-3-yloxy)octyl)amino)octanoate (130 mg, 69%) as a light yellow oil. m/z ($MH^+$) 894.6 for $C_{51}H_{99}N_5O_5S$. $^1H$ NMR (300 MHz, $CDCl_3$): δ 0.81-0.89 (m, 12H); 1.15-1.75 (m, 66H); 2.25-2.69 (m, 10H); 3.22 (s, 6H); 3.59-3.62 (m, 2H); 4.80-4.85 (m, 2H); 8.4 (br s, 1H).

BZ. Compound 86. Heptadecan-9-yl (E)-8-((3-(N'-(methylsulfonyl)formimidamido)propyl)(8-oxo-8-(undecan-3-yloxy)octyl)amino)octanoate

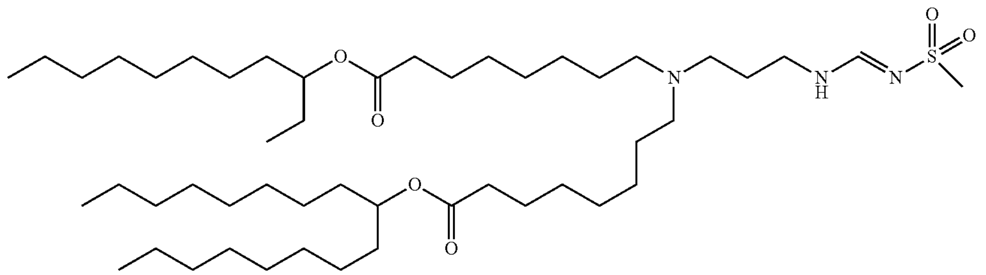

Chemical Formula: $C_{49}H_{97}N_3O_6S$
Molecular Weight: 856.4

A mixture of heptadecan-9-yl 8-((3-aminopropyl)(8-oxo-8-(undecan-3-yloxy)octyl)amino)octanoate (100 mg, 0.13 mmol) and trimethyl orthoformate (2 mL) in n-BuOH (5 mL) was refluxed for 1 h. After completion of the reaction the excess solvents were evaporated. The residue was dissolved in MeOH (10 mL), methanesulfonamide (15 mg, 0.16 mmol) added and the resultant mixture was heated to 100° C. for 1 h. The mixture was allowed to cool to room temperature and conc. The reaction was repeated with 200 mg (0.26 mmol) of heptadecan-9-yl 8-((3-aminopropyl)(8-oxo-8-(undecan-3-yloxy)octyl)amino)octanoate as above and the combined crude material was purified by silica gel chromatography with 0-10% methanol in dichloromethane to give heptadecan-9-yl (E)-8-((3-(N-(methylsulfonyl)formimidamido)propyl)(8-oxo-8-(undecan-3-yloxy)octyl)amino)octanoate (130 mg, 38%) as a light yellow oil. m/z ($MH^+$) 856.7 for $C_{49}H_{97}N_3O_6S$. $^1$H NMR (300 MHz, $CDCl_3$): δ 0.83-0.89 (m, 12H); 1.15-1.8 (m, 66H); 2.2-2.7 (m, 10H); 2.9 (s, 3H); 3.48-3.51 (m, 2H); 4.80-4.87 (m, 2H); 8.1 (br m, 1H); 9.15 (br s, 1H).

CA. Compound 87. Heptadecan-9-yl 8-((3-((3-amino-1-methyl-1H-1,2,4-triazol-5-yl)amino)propyl)(8-oxo-8-(undecan-3-yloxy)octyl)amino)octanoate

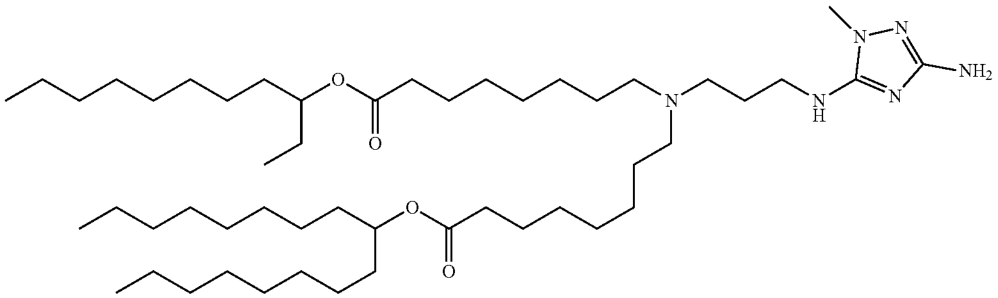

Chemical Formula: $C_{50}H_{98}N_6O_4$
Molecular Weight: 847.4

To a mixture of heptadecan-9-yl 8-((3-aminopropyl)(8-oxo-8-(undecan-3-yloxy)octyl)amino)octanoate (300 mg, 0.4 mmol) and diphenyl cyanocarbonimidate (95 mg, 0.4 mmol) in 2-propanol (9 mL) was added DIPEA (69 μL, 0.4 mmol). The resultant mixture was stirred at room temperature for 1 h. After complete conversion had occurred methylhydrazine (21 μL, 0.4 mmol) was added to the above mixture. The resultant mixture was refluxed for 18 h. The excess solvent was evaporated and purified by silica gel chromatography with 0-10% methanol in dichloromethane to give heptadecan-9-yl 8-((3-((3-amino-1-methyl-1H-1,2,4-triazol-5-yl)amino)propyl)(8-oxo-8-(undecan-3-yloxy)octyl)amino)octanoate (120 mg, 35%) as a light brown oil. m/z ($MH^+$) 847.7 for $C_{50}H_{98}N_6O_4$. $^1$H NMR (300 MHz, $CDCl_3$): δ 0.83-0.89 (m, 12H); 1.15-1.8 (m, 66H); 2.2-2.6 (m, 10H); 3.3 (s, 3H); 3.38-3.48 (m, 2H); 3.81 (br s, 2H), 4.80-4.87 (m, 2H); 6.31-6.35 (br m, 1H).

CB. Compound 88. Heptadecan-9-yl 8-((3-((3-nitro-1H-pyrrol-2-yl)amino)propyl)(8-oxo-8-(undecan-3-yloxy)octyl)amino)octanoate (Z)—N-(2,2-Diethoxyethyl)-1-(methylthio)-2-nitroethen-1-amine

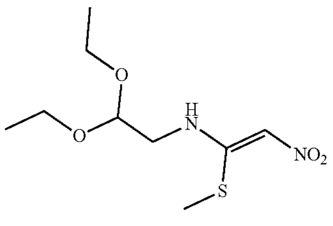

Chemical Formula: $C_9H_{18}N_2O_4S$
Molecular Weight: 250.3

A mixture of glycinaldehyde diethylacetal (2.0 g, 15 mmol)) and 1,1-bis(methylthio)-2-nitroethene (2.5 g, 15 mmol) in ethanol (25 mL) was refluxed for 20 h. After completion of the reaction, the solvents were removed by rotary evaporator. The crude product was purified by silica gel chromatography with 0-5% acetone in dichloromethane to give (Z)—N-(2,2-diethoxyethyl)-1-(methylthio)-2-nitroethen-1-amine (2.2 g, 60%). $^1$H NMR (300 MHz, $CDCl_3$): δ 1.22-1.26 (m, 6H); 2.43 (s, 3H); 3.51-3.58 (m, 4H); 3.71-3.81 (m, 2H); 4.613-4.66 (m, 1H); 6.56 (s, 1H); 10.45 (br s, 1H).

2-(Methylthio)-3-nitro-1H-pyrrole

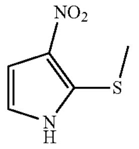

Chemical Formula: $C_5H_6N_2O_2S$
Molecular Weight: 158.2

Dry HCl gas was passed through a mixture of (Z)—N-(2,2-diethoxyethyl)-1-(methylthio)-2-nitroethen-1-amine (1.25 g, 5 mmol)) in ether (100 mL) at 5-10° C. for 3 h. After completion of the reaction, the mixture was quenched with 10% $K_2CO_3$ solution. The organic layer was dried over anhydrous $Na_2SO_4$, filtered and evaporated to give 2-(methylthio)-3-nitro-1H-pyrrole (730 mg, 92%). $^1$H NMR (300 MHz, DMSO-d6): δ 2.57 (s, 3H); 6.71 (m, 1H); 6.92 (m, 1H); 10.82 (br s, 1H).

2-(Methylsulfinyl)-3-nitro-1H-pyrrole

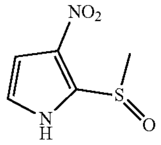

Chemical Formula: $C_5H_6N_2O_3S$
Molecular Weight: 174.2

To a mixture of 2-(methylthio)-3-nitro-1H-pyrrole (100 mg, 0.63 mmol)) in $CH_2Cl_2$:MeOH (3:1, 9 mL) was added mCPBA (141 mg, 0.63 mmol, 77% approx) at 0° C. The resultant mixture was stirred for 30 min (monitored by TLC). After completion of the reaction, the mixture was diluted with $CH_2Cl_2$ (10 mL), washed with saturated $NaHCO_3$, dried over anhydrous $Na_2SO_4$, filtered and evaporated to give 2-(methylsulfinyl)-3-nitro-1H-pyrrole (60 mg, 54%). $^1$H NMR (300 MHz, DMSO-d6): δ 2.95 (s, 3H); 6.82 (m, 1H); 7.1 (m, 1H); 11.2 (br s, 1H).

Heptadecan-9-yl 8-((3-((3-nitro-1H-pyrrol-2-yl)amino)propyl)(8-oxo-8-(undecan-3-yloxy)octyl)amino)octanoate

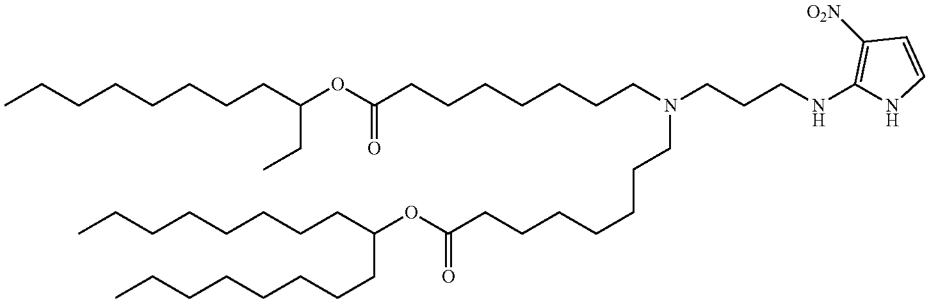

Chemical Formula: $C_{51}H_{96}N_4O_6$
Molecular Weight: 861.4

A mixture of heptadecan-9-yl 8-((3-aminopropyl)(8-oxo-8-(undecan-3-yloxy)octyl)amino)octanoate (500 mg, 0.66 mmol) and 2-(methylsulfinyl)-3-nitro-1H-pyrrole (172 mg, 0.98 mmol in n-BuOH (2 mL) was heated at 100° C. for 65 h. The excess solvents were removed in rotary evaporator and the residue purified by silica gel chromatography with 0-10% methanol in dichloromethane to give heptadecan-9-yl 8-((3-((3-nitro-1H-pyrrol-2-yl)amino)propyl)(8-oxo-8-(undecan-3-yloxy)octyl)amino)octanoate (120 mg, 21%) as a light brown oil. m/z ($MH^+$) 861.7 for $C_{51}H_{96}N_4O_6$. $^1$H NMR (300 MHz, $CDCl_3$): δ 0.83-0.89 (m, 12H); 1.15-1.69 (m, 65H); 1.8-1.95 (m, 2H); 2.19-2.32 (m, 4H); 2.5-2.75 (m, 6H); 3.35-3.63 (m, 2H); 4.80-4.87 (m, 2H); 6.09-6.12 (m, 1H); 6.39-6.42 (m, 1H); 7.61-7.7 (m, 1H).

CC. Compound 89: Heptadecan-9-yl 8-((3-(ethylsulfonamido)propyl)(8-((2-methylnonyl)oxy)-8-oxooctyl)amino)octanoate 2-Methylnonyl 8-bromooctanoate

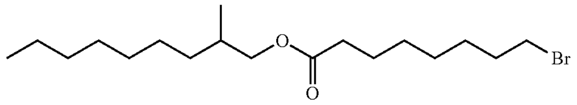

Chemical Formula: $C_{18}H_{35}BrO_2$
Molecular Weight: 363.38

To a solution of 8-bromooctanoic acid (3.83 g, 17.18 mmol), 2-methylnonan-1-ol (2.72 g, 17.18 mmol), 4-dimethylaminopyridine (0.42 g, 3.44 mmol) in DCM (25 mL) under $N_2$ was added (3-{[(ethylimino)methylidene]amino}propyl)dimethylamine hydrochloride (3.29 g, 17.18 mmol). The reaction was allowed to stir at rt for 16 h. The reaction was diluted with DCM and washed with sat. $NaHCO_3$, followed by brine. The organic layer was separated, dried over $Na_2SO_4$, filtered, and evaporated under vacuum. The residue was purified by silica gel chromatography with (0-20%) EtOAc in hexanes to obtain 2-methylnonyl 8-bromooctanoate (5.1 g, 14.04 mmol, 82%). $^1$H NMR (300 MHz, $CDCl_3$) δ: ppm 3.98 (m, 2H); 3.43 (t, 2H); 2.33 (t, 2H); 1.93-1.74 (m, 3H); 1.72-1.09 (m, 20H); 0.93 (m, 6H).

Heptadecan-9-yl 8-((3-((tert-butoxycarbonyl)amino)propyl)amino)octanoate

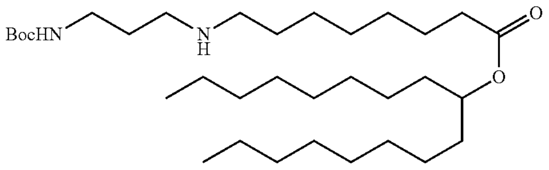

Chemical Formula: $C_{33}H_{66}N_2O_4$
Molecular Weight: 554.90

A solution of heptadecan-9-yl 8-bromooctanoate 4 (69.2 g, 0.15 mole) and tert-butyl (3-aminopropyl)carbamate (130.6 g, 0.75 mole) in 500 mL ethanol was heated to 65° C. overnight. The reaction mixture was concentrated, and the crude was purified by flash column chromatography ($SiO_2$: methanol/dichloromethane 0-20%) to get heptadecan-9-yl 8-((3-((tert-butoxycarbonyl)amino)propyl)amino)octanoate (62 g, 74%) as light yellow oil. MS (CI): m/z ($MH^+$) 555.5 for $C_{33}H_{66}N_2O_4$. $^1$H NMR (300 MHz, $CDCl_3$): δ ppm 5.15 (bs, 1H); 4.85 (quint., 1H, J=6.0 Hz); 3.17 (m, 2H); 2.65 (t, 2H, J=6.6 Hz); 2.56 (t, 2H, J=6.8 Hz); 2.26 (t, 2H, J=7.6 Hz); 1.68-1.56 (m, 6H); 1.46 (m, 5H); 1.43 (s, 9H); 1.24 (m, 30H); 0.86 (t, 6H, J=6.6 Hz).

Heptadecan-9-yl 8-((3-((tert-butoxycarbonyl)amino)propyl)(8-((2-methylnonyl)oxy)-8-oxooctyl)amino)octanoate

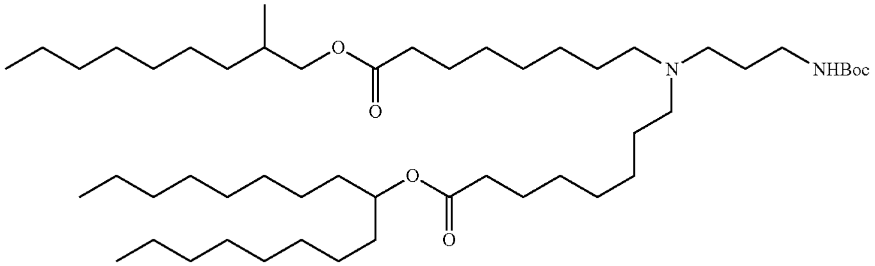

Chemical Formula: $C_{51}H_{100}N_2O_6$
Molecule Weight: 837.37

To a solution of heptadecan-9-yl 8-((3-((tert-butoxycarbonyl)amino)propyl)amino)octanoate (5.0 g, 8.9 mmol) and 2-methylnonyl 8-bromooctanoate (3.76 g, 10.2 mmol) in 27 mL propionitrile was added potassium carbonate (1.87 g, 13.4 mmol) and potassium iodide (0.22 g, 1.3 mmol) to give a white mixture. This was heated to 80° C. and stirred for 14 hours. The mixture was allowed to cool to room temp., filtered through Celite, the filter solids washed with propionitrile and the filtrate conc. The residue was dissolved in heptane, washed twice with acetonitrile and conc. to a slightly yellow oil. This residue was purified by silica gel chromatography (0-20% ethyl acetate in hexanes) to give heptadecan-9-yl 8-((3-((tert-butoxycarbonyl)amino)propyl)(8-((2-methylnonyl)oxy)-8-oxooctyl)amino)octanoate (6.12 g, 7.3 mmol, 82%) as a slightly yellow oil. MS (CI): m/z ($MH^+$) 837.6 for $C_{51}H_{100}N_2O_6$. $^1H$ NMR (300 MHz, $CDCl_3$): δ ppm 5.65 (br s, 1H); 4.86 (m, 1H); 3.98-3.81 (m, 2H); 3.81 (m, 2H), 2.44 (t, 2H, J=6.3 Hz); 2.36-2.25 (m, 8H); 1.77 (m, 1H), 1.64-1.57 (m, 6H); 1.55-1.39 (m, 17H); 1.37-1.14 (m, 48H); 0.93-0.84 (m, 12H).

Heptadecan-9-yl 8-((3-aminopropyl)(8-((2-methylnonyl)oxy)-8-oxooctyl)amino)octanoate

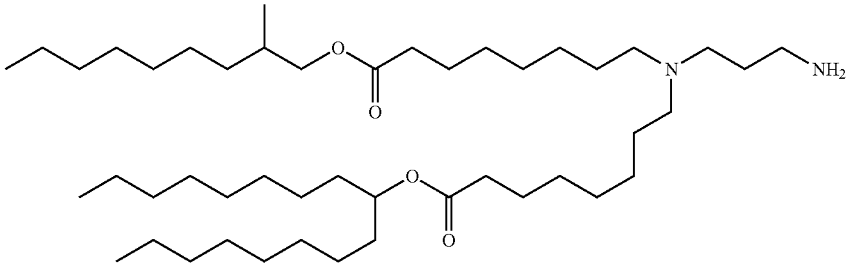

Chemical Formula: $C_{46}H_{92}N_2O_4$
Molecule Weight: 737.25

To a solution of heptadecan-9-yl 8-((3-((tert-butoxycarbonyl)amino)propyl)(8-((2-methylnonyl)oxy)-8-oxooctyl) amino)octanoate (760 mg, 0.91 mmol) in 2 mL methyl cyclopentyl ether (MCPE) was added a 3M HCl solution in MCPE, the reaction vessel sealed and the reaction heated to 40° C. for two hours with stirring. The reaction was allowed to cool to room temp., diluted with ca. 5 mL of an aqueous 10% sodium carbonate solution and extracted three times with EtOAc. The organics were combined, dried ($Na_2SO_4$), filtered and the filtrate conc. to a yellow oil. This was dissolved in heptane, washed twice with acetonitrile, then conc. and dried under vacuum to give heptadecan-9-yl 8-((3-aminopropyl)(8-((2-methylnonyl)oxy)-8-oxooctyl) amino)octanoate (570 mg, 0.77 mmol, 85%) as a colorless oil. MS (CI): m/z ($MH^+$) 737.5 for $C_{46}H_{92}N_2O_4$. $^1H$ NMR (300 MHz, $CDCl_3$): δ ppm 4.87-4.79 (m, 2H); 3.65 (m, 2H), 3.41-3.34 (m, 2H), 2.70 (t, 2H, J=6.6 Hz); 2.42-2.33 (m, 6H); 2.30-2.25 (m, 4H); 1.68-1.46 (m, 16H); 1.44-1.35 (m, 4H); 1.34-1.16 (m, 42H); 0.92-0.84 (m, 12H).

Heptadecan-9-yl 8-((3-(ethylsulfonamido)propyl)(8-((2-methylnonyl)oxy)-8-oxooctyl)amino)octanoate

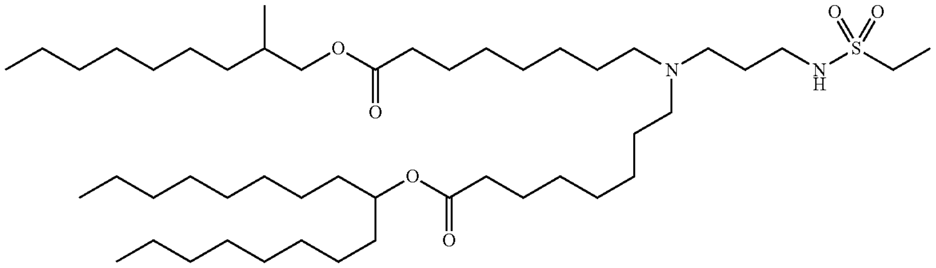

Chemical Formula: $C_{48}H_{96}N_2O_6S$
Molecular Weight: 829.36

To a solution of heptadecan-9-yl 8-((3-aminopropyl)(8-((2-methylnonyl)oxy)-8-oxooctyl)amino)octanoate (200 mg, 0.271 mmol) and triethylamine (200 μL, 1.43 mmol) in DCM (6.782 mL) at 0° C. was added ethanesulfonyl chloride (41.854 mg, 0.326 mmol) in DCM (1 mL). The reaction mixture stirred at 0° C. for 1 h and at room temperature overnight. The reaction mixture was diluted with additional DCM (10 mL) and washed brine solution (15 mL). The DCM layer was separated and dried over magnesium sulfate. The solution was concentrated and purified by silica gel chromatography (0-100% (mixture of 1% $NH_4OH$, 20% MeOH in DCM) in DCM) to give heptadecan-9-yl 8-((3-(ethylsulfonamido)propyl)(8-((2-methylnonyl)oxy)-8-oxooctyl)amino)octanoate (101.2 mg, 45%) as an oil. UPLC/ELSD: RT=2.90 min. MS (CI): m/z ($MH^+$) 829.964 for $C_{48}H_{96}N_2O_6S$. $^1H$ NMR (300 MHz, $CDCl_3$): δ ppm 6.93 (br s, 1H); 4.93-4.78 (m, 1H); 4.04-3.77 (m, 2H); 3.38-3.12 (m, 3H); 3.11-2.90 (m, 5H); 2.67-2.22 (m, 8H); 1.90-1.44 (m, 16H); 1.43-1.19 (m, 48H); 0.98-0.81 (m, 12H).

CD. Compound 90: Heptadecan-9-yl 8-((3-(cyclopropanesulfonamido)propyl)(8-((2-methylnonyl)oxy)-8-oxooctyl)amino)octanoate

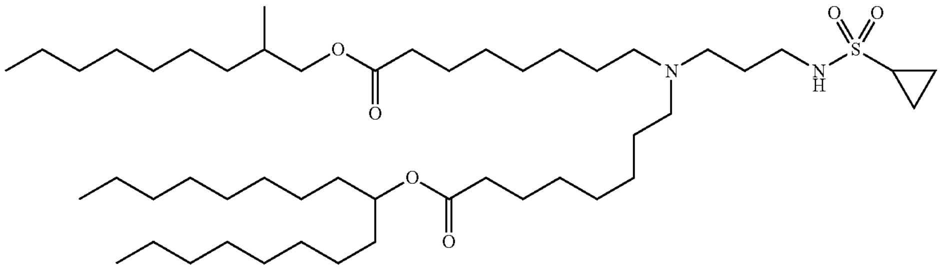

Chemical Formula: $C_{49}H_{96}N_2O_6S$
Molecular Weight: 841.38

To a solution of heptadecan-9-yl 8-((3-aminopropyl)(8-((2-methylnonyl)oxy)-8-oxooctyl)amino)octanoate (200 mg, 0.271 mmol) and triethylamine (200 μL, 1.43 mmol) in DCM (6.782 mL) at 0° C. was added cyclopropanesulfonyl chloride (45.763 mg, 0.326 mmol) in DCM (1 mL). The reaction mixture stirred at 0° C. for 1 h and at room temperature overnight. The reaction mixture was diluted with additional DCM (10 mL) and washed with brine solution (15 mL). The DCM layer was separated and dried over magnesium sulfate. The solution was concentrated and purified by silica gel chromatography (0-100% (mixture of 1% $NH_4OH$, 20% MeOH in DCM) in DCM) to give heptadecan-9-yl 8-((3-(cyclopropanesulfonamido)propyl)(8-((2-methylnonyl)oxy)-8-oxooctyl)amino)octanoate (150.2 mg, 66%) as an oil. UPLC/ELSD: RT=2.98 min. MS (CI): m/z ($MH^+$) 841.558 for $C_{49}H_{96}N_2O_6S$. $^1H$ NMR (300 MHz, $CDCl_3$): δ ppm 6.98 (br s, 1H); 4.93-4.80 (m, 1H); 4.05-3.75 (m, 2H); 3.40-3.14 (m, 2H); 2.65-2.48 (m, 2H); 2.47-2.18 (m, 9H); 1.86-1.39 (m, 19H); 1.3-1.06 (m, 48H); 1.00-0.80 (m, 12H).

CE. Compound 91: Heptadecan-9-yl 8-((3-((isoxazol-3-ylmethyl)sulfonamido)propyl)(8-((2-methylnonyl)oxy)-8-oxooctyl)amino)octanoate

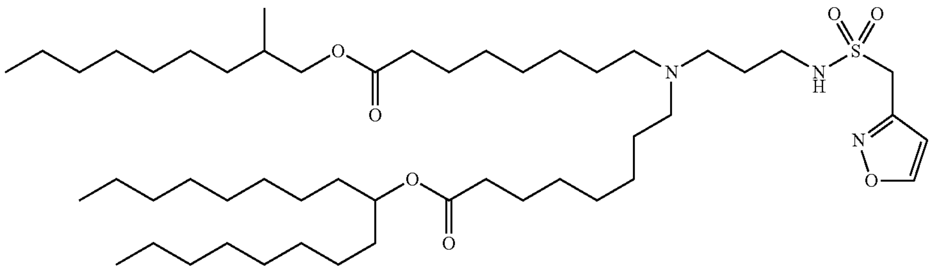

Chemical Formula: $C_{50}H_{95}N_3O_7S$
Molecular Weight: 882.38

To a solution of heptadecan-9-yl 8-((3-aminopropyl)(8-((2-methylnonyl)oxy)-8-oxooctyl)amino)octanoate (200 mg, 0.271 mmol) and triethylamine (200 μL, 1.43 mmol) in DCM (6.782 mL) at 0° C. was added cyclopropanesulfonyl chloride (59.114 mg, 0.326 mmol) in DCM (1 mL). The reaction mixture stirred at 0° C. for 1 h and at room temperature overnight. The reaction was heated to 30° C. for 2 h. The reaction mixture was diluted with additional DCM (10 mL) and washed with brine solution (15 mL). The DCM layer was separated and dried over magnesium sulfate. The solution was concentrated and purified by silica gel chromatography (0-100% (mixture of 1% $NH_4OH$, 20% MeOH in DCM) in DCM) to give heptadecan-9-yl 8-((3-((isoxazol-3-ylmethyl)sulfonamido)propyl)(8-((2-methylnonyl)oxy)-8-oxooctyl)amino)octanoate (80.7 mg, 34%) as an oil. UPLC/ELSD: RT=2.95 min. MS (CI): m/z ($MH^+$) 882.878 for $C_{50}H_{95}N_3O7S$. $^1H$ NMR (300 MHz, $CDCl_3$): δ ppm 8.44 (s, 1H); 7.64 (br s, 1H); 6.62 (s, 1H); 4.92-4.78 (m, 1H); 4.45-4.31 (s, 2H); 4.00-3.79 (m, 2H); 3.29-3.10 (m, 2H); 2.61-2.44 (m, 2H); 2.39-2.22 (m, 8H); 1.88-1.43 (m, 16H); 1.42-1.01 (m, 48H); 0.98-0.77 (m, 12H).

CF. Compound 94. Heptadecan-9-yl 8-{[3-(methylsulfamoyl)propyl][8-oxo-8-(undecan-3-yloxy)octyl]amino}octanoate

Undecan-3-yl 8-{[(4-methoxyphenyl)methyl]amino}octanoate

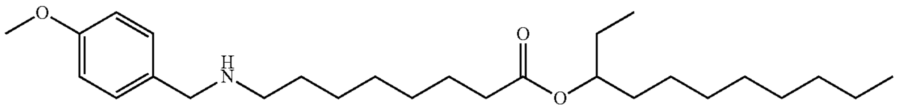

Chemical Formula: $C_{27}H_{47}NO_3$
Molecular Weight: 433.68

To a suspension of cesium carbonate (4.988 g, 15.31 mmol) in DMF (52 mL) was added 4-methoxybenzylamine (4.00 mL, 30.6 mmol). The suspension stirred at room temperature for 30 min, then undecan-3-yl 8-bromooctanoate (5.777 g, 15.31 mmol) in DMF (4.0 mL) was added. The reaction mixture stirred at room temperature and was monitored by LCMS. At 16 h, the reaction mixture was diluted with MTBE (75 mL), filtered through a pad of celite, and then the filtrate was concentrated. The residue was taken up in MTBE (300 mL), washed with water (3×) and brine, dried over $Na_2SO_4$, and concentrated. The crude material was purified via automated silica gel flash chromatography (0-20% MeOH in DCM) to afford undecan-3-yl 8-{[(4-methoxyphenyl)methyl]amino}octanoate (3.500 g, 8.071 mmol, 52.72%) as a clear yellow oil. UPLC/ELSD: RT=1.72 min. MS (ES): m/z ($MH^+$) 434.09 for $C_{27}H_{47}NO_3$. $^1H$ NMR (300 MHz, $CDCl_3$) δ: ppm 7.20-7.26 (m, 2H); 6.82-6.90 (m, 2H); 4.75-4.86 (m, 1H); 3.80 (s, 3H); 3.72 (s, 2H); 2.60 (t, 2H, J=7.5 Hz); 2.28 (t, 2H, J=7.5 Hz); 1.41-1.67 (m, 8H); 1.19-1.40 (m, 18H); 0.82-0.92 (m, 6H).

Heptadecan-9-yl 8-{[(4-methoxyphenyl)methyl][8-oxo-8-(undecan-3-yloxy)octyl]amino}octanoate

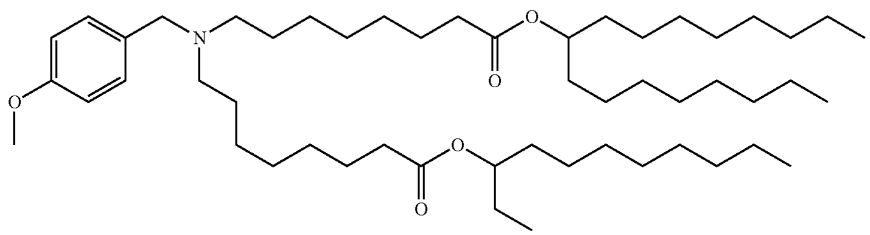

Chemical Formula: $C_{52}H_{95}NO_5$
Molecular Weight: 814.33

Heptadecan-9-yl 8-bromooctanoate (4.268 g, 9.195 mmol), potassium carbonate (1.733 g, 12.54 mmol), potassium iodide (0.278 g, 1.67 mmol), undecan-3-yl 8-{[(4-methoxyphenyl)methyl]amino}octanoate (3.625 g, 8.359 mmol) and dioxane (28.0 mL) were combined in a sealed tube. The reaction mixture stirred at 110° C. and was monitored by LCMS. At 65 h, the reaction mixture was cooled to room temperature, poured into MTBE (50 mL), and filtered through a pad of celite rinsing with MTBE. The filtrate was washed with water and brine, dried over $Na_2SO_4$, and concentrated. The crude material was purified via automated silica gel flash chromatography (5-40% EtOAc in hexanes) to afford heptadecan-9-yl 8-{[(4-methoxyphenyl)methyl][8-oxo-8-(undecan-3-yloxy)octyl]amino}octanoate (5.001 g, 6.141 mmol, 73.47%) as a yellow oil. UPLC/ELSD: RT=3.13 min. MS (ES): m/z ($MH^+$) 814.34 for $C_{52}H_{95}NO_5$. $^1H$ NMR (300 MHz, $CDCl_3$) δ: ppm 7.18-7.24 (m, 2H); 6.80-6.86 (m, 2H); 4.76-4.91 (m, 2H); 3.80 (s, 3H); 3.47 (s, 2H); 2.31-2.40 (m, 4H); 2.22-2.31 (m, 4H); 1.37-1.66 (m, 16H); 1.16-1.36 (m, 48H); 0.82-0.93 (m, 12H).

Heptadecan-9-yl 8-{[8-oxo-8-(undecan-3-yloxy)octyl]amino}octanoate

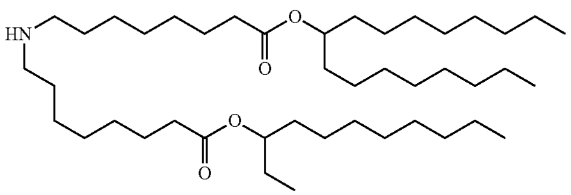

Chemical Formula: $C_{44}H_{87}NO_4$
Molecular Weight: 694.18

A mixture of 20% palladium (II) hydroxide on carbon (1.721 g, 1.226 mmol) and methoxyphenyl)methyl][8-oxo-8-(undecan-3-yloxy)octyl]amino}octanoate (4.99 g, 6.128 mmol, 1 equiv.) in ethyl acetate (40.0 mL) and acetic acid (10.0 mL) was stirred under an atmosphere of H2 (balloon pressure) at room temperature. Reaction was monitored by LCMS. At 16 h, the reaction mixture was filtered through a pad of celite rinsing with EtOAc. Water (ca. 200 mL) was added to the filtrate, then $Na_2CO_3$ was added to the stirred biphasic mixture until pH~10. The layers were separated, the organics were washed with water and brine, dried over $Na_2SO_4$, and concentrated. The crude material was purified via automated silica gel flash chromatography (0-20% (5% conc. aq. $NH_4OH$ in MeOH) in DCM) to afford heptadecan-9-yl 8-{[8-oxo-8-(undecan-3-yloxy)octyl]amino}octanoate (3.300 g, 4.754 mmol, 77.58%) as a clear yellowish oil. UPLC/ELSD: RT=2.99 min. MS (ES): m/z ($MH^+$) 694.32 for $C_{44}H_{87}NO_4$. $^1H$ NMR (300 MHz, $CDCl_3$) δ: ppm 4.75-4.91 (m, 2H); 2.57 (t, 4H, J=7.5 Hz); 2.23-2.33 (m, 4H); 1.40-1.70 (m, 16H); 1.16-1.40 (m, 48H); 0.83-0.92 (m, 12H).

3-{[8-(heptadecan-9-yloxy)-8-oxooctyl][8-oxo-8-(undecan-3-yloxy)octyl]amino}propane-1-sulfonic Acid

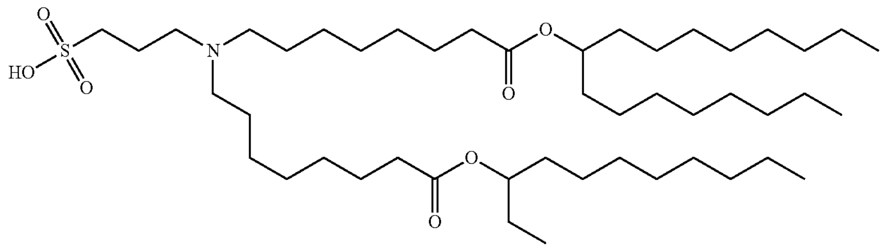

Chemical Formula: $C_{47}H_{93}NO_7S$
Molecular Weight: 816.32

A solution of heptadecan-9-yl 8-{[8-oxo-8-(undecan-3-yloxy)octyl]amino}octanoate (0.313 g, 0.450 mmol) and 1,3-propane sultone (0.066 g, 0.54 mmol) in acetone (2.25 mL) was heated at 55° C. while stirring. The reaction was monitored by LCMS. At 25 h, the reaction mixture was cooled to room temperature, 1,3-propane sultone (28 mg, 0.23 mmol) was added, and the reaction mixture was stirred at 55° C. At 42 h, the reaction mixture was cooled to room temperature. Water (2.5 mL) was added, and the reaction mixture stirred for 5 min at room temperature. After this time, the reaction mixture was concentrated to remove volatile organics. The residue was taken up in EtOAc and water. The aqueous was extracted with EtOAc (2×) and 19:1 DCM/MeOH. The combined organics were washed with brine, dried over $Na_2SO_4$, and concentrated. The crude material was purified via automated silica gel flash chromatography (0-20% MeOH in DCM) to afford 3-{[8-(heptadecan-9-yloxy)-8-oxooctyl][8-oxo-8-(undecan-3-yloxy)octyl]amino}propane-1-sulfonic acid (0.277 g, 0.339 mmol, 75.34%) as a clear pink oil. UPLC/ELSD: RT=3.45 min. MS (ES): m/z ($MNa^+$) 838.84 for $C_{47}H_{93}NO_7S$. $^1H$ NMR (300 MHz, $CDCl_3$) δ: ppm 11.18 (br s, 1H); 4.75-4.91 (m, 2H); 3.14-3.23 (m, 2H); 2.97-3.13 (m, 6H); 2.22-2.34 (m, 6H); 1.44-1.83 (m, 16H); 1.15-1.43 (m, 48H); 0.82-0.94 (m, 12H).

Heptadecan-9-yl 8-{[3-(chlorosulfonyl)propyl][8-oxo-8-(undecan-3-yloxy)octyl]amino}octanoate

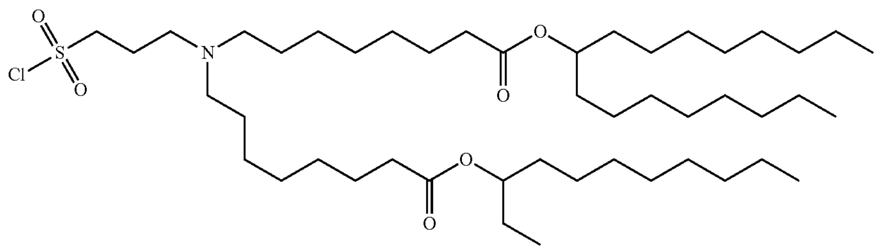

Chemical Formula: $C_{47}H_{92}ClNO_6S$
Molecular Weight: 834.76

To a solution of 3-{[8-(heptadecan-9-yloxy)-8-oxooctyl][8-oxo-8-(undecan-3-yloxy)octyl]amino}propane-1-sulfonic acid (0.150 g, 0.184 mmol) and DMF (cat.) in 1,2-dichloroethane (0.75 mL) was added thionyl chloride (70 uL, 0.92 mmol). The reaction mixture stirred at 70° C. and was monitored by LCMS. At 1 h, the reaction mixture was cooled to room temperature and then concentrated. The residue was concentrated from PhMe (3×) to afford heptadecan-9-yl 8-{[3-(chlorosulfonyl)propyl][8-oxo-8-(undecan-3-yloxy)octyl]amino}octanoate as an amber oil which was carried forward as is assuming quant. yield.

Heptadecan-9-yl 8-{[3-(methylsulfamoyl)propyl][8-oxo-8-(undecan-3-yloxy)octyl]amino}octanoate

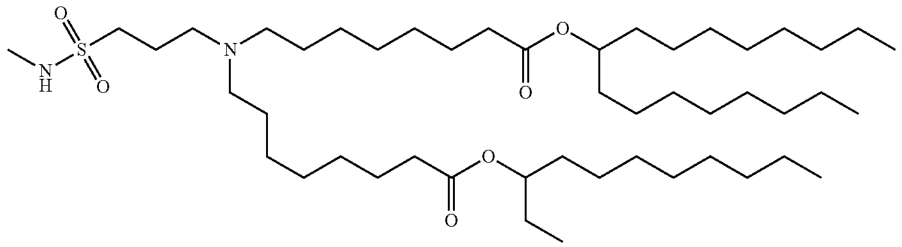

Chemical Formula: $C_{48}H_{96}N_2O_6S$
Molecular Weight: 829.36

A stirred solution of heptadecan-9-yl 8-{[3-(chlorosulfonyl)propyl][8-oxo-8-(undecan-3-yloxy)octyl]amino}octanoate (0.075 g, 0.090 mmol) in DCM (1.5 mL) was cooled to 0° C. in an ice bath. Then, methylamine (0.22 mL, 0.45 mmol, 2.0 M in THF) was added dropwise. The reaction mixture was allowed to come to room temperature and was monitored by LCMS. At 17 h, the reaction mixture was diluted with DCM and washed with satd. aq. $NaHCO_3$. The aqueous was extracted with DCM (2×). The combined organics were passed through a hydrophobic frit, dried over $Na_2SO_4$, and concentrated. The crude material was purified via automated silica gel flash chromatography (0-8% (5% conc. aq. $NH_4OH$ in MeOH) in DCM) to afford heptadecan-9-yl 8-{[3-(methylsulfamoyl)propyl][8-oxo-8-(undecan-3-yloxy)octyl]amino}octanoate (0.041 g, 0.047 mmol, 52%) as a clear yellow oil. UPLC/ELSD: RT=2.95 min. MS (ES): m/z ($MH^+$) 830.34 for $C_{48}H_{96}N_2O_6S$. $^1H$ NMR (300 MHz, $CDCl_3$) δ: ppm 4.75-4.92 (m, 3H); 3.03-3.13 (m, 2H); 2.79 (s, 3H); 2.45-2.59 (m, 2H); 2.33-2.45 (m, 4H); 2.23-2.33 (m, 4H); 1.87-2.01 (m, 2H); 1.45-1.69 (m, 14H); 1.16-1.45 (m, 50H); 0.81-0.95 (m, 12H).

CG. Compound 95. Heptadecan-9-yl 8-{[3-(ethylsulfamoyl)propyl][8-oxo-8-(undecan-3-yloxy)octyl]amino}octanoate

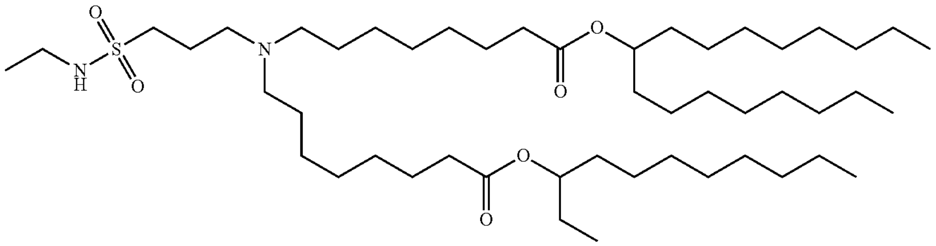

Chemical Formula: $C_{49}H_{98}N_2O_6S$
Molecular Weight: 843.39

A stirred solution of heptadecan-9-yl 8-{[3-(chlorosulfonyl)propyl][8-oxo-8-(undecan-3-yloxy)octyl]amino}octanoate (0.075 g, 0.090 mmol) in DCM (1.5 mL) was cooled to 0° C. in an ice bath. Then, ethylamine (0.22 mL, 0.45 mmol, 2.0 M in THF) was added dropwise. The reaction mixture was allowed to come to room temperature and was monitored by LCMS. At 17 h, the reaction mixture was diluted with DCM and washed with satd. aq. $NaHCO_3$. The aqueous was extracted with DCM (2×). The combined organics were passed through a hydrophobic frit, dried over $Na_2SO_4$, and concentrated. The crude material was purified via automated silica gel flash chromatography (0-8% (5% conc. aq. $NH_4OH$ in MeOH) in DCM) to afford heptadecan-9-yl 8-{[3-(ethylsulfamoyl)propyl][8-oxo-8-(undecan-3-yloxy)octyl]amino}octanoate (0.048 g, 0.056 mmol, 62%) as a clear, light yellow oil. UPLC/ELSD: RT=2.97 min. MS (ES): m/z ($MH^+$) 844.15 for $C_{49}H_{98}N_2O_6S$. $^1H$ NMR (300 MHz, $CDCl_3$) δ: ppm 4.75-4.92 (m, 2H); 4.55 (br s, 1H); 3.11-3.23 (m, 2H); 3.02-3.11 (m, 2H); 2.44-2.55 (m, 2H); 2.32-2.44 (m, 4H); 2.23-2.32 (m, 4H); 1.83-2.01 (m, 2H); 1.45-1.73 (m, 14H); 1.18-1.45 (m, 50H); 1.22 (t, 3H, J=7.5 Hz); 0.82-0.94 (m, 12H).

CH. Compound 96. Heptadecan-9-yl 8-{[3-(cyclopropylsulfamoyl)propyl][8-oxo-8-(undecan-3-yloxy)octyl]amino}octanoate

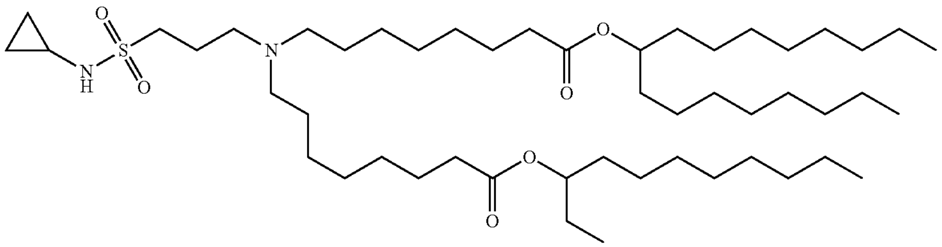

Chemical Formula: $C_{50}H_{98}N_2O_6S$
Molecular Weight: 855.40

A stirred solution of heptadecan-9-yl 8-{[3-(chlorosulfonyl)propyl][8-oxo-8-(undecan-3-yloxy)octyl]amino}octanoate (0.085 g, 0.10 mmol) in DCM (1.7 mL) was cooled to 0° C. in an ice bath. Then, cyclopropylamine (35 uL, 0.51 mmol) was added dropwise. The reaction mixture was allowed to come to room temperature and was monitored by LCMS. At 15 min, the reaction mixture was diluted with DCM and washed with satd. aq. $NaHCO_3$. The aqueous was extracted with DCM. The combined organics were passed through a hydrophobic frit, dried over $Na_2SO_4$, and concentrated. The crude material was purified via automated silica gel flash chromatography (0-8% (5% conc. aq. $NH_4OH$ in MeOH) in DCM) to afford heptadecan-9-yl 8-{[3-(cyclopropylsulfamoyl)propyl][8-oxo-8-(undecan-3-yloxy)octyl]amino}octanoate (0.039 g, 0.043 mmol, 43%) as a clear, light yellow oil. UPLC/ELSD: RT=2.98 min. MS (ES): m/z ($MH^+$) 856.24 for $C_{50}H98N_2O_6S$. $^1H$ NMR (300 MHz, $CDCl_3$) δ: ppm 5.16 (br s, 1H); 4.76-4.91 (m, 2H); 3.09-3.20 (m, 2H); 2.45-2.60 (m, 3H); 2.33-2.45 (m, 4H); 2.22-2.33 (m, 4H); 1.85-1.99 (m, 2H); 1.43-1.70 (m, 14H); 1.14-1.43 (m, 50H); 0.81-0.97 (m, 12H); 0.67-0.75 (m, 4H).

CI. Compound 97. Heptadecan-9-yl 8-{[3-(tert-butylsulfamoyl)propyl][8-oxo-8-(undecan-3-yloxy)octyl]amino}octanoate

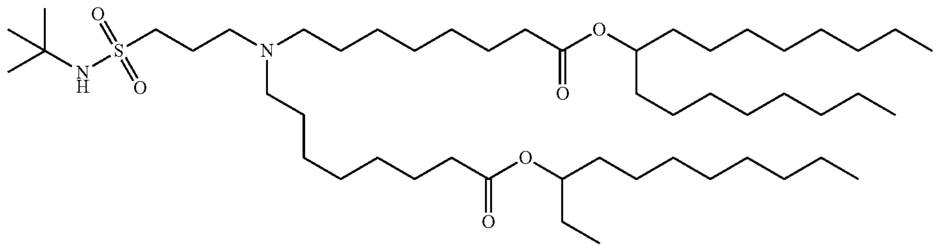

Chemical Formula: $C_{51}H_{102}N_2O_6S$
Molecular Weight: 871.45

A stirred solution of heptadecan-9-yl 8-{[3-(chlorosulfonyl)propyl][8-oxo-8-(undecan-3-yloxy)octyl]amino}octanoate (0.085 g, 0.10 mmol) in DCM (1.7 mL) was cooled to 0° C. in an ice bath. Then, tert-butylamine (54 uL, 0.51 mmol) was added dropwise. The reaction mixture was allowed to come to room temperature and was monitored by LCMS. At 15 min, the reaction mixture was diluted with DCM and washed with satd. aq. $NaHCO_3$. The aqueous was extracted with DCM. The combined organics were passed through a hydrophobic frit, dried over $Na_2SO_4$, and concentrated. The crude material was purified via automated silica gel flash chromatography (0-10% (5% conc. aq. $NH_4OH$ in MeOH) in DCM) to afford heptadecan-9-yl 8-{[3-(tert-butylsulfamoyl)propyl][8-oxo-8-(undecan-3-yloxy)octyl]amino}octanoate (0.053 g, 0.058 mmol, 57%) as a clear, light yellow oil. UPLC/ELSD: RT=3.01 min. MS (ES): m/z ($MH^+$) 872.15 for $C_{52}H_{102}N_2O_6S$. $^1H$ NMR (300 MHz, $CDCl_3$) δ: ppm 4.76-4.91 (m, 2H); 4.15 (br s, 1H); 3.03-3.15 (m, 2H); 2.43-2.56 (m, 2H); 2.32-2.43 (m, 4H); 2.22-2.32 (m, 4H); 1.84-2.00 (m, 2H); 1.44-1.69 (m, 14H); 1.18-1.44 (50H); 1.37 (s, 9H); 0.82-0.94 (m, 12H).-

CJ. Compound 98. Heptadecan-9-yl 8-((3-(3H-imidazo[4,5-b]pyridin-3-yl)propyl)(8-oxo-8-(undecan-3-yloxy)octyl)amino)octanoate

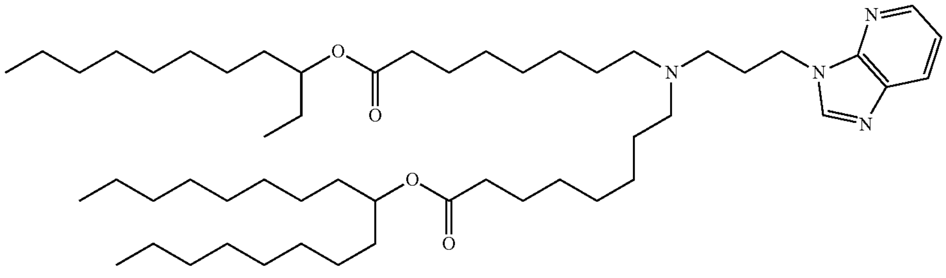

Chemical Formula: $C_{53}H_{96}N_4O_4$
Molecular Weight: 853.38

To a solution of heptadecan-9-yl 8-((3-((3-aminopyridin-2-yl)amino)propyl)(8-oxo-8-(undecan-3-yloxy)octyl) amino)octanoate (50 mg, 0.059 mmol) in 1 mL of trimethyl orthoformate was added a drop of TFA. The reaction mixture was stirred at 130° C. for 1.5 h. After cooling, the excess solvent was evaporated and dried. To this crude product in THF (1 mL) was added sodium triacetoxyborohydride (30 mg, 0.23 mmol) and a drop of AcOH and the resultant mixture stirred overnight at room temperature. The mixture was diluted with EtOAc (10 mL), washed with water, dried over anhydrous $Na_2SO_4$ and concentrated. The crude product was purified by silica gel chromatography with 0-10% methanol in dichloromethane to give heptadecan-9-yl 8-((3-(3H-imidazo[4,5-b]pyridin-3-yl)propyl)(8-oxo-8-(undecan-3-yloxy)octyl)amino)octanoate (21 mg, 42%) as brown oil. m/z ($MH^+$) 853.7 for $C_{53}H_{96}N_4O_4$. $^1H$ NMR (300 MHz, $CDCl_3$): δ 0.84-0.88 (m, 12H); 1.14-1.80 (m, 66H); 2.1-2.45 (m, 10H); 4.34-4.39 (m, 2H); 4.79-4.85 (m, 2H); 7.23-7.25 (m, 1H); 8.05-8.07 (m, 2H); 8.37-8.39 (m, 1H).

CK. Compound 99. Heptadecan-9-yl 8-((3-(2-((furan-2-ylmethyl)thio)acetamido)propyl)(8-oxo-8-(undecan-3-yloxy)octyl)amino)octanoate 2-((Furan-2-ylmethyl)thio)acetic Acid

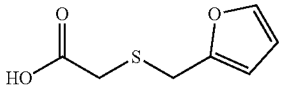

Chemical Formula: $C_7H_8O_3S$
Molecular Weight: 172.2

To a mixture of methyl 2-((furan-2-ylmethyl)thio)acetate (2.0 g, 10.7 mmol)) in methanol (12 mL) was added KOH (850 mg, 15.1 mmol) dissolved in 3 mL of water. The resultant mixture was stirred for 1 h at room temperature. After completion of the reaction, the pH of the mixture was adjusted to 5 with 2N HCl. The mixture was diluted with EtOAc:water (1:1, 100 mL) and the organic layer was separated. The organic layer was dried over anhydrous $Na_2SO_4$, filtered and evaporated. The crude product was purified by silica gel chromatography with 0-10% methanol in dichloromethane to give 2-((furan-2-ylmethyl)thio)acetic acid (770 mg, 42%). $^1H$ NMR (300 MHz, $CDCl_3$): δ 3.21 (s, 2H); 3.88 (s, 2H); 6.24-6.31 (m, 2H); 7.38 (s, 1H).

Heptadecan-9-yl 8-((3-(2-((furan-2-ylmethyl)thio) acetamido)propyl)(8-oxo-8-(undecan-3-yloxy)octyl) amino)octanoate

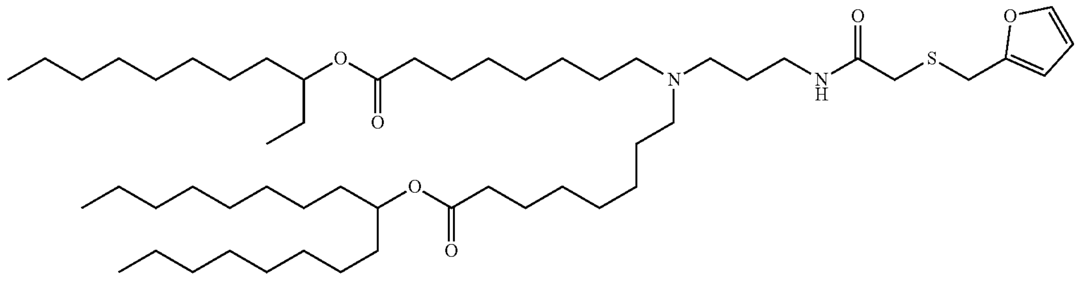

Chemical Formula: $C_{54}H_{100}N_2O_6S$
Molecular Weight: 905.5

A mixture of heptadecan-9-yl 8-((3-aminopropyl)(8-oxo-8-(undecan-3-yloxy)octyl)amino)octanoate (170 mg, 0.22 mmol), EDCI (65 mg, 0.33 mmol), HOBt (46 mg, 0.33 mmol), TEA (70 μL, 0.45 mmol) and 2-((furan-2-ylmethyl) thio)acetic acid (58 mg, 0.33 mmol) in acetonitrile (3 mL) was stirred overnight at room temperature. The mixture was diluted with EtOAc (20 mL), washed with water and brine. The organic layer was dried over anhydrous $Na_2SO_4$ and evaporated. The crude product was purified by silica gel chromatography with 0-10% methanol in dichloromethane to give heptadecan-9-yl 8-((3-(2-((furan-2-ylmethyl)thio)acetamido)propyl)(8-oxo-8-(undecan-3-yloxy)octyl)amino) octanoate (130 mg, 64%) as a light brown oil. m/z ($MH^+$) 905.7 for $C_{54}H_{100}N_2O_6S$. $^1$H NMR (300 MHz, $CDCl_3$): δ 0.83-0.89 (m, 12H); 1.15-1.79 (m, 66H); 2.2-2.56 (m, 10H); 3.16 (s, 2H); 3.28-3.22 (m, 2H); 3.75 (s, 2H), 4.80-4.87 (m, 2H); 6.2-6.29 (m, 2H); 7.35 (d, 1H, J=1.6 Hz); 7.65 (br s, 1H).

CL. Compound 100. Heptadecan-9-yl 8-((3-(2-((furan-2-ylmethyl)sulfinyl)acetamido)propyl)(8-oxo-8-(undecan-3-yloxy)octyl)amino)octanoate Methyl 2-((furan-2-ylmethyl)sulfinyl)acetate

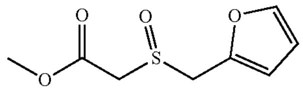

Chemical Formula: $C_8H_{10}O_4S$
Molecular Weight: 202.2

To a mixture of methyl 2-((furan-2-ylmethyl)thio)acetate (1.0 g, 4.95 mmol)) in methanol (9 mL) was added sodium metaperiodate (1.25 g, 5.8 mmol) in 10 ml water dropwise at 0° C. The resultant mixture was stirred at room temperature overnight. The mixture was extracted with $CH_2Cl_2$ (50 mL×2), washed with water, dried over anhydrous $Na_2SO_4$, filtered and evaporated. The crude product was purified by silica gel chromatography with 0-10% methanol in dichloromethane to give methyl 2-((furan-2-ylmethyl)sulfinyl)acetate (880 mg, 81%). $^1$H NMR (300 MHz, $CDCl_3$): δ 3.55-3.79 (m, 5H); 4.15-4.3 (m, 2H); 6.41-6.45 (m, 2H); 7.45 (s, 1H).

2-((Furan-2-ylmethyl)sulfinyl)acetic Acid

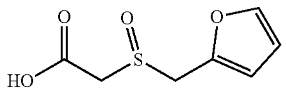

Chemical Formula: $C_7H_8O_4S$
Molecular Weight: 188.2

To a mixture of methyl 2-((furan-2-ylmethyl)sulfinyl) acetate (278 mg, 1.37 mmol)) in methanol (7 mL) was added KOH (115 mg, 2 mmol) dissolved in 0.4 mL of water. The resultant mixture was stirred for 1 h at room temperature. After completion of the reaction, the pH of the mixture was adjusted to 5 with 2N HCl. The mixture was diluted with EtOAc:water (1:1, 20 mL) and the organic layer separated. The organic layer was dried over anhydrous $Na_2SO_4$, filtered and evaporated. The crude product was purified by silica gel chromatography with 0-10% methanol in dichloromethane to give 2-((furan-2-ylmethyl)sulfinyl)acetic acid (86 mg, 33%). The structure was confirmed by MS and used in the next step.

Heptadecan-9-yl 8-((3-(2-((furan-2-ylmethyl)sulfinyl)acetamido)propyl)(8-oxo-8-(undecan-3-yloxy)octyl)amino)octanoate

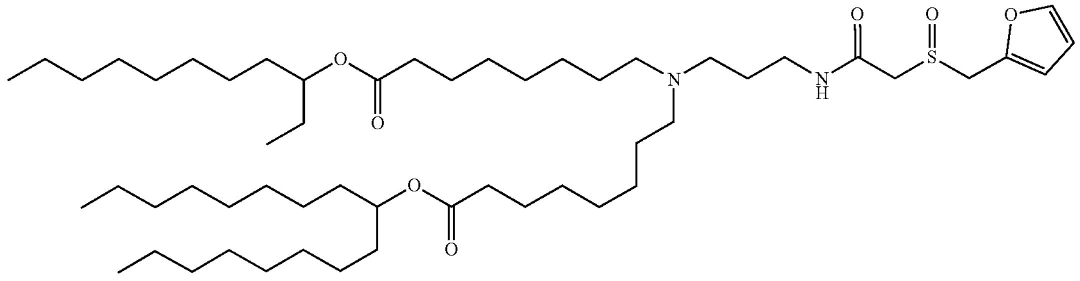

Chemical Formula: $C_{54}H_{100}N_2O_7S$
Molecular Weight: 921.5

A mixture of heptadecan-9-yl 8-((3-aminopropyl)(8-oxo-8-(undecan-3-yloxy)octyl)amino)octanoate (188 mg, 0.3 mmol), EDCI (87 mg, 0.45 mmol), HOBt (61 mg, 0.45 mmol), TEA (50 μL, 0.6 mmol) and 2-((furan-2-ylmethyl)sulfinyl)acetic acid (86 mg, 0.45 mmol) in acetonitrile (3 mL) was stirred overnight at room temperature. The mixture was diluted with EtOAc (20 mL), washed with water and brine. The organic layer was dried over anhydrous $Na_2SO_4$ and evaporated. The crude product was purified by silica gel chromatography with 0-10% methanol in dichloromethane to give heptadecan-9-yl 8-((3-((2-((furan-2-ylmethyl)sulfinyl)acetamido)propyl)(8-oxo-8-(undecan-3-yloxy)octyl)amino)octanoate (125 mg, 57%) as a light brown oil. m/z ($MH^+$) 921.6 for $C_{54}H_{100}N_2O_7S$. $^1H$ NMR (300 MHz, $CDCl_3$): δ 0.83-0.89 (m, 12H); 1.15-1.79 (m, 66H); 2.2-2.56 (m, 10H); 3.21-3.57 (m, 4H); 4.15-4.32 (m, 2H); 4.80-4.87 (m, 2H); 6.39-6.247 (m, 2H); 7.43 (d, 1H, J=1.6 Hz); 7.65 (br s, 1H).

CM. Compound 101. Heptadecan-9-yl 8-((3-(2-((furan-2-ylmethyl)sulfonyl)acetamido)propyl)(8-oxo-8-(undecan-3-yloxy)octyl)amino)octanoate Methyl 2-((furan-2-ylmethyl)sulfonyl)acetate

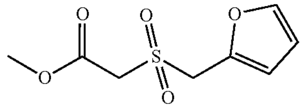

Chemical Formula: $C_8H_{10}O_5S$
Molecular Weight: 218.2

To a mixture of methyl 2-((furan-2-ylmethyl)sulfinyl)acetate (110 mg, 0.54 mmol)) in $CH_2Cl_2$ (2 mL) was added mCPBA (159 mg, 0.65 mmol, 77% approx) at 0° C. The resultant mixture was stirred for 1 h (monitored by TLC). After completion of the reaction, the mixture was diluted with $CH_2Cl_2$ (10 mL), washed with saturated $NaHCO_3$, dried over anhydrous $Na_2SO_4$, filtered and evaporated to give methyl 2-((furan-2-ylmethyl)sulfonyl)acetate (118 mg, quant). $^1H$ NMR (300 MHz, $CDCl_3$): δ 3.85 (s, 3H); 3.93 (s, 2H); 4.62 (s, 2H); 6.44 (s, 1H); 6.57 (s, 1H); 7.49 (s, 1H).

2-((Furan-2-ylmethyl)sulfonyl)acetic Acid

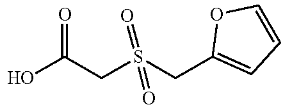

Chemical Formula: $C_7H_8O_5S$
Molecular Weight: 204.2

To a mixture of methyl 2-((furan-2-ylmethyl)sulfonyl)acetate (118 mg, 0.54 mmol)) in methanol (3 mL) was added KOH (45 mg, 0.81 mmol) dissolved in 0.2 mL of water. The resultant mixture was stirred for 1 h at room temperature. After completion of the reaction, the pH of the mixture was adjusted to 5 with 2N HCl. The mixture was diluted with EtOAc:water (1:1, 10 mL) and the organic layer was separated. The organic layer dried over anhydrous $Na_2SO_4$, filtered and evaporated give 2-((furan-2-ylmethyl)sulfonyl)acetic acid (40 mg, 34%). $^1H$ NMR (300 MHz, $CDCl_3$): δ 3.99 (s, 2H); 4.63 (s, 2H); 6.44-6.59 (m, 2H); 7.5 (s, 1H).

Heptadecan-9-yl 8-((3-(2-((furan-2-ylmethyl)sulfonyl)acetamido)propyl)(8-oxo-8-(undecan-3-yloxy)octyl)amino)octanoate

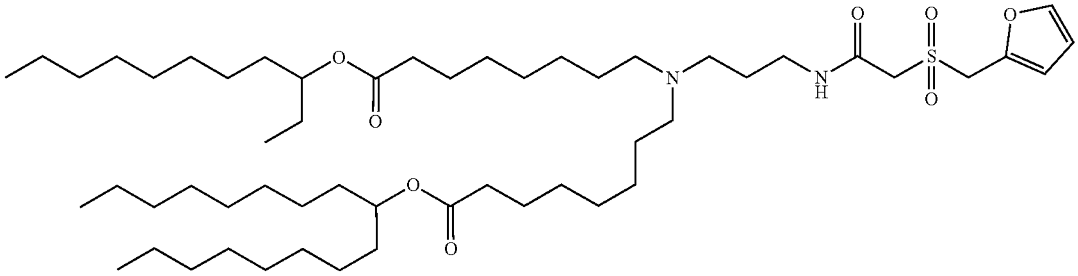

Chemical Formula: $C_{54}H_{100}N_2O_8S$
Molecular Weight: 937.5

A mixture of heptadecan-9-yl 8-((3-aminopropyl)(8-oxo-8-(undecan-3-yloxy)octyl)amino)octanoate (40 mg, 0.19 mmol), EDCI (47 mg, 0.23 mmol), HOBt (33 mg, 0.24 mmol), TEA (40 μL, 0.32 mmol) and 2-((furan-2-ylmethyl)sulfonyl)acetic acid (122 mg, 0.16 mmol) in acetonitrile (2 mL) was stirred overnight at room temperature. The mixture was diluted with EtOAc (10 mL), washed with water and brine. The organic layer was dried over anhydrous $Na_2SO_4$ and evaporated. The crude product was purified by silica gel chromatography with 0-10% methanol in dichloromethane to give heptadecan-9-yl 8-((3-(2-((furan-2-ylmethyl)sulfonyl)acetamido)propyl)(8-oxo-8-(undecan-3-yloxy)octyl)amino)octanoate (35 mg, 23%) as a light yellow oil. m/z ($MH^+$) 937.7 for $C_{54}H_{100}N_2O_8S$. $^1H$ NMR (300 MHz, $CDCl_3$): δ 0.83-0.89 (m, 12H); 1.15-1.79 (m, 66H); 2.2-2.56 (m, 10H); 3.39-3.43 (m, 2H); 3.72 (s, 2H); 4.63 (s, 2H); 4.80-4.87 (m, 2H); 6.41-6.42 (m, 1H); 6.61-6.62 (m, 1H); 7.48 (d, 1H, J=1.6 Hz); 8.35 (br s, 1H).

CN. Compound 102: Heptadecan-9-yl 8-((8-oxo-8-(undecan-3-yloxy)octyl)(3-(propylsulfonamido)propyl)amino)octanoate

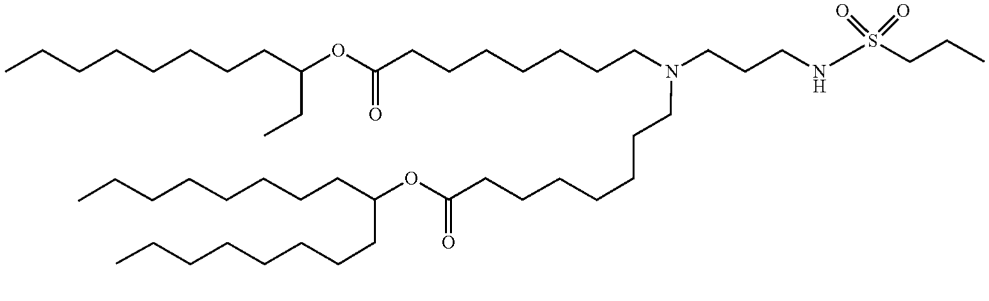

Chemical Formula: $C_{50}H_{100}N_2O_6S$
Molecular Weight: 857.42

To a solution of heptadecan-9-yl 8-((3-aminopropyl)(8-oxo-8-(undecan-3-yloxy)octyl) amino)octanoate (150 mg, 0.2 mmol) and triethylamine (33.39 μL, 0.24 mmol) in DCM (5 mL) at 0° C. was added propane-1-sulfonyl chloride (34.166 mg, 0.24 mmol) in DCM (1 mL). The reaction mixture stirred at 0° C. for 1 h and at room temperature for 4 h. The reaction mixture was diluted with additional DCM (10 mL) and washed with saturated sodium bicarbonate solution (15 mL) followed by brine solution (15 mL). The DCM layer was separated and dried over magnesium sulfate. The solution was concentrated and purified by silica gel chromatography (0-100% (mixture of 1% $NH_4OH$, 20% MeOH in DCM) in DCM) to give heptadecan-9-yl 8-((8-oxo-8-(undecan-3-yloxy)octyl)(3-(propylsulfonamido)propyl)amino)octanoate (141.4 mg, 83%) as an oil. UPLC/ELSD: RT=2.93 min. MS (CI): m/z ($MH^+$) 857.963 for $C_{50}H_{100}N_2O_6S$. $^1H$ NMR (300 MHz, $CDCl_3$): δ ppm 6.91 (br s, 1H); 4.98-4.73 (m, 2H); 3.20 (t, 2H, J=5.1 Hz); 3.01-2.87 (m, 2H); 2.62-2.50 (m, 2H); 2.45-2.33 (m, 4H); 2.28 (td, 4H, J=7.4, 3 Hz); 1.91-1.76 (m, 2H); 1.74-1.38 (m, 18H); 1.37-1.17 (m, 48H); 1.05 (t, 3H, J=7.5 Hz) 0.97-0.80 (m, 12H).

CO. Compound 103: Heptadecan-9-yl 8-((3-(butylsulfonamido)propyl)(8-oxo-8-(undecan-3-yloxy) octyl)amino)octanoate

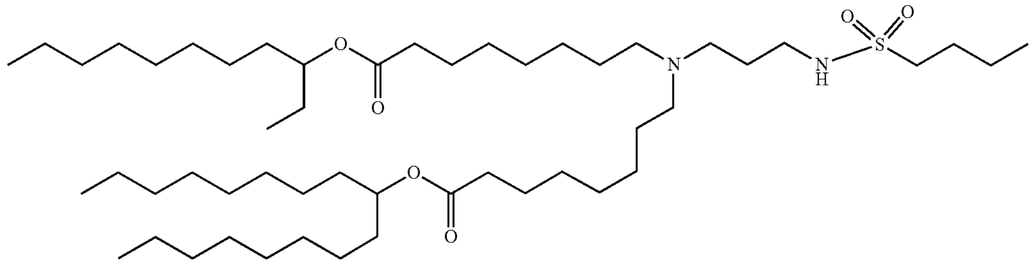

Chemical Formula: $C_{51}H_{102}N_2O_6S$
Molecular Weight: 871.45

To a solution of heptadecan-9-yl 8-((3-aminopropyl)(8-oxo-8-(undecan-3-yloxy)octyl) amino)octanoate (150 mg, 0.2 mmol) and triethylamine (33.39 μL, 0.24 mmol) in DCM (5 mL) at 0° C. was added 1-butanesulfonyl chloride (37.525 mg, 0.24 mmol) in DCM (1 mL). The reaction mixture stirred at 0° C. for 1 h and at room temperature for 4 h. The reaction mixture was diluted with additional DCM (10 mL) and washed with saturated sodium bicarbonate solution (15 mL) followed by brine solution (15 mL). The DCM layer was separated and dried over magnesium sulfate. The solution was concentrated and purified by silica gel chromatography (0-100% (mixture of 1% $NH_4OH$, 20% MeOH in DCM) in DCM) to give heptadecan-9-yl 8-((3-(butylsulfonamido)propyl)(8-oxo-8-(undecan-3-yloxy)octyl)amino)octanoate (158.3 mg, 91%) as an oil. UPLC/ELSD: RT=3.01 min. MS (CI): m/z ($MH^+$) 871.900 for $C_{51}H_{102}N_2O_6S$. $^1H$ NMR (300 MHz, $CDCl_3$): δ ppm 6.87 (br s, 1H); 5.03-4.69 (m, 2H); 3.23 (m, 2H); 3.04-2.91 (m, 2H); 2.72-2.21 (m, 10H); 1.88-1.70 (m, 4H); 1.70-1.39 (m, 18H); 1.38-1.16 (m, 48H); 0.95 (t, 3H, J=7.3 Hz) 0.91-0.83 (m, 12H).

CP. Compound 104: Heptadecan-9-yl 8-((3-(allylsulfonamido)propyl)(8-oxo-8-(undecan-3-yloxy)octyl)amino)octanoate

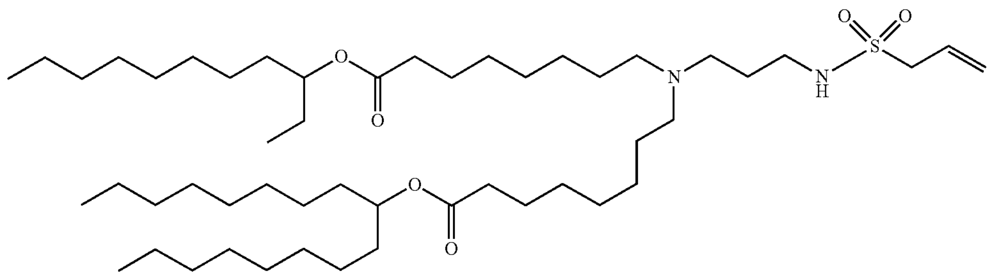

Chemical Formula: $C_{50}H_{98}N_2O_6S$
Molecular Weight: 855.40

To a solution of heptadecan-9-yl 8-((3-aminopropyl)(8-oxo-8-(undecan-3-yloxy)octyl) amino)octanoate (150 mg, 0.2 mmol) and triethylamine (33.39 μL, 0.24 mmol) in DCM (5 mL) at 0° C. was added prop-2-ene-1-sulfonyl chloride (33.682 mg, 0.24 mmol) in DCM (1 mL). The reaction mixture stirred at 0° C. for 1 h and at room temperature for 4 h. The reaction mixture was diluted with additional DCM (10 mL) and washed with saturated sodium bicarbonate solution (15 mL) followed by brine solution (15 mL). The DCM layer was separated and dried over magnesium sulfate. The solution was concentrated and purified by silica gel chromatography (0-100% (mixture of 1% $NH_4OH$, 20% MeOH in DCM) in DCM) to give heptadecan-9-yl 8-((3-(allylsulfonamido)propyl)(8-oxo-8-(undecan-3-yloxy)octyl) amino)octanoate (128.6 mg, 75%) as an oil. UPLC/ELSD: RT=2.98 min. MS (CI): m/z ($MH^+$) 855.989 for $C_{50}H98N_2O_6S$. $^1H$ NMR (300 MHz, $CDCl_3$): δ ppm 7.10 (br s, 1H); 6.30-5.83 (m, 1H); 5.50-5.31 (m, 2H); 4.96-4.72 (m, 2H); 3.77-3.65 (m, 2H); 3.23 (t, 2H, J=5.0 Hz); 2.65-2.47 (m, 2H); 2.46-2.32 (m, 4H); 2.31-2.23 (td, 4H, J=7.4, 3.0 Hz); 1.78-1.39 (m, 18H); 1.38-1.16 (m, 48H); 0.96-0.79 (m, 12H).

CQ. Compound 105: Heptadecan-9-yl 8-((3-((2-methoxyethyl)sulfonamido)propyl)(8-oxo-8-(undecan-3-yloxy)octyl)amino)octanoate

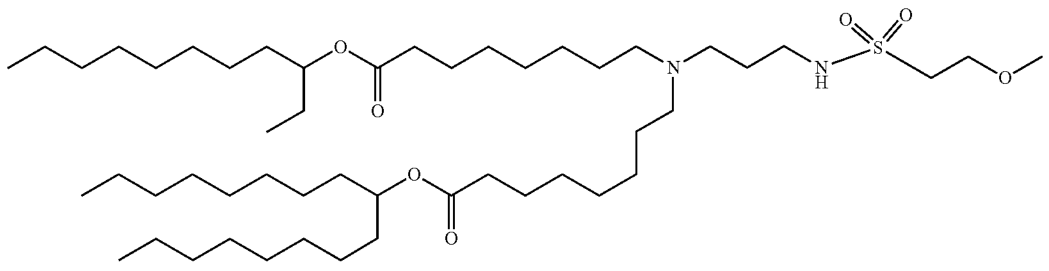

Chemical Formula: $C_{50}H_{100}N_2O_7S$
Molecular Weight: 873.42

To a solution of heptadecan-9-yl 8-((3-aminopropyl)(8-oxo-8-(undecan-3-yloxy)octyl) amino)octanoate (150 mg, 0.2 mmol) and triethylamine (33.39 μL, 0.24 mmol) in DCM (5 mL) at 0° C. was added 2-methoxyethanesulfonyl chloride (37.999 mg, 0.24 mmol) in DCM (1 mL). The reaction mixture stirred at 0° C. for 1 h and at room temperature for 4 h. The reaction mixture was diluted with additional DCM (10 mL) and washed with saturated sodium bicarbonate solution (15 mL) followed by brine solution (15 mL). The DCM layer was separated and dried over magnesium sulfate. The solution was concentrated and purified by silica gel chromatography (0-100% (mixture of 1% $NH_4OH$, 20% MeOH in DCM) in DCM) to give heptadecan-9-yl 8-((3-((2-methoxyethyl)sulfonamido)propyl)(8-oxo-8-(undecan-3-yloxy)octyl)amino)octanoate (138.3 mg, 79%) as an oil. UPLC/ELSD: RT=2.92 min. MS (CI): m/z ($MH^+$) 873.874 for $C_{50}H_{100}N_2O_7S$. $^1H$ NMR (300 MHz, $CDCl_3$): δ ppm 6.66 (br s, 1H); 4.93-4.73 (m, 2H); 3.78 (t, 2H, J=6.2 Hz); 3.37 (s, 3H); 3.28-3.13 (m, 4H); 2.59-2.48 (m, 2H); 2.44-2.33 (m, 4H); 2.28 (td, 4H, J=7.4, 3.0 Hz); 1.78-1.39 (m, 18H); 1.38-1.17 (m, 48H); 0.96-0.79 (m, 12H).

CR. Compound 106: Heptadecan-9-yl 8-((3-((cyclopropylmethyl)sulfonamido)propyl)(8-oxo-8-(undecan-3-yloxy)octyl)amino)octanoate

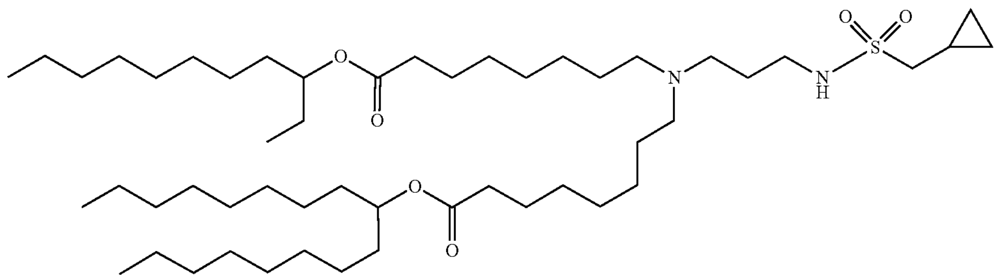

Chemical Formula: $C_{51}H_{100}N_2O_6S$
Molecular Weight: 869.43

To a solution of heptadecan-9-yl 8-((3-aminopropyl)(8-oxo-8-(undecan-3-yloxy)octyl) amino)octanoate (150 mg, 0.2 mmol) and triethylamine (33.39 μL, 0.24 mmol) in DCM (5 mL) at 0° C. was added cyclopropylmethanesulfonyl chloride (37.043 mg, 0.24 mmol) in DCM (1 mL). The reaction mixture stirred at 0° C. for 1 h and at room temperature for 4 h. The reaction mixture was diluted with additional DCM (10 mL) and washed with saturated sodium bicarbonate solution (15 mL) followed by brine solution (15 mL). The DCM layer was separated and dried over magnesium sulfate. The solution was concentrated and purified by silica gel chromatography (0-100% (mixture of 1% $NH_4OH$, 20% MeOH in DCM) in DCM) to give heptadecan-9-yl 8-((3-((cyclopropylmethyl)sulfonamido)propyl)(8-oxo-8-(undecan-3-yloxy)octyl)amino)octanoate (83 mg, 48%) as an oil. UPLC/ELSD: RT=3.00 min. MS (CI): m/z ($MH^+$) 870.174 for $C_{51}H_{100}N_2O_6S$. $^1H$ NMR (300 MHz, $CDCl_3$): δ ppm 6.83 (br s, 1H); 4.94-4.76 (m, 2H); 3.23 (t, 2H, J=5.3 Hz); 2.95-2.83 (m, 2H); 2.60-2.49 (t, 2H, J=5.6 Hz); 2.38 (t, 4H, J=6.8 Hz); 2.28 (td, 4H, J=7.4, 3.0 Hz); 1.76-1.39 (m, 19H); 1.38-1.19 (m, 48H); 0.96-0.81 (m, 12H); 0.73-0.63 (m, 2H); 0.42-0.33 (m, 2H).

CS. Compound 107: Heptadecan-9-yl 8-((3-(((3-methyloxetan-3-yl)methyl)sulfonamido)propyl)(8-oxo-8-(undecan-3-yloxy)octyl)amino)octanoate

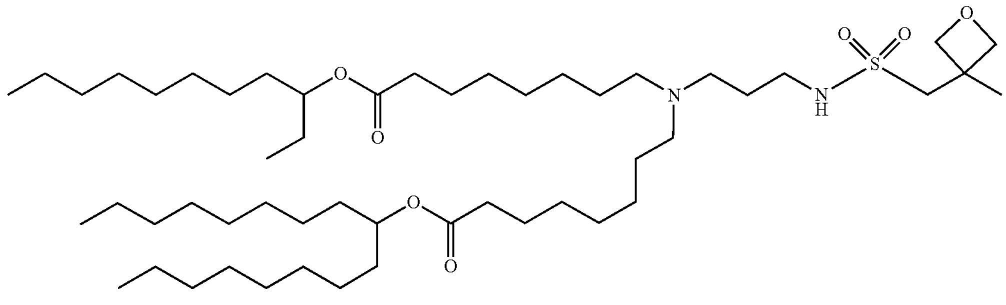

Chemical Formula: $C_{52}H_{102}N_2O_7S$
Molecular Weight: 899.46

To a solution of heptadecan-9-yl 8-((3-aminopropyl)(8-oxo-8-(undecan-3-yloxy)octyl) amino)octanoate (150 mg, 0.2 mmol) and triethylamine (33.39 µL, 0.24 mmol) in DCM (5 mL) at 0° C. was added (3-methyloxetan-3-yl)methanesulfonyl chloride (44.236 mg, 0.24 mmol) in DCM (1 mL). The reaction mixture stirred at 0° C. for 1 h and at room temperature for 4 h. The reaction mixture was diluted with additional DCM (10 mL) and washed with saturated sodium bicarbonate solution (15 mL) followed by brine solution (15 mL). The DCM layer was separated and dried over magnesium sulfate. The solution was concentrated and purified by silica gel chromatography (0-100% (mixture of 1% $NH_4OH$, 20% MeOH in DCM) in DCM) to give heptadecan-9-yl 8-((3-(((3-methyloxetan-3-yl)methyl)sulfonamido)propyl)(8-oxo-8-(undecan-3-yloxy)octyl)amino)octanoate (120.4 mg, 67%) as an oil. UPLC/ELSD: RT=2.99 min. MS (CI): m/z ($MH^+$) 899.652 for $C_{52}H_{102}N_2O_7S$. $^1H$ NMR (300 MHz, $CDCl_3$): δ ppm 7.35 (br s, 1H); 4.93-4.75 (m, 2H); 4.66 (d, 2H, J=6.2 Hz); 4.41 (d, 2H, J=6.2 Hz); 3.33 (s, 2H); 2.59-2.48 (m, 2H); 2.44-2.33 (m, 4H); 2.28 (td, 4H, J=7.4, 3.0 Hz); 1.77-1.39 (m, 20H); 1.38-1.16 (m, 51H); 0.96-0.79 (m, 12H).

CT. Compound 108: Heptadecan-9-yl 8-((3-((1-methylcyclopropane)-1-sulfonamido)propyl)(8-oxo-8-(undecan-3-yloxy)octyl)amino)octanoate

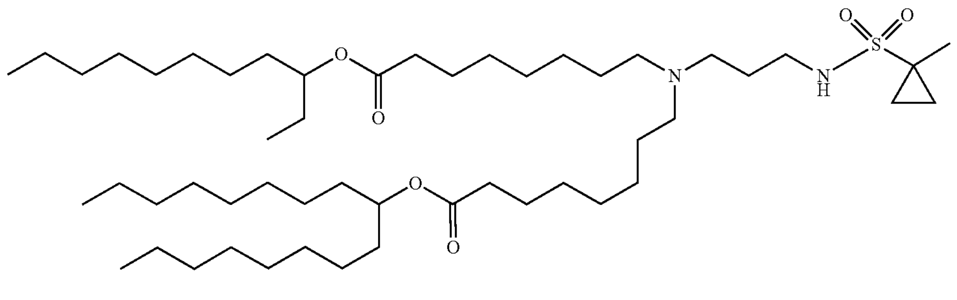

Chemical Formula: $C_{51}H_{100}N_2O_6S$
Molecular Weight: 869.43

To a solution of heptadecan-9-yl 8-((3-aminopropyl)(8-oxo-8-(undecan-3-yloxy)octyl) amino)octanoate (150 mg, 0.2 mmol) and triethylamine (33.39 μL, 0.24 mmol) in DCM (5 mL) at 0° C. was added 1-methylcyclopropane-1-sulfonyl chloride (37.043 mg, 0.24 mmol) in DCM (1 mL). The reaction mixture stirred at 0° C. for 1 h and at room temperature for 4 h. The reaction mixture was diluted with additional DCM (10 mL) and washed with saturated sodium bicarbonate solution (15 mL) followed by brine solution (15 mL). The DCM layer was separated and dried over magnesium sulfate. The solution was concentrated and purified by silica gel chromatography (0-100% (mixture of 1% $NH_4OH$, 20% MeOH in DCM) in DCM) to give heptadecan-9-yl 8-((3-((1-methylcyclopropane)-1-sulfonamido)propyl)(8-oxo-8-(undecan-3-yloxy)octyl)amino)octanoate (108.9 mg, 63%) as an oil. UPLC/ELSD: RT=3.00 min. MS (CI): m/z ($MH^+$) 869.927 for $C_{51}H_{100}N_2O_6S$. $^1H$ NMR (300 MHz, $CDCl_3$): δ ppm 6.79 (br s, 1H); 5.00-4.69 (m, 2H); 3.23 (t, 2H, J=5.6 Hz); 2.55 (t, 2H, J=5.6 Hz); 2.38 (t, 4H, J=7.7 Hz); 2.28 (td, 4H, J=7.4, 3.0 Hz); 1.78-1.39 (m, 21H); 1.38-1.17 (m, 50H); 0.96-0.79 (m, 12H); 0.77-0.68 (m, 2H).

CU. Compound 109: Heptadecan-9-yl 8-((3-(cyclobutanesulfonamido)propyl)(8-oxo-8-(undecan-3-yloxy)octyl)amino)octanoate

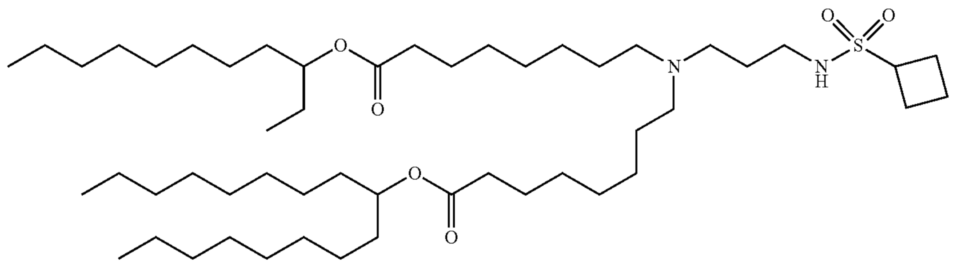

Chemical Formula: $C_{51}H_{100}N_2O_6S$
Molecular Weight: 869.43

To a solution of heptadecan-9-yl 8-((3-aminopropyl)(8-oxo-8-(undecan-3-yloxy)octyl) amino)octanoate (150 mg, 0.2 mmol) and triethylamine (33.39 μL, 0.24 mmol) in DCM (5 mL) at 0° C. was added cyclobutanesulfonyl chloride (37.043 mg, 0.24 mmol) in DCM (1 mL). The reaction mixture stirred at 0° C. for 1 h and at room temperature for 4 h. The reaction mixture was diluted with additional DCM (10 mL) and washed with saturated sodium bicarbonate solution (15 mL) followed by brine solution (15 mL). The DCM layer was separated and dried over magnesium sulfate. The solution was concentrated and purified by silica gel chromatography (0-100% (mixture of 1% $NH_4OH$, 20% MeOH in DCM) in DCM) to give heptadecan-9-yl 8-((3-(cyclobutanesulfonamido)propyl)(8-oxo-8-(undecan-3-yloxy)octyl)amino)octanoate (32.9 mg, 19%) as an oil. UPLC/ELSD: RT=2.93 min. MS (CI): m/z ($MH^+$) 869.927 for $C_{51}H_{100}N_2O_6S$. $^1H$ NMR (300 MHz, $CDCl_3$): δ ppm 6.72 (br s, 1H); 4.94-4.72 (m, 2H); 3.91-3.65 (m, 1H); 3.52-2.71 (m, 2H); 2.67-2.20 (m, 12H); 2.09-1.02 (m, 2H); 1.78-1.41 (m, 18H); 1.40-1.18 (m, 50H); 0.96-0.79 (m, 12H).

CV. Compound 110: Heptadecan-9-yl 8-((3-(oxetane-3-sulfonamido)propyl)(8-oxo-8-(undecan-3-yloxy)octyl)amino)octanoate

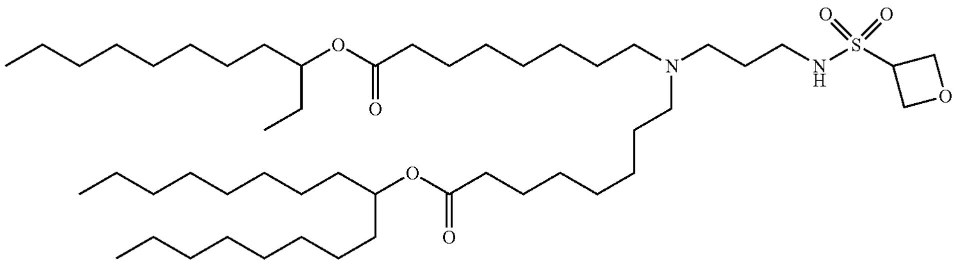

Chemical Formula: $C_{50}H_{98}N_2O_7S$
Molecular Weight: 871.40

To a solution of heptadecan-9-yl 8-((3-aminopropyl)(8-oxo-8-(undecan-3-yloxy)octyl) amino)octanoate (150 mg, 0.2 mmol) and triethylamine (33.39 μL, 0.24 mmol) in DCM (5 mL) at 0° C. was added oxetane-3-sulfonyl chloride (37.515 mg, 0.24 mmol) in DCM (1 mL). The reaction mixture stirred at 0° C. for 1 h and at room temperature for 4 h. The reaction mixture was diluted with additional DCM (10 mL) and washed with saturated sodium bicarbonate solution (15 mL) followed by brine solution (15 mL). The DCM layer was separated and dried over magnesium sulfate. The solution was concentrated and purified by silica gel chromatography (0-100% (mixture of 1% $NH_4OH$, 20% MeOH in DCM) in DCM) to give heptadecan-9-yl 8-((3-(oxetane-3-sulfonamido)propyl)(8-oxo-8-(undecan-3-yloxy)octyl)amino)octanoate (126 mg, 72%) as an oil. UPLC/ELSD: RT=2.98 min. MS (CI): m/z ($MH^+$) 872.640 for $C_{50}H_{98}H_2O_7S$. $^1H$ NMR (300 MHz, $CDCl_3$): δ ppm 7.76 (br s, 1H); 4.96-4.77 (m, 6H); 4.38 (q, 1H, J=1H, 7.1 Hz); 3.29 (t, 2H, J=5.3 Hz); 2.65-2.51 (m, 2H); 2.47-2.34 (m, 4H); 2.28 (td, 4H, J=7.4, 3.0 Hz); 1.78-1.39 (m, 18H); 1.38-1.15 (m, 48H); 0.98-0.81 (m, 12H).

CW. Compound 111: Heptadecan-9-yl 8-((3-(cyclopentanesulfonamido)propyl)(8-oxo-8-(undecan-3-yloxy)octyl)amino)octanoate

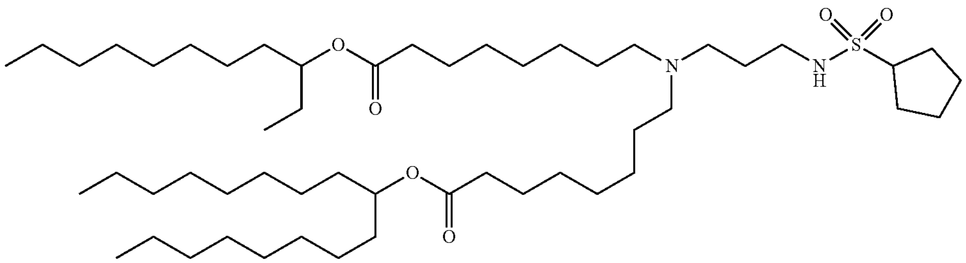

Chemical Formula: $C_{52}H_{102}N_2O_6S$
Molecular Weight: 883.46

To a solution of heptadecan-9-yl 8-((3-aminopropyl)(8-oxo-8-(undecan-3-yloxy)octyl) amino)octanoate (150 mg, 0.2 mmol) and triethylamine (33.39 μL, 0.24 mmol) in DCM (5 mL) at 0° C. was added cyclopentanesulfonyl chloride (40.405 mg, 0.24 mmol) in DCM (1 mL). The reaction mixture stirred at 0° C. for 1 h and at room temperature for 4 h. The reaction mixture was diluted with additional DCM (10 mL) and washed with saturated sodium bicarbonate solution (15 mL) followed by brine solution (15 mL). The DCM layer was separated and dried over magnesium sulfate. The solution was concentrated and purified by silica gel chromatography (0-100% (mixture of 1% $NH_4OH$, 20% MeOH in DCM) in DCM) to give heptadecan-9-yl 8-((3-(cyclopentanesulfonamido)propyl)(8-oxo-8-(undecan-3-yloxy)octyl)amino)octanoate (23.6 mg, 13%) as an oil. UPLC/ELSD: RT=2.93 min. MS (CI): m/z ($MH^+$) 883.618 for $C_{52}H_{102}N_2O_6S$. $^1H$ NMR (300 MHz, $CDCl_3$): δ ppm 6.72 (br s, 1H); 4.94-4.75 (m, 2H); 3.51-3.36 (m, 1H); 3.32-3.17 (m, 2H); 2.61-2.47 (m, 2H); 2.46-2.33 (m, 4H); 2.28 (td, 4H, J=7.4, 3.0 Hz); 2.06-1.94 (m, 4H); 1.89-1.75 (m, 2H); 1.74-1.40 (m, 20H); 1.39-1.17 (m, 48H); 0.96-0.80 (m, 12H).

CX. Compound 112: Heptadecan-9-yl 8-((8-oxo-8-(undecan-3-yloxy)octyl)(3-((tetrahydrofuran)-3-sulfonamido)propyl)amino)octanoate

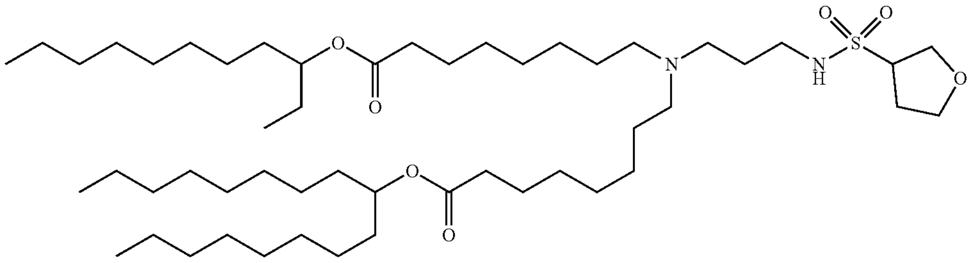

Chemical Formula: $C_{51}H_{100}N_2O_7S$
Molecular Weight: 885.43

To a solution of heptadecan-9-yl 8-((3-aminopropyl)(8-oxo-8-(undecan-3-yloxy)octyl) amino)octanoate (150 mg, 0.2 mmol) and triethylamine (33.39 μL, 0.24 mmol) in DCM (5 mL) at 0° C. was added oxolane-3-sulfonyl chloride (40.877 mg, 0.24 mmol) in DCM (1 mL). The reaction mixture stirred at 0° C. for 1 h and at room temperature for 4 h. The reaction mixture was diluted with additional DCM (10 mL) and washed with saturated sodium bicarbonate solution (15 mL) followed by brine solution (15 mL). The DCM layer was separated and dried over magnesium sulfate. The solution was concentrated and purified by silica gel chromatography (0-100% (mixture of 1% $NH_4OH$, 20% MeOH in DCM) in DCM) to give heptadecan-9-yl 8-((8-oxo-8-(undecan-3-yloxy)octyl)(3-((tetrahydrofuran)-3-sulfonamido)propyl)amino)octanoate (122.7 mg, 69%) as an oil. UPLC/ELSD: RT=2.94 min. MS (CI): m/z ($MH^+$) 885.961 for $C_{51}H_{100}N_2O_7S$. $^1H$ NMR (300 MHz, $CDCl_3$): δ ppm 7.40 (br s, 1H); 4.95-4.74 (m, 2H); 4.05 (d, 2H, J=7.0 Hz); 4.02-3.90 (m, 1H); 3.89-3.79 (m, 1H); 3.78-3.65 (m, 1H); 3.33-3.21 (m, 2H); 2.63-2.51 (m, 2H); 2.46-2.33 (m, 4H); 2.28 (td, 4H, J=7.4, 3.0 Hz); 1.75-1.39 (m, 18H); 1.38-1.16 (m, 50H); 0.94-0.81 (m, 12H).

CY. Compound 113: Heptadecan-9-yl 8-((3-((1,1-dioxidotetrahydrothiophene)-3-sulfonamido)propyl)(8-oxo-8-(undecan-3-yloxy)octyl)amino)octanoate

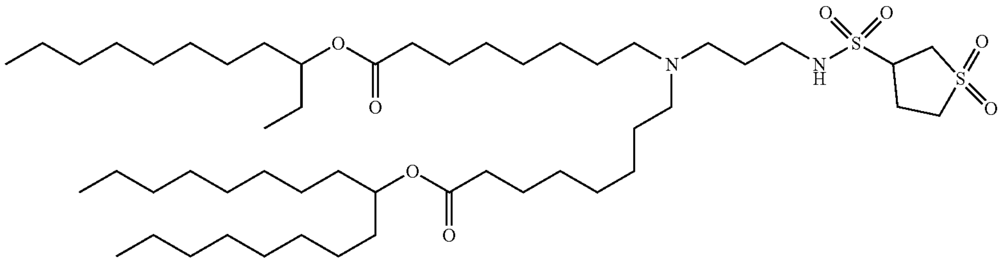

Chemical Formula: $C_{51}H_{100}N_2O_8S_2$
Molecular Weight: 933.49

To a solution of heptadecan-9-yl 8-((3-aminopropyl)(8-oxo-8-(undecan-3-yloxy)octyl) amino)octanoate (150 mg, 0.2 mmol) and triethylamine (33.39 μL, 0.24 mmol) in DCM (5 mL) at 0° C. was added 1,1-dioxo-1$\lambda^6$-thiolane-3-sulfonyl chloride (52.391 mg, 0.24 mmol) in DCM (1 mL). The reaction mixture stirred at 0° C. for 1 h and at room temperature for 4 h. The reaction mixture was diluted with additional DCM (10 mL) and washed with saturated sodium bicarbonate solution (15 mL) followed by brine solution (15 mL). The DCM layer was separated and dried over magnesium sulfate. The solution was concentrated and purified by silica gel chromatography (0-100% (mixture of 1% $NH_4OH$, 20% MeOH in DCM) in DCM) to give heptadecan-9-yl 8-((3-((1,1-dioxidotetrahydrothiophene)-3-sulfonamido)propyl)(8-oxo-8-(undecan-3-yloxy)octyl)amino)octanoate (115.3 mg, 62%) as an oil. UPLC/ELSD: RT=2.97 min. MS (CI): m/z ($MH^+$) 885.961 for $C_{51}H_{100}N_2O_8S$. $^1H$ NMR (300 MHz, $CDCl_3$): δ ppm 8.01 (br s, 1H); 4.95-4.72 (m, 2H); 3.91-3.71 (m, 1H); 3.49-3.21 (m, 5H); 3.20-3.02 (m, 1H); 2.71-2.49 (m, 4H); 2.48-2.35 (m, 4H); 2.28 (td, 4H, J=7.4, 3.0 Hz); 1.82-1.39 (m, 18H); 1.40-1.16 (m, 50H); 0.94-0.81 (m, 12H).

CZ. Compound 114: Heptadecan-9-yl 8-((8-oxo-8-(undecan-3-yloxy)octyl)(3-((tetrahydro-2H-pyran)-4-sulfonamido)propyl)amino)octanoate

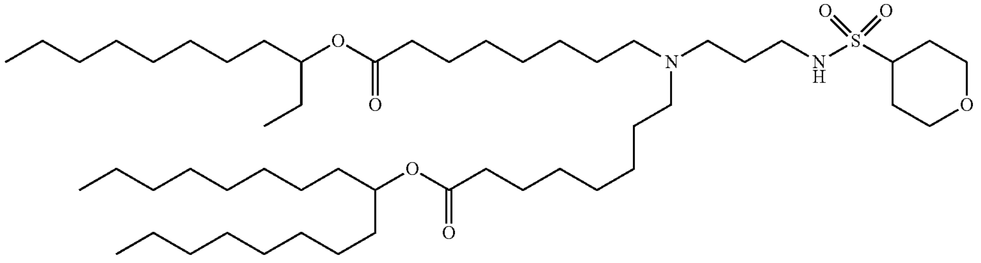

Chemical Formula: $C_{52}H_{102}N_2O_7S$
Molecular Weight: 899.46

To a solution of heptadecan-9-yl 8-((3-aminopropyl)(8-oxo-8-(undecan-3-yloxy)octyl) amino)octanoate (150 mg, 0.2 mmol) and triethylamine (33.39 μL, 0.24 mmol) in DCM (5 mL) at 0° C. was added oxane-4-sulfonyl chloride (44.236 mg, 0.24 mmol) in DCM (1 mL). The reaction mixture stirred at 0° C. for 1 h and at room temperature for 4 h. The reaction mixture was diluted with additional DCM (10 mL) and washed with saturated sodium bicarbonate solution (15 mL) followed by brine solution (15 mL). The DCM layer was separated and dried over magnesium sulfate. The solution was concentrated and purified by silica gel chromatography (0-100% (mixture of 1% $NH_4OH$, 20% MeOH in DCM) in DCM) to give heptadecan-9-yl 8-((8-oxo-8-(undecan-3-yloxy)octyl)(3-((tetrahydro-2H-pyran)-4-sulfonamido)propyl)amino)octanoate (72.5 mg, 40%) as an oil. UPLC/ELSD: RT=3.00 min. MS (CI): m/z ($MH^+$) 900.146 for $C_{52}H_{102}N_2O_7S$. $^1H$ NMR (300 MHz, $CDCl_3$): δ ppm 7.03 (br s, 1H); 4.99-4.72 (m, 2H); 4.15-4.03 (m, 2H); 3.45-3.31 (m, 2H); 3.30-2.83 (m, 4H); 2.63-2.50 (m, 1H); 2.46-2.34 (m, 2H); 2.28 (td, 4H, J=7.4, 3.0 Hz); 2.15-1.96 (m, 3H); 1.95-1.77 (m, 3H); 1.76-1.42 (m, 18H); 1.40-1.16 (m, 48H); 0.97-0.80 (m, 12H).

DA. Compound 115: Heptadecan-9-yl 8-((3-((((1S,4S)-7,7-dimethyl-2-oxobicyclo[2.2.1]heptan-1-yl)methyl)sulfonamido)propyl)(8-oxo-8-(undecan-3-yloxy)octyl)amino)octanoate

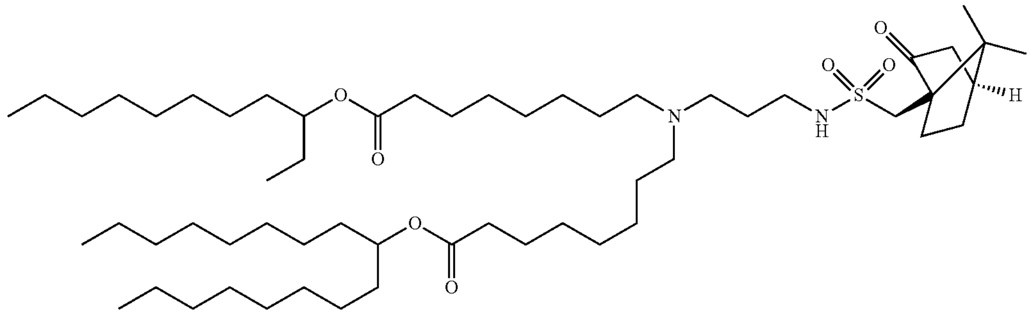

Chemical Formula: $C_{57}H_{108}N_2O_7S$
Molecular Weight: 965.56

To a solution of heptadecan-9-yl 8-((3-aminopropyl)(8-oxo-8-(undecan-3-yloxy)octyl) amino)octanoate (150 mg, 0.2 mmol) and triethylamine (33.39 μL, 0.24 mmol) in DCM (5 mL) at 0° C. was added [(45)-7,7-dimethyl-2-oxobicyclo[2.2.1]heptan-1-yl]methanesulfonyl chloride (60.075 mg, 0.24 mmol) in DCM (1 mL). The reaction mixture stirred at 0° C. for 1 h and at room temperature for 4 h. The reaction mixture was diluted with additional DCM (10 mL) and washed with saturated sodium bicarbonate solution (15 mL) followed by brine solution (15 mL). The DCM layer was separated and dried over magnesium sulfate. The solution was concentrated and purified by silica gel chromatography (0-100% (mixture of 1% $NH_4OH$, 20% MeOH in DCM) in DCM) to give heptadecan-9-yl 8-((3-((((1S,4S)-7,7-dimethyl-2-oxobicyclo[2.2.1]heptan-1-yl)methyl)sulfonamido)propyl)(8-oxo-8-(undecan-3-yloxy)octyl)amino)octanoate (60.9 mg, 32%) as an oil. UPLC/ELSD: RT=3.01 min. MS (CI): m/z ($MH^+$) 965.887 for $C_{57}H_{108}N_2O_7S$. $^1H$ NMR (300 MHz, $CDCl_3$): δ ppm 7.03 (br s, 1H); 4.99-4.72 (m, 2H); 4.15-4.03 (m, 2H); 3.45-3.31 (m, 2H); 3.30-2.83 (m, 4H); 2.63-2.50 (m, 1H); 2.46-2.34 (m, 2H); 2.28 (td, 4H, J=7.4, 3.0 Hz); 2.15-1.96 (m, 3H); 1.95-1.77 (m, 3H); 1.76-1.42 (m, 18H); 1.40-1.16 (m, 48H); 0.97-0.80 (m, 12H).

DB. Compound 116: Heptadecan-9-yl 8-((3-(((6-chloropyridin-3-yl)methyl)sulfonamido)propyl)(8-oxo-8-(undecan-3-yloxy)octyl)amino)octanoate

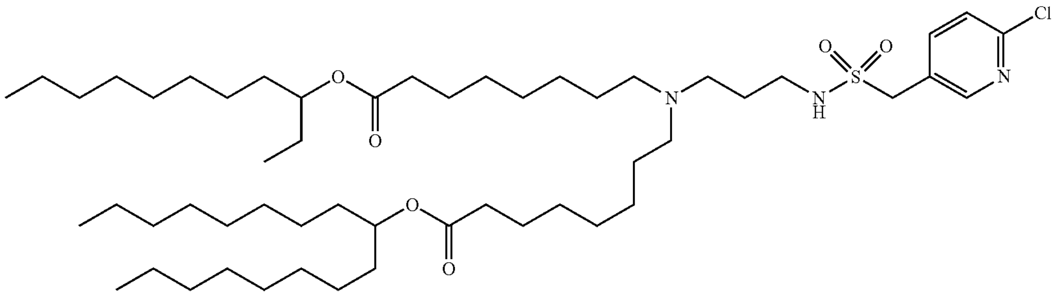

Chemical Formula: $C_{53}H_{98}ClN_3O_6S$
Molecular Weight: 940.89

To a solution of heptadecan-9-yl 8-((3-aminopropyl)(8-oxo-8-(undecan-3-yloxy)octyl) amino)octanoate (150 mg, 0.2 mmol) and triethylamine (33.39 μL, 0.24 mmol) in DCM (5 mL) at 0° C. was added (6-chloropyridin-3-yl)methanesulfonyl chloride (54.164 mg, 0.24 mmol) in DCM (1 mL). The reaction mixture stirred at 0° C. for 1 h and at room temperature for 4 h. The reaction mixture was diluted with additional DCM (10 mL) and washed with saturated sodium bicarbonate solution (15 mL) followed by brine solution (15 mL). The DCM layer was separated and dried over magnesium sulfate. The solution was concentrated and purified by silica gel chromatography (0-100% (mixture of 1% $NH_4OH$, 20% MeOH in DCM) in DCM) to give heptadecan-9-yl 8-((3-(((6-chloropyridin-3-yl)methyl)sulfonamido)propyl) (8-oxo-8-(undecan-3-yloxy)octyl)amino)octanoate (89.6 mg, 48%) as an oil. UPLC/ELSD: RT=3.03 min. MS (CI): m/z ($MH^+$) 940.725 for $C_{53}H_{98}ClN_3O_6S$. $^1H$ NMR (300 MHz, $CDCl_3$): δ ppm 8.36 (s, 1H); 7.78 (dd, 1H, J=8.2, 2.4 Hz); 7.69 (br s, 1H); 7.36 (d, 1H, J=8.2 Hz); 4.92-4.74 (m, 2H); 4.27-4.06 (m, 2H); 3.22-3.05 (m, 2H); 2.66-2.44 (s, 1H); 2.46-2.34 (m, 2H); 2.40-2.20 (m, 7H); 1.75-1.42 (m, 18H); 1.43-1.15 (m, 48H); 0.99-0.78 (m, 12H).

DC. Compound 117: Heptadecan-9-yl 8-((3-(((5-methylisoxazol-3-yl)methyl)sulfonamido)propyl)(8-oxo-8-(undecan-3-yloxy)octyl)amino)octanoate

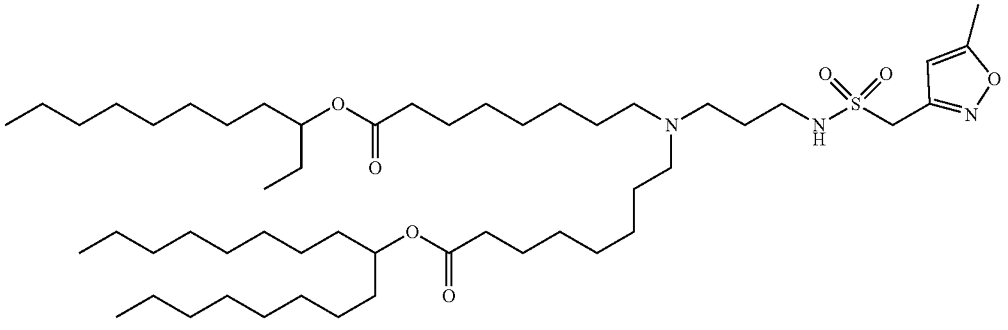

Chemical Formula: $C_{52}H_{99}N_3O_7S$
Molecular Weight: 910.44

To a solution of heptadecan-9-yl 8-((3-aminopropyl)(8-oxo-8-(undecan-3-yloxy)octyl) amino)octanoate (150 mg, 0.2 mmol) and triethylamine (33.39 μL, 0.24 mmol) in DCM (5 mL) at 0° C. was added (5-methyl-1,2-oxazol-3-yl) methanesulfonyl chloride (46.869 mg, 0.24 mmol) in DCM (1 mL). The reaction mixture stirred at 0° C. for 1 h and at room temperature for 4 h. The reaction mixture was diluted with additional DCM (10 mL) and washed with saturated sodium bicarbonate solution (15 mL) followed by brine solution (15 mL). The DCM layer was separated and dried over magnesium sulfate. The solution was concentrated and purified by silica gel chromatography (0-100% (mixture of 1% $NH_4OH$, 20% MeOH in DCM) in DCM) to give heptadecan-9-yl 8-((3-(((5-methylisoxazol-3-yl)methyl) sulfonamido)propyl)(8-oxo-8-(undecan-3-yloxy)octyl) amino)octanoate (86 mg, 47%) as an oil. UPLC/ELSD: RT=2.87 min. MS (CI): m/z ($MH^+$) 911.000 for $C_{52}H_{99}N_3O_7S$. $^1H$ NMR (300 MHz, $CDCl_3$): δ ppm 7.55 (br s, 1H); 4.95-4.72 (m, 2H); 4.47-4.19 (m, 2H); 3.38-2.82 (m, 4H); 2.61-2.22 (m, 11H); 2.08 (br s, 1H); 1.89-1.45 (m, 18H); 1.44-1.16 (m, 48H); 0.96-0.80 (m, 12H).

DD. Compound 118: Heptadecan-9-yl 8-((3-(((4-methylisoxazol-3-yl)methyl)sulfonamido)propyl)(8-oxo-8-(undecan-3-yloxy)octyl)amino)octanoate

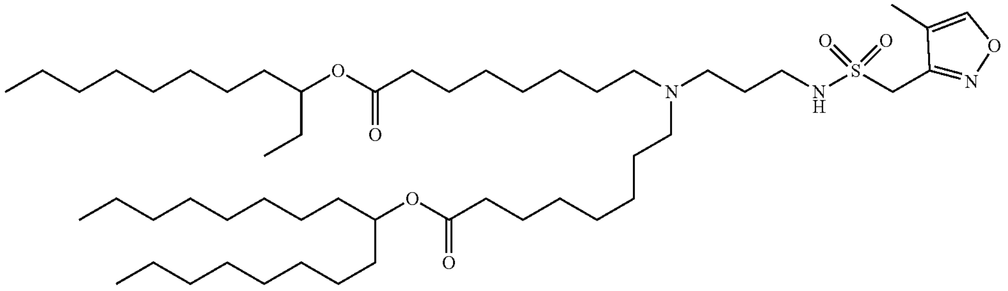

Chemical Formula: $C_{52}H_{99}N_3O_7S$
Molecular Weight: 910.44

To a solution of heptadecan-9-yl 8-((3-aminopropyl)(8-oxo-8-(undecan-3-yloxy)octyl) amino)octanoate (150 mg, 0.2 mmol) and triethylamine (33.39 μL, 0.24 mmol) in DCM (5 mL) at 0° C. was added (4-methyl-1,2-oxazol-3-yl) methanesulfonyl chloride (46.869 mg, 0.24 mmol) in DCM (1 mL). The reaction mixture stirred at 0° C. for 1 h and at room temperature for 4 h. The reaction mixture was diluted with additional DCM (10 mL) and washed with saturated sodium bicarbonate solution (15 mL) followed by brine solution (15 mL). The DCM layer was separated and dried over magnesium sulfate. The solution was concentrated and purified by silica gel chromatography (0-100% (mixture of 1% $NH_4OH$, 20% MeOH in DCM) in DCM) to give heptadecan-9-yl 8-((3-(((4-methylisoxazol-3-yl)methyl) sulfonamido)propyl)(8-oxo-8-(undecan-3-yloxy)octyl) amino)octanoate (86 mg, 47%) as an oil. UPLC/ELSD: RT=2.88 min. MS (CI): m/z ($MH^+$) 911.000 for $C_{52}H_{99}N_3O_7S$. $^1H$ NMR (300 MHz, $CDCl_3$): δ ppm 8.20 (s, 1H); 7.59 (br s, 1H); 4.92-4.73 (m, 2H); 4.44-4.24 (m, 2H); 3.37-2.84 (m, 4H); 2.62-2.49 (m, 1H); 2.45-2.21 (m, 7H); 2.20-2.08 (m, 3H); 1.88-1.44 (m, 18H); 1.43-1.15 (m, 48H); 0.96-0.81 (m, 12H).

DE. Compound 119: Heptadecan-9-yl 8-((3-(((5-(methoxymethyl)isoxazol-3-yl)methyl)sulfonamido)propyl)(8-oxo-8-(undecan-3-yloxy)octyl)amino)octanoate

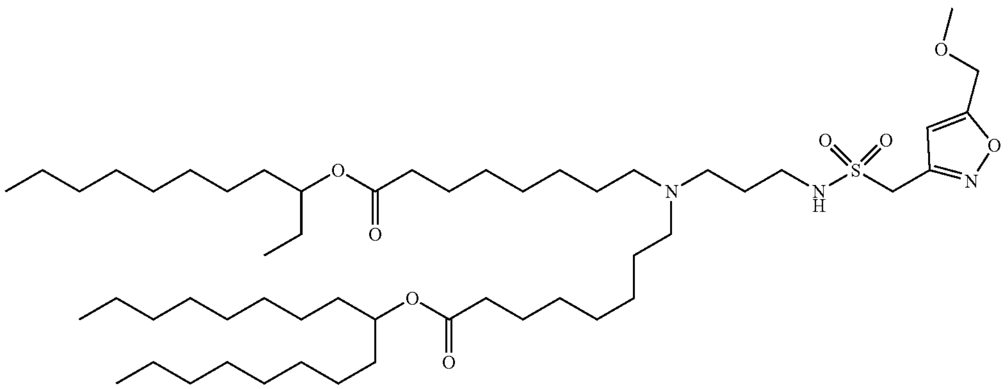

Chemical Formula: $C_{53}H_{101}N_3O_8S$
Molecular Weight: 940.46

To a solution of heptadecan-9-yl 8-((3-aminopropyl)(8-oxo-8-(undecan-3-yloxy)octyl) amino)octanoate (150 mg, 0.2 mmol) and triethylamine (33.39 μL, 0.24 mmol) in DCM (5 mL) at 0° C. was added [5-(methoxymethyl)-1,2-oxazol-3-yl]methanesulfonyl chloride (54.061 mg, 0.24 mmol) in DCM (1 mL). The reaction mixture stirred at 0° C. for 1 h and at room temperature for 4 h. The reaction mixture was diluted with additional DCM (10 mL) and washed with saturated sodium bicarbonate solution (15 mL) followed by brine solution (15 mL). The DCM layer was separated and dried over magnesium sulfate. The solution was concentrated and purified by silica gel chromatography (0-100% (mixture of 1% $NH_4OH$, 20% MeOH in DCM) in DCM) to give heptadecan-9-yl 8-((3-(((5-(methoxymethyl)isoxazol-3-yl)methyl)sulfonamido)propyl)(8-oxo-8-(undecan-3-yloxy)octyl)amino)octanoate (78.6 mg, 42%) as an oil. UPLC/ELSD: RT=2.92 min. MS (CI): m/z ($MH^+$) 940.972 for $C_{53}H_{101}N_3O_8S$. $^1H$ NMR (300 MHz, $CDCl_3$): δ ppm 7.61 (br s, 1H); 6.51 (s, 1H); 4.93-4.74 (m, 2H); 4.59-4.51 (m, 2H); 4.44-4.28 (m, 2H); 3.51-3.39 (m, 3H); 3.37-2.79 (m, 3H); 2.63-2.44 (m, 2H); 2.43-1.91 (m, 7H); 1.88-1.43 (m, 18H); 1.43-1.13 (m, 48H); 0.97-0.79 (m, 12H).

Example 2: Sample Formulations

Nanoparticle compositions including a therapeutic and/or prophylactic can be optimized according to the selection of a compound according to Formula (I), (I-1), (A), (A-1), (A-1a), or (A-1b), the selection of additional lipids, the amount of each lipid in the lipid component, and the wt:wt ratio of the lipid component to the therapeutic and/or prophylactic. Nanoparticle compositions including DSPC as a phospholipid, cholesterol as a structural lipid, PEG 2 as a PEG lipid, and a compound according to Formula (I), (I-1), (A), (A-1), (A-1a), or (A-1b) were prepared. The ratios of the lipids were 50:10:38:2 mol % for the lipid according to Formula (I), (I-1), (A), (A-1), (A-1a), or (A-1b):DSPC:cholesterol:PEG 2. Tables 2a, 2b, and 3-5 summarize the characteristics of the formulations.

As shown in Tables 2a and 2b, the choice of compound according to Formula (I), (I-1), (A), (A-1), (A-1a), or (A-1b) affects the size (e.g., diameter), polydispersity index ("PDI"), and encapsulation efficiency ("% EE") of the compositions. Table 3 shows the pKa of nanoparticles comprising compounds of the disclosure. Table 4 summarizes the surface hydrophobicity of nanoparticles comprising compounds of the disclosure as determined by Generalized Polarization by Laurdan (GPL). Laurdan, a fluorescent aminonaphthalene ketone lipid, was post-inserted into the nanoparticle surface and the fluorescence spectrum of Laurdan was collected to determine the normalized Generalized Polarization (N-GP). Higher N-GP indicates a less polar surface. Table 5 shows heparin-sepharose binding of nanoparticles comprising compounds of the disclosure.

TABLE 2a

Characteristics of nanoparticles comprising compounds of the disclosure

| Cmpd No. | Size (nm) | PDI | % EE (ribogreen) | % EE (ribostar) |
|---|---|---|---|---|
| 1 | 67.6 | 0.131 | 97.5 | 61.4 |
| 2 | 60.8 | 0.104 | 95.1 | |
| 17 | 80.8 | 0.178 | 98.4 | |
| 12 | 78.9 | 0.139 | 85.0 | |
| 6 | 68.4 | 0.088 | 97.9 | |
| 24 | 60.8 | 0.114 | 98.8 | |
| 11 | 79.4 | 0.219 | 99.6 | |
| 14 | 91.2 | 0.167 | 98.9 | |
| 34 | 108.2 | 0.211 | 75.4 | 41.6 |
| 21 | 62.5 | 0.141 | 99.4 | |
| 9 | 77.1 | 0.154 | 92.9 | 68.9 |
| 50 | 69.8 | 0.18 | 98.1 | |
| 29 | 63.5 | 0.199 | 98.9 | |
| 48 | 54.3 | 0.196 | −11.2 | |
| 52 | 53.7 | 0.22 | 98.2 | |
| 59 | 72.7 | 0.16 | 98.3 | |
| 72 | 76.7 | 0.090 | 91.2 | 78.6 |

TABLE 2b

| Characteristics of nanoparticles comprising compounds of the disclosure | | | | |
|---|---|---|---|---|
| Cmpd No. | Size (nm) | PDI | % EE (ribogreen) | % EE (ribostar) |
| 60 | 90.8 | 0.192 | 41.5 | 20.5 |
| 61 | 79.6 | 0.375 | 49.1 | |
| 45 | 81.8 | 0.141 | 98.5 | |
| 57 | 58.8 | 0.132 | 98.2 | |
| 62 | 124.3 | 0.233 | 28.3 | |
| 63 | 126.4 | 0.273 | 37.7 | |
| 64 | 105.3 | 0.121 | 93.7 | |
| 35 | 91.2 | 0.176 | 96 | |
| 58 | 86.9 | 0.142 | 98.6 | |
| 65 | 73.2 | 0.155 | 96.8 | |
| 66 | 70.1 | 0.125 | 91.8 | 59.1 |
| 67 | 71.7 | 0.123 | 84.1 | 48.5 |
| 68 | 63.2 | 0.109 | 96.6 | |
| 69 | 66.8 | 0.108 | 97 | |
| 70 | 72.6 | 0.123 | 89.9 | 60.7 |
| 71 | 64.7 | 0.109 | 90.8 | 50.7 |

*determined by 2-(p-toluidino)-6-napthalene sulfonic acid (TNS) assay.

TABLE 3

| pKa of nanoparticles comprising compounds of the disclosure | |
|---|---|
| Compound # | LogIC50 (pKa)* |
| 1 | 6.94 |
| 2 | 7.65 |
| 17 | 7.23 |
| 12 | 6.13 |
| 6 | 6.00 |
| 24 | 6.56 |
| 11 | 6.88 |
| 14 | 7.20 |
| 21 | 7.59 |
| 9 | −0.39 |
| 50 | 6.09 |
| 29 | 6.68 |
| 48 | 6.41 |
| 55/56 | 5.61 |
| 59 | 6.74 |
| 60 | 6.69 |
| 61 | 5.95 |
| 45 | 6.85 |
| 57 | 6.52 |
| 62 | 6.80 |
| 63 | 6.41 |
| 64 | 7.10 |
| 35 | 7.27 |
| 58 | 7.05 |
| 65 | 6.81 |
| 66 | 6.64 |
| 67 | 6.67 |
| 68 | 6.71 |
| 69 | 6.56 |
| 70 | 6.75 |
| 71 | 6.54 |
| 73 | 6.61 |
| 74 | 6.42 |
| 75 | 6.50 |
| 76 | 6.92 |
| 77 | 6.80 |
| 78 | 6.94 |
| 51/52 | 6.48 |
| 79 | 6.23 |
| 34 | 6.87 |
| 80 | 6.75 |
| 25 | 7.46 |

TABLE 3-continued

| pKa of nanoparticles comprising compounds of the disclosure | |
|---|---|
| Compound # | LogIC50 (pKa)* |
| 16 | 7.01 |
| 72 | 6.39 |
| 81 | 6.48 |
| 82 | 6.25 |
| 86 | 6.59 |

*determined by 2-(p-toluidino)-6-napthalene sulfonic acid (TNS) assay. "IC50" refers to the pH value at which half of the maximum fluorescence is reached. This value is reported as the apparent LNP pKa.

TABLE 4

| Surface-hydrophobicity of nanoparticles comprising compounds of the disclosure | |
|---|---|
| Compound # | Average N-GP |
| 59 | 0.762 |
| 60 | 1.055 |
| 61 | 0.900 |
| 45 | 0.655 |
| 57 | 0.582 |
| 62 | 0.890 |
| 63 | 0.866 |
| 64 | 0.382 |
| 35 | 0.888 |
| 58 | 0.493 |
| 65 | 0.713 |
| 66 | 0.837 |
| 67 | 0.890 |
| 68 | 0.822 |
| 69 | 0.812 |
| 70 | 0.902 |
| 71 | 0.874 |
| 73 | 0.747 |
| 74 | 0.938 |
| 75 | 0.831 |
| 76 | 0.683 |
| 77 | 0.824 |
| 78 | 0.622 |
| 51/52 | 0.921 |
| 79 | 0.683 |
| 34 | 1.001 |
| 80 | 0.703 |
| 25 | 0.869 |
| 16 | 0.595 |
| 72 | 0.988 |
| 81 | 0.752 |
| 82 | 0.920 |
| 86 | 0.737 |

*Generalized Polarization by Laurdan (GPL)

TABLE 5

| Heparin-sepharose binding of nanoparticles comprising compounds of the disclosure | |
|---|---|
| Compound # | Relative % Area Bound byLNP |
| 1 | 0 |
| 2 | 21.86 |
| 17 | 37.96 |
| 12 | 1.43 |
| 6 | 0 |
| 24 | 0 |
| 11 | 39.54 |
| 14 | 69.04 |
| 21 | 50.19 |
| 9 | 0 |

TABLE 5-continued

| Heparin-sepharose binding of nanoparticles comprising compounds of the disclosure | |
|---|---|
| Compound # | Relative % Area Bound byLNP |
| 50 | 0 |
| 29 | 6.45 |
| 48 | 0 |
| 55/56 | 0 |
| 59 | 0 |
| 60 | 5.65 |
| 61 | 1.73 |
| 45 | 31.46 |
| 57 | 1.09 |
| 62 | 3.99 |
| 63 | 6.25 |
| 64 | 74.32 |
| 35 | 2.90 |
| 58 | 47.35 |
| 65 | 4.86 |
| 66 | 3.54 |
| 67 | 6.69 |
| 68 | 1.12 |
| 69 | 0.93 |
| 70 | 0 |
| 71 | 0 |
| 73 | 0 |
| 74 | 6.14 |
| 75 | 1.97 |
| 76 | 31.61 |
| 77 | 0 |
| 78 | 36.14 |
| 51/52 | 2.25 |
| 79 | 0 |
| 34 | 2.90 |
| 80 | 10.99 |
| 25 | 0 |
| 16 | 57.65 |
| 72 | 0 |
| 81 | 0 |
| 82 | 1.67 |
| 86 | 0 |

Example 3: Expression of hEPO and ApoE Binding Induced by Sample Formulations The expression of hEPO mRNA in CD1-mice was measured 6 h after intravenous administration of nanoparticles comprising a compound of the disclosure, DSPC, cholesterol, and PEG 2 in a ratio of 50:10:38:2. The nanoparticles had a molar ratio of lipid nitrogen to RNA phosphate (N:P) of 3.4. Each composition was dosed to 8 animals at an mRNA dose of 0.5 mg/kg. The hEPO expression of nanoparticles of the disclosure is summarized in Table 6.

The ApoE binding affinity, i.e., the affinity of binding between nanoparticles comprising compounds of the disclosure and the serum protein ApoE, was determined by binding the nanoparticles to beads, then incubating them with known quantities of immunoglobulin (IgM). The quantity of protein bound to the nanoparticle was then determined by flow cytometry. The ApoE binding affinity of nanoparticles of the disclosure is summarized in Table 7.

TABLE 6

| RNA hEPO expression of nanoparticles comprising compounds of the disclosure | |
|---|---|
| Compound# | Avg. [hEPO] mIU/mL |
| 1 | 6.38E+05 |
| 2 | 6.57E+04 |
| 17 | 7.95E+04 |
| 12 | 2.29E+05 |
| 6 | 8.12E+04 |
| 24 | 2.05E+05 |
| 11 | 1.69E+04 |
| 14 | 6.20E+04 |
| 21 | 7.04E+04 |
| 9 | 5.32E+05 |
| 50 | 1.91E+05 |
| 29 | 8.93E+04 |
| 48 | 0 |
| 55/56 | 1.37E+05 |
| 59 | 2.49E+05 |
| 60 | 7.34E+05 |
| 61 | 1.52E+03 |
| 45 | 1.15E+05 |
| 57 | 4.21E+04 |
| 62 | 1.60E+05 |
| 63 | 1.90E+05 |
| 64 | 3.17E+04 |
| 35 | 3.71E+05 |
| 58 | 9.03E+04 |
| 65 | 3.64E+05 |
| 66 | 1.57E+06 |
| 67 | 1.43E+06 |
| 68 | 4.29E+05 |
| 69 | 2.61E+05 |
| 70 | 9.18E+05 |
| 71 | 1.50E+06 |
| 73 | 4.64E+05 |
| 74 | 1.21E+05 |
| 75 | 6.24E+05 |
| 76 | 1.50E+05 |
| 77 | 7.75E+04 |
| 78 | 1.11E+05 |
| 51/52 | 1.86E+05 |
| 79 | 4.04E+04 |
| 34 | 8.06E+05 |
| 80 | 7.69E+04 |
| 25 | 4.29E+05 |
| 16 | 1.72E+05 |
| 72 | 7.36E+05 |
| 81 | 4.96E+05 |
| 82 | 2.18E+05 |

TABLE 7

| ApoE binding affinity of nanoparticles comprising compounds of the disclosure | |
|---|---|
| Compound # | Median Fluorescence Intensity, PE |
| 1 | 182846 |
| 9 | 56008 |
| 60 | 41093 |
| 66 | 112648 |
| 67 | 146715 |
| 70 | 121247 |
| 71 | 147047 |
| 34 | 3133 |
| 72 | 78901 |

Example 4: mRNA Integrity Induced by Sample Formulations

Integrity of mRNA comprised in nanoparticles of the disclosure, i.e., the percentages of intact mRNA, mRNA adducts, and mRNA hydrolysis products, after 2 weeks of storage at 25° C. was determined by RP-IP (Reverse-Phase Ion-Pairing HPLC) using UV detection at 260 nm. Total purity and impurities are calculated as percent peak area.

TABLE 8a

| mRNA integrity at t = 0 | | | | | | | | |
|---|---|---|---|---|---|---|---|---|
| Compound | 60 | 66 | 67 | 70 | 71 | 34 | 72 | naked NPI Luc |
| Hydrolysis Product | 51.8% | 32.9% | 32.8% | 40.2% | 30.8% | 36.4% | 16.8% | 11.1% |
| Adduct | 6.0% | 13.1% | 10.1% | 10.3% | 8.7% | 3.8% | 5.6% | 2.4% |
| Intact | 42.2% | 54.0% | 57.1% | 49.5% | 60.6% | 59.8% | 77.7% | 86.5% |

TABLE 8a

| mRNA integrity after 2 weeks at 25° C. | | | | | | | | |
|---|---|---|---|---|---|---|---|---|
| Compound | 60 | 66 | 67 | 70 | 71 | 34 | 72 | naked NPI Luc |
| Hydrolysis Product | 77.2% | 32.9% | 39.0% | 50.1% | 35.9% | 51.4% | 23.5% | 38.5% |
| Adduct | 8.5% | 27.2% | 26.3% | 12.7% | 20.2% | 7.9% | 24.9% | 4.5% |
| Intact | 14.3% | 39.9% | 34.7% | 37.2% | 43.9% | 40.8% | 51.6% | 57.1% |

Embodiments

Embodiment 1. A compound of Formula (I):

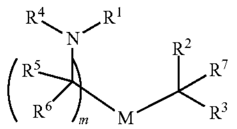

(I)

or its N-oxide, or a salt or isomer thereof, wherein:

$R^1$ is selected from the group consisting of $C_{5-30}$ alkyl, $C_{5-20}$ alkenyl, —R*YR*", —YR*", and —R"M'R';

$R^2$ and $R^3$ are each independently selected from the group consisting of H, $C_{1-14}$ alkyl, $C_{2-14}$ alkenyl, —R*YR*", —YR*", and —R*OR*", or $R^2$ and $R^3$, together with the atom to which they are attached, form a heterocycle or carbocycle;

$R^4$ is selected from the group consisting of $-(CH_2)_nQ$, $-(CH_2)_nCHQR$, $-(CH_2)OC(R^{12})_2(CH_2)_{n-o}Q$, —CHQR, $-CQ(R)_2$, and —C(O)NQR, where Q is selected from $NC(R){=}R^{11}$, $NC({=}NR^{15})R^{11}$, $NRC(C(O)NR^{14}R^{14'})_2$, $-NRC(O)(CH_2)_pC(O)NR^{14}R^{14'}$, and

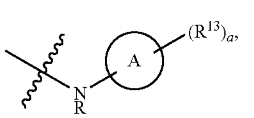

wherein A is $C_{6-10}$ aryl or a heterocycle; and each o is independently selected from 1, 2, 3, and 4; p is 0, 1, 2, 3, or 4; a is 1, 2, 3, or 4; and each n is independently selected from 1, 2, 3, 4, and 5;

each $R^5$ is independently selected from the group consisting of OH, $C_{1-3}$ alkyl, $C_{2-3}$ alkenyl, and H;

each $R^6$ is independently selected from the group consisting of OH, $C_{1-3}$ alkyl, $C_{2-3}$ alkenyl, and H;

M and M' are each independently selected from —OC(O)O—, —C(O)O—, —OC(O)—, —OC(O)-M"-C(O)O—, $-OC(O)-NR^M-C(O)O-$, —O-M"-O—, $-C(O)N(R^M)-$, $-N(R^M)C(O)-$, $-OC(O)N(R^M)-$, $-N(R^M)C(O)O-$, $-NR^MC(O)NR^M-$, $-O-N{=}C(R^M)-$, —C(O)—, —C(S)—, —C(S)S—, —SC(S)—, —CH(OH)—, $-P(O)(OR^M)O-$, $-S(O)_2-$, —S—S—, —SO—, —OS—, $S(R^M)_2O-$, $-O-S(R^M)_2-$, —S(O)O—, —OS(O)—, an aryl group, and a heteroaryl group, in which M" is a bond, $-(CH_2)_zC(O)-$, $C_{1-13}$ alkyl, $C_{2-13}$ alkenyl, —B(R)—, $-Si(R^{})_2-$, $-S(R^{**})_2-$, or —S(O)—, wherein z is 1, 2, 3, or 4;

$R^7$ is selected from the group consisting of $C_{1-3}$ alkyl, $C_{2-3}$ alkenyl, and H;

$R^{11}$ is selected from the group consisting of $C_{3-6}$ carbocycle and heterocycle, wherein the $C_{3-6}$ carbocycle and heterocycle are each optionally substituted with one or more $R^{13}$;

$R^{12}$ is selected from the group consisting of H, OH, $C_{1-3}$ alkyl, and $C_{2-3}$ alkenyl;

each $R^{13}$ is selected from the group consisting of OH, oxo, halo, $C_{1-6}$ alkyl, $C_{1-6}$ alkoxy, $C_{2-6}$ alkenyl, $C_{1-6}$ alkylamino, di-($C_{1-6}$ alkyl) amino, $NH_2$, $C(O)NH_2$, CN, and $NO_2$;

each $R^{14}$ is independently selected from the group consisting of H, OH, $C_{1-6}$ alkyl, and $C_{2-3}$ alkenyl;

each $R^{14'}$ is independently selected from the group consisting of H, OH, $C_{1-6}$ alkyl, and $C_{2-3}$ alkenyl;

$R^{15}$ is independently selected from the group consisting of H, OH, $C_{1-6}$ alkyl, and $C_{2-3}$ alkenyl;

each R is independently selected from the group consisting of H, OH, $C_{1-6}$ alkyl, and $C_{2-6}$ alkenyl;

each R' is independently selected from the group consisting of $C_{1-18}$ alkyl, $C_{2-18}$ alkenyl, —R*YR*", —YR*", $(CH_2)_qOR*$, and H;

each $R^M$ is independently selected from the group consisting of H, $C_{1-6}$ alkyl and $C_{2-6}$ alkenyl;

each R" is independently selected from the group consisting of $C_{3-15}$ alkyl and $C_{3-15}$ alkenyl;

each R*" is selected from the group consisting of $C_{1-15}$ alkyl and $C_{2-15}$ alkenyl;

each R* is independently selected from the group consisting of $C_{1-12}$ alkyl and $C_{2-12}$ alkenyl;

each R** is independently selected from the group consisting of H, OH, $C_{1-12}$ alkyl, $C_{2-12}$ alkenyl, $(CH_2)_qOR*$, and $(CH_2)_qOH$;

each Y is independently a $C_{3-6}$ carbocycle;

each q is independently selected from 1, 2, and 3; and m is selected from 5, 6, 7, 8, 9, 10, 11, 12, and 13.

Embodiment 2. A compound of Formula (IA):

(IA)

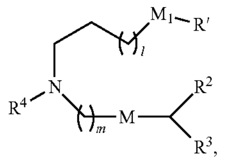

or its N-oxide, or a salt or isomer thereof, wherein l is selected from 1, 2, 3, 4, and 5;

m is selected from 5, 6, 7, 8, and 9;

$M_1$ is a bond or M'; and $R^2$ and $R^3$ are each independently selected from the group consisting of H, $C_{1-14}$ alkyl, and $C_{2-14}$ alkenyl;

$R^4$ is selected from the group consisting of $—(CH_2)_nQ$, $—(CH_2)_nCHQR$, $—(CH_2)_oC(R^{12})_2(CH_2)_{n-p}Q$, —CHQR, $—CQ(R)_2$, and —C(O)NQR, where Q is selected from $NC(R)═R^{11}$, $NC(═NR^{15})R^{11}$, $NRC(C(O)NR^{14}R^{14\prime})_2$, $—NRC(O)(CH_2)_pC(O)NR^{14}R^{14\prime}$, and

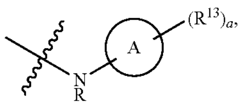

wherein A is $C_{6-10}$ aryl or a heterocycle; and each o is independently selected from 1, 2, 3, and 4; p is 0, 1, 2, 3, or 4; a is 1, 2, 3, or 4; and each n is independently selected from 1, 2, 3, 4, and 5;

M and M' are each independently selected from —OC(O)O—, —C(O)O—, —OC(O)—, —OC(O)-M"-C(O)O—, $—OC(O)—NR^M—C(O)O—$, —O-M"-O—, $—C(O)N(R^M)—$, $—N(R^M)C(O)—$, $—OC(O)N(R^M)—$, $—N(R^M)C(O)O—$, $—NR^MC(O)NR^M—$, $—O—N═C(R^M)—$, —C(O)—, —C(S)—, —C(S)S—, —SC(S)—, —CH(OH)—, $—P(O)(OR^M)O—$, $—S(O)_2—$, —S—S—, —SO—, —OS—, $S(R^M)_2O—$, $—O—S(R^M)_2—$, —S(O)O—, —OS(O)—, an aryl group, and a heteroaryl group, in which M" is a bond, $—(CH_2)_zC(O)—$, $C_{1-13}$ alkyl, $C_{2-13}$ alkenyl, —B(R)—, $—Si(R)_2—$, $—S(R**)_2—$, or —S(O)—, wherein z is 1, 2, 3, or 4;

$R^{11}$ is selected from the group consisting of $C_{3-6}$ carbocycle and heterocycle, wherein the $C_{3-6}$ carbocycle and heterocycle are each optionally substituted with one or more $R^{13}$;

$R^{12}$ is selected from the group consisting of H, OH, $C_{1-3}$ alkyl, and $C_{2-3}$ alkenyl;

each $R^{13}$ is selected from the group consisting of OH, oxo, halo, $C_{1-6}$ alkyl, $C_{1-6}$ alkoxy, $C_{2-6}$ alkenyl, $C_{1-6}$ alkylamino, di-($C_{1-6}$ alkyl) amino, $NH_2$, $C(O)NH_2$, CN, and $NO_2$;

each $R^{14}$ is independently selected from the group consisting of H, OH, $C_{1-6}$ alkyl, and $C_{2-3}$ alkenyl;

each $R^{14\prime}$ is independently selected from the group consisting of H, OH, $C_{1-6}$ alkyl, and $C_{2-3}$ alkenyl;

$R^{15}$ is independently selected from the group consisting of H, OH, $C_{1-6}$ alkyl, and $C_{2-3}$ alkenyl;

each R is independently selected from the group consisting of H, OH, $C_{1-6}$ alkyl, and $C_{2-6}$ alkenyl;

each R' is independently selected from the group consisting of $C_{1-18}$ alkyl, $C_{2-18}$ alkenyl, —R*YR*", —YR*", $(CH_2)_qOR*$, and H;

each $R^M$ is independently selected from the group consisting of H, $C_{1-6}$ alkyl and $C_{2-6}$ alkenyl;

each R" is independently selected from the group consisting of $C_{3-15}$ alkyl and $C_{3-15}$ alkenyl;

each R*" is selected from the group consisting of $C_{1-15}$ alkyl and $C_{2-15}$ alkenyl;

each R* is independently selected from the group consisting of $C_{1-12}$ alkyl and $C_{2-12}$ alkenyl;

each R** is independently selected from the group consisting of H, OH, $C_{1-12}$ alkyl, $C_{2-12}$ alkenyl, $(CH_2)_qOR*$, and $(CH_2)_qOH$;

each Y is independently a $C_{3-6}$ carbocycle; and each q is independently selected from 1, 2, and 3.

Embodiment 3. The compound of any one of the preceding embodiments, wherein $R^4$ is $—(CH_2)_nQ$.

Embodiment 4. The compound of any one of the preceding embodiments, wherein Q is

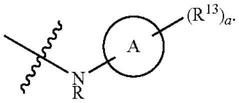

Embodiment 5. The compound of any one of the preceding embodiments, wherein M and M' are each —C(O)O—.

Embodiment 6. A compound of Formula (I-1):

(I-1)

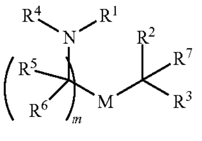

or its N-oxide, or a salt or isomer thereof, wherein:

$R^1$ is R"M'R' and R' is a branched $C_{1-18}$ alkyl;

$R^2$ and $R^3$ are each independently selected from the group consisting of H, $C_{1-14}$ alkyl, $C_{2-14}$ alkenyl, —R*YR*", —YR*", and —R*OR*", or $R^2$ and $R^3$, together with the atom to which they are attached, form a heterocycle or carbocycle;

$R^4$ is $—(CH_2)_nQ$, where Q is

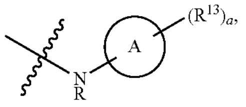

wherein A is $C_{6-10}$ aryl or a heterocycle; a is 1, 2, 3, or 4; and each n is independently selected from 1, 2, 3, 4, and 5;

each $R^5$ is independently selected from the group consisting of OH, $C_{1-3}$ alkyl, $C_{2-3}$ alkenyl, and H;

each $R^6$ is independently selected from the group consisting of OH, $C_{1-3}$ alkyl, $C_{2-3}$ alkenyl, and H;

M and M' are each independently selected from —OC(O)O—, —C(O)O—, —OC(O)—, —OC(O)-M"-C(O)O—, —OC(O)—$NR^M$—C(O)O—, —O-M"-O—, —C(O)N($R^M$)—, —N($R^M$)C(O)—, —OC(O)N($R^M$)—, —N($R^M$)C(O)O—, —$NR^M$C(O)$NR^M$—, —O—N═C($R^M$)—, —C(O)—, —C(S)—, —C(S)S—, —SC(S)—, —CH(OH)—, —P(O)($OR^M$)O—, —$S(O)_2$—, —S—S—, —SO—, —OS—, $S(R^M)_2O$—, —O—$S(R^M)_2$—, —S(O)O—, —OS(O)—, an aryl group, and a heteroaryl group, in which M" is a bond, —$(CH_2)_z$C(O)—, $C_{1-13}$ alkyl, $C_{2-13}$ alkenyl, —B(R)—, —Si$(R^{})_2$—, —S$(R^{**})_2$—, or —S(O)—, wherein z is 1, 2, 3, or 4;

$R^7$ is selected from the group consisting of $C_{1-3}$ alkyl, $C_{2-3}$ alkenyl, and H;

each $R^{13}$ is selected from the group consisting of OH, oxo, halo, $C_{1-6}$ alkyl, $C_{1-6}$ alkoxy, $C_{2-6}$ alkenyl, $C_{1-6}$ alkylamino, di-($C_{1-6}$ alkyl) amino, $NH_2$, $C(O)NH_2$, CN, and $NO_2$;

each $R^M$ is independently selected from the group consisting of H, $C_{1-6}$ alkyl and $C_{2-6}$ alkenyl;

each R" is independently selected from the group consisting of $C_{3-15}$ alkyl and $C_{3-15}$ alkenyl;

each R*" is selected from the group consisting of $C_{1-15}$ alkyl and $C_{2-15}$ alkenyl;

each R* is independently selected from the group consisting of $C_{1-12}$ alkyl and $C_{2-12}$ alkenyl;

each R** is independently selected from the group consisting of H, OH, $C_{1-12}$ alkyl, $C_{2-12}$ alkenyl, $(CH_2)_qOR^*$, and $(CH_2)_qOH$;

each Y is independently a $C_{3-6}$ carbocycle;

m is selected from 5, 6, 7, 8, 9, 10, 11, 12, and 13; and each q is independently selected from 1, 2, and 3.

Embodiment 7. The compound of any one of the preceding embodiments, wherein $R^2$ and $R^3$ are each $C_{1-14}$ alkyl.

Embodiment 8. The compound of any one of the preceding embodiments, wherein $R^1$ is

—R"M'R'.

Embodiment 9. The compound of any one of the preceding embodiments, wherein M' is

—C(O)O—.

Embodiment 10. The compound of any one of the preceding embodiments, wherein R" is $C_{3-15}$ alkyl.

Embodiment 11. The compound of any one of the preceding embodiments, wherein R" is $C_5$ alkyl.

Embodiment 12. The compound of any one of the preceding embodiments, wherein R' is $C_{1-18}$ alkyl.

Embodiment 13. The compound of any one of the preceding embodiments, wherein $R^5$, $R^5$, and $R^5$ are each H.

Embodiment 14. The compound of any one of the preceding embodiments, wherein m is 7.

Embodiment 15. The compound of any one of the preceding embodiments, wherein 1 is 5.

Embodiment 16. The compound of any one of the preceding embodiments wherein $R^1$ is R"M'R' and R' is a branched alkyl.

Embodiment 17. The compound of any one of the preceding embodiments, wherein $R^1$ is R"M'R' and R" is a branched alkyl.

Embodiment 18. The compound of any one of the preceding embodiments, wherein M and M' are each —C(O)O—.

Embodiment 19. The compound of any one of the preceding embodiments, wherein $R^4$ is $—(CH_2)_nQ$.

Embodiment 20. The compound of any one of the preceding embodiments, wherein Q is NC(R)═$R^{11}$.

Embodiment 21. The compound of any one of the preceding embodiments, wherein Q is NC(═$NR^{15}$)$R^{11}$.

Embodiment 22. The compound of any one of the preceding embodiments, wherein RH is a heterocycle.

Embodiment 23. The compound of any one of the preceding embodiments, wherein RH is further substituted with one or two $R^{13}$.

Embodiment 24. The compound of any one of the preceding embodiments, wherein $R^{13}$ is oxo, $NH_2$, or $C_{1-6}$ alkylamino.

Embodiment 25. The compound of any one of the preceding embodiments, wherein RH is selected from imidazole, imidazole-2,5-dione, 1,2,5-oxadiazole, N-methyl-1,2,5-oxadiazol-3-amine, and 1,2,5-oxadiazol-3-amine.

Embodiment 26. The compound of any one of the preceding embodiments, wherein Q is $NRC(C(O)NR^{14}R^{14'})_2$.

Embodiment 27. The compound of any one of the preceding embodiments, wherein Q is $—NRC(O)(CH_2)_pC(O)NR^{14}R^{14'}$.

Embodiment 28. The compound of any one of the preceding embodiments, wherein Q is

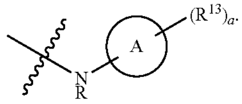

Embodiment 29. The compound of any one of the preceding embodiments, wherein A is phenyl.

Embodiment 30. The compound of any one of the preceding embodiments, wherein A is a heterocycle.

Embodiment 31. The compound of any one of the preceding embodiments, wherein A is selected from 1,2,5-thiadiazole, pyrrole, imidazole, imidazoline, 1,2-dihydropyridazine, 1,2,4 triazole, 1,2,5 oxadiazole, 1,2,4-oxadiazole, pyrimidine, pyrazine, pyridazine, pyridine, pyrazole, 2,5-dihydro-1H-pyrrole, and 2,3-dihydro-1H-pyrazole.

Embodiment 32. The compound of any one of the preceding embodiments, wherein A is selected from 7-H purine, 9-H purine, indole, and indazole.

Embodiment 33. The compound of any one of the preceding embodiments, wherein

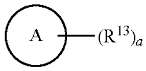

is selected from 1,2,5-thiadiazole 1-oxide, 1,2,5-thiadiazole 1,1-dioxide, 1H-pyrrole-2,5-dione, 1,2-dihydropyridazine-3,6-dione, imidazolidine-2,5-dione, imidazolidine-2,4-dione, imidazolidin-2-one, imidazole-2,5-dione, pyrimidine-2,4,6-trione, pyrimidin-2-one, pyrimidin-4-one, pyrimidine-2,4-dione, pyrimidine-2,4,6-trione, pyridin-2-one, 1,5-dihydro-2H-pyrrol-2-one, 1,2-dihydro-3H-pyrazol-3-one, pyridazine-3,6-dione, 1,9-dihydro-6H-purin-6-one, and imidazole-2,5-dione, each optionally substituted with one or more groups selected from $C_{1-6}$ alkyl, $C_{1-6}$ alkylamino, or halo.

Embodiment 34. A compound of Formula (A):
wherein:

(A)

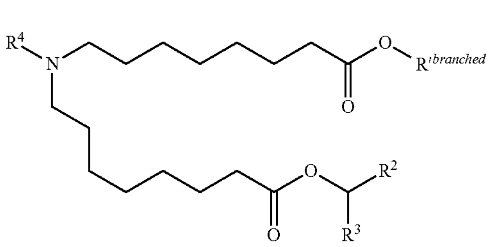

or its N-oxide, or a salt or isomer thereof, $R'^{branched}$ is

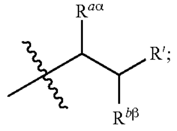

wherein

denotes a point of attachment;

wherein $R^{a\alpha}$ and $R^{a\beta}$ are each independently selected from the group consisting of H and $C_{1-2}$ alkyl, wherein at least one of $R^{a\alpha}$ and $R^{a\beta}$ is a $C_1$ or $C_2$ alkyl;

R' is selected from the group consisting of $C_{1-18}$ alkyl and $C_{2-18}$ alkenyl;

$R^2$ and $R^3$ are each independently selected from the group consisting of $C_{1-14}$ alkyl and $C_{2-14}$ alkenyl;

$R^4$ is —$(CH_2)_n$Q, wherein n is selected from 1, 2, 3, 4, and 5, where Q is selected from —NR(S(O)(NR))$R^{SX}$, —NRS$(O)_2$NRR$^{SX}$, —NRC(S)$R^{SX}$, —NRC(O)$R^{SX}$, —NRP(O)(O$R^{P'}$)$R^P$, —NRS$(O)_2R^{SX}$, —NC(R)═$R^{11}$, —NC(═$NR_{15}$)$R^{11}$, —NRC(C(O)N$R^{14}R^{14'}$)$_2$, —NRC(O)$(CH_2)_p$C(O)N$R^{14}R^{14'}$, —NC(R)═NS$(O)_2R^{SX}$, —S$(O)_2$NRR$^{SX}$, and

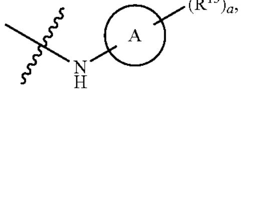

wherein A is a 3-14 membered heterocycle containing one or more heteroatoms selected from N, O and S; p is 0, 1, 2, 3, or 4; and a is 1, 2, 3, 4, or 5; wherein

denotes a point of attachment;

each R is independently selected from the group consisting of H and $C_{1-3}$ alkyl;

$R^{SX}$ is selected from a $C_{3-8}$ carbocycle, a 3-14 membered heterocycle containing one or more heteroatoms selected from N, O and S, $C_{1-6}$ alkyl, $C_{2-6}$ alkenyl, $(CH_2)_{p1}O(CH_2)_{p2}R^{SX1}$, $(CH_2)_{p1}S(CH_2)_{p2}R^{SX1}$, $(CH_2)_{p1}S(O)(CH_2)_{p2}R^{SX1}$, $(CH_2)_{p1}S(O)_2(CH_2)_{p2}R^{SX1}$, $(CH_2)_{p1}S(O)NR^{SX1}$, $(CH_2)_{p1}S(O)_2NR^{SX1}$, and $(CH_2)_{p1}R^{SX1}$, wherein the carbocycle and heterocycle are optionally substituted with one or more groups selected from OH, oxo, $C_{1-6}$ alkyl and $C_{1-6}$ alkoxy;

$R^P$ and $R^{P'}$ are each independently selected from H, $C_{1-3}$ alkyl, and $C_{2-3}$ alkenyl;

$R^{SX1}$ is selected from $C_{1-3}$ alkyl, $NR^{14}R^{14'}$, C(O)$NR^{14}R^{14'}$, S$(O)_2NR^{14}R^{14'}$, a $C_{3-8}$ carbocycle, and a 3-14 membered heterocycle containing one or more heteroatoms selected from N, O and S, wherein the carbocycle and heterocycle are each optionally substituted with one or more groups selected from oxo, halo, $C_{1-3}$ alkyl, $C_{1-3}$ alkoxy, ($C_{1-3}$ alkoxy)-$C_{1-3}$ alkyl, $C_{1-6}$ alkylamino, di-($C_{1-6}$ alkyl) amino, and $NH_2$;

$R^{11}$ is selected from the group consisting of $C_{3-6}$ carbocycle and a 3-14 membered heterocycle containing one or more heteroatoms selected from N, O and S, wherein the carbocycle and heterocycle are each optionally substituted with one or more $R^{13}$;

each $R^{13}$ is independently selected from the group consisting of OH, oxo, halo, $C_{1-6}$ alkyl, $C_{1-6}$ alkoxy, $C_{2-6}$ alkenyl, $C_{1-6}$ alkylamino, di-($C_{1-6}$ alkyl) amino, $NH_2$, C(O)$NH_2$, CN, and $NO_2$; wherein $C_{1-6}$ alkyl and $C_{2-6}$ alkenyl are optionally substituted with $C_{1-6}$ alkoxy;

$R^{14}$ and $R^{14'}$ are each independently selected from the group consisting of H, OH, $C_{1-6}$ alkyl;

$R^{15}$ is H or OH;

$p_1$ is selected from 1, 2, 3, 4, and 5; and $p_2$ is selected from 1, 2, 3, 4, and 5.

Embodiment 35. The compound of any one of the preceding embodiments, wherein $R^{a\alpha}$ is H and $R^{a\beta}$ is a $C_1$ or $C_2$ alkyl.

Embodiment 36. The compound of any one of the preceding embodiments, wherein $R^{a\alpha}$ is $C_1$ or $C_2$ alkyl and $R^{a\beta}$ is H.

Embodiment 37. The compound of any one of the preceding embodiments, wherein Q is —NR(S(O)(NR))$R^{SX}$.

Embodiment 38. The compound of any one of the preceding embodiments, wherein Q is —NRS$(O)_2$NRR$^{SX}$.

Embodiment 39. The compound of any one of the preceding embodiments, wherein Q is —NRC(S)$R^{SX}$.

Embodiment 40. The compound of any one of the preceding embodiments, wherein Q is —NRC(O)$R^{SX}$.

Embodiment 41. The compound of any one of the preceding embodiments, wherein Q is —NRS$(O)_2R^{SX}$.

Embodiment 42. The compound of any one of the preceding embodiments, wherein Q is —NC(R)═NS$(O)_2R^{SX}$.

Embodiment 43. The compound of any one of the preceding embodiments, wherein $R^{SX}$ is selected from a $C_{3-8}$ carbocycle, a 3-14 membered heterocycle containing one or more heteroatoms selected from N, O and S, $C_{1-6}$ alkyl, and $C_{2-6}$ alkenyl, wherein the carbocycle and heterocycle are optionally substituted with one or more groups selected from OH, oxo, $C_{1-6}$ alkyl and $C_{1-6}$ alkoxy.

Embodiment 44. The compound of any one of the preceding embodiments, wherein $R^{SX}$ is selected from an unsubstituted $C_{3-8}$ carbocycle, a unsubstituted 3-14 membered heterocycle containing one or more heteroatoms selected from N, O and S, $C_{1-6}$ alkyl, and $C_{2-6}$ alkenyl.

Embodiment 45. The compound of any one of the preceding embodiments, wherein $R^{SX}$ is $(CH_2)_{p1}O(CH_2)_{p2}R^{SX1}$.

Embodiment 46. The compound of any one of the preceding embodiments, wherein $R^{SX}$ is $(CH_2)_{p2}S(CH_2)_{p2}R^{SX1}$.

Embodiment 47. The compound of any one of the preceding embodiments, wherein $R^{SX}$ is $(CH_2)_pS(O)NR^{SX1}$.

Embodiment 48. The compound of any one of the preceding embodiments, wherein $R^{SX}$ is $(CH_2)_pS(O)_2NR^{SX1}$.

Embodiment 49. The compound of any one of the preceding embodiments, wherein $R^{SX}$ is $(CH_2)_{p1}R^{SX1}$.

Embodiment 50. The compound of any one of the preceding embodiments, wherein $R^{SX1}$ is $NR^{14}R^{14'}$.

Embodiment 51. The compound of any one of the preceding embodiments, wherein $R^{SX1}$ is $C(O)NR^{14}R^{14'}$.

Embodiment 52. The compound of any one of the preceding embodiments. wherein $R^4$ is selected from:

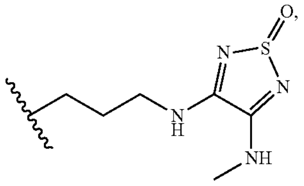

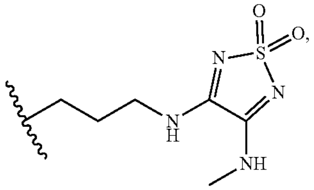

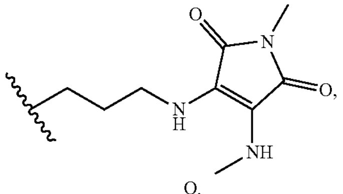

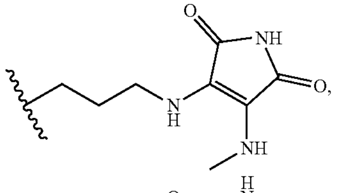

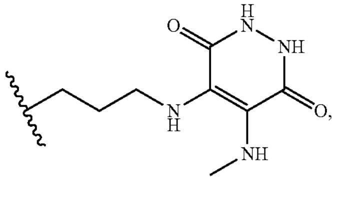

-continued

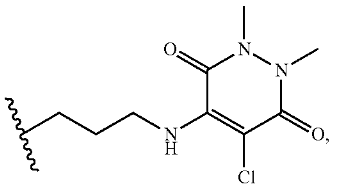

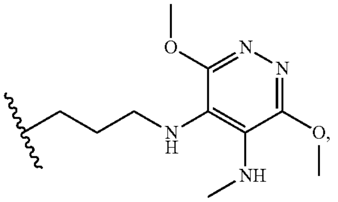

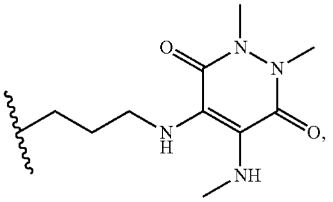

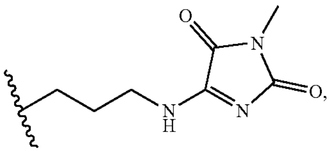

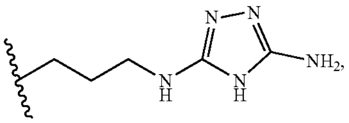

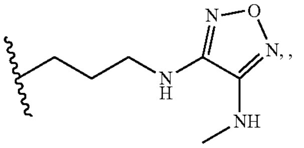

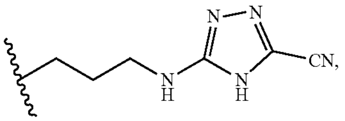

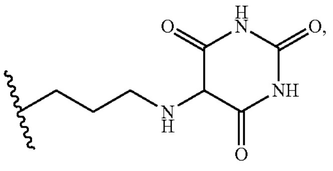

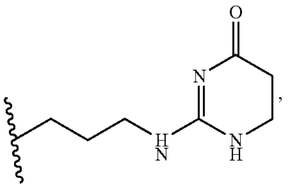

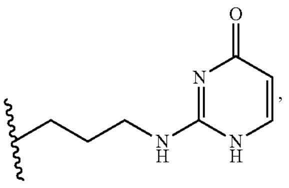

-continued
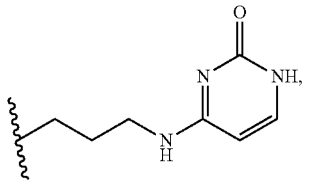
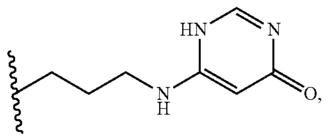
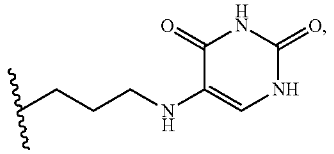
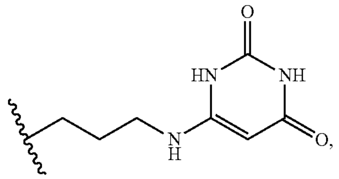
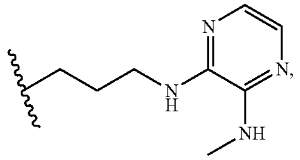
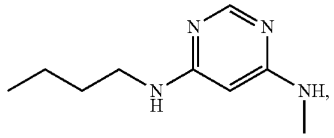
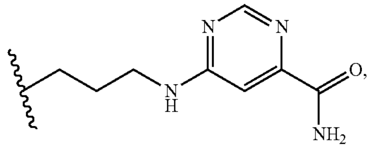
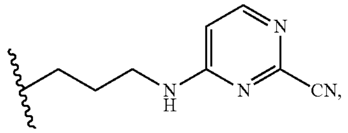
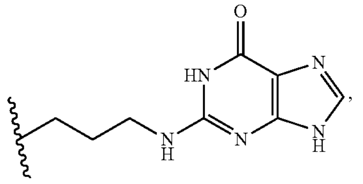
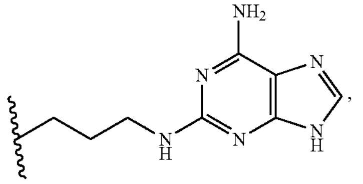
-continued
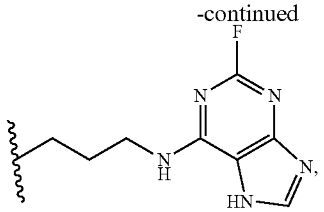
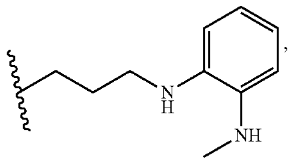
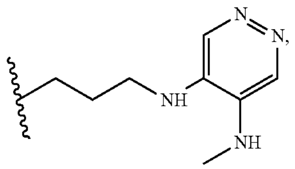
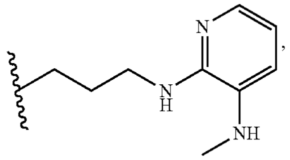
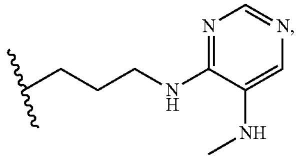
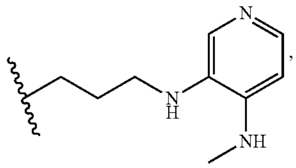
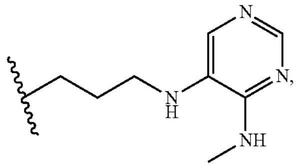
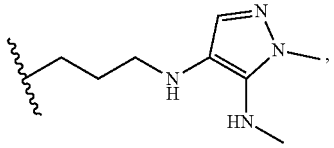
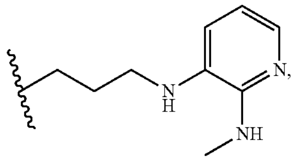
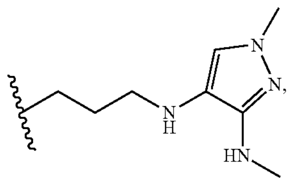

-continued
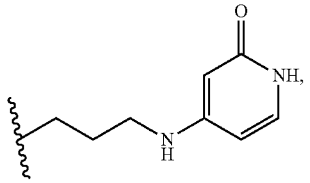
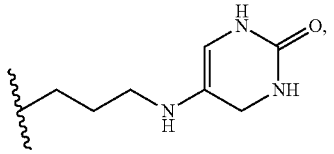
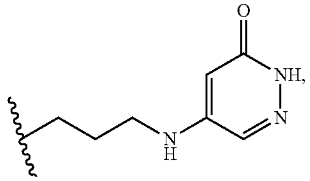
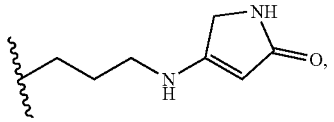
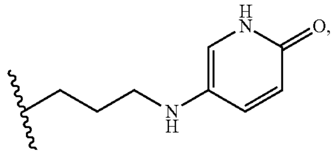
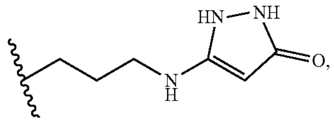
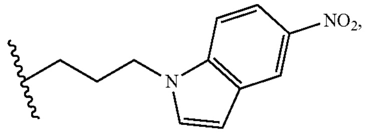
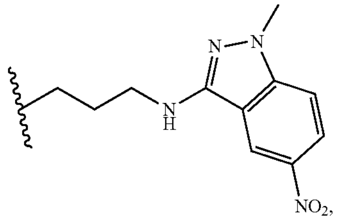
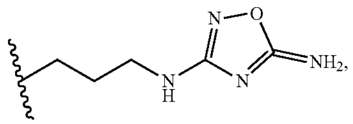
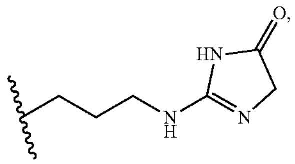
-continued
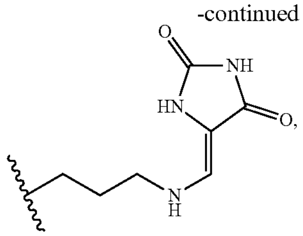
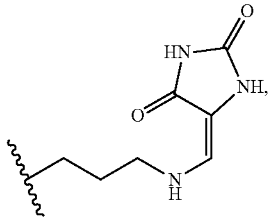
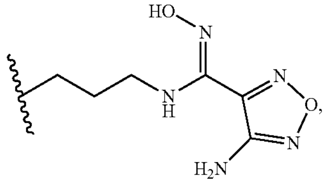
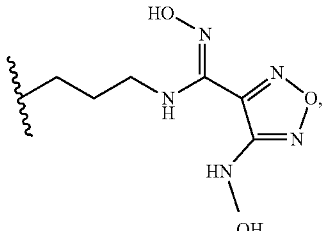
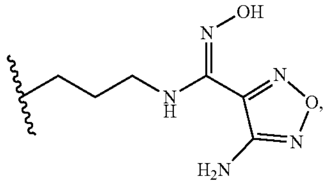
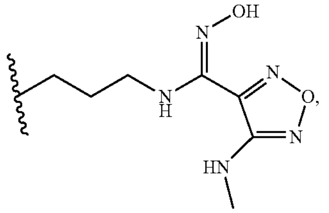
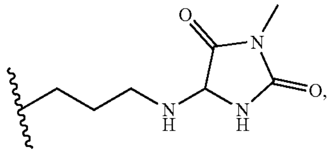
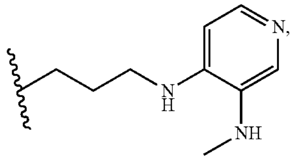
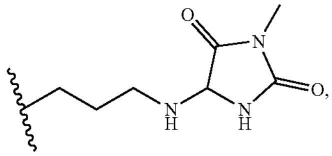

-continued
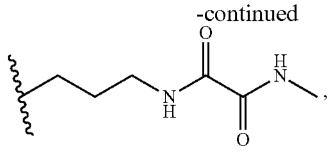
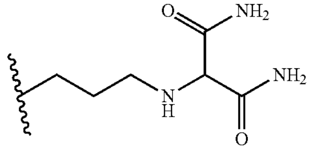
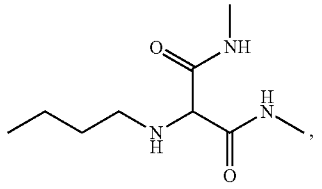
and
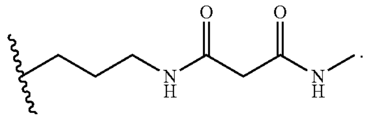
Embodiment 53. The compound of any one of the preceding claims, wherein $R^4$ is selected from
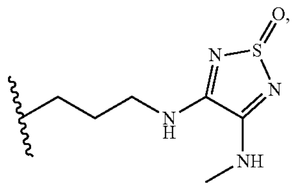
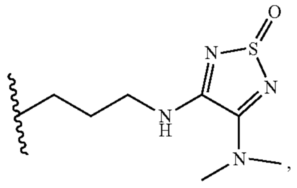
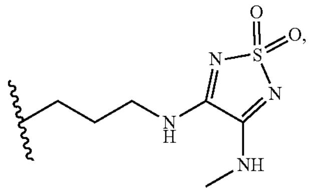
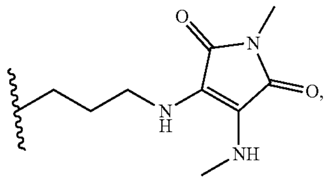
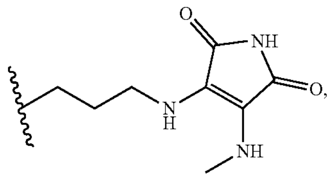
-continued
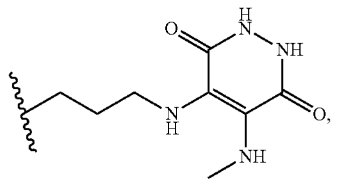
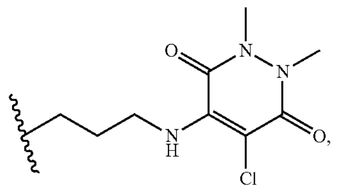
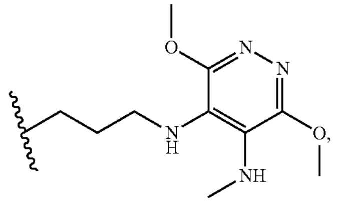
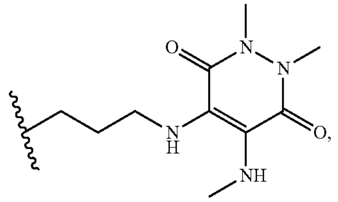
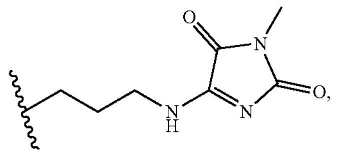
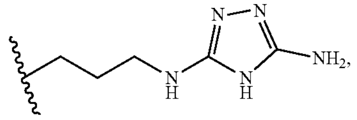
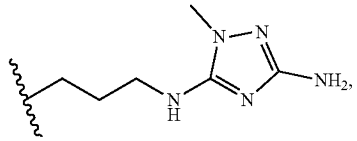
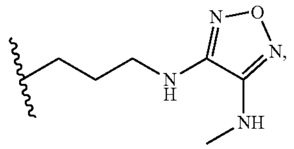
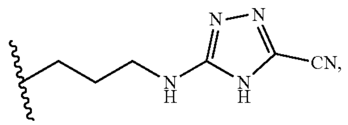
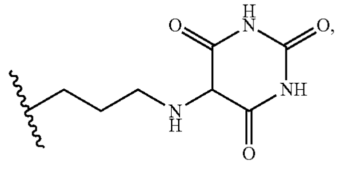

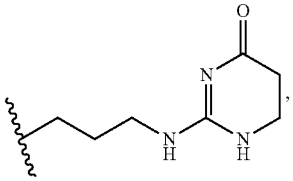,
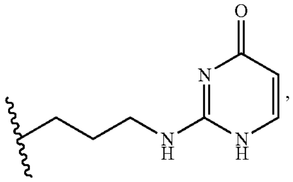,
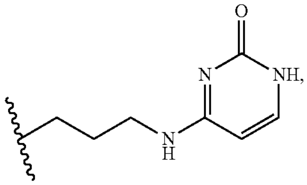,
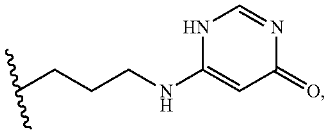,
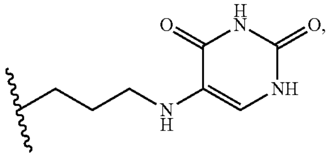,
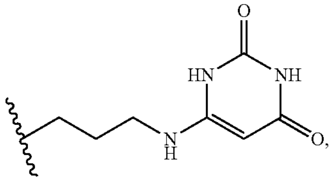,
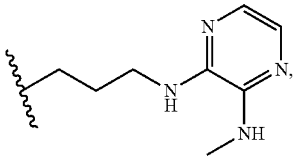,
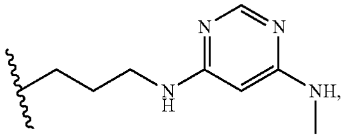,
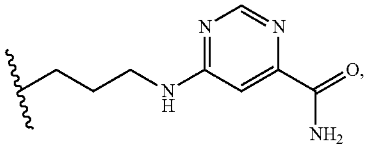,
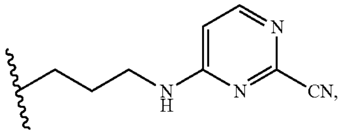,
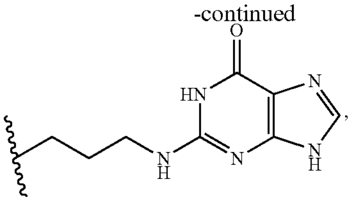,
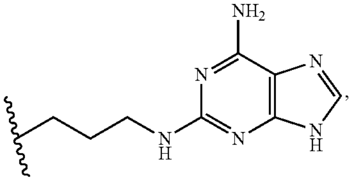,
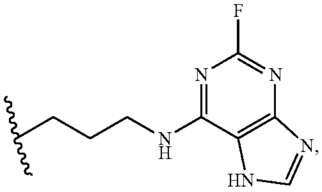,
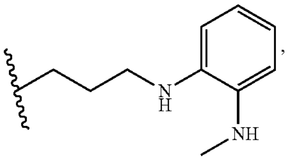,
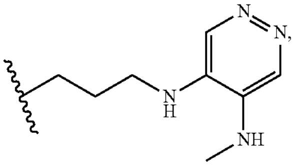,
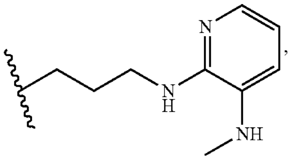,
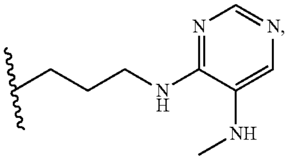,
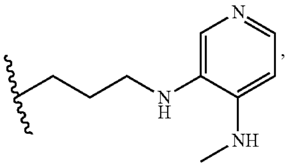,
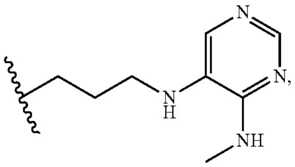,
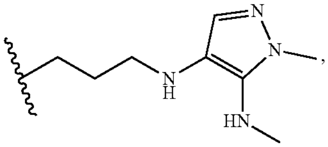, -continued
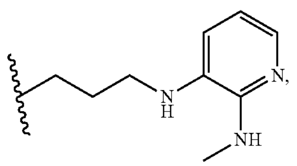
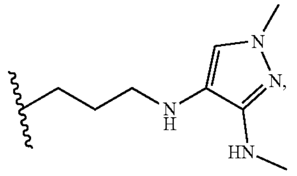
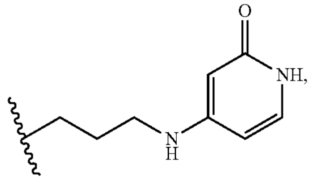
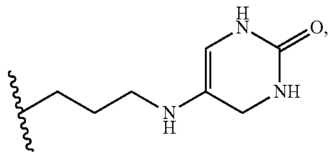
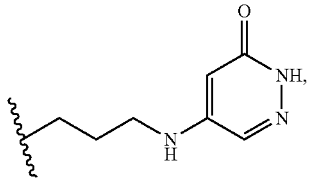
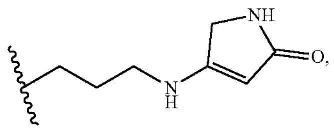
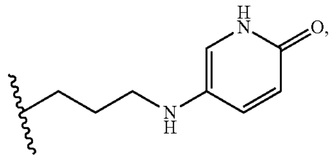
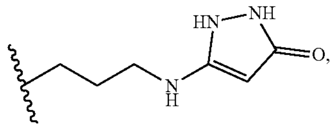
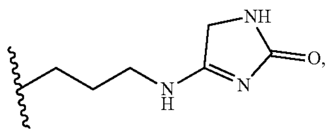
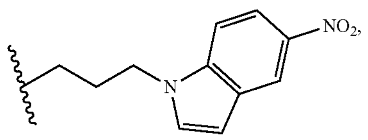
-continued
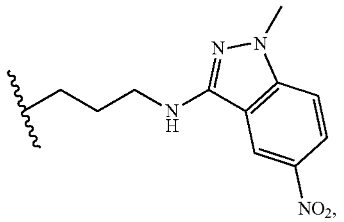
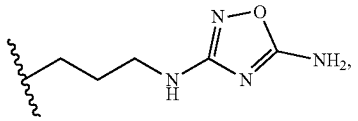
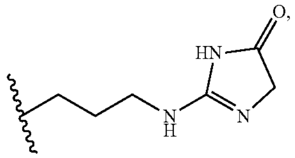
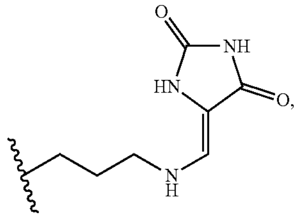
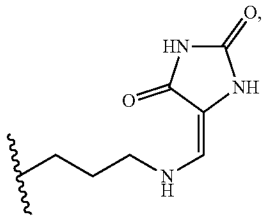
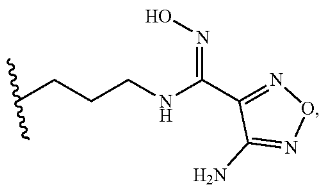
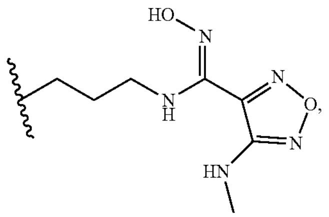
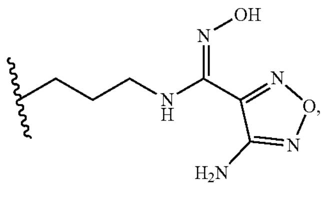

-continued
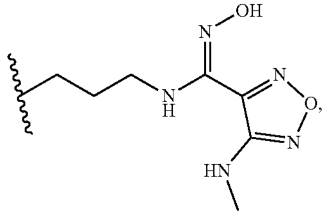
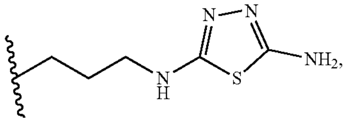
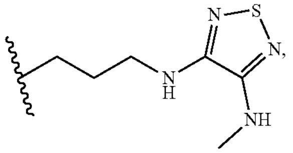
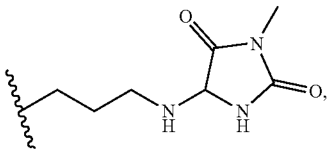
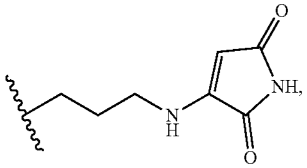
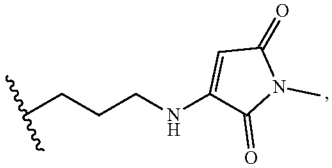
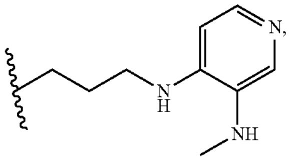
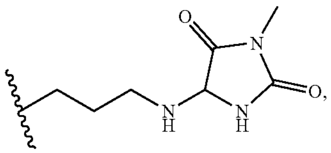
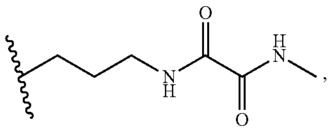
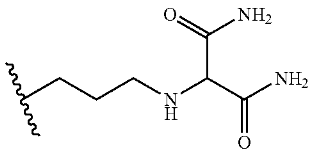
-continued
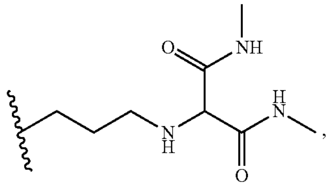
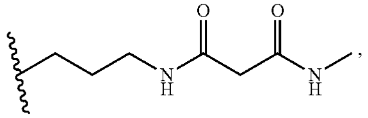
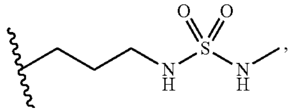
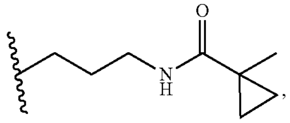
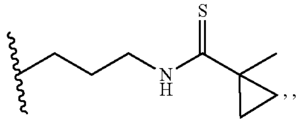
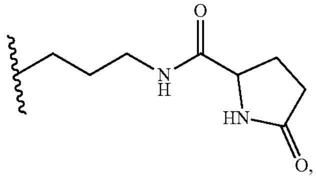
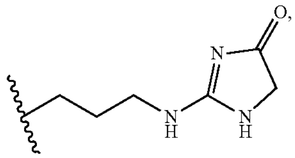
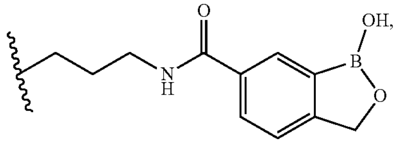
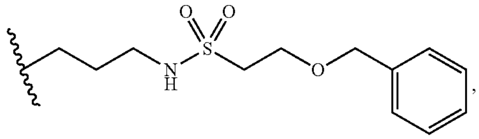
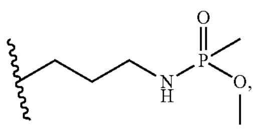
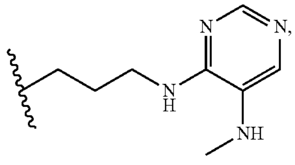
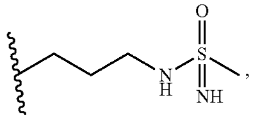

-continued
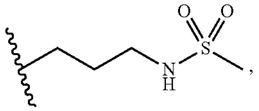
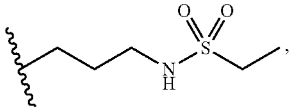
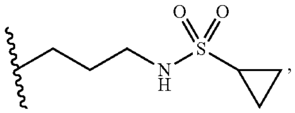
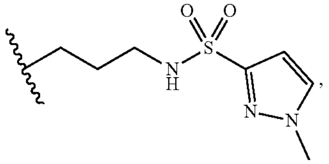
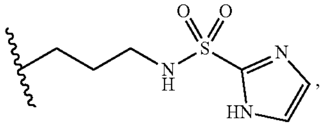
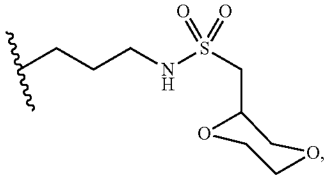
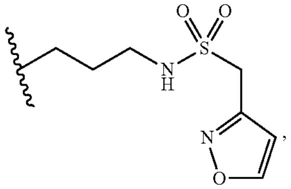
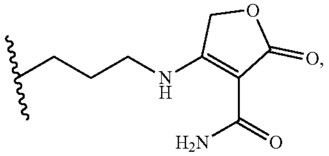
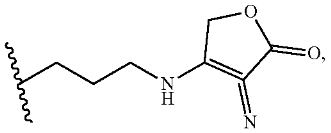
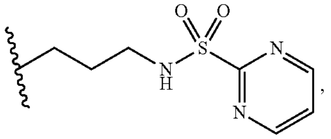
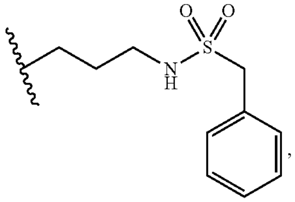
-continued
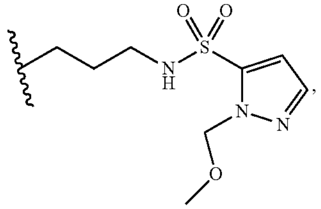
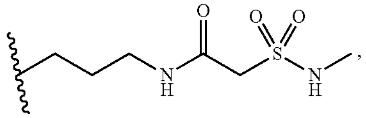
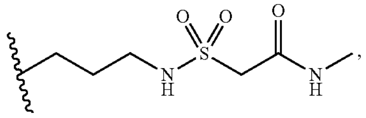
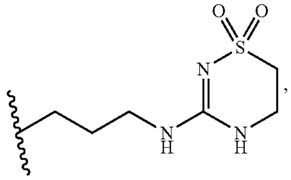
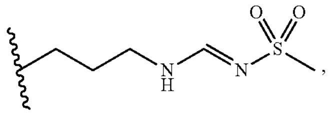
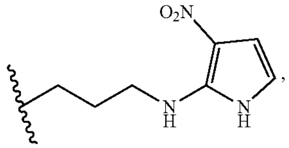
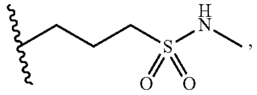
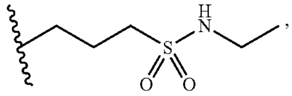 and
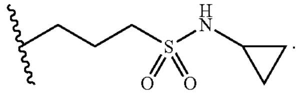
Embodiment 54. A compound of Formula (A-1):
(A-1)
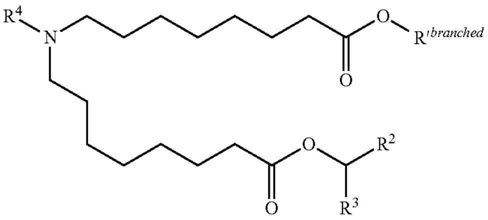
or its N-oxide, or a salt or isomer thereof, wherein:

$R'^{branched}$ is

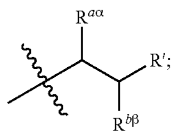

wherein

denotes a point of attachment;

wherein $R^{a\alpha}$ and $R^{a\beta}$ are each independently selected from the group consisting of H and $C_{1-2}$ alkyl, wherein at least one of $R^{a\alpha}$ and $R^{a\beta}$ is a $C_1$ or $C_2$ alkyl;

R' is selected from the group consisting of $C_{1-18}$ alkyl and $C_{2-18}$ alkenyl;

$R^2$ and $R^3$ are each independently selected from the group consisting of $C_{1-14}$ alkyl and $C_{2-14}$ alkenyl;

$R^4$ is —$(CH_2)_nQ$, wherein n is independently selected from 1, 2, 3, 4, and 5, where Q is selected from $NRS(O)_2R^{SX}$ and

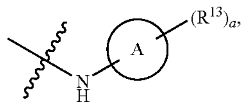

wherein A is a 3-14 membered heterocycle containing one or more heteroatoms selected from N, O and S; and a is 1, 2, 3, or 4; wherein

denotes a point of attachment;

R is selected from H and $C_{1-3}$ alkyl;

$R^{SX}$ is selected from a $C_{3-8}$ carbocycle, a 3-14 membered heterocycle containing one or more heteroatoms selected from N, O and S, $C_{1-6}$ alkyl, $C_{2-6}$ alkenyl, $(C_{1-3}$ alkoxy$)C_{1-3}$ alkyl, $(CH_2)_{p1}O(CH_2)_{p2}R^{SX1}$, and $(CH_2)_{p1}R^{SX1}$, where in the carbocycle and heterocycle are optionally substituted with one or more groups selected from oxo, $C_{1-6}$ alkyl, and $(C_{1-3}$ alkoxy$)C_{1-3}$ alkyl;

$R^{SX1}$ is selected from $C(O)NR^{14}R^{14\prime}$, a $C_{3-8}$ carbocycle, and a 3-14 membered heterocycle containing one or more heteroatoms selected from N, O and S, wherein the carbocycle and heterocycle are each optionally substituted with one or more groups selected from oxo, halo, $C_{1-3}$ alkyl, $(C_{1-3}$ alkoxy$)C_{1-3}$ alkyl, $C_{1-6}$ alkylamino, di-$(C_{1-6}$ alkyl) amino, and $NH_2$;

each $R^{13}$ is selected from the group consisting of OH, oxo, halo, $C_{1-6}$ alkyl, $C_{1-6}$ alkoxy, $C_{2-6}$ alkenyl, $C_{1-6}$ alkylamino, di-$(C_{1-6}$ alkyl) amino, $NH_2$, $C(O)NH_2$, CN, and $NO_2$;

$R^{14}$ and $R^{14\prime}$ are each independently selected from the group consisting of H and $C_{1-6}$ alkyl;

$p_1$ is selected from 1, 2, 3, 4, and 5; and $p_2$ is selected from 1, 2, 3, 4, and 5.

Embodiment 55. The compound of any one of the preceding embodiments, having one of the following structures:

(A-1a)

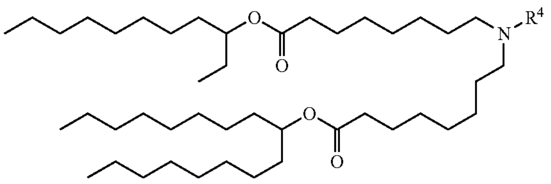

(A-1b)

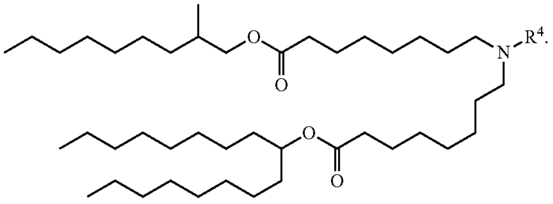

Embodiment 56. The compound of any one of the preceding embodiments, wherein n is 3.

Embodiment 57. The compound of any one of the preceding embodiments, wherein Q is $NRS(O)_2R^{SX}$.

Embodiment 58. The compound of any one of the preceding embodiments, wherein R is H.

Embodiment 59. The compound of any one of the preceding embodiments, wherein $R^{SX}$ is ethyl, propyl, or butyl.

Embodiment 60. The compound of any one of the preceding embodiments, wherein $R^{SX}$ is selected from a $C_{3-6}$ carbocycle and a $C_{1-3}$ alkyl.

Embodiment 61. The compound of any one of the preceding embodiments, wherein $R^{SX}$ is ethyl.

Embodiment 62. The compound of any one of the preceding embodiments, wherein $R^{SX}$ is a $C_{2-6}$ alkenyl.

Embodiment 63. The compound of any one of the preceding embodiments, wherein $R^{SX}$ is cyclopropyl.

Embodiment 64. The compound of any one of the preceding embodiments, wherein $R^{SX}$ is $(CH_2)_{p1}O(CH_2)_{p2}R^{SX1}$.

Embodiment 65. The compound of any one of the preceding embodiments, wherein $R^{SX1}$ is $C_{1-3}$ alkyl.

Embodiment 66. The compound of any one of the preceding embodiments, wherein $R^{SX}$ is $(CH_2)_{p1}R^{SX1}$.

Embodiment 67. The compound of any one of the preceding embodiments, wherein $p_1$ is 1 and $R^{SX1}$ is a $C_{3-8}$ carbocycle or a 3-14 membered heterocycle.

Embodiment 68. The compound of any one of the preceding embodiments, wherein $p_1$ is 1 and $R^{SX1}$ is a 6-membered heterocycloalkyl, a 5-membered heteroaryl, or phenyl.

Embodiment 69. The compound of any one of the preceding embodiments, wherein $R^{SX1}$ is a 5-membered heteroaryl.

Embodiment 70. The compound of any one of the preceding embodiments, wherein $R^{SX1}$ is oxazole or isoxazole.

Embodiment 71. The compound of any one of the preceding embodiments, wherein Q is

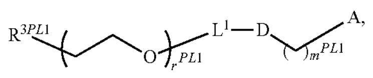

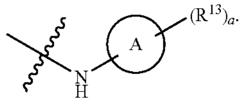

Embodiment 72. The compound of any one of the preceding embodiments, wherein A is a 5-membered heteroaryl.

Embodiment 73. The compound of any one of the preceding embodiments, wherein A is a thiadiazole.

Embodiment 74. The compound of any one of the preceding embodiments, wherein each $R^{13}$ is selected from the group consisting of oxo, $C_{1-6}$ alkylamino, di-($C_{1-6}$ alkyl) amino, and $NH_2$.

Embodiment 75. The compound of any one of the preceding embodiments, wherein $R^4$ is

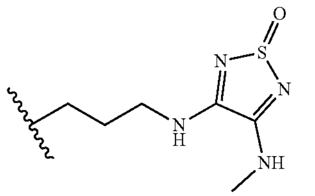

or

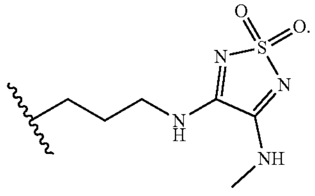

Embodiment 76. A compound selected from:

| Structure |
| --- |
| 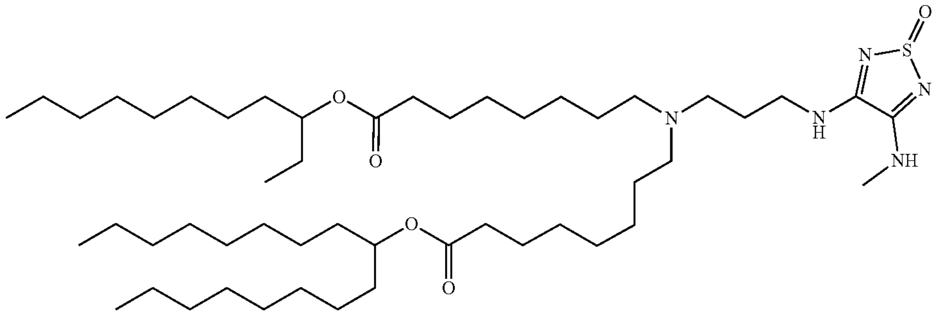 [SMILES: CCCCCCCCC(CC)OC(=O)CCCCCCCN(CCCCCCCC(=O)OC(CCCCCCCC)CCCCCCCC)CCCNC1=NS(=O)N=C1NC] |
| 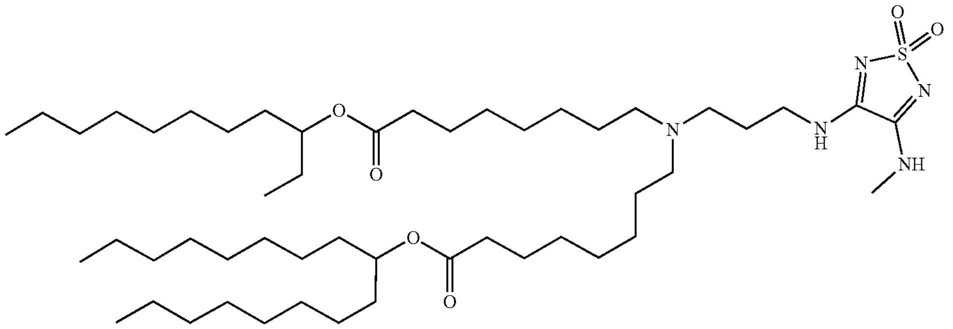 [SMILES: CCCCCCCCC(CC)OC(=O)CCCCCCCN(CCCCCCCC(=O)OC(CCCCCCCC)CCCCCCCC)CCCNC1=NS(=O)(=O)N=C1NC] |
| 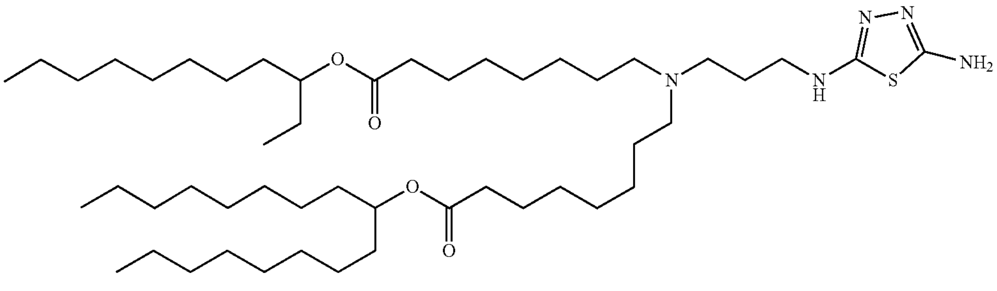 [SMILES: CCCCCCCCC(CC)OC(=O)CCCCCCCN(CCCCCCCC(=O)OC(CCCCCCCC)CCCCCCCC)CCCNc1nnc(N)s1] |

-continued
| Structure |
| --- |
| 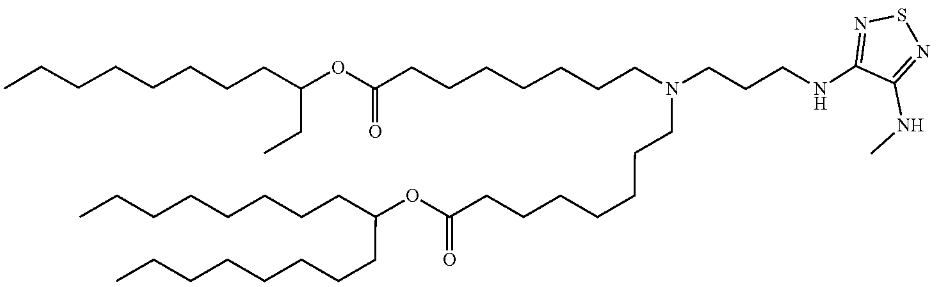 [SMILES: CCCCCCCCC(CC)OC(=O)CCCCCCCN(CCCCCCCC(=O)OC(CCCCCCCC)CCCCCCCC)CCCNc1nsnc1NC] |
| 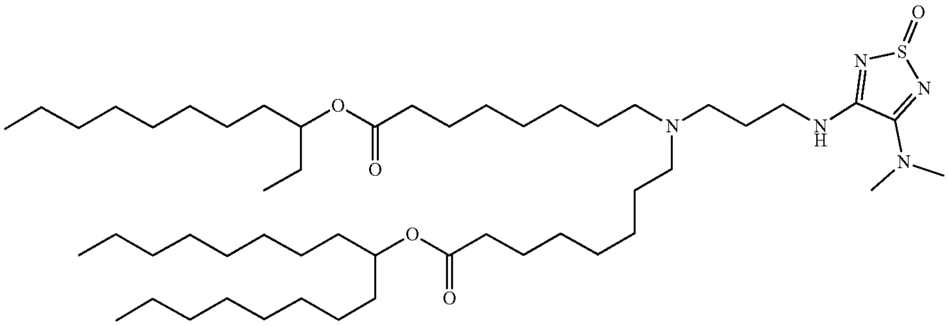 [SMILES: CCCCCCCCC(CC)OC(=O)CCCCCCCN(CCCCCCCC(=O)OC(CCCCCCCC)CCCCCCCC)CCCNC1=NS(=O)N=C1N(C)C] |
| 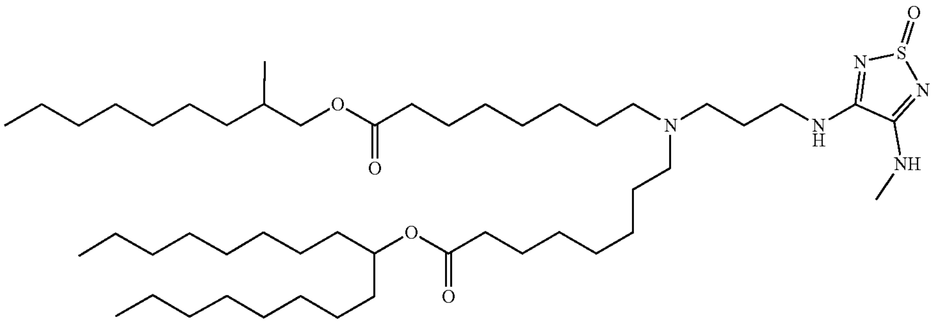 [SMILES: CCCCCCCCC(CCCCCCCC)OC(=O)CCCCCCCN(CCCCCCCC(=O)OCC(C)CCCCCCC)CCCNC1=NS(=O)N=C1NC] |
| 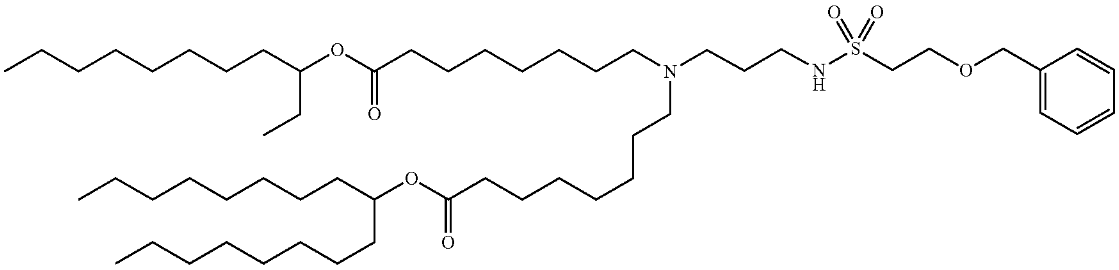 [SMILES: CCCCCCCCC(CC)OC(=O)CCCCCCCN(CCCCCCCC(=O)OC(CCCCCCCC)CCCCCCCC)CCCNS(=O)(=O)CCOCc1ccccc1] |
| 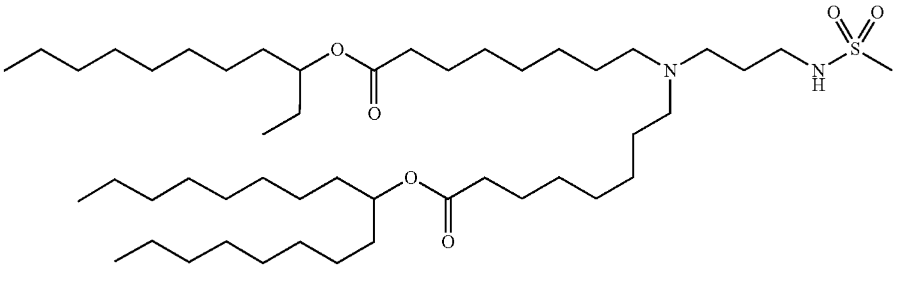 [SMILES: CCCCCCCCC(CC)OC(=O)CCCCCCCN(CCCCCCCC(=O)OC(CCCCCCCC)CCCCCCCC)CCCNS(C)(=O)=O] |

-continued
| Structure |
| --- |
| 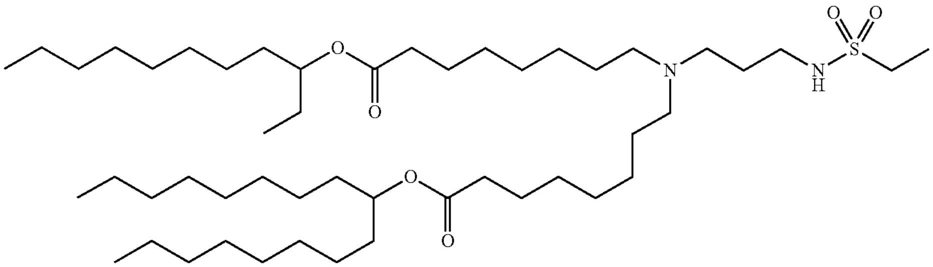 [SMILES: CCCCCCCCC(CC)OC(=O)CCCCCCCN(CCCCCCCC(=O)OC(CCCCCCCC)CCCCCCCC)CCCNS(=O)(=O)CC] |
| 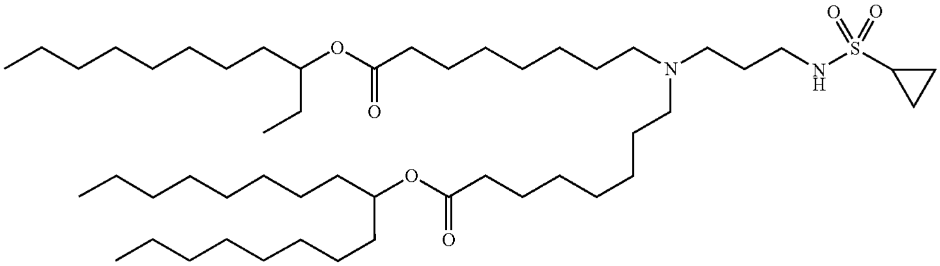 [SMILES: CCCCCCCCC(CC)OC(=O)CCCCCCCN(CCCCCCCC(=O)OC(CCCCCCCC)CCCCCCCC)CCCNS(=O)(=O)C1CC1] |
| 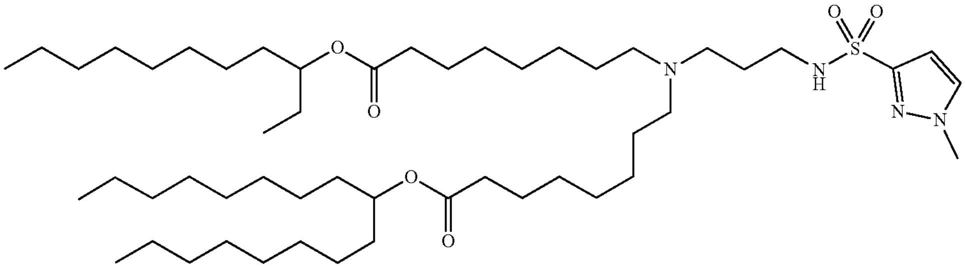 [SMILES: CCCCCCCCC(CC)OC(=O)CCCCCCCN(CCCCCCCC(=O)OC(CCCCCCCC)CCCCCCCC)CCCNS(=O)(=O)c1ccn(C)n1] |
| 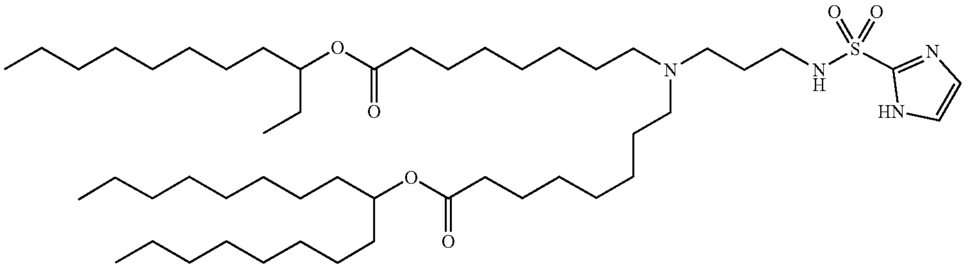 [SMILES: CCCCCCCCC(CC)OC(=O)CCCCCCCN(CCCCCCCC(=O)OC(CCCCCCCC)CCCCCCCC)CCCNS(=O)(=O)c1ncc[nH]1] |
| 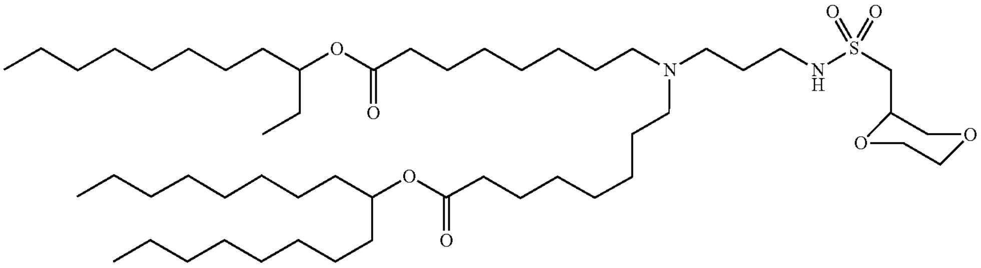 [SMILES: CCCCCCCCC(CC)OC(=O)CCCCCCCN(CCCCCCCC(=O)OC(CCCCCCCC)CCCCCCCC)CCCNS(=O)(=O)CC1COCCO1] |

-continued
| Structure |
| --- |
| 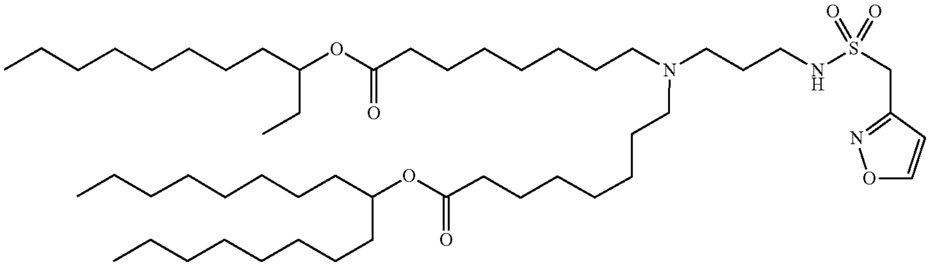 [SMILES: CCCCCCCCC(CC)OC(=O)CCCCCCCN(CCCCCCCC(=O)OC(CCCCCCCC)CCCCCCCC)CCCNS(=O)(=O)Cc1ccon1] |
| 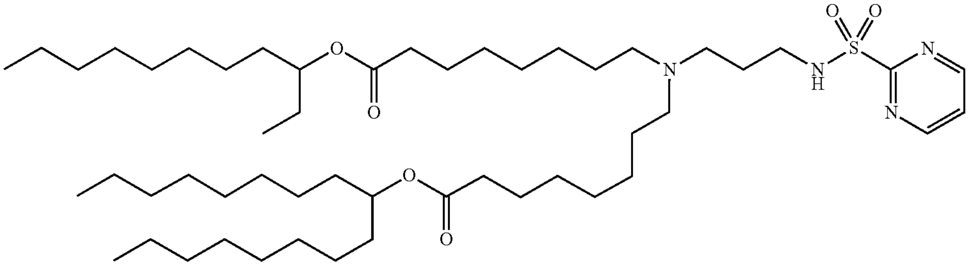 [SMILES: CCCCCCCCC(CC)OC(=O)CCCCCCCN(CCCCCCCC(=O)OC(CCCCCCCC)CCCCCCCC)CCCNS(=O)(=O)c1ncccn1] |
| 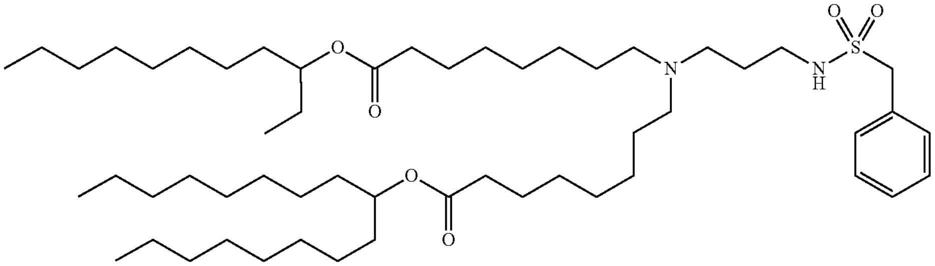 [SMILES: CCCCCCCCC(CC)OC(=O)CCCCCCCN(CCCCCCCC(=O)OC(CCCCCCCC)CCCCCCCC)CCCNS(=O)(=O)Cc1ccccc1] |
| 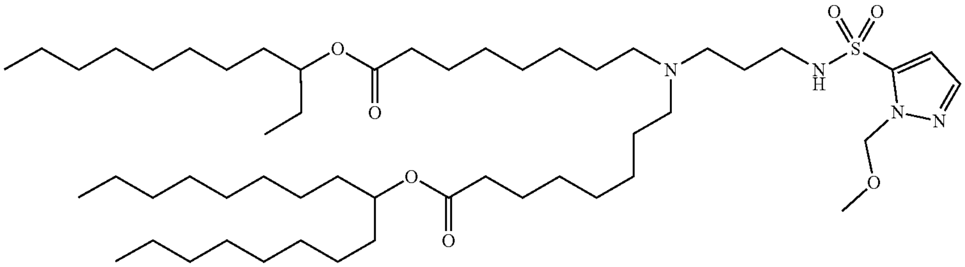 [SMILES: CCCCCCCCC(CC)OC(=O)CCCCCCCN(CCCCCCCC(=O)OC(CCCCCCCC)CCCCCCCC)CCCNS(=O)(=O)c1ccnn1COC] |
| 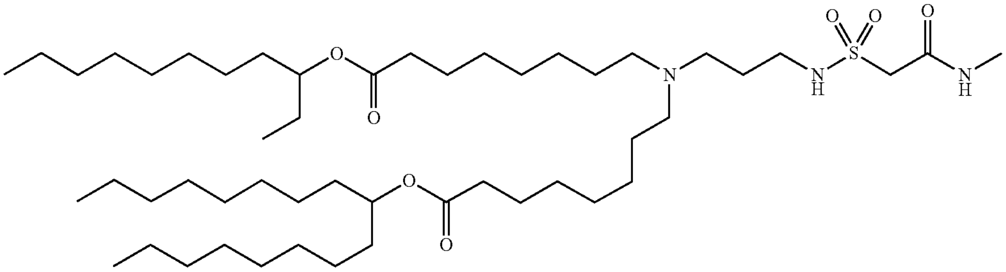 [SMILES: CCCCCCCCC(CC)OC(=O)CCCCCCCN(CCCCCCCC(=O)OC(CCCCCCCC)CCCCCCCC)CCCNS(=O)(=O)CC(=O)NC] |

-continued
| Structure |
| --- |
| 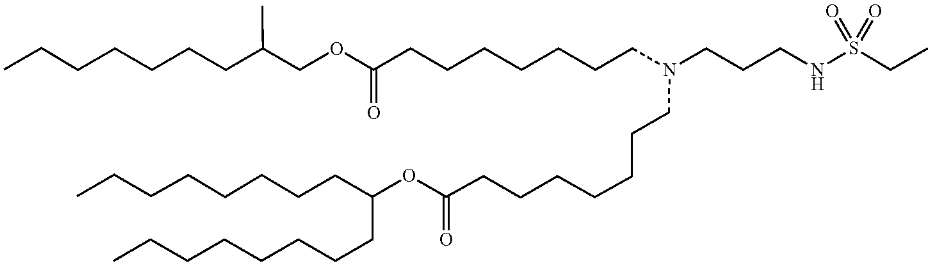 |
| 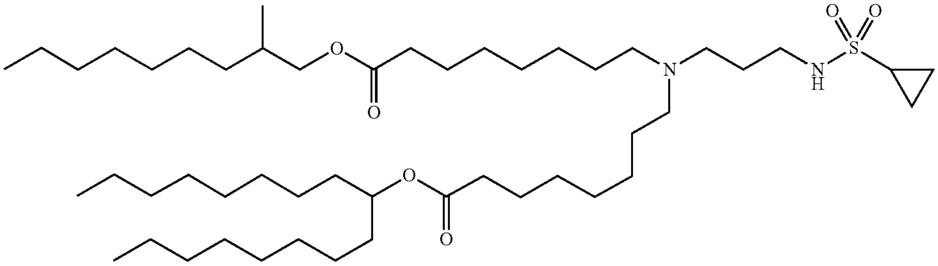 [SMILES: CCCCCCCCC(CCCCCCCC)OC(=O)CCCCCCCN(CCCCCCCC(=O)OCC(C)CCCCCCC)CCCNS(=O)(=O)C1CC1] |
| 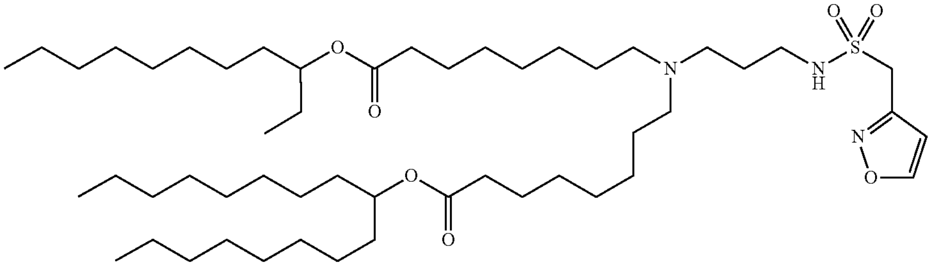 [SMILES: CCCCCCCCC(CC)OC(=O)CCCCCCCN(CCCCCCCC(=O)OC(CCCCCCCC)CCCCCCCC)CCCNS(=O)(=O)Cc1ccon1] |
| 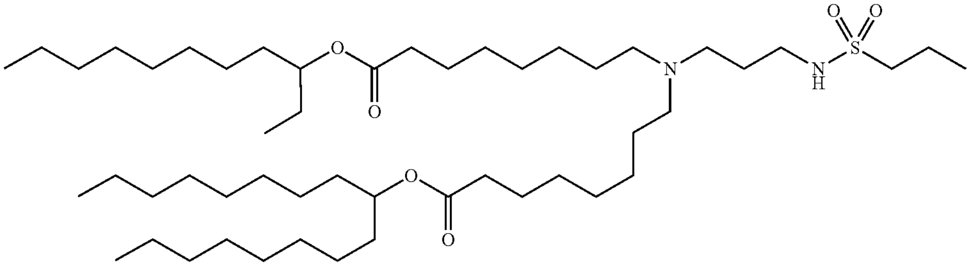 [SMILES: CCCCCCCCC(CC)OC(=O)CCCCCCCN(CCCCCCCC(=O)OC(CCCCCCCC)CCCCCCCC)CCCNS(=O)(=O)CCC] |
| 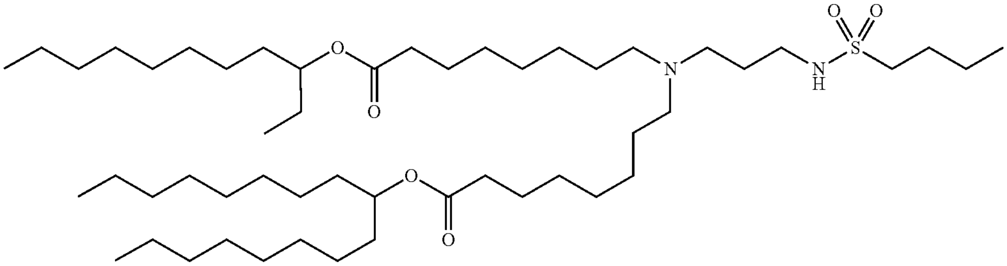 [SMILES: CCCCCCCCC(CC)OC(=O)CCCCCCCN(CCCCCCCC(=O)OC(CCCCCCCC)CCCCCCCC)CCCNS(=O)(=O)CCCC] |

-continued
| Structure |
|---|
| 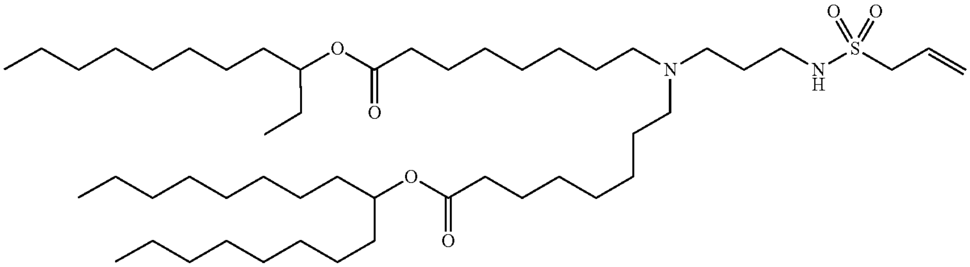 [SMILES: C=CCS(=O)(=O)NCCCN(CCCCCCCC(=O)OC(CC)CCCCCCCC)CCCCCCCC(=O)OC(CCCCCCCC)CCCCCCCC] |
| 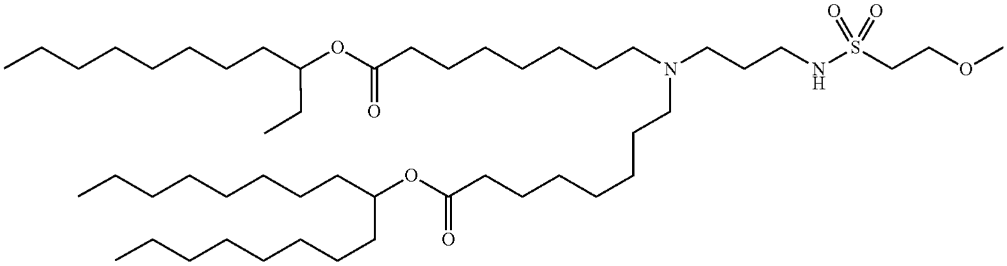 [SMILES: CCCCCCCCC(CC)OC(=O)CCCCCCCN(CCCCCCCC(=O)OC(CCCCCCCC)CCCCCCCC)CCCNS(=O)(=O)CCOC] |
| 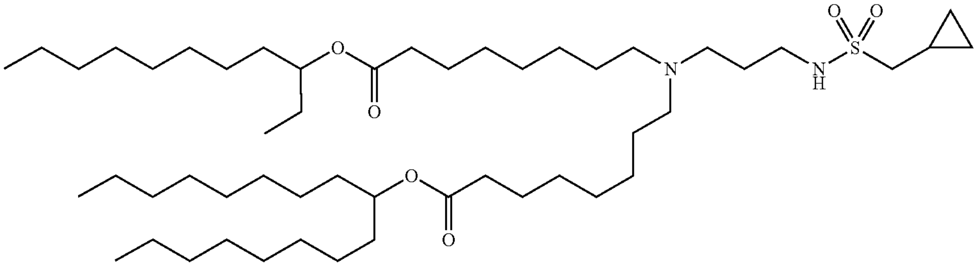 [SMILES: CCCCCCCCC(CC)OC(=O)CCCCCCCN(CCCCCCCC(=O)OC(CCCCCCCC)CCCCCCCC)CCCNS(=O)(=O)CC1CC1] |
| 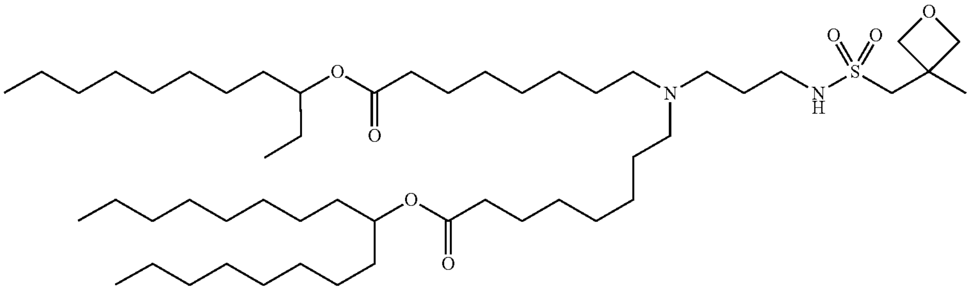 [SMILES: CCCCCCCCC(CC)OC(=O)CCCCCCCN(CCCCCCCC(=O)OC(CCCCCCCC)CCCCCCCC)CCCNS(=O)(=O)CC1(C)COC1] |
| 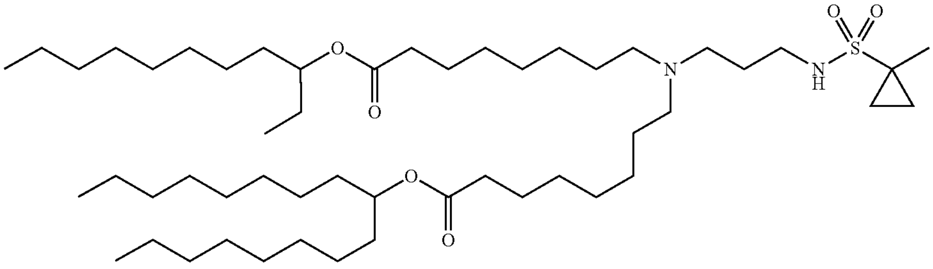 [SMILES: CCCCCCCCC(CC)OC(=O)CCCCCCCN(CCCCCCCC(=O)OC(CCCCCCCC)CCCCCCCC)CCCNS(=O)(=O)C1(C)CC1] |

-continued
| Structure |
| --- |
| 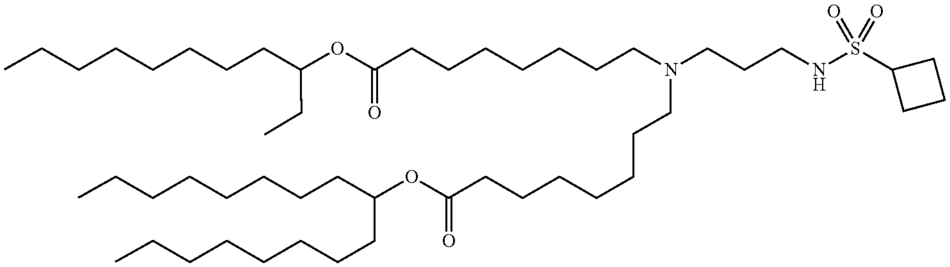 [SMILES: CCCCCCCCC(CC)OC(=O)CCCCCCCN(CCCCCCCC(=O)OC(CCCCCCCC)CCCCCCCC)CCCNS(=O)(=O)C1CCC1] |
| 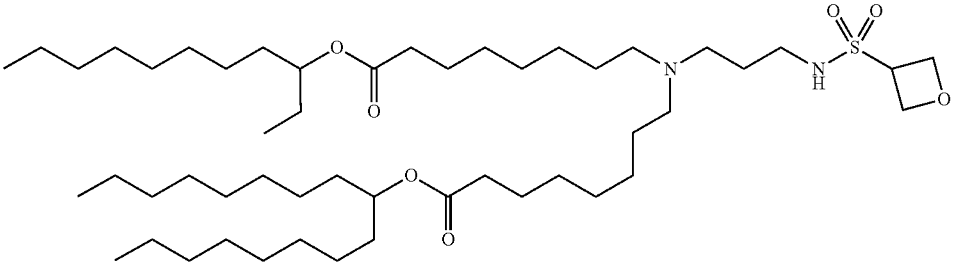 [SMILES: CCCCCCCCC(CC)OC(=O)CCCCCCCN(CCCCCCCC(=O)OC(CCCCCCCC)CCCCCCCC)CCCNS(=O)(=O)C1COC1] |
| 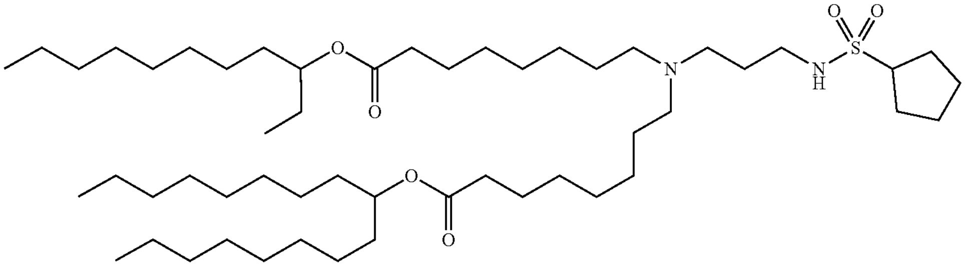 [SMILES: CCCCCCCCC(CC)OC(=O)CCCCCCCN(CCCCCCCC(=O)OC(CCCCCCCC)CCCCCCCC)CCCNS(=O)(=O)C1CCCC1] |
| 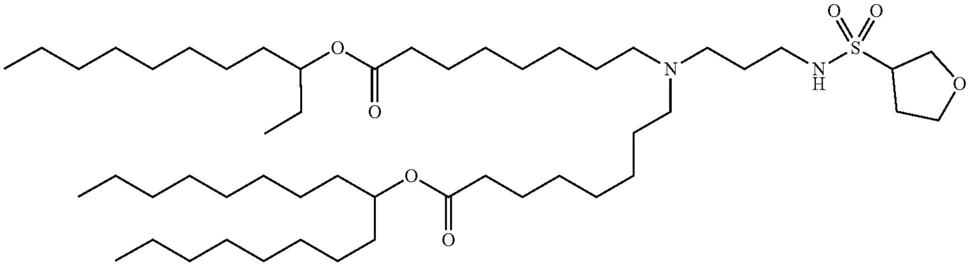 [SMILES: CCCCCCCCC(CC)OC(=O)CCCCCCCN(CCCCCCCC(=O)OC(CCCCCCCC)CCCCCCCC)CCCNS(=O)(=O)C1CCOC1] |
| 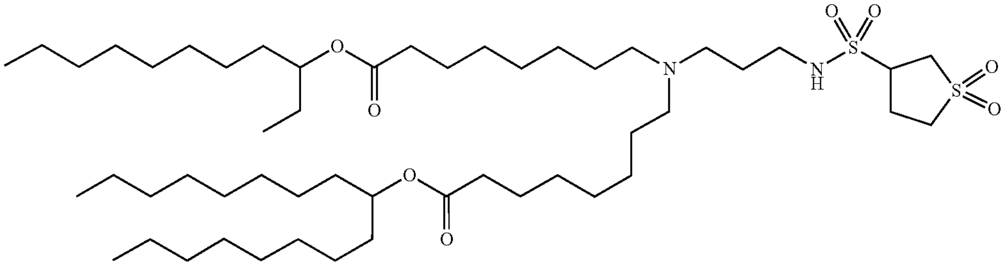 [SMILES: CCCCCCCCC(CC)OC(=O)CCCCCCCN(CCCCCCCC(=O)OC(CCCCCCCC)CCCCCCCC)CCCNS(=O)(=O)C1CCS(=O)(=O)C1] |

-continued
| Structure |
| --- |
| 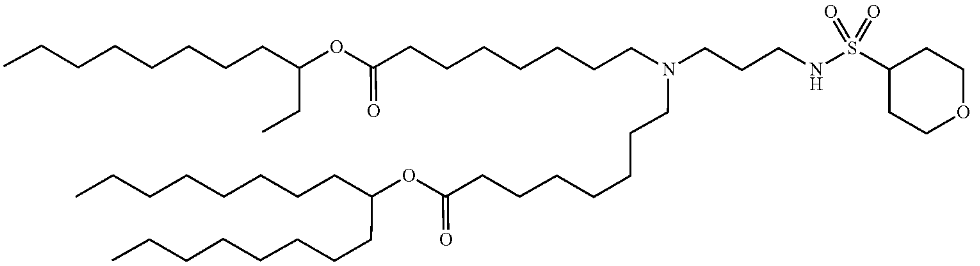 [SMILES: CCCCCCCCC(CC)OC(=O)CCCCCCCN(CCCCCCCC(=O)OC(CCCCCCCC)CCCCCCCC)CCCNS(=O)(=O)C1CCOCC1] |
| 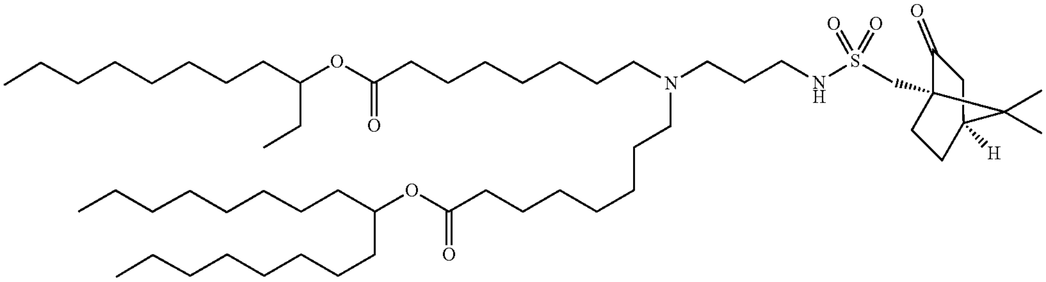 [SMILES: CCCCCCCCC(CC)OC(=O)CCCCCCCN(CCCCCCCC(=O)OC(CCCCCCCC)CCCCCCCC)CCCNS(=O)(=O)C[C@]12CC[C@@H](CC1=O)C2(C)C] |
| 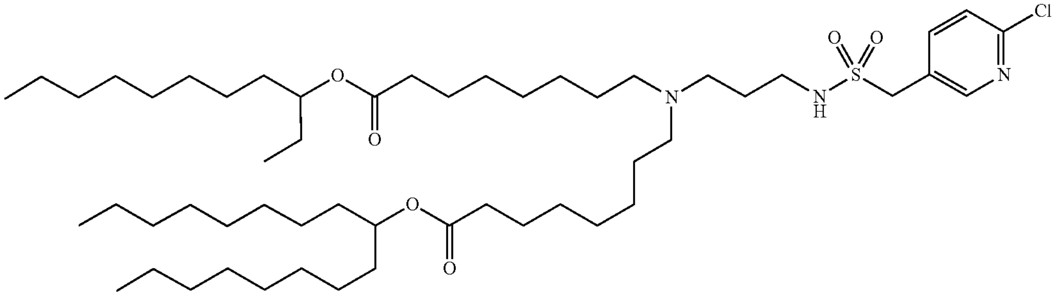 [SMILES: CCCCCCCCC(CC)OC(=O)CCCCCCCN(CCCCCCCC(=O)OC(CCCCCCCC)CCCCCCCC)CCCNS(=O)(=O)Cc1ccc(Cl)nc1] |
| 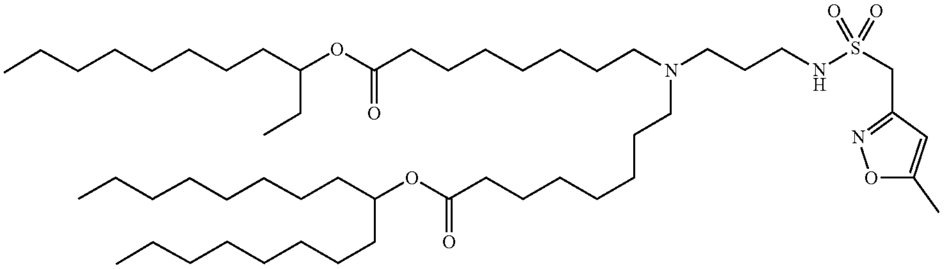 [SMILES: CCCCCCCCC(CC)OC(=O)CCCCCCCN(CCCCCCCC(=O)OC(CCCCCCCC)CCCCCCCC)CCCNS(=O)(=O)Cc1cc(C)on1] |
| 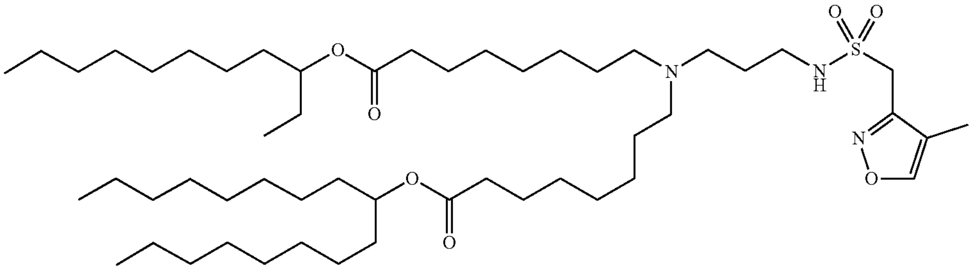 [SMILES: CCCCCCCCC(CC)OC(=O)CCCCCCCN(CCCCCCCC(=O)OC(CCCCCCCC)CCCCCCCC)CCCNS(=O)(=O)Cc1nocc1C] |

-continued
| Structure |
|---|
| 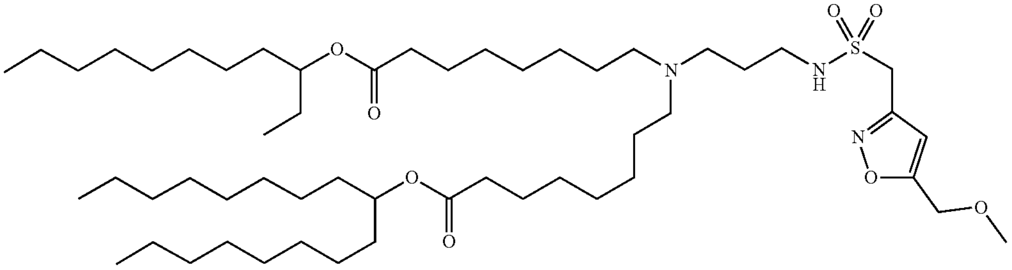 [SMILES: CCCCCCCCC(CC)OC(=O)CCCCCCCN(CCCCCCCC(=O)OC(CCCCCCCC)CCCCCCCC)CCCNS(=O)(=O)Cc1cc(COC)on1] |
Embodiment 77. A compound selected from:
| Cpd | Structure |
|---|---|
| 1 | 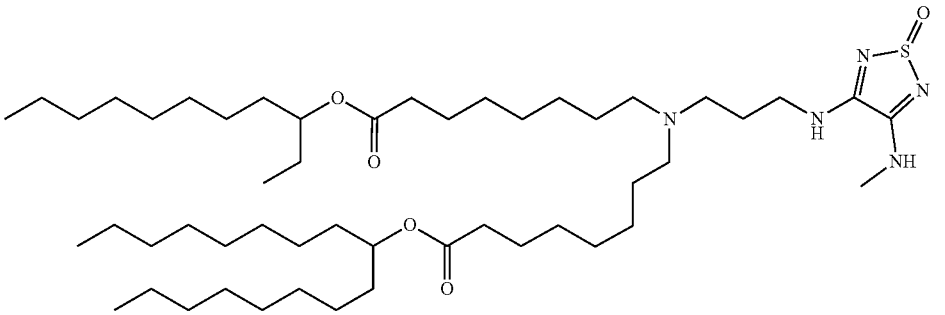 [SMILES: CCCCCCCCC(CC)OC(=O)CCCCCCCN(CCCCCCCC(=O)OC(CCCCCCCC)CCCCCCCC)CCCNC1=NS(=O)N=C1NC] |
| 2 | 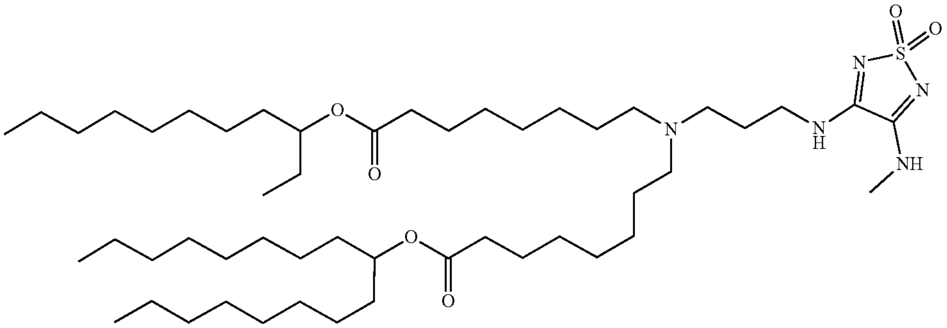 [SMILES: CCCCCCCCC(CC)OC(=O)CCCCCCCN(CCCCCCCC(=O)OC(CCCCCCCC)CCCCCCCC)CCCNC1=NS(=O)(=O)N=C1NC] |
| 3 | 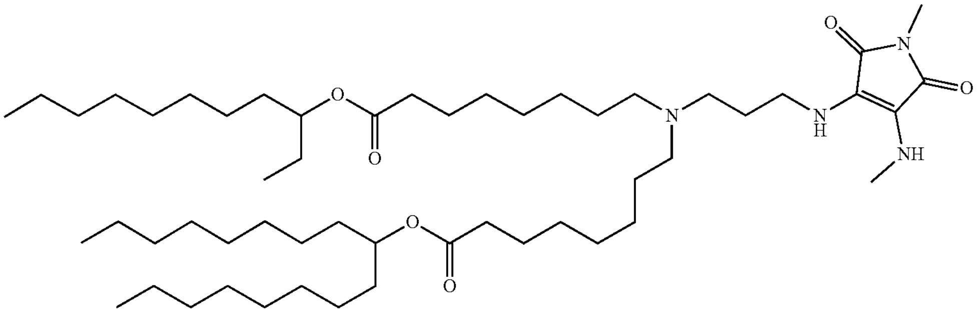 [SMILES: CCCCCCCCC(CC)OC(=O)CCCCCCCN(CCCCCCCC(=O)OC(CCCCCCCC)CCCCCCCC)CCCNC1=C(NC)C(=O)N(C)C1=O] |

-continued
| Cpd | Structure |
| --- | --- |
| 4 | 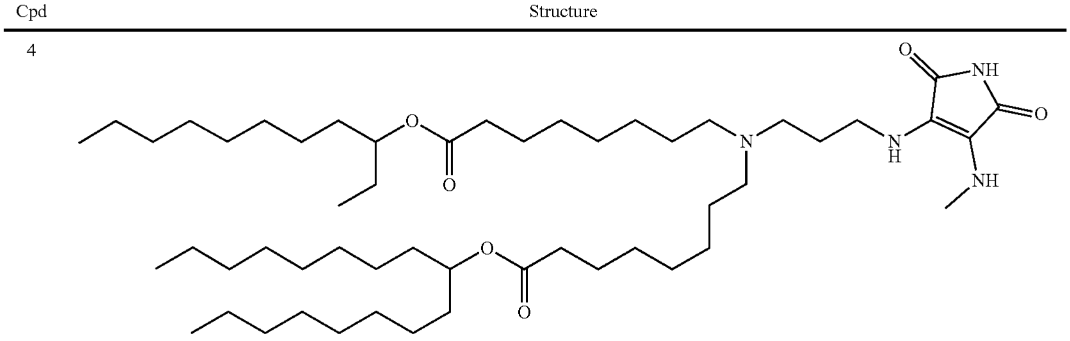 |
| 5 | 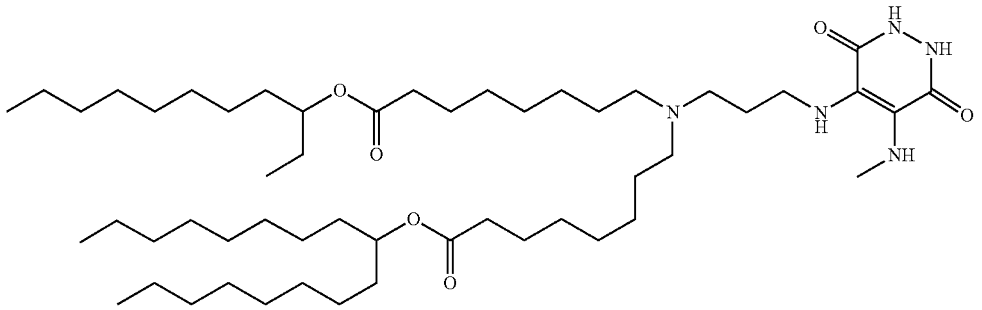 [SMILES: CCCCCCCCC(CC)OC(=O)CCCCCCCN(CCCCCCCC(=O)OC(CCCCCCCC)CCCCCCCC)CCCNc1c(NC)c(=O)[nH][nH]c1=O] |
| 6 | 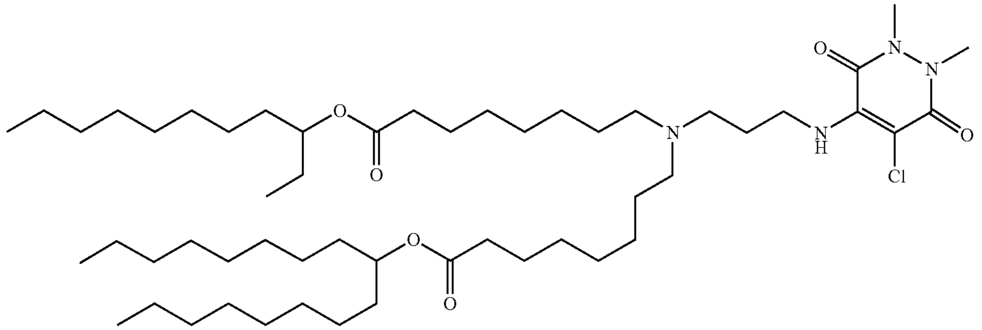 [SMILES: CCCCCCCCC(CC)OC(=O)CCCCCCCN(CCCCCCCC(=O)OC(CCCCCCCC)CCCCCCCC)CCCNc1c(Cl)c(=O)n(C)n(C)c1=O] |
| 7 | 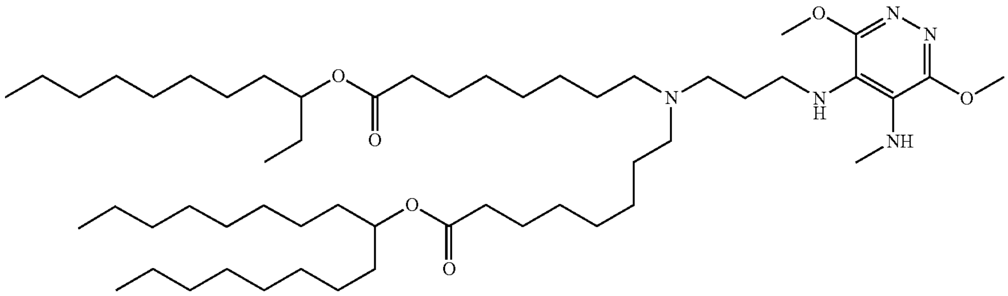 [SMILES: CCCCCCCCC(CC)OC(=O)CCCCCCCN(CCCCCCCC(=O)OC(CCCCCCCC)CCCCCCCC)CCCNc1c(OC)nnc(OC)c1NC] |
| 8 | 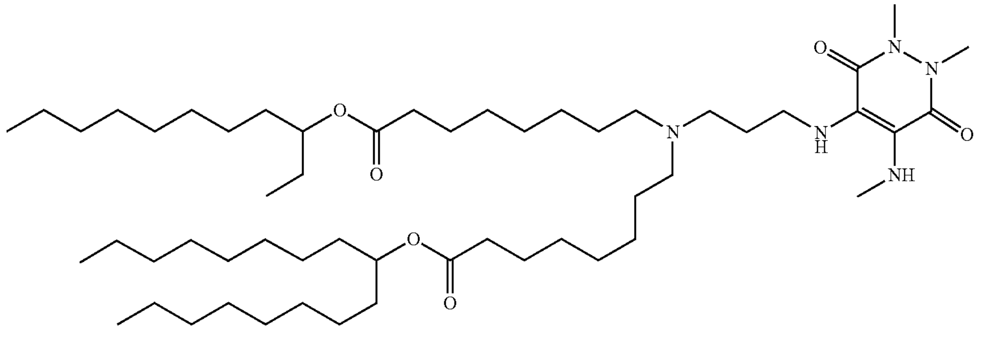 [SMILES: CCCCCCCCC(CC)OC(=O)CCCCCCCN(CCCCCCCC(=O)OC(CCCCCCCC)CCCCCCCC)CCCNc1c(NC)c(=O)n(C)n(C)c1=O] |

-continued
| Cpd | Structure |
|---|---|
| 9 | 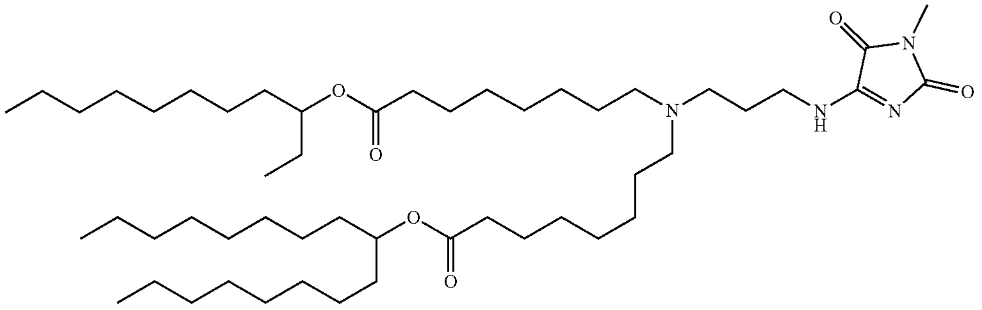 [SMILES: CCCCCCCCC(CC)OC(=O)CCCCCCCN(CCCCCCCC(=O)OC(CCCCCCCC)CCCCCCCC)CCCNC1=NC(=O)N(C)C1=O] |
| 10 | 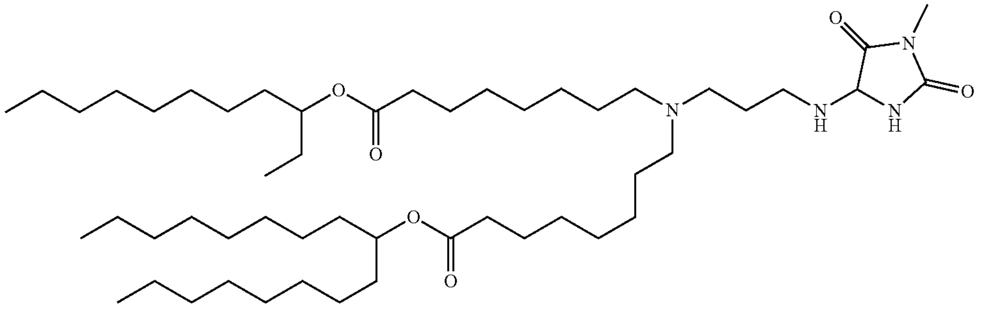 [SMILES: CCCCCCCCC(CC)OC(=O)CCCCCCCN(CCCCCCCC(=O)OC(CCCCCCCC)CCCCCCCC)CCCNC1NC(=O)N(C)C1=O] |
| 11 | 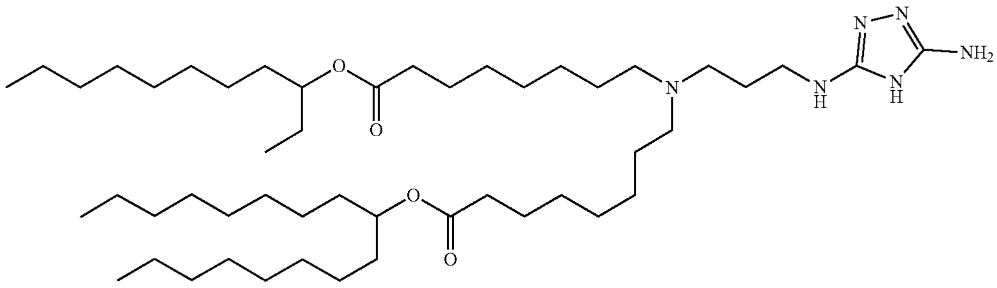 [SMILES: CCCCCCCCC(CC)OC(=O)CCCCCCCN(CCCCCCCC(=O)OC(CCCCCCCC)CCCCCCCC)CCCNc1nnc(N)[nH]1] |
| 12 | 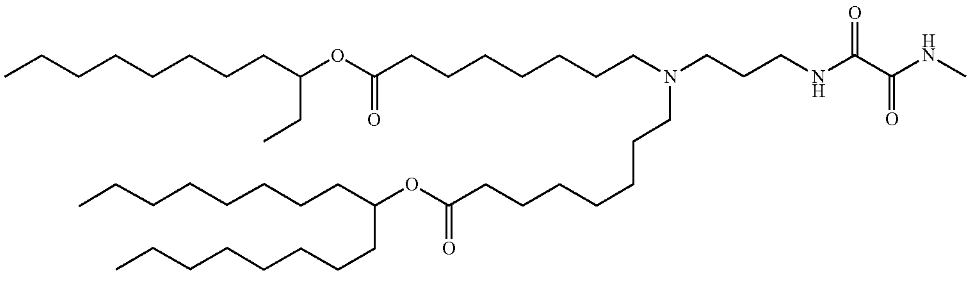 [SMILES: CCCCCCCCC(CC)OC(=O)CCCCCCCN(CCCCCCCC(=O)OC(CCCCCCCC)CCCCCCCC)CCCNC(=O)C(=O)NC] |
| 13 | 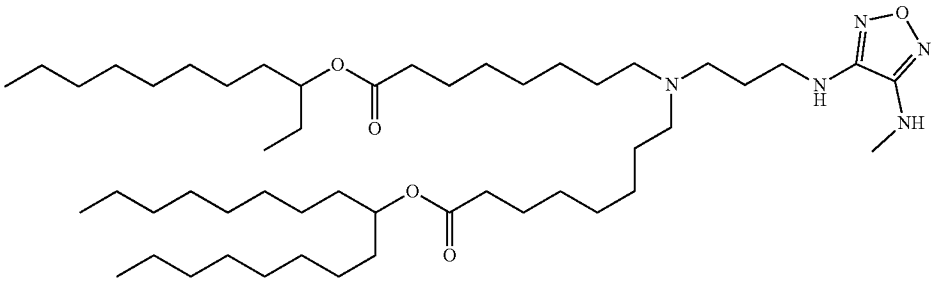 [SMILES: CCCCCCCCC(CC)OC(=O)CCCCCCCN(CCCCCCCC(=O)OC(CCCCCCCC)CCCCCCCC)CCCNc1nonc1NC] |

-continued
| Cpd | Structure |
| --- | --- |
| 14 | 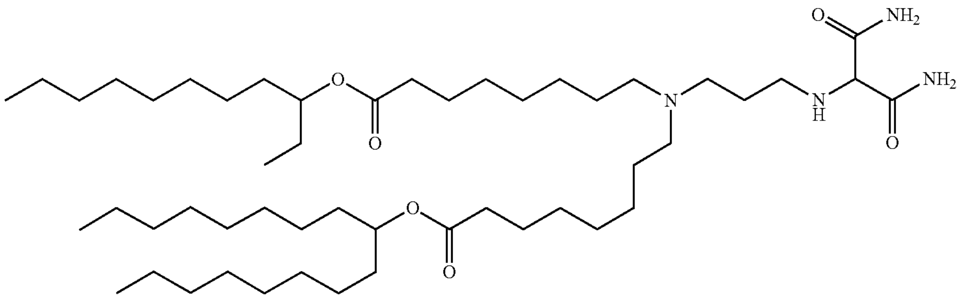 [SMILES: CCCCCCCCC(CC)OC(=O)CCCCCCCN(CCCCCCCC(=O)OC(CCCCCCCC)CCCCCCCC)CCCNC(C(N)=O)C(N)=O] |
| 15 | 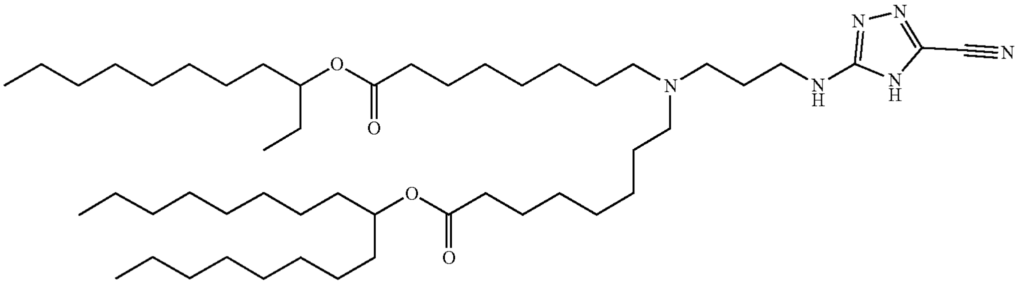 [SMILES: CCCCCCCCC(CC)OC(=O)CCCCCCCN(CCCCCCCC(=O)OC(CCCCCCCC)CCCCCCCC)CCCNc1nnc(C#N)[nH]1] |
| 16 | 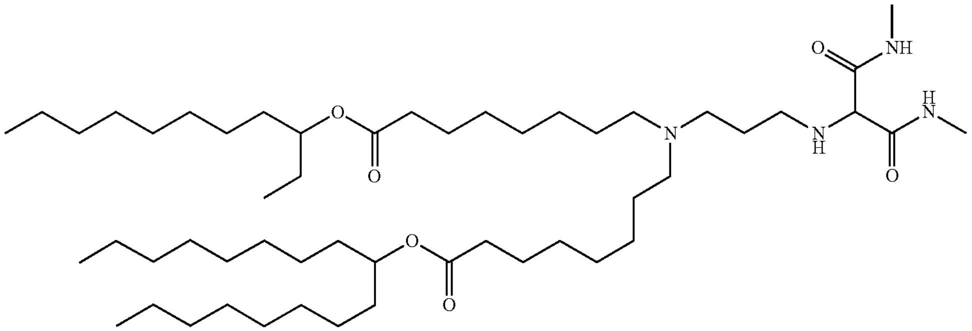 [SMILES: CCCCCCCCC(CC)OC(=O)CCCCCCCN(CCCCCCCC(=O)OC(CCCCCCCC)CCCCCCCC)CCCNC(C(=O)NC)C(=O)NC] |
| 17 | 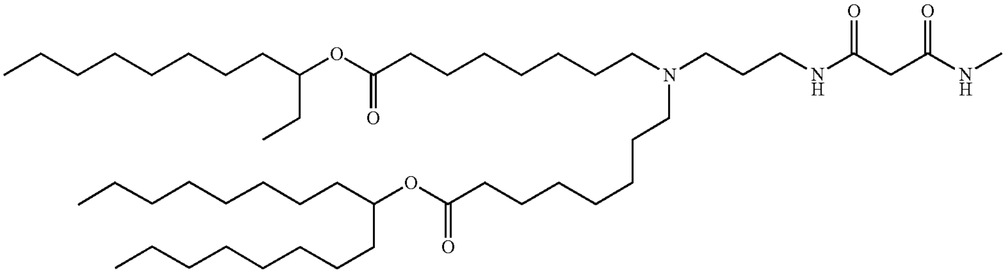 [SMILES: CCCCCCCCC(CC)OC(=O)CCCCCCCN(CCCCCCCC(=O)OC(CCCCCCCC)CCCCCCCC)CCCNC(=O)CC(=O)NC] |
| 18 | 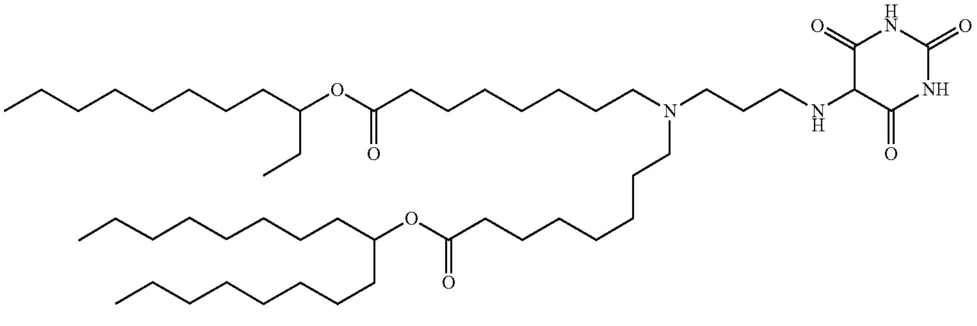 [SMILES: CCCCCCCCC(CC)OC(=O)CCCCCCCN(CCCCCCCC(=O)OC(CCCCCCCC)CCCCCCCC)CCCNC1C(=O)NC(=O)NC1=O] |

-continued
| Cpd | Structure |
|---|---|
| 19 | 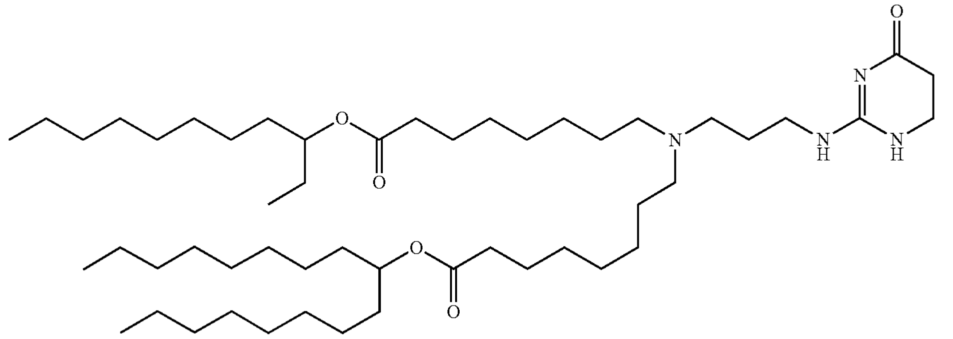 [SMILES: CCCCCCCCC(CC)OC(=O)CCCCCCCN(CCCCCCCC(=O)OC(CCCCCCCC)CCCCCCCC)CCCNC1=NC(=O)CCN1] |
| 20 | 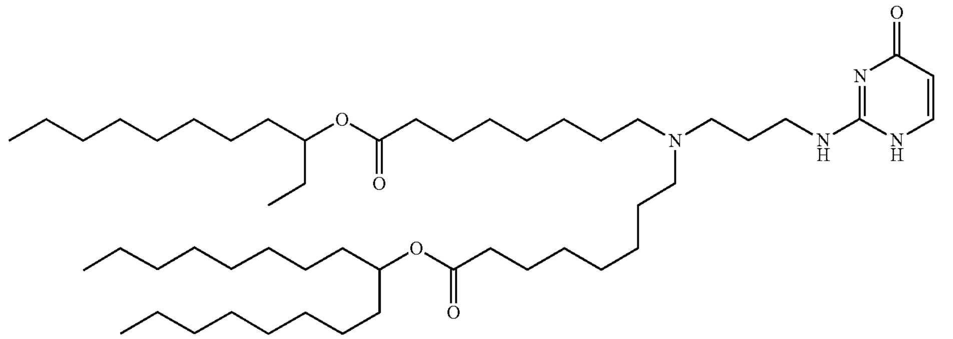 [SMILES: CCCCCCCCC(CC)OC(=O)CCCCCCCN(CCCCCCCC(=O)OC(CCCCCCCC)CCCCCCCC)CCCNc1nc(=O)cc[nH]1] |
| 21 | 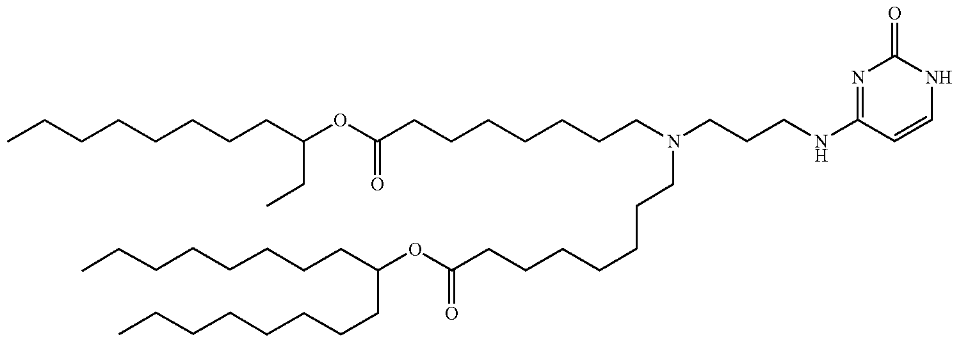 [SMILES: CCCCCCCCC(CC)OC(=O)CCCCCCCN(CCCCCCCC(=O)OC(CCCCCCCC)CCCCCCCC)CCCNc1cc[nH]c(=O)n1] |
| 22 | 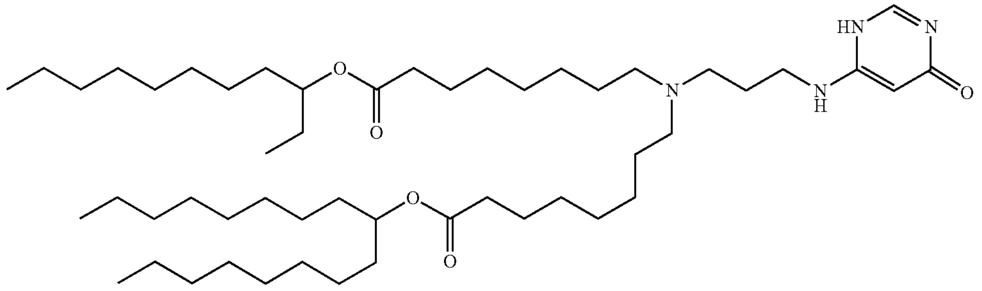 [SMILES: CCCCCCCCC(CC)OC(=O)CCCCCCCN(CCCCCCCC(=O)OC(CCCCCCCC)CCCCCCCC)CCCNc1cc(=O)nc[nH]1] |

-continued
| Cpd | Structure |
| --- | --- |
| 23 | 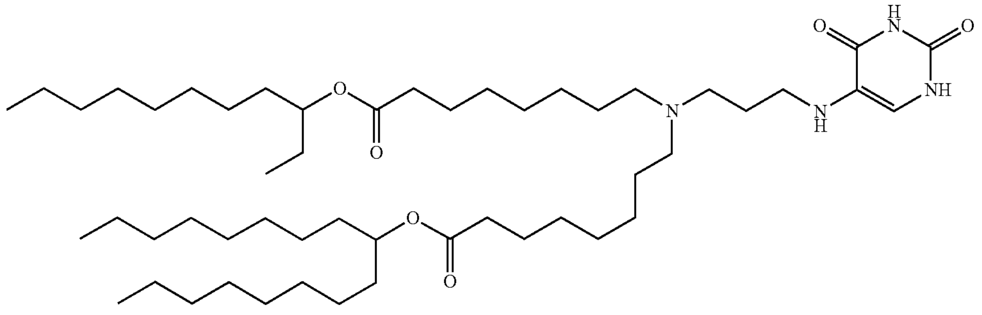 [SMILES: CCCCCCCCC(CC)OC(=O)CCCCCCCN(CCCCCCCC(=O)OC(CCCCCCCC)CCCCCCCC)CCCNc1c[nH]c(=O)[nH]c1=O] |
| 24 | 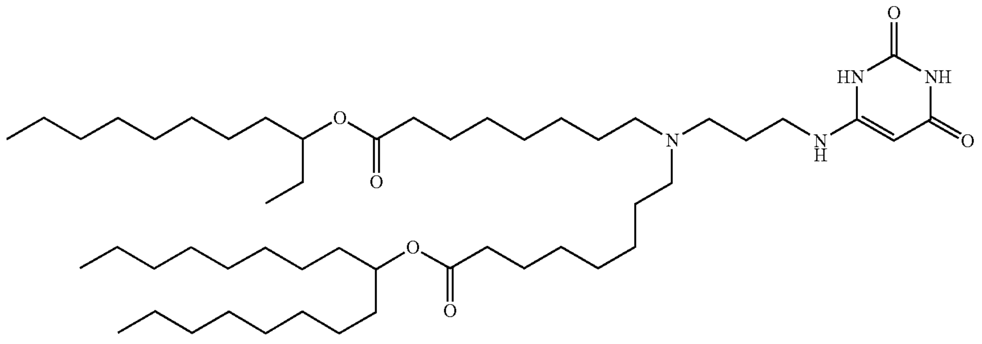 [SMILES: CCCCCCCCC(CC)OC(=O)CCCCCCCN(CCCCCCCC(=O)OC(CCCCCCCC)CCCCCCCC)CCCNc1cc(=O)[nH]c(=O)[nH]1] |
| 25 | 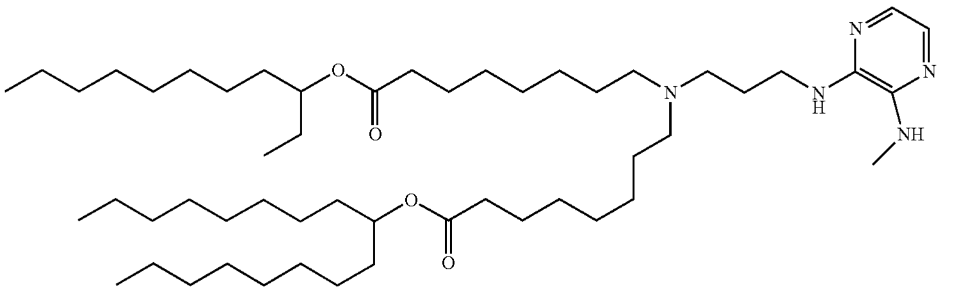 [SMILES: CCCCCCCCC(CC)OC(=O)CCCCCCCN(CCCCCCCC(=O)OC(CCCCCCCC)CCCCCCCC)CCCNc1nccnc1NC] |
| 26 | 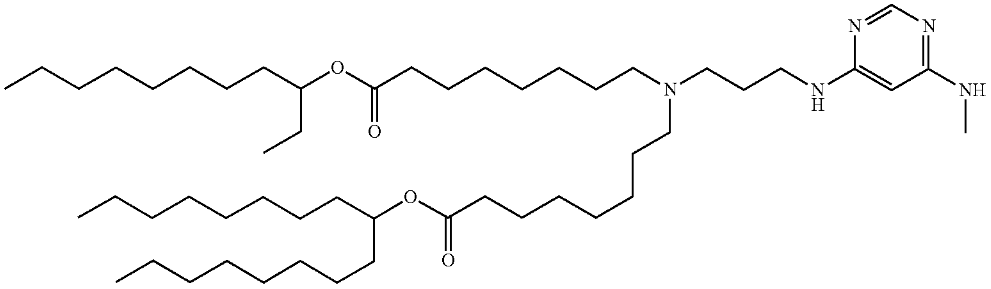 [SMILES: CCCCCCCCC(CC)OC(=O)CCCCCCCN(CCCCCCCC(=O)OC(CCCCCCCC)CCCCCCCC)CCCNc1cc(NC)ncn1] |
| 27 | 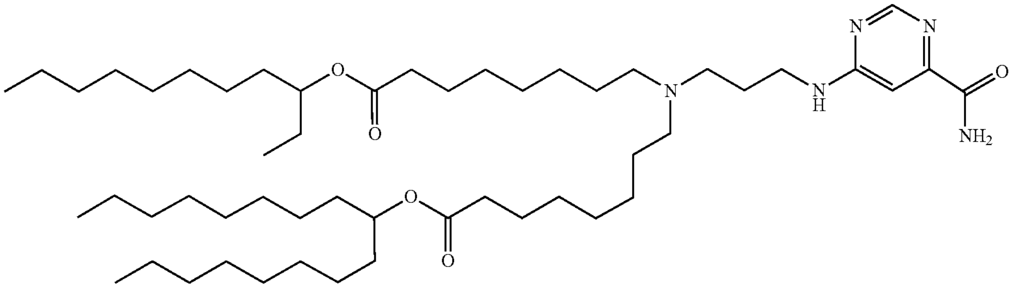 [SMILES: CCCCCCCCC(CC)OC(=O)CCCCCCCN(CCCCCCCC(=O)OC(CCCCCCCC)CCCCCCCC)CCCNc1cc(C(N)=O)ncn1] |

-continued
| Cpd | Structure |
|---|---|
| 28 | 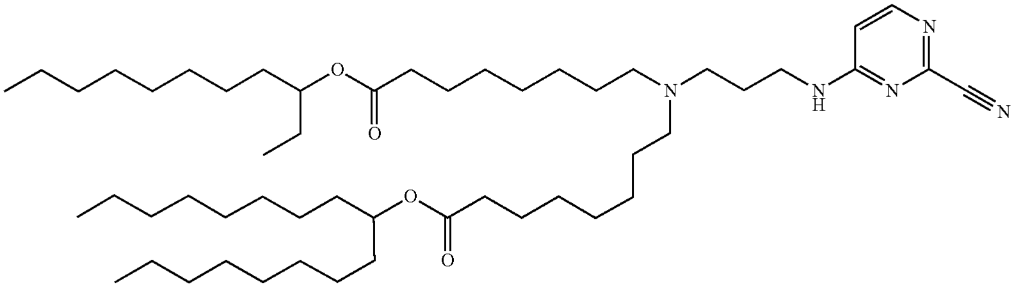 [SMILES: CCCCCCCCC(CC)OC(=O)CCCCCCCN(CCCCCCCC(=O)OC(CCCCCCCC)CCCCCCCC)CCCNc1ccnc(C#N)n1] |
| 29 | 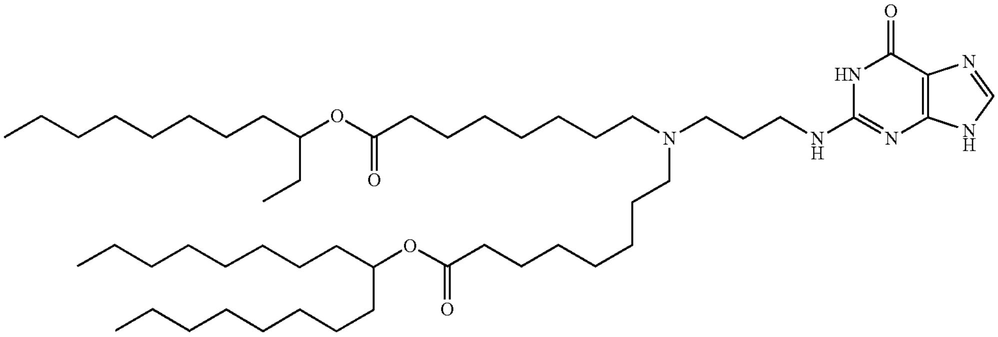 [SMILES: CCCCCCCCC(CC)OC(=O)CCCCCCCN(CCCCCCCC(=O)OC(CCCCCCCC)CCCCCCCC)CCCNc1nc2[nH]cnc2c(=O)[nH]1] |
| 30 | 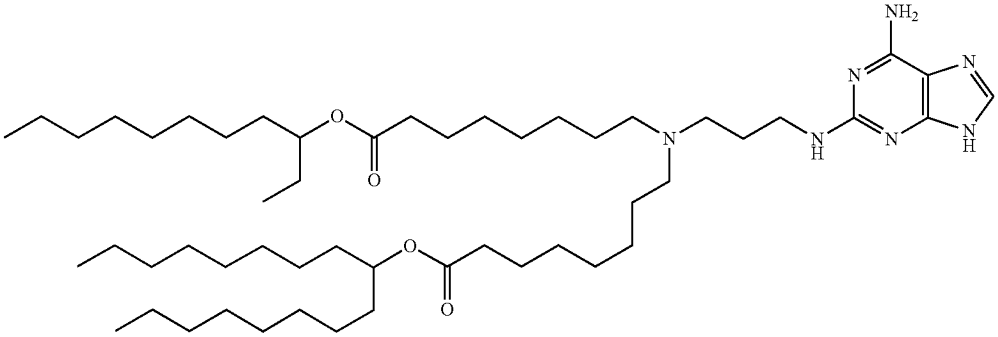 [SMILES: CCCCCCCCC(CC)OC(=O)CCCCCCCN(CCCCCCCC(=O)OC(CCCCCCCC)CCCCCCCC)CCCNc1nc(N)c2nc[nH]c2n1] |
| 31 | 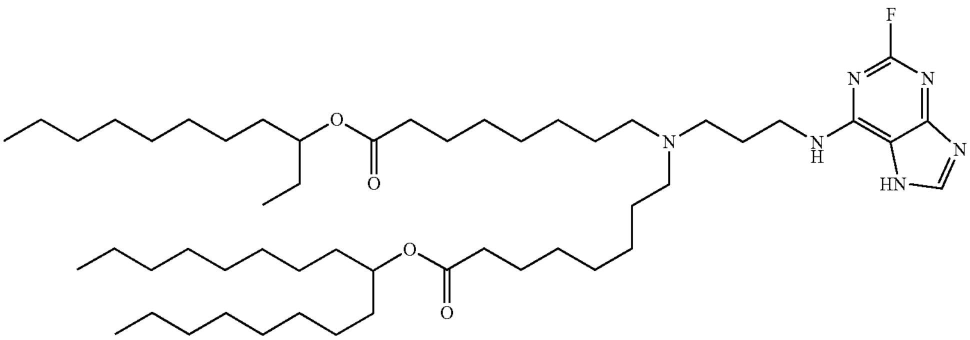 [SMILES: CCCCCCCCC(CC)OC(=O)CCCCCCCN(CCCCCCCC(=O)OC(CCCCCCCC)CCCCCCCC)CCCNc1nc(F)nc2nc[nH]c12] |

-continued
| Cpd | Structure |
| --- | --- |
| 32 | 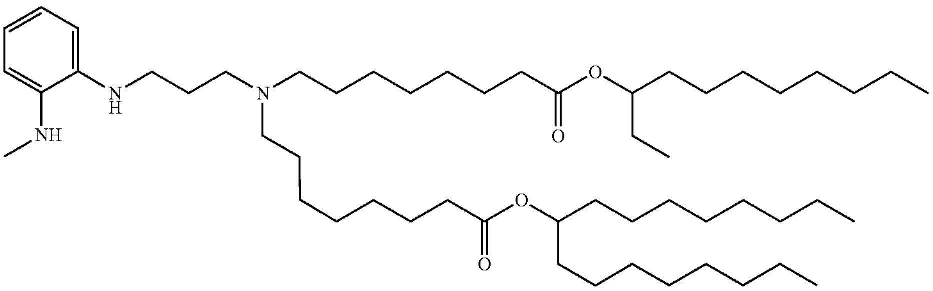 [SMILES: CCCCCCCCC(CC)OC(=O)CCCCCCCN(CCCCCCCC(=O)OC(CCCCCCCC)CCCCCCCC)CCCNc1ccccc1NC] |
| 33 | 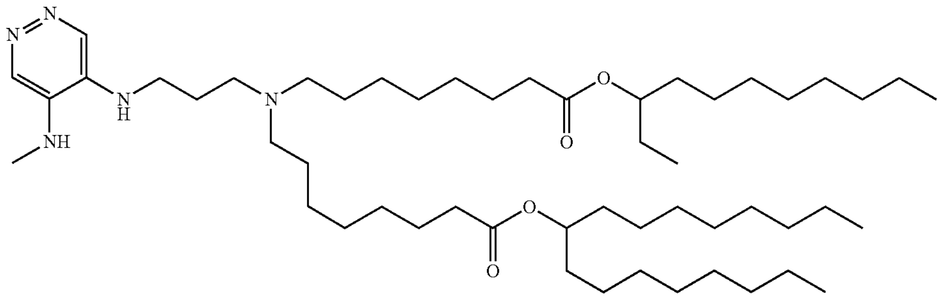 [SMILES: CCCCCCCCC(CC)OC(=O)CCCCCCCN(CCCCCCCC(=O)OC(CCCCCCCC)CCCCCCCC)CCCNc1cnncc1NC] |
| 34 | 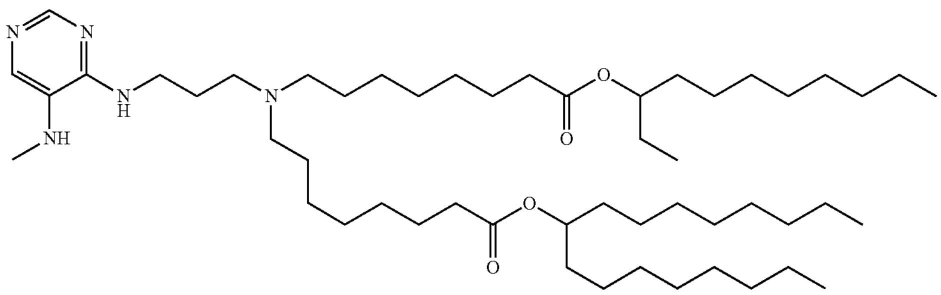 [SMILES: CCCCCCCCC(CC)OC(=O)CCCCCCCN(CCCCCCCC(=O)OC(CCCCCCCC)CCCCCCCC)CCCNc1ncncc1NC] |
| 35 | 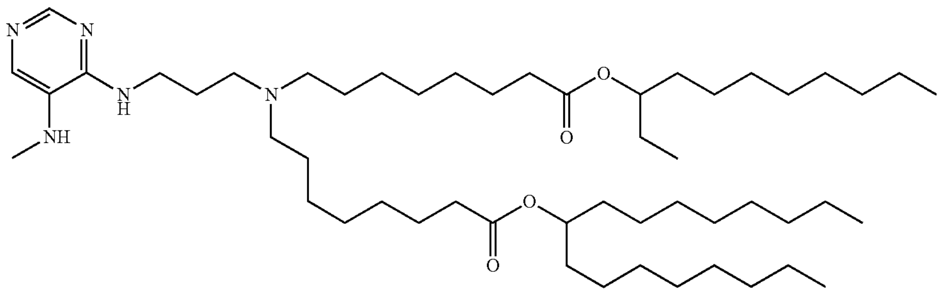 [SMILES: CCCCCCCCC(CC)OC(=O)CCCCCCCN(CCCCCCCC(=O)OC(CCCCCCCC)CCCCCCCC)CCCNc1ncncc1NC] |
| 36 | 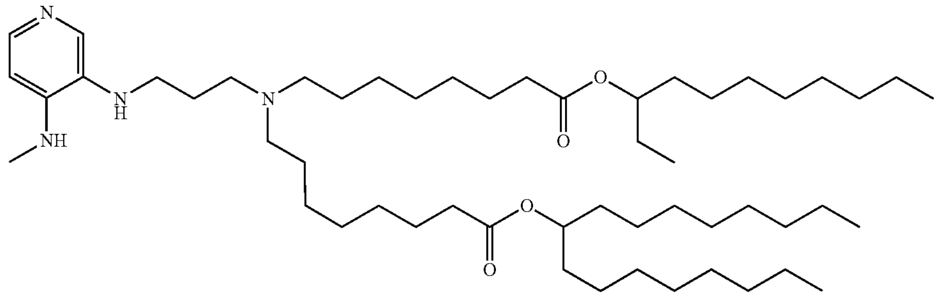 [SMILES: CCCCCCCCC(CC)OC(=O)CCCCCCCN(CCCCCCCC(=O)OC(CCCCCCCC)CCCCCCCC)CCCNc1cnccc1NC] |

-continued
| Cpd | Structure |
|---|---|
| 37 | 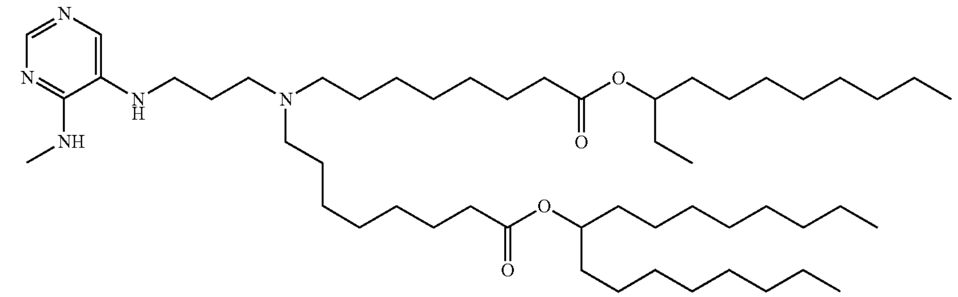 |
| 38 | 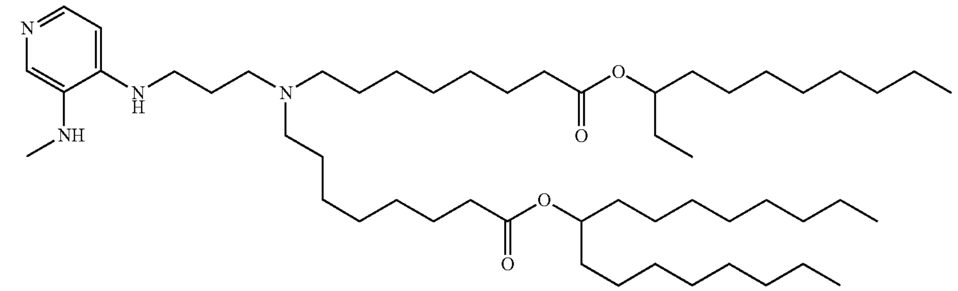 [SMILES: CCCCCCCCC(CC)OC(=O)CCCCCCCN(CCCCCCCC(=O)OC(CCCCCCCC)CCCCCCCC)CCCNc1ccncc1NC] |
| 39 | 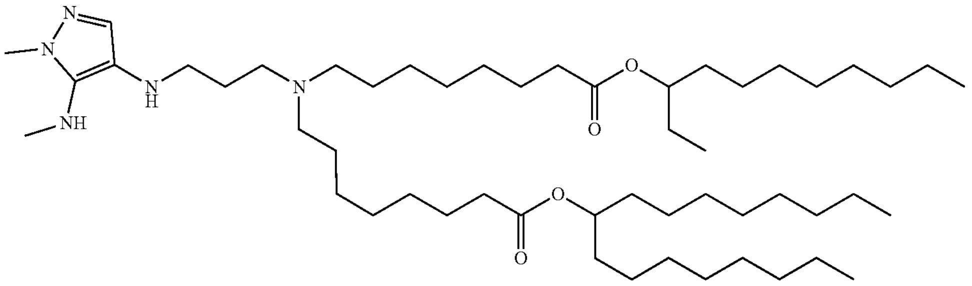 [SMILES: CCCCCCCCC(CC)OC(=O)CCCCCCCN(CCCCCCCC(=O)OC(CCCCCCCC)CCCCCCCC)CCCNc1cnn(C)c1NC] |
| 40 | 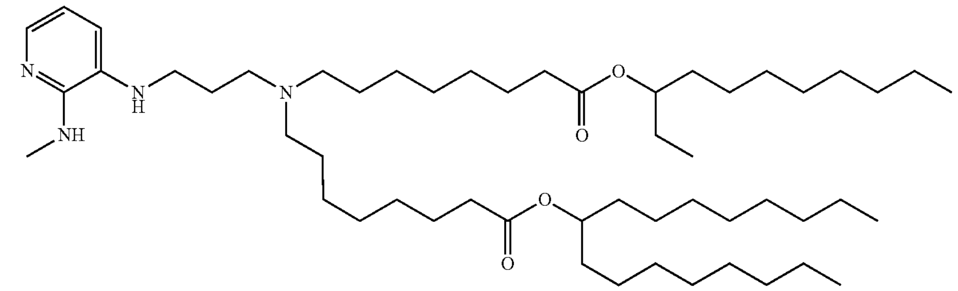 [SMILES: CCCCCCCCC(CC)OC(=O)CCCCCCCN(CCCCCCCC(=O)OC(CCCCCCCC)CCCCCCCC)CCCNc1cccnc1NC] |
| 41 | 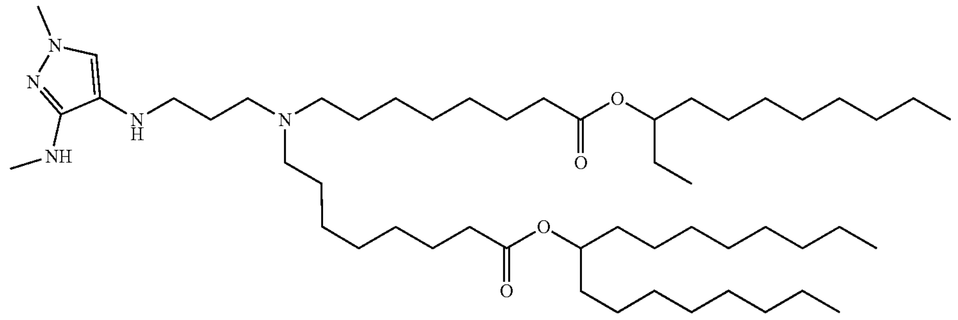 [SMILES: CCCCCCCCC(CC)OC(=O)CCCCCCCN(CCCCCCCC(=O)OC(CCCCCCCC)CCCCCCCC)CCCNc1cn(C)nc1NC] |

-continued
| Cpd | Structure |
| --- | --- |
| 42 | 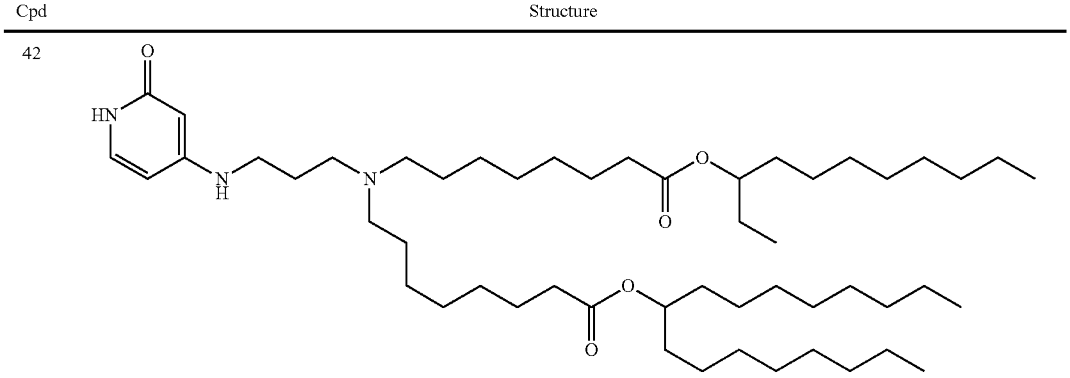 |
| 43 | 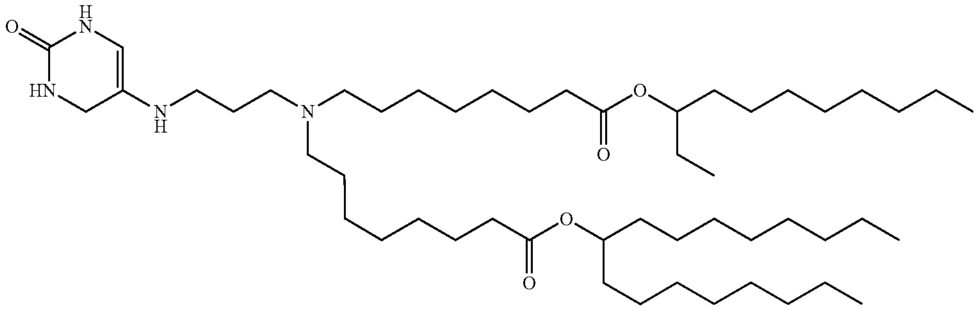 [SMILES: CCCCCCCCC(CC)OC(=O)CCCCCCCN(CCCCCCCC(=O)OC(CCCCCCCC)CCCCCCCC)CCCNC1=CNC(=O)NC1] |
| 44 | 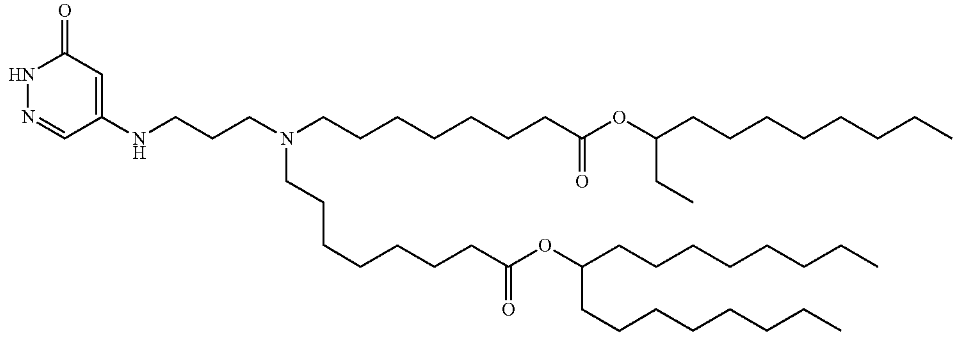 [SMILES: CCCCCCCCC(CC)OC(=O)CCCCCCCN(CCCCCCCC(=O)OC(CCCCCCCC)CCCCCCCC)CCCNc1cn[nH]c(=O)c1] |
| 45 | 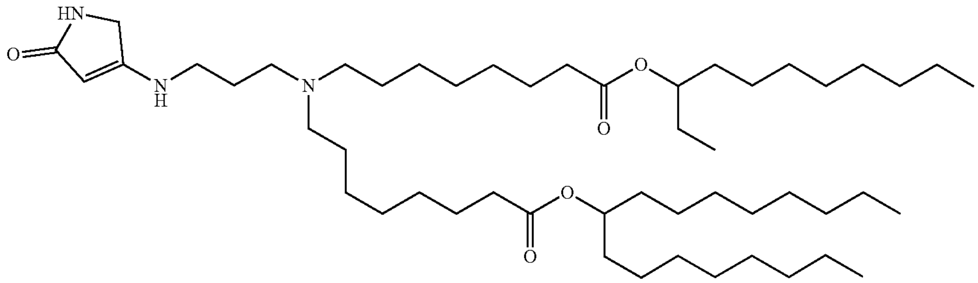 [SMILES: CCCCCCCCC(CC)OC(=O)CCCCCCCN(CCCCCCCC(=O)OC(CCCCCCCC)CCCCCCCC)CCCNC1=CC(=O)NC1] |
| 46 | 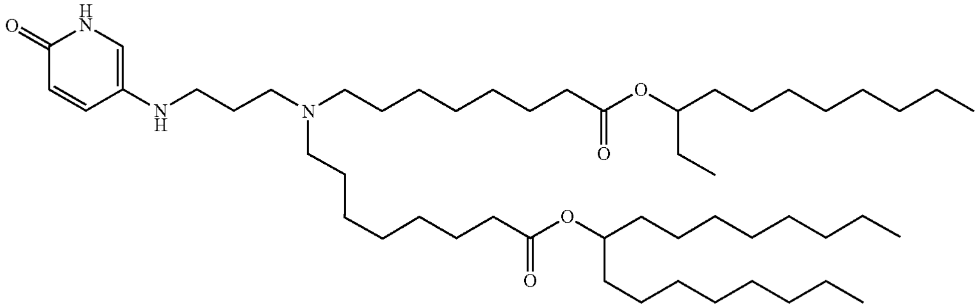 [SMILES: CCCCCCCCC(CC)OC(=O)CCCCCCCN(CCCCCCCC(=O)OC(CCCCCCCC)CCCCCCCC)CCCNc1ccc(=O)[nH]c1] |

-continued
| Cpd | Structure |
| --- | --- |
| 47 | 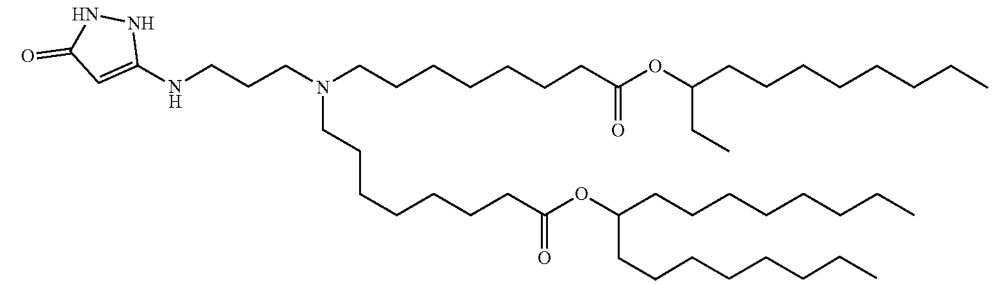 [SMILES: CCCCCCCCC(CC)OC(=O)CCCCCCCN(CCCCCCCC(=O)OC(CCCCCCCC)CCCCCCCC)CCCNc1cc(=O)[nH][nH]1] |
| 48 | 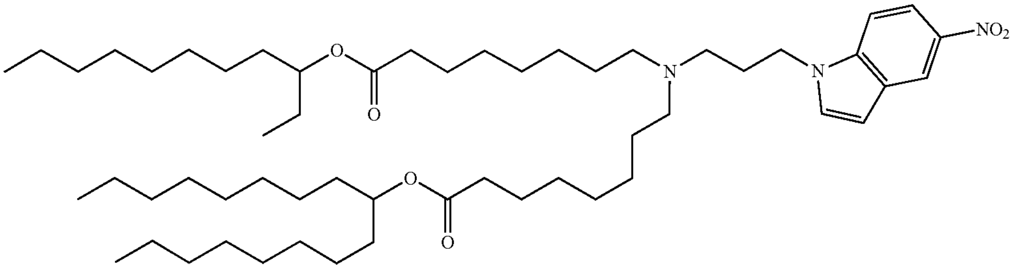 [SMILES: CCCCCCCCC(CC)OC(=O)CCCCCCCN(CCCCCCCC(=O)OC(CCCCCCCC)CCCCCCCC)CCCn1ccc2cc([N+](=O)[O-])ccc21] |
| 49 | 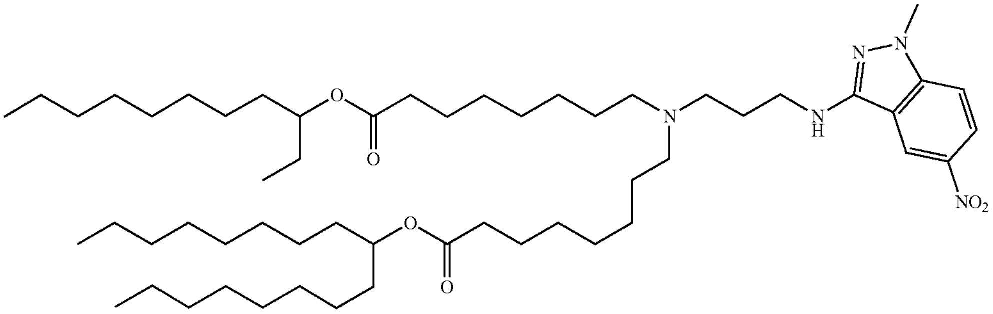 [SMILES: CCCCCCCCC(CC)OC(=O)CCCCCCCN(CCCCCCCC(=O)OC(CCCCCCCC)CCCCCCCC)CCCNc1nn(C)c2ccc([N+](=O)[O-])cc12] |
| 50 | 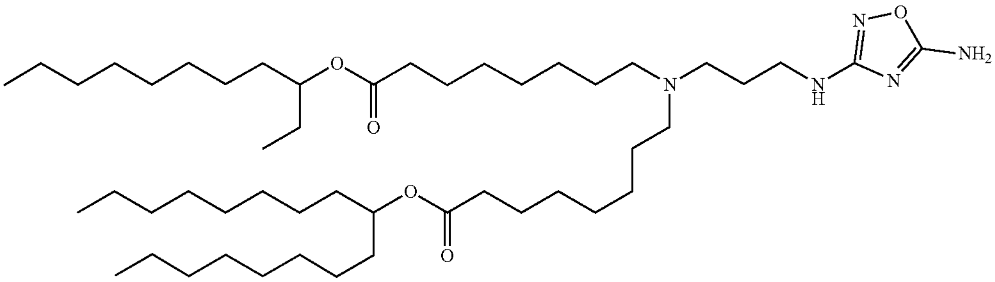 [SMILES: CCCCCCCCC(CC)OC(=O)CCCCCCCN(CCCCCCCC(=O)OC(CCCCCCCC)CCCCCCCC)CCCNc1noc(N)n1] |
| 51 | 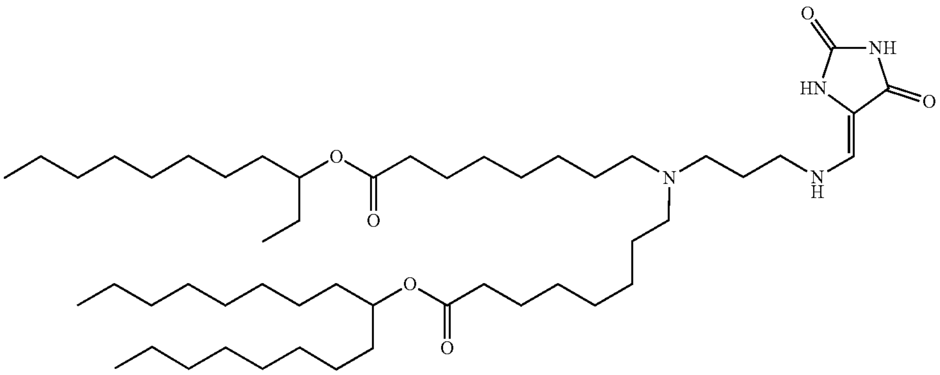 [SMILES: CCCCCCCCC(CC)OC(=O)CCCCCCCN(CCCCCCCC(=O)OC(CCCCCCCC)CCCCCCCC)CCCN/C=C1\NC(=O)NC1=O] |

-continued
| Cpd | Structure |
| --- | --- |
| 52 | 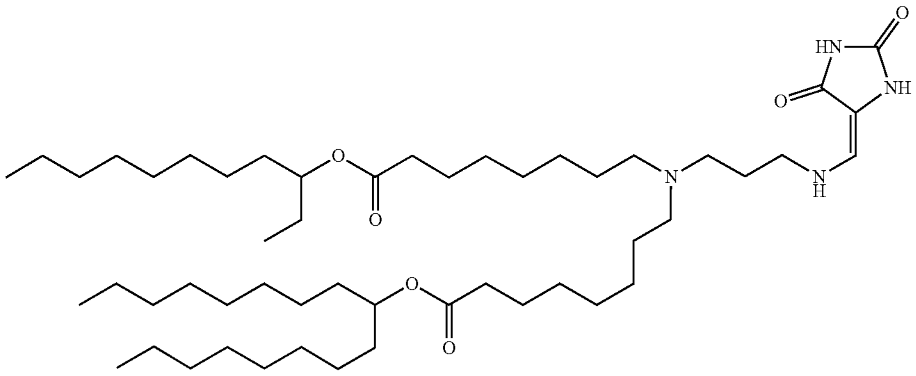 [SMILES: CCCCCCCCC(CC)OC(=O)CCCCCCCN(CCCCCCCC(=O)OC(CCCCCCCC)CCCCCCCC)CCCN/C=C1/NC(=O)NC1=O] |
| 53 | 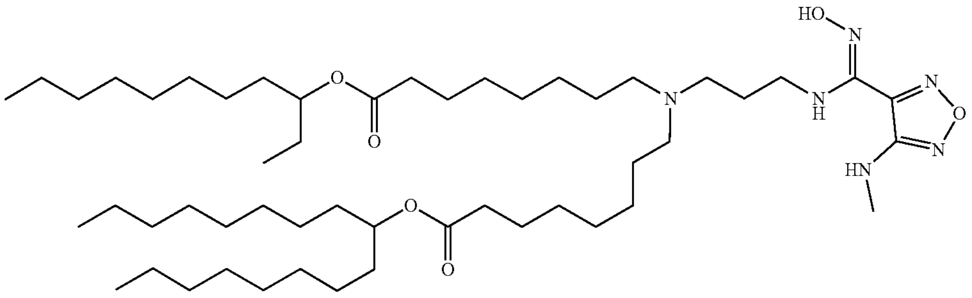 [SMILES: CCCCCCCCC(CC)OC(=O)CCCCCCCN(CCCCCCCC(=O)OC(CCCCCCCC)CCCCCCCC)CCCN/C(=N\O)c1nonc1NC] |
| 54 | 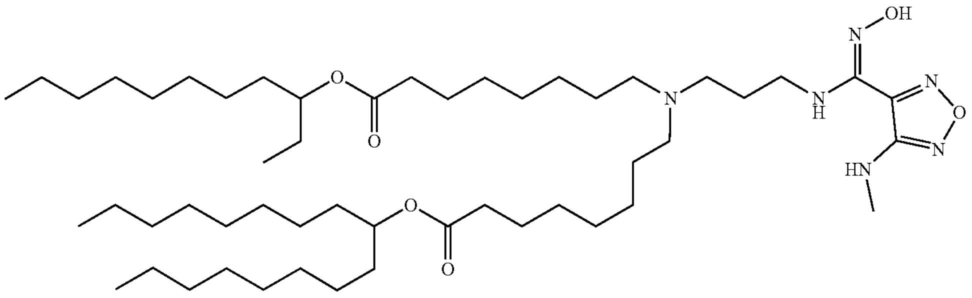 [SMILES: CCCCCCCCC(CC)OC(=O)CCCCCCCN(CCCCCCCC(=O)OC(CCCCCCCC)CCCCCCCC)CCCN/C(=N/O)c1nonc1NC] |
| 55 | 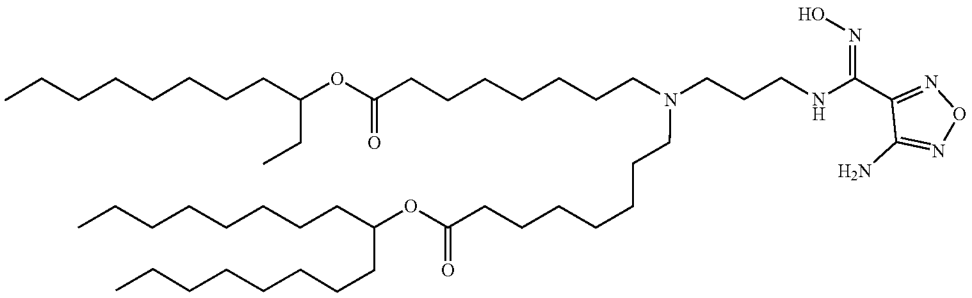 [SMILES: CCCCCCCCC(CC)OC(=O)CCCCCCCN(CCCCCCCC(=O)OC(CCCCCCCC)CCCCCCCC)CCCN/C(=N\O)c1nonc1N] |
| 56 | 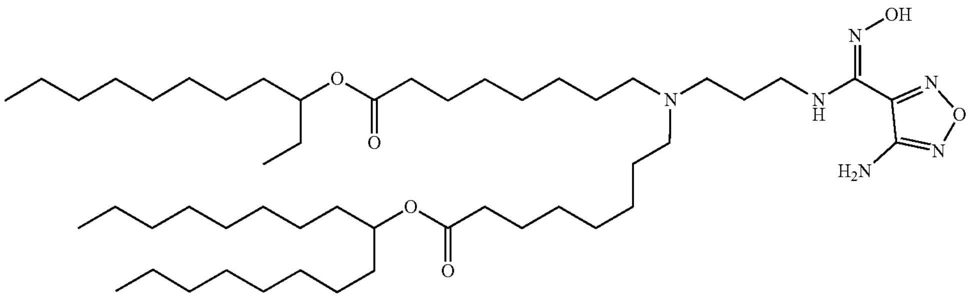 [SMILES: CCCCCCCCC(CC)OC(=O)CCCCCCCN(CCCCCCCC(=O)OC(CCCCCCCC)CCCCCCCC)CCCN/C(=N/O)c1nonc1N] |

-continued
| Cpd | Structure |
|---|---|
| 57 | 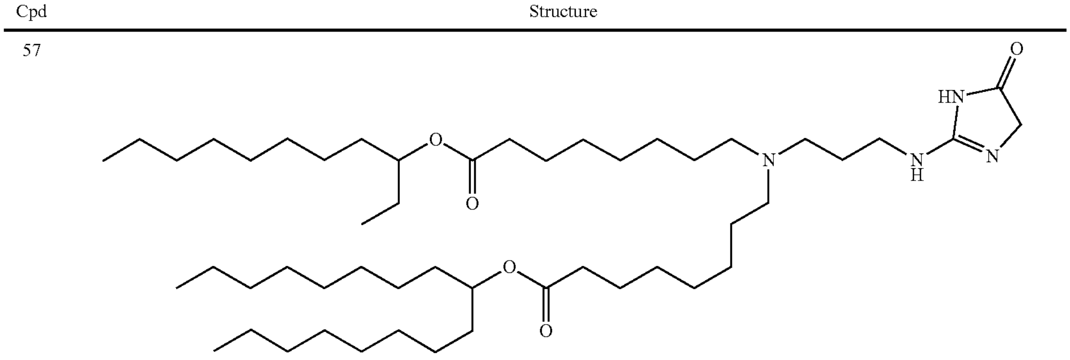 |
Embodiment 78. A compound selected from:
| | |
|---|---|
| 58 | 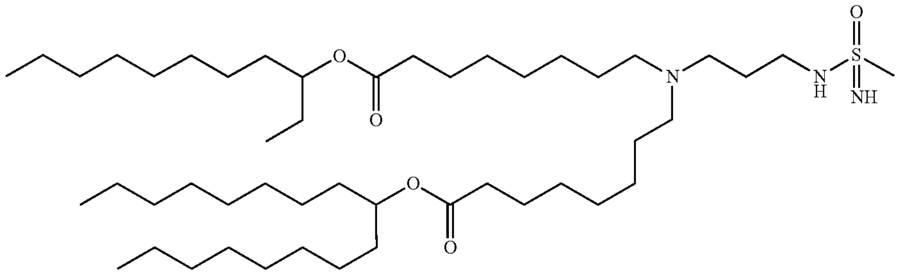 [SMILES: CCCCCCCCC(CC)OC(=O)CCCCCCCN(CCCCCCCC(=O)OC(CCCCCCCC)CCCCCCCC)CCCNS(C)(=N)=O] |
| 59 | 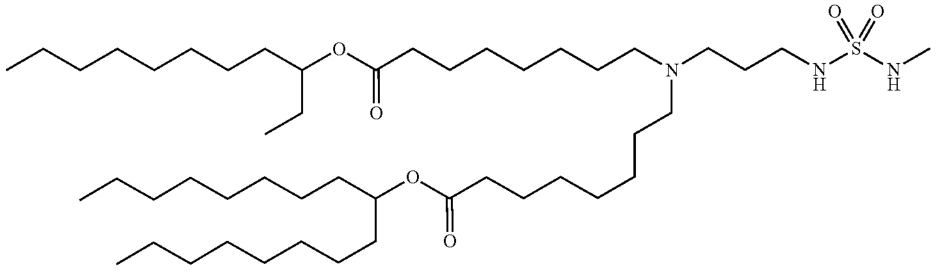 [SMILES: CCCCCCCCC(CC)OC(=O)CCCCCCCN(CCCCCCCC(=O)OC(CCCCCCCC)CCCCCCCC)CCCNS(=O)(=O)NC] |
| 60 | 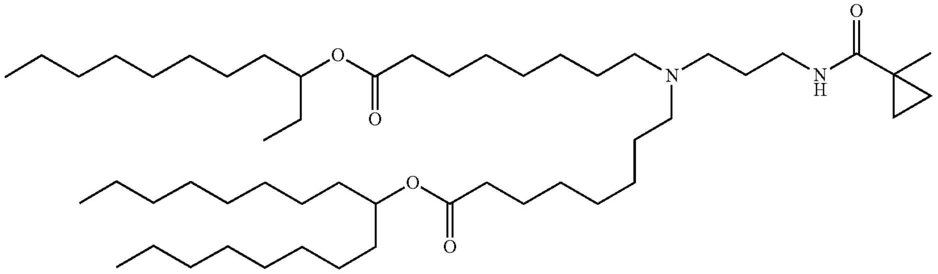 [SMILES: CCCCCCCCC(CC)OC(=O)CCCCCCCN(CCCCCCCC(=O)OC(CCCCCCCC)CCCCCCCC)CCCNC(=O)C1(C)CC1] |
| 61 | 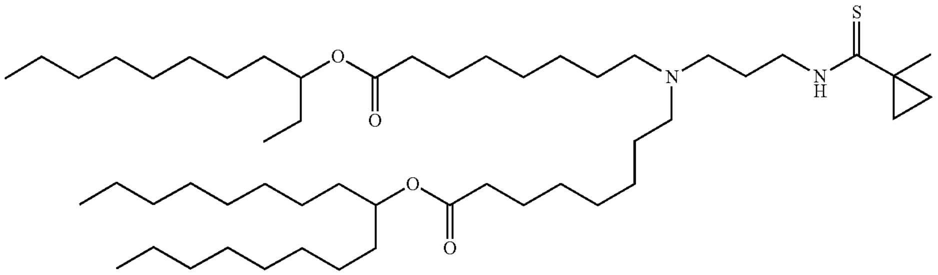 [SMILES: CCCCCCCCC(CC)OC(=O)CCCCCCCN(CCCCCCCC(=O)OC(CCCCCCCC)CCCCCCCC)CCCNC(=S)C1(C)CC1] |

-continued
62
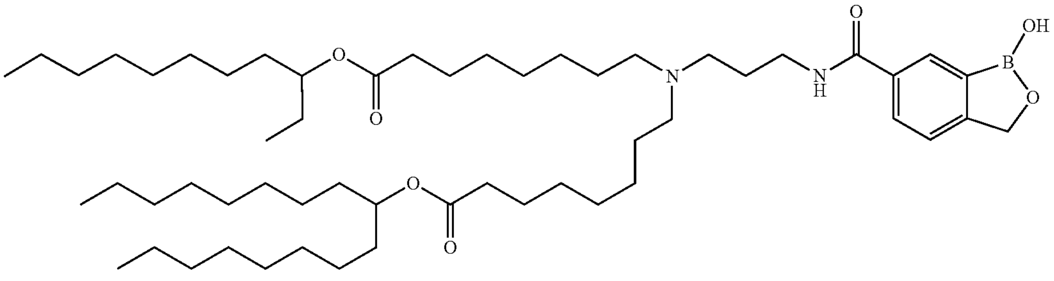 [SMILES: CCCCCCCCC(CC)OC(=O)CCCCCCCN(CCCCCCCC(=O)OC(CCCCCCCC)CCCCCCCC)CCCNC(=O)c1ccc2c(c1)B(O)OC2]
63
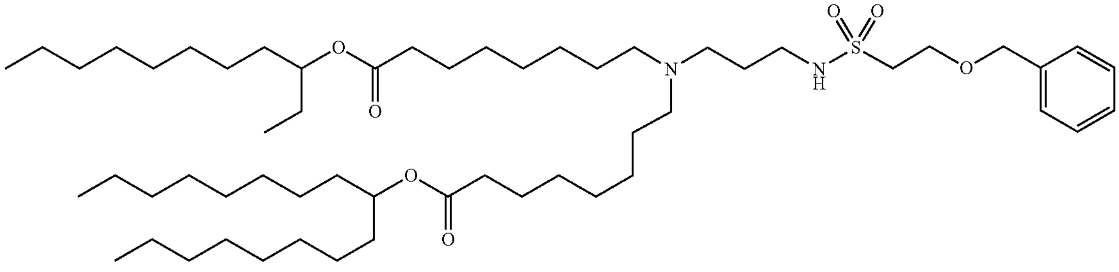 [SMILES: CCCCCCCCC(CC)OC(=O)CCCCCCCN(CCCCCCCC(=O)OC(CCCCCCCC)CCCCCCCC)CCCNS(=O)(=O)CCOCc1ccccc1]
64
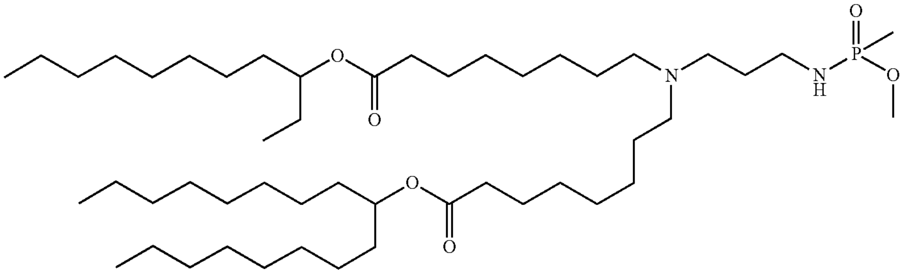 [SMILES: CCCCCCCCC(CC)OC(=O)CCCCCCCN(CCCCCCCC(=O)OC(CCCCCCCC)CCCCCCCC)CCCNP(C)(=O)OC]
65
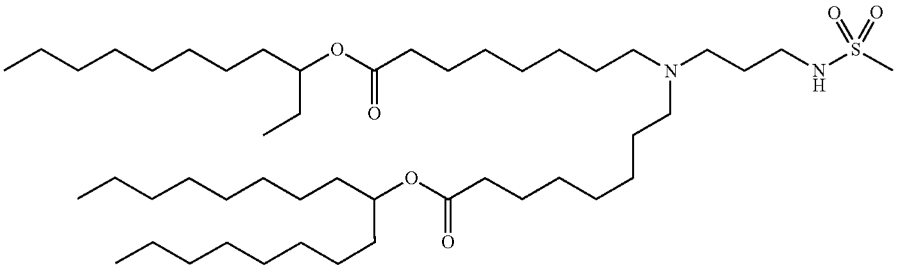 [SMILES: CCCCCCCCC(CC)OC(=O)CCCCCCCN(CCCCCCCC(=O)OC(CCCCCCCC)CCCCCCCC)CCCNS(C)(=O)=O]
66
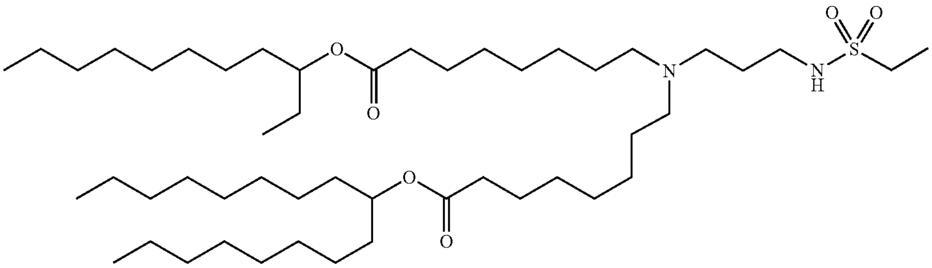 [SMILES: CCCCCCCCC(CC)OC(=O)CCCCCCCN(CCCCCCCC(=O)OC(CCCCCCCC)CCCCCCCC)CCCNS(=O)(=O)CC]

-continued
67
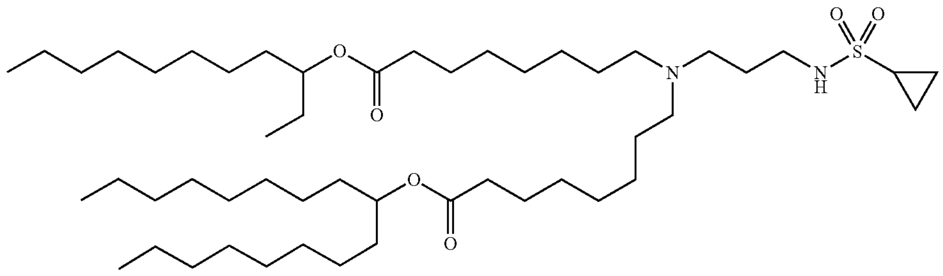 [SMILES: CCCCCCCCC(CC)OC(=O)CCCCCCCN(CCCCCCCC(=O)OC(CCCCCCCC)CCCCCCCC)CCCNS(=O)(=O)C1CC1]
68
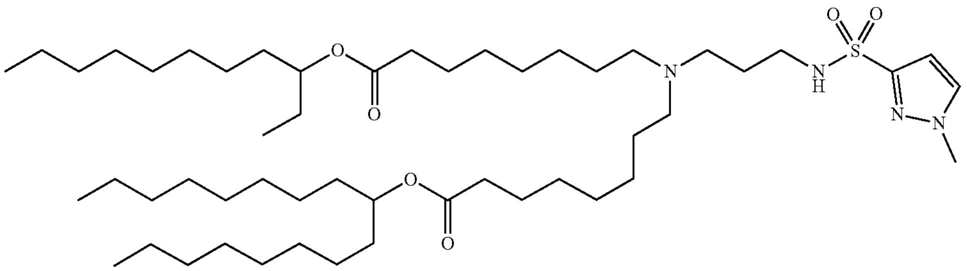 [SMILES: CCCCCCCCC(CC)OC(=O)CCCCCCCN(CCCCCCCC(=O)OC(CCCCCCCC)CCCCCCCC)CCCNS(=O)(=O)c1ccn(C)n1]
69
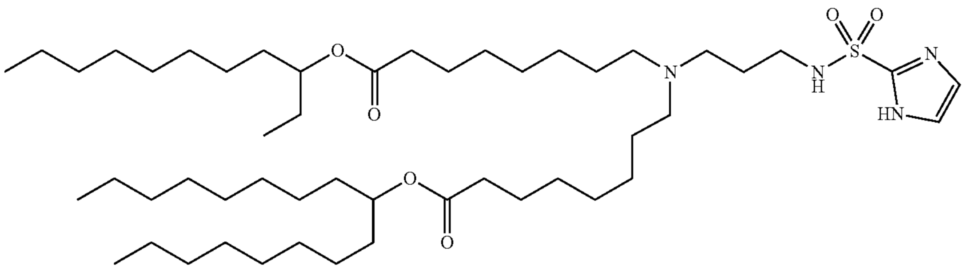 [SMILES: CCCCCCCCC(CC)OC(=O)CCCCCCCN(CCCCCCCC(=O)OC(CCCCCCCC)CCCCCCCC)CCCNS(=O)(=O)c1ncc[nH]1]
70
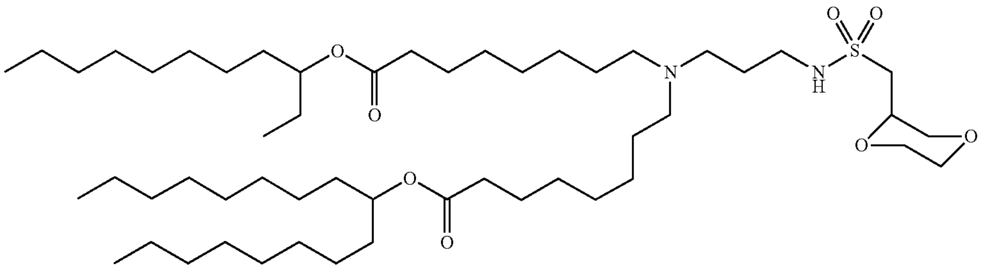 [SMILES: CCCCCCCCC(CC)OC(=O)CCCCCCCN(CCCCCCCC(=O)OC(CCCCCCCC)CCCCCCCC)CCCNS(=O)(=O)CC1COCCO1]
71
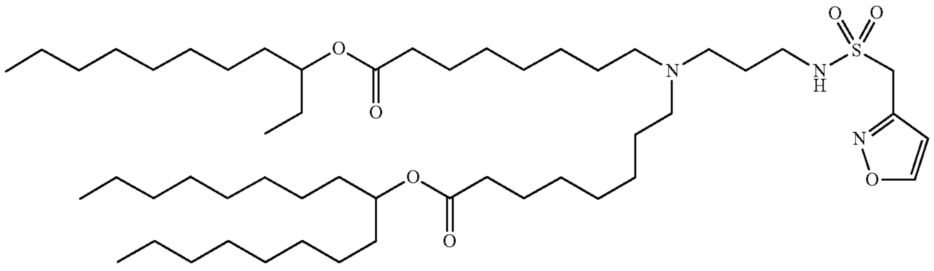 [SMILES: CCCCCCCCC(CC)OC(=O)CCCCCCCN(CCCCCCCC(=O)OC(CCCCCCCC)CCCCCCCC)CCCNS(=O)(=O)Cc1ccon1]

-continued
72
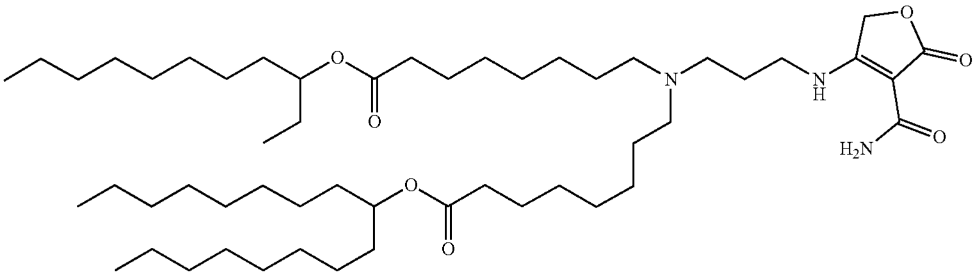 [SMILES: CCCCCCCCC(CC)OC(=O)CCCCCCCN(CCCCCCCC(=O)OC(CCCCCCCC)CCCCCCCC)CCCNC1=C(C(N)=O)C(=O)OC1]
73
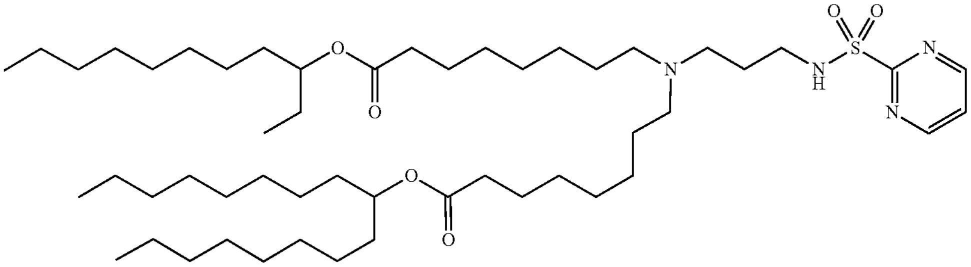 [SMILES: CCCCCCCCC(CC)OC(=O)CCCCCCCN(CCCCCCCC(=O)OC(CCCCCCCC)CCCCCCCC)CCCNS(=O)(=O)c1ncccn1]
74
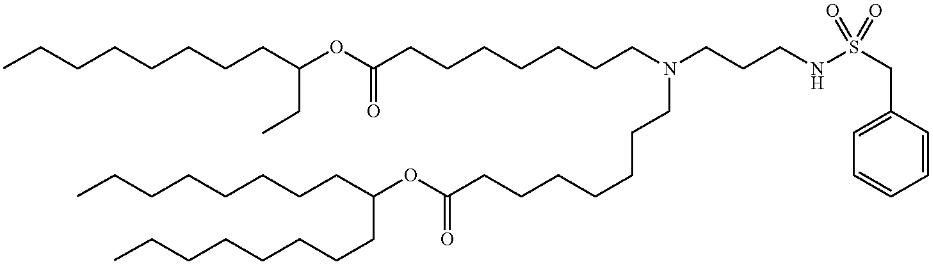 [SMILES: CCCCCCCCC(CC)OC(=O)CCCCCCCN(CCCCCCCC(=O)OC(CCCCCCCC)CCCCCCCC)CCCNS(=O)(=O)Cc1ccccc1]
75
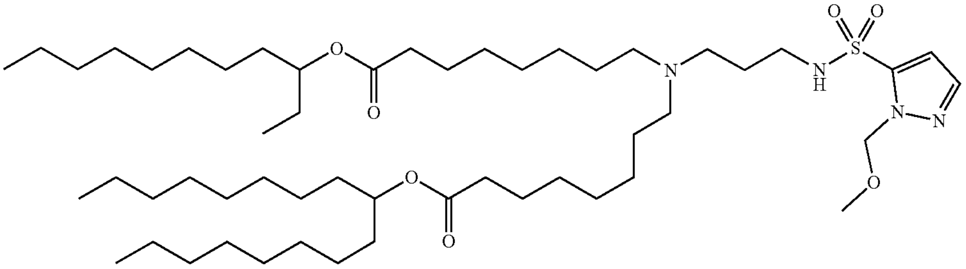 [SMILES: CCCCCCCCC(CC)OC(=O)CCCCCCCN(CCCCCCCC(=O)OC(CCCCCCCC)CCCCCCCC)CCCNS(=O)(=O)c1ccnn1COC]
76
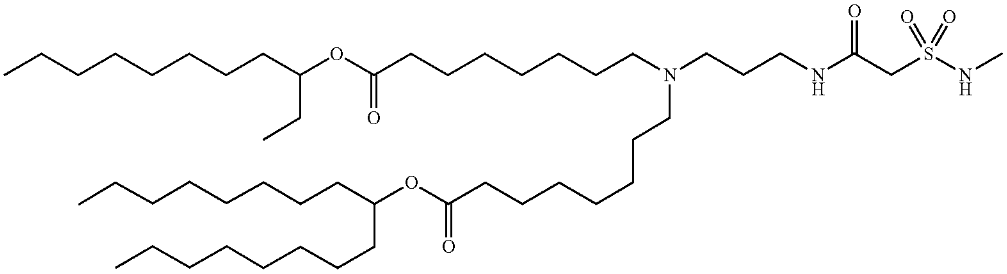 [SMILES: CCCCCCCCC(CC)OC(=O)CCCCCCCN(CCCCCCCC(=O)OC(CCCCCCCC)CCCCCCCC)CCCNC(=O)CS(=O)(=O)NC]

-continued
77
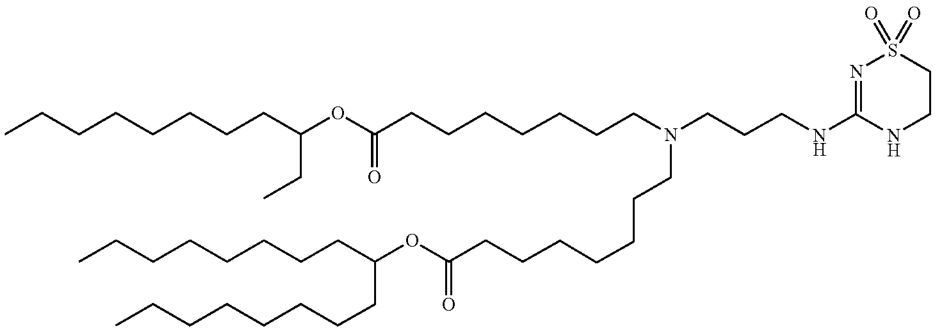 [SMILES: CCCCCCCCC(CC)OC(=O)CCCCCCCN(CCCCCCCC(=O)OC(CCCCCCCC)CCCCCCCC)CCCNC1=NS(=O)(=O)CCN1]
78
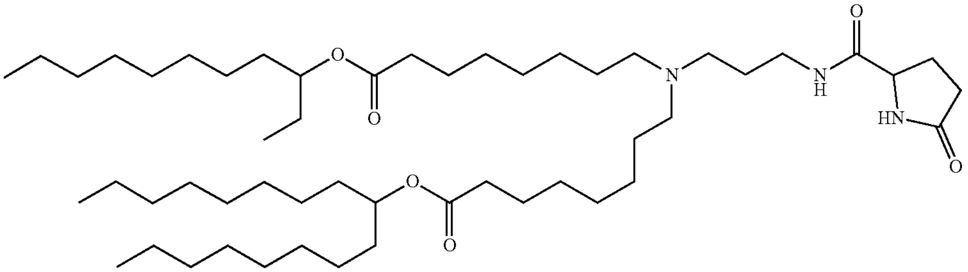 [SMILES: CCCCCCCCC(CC)OC(=O)CCCCCCCN(CCCCCCCC(=O)OC(CCCCCCCC)CCCCCCCC)CCCNC(=O)C1CCC(=O)N1]
79
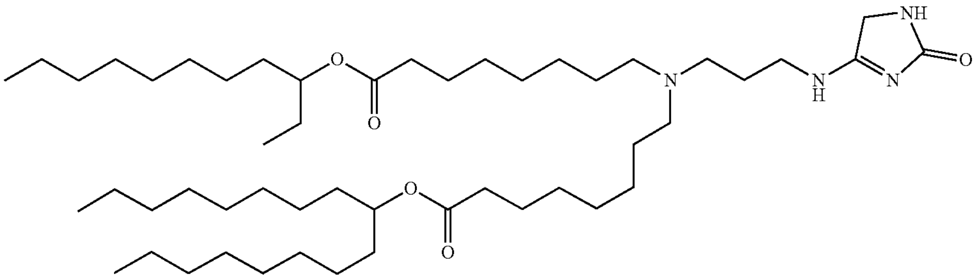 [SMILES: CCCCCCCCC(CC)OC(=O)CCCCCCCN(CCCCCCCC(=O)OC(CCCCCCCC)CCCCCCCC)CCCNC1=NC(=O)NC1]
80
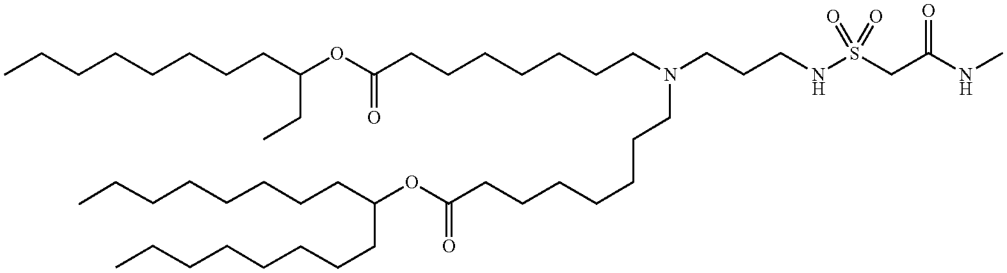 [SMILES: CCCCCCCCC(CC)OC(=O)CCCCCCCN(CCCCCCCC(=O)OC(CCCCCCCC)CCCCCCCC)CCCNS(=O)(=O)CC(=O)NC]
81
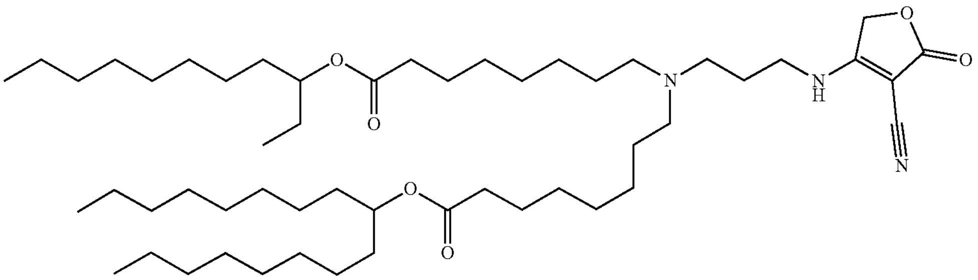 [SMILES: CCCCCCCCC(CC)OC(=O)CCCCCCCN(CCCCCCCC(=O)OC(CCCCCCCC)CCCCCCCC)CCCNC1=C(C#N)C(=O)OC1]

-continued
82
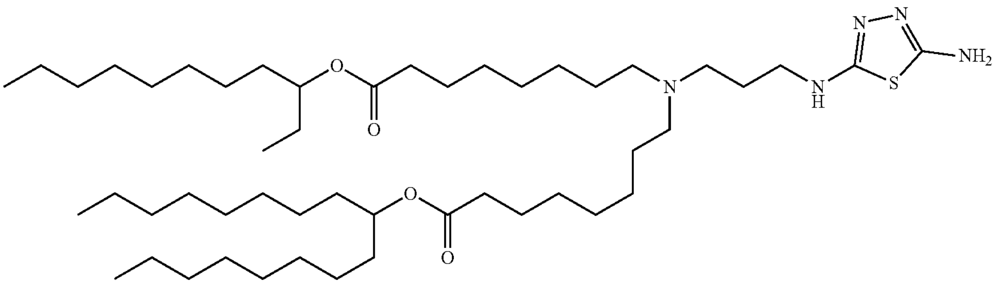 [SMILES: CCCCCCCCC(CC)OC(=O)CCCCCCCN(CCCCCCCC(=O)OC(CCCCCCCC)CCCCCCCC)CCCNc1nnc(N)s1]
83
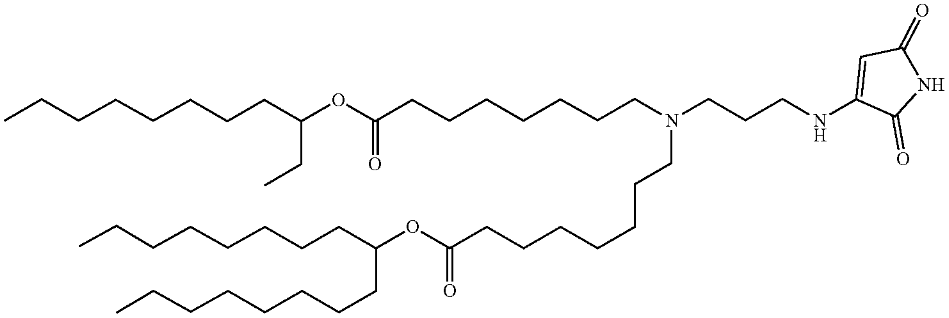 [SMILES: CCCCCCCCC(CC)OC(=O)CCCCCCCN(CCCCCCCC(=O)OC(CCCCCCCC)CCCCCCCC)CCCNC1=CC(=O)NC1=O]
84
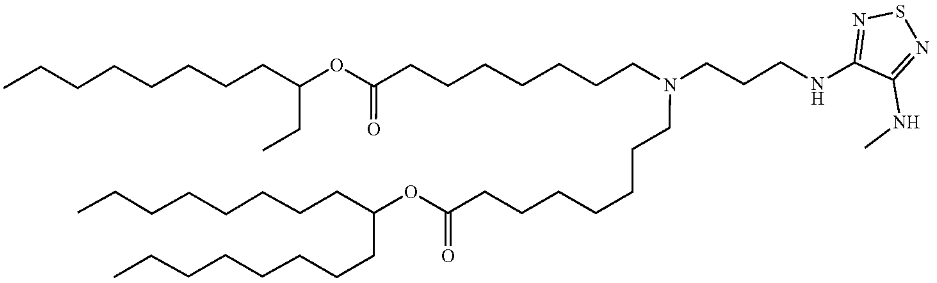
85
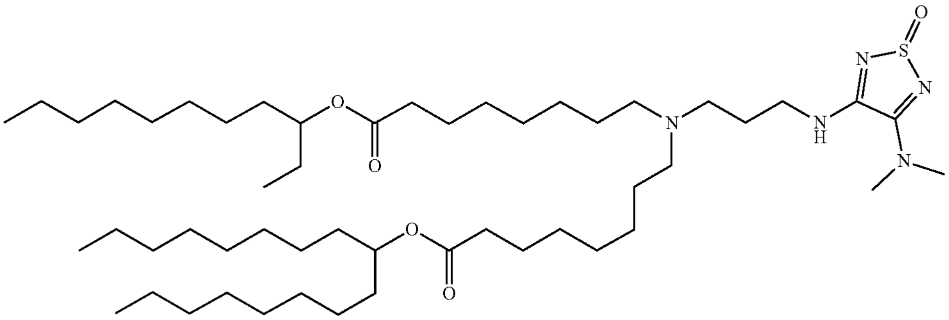 [SMILES: CCCCCCCCC(CC)OC(=O)CCCCCCCN(CCCCCCCC(=O)OC(CCCCCCCC)CCCCCCCC)CCCNC1=NS(=O)N=C1N(C)C]
86
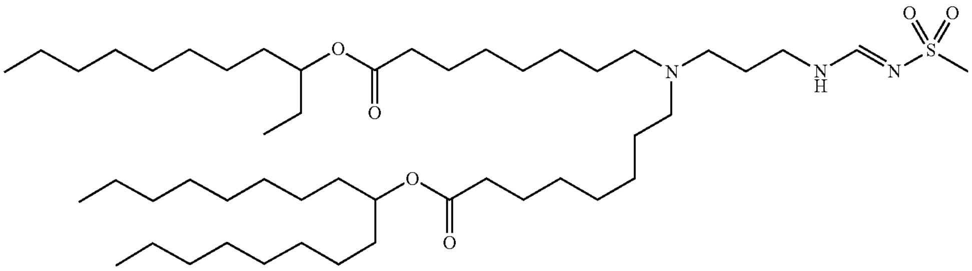 [SMILES: CCCCCCCCC(CC)OC(=O)CCCCCCCN(CCCCCCCC(=O)OC(CCCCCCCC)CCCCCCCC)CCCN/C=N/S(C)(=O)=O]

-continued
87
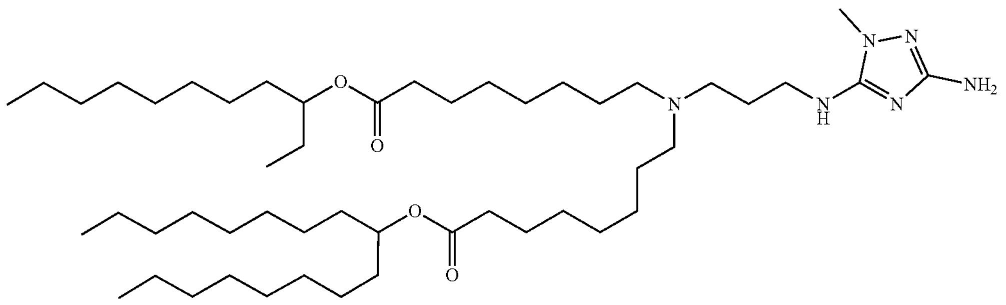 [SMILES: CCCCCCCCC(CC)OC(=O)CCCCCCCN(CCCCCCCC(=O)OC(CCCCCCCC)CCCCCCCC)CCCNc1nc(N)nn1C]
88
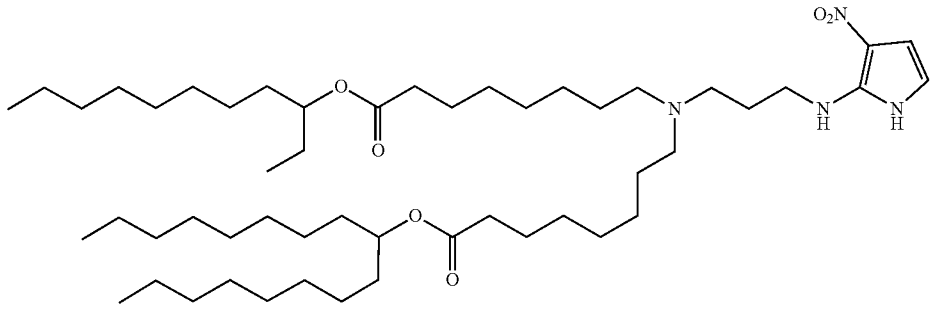 [SMILES: CCCCCCCCC(CC)OC(=O)CCCCCCCN(CCCCCCCC(=O)OC(CCCCCCCC)CCCCCCCC)CCCNc1[nH]ccc1[N+](=O)[O-]]
89
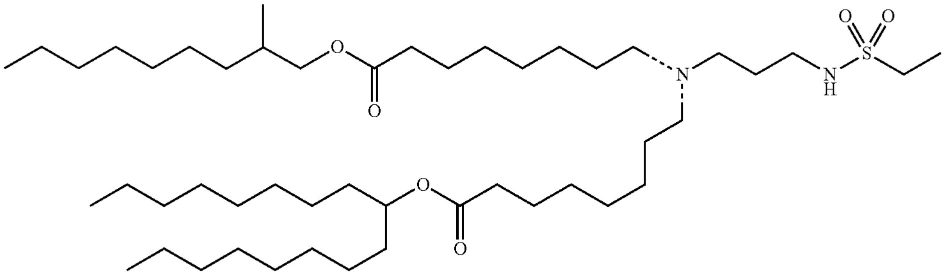
90
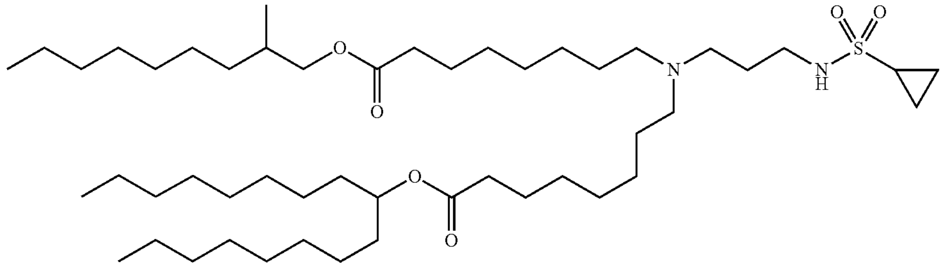 [SMILES: CCCCCCCCC(CCCCCCCC)OC(=O)CCCCCCCN(CCCCCCCC(=O)OCC(C)CCCCCCC)CCCNS(=O)(=O)C1CC1]
91
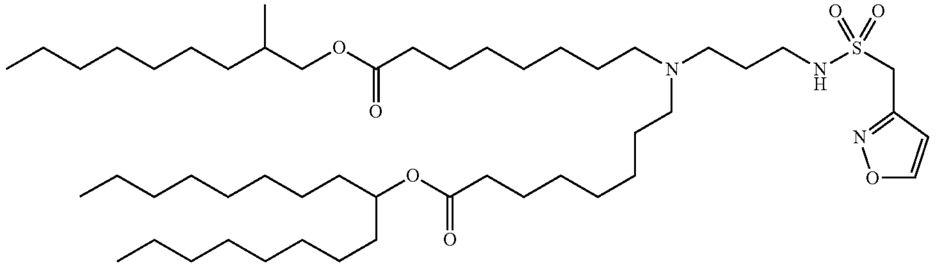 [SMILES: CCCCCCCCC(CCCCCCCC)OC(=O)CCCCCCCN(CCCCCCCC(=O)OCC(C)CCCCCCC)CCCNS(=O)(=O)Cc1ccon1]

-continued
92
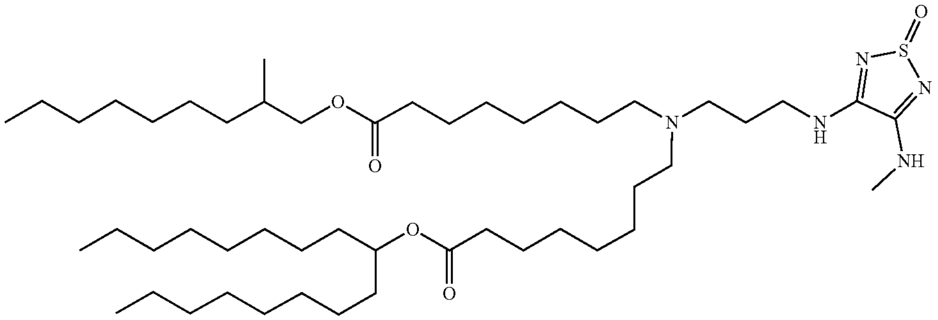 [SMILES: CCCCCCCCC(CCCCCCCC)OC(=O)CCCCCCCN(CCCCCCCC(=O)OCC(C)CCCCCCC)CCCNC1=NS(=O)N=C1NC]
93
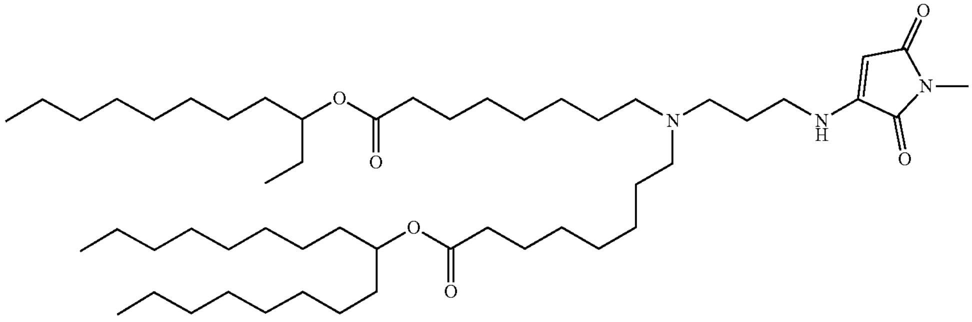 [SMILES: CCCCCCCCC(CC)OC(=O)CCCCCCCN(CCCCCCCC(=O)OC(CCCCCCCC)CCCCCCCC)CCCNC1=CC(=O)N(C)C1=O]
94
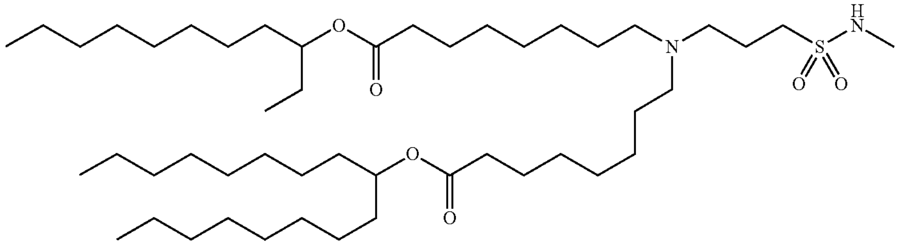 [SMILES: CCCCCCCCC(CC)OC(=O)CCCCCCCN(CCCCCCCC(=O)OC(CCCCCCCC)CCCCCCCC)CCCS(=O)(=O)NC]
95
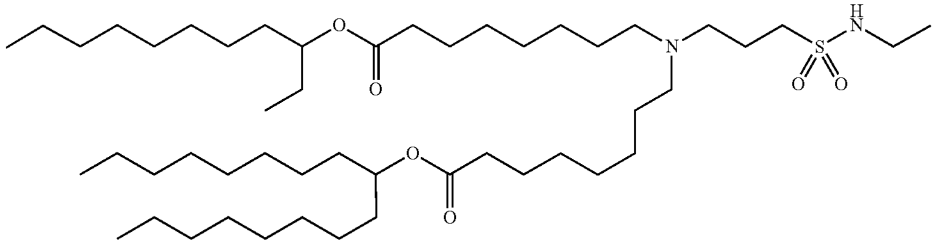 [SMILES: CCCCCCCCC(CC)OC(=O)CCCCCCCN(CCCCCCCC(=O)OC(CCCCCCCC)CCCCCCCC)CCCS(=O)(=O)NCC]
96
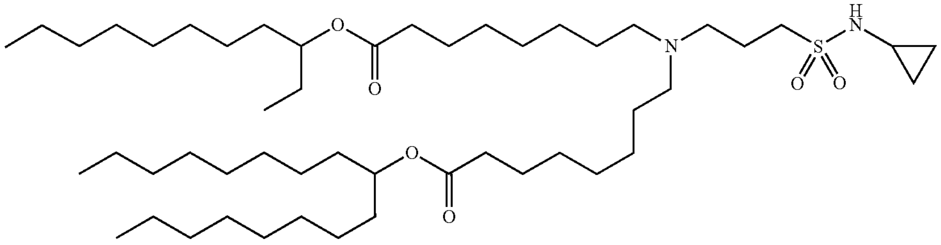 [SMILES: CCCCCCCCC(CC)OC(=O)CCCCCCCN(CCCCCCCC(=O)OC(CCCCCCCC)CCCCCCCC)CCCS(=O)(=O)NC1CC1]

-continued
97
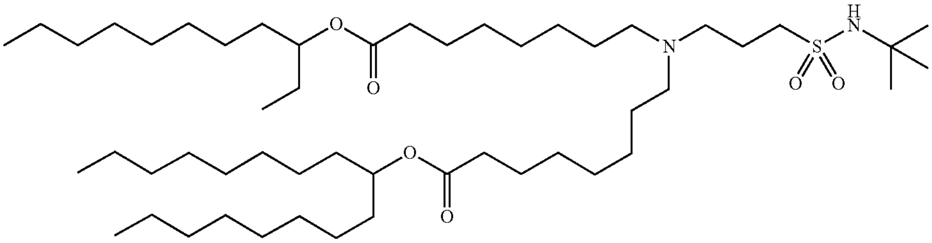 [SMILES: CCCCCCCCC(CC)OC(=O)CCCCCCCN(CCCCCCCC(=O)OC(CCCCCCCC)CCCCCCCC)CCCS(=O)(=O)NC(C)(C)C]
99
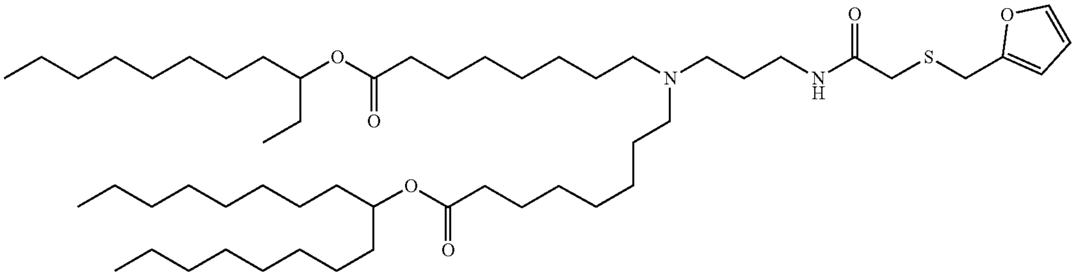 [SMILES: CCCCCCCCC(CC)OC(=O)CCCCCCCN(CCCCCCCC(=O)OC(CCCCCCCC)CCCCCCCC)CCCNC(=O)CSCc1ccco1]
100
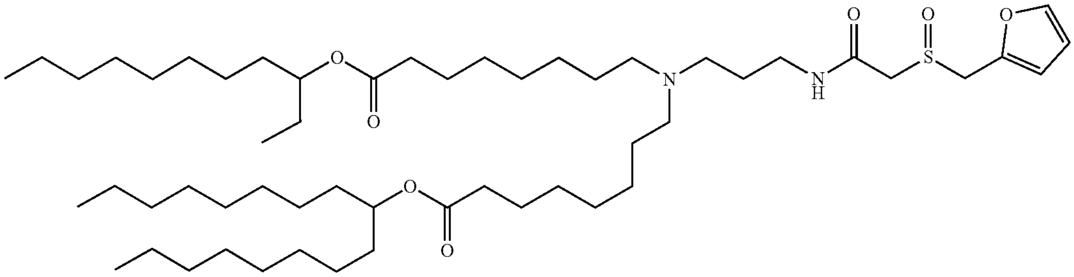 [SMILES: CCCCCCCCC(CC)OC(=O)CCCCCCCN(CCCCCCCC(=O)OC(CCCCCCCC)CCCCCCCC)CCCNC(=O)CS(=O)Cc1ccco1]
101
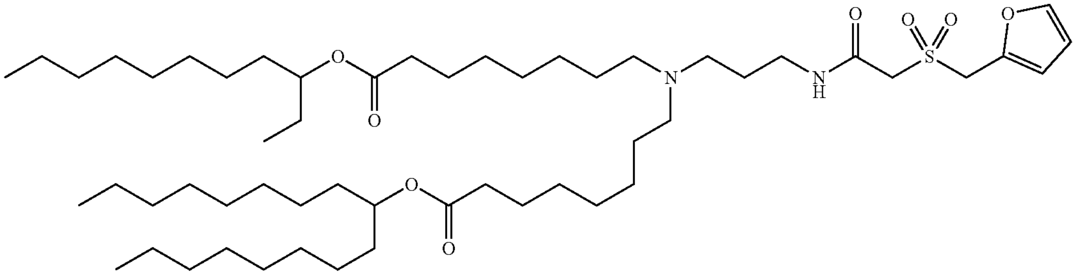 [SMILES: CCCCCCCCC(CC)OC(=O)CCCCCCCN(CCCCCCCC(=O)OC(CCCCCCCC)CCCCCCCC)CCCNC(=O)CS(=O)(=O)Cc1ccco1]
102
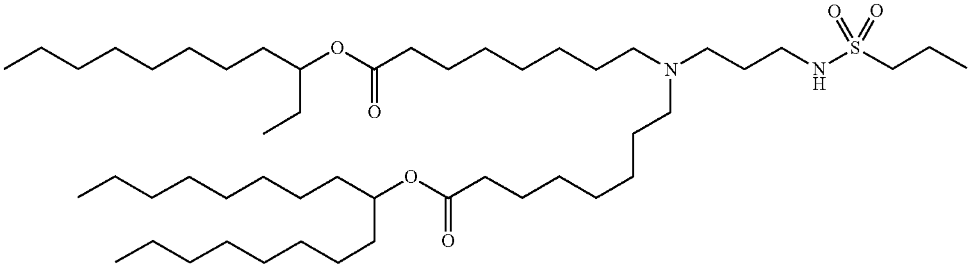 [SMILES: CCCCCCCCC(CC)OC(=O)CCCCCCCN(CCCCCCCC(=O)OC(CCCCCCCC)CCCCCCCC)CCCNS(=O)(=O)CCC]
103
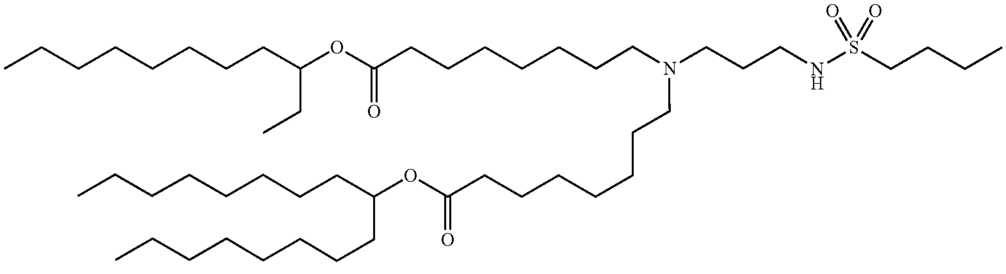 [SMILES: CCCCCCCCC(CC)OC(=O)CCCCCCCN(CCCCCCCC(=O)OC(CCCCCCCC)CCCCCCCC)CCCNS(=O)(=O)CCCC]

-continued
104
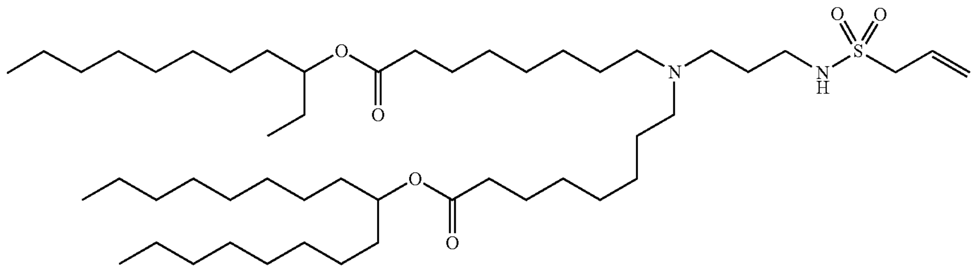 [SMILES: C=CCS(=O)(=O)NCCCN(CCCCCCCC(=O)OC(CC)CCCCCCCC)CCCCCCCC(=O)OC(CCCCCCCC)CCCCCCCC]
105
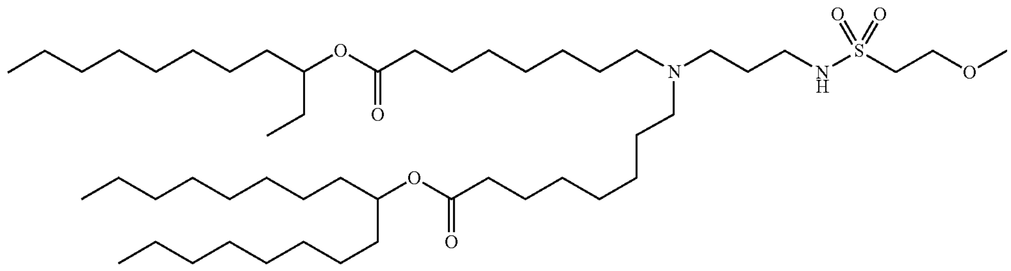 [SMILES: CCCCCCCCC(CC)OC(=O)CCCCCCCN(CCCCCCCC(=O)OC(CCCCCCCC)CCCCCCCC)CCCNS(=O)(=O)CCOC]
106
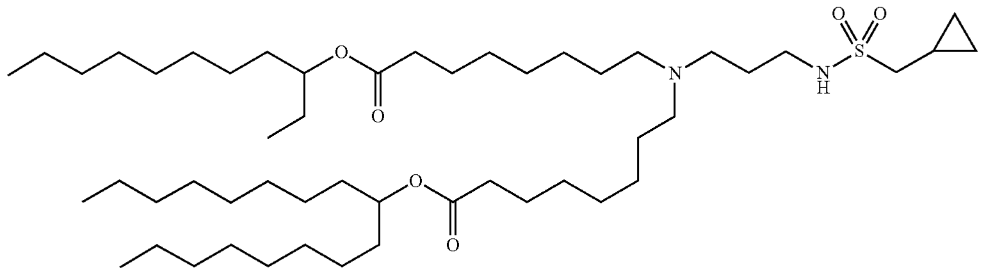 [SMILES: CCCCCCCCC(CC)OC(=O)CCCCCCCN(CCCCCCCC(=O)OC(CCCCCCCC)CCCCCCCC)CCCNS(=O)(=O)CC1CC1]
107
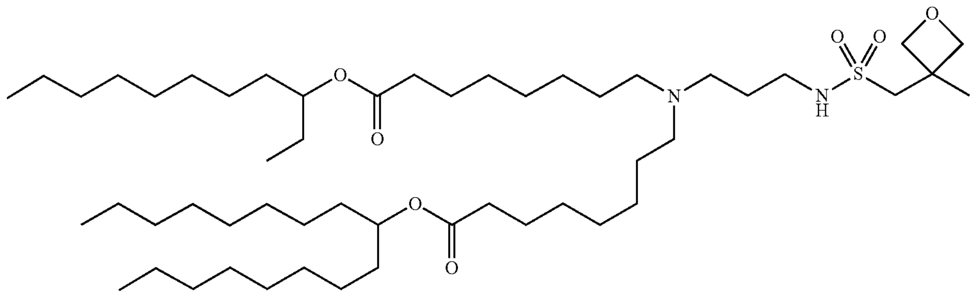 [SMILES: CCCCCCCCC(CC)OC(=O)CCCCCCCN(CCCCCCCC(=O)OC(CCCCCCCC)CCCCCCCC)CCCNS(=O)(=O)CC1(C)COC1]
108
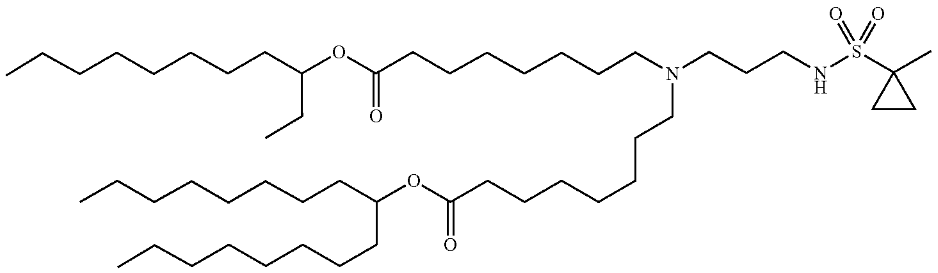 [SMILES: CCCCCCCCC(CC)OC(=O)CCCCCCCN(CCCCCCCC(=O)OC(CCCCCCCC)CCCCCCCC)CCCNS(=O)(=O)C1(C)CC1]

-continued
109
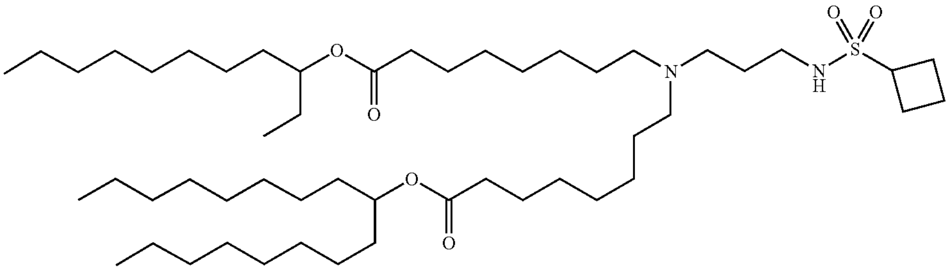 [SMILES: CCCCCCCCC(CC)OC(=O)CCCCCCCN(CCCCCCCC(=O)OC(CCCCCCCC)CCCCCCCC)CCCNS(=O)(=O)C1CCC1]
110
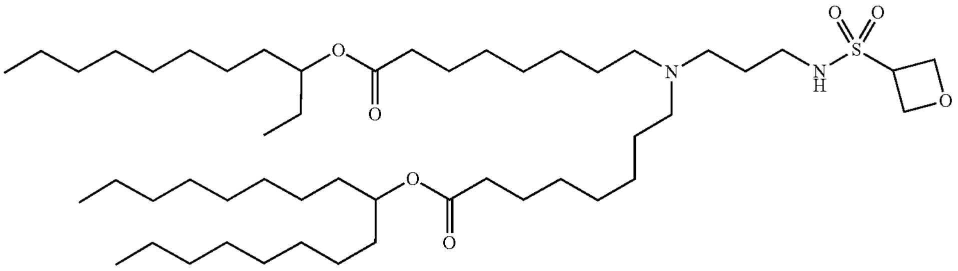 [SMILES: CCCCCCCCC(CC)OC(=O)CCCCCCCN(CCCCCCCC(=O)OC(CCCCCCCC)CCCCCCCC)CCCNS(=O)(=O)C1COC1]
111
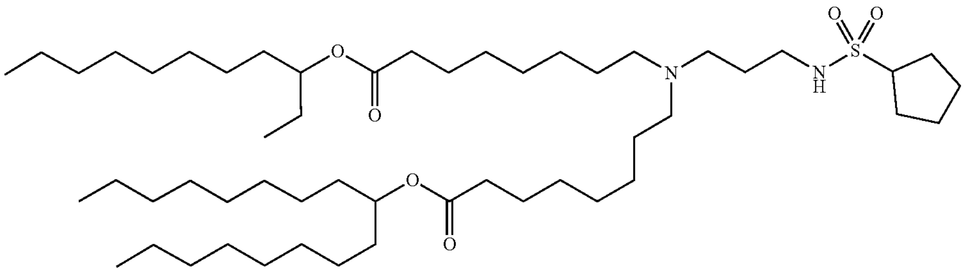 [SMILES: CCCCCCCCC(CC)OC(=O)CCCCCCCN(CCCCCCCC(=O)OC(CCCCCCCC)CCCCCCCC)CCCNS(=O)(=O)C1CCCC1]
112
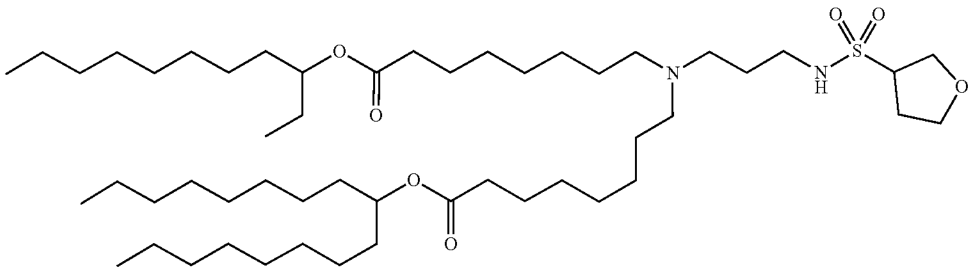 [SMILES: CCCCCCCCC(CC)OC(=O)CCCCCCCN(CCCCCCCC(=O)OC(CCCCCCCC)CCCCCCCC)CCCNS(=O)(=O)C1CCOC1]
113
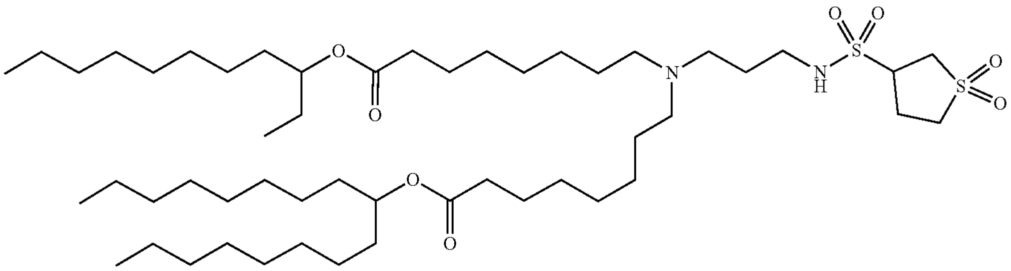 [SMILES: CCCCCCCCC(CC)OC(=O)CCCCCCCN(CCCCCCCC(=O)OC(CCCCCCCC)CCCCCCCC)CCCNS(=O)(=O)C1CCS(=O)(=O)C1]

-continued
114
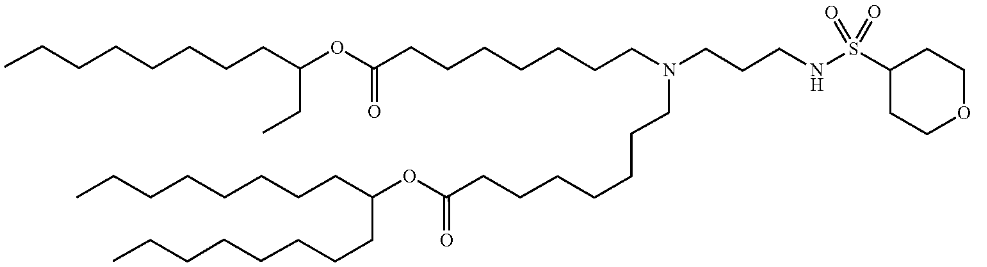 [SMILES: CCCCCCCCC(CC)OC(=O)CCCCCCCN(CCCCCCCC(=O)OC(CCCCCCCC)CCCCCCCC)CCCNS(=O)(=O)C1CCOCC1]
115
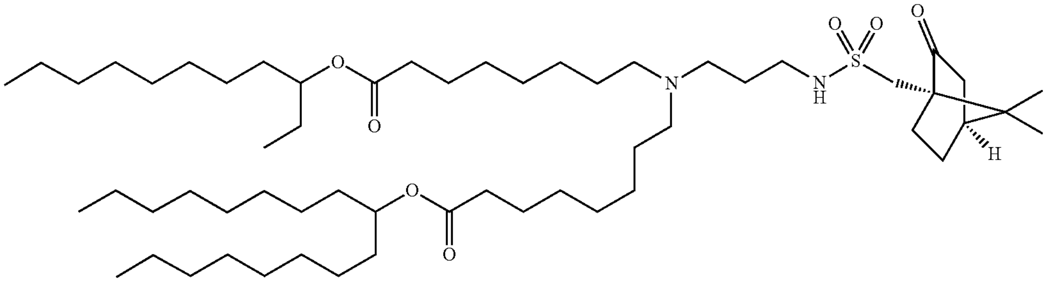 [SMILES: CCCCCCCCC(CC)OC(=O)CCCCCCCN(CCCCCCCC(=O)OC(CCCCCCCC)CCCCCCCC)CCCNS(=O)(=O)C[C@]12CC[C@@H](CC1=O)C2(C)C]
116
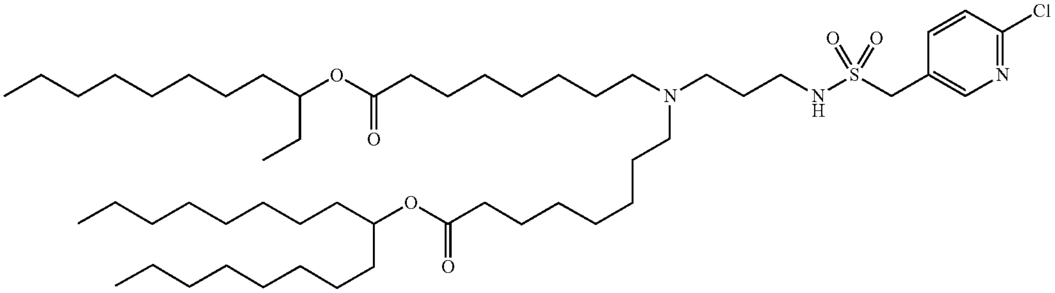 [SMILES: CCCCCCCCC(CC)OC(=O)CCCCCCCN(CCCCCCCC(=O)OC(CCCCCCCC)CCCCCCCC)CCCNS(=O)(=O)Cc1ccc(Cl)nc1]
117
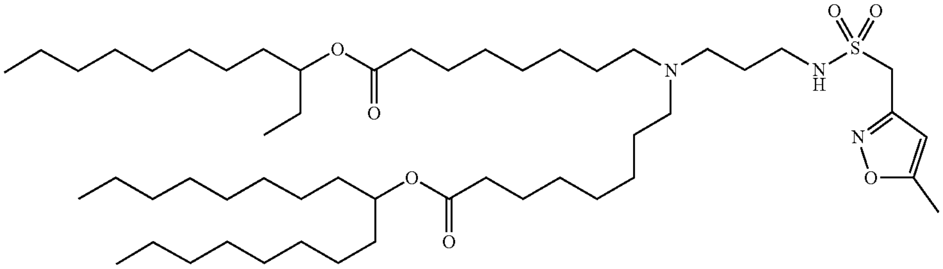 [SMILES: CCCCCCCCC(CC)OC(=O)CCCCCCCN(CCCCCCCC(=O)OC(CCCCCCCC)CCCCCCCC)CCCNS(=O)(=O)Cc1cc(C)on1]
118
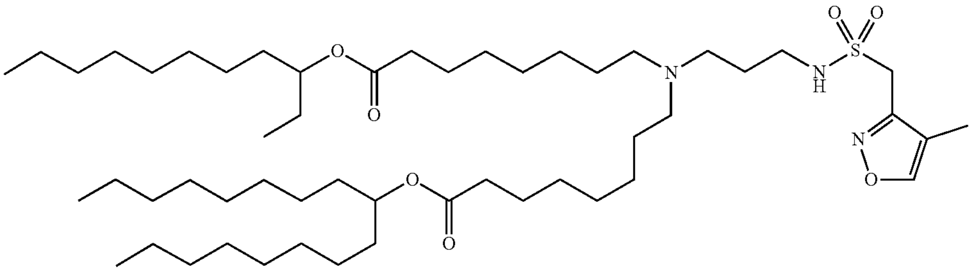 [SMILES: CCCCCCCCC(CC)OC(=O)CCCCCCCN(CCCCCCCC(=O)OC(CCCCCCCC)CCCCCCCC)CCCNS(=O)(=O)Cc1nocc1C]

-continued

119

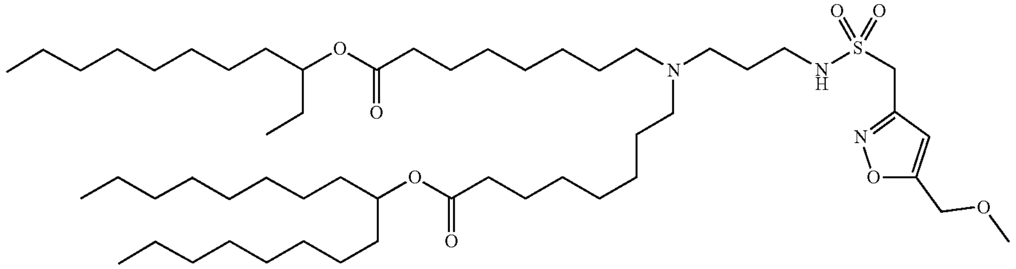 [SMILES: CCCCCCCCC(CC)OC(=O)CCCCCCCN(CCCCCCCC(=O)OC(CCCCCCCC)CCCCCCCC)CCCNS(=O)(=O)Cc1cc(COC)on1]

Embodiment 79. A compound having the following structure:

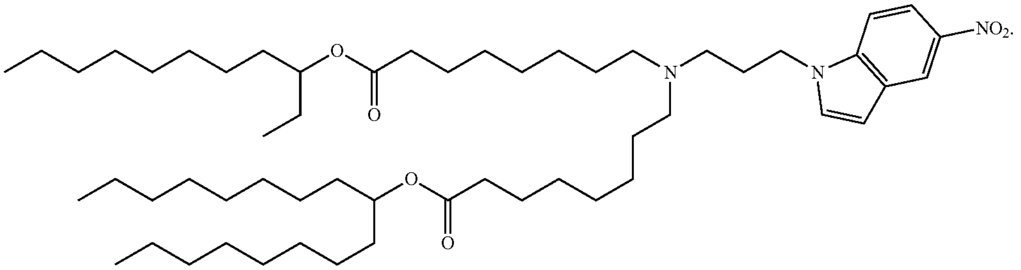 [SMILES: CCCCCCCCC(CC)OC(=O)CCCCCCCN(CCCCCCCC(=O)OC(CCCCCCCC)CCCCCCCC)CCCn1ccc2cc([N+](=O)[O-])ccc21]

Embodiment 80. A compound having the following structure

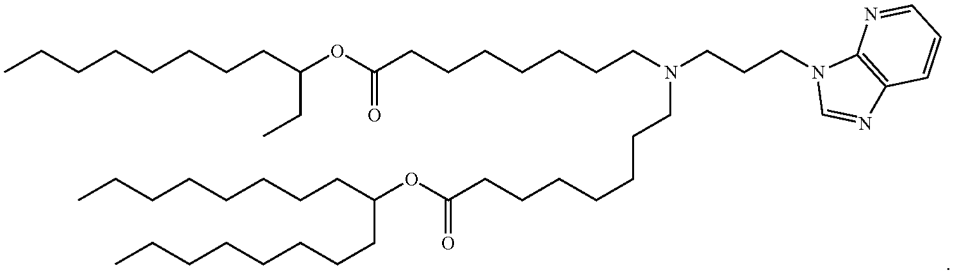 [SMILES: CCCCCCCCC(CC)OC(=O)CCCCCCCN(CCCCCCCC(=O)OC(CCCCCCCC)CCCCCCCC)CCCn1cnc2cccnc21 ; "."]

Embodiment 81. An empty lipid nanoparticle (empty LNP) comprising a compound of any one of the preceding embodiments, a phospholipid, a structural lipid, and a PEG lipid.

Embodiment 82. A loaded lipid nanoparticle (loaded LNP) comprising a compound of any one of the preceding embodiments, a phospholipid, a structural lipid, a PEG lipid, and one or more therapeutic and/or prophylactic agents.

Embodiment 83. The empty LNP or loaded LNP of any one of the preceding embodiments, comprising the compound in an amount from about 40% to about 60%.

Embodiment 84. The empty LNP or loaded LNP of any one of the preceding embodiments, comprising the phospholipid in an amount from about 0% to about 20%.

Embodiment 85. The empty LNP or loaded LNP of any one of the preceding embodiments, comprising the structural lipid in an amount from about 30% to about 50%.

Embodiment 86. The empty LNP or loaded LNP of any one of the preceding embodiments, comprising the PEG lipid in an amount from about 0% to about 5%.

Embodiment 87. The empty LNP or loaded LNP of any one of the preceding embodiments, comprising about 40 mol % to about 60 mol % of the compound of any one of the preceding embodiments, about 0 mol % to about 20 mol % phospholipid, about 30 mol % to about 50 mol % structural lipid, and about 0 mol % to about 5 mol % PEG lipid.

Embodiment 88. The empty LNP or loaded LNP of any one of the preceding embodiments, comprising about 30 mol % to about 60 mol % of the compound of any one of the preceding embodiments, about 0 mol % to about 30 mol % phospholipid, about 18.5 mol % to about 48.5 mol % structural lipid, and about 0 mol % to about 10 mol % PEG lipid.

Embodiment 89. The loaded LNP of any one of the preceding embodiments, wherein the one or more therapeutic and/or prophylactic agents is a polynucleotide or a polypeptide.

Embodiment 90. The loaded LNP of any one of the preceding embodiments, wherein the one or more therapeutic and/or prophylactic agents is a nucleic acid.

Embodiment 91. The loaded LNP of any one of the preceding embodiments, wherein the one or more therapeutic and/or prophylactic agents is selected from the group consisting of a ribonucleic acid (RNA) and a deoxyribonucleic acid (DNA).

Embodiment 92. The loaded LNP of any one of the preceding embodiments, wherein the DNA is selected from the group consisting of a double-stranded DNA, a single-stranded DNA (ssDNA), a partially double-stranded DNA, a triple stranded DNA, and a partially triple-stranded DNA.

Embodiment 93. The loaded LNP of any one of the preceding embodiments, wherein the DNA is selected from the group consisting of a circular DNA, a linear DNA, and mixtures thereof.

Embodiment 94. The loaded LNP of any one of the preceding embodiments, wherein the one or more therapeutic and/or prophylactic agents is selected from the group consisting of a plasmid expression vector, a viral expression vector, and mixtures thereof.

Embodiment 95. The loaded LNP of any one of the preceding embodiments, wherein the one or more therapeutic and/or prophylactic agents is a RNA.

Embodiment 96. The loaded LNP of any one of the preceding embodiments, wherein the RNA is selected from the group consisting of a single-stranded RNA, a double-stranded RNA (dsRNA), a partially double-stranded RNA, and mixtures thereof.

Embodiment 97. The loaded LNP of any one of the preceding embodiments, wherein the RNA is selected from the group consisting of a circular RNA, a linear RNA, and mixtures thereof.

Embodiment 98. The loaded LNP of any one of the preceding embodiments, wherein the RNA is selected from the group consisting of is selected from the group consisting of a short interfering RNA (siRNA), an asymmetrical interfering RNA (aiRNA), a RNA interference (RNAi) molecule, a microRNA (miRNA), an antagomir, an antisense RNA, a ribozyme, a Dicer-substrate RNA (dsRNA), a small hairpin RNA (shRNA), a messenger RNA (mRNA), and mixtures thereof.

Embodiment 99. The loaded LNP of any one of the preceding embodiments, wherein the RNA is an mRNA.

Embodiment 100. The loaded LNP of any one of the preceding embodiments, wherein the mRNA is a modified mRNA (mmRNA).

Embodiment 101. The loaded LNP of any one of the preceding embodiments, wherein the mRNA incorporates a micro-RNA binding site (miR binding site).

Embodiment 102. The loaded LNP of any one of the preceding embodiments, wherein the mRNA includes one or more of a stem loop, a chain terminating nucleoside, a polyA sequence, a polyadenylation signal, and/or a 5' cap structure.

Embodiment 103. The empty LNP or loaded LNP of any one of the preceding embodiments, wherein the phospholipid is selected from the group consisting of 1,2-dilinoleoyl-sn-glycero-3-phosphocholine (DLPC), 1,2-dimyristoyl-sn-glycero-phosphocholine (DMPC), 1,2-dioleoyl-sn-glycero-3-phosphocholine (DOPC), 1,2-dipalmitoyl-sn-glycero-3-phosphocholine (DPPC), 1,2-distearoyl-sn-glycero-3-phosphocholine (DSPC), 1,2-diundecanoyl-sn-glycero-phosphocholine (DUPC), 1-palmitoyl-2-oleoyl-sn-glycero-3-phosphocholine (POPC), 1,2-di-O-octadecenyl-sn-glycero-3-phosphocholine (18:0 Diether PC), 1-oleoyl-2-cholesterylhemisuccinoyl-sn-glycero-3-phosphocholine (OChemsPC), 1-hexadecyl-sn-glycero-3-phosphocholine (C16 Lyso PC), 1,2-dilinolenoyl-sn-glycero-3-phosphocholine, 1,2-diarachidonoyl-sn-glycero-3-phosphocholine, 1,2-didocosahexaenoyl-sn-glycero-3-phosphocholine, 1,2-dioleoyl-sn-glycero-3-phosphoethanolamine (DOPE), 1,2-diphytanoyl-sn-glycero-3-phosphoethanolamine (ME 16.0 PE), 1,2-distearoyl-sn-glycero-3-phosphoethanolamine, 1,2-dilinoleoyl-sn-glycero-3-phosphoethanolamine, 1,2-dilinolenoyl-sn-glycero-3-phosphoethanolamine, 1,2-diarachidonoyl-sn-glycero-3-phosphoethanolamine, 1,2-didocosahexaenoyl-sn-glycero-3-phosphoethanolamine, 1,2-dioleoyl-sn-glycero-3-phospho-rac-(1-glycerol) sodium salt (DOPG), sphingomyelin, and mixtures thereof.

Embodiment 104. The empty LNP or loaded LNP of any one of the preceding embodiments, wherein the phospholipid is 1,2-distearoyl-sn-glycero-3-phosphocholine (DSPC).

Embodiment 105. The empty LNP or loaded LNP of any one of the preceding embodiments, wherein the structural lipid is selected from the group consisting of cholesterol, fecosterol, sitosterol, ergosterol, campesterol, stigmasterol, brassicasterol, tomatidine, ursolic acid, alpha-tocopherol, and mixtures thereof.

Embodiment 106. The empty LNP or loaded LNP of any one of the preceding embodiments, wherein the structural lipid is (SL-1)

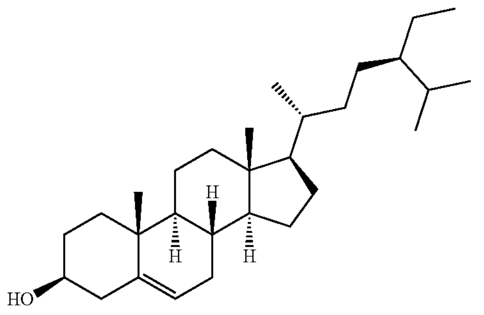

or a salt thereof.

Embodiment 107. The empty LNP or loaded LNP of any one of the preceding embodiments, wherein the structural lipid is cholesterol:

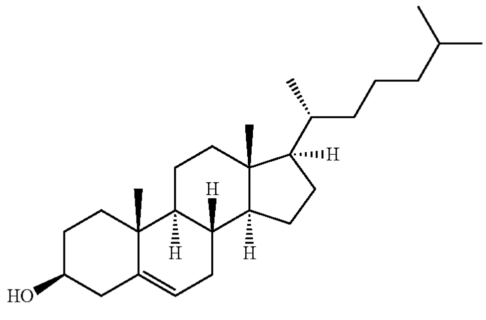

or a salt thereof.

Embodiment 108. The empty LNP or loaded LNP of any one of the preceding embodiments, wherein the PEG lipid is selected from the group consisting of a PEG-modified phosphatidylethanolamine, a PEG-modified, phosphatidic acid, a PEG-modified ceramide, PEG-modified dialkylamine, a PEG-modified diacylglycerol, and a PEG-modified diacylglycerol, and mixtures thereof.

Embodiment 109. The empty LNP or loaded LNP of any one of the preceding embodiments, wherein the PEG lipid is selected from the group consisting of 1,2-dimyristoyl-sn-glycerol methoxypolyethylene glycol (PEG-DMG), 1,2-distearoyl-sn-glycero-3-phosphoethanolamine-N-[amino(polyethylene glycol)] (PEG-DSPE), PEG-disteryl glycerol (PEG-DSG), PEG-dipalmetoleyl, PEG-dioleyl, PEG-distearyl, PEG-diacylglycamide (PEG-DAG), PEG-dipalmitoyl phosphatidylethanolamine (PEG-DPPE), or PEG-1,2-dimyristyloxlpropyl-3-amine (PEG-c-DMA).

Embodiment 110. The empty LNP or loaded LNP of any one of the preceding embodiments, wherein the PEG lipid is PEG-DMG.

Embodiment 111. The empty LNP or loaded LNP of any one of the preceding embodiments, wherein the PEG lipid is a compound of Formula (PL-I):

(PL-I)

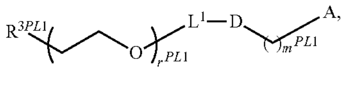

or a salt thereof, wherein:

$R^{3PL1}$ is —$OR^{OPL1}$;

$R^{OPL1}$ is hydrogen, optionally substituted alkyl, or an oxygen protecting group;

$r^{PL1}$ is an integer between 1 and 100, inclusive;

$L^1$ is optionally substituted $C_{1-10}$ alkylene, wherein at least one methylene of the optionally substituted $C_{1-10}$ alkylene is independently replaced with optionally substituted carbocyclylene, optionally substituted heterocyclylene, optionally substituted arylene, optionally substituted heteroarylene, O, $N(R^{NPL1})$, S, C(O), C(O)$N(R^{NPL1})$, $NR^{NPL1}C(O)$, —C(O)O, OC(O), OC(O)O, OC(O)$N(R^{NPL1})$, $NR^{NPL1}C(O)O$, or $NR^{NPL1}C(O)N(R^{NPL1})$;

D is a moiety obtained by click chemistry or a moiety cleavable under physiological conditions;

$m^{PL1}$ is 0, 1, 2, 3, 4, 5, 6, 7, 8, 9, or 10;

A is of the formula:

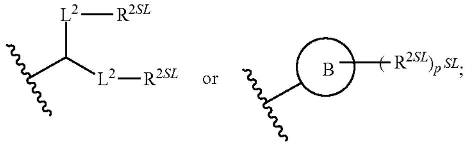

each instance of $L^2$ is independently a bond or optionally substituted $C_{1-6}$ alkylene, wherein one methylene unit of the optionally substituted $C_{1-6}$ alkylene is optionally replaced with O, $N(R^{NPL1})$, S, C(O), C(O)$N(R^{NPL1})$, $NR^{NPL1}C(O)$, C(O)O, OC(O), OC(O)O, —OC(O)N$(R^{NPL1})$, $NR^{NPL1}C(O)O$, or $NR^{NPL1}C(O)N(R^{NPL1})$;

each instance of $R^{2SL}$ is independently optionally substituted $C_{1-30}$ alkyl, optionally substituted $C_{1-30}$ alkenyl, or optionally substituted $C_{1-30}$ alkynyl; optionally wherein one or more methylene units of $R^{2SL}$ are independently replaced with optionally substituted carbocyclylene, optionally substituted heterocyclylene, optionally substituted arylene, optionally substituted heteroarylene, $N(R^{NPL1})$, O, S, C(O), C(O)$N(R^{NPL1})$, $NR^{NPL1}C(O)$, —$NR^{NPL1}C(O)N(R^{NPL1})$, C(O)O, OC(O), OC(O)O, OC(O)$N(R^{NPL1})$, $NR^{NPL1}C(O)O$, C(O)S, —SC(O), C(=$NR^{NPL1}$), C(=$NR^{NPL1}$)N$(R^{NPL1})$, $NR^{NPL1}C(=NR^{NPL1})$, —$NR^{NPL1}$C(=$NR^{NPL1}$)N$(R^{NPL1})$, C(S), C(S)$N(R^{NPL1})$, $NR^{NPL1}$C(S), $NR^{NPL1}C(S)N(R^{NPL1})$, S(O) OS(O), S(O)O, OS(O)O, $OS(O)_2$, $S(O)_2O$, $OS(O)_2O$, $N(R^{NPL1})S(O)$, S(O)$N(R^{NPL1})$, —$N(R^{NPL1})S(O)N(R^{NPL1})$, OS(O)N$(R^{NPL1})$, $N(R^{NPL1})S(O)O$, $S(O)_2$, $N(R^{NPL1})S(O)_2$, —$S(O)_2N(R^{NPL1})$, $N(R^{NPL1})S(O)_2N(R^{NPL1})$, $OS(O)_2N(R^{NPL1})$, or $N(R^{NPL1})S(O)_2O$;

each instance of $R^{NPL1}$ is independently hydrogen, optionally substituted alkyl, or a nitrogen protecting group;

Ring B is optionally substituted carbocyclyl, optionally substituted heterocyclyl, optionally substituted aryl, or optionally substituted heteroaryl; and $p^{SL}$ is 1 or 2.

Embodiment 112. The empty LNP or loaded LNP of any one of the preceding embodiments, wherein the PEG lipid is a compound of Formula (PL-I—OH):

(PL-I-OH)

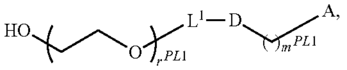

or a salt thereof.

Embodiment 113. The empty LNP or loaded LNP of any one of the preceding embodiments, wherein the PEG lipid is a compound of Formula (PL-II-OH):

(PL-II-OH)

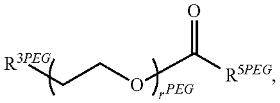

or a salt or isomer thereof, wherein:

$R^{3PEG}$ is —$OR^O$;

$R^O$ is hydrogen, $C_{1-6}$ alkyl or an oxygen protecting group;

$r^{PEG}$ is an integer between 1 and 100;

$R^{5PEG}$ is $C_{10-40}$ alkyl, $C_{10-40}$ alkenyl, or $C_{10-40}$ alkynyl; and optionally one or more methylene groups of $R^{5PEG}$ are each independently replaced with $C_{3-10}$ carbocyclylene, 4 to 10 membered heterocyclylene, $C_{6-10}$ arylene, 4 to 10 membered heteroarylene, —$N(R^{NPEG})$—, —O—, —S—, —C(O)—, —C(O)N$(R^{NPEG})$—, —$NR^{NPEG}C(O)$—, —$NR^{NPEG}C(O)N(R^{NPEG})$—, —C(O)O—, —OC(O)—, —OC(O)O—, —OC(O)$N(R^{NPEG})$—, —$NR^{NPEG}C(O)O$—, —C(O)S—, —SC(O)—, —C(=$NR^{NPEG}$—, —C(=$NR^{NPEG}$)N$(R^{NPEG})$—, —$NR^{NPEG}C(=NR^{NPEG})$—, —$NR^{NPEG}C(=NR^{NPEG})N(R^{NPEG})$—, —C(S)—, —C(S)$N(R^{NPEG})$—, —$NR^{NPEG}C(S)$—, —$NR^{NPEG}C(S)N(R^{NPEG})$—, —OS(O)—, —S(O)O—, —OS(O)O—, —$OS(O)_2$—, —$S(O)_2O$—, —$OS(O)_2O$—, —$N(R^{NPEG})S(O)$—, —S(O)$N(R^{NPEG})$—, —$N(R^{NPEG})S(O)N(R^{NPEG})$—, —OS(O)$N(R^{NPEG})$—, —$N(R^{NPEG})S(O)O$—, —$S(O)_2$—, —$N(R^{NPEG})S(O)_2$—, —$S(O)_2N(R^{NPEG})$—, —$N(R^{NPEG})S(O)_2N(R^{NPEG})$—, —$OS(O)_2N(R^{NPEG})$—, or —$N(R^{NPEG})S(O)_2O$—; and each instance of $R^{NPEG}$ is independently hydrogen, $C_{1-6}$ alkyl, or a nitrogen protecting group.

Embodiment 114. The empty LNP or loaded LNP of any one of the preceding embodiments, wherein in the PEG lipid of Formula (PL-II-OH), r is an integer between 40 and 50.

Embodiment 115. The empty LNP or loaded LNP of any one of the preceding embodiments, wherein in the PEG lipid of Formula (PL-II-OH), r is 45.

Embodiment 116. The empty LNP or loaded LNP of any one of the preceding embodiments, wherein in the PEG lipid of Formula (PL-II-OH), $R^5$ is $C_{17}$ alkyl.

Embodiment 117. The empty LNP or loaded LNP of any one of the preceding embodiments, wherein the PEG lipid is a compound of Formula (PL-II):

(PL-II)

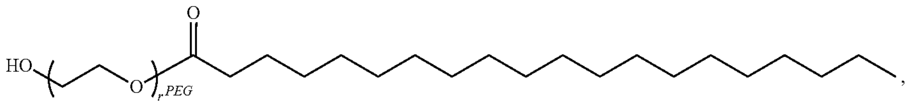

wherein $r^{PEG}$ is an integer between 1 and 100.

Embodiment 118. The empty LNP or loaded LNP of any one of the preceding embodiments, wherein the PEG lipid is a compound of Formula (PEG-1):

(PEG-1)

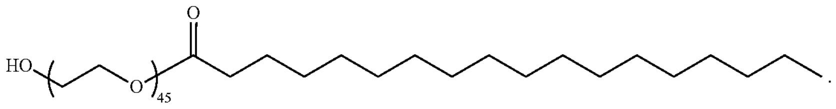

Embodiment 119. The empty LNP or loaded LNP of any one of the preceding embodiments, wherein the PEG lipid is a compound of Formula (PL-III):

(PL-III)

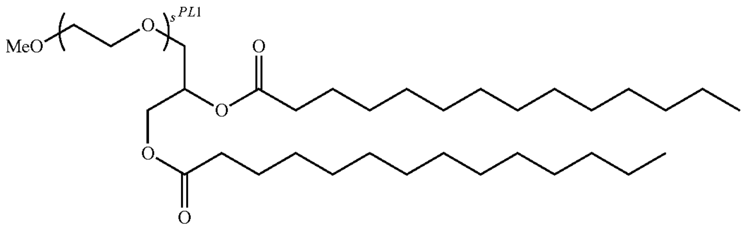

, or a salt or isomer thereof, wherein $S^{PL1}$ is an integer between 1 and 100.

Embodiment 120. The empty LNP or loaded LNP of any one of the preceding embodiments, wherein the PEG lipid is a compound of following formula:

($PEG_{2k}$-DMG)

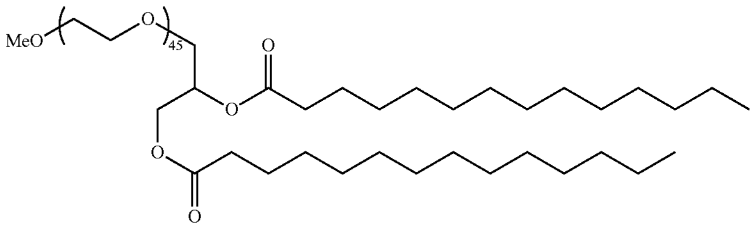

Embodiment 121. An empty lipid nanoparticle (empty LNP) comprising a compound of any one of the preceding embodiments, a phospholipid, a structural lipid, and a PEG lipid, wherein the phospholipid is DSPC and the structural lipid is cholesterol.

Embodiment 122. An empty lipid nanoparticle (empty LNP) comprising a compound of any one of the preceding embodiments, a phospholipid, a structural lipid, and a PEG lipid, wherein the structural lipid is cholesterol and the PEG lipid is $PEG_{2k}$-DMG.

Embodiment 123. An empty lipid nanoparticle (empty LNP) comprising a compound of any one of the preceding embodiments, a phospholipid, a structural lipid, and a PEG lipid, wherein the structural lipid is cholesterol and the PEG lipid is PEG-1.

Embodiment 124. An empty lipid nanoparticle (empty LNP) comprising a compound of any one of the preceding embodiments, a phospholipid, a structural lipid, and a PEG lipid, wherein the phospholipid is DSPC and the PEG lipid is $PEG_{2k}$-DMG.

Embodiment 125. An empty lipid nanoparticle (empty LNP) comprising a compound of any one of the preceding embodiments, a phospholipid, a structural lipid, and a PEG lipid, wherein the phospholipid is DSPC and the PEG lipid is PEG-1.

Embodiment 126. An empty lipid nanoparticle (empty LNP) comprising a compound of any one of the preceding embodiments, a phospholipid, a structural lipid, and a PEG lipid, wherein the phospholipid is DSPC, the structural lipid is cholesterol, and the PEG lipid is $PEG_{2k}$-DMG.

Embodiment 127. An empty lipid nanoparticle (empty LNP) comprising a compound of any one of the preceding embodiments, a phospholipid, a structural lipid, and a PEG lipid, wherein the phospholipid is DSPC, the structural lipid is cholesterol, and the PEG lipid is PEG-1.

Embodiment 128. A loaded lipid nanoparticle (loaded LNP) comprising a compound of any one of the preceding embodiments, a phospholipid, a structural lipid, and a PEG lipid, wherein the phospholipid is DSPC and the structural lipid is cholesterol, and one or more therapeutic and/or prophylactic agents.

Embodiment 129. A loaded lipid nanoparticle (loaded LNP) comprising a compound of any one of the preceding embodiments, a phospholipid, a structural lipid, and a PEG lipid, wherein the structural lipid is cholesterol and the PEG lipid is $PEG_{2k}$-DMG, and one or more therapeutic and/or prophylactic agents.

Embodiment 130. A loaded lipid nanoparticle (loaded LNP) comprising a compound of any one of the preceding embodiments, a phospholipid, a structural lipid, and a PEG lipid, wherein the structural lipid is cholesterol and the PEG lipid is PEG-1, and one or more therapeutic and/or prophylactic agents.

Embodiment 131. A loaded lipid nanoparticle (loaded LNP) comprising a compound of any one of the preceding embodiments, a phospholipid, a structural lipid, and a PEG lipid, wherein the phospholipid is DSPC and the PEG lipid is $PEG_{2k}$-DMG, and one or more therapeutic and/or prophylactic agents.

Embodiment 132. A loaded lipid nanoparticle (loaded LNP) comprising a compound of any one of the preceding embodiments, a phospholipid, a structural lipid, and a PEG lipid, wherein the phospholipid is DSPC and the PEG lipid is PEG-1, and one or more therapeutic and/or prophylactic agents.

Embodiment 133. A loaded lipid nanoparticle (loaded LNP) comprising a compound of any one of the preceding embodiments, a phospholipid, a structural lipid, and a PEG lipid, wherein the phospholipid is DSPC, the structural lipid is cholesterol, and the PEG lipid is $PEG_{2k}$-DMG, and one or more therapeutic and/or prophylactic agents.

Embodiment 134. A loaded lipid nanoparticle (loaded LNP) comprising a compound of any one of the preceding embodiments, a phospholipid, a structural lipid, and a PEG lipid, wherein the phospholipid is DSPC, the structural lipid is cholesterol, and the PEG lipid is PEG-1, and one or more therapeutic and/or prophylactic agents.

Embodiment 135. The empty LNP or loaded LNP of any one of the preceding embodiments, comprising DSPC in an amount from about 0% to about 20%.

Embodiment 136. The empty LNP or loaded LNP of any one of the preceding embodiments, comprising cholesterol in an amount from about 30% to about 50%.

Embodiment 137. The empty LNP or loaded LNP of any one of the preceding embodiments, comprising $PEG_{2k}$-DMG in an amount from about 0% to about 5%.

Embodiment 138. The empty LNP or loaded LNP of any one of the preceding embodiments, comprising PEG-1 in an amount from about 0% to about 5%.

Embodiment 139. The empty LNP or loaded LNP of any one of the preceding embodiments, comprising about 40 mol % to about 60 mol % of the compound of any one of the preceding embodiments, about 0 mol % to about 20 mol % DSPC, about 30 mol % to about 50 mol % cholesterol, and about 0 mol % to about 5 mol % $PEG_{2k}$-DMG.

Embodiment 140. The empty LNP or loaded LNP of any one of the preceding embodiments, comprising about 40 mol % to about 60 mol % of the compound of any one of the preceding embodiments, about 0 mol % to about 20 mol % DSPC, about 30 mol % to about 50 mol % cholesterol, and about 0 mol % to about 5 mol % PEG-1.

Embodiment 141. The loaded LNP of any one of the preceding embodiments the encapsulation efficiency of the therapeutic and/or prophylactic agent is between 80% and 100%.

Embodiment 142. The loaded LNP of any one of the preceding embodiments, wherein the wt/wt ratio of the lipid component to the mRNA is from about 10:1 to about 60:1.

Embodiment 143. The loaded LNP of any one of the preceding embodiments, wherein the wt/wt ratio of the lipid component to the mRNA is about 20:1.

Embodiment 144. The loaded LNP of any one of the preceding embodiments, wherein the N:P ratio is from about 5:1 to about 8:1.

Embodiment 145. A pharmaceutical composition comprising the loaded LNP of any one of the preceding embodiments and a pharmaceutically acceptable carrier.

Embodiment 146. The pharmaceutical composition of any one of the preceding embodiments, further comprising a cryoprotectant, a buffer, or a combination thereof.

Embodiment 147. The pharmaceutical composition of any one of the preceding embodiments, wherein the cryoprotectant comprises sucrose.

Embodiment 148. The pharmaceutical composition of any one of the preceding embodiments, wherein the cryoprotectant comprises sodium acetate.

Embodiment 149. The pharmaceutical composition of any one of the preceding embodiments, wherein the cryoprotectant comprises sucrose and sodium acetate.

Embodiment 150. The pharmaceutical composition of any one of the preceding embodiments, wherein the buffer is selected from the group consisting of an acetate buffer, a citrate buffer, a phosphate buffer, and a tris buffer.

Embodiment 151. A method of delivering a therapeutic and/or prophylactic agent to a cell within a subject, the method comprising administering to the subject the loaded LNP of any one of the preceding embodiments.

Embodiment 152. A method of specifically delivering a therapeutic and/or prophylactic agent to an organ of a subject, the method comprising administering to the subject the loaded LNP of any one of the preceding embodiments.

Embodiment 153. A method for the enhanced delivery of a therapeutic and/or prophylactic to a target tissue of a subject, the method comprising administering to the subject the loaded LNP of any one of the preceding embodiments.

Embodiment 154. A method of producing a polypeptide of interest in a cell within a subject, the method comprising administering to the subject the loaded LNP of any one of the preceding embodiments.

Embodiment 155. A method of treating a disease or disorder in a subject in need thereof, the method comprising administering to the subject a therapeutically effective amount of the loaded LNP of any one of the preceding embodiments.

Embodiment 156. Use of a loaded LNP of any one of the preceding embodiments, in the manufacture of a medicament for delivering a therapeutic and/or prophylactic agent to a cell within a subject.

Embodiment 157. Use of a loaded LNP of any one of the preceding embodiments, in the manufacture of a medicament for specifically delivering a therapeutic and/or prophylactic agent to an organ of a subject.

Embodiment 158. Use of a loaded LNP of any one of the preceding embodiments, in the manufacture of a medicament for the enhanced delivery of a therapeutic and/or prophylactic to a target tissue of a subject.

Embodiment 159. Use of a loaded LNP of any one of the preceding embodiments, in the manufacture of a medicament for producing a polypeptide of interest in a cell within a subject.

Embodiment 160. Use of a loaded LNP of any one of the preceding embodiments, in the manufacture of a medicament for treating a disease or disorder in a subject in need thereof.

Embodiment 161. A loaded LNP of any one of the preceding embodiments, for use in delivering a therapeutic and/or prophylactic agent to a cell within a subject, wherein the delivering comprises administering a therapeutically effective amount of the loaded LNP to the subject.

Embodiment 162. A loaded LNP of any one of the preceding embodiments, for use in specifically delivering a therapeutic and/or prophylactic agent to an organ of a subject, wherein the delivering comprises administering a therapeutically effective amount of the loaded LNP to the subject.

Embodiment 163. A loaded LNP of any one of the preceding embodiments, for use in the enhanced delivery of a therapeutic and/or prophylactic to a target tissue of a subject, wherein the use comprises administering to the subject the loaded LNP of any one of the preceding embodiments.

Embodiment 164. A loaded LNP of any one of the preceding embodiments, for use in producing a polypeptide of interest in a cell within a subject, the use comprises administering to the subject the loaded LNP of any one of the preceding embodiments.

Embodiment 165. A loaded LNP of any one of the preceding embodiments, for use in the treatment of a disease or disorder in a subject in need thereof, wherein the treatment comprises administering a therapeutically effective amount of the loaded LNP to a subject.

Embodiment 166. A method of delivering a therapeutic and/or prophylactic agent to a cell within a subject, the method comprising administering to the subject the pharmaceutical composition of any one of the preceding embodiments.

Embodiment 167. A method of specifically delivering a therapeutic and/or prophylactic agent to an organ of a subject, the method comprising administering to the subject the pharmaceutical composition of any one of the preceding embodiments.

Embodiment 168. A method for the enhanced delivery of a therapeutic and/or prophylactic to a target tissue of a subject, the method comprising administering to the subject the pharmaceutical composition of any one of the preceding embodiments.

Embodiment 169. A method of producing a polypeptide of interest in a cell within a subject, the method comprising administering to the subject the loaded LNP of any one of the preceding embodiments.

Embodiment 170. A method of treating a disease or disorder in a subject in need thereof, the method comprising administering to the subject a therapeutically effective amount of the pharmaceutical composition of any one of the preceding embodiments.

Embodiment 171. Use of a pharmaceutical composition of any one of the preceding embodiments, in the manufacture of a medicament for delivering a therapeutic and/or prophylactic agent to a cell within a subject.

Embodiment 172. Use of a pharmaceutical composition of any one of the preceding embodiments, in the manufacture of a medicament for specifically delivering a therapeutic and/or prophylactic agent to an organ of a subject.

Embodiment 173. Use of a pharmaceutical composition of any one of the preceding embodiments, in the manufacture of a medicament for the enhanced delivery of a therapeutic and/or prophylactic to a target tissue of a subject, the method comprising administering to the subject the pharmaceutical composition of any one of the preceding embodiments.

Embodiment 174. Use of a pharmaceutical composition of any one of the preceding embodiments, in the manufacture of a medicament for producing a polypeptide of interest in a cell within a subject.

Embodiment 175. Use of a pharmaceutical composition of any one of the preceding embodiments, in the manufacture of a medicament for treating a disease or disorder in a subject in need thereof.

Embodiment 176. A pharmaceutical composition of any one of the preceding embodiments, for use in delivering a therapeutic and/or prophylactic agent to a cell within a subject, wherein the delivering comprises administering a therapeutically effective amount of the pharmaceutical composition to the subject.

Embodiment 177. A pharmaceutical composition of any one of the preceding embodiments, for use in specifically delivering a therapeutic and/or prophylactic agent to an organ of a subject, wherein the delivering comprises administering a therapeutically effective amount of the pharmaceutical composition to the subject.

Embodiment 178. A pharmaceutical composition of any one of the preceding embodiments, for use in the enhanced delivery of a therapeutic and/or prophylactic to a target tissue of a subject, wherein the use comprises administering to the subject the pharmaceutical composition of any one of the preceding embodiments.

Embodiment 179. A pharmaceutical composition of any one of the preceding embodiments, for use in producing a polypeptide of interest in a cell within a subject, the use comprises administering to the subject the pharmaceutical composition of any one of the preceding embodiments Embodiment 180. A pharmaceutical composition of any one of the preceding embodiments, for use in the treatment of a disease or disorder in a subject in need thereof, wherein the treatment comprises administering a therapeutically effective amount of the pharmaceutical composition to a subject.

Embodiment 181. The method, use, or loaded LNP or pharmaceutical composition for use, of any one of the preceding embodiments, wherein the organ is selected from the group consisting of liver, kidney, lung, spleen, and femur.

Embodiment 182. The method, use, or loaded LNP or pharmaceutical composition for use, of any one of the preceding embodiments, wherein the target tissue is selected from the group consisting of liver, kidney, lung, spleen, and femur.

Embodiment 183. The method or loaded LNP or pharmaceutical composition for use of any one of the preceding embodiments, wherein the administering is performed parenterally.

Embodiment 184. The method or loaded LNP or pharmaceutical composition for use wherein the administering is performed intramuscularly, intradermally, subcutaneously, and/or intravenously.

Embodiment 185. The use of any one of the preceding embodiments, wherein the medicament is for parenteral administration.

Embodiment 186. The use of any one of the preceding embodiments, wherein the medicament is for intramuscular, intradermal, subcutaneous, and/or intravenous administration.

Embodiment 187. The method, use, or loaded LNP or pharmaceutical composition for use, of any one of the preceding embodiments, wherein the subject is human.

EQUIVALENTS

It is to be understood that while the present disclosure has been described in conjunction with the detailed description thereof, the foregoing description is intended to illustrate and not limit the scope of the present disclosure, which is defined by the scope of the appended claims. Other aspects, advantages, and alterations are within the scope of the following claims.

The invention claimed is:

1. A is a thiadiazole to

A is a 1,2,5-thiadiazole.

2. The compound of claim 1, having one of the following structures:

(A-1a)

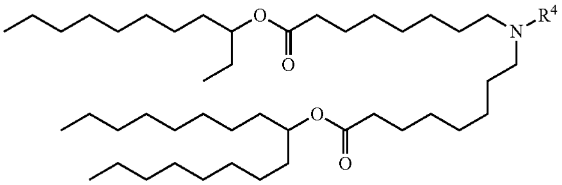

-continued (A-1b)

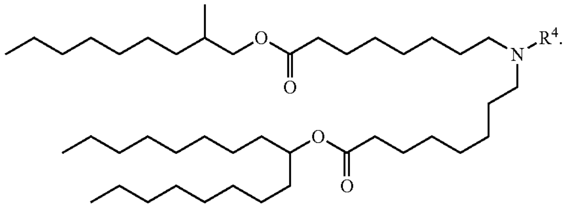

3. The compound of claim 1, wherein $R^4$ is

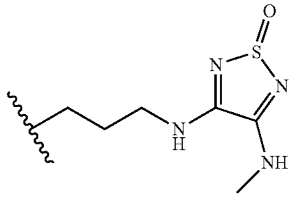

or

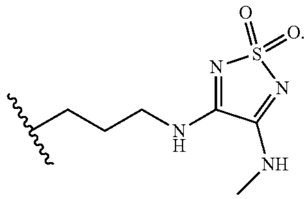

4. A compound selected from Compounds 1, 2, 82, 84, 85, and 92:

| Cpd | Structure |
|---|---|
| 1 | 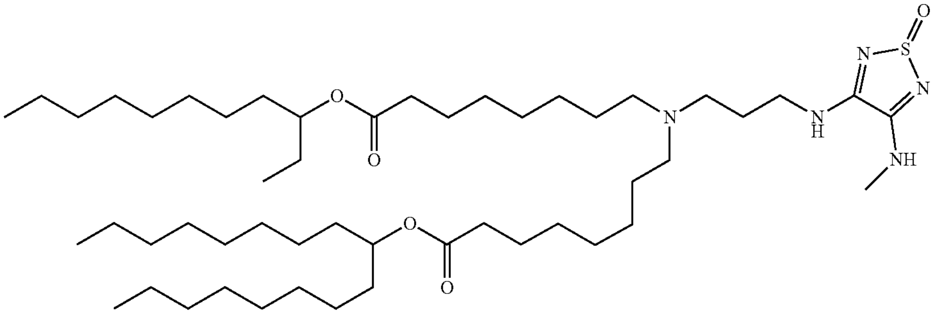 [SMILES: CCCCCCCCC(CC)OC(=O)CCCCCCCN(CCCCCCCC(=O)OC(CCCCCCCC)CCCCCCCC)CCCNC1=NS(=O)N=C1NC] |

-continued
| Cpd | Structure |
| --- | --- |
| 2 | 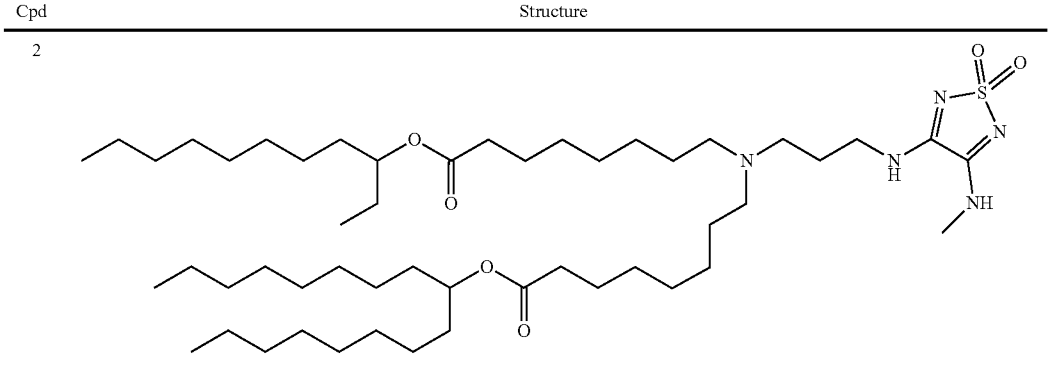 |
| 82 | 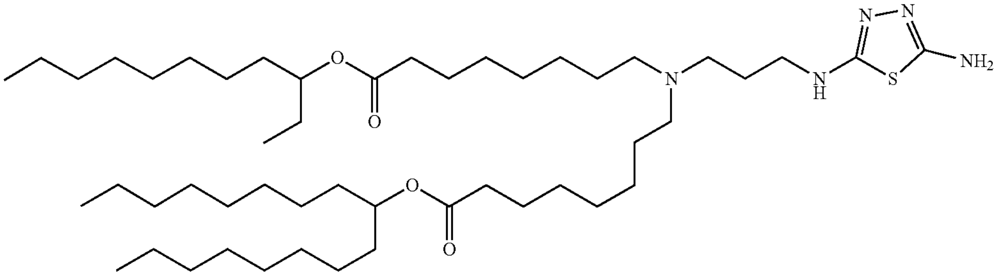 [SMILES: CCCCCCCCC(CC)OC(=O)CCCCCCCN(CCCCCCCC(=O)OC(CCCCCCCC)CCCCCCCC)CCCNc1nnc(N)s1] |
| 84 | 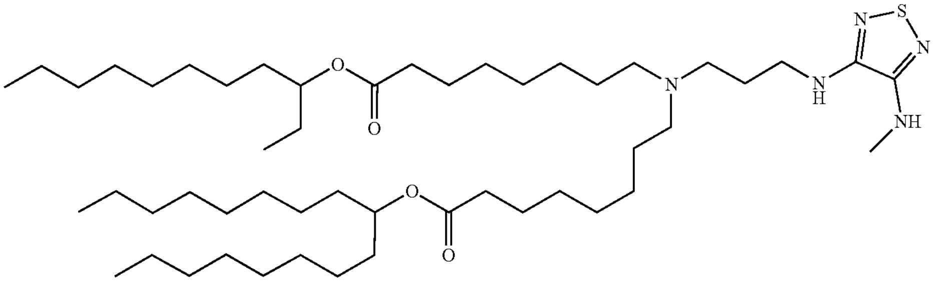 |
| 85 | 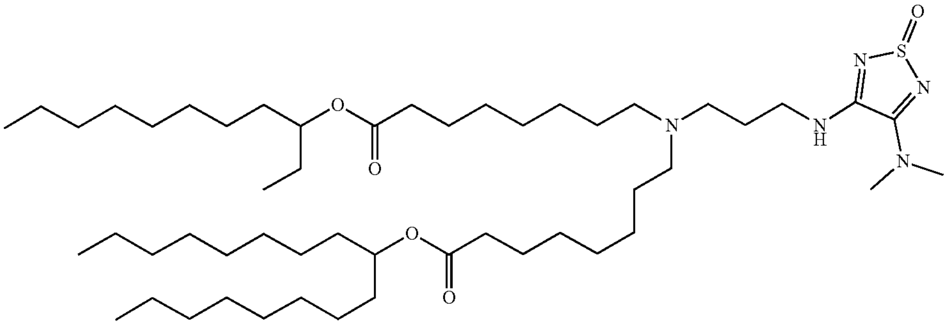 [SMILES: CCCCCCCCC(CC)OC(=O)CCCCCCCN(CCCCCCCC(=O)OC(CCCCCCCC)CCCCCCCC)CCCNC1=NS(=O)N=C1N(C)C] |
| 92 | 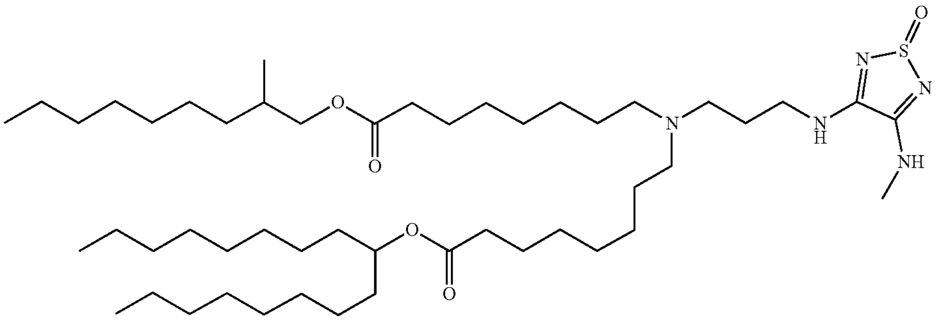 [SMILES: CCCCCCCCC(CCCCCCCC)OC(=O)CCCCCCCN(CCCCCCCC(=O)OCC(C)CCCCCCC)CCCNC1=NS(=O)N=C1NC] |
and N-oxides and salts thereof.

5. An empty lipid nanoparticle (empty LNP) comprising a compound of claim 1, a phospholipid, a structural lipid, and a PEG lipid.

6. The empty LNP of claim 5, comprising about 40 mol % to about 60 mol % said compound, about 0 mol % to about 20 mol % phospholipid, about 30 mol % to about 50 mol % structural lipid, and about 0 mol % to about 5 mol % PEG lipid;

wherein the phospholipid is selected from the group consisting of:

1,2-dilinoleoyl-sn-glycero-3-phosphocholine (DLPC), 1,2-dimyristoyl-sn-glycero-phosphocholine (DMPC), 1,2-dioleoyl-sn-glycero-3-phosphocholine (DOPC), 1,2-dipalmitoyl-sn-glycero-3-phosphocholine (DPPC), 1,2-distearoyl-sn-glycero-3-phosphocholine (DSPC), 1,2-diundecanoyl-sn-glycero-phosphocholine (DUPC), 1-palmitoyl-2-oleoyl-sn-glycero-3-phosphocholine (POPC), 1,2-di-O-octadecenyl-sn-glycero-3-phosphocholine (18:0 Diether PC), 1-oleoyl-2-cholesterylhemisuccinoyl-sn-glycero-3-phosphocholine (OChemsPC), 1-hexadecyl-sn-glycero-3-phosphocholine (C16 Lyso PC), 1,2-dilinolenoyl-sn-glycero-3-phosphocholine, 1,2-diarachidonoyl-sn-glycero-3-phosphocholine, 1,2-didocosahexaenoyl-sn-glycero-3-phosphocholine, 1,2-dioleoyl-sn-glycero-3-phosphoethanolamine (DOPE), 1,2-diphytanoyl-sn-glycero-3-phosphoethanolamine (ME 16.0 PE), 1,2-distearoyl-sn-glycero-3-phosphoethanolamine, 1,2-dilinoleoyl-sn-glycero-3-phosphoethanolamine, 1,2-dilinolenoyl-sn-glycero-3-phosphoethanolamine, 1,2-diarachidonoyl-sn-glycero-3-phosphoethanolamine, 1,2-didocosahexaenoyl-sn-glycero-3-phosphoethanolamine, 1,2-dioleoyl-sn-glycero-3-phospho-rac-(1-glycerol) sodium salt (DOPG), sphingomyelin, and mixtures thereof;

wherein the structural lipid is selected from the group consisting of cholesterol, fecosterol, sitosterol, ergosterol, campesterol, stigmasterol, brassicasterol, and mixtures thereof; and/or wherein the PEG lipid is selected from the group consisting of a PEG-modified phosphatidylethanolamine, a PEG-modified phosphatidic acid, a PEG-modified ceramide, a PEG-modified dialkylamine, a PEG-modified diacylglycerol, a PEG-modified dialkylglycerol, and mixtures thereof.

7. The empty LNP of claim 5, wherein the PEG lipid is selected from $PEG_{2k}$-DMG and PEG-1:

($PEG_{2k}$-DMG)

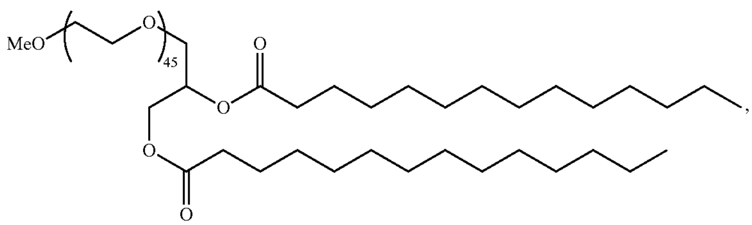

, (PEG-1)

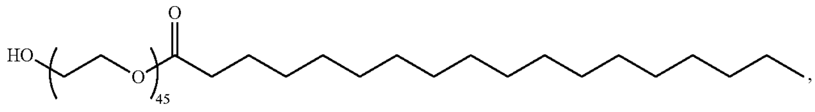

, and mixtures thereof.

8. A loaded lipid nanoparticle (loaded LNP), which comprises the empty LNP of claim 5 and one or more therapeutic and/or prophylactic agents.

9. The loaded LNP of claim 8, wherein the one or more therapeutic and/or prophylactic agents is a nucleic acid, wherein the nucleic acid is an RNA, and wherein the RNA is selected from the group consisting of a short interfering RNA (siRNA), an asymmetrical interfering RNA (aiRNA), a RNA interference (RNAi) molecule, a microRNA (miRNA), an antagomir, an antisense RNA, a ribozyme, a Dicer-substrate RNA (dsRNA), a small hairpin RNA (shRNA), a messenger RNA (mRNA), and mixtures thereof.

10. The loaded LNP of claim 9, wherein the RNA is an mRNA.

11. A pharmaceutical composition comprising the loaded LNP of claim 8 and a pharmaceutically acceptable carrier.

12. A method of delivering a therapeutic and/or prophylactic agent to a cell within a subject, and/or to the organ of a subject, the method comprising administering to the subject the loaded LNP of claim 8.

13. A method of producing a polypeptide of interest in a cell within a subject, the method comprising administering to the subject the loaded LNP of claim 10.

14. A method of treating a disease or disorder in a subject in need thereof, the method comprising administering to the subject a therapeutically effective amount of the loaded LNP of claim 8.

* * * * *